US012807611B2

(12) United States Patent
Katamreddy et al.

(10) Patent No.: US 12,807,611 B2
(45) Date of Patent: Nov. 24, 2026

(54) CYCLIN-DEPENDENT KINASE INHIBITORS

(71) Applicant: SPV THERAPEUTICS INC., Research Triangle Park, NC (US)

(72) Inventors: Subba R. Katamreddy, Research Triangle Park, NC (US); Yousry Sayed, Research Triangle Park, NC (US); Naresh Ramireddy, Research Triangle Park, NC (US)

(73) Assignee: SPV THERAPEUTICS INC., Research Triangle Park, NC (US)

( * ) Notice: Subject to any disclaimer, the term of this patent is extended or adjusted under 35 U.S.C. 154(b) by 1267 days.

(21) Appl. No.: 17/416,971

(22) PCT Filed: Dec. 27, 2019

(86) PCT No.: PCT/US2019/068775
§ 371 (c)(1),
(2) Date: Jun. 21, 2021

(87) PCT Pub. No.: WO2020/140055
PCT Pub. Date: Jul. 2, 2020

(65) Prior Publication Data

US 2023/0048132 A1 Feb. 16, 2023

Related U.S. Application Data

(60) Provisional application No. 62/785,849, filed on Dec. 28, 2018.

(51) Int. Cl.
*C07D 471/20* (2006.01)
*C07D 487/04* (2006.01)
*C07D 519/00* (2006.01)

(52) U.S. Cl.
CPC ......... *C07D 471/20* (2013.01); *C07D 487/04* (2013.01); *C07D 519/00* (2013.01)

(58) Field of Classification Search
CPC ... C07D 471/20; C07D 487/04; C07D 519/00
See application file for complete search history.

(56) References Cited

U.S. PATENT DOCUMENTS

| | | | |
|---|---|---|---|
| 6,936,612 B2 | 8/2005 | Barvian et al. | |
| 7,713,994 B2 | 5/2010 | Tsou et al. | |
| 7,776,869 B2 | 8/2010 | Chaffee et al. | |
| 8,324,225 B2 | 12/2012 | Brain et al. | |
| 8,598,186 B2 | 12/2013 | Tavares et al. | |
| 8,685,980 B2 | 4/2014 | Besong et al. | |
| 9,850,244 B2 * | 12/2017 | Xu | C08K 5/34 |
| 2003/0064928 A1 | 4/2003 | Backstrom et al. | |
| 2005/0222163 A1 | 10/2005 | Eck et al. | |
| 2005/0261307 A1 | 11/2005 | Cai et al. | |
| 2007/0212736 A1 | 9/2007 | Chen-Kiang et al. | |
| 2009/0093497 A1 | 4/2009 | Bolin et al. | |
| 2012/0220572 A1 | 8/2012 | Tong et al. | |
| 2012/0309775 A1 | 12/2012 | Cheng et al. | |
| 2013/0035336 A1 | 2/2013 | Borland et al. | |
| 2014/0107094 A1 | 4/2014 | Leonard et al. | |
| 2016/0220569 A1 | 8/2016 | Strum et al. | |
| 2018/0044344 A1 | 2/2018 | Behenna et al. | |
| 2018/0072707 A1 | 3/2018 | Ding et al. | |
| 2018/0155351 A1 | 6/2018 | Besong et al. | |
| 2018/0208564 A1 | 7/2018 | Mansour | |
| 2019/0184023 A1 | 6/2019 | Miyamoto et al. | |
| 2022/0056037 A1 | 2/2022 | Katamreddy et al. | |
| 2022/0220103 A1 | 7/2022 | Katamreddy et al. | |
| 2023/0065740 A1 | 3/2023 | Katamreddy et al. | |

FOREIGN PATENT DOCUMENTS

| | | | |
|---|---|---|---|
| WO | 9909030 A1 | 2/1999 | |
| WO | 1999048858 A2 | 9/1999 | |
| WO | 0024744 A1 | 5/2000 | |
| WO | 2001068643 A1 | 9/2001 | |
| WO | 0212238 A2 | 2/2002 | |
| WO | 2002010146 A1 | 2/2002 | |
| WO | 2003015776 A1 | 2/2003 | |
| WO | 2003062236 | 7/2003 | |
| WO | 2004011438 A1 | 2/2004 | |
| WO | 2004056822 A1 | 7/2004 | |
| WO | 2004080980 A1 | 9/2004 | |
| WO | 2005009443 A1 | 2/2005 | |

(Continued)

OTHER PUBLICATIONS

European Patent Office Extended European Search Report for Application No. 19905411.5 dated Jan. 31, 2023 (14 pages).
European Patent Office Partial Supplementary Search Report for Application No. 19903619.5 dated Aug. 10, 2022 (16 pages).
Katz, J. D., et al. "Structure guided design of a series of selective pyrrolopyrimidinone MARK inhibitors." Bioorganic & medicinal chemistry letters 27.1 (2017): 114-120.
Shao, Y., et al. "Synthesis and SAR studies of trisubstituted purinones as potent and selective adenosine A2A receptor antagonists." Bioorganic & Medicinal Chemistry Letters 19.5 (2009): 1399-1402.
European Patent Office Partial Supplementary Search Report for Application No. 19905411.5 dated Oct. 31, 2022 (18 pages).
European Patent Office Extended European Search Report for Application No. 19903619.5 dated Nov. 14, 2022 (13 pages).

(Continued)

*Primary Examiner* — Adam C Milligan
*Assistant Examiner* — Karen Cheng
(74) *Attorney, Agent, or Firm* — Hovey Williams LLP; Crissa A. Cook

(57) ABSTRACT

Described herein are compounds and their pharmaceutically acceptable salts, pharmaceutical compositions thereof, methods of treatment, and medical uses. The compounds described herein are modulators of cyclin-dependent kinases, and are useful in the treatment or alleviation of protein kinase associated disorders, including cancer, infectious diseases, autoimmune diseases, or cardiovascular diseases.

23 Claims, 5 Drawing Sheets

(56) References Cited

FOREIGN PATENT DOCUMENTS

| | | | |
|---|---|---|---|
| CN | 105294737 | A | 2/2016 |
| CN | 106749259 | B | 2/2019 |
| TD | 2012082817 | A1 | 6/2012 |
| WO | 2006004200 | A1 | 1/2006 |
| WO | 2007015877 | A2 | 2/2007 |
| WO | 2007033232 | A1 | 3/2007 |
| WO | 2007089768 | A2 | 8/2007 |
| WO | 2007131991 | A1 | 11/2007 |
| WO | 2007140222 | A2 | 12/2007 |
| WO | 2008032162 | A1 | 3/2008 |
| WO | 2008033999 | A2 | 3/2008 |
| WO | 2008051547 | A1 | 5/2008 |
| WO | 2008113711 | A1 | 9/2008 |
| WO | 2008152013 | A1 | 12/2008 |
| WO | 2009037467 | A1 | 3/2009 |
| WO | 2009076140 | A1 | 6/2009 |
| WO | 2009079597 | A1 | 6/2009 |
| WO | 2009085185 | A1 | 7/2009 |
| WO | 2009156284 | A1 | 12/2009 |
| WO | 2010020675 | A1 | 2/2010 |
| WO | 2010027005 | A1 | 3/2010 |
| WO | 2010090764 | A1 | 8/2010 |
| WO | 2010149755 | A1 | 12/2010 |
| WO | 2009096435 | A1 | 5/2011 |
| WO | 2011112995 | A1 | 9/2011 |
| WO | 2012018540 | A1 | 2/2012 |
| WO | 2012053606 | A1 | 4/2012 |
| WO | 2012058392 | A1 | 5/2012 |
| WO | 2012059932 | A1 | 5/2012 |
| WO | 2012069680 | A1 | 5/2012 |
| WO | 2012145569 | A1 | 10/2012 |
| WO | 2014012360 | A1 | 1/2014 |
| WO | 2014108452 | A1 | 7/2014 |
| WO | 2014134308 | A1 | 9/2014 |
| WO | 2015038417 | A1 | 3/2015 |
| WO | 2015092431 | A1 | 6/2015 |
| WO | 2015128334 | A1 | 9/2015 |
| WO | 2015132799 | A2 | 9/2015 |
| WO | 2016015605 | A1 | 2/2016 |
| WO | 2016040858 | A1 | 3/2016 |
| WO | 2016049211 | A1 | 3/2016 |
| WO | 2016197032 | A1 | 12/2016 |
| WO | 2016013657 | A1 | 4/2017 |
| WO | 2017064657 | A1 | 4/2017 |
| WO | 2017066428 | A1 | 4/2017 |
| WO | 2017076355 | A1 | 5/2017 |
| WO | 2017079267 | A1 | 5/2017 |
| WO | 2017084096 | A1 | 5/2017 |
| WO | 2017143842 | A1 | 8/2017 |
| WO | 2017161119 | A1 | 9/2017 |
| WO | 2017176812 | A1 | 10/2017 |
| WO | 2017185023 | A1 | 10/2017 |
| WO | 2017197036 | A1 | 11/2017 |
| WO | 2017211216 | A1 | 12/2017 |
| WO | 2018005193 | A1 | 1/2018 |
| WO | 2018005860 | A1 | 1/2018 |
| WO | 2018005865 | A1 | 1/2018 |
| WO | 2018007331 | A1 | 1/2018 |
| WO | 2018009625 | A1 | 1/2018 |
| WO | 2018011164 | A1 | 1/2018 |
| WO | 2011101409 | A1 | 5/2018 |
| WO | 2018081211 | A1 | 5/2018 |
| WO | 2018106870 | A1 | 6/2018 |
| WO | 2018124001 | A1 | 7/2018 |
| WO | 2018160774 | A1 | 9/2018 |
| WO | 2018161922 | A1 | 9/2018 |
| WO | 2018183112 | A1 | 10/2018 |
| WO | 2019060742 | A1 | 3/2019 |
| WO | 2019140387 | A1 | 7/2019 |
| WO | 2019195609 | A2 | 10/2019 |
| WO | 2020023917 | A1 | 1/2020 |
| WO | 2020041331 | A1 | 2/2020 |
| WO | 2020140052 | A1 | 7/2020 |
| WO | 2020140053 | A1 | 7/2020 |
| WO | 2020140054 | A1 | 7/2020 |

OTHER PUBLICATIONS

Axten et al., "Discovery of 7-methyl-5-(1-{[3-(trifluoromethyl)phenyl]acetyl}-2,3-dihydro-1H-indol-5-yl)-7H-pyrrolo[2,3-d]pyrimidin-4-amine (GSK2606414), a potent and selective first-in-class inhibitor of protein kinase R (PKR)-like endoplasmic reticulum kinase (PERK)", J. Med. Chem., vol. 55, No. 16, 2012, pp. 7193-7207.

Berge et al., "Review Article: Pharmaceutical Salts", J. Pharm Sci, vol. 66, 1977, pp. 1-19.

Cue et al., "Green process chemistry in the pharmaceutical industry", Green Chemistry Letters and Reviews, vol. 10, No. 1, 2017, pp. 42-47.

Dolomanov et al., "OLEX2: A complete structure solution, refinement and analysis program", J. Appl. Cryst., vol. 42, 2009, pp. 339-341.

Fleisher et al., "Improved oral drug delivery: solubility limitations overcome by the use of prodrugs", Advanced Drug Delivery Reviews, vol. 19, 1996, pp. 115-130.

Harwell et al., "Activation of Cyclin-dependent Kinase 2 by Full Length and Low Molecular Weight Forms of Cyclin E in Breast Cancer Cells", J. Biol. Chem, vol. 279, No. 13, 2004, pp. 12695-12705.

Harwell et al., "Processing of Cyclin E Differs between Normal and Tumor Breast Cells", Cancer Res., vol. 60, 2000, pp. 481-489.

Higuchi, "The Chemistry of a Novel 5,5-Diphenylhydantoin Pro-Drug", Pro-Drugs as Novel Delivery Systems, ACS Symposium Series, vol. 14, 1975, pp. 154-183.

Hou et al., "Design, synthesis and biological evaluation of novel 7-amino-[1,2,4] triazolo[4,3-f]pteridinone, and 7-aminotetrazolo[1,5-f]pteridinone derivative as potent antitumor agents", eJMC, 2019, vol. 163, pp. 690-709.

Howe et al., "Real-Time Quantitative Reverse Transcription PCR for Cyclin D1 mRNA in Blood, Marrow, and Tissue Specimens for Diagnosis of Mantle Cell Lymphoma", Clin. Chem., vol. 50, No. 1, 2004, pp. 80-87.

Jones et al., "CyclinD1/CyclinD3 Ratio by Real-Time PCR Improves Specificity for the Diagnosis of Mantle Cell Lymphoma", J. Mol. Diagn., vol. 6, No. 2, 2004, pp. 84-89.

Jorda et al., "How selective are pharmacological inhibitors of cell-cycle-regulating cyclin-dependent kinases?", Journal of Medicinal Chemistry, vol. 61, No. 20, 2018, pp. 9105-9120.

Lawhorn et al., "Identification of Purines and 7-Deazapurines as Potent and Selective Type 1 Inhibitors of Troponin I-Interacting Kinase (TNNI3K)", J. Med. Chem., vol. 58, No. 18, 2015, pp. 7431-7448.

Li et al., "Towards Optimization of Arylamides as Novel, Potent, and Brain-Penetrant Antiprion Lead Compounds", ACS Med. Chem. Lett., vol. 4, No. 7, 2013, pp. 647-650.

Lohmann et al., "Retinoblastoma", Gene Reviews, 2000, 21 pages.

Lu et al., "Discovery of biphenyl-based VEGFR-2 inhibitors. Part 3: design, synthesis and 3D-QSAR studies.", BMCL 2015, vol. 23, pp. 1044-1054.

Maffrand et al., "1,3-Dipolar cycloaddition reactions of Munchnone and Sydnone derivatives obtained from 4,5,6,7-tetrahydrothieno(3,2-c)pyridine-4 and -6 carboxylic acids", Heterocycles, vol. 16, No. 1, 1981, pp. 35-37.

Parsam et al., "A comprehensive, sensitive and economical approach for the detection of mutations in the RB1 gene in retinoblastoma", J. Genetics, vol. 88, No. 4, 2009, pp. 517-527.

Perumal et al., "Dual Targeting of CDK4 and ARK5 using a novel kinase inhibitor ON123300 exerts potent anticancer activity against multiple myeloma", Cancer Research, vol. 76, No. 5, 2016, pp. 1225-1236.

Rajagopalan et al., "Inactivation of hCDC4 can cause chromosomal instability", Nature, vol. 428, No. 6978, 2004, pp. 77-81.

Reddy et al., "Discovery of the 8-cyclopentyl-2-[4-(4-methyl-piperazin-1-yl)-phenylamniol]-7-oxo-7, 8-dihydro-pyrido [2,3-d] pyrimidine-6-carbonitrile (7x) as a potent inhibitor of cyclin-dependent

(56) References Cited

OTHER PUBLICATIONS kinase 4 (CDK4) and AMPK-related kinase 5 (ARK5)", Journal of Medicinal Chemistry, vol. 57, No. 3, 2014, pp. 578-599.
Riggs et al., "Design and Optimization Leading to an Orally Active TTK Protein Kinase Inhibitor with Robust Single Agent Efficacy", JMC, 2019, vol. 62, pp. 4401-4410.
Saeed et al, "2-Chloro-4-[[(1R,2R)-2-hydroxy-2-methyl-cyclopentyl]amino]-3-methyl-benzonitrile: A Transdermal Selective Androgen Receptor Modulator (SARM) for Muscle Atrophy", JMC, 2016, vol. 59, pp. 750-755.
Singh et al., "Discovery and development of spleen tyrosine kinase (SYK) inhibitors", J. Med. Chem., vol. 55, 2012, pp. 3614-3643.
Spruck et al., "hCDC4 Gene Mutations in Endometrial Cancer", Cancer Res., vol. 62, No. 16, 2002, pp. 4535-4539.
TenBrink et al., "High Affinity Partial Agonist Imidazo[1,5-a]quinoxaline Amides, Carbamates, and Ureas at the y-Aminobutyric Acid A/ Benzodiazepine Receptor Complex", J. Med. Chem. vol. 39, 1996, pp. 158-175.
Tsou et al, "4-(Phenylaminomethylene)isoquinoline-1,3(2H,4H)-diones as potent and selective inhibitors of the cyclin-dependent kinase 4 (CDK4)", J. Med. Chem., vol. 51, No. 12, 2008, pp. 3507-3525.
International Search Report and Written Opinion for Application No. PCT/US2019/068775 dated May 1, 2020 (16 pages).
VanderWel et al., "Pyrido[2,3-d]pyrimidin-7-ones as Specific Inhibitors of Cyclin-Dependent Kinase 4", JMC, 2005, vol. 48, pp. 2371-2387.
Walia et al., "Microwave-assisted Protection of Primary Amines as 2,5-Dimethylpyrroles and Their Orthogonal Deprotection", J. Org. Chem., vol. 78, No. 21, 2013, pp. 10931-10937.
Yatabe et al., "Significance of cyclin D1 overexpression for the diagnosis of mantle cell lymphoma: a clinicopathologic comparison of cyclin D1-positive MCL and cyclin D1-negative MCL-like B-cell lymphoma", Blood, vol. 95, No. 7, 2000, pp. 2253-2261.
Zhu et al., "Ligand-Free Copper-Catalyzed One-Pot Synthesis of Indole-2-carboxylic Esters", Eur. J. Org. Chem., vol. 3, 2014, pp. 511-514.
An et al., "Small-molecule PROTACs: An emerging and promising approach for the development of targeting therapy drugs", EBioMedicine, vol. 36, 2018, pp. 553-562.
Banerjee, Souvik, et al. "A stereoselective cyclization strategy for the preparation of γ-lactams and their use in the synthesis of α-methyl-β-proline." The Journal of Organic Chemistry 77.23 (2012): 10925-10930.
Brand, M., et al. "Homolog-Selective Degradation as a Strategy to Probe the Function of CDK6 in AML." Cell chemical biology 26.2 (2019): 300-306.
Crews, C. M. "Inducing protein degradation as a therapeutic strategy." Journal of Medicinal Chemistry 61.2 (2018): 403-404.
Dieltiens, N., et al. "[1, 2] Boc migration during pyroglutamate alkylations." Tetrahedron 61.28 (2005): 6749-6756.
Dierks, A. et al. "Synthesis of Annulated Indolines by Reductive Fischer Indolization." Chemistry—A European Journal 25.21 (2019): 5451-5462.
Guitot, Karine, et al. "Synthesis of (S)-and (R)-5-Oxo-piperazine-2-Carboxylic Acid and Its Application to Peptidomimetics." The Journal of Organic Chemistry 74.21 (2009): 8433-8436.
Habibi, Azizollah, Enayatollah Seikhhosseini Lori, and Abbas Shockravi. "Synthesis of novel furo-pyran derivatives via reaction between an isocyanide and alkylidene-substituted Meldrum's acid." Tetrahedron Letters 50.9 (2009): 1075-1078.
Hu, X., et al. "Synthesis and biological evaluation of novel 5, 6-dihydropyrimido [4, 5-f] quinazoline derivatives as potent CDK2 inhibitors." Bioorganic & Medicinal Chemistry Letters 28.20 (2018): 3385-3390.
Huang et al., "A Chemoproteomic Approach to Query the Degradable Kinome Using a Multi-Kinase Degraders", Cell. Chem. Biol., vol. 25, No. 1, 2018, pp. 88-99.
Huang, H., et al. "Design and synthesis of a pyrido [2, 3-d] pyrimidin-5-one class of anti-inflammatory FMS inhibitors." Bioorganic & medicinal chemistry letters 18.7 (2008): 2355-2361.
International Search Report and Written Opinion for Application No. PCT/US2021/038837 dated Sep. 29, 2021 (10 pages).
Kyei, A. S., et al. "Radical dearomatising spirocyclisations onto the C-2 position of benzofuran and indole." Tetrahedron letters 45.48 (2004): 8931-8934.
Lindstrom, K. J., et al. "An Improved Preparation of Ethyl 2-Oxo-3-Pyrrolidinecarboxylate." Synthetic Communications 20.15 (1990): 2335-2337.
Mao, T.-Q., et al. "Anti-HIV diarylpyrimidine-quinolone hybrids and their mode of action." Bioorganic & medicinal chemistry 23.13 (2015): 3860-3868.
Meng, G. et al. "Rhodium-catalyzed C—H bond functionalization with amides by double C—H/C—N bond activation." Organic letters 18.4 (2016): 796-799.
Park, Y., et al. "Highly Enantioselective Phase-Transfer Catalytic α-Alkylation of α-tert-Butoxycarbonyllactams: Construction of β-Quaternary Chiral Pyrrolidine and Piperidine Systems." Advanced Synthesis & Catalysis 353.18 (2011): 3313-3318.
Pei, H., et al. "Small molecule PROTACs: an emerging technology for targeted therapy in drug discovery." RSC advances 9.30 (2019): 16967-16976.
Putey, A., et al. "Indolobenzazepin-7-ones and 6-, 8-, and 9-membered ring derivatives as tubulin polymerization inhibitors: synthesis and structure-activity relationship studies." Journal of medicinal chemistry 52.19 (2009): 5916-5925.
Reddy, MV Ramana, et al. "Discovery of 8-cyclopentyl-2-[4-(4-methyl-piperazin-1-yl)-phenylamino]-7-oxo-7, 8-dihydro-pyrido [2, 3-d] pyrimidine-6-carbonitrile (7x) as a potent inhibitor of cyclin-dependent kinase 4 (CDK4) and AMPK-related kinase 5 (ARK5)." Journal of medicinal chemistry 57.3 (2014): 578-599.
Roskoski Jr, R.. "Cyclin-dependent protein serine/threonine kinase inhibitors as anticancer drugs." Pharmacological research 139 (2019): 471-488.
Sakamoto, T., et al. "8-(3-Chloro-4-methoxybenzyl)-8H-pyrido [2, 3-d] pyrimidin-7-one derivatives as potent and selective phosphodiesterase 5 inhibitors." Bioorganic & Medicinal Chemistry Letters 25.7 (2015): 1431-1435.
Sun, Z., et al. "π-Extended C 2-symmetric double NBN-heterohelicenes with exceptional luminescent properties." Organic letters 22.1 (2019): 209-213.
Toshima, M., et al. "First Kilogram-Scale Application of the Lanthanum Catalyzed Asymmetric Amination to Synthesis of the Chiral Succinimide Derivative, A Key Intermediate for the Preparation of AS-3201." Organic Process Research & Development 20.7 (2016): 1239-1245.
Trost, B. M., et al. "Palladium-catalyzed decarboxylative asymmetric allylic alkylation of dihydroquinolinones." Organic letters 21.6 (2019): 1784-1788.
Xie, H., et al. "Intramolecular cycloaddition of azomethine ylides activated by aromatic rings: scope and limitations." Chemistry of Heterocyclic Compounds 52 (2016): 484-492.
Yang, W., et al. "Facile synthesis of spirocyclic lactams from β-keto carboxylic acids." Organic letters 17.12 (2015): 3070-3073.
Zou, Y. et al. "The PROTAC technology in drug development." Cell biochemistry and function 37.1 (2019): 21-30.
Australian Patent Office Examination Report No. 1 for Application No. 2019413683, dated May 15, 2024 (4 pages).
Office Action in co-pending Canadian Patent Application Serial No. 3,124,574, dated Nov. 22, 2024.

* cited by examiner

A

B

CYCLIN-DEPENDENT KINASE INHIBITORS

CROSS-REFERENCE TO RELATED APPLICATIONS

The present application is a U.S. national stage entry of International Patent Application No. PCT/US2019/068775, filed on Dec. 27, 2019, which claims the benefit of U.S. Provisional Patent Application No. 62/785,849, filed on Dec. 28, 2018, which are hereby incorporated herein by reference in their entirety.

TECHNICAL FIELD

Described herein are compounds and their pharmaceutically acceptable salts, pharmaceutical compositions thereof, methods of treatment, and medical uses. The compounds described herein are modulators of cyclin-dependent kinases and are useful in the treatment or alleviation of protein kinase associated disorders, including cancer, infectious diseases, autoimmune diseases, or cardiovascular diseases.

BACKGROUND

The cell cycle is a complex series of events that cause a cell to divide and duplicate. The phases of the cell cycle include mitosis (M), gap 1 phase (G1), synthesis phase (S) and gap 2 phase (G2). Checkpoints in the cell cycle ensure that division only occurs after sufficient growth and faithful DNA replication and under favorable conditions. At each checkpoint, a variety of proteins engage in a series of carefully coordinated biochemical reactions. This complexity allows for precise regulation of all steps in the cell cycle.

Cyclin-dependent kinases (CDKs) are powerful protein kinase enzymes that drive cell cycle regulation in biochemical pathways by modulating the activity of various target proteins of the cell cycle. In response to a variety either intra- or extracellular cues, the enzymes function by the transfer of phosphate groups from intracellular adenosine triphosphate (ATP) to the serine or threonine amino acids of target proteins involved in a signaling pathway. These activating or inhibitory phosphorylation events act as the signals that either activate or deactivate target protein activity, and thus stimulate or inhibit the cell from entering the cell cycle and dividing.

CDKs themselves require the presence of cyclin proteins to activate. A variety of cyclin proteins exist, each of which is present at varying protein levels and act during a specific stage of the cell cycle by binding to specific CDKs. The cyclin-CDK complexes then recognize and modify multiple target substrates and thus coordinate multiple events during each phase of the cell cycle. Thus, the various activities of the cell cycle are determined by the specific combination of cyclins and CDKs that are active at each stage. For example, cyclin D and CDK4 and CDK6 have been found to be active during the G1 phase of the cell cycle and react to external signals such as growth factors and mitogens. Cyclins A and E and CDK2 have been found to be active during G1/S phase of the cell cycle and are thought to regulate centrosome duplication. Some cyclin-CDK complexes are found to be involved in transcription activities, such as cyclin A, cyclin E and CDK2 which are thought to target helicase and polymerase protein enzymes. CDK-cyclin controlled protein phosphorylation thus plays an important role in many key cellular processes including cell division, metabolism, survival, and apoptosis.

The ubiquitous nature of CDKs coupled with the highly regulated and complex nature of CDK dependent phosphorylation makes it susceptible to malfunction. Thus, CDKs are implicated in a variety of cell-cycle dependent diseases, including cancers, cardiovascular diseases, neurodegenerative disorders, autoimmune diseases and infectious diseases with the CDKs either the causative agents or as therapeutic targets.

Of particular interest are CDK4, CDK6, and CDK9 as therapeutic targets. These cyclin-dependent kinases are involved in cell cycle regulation and have been found to be deregulated and overactive in cancer cells as result of overexpression of relevant genes or loss of naturally occurring, endogenous inhibitors by gene deletion or mutation. Thus, inhibitors of CDK4/6/9 among other cyclin dependent kinases are important targets for cancer therapeutics, alone or in combination with other drugs.

Thus, there remains a need for additional cyclin dependent kinase inhibitors suitable for pharmaceuticals.

SUMMARY

One embodiment described herein is a compound or a pharmaceutically acceptable salt thereof comprising Formula I or II:

(I)

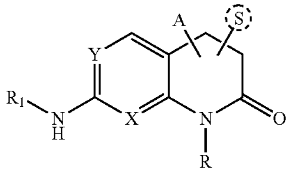

or (II)

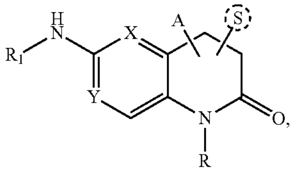

wherein A is none, Me, CO, or gem-difluoro;

X and Y are independently, C, N, or C—F;

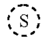

is:

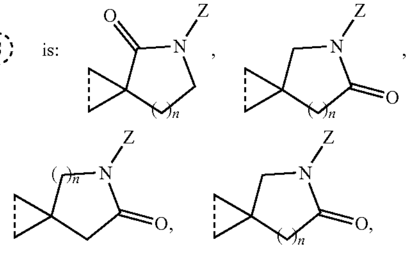

bonded in a spiro-manner,

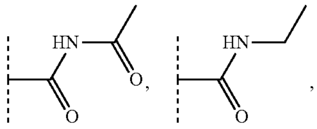

,

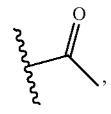

,

-continued
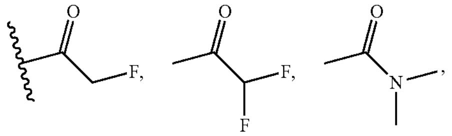
CN;
where Z is H, Me, or $CH_2CH_2OH$, $CH_2CH_2CN$, $CH_2CH_2F$, $COCH_3$, $COCH{=}CH$; and n is 0, 1, 2, or R is $(CH_2)_n$,
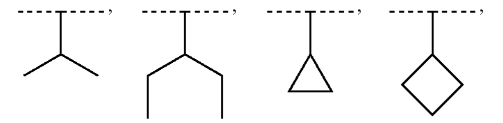
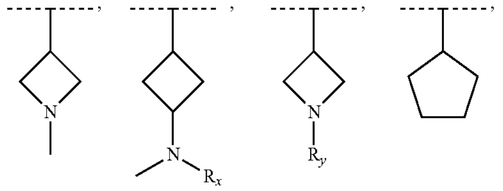
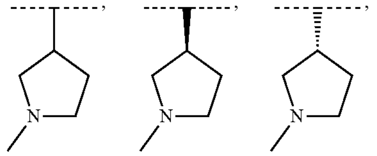
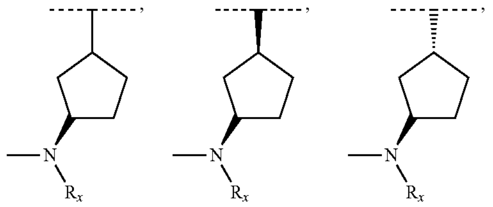
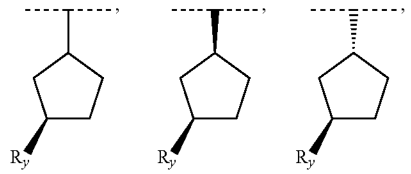
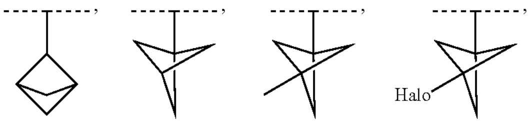
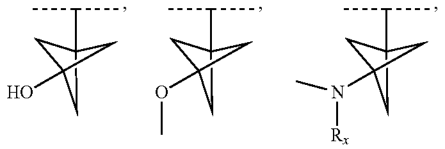
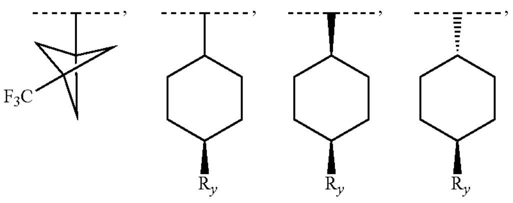
-continued
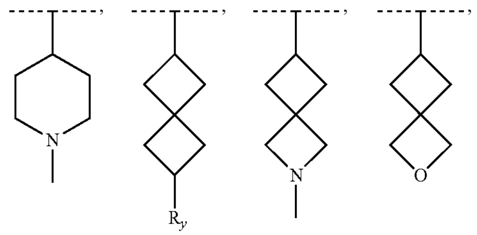
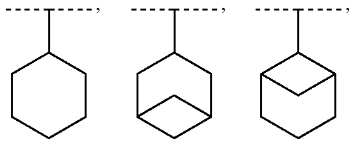
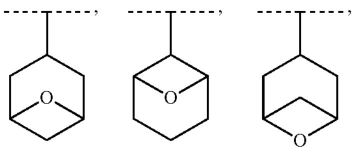
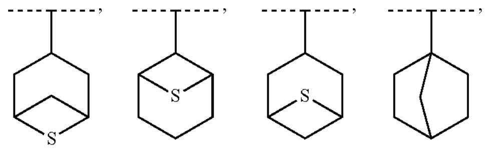
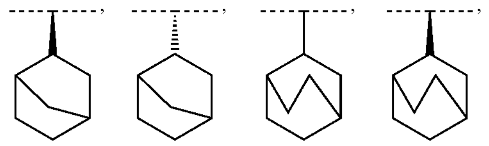
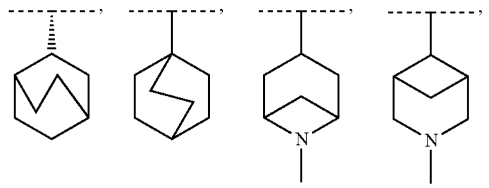
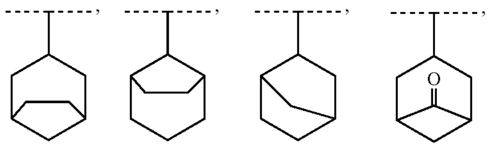
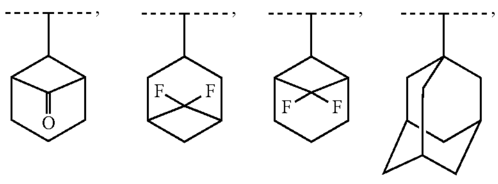
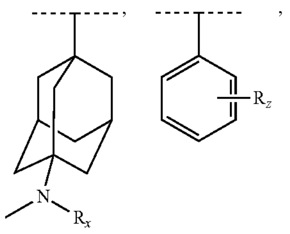

-continued
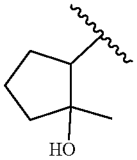
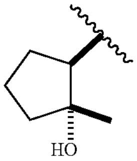
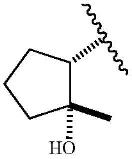
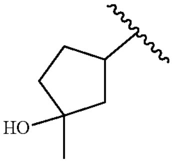
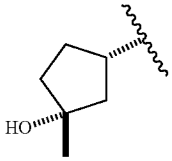
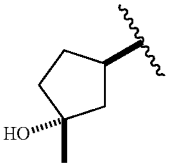
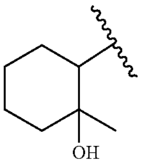
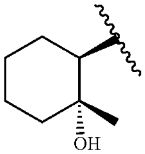
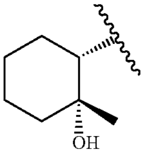
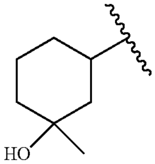
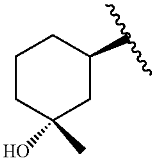
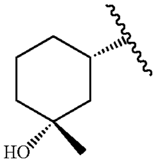
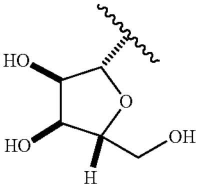
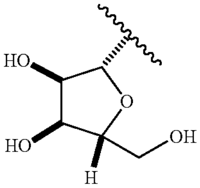
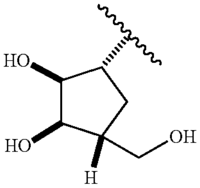
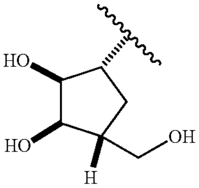
or
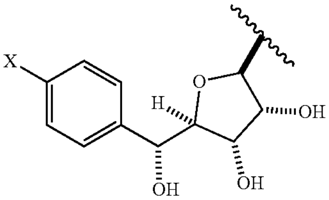
X = F, Cl
where $R_x$ is H or Me, $R_y$ is Me, OH, or OMe; $R_z$ is H, Me, OMe, OH, N, F, or $CF_3$; and n is 1 to 11; and
$R_1$ is:
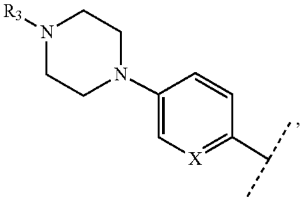
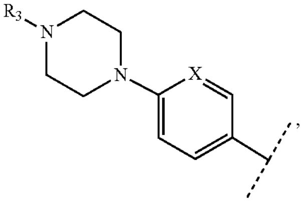
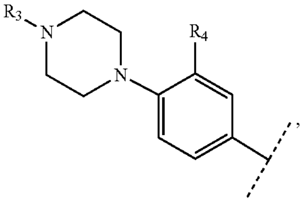
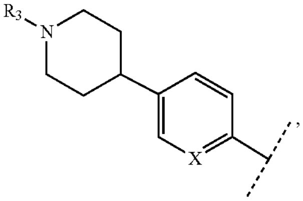
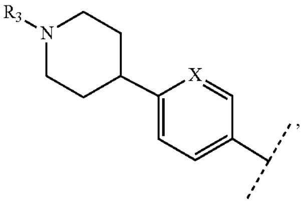
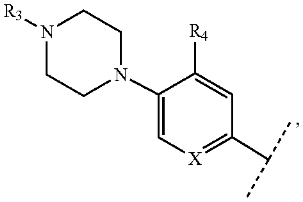
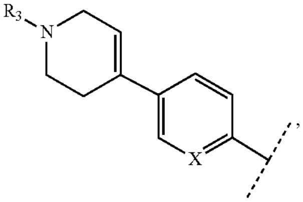
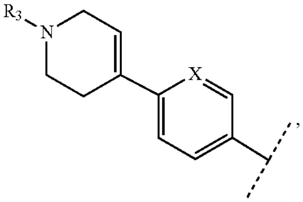

-continued
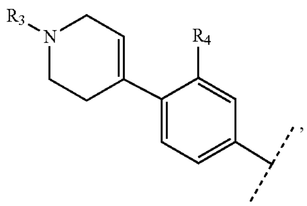
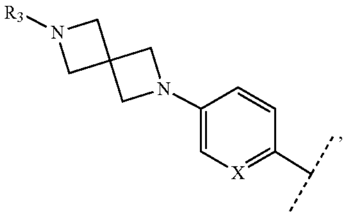
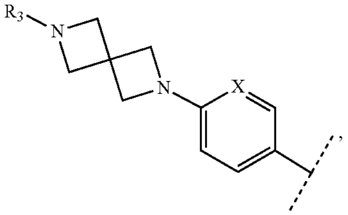
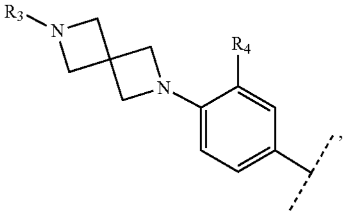
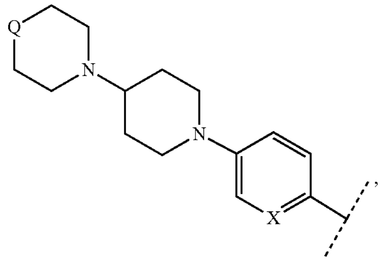
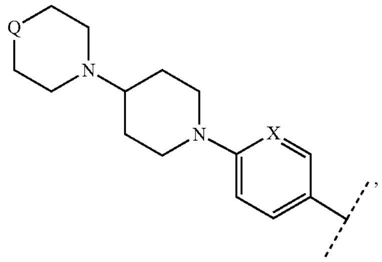
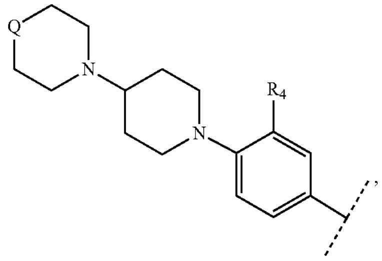
-continued
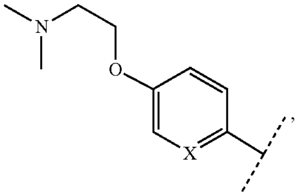
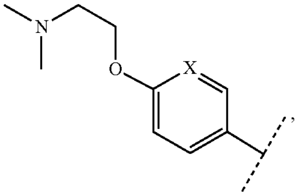
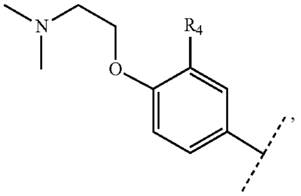
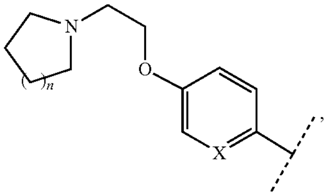
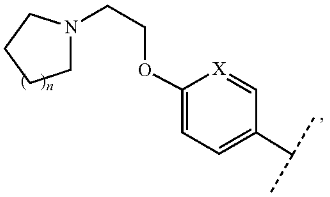
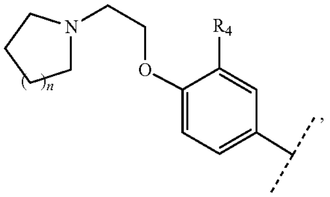
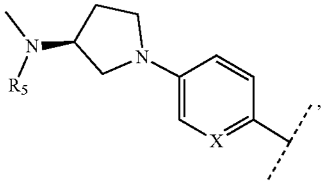
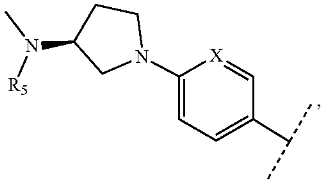
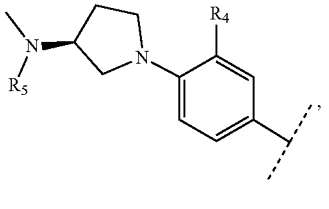

-continued
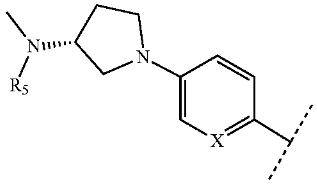,
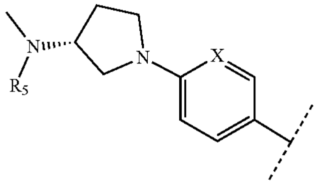,
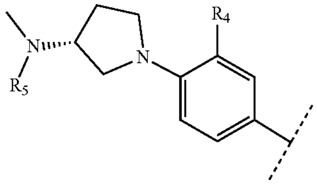,
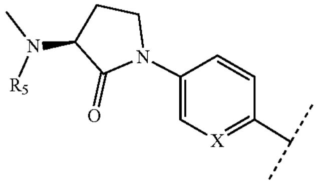,
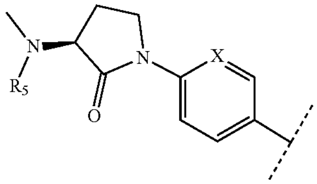,
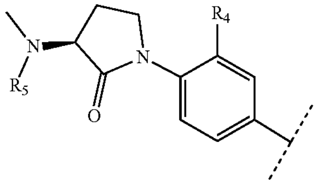,
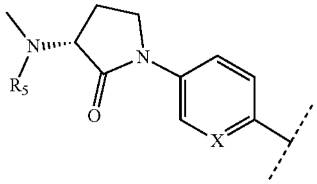,
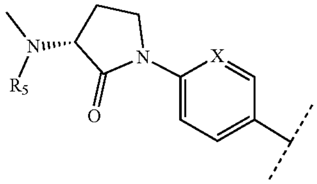,
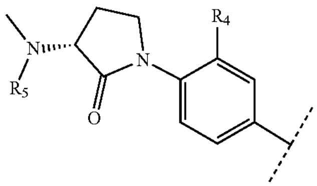,
-continued
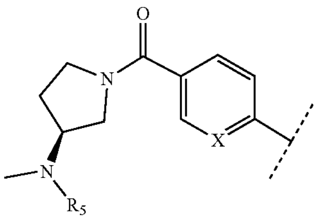,
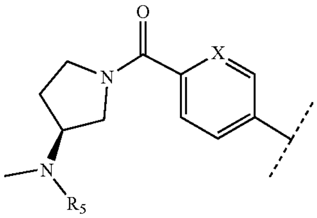,
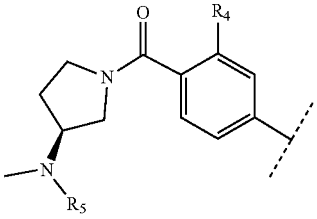,
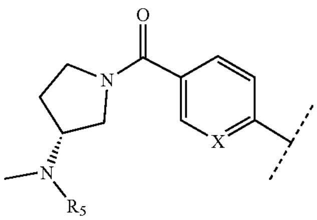,
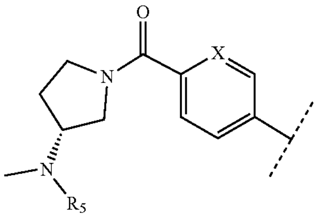,
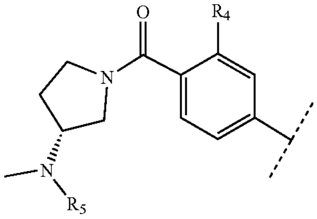,
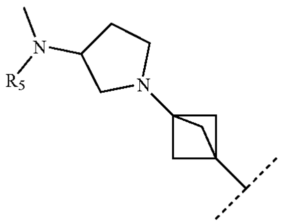, -continued
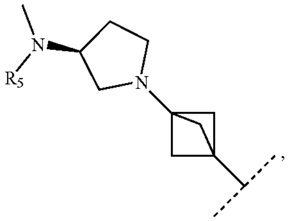,
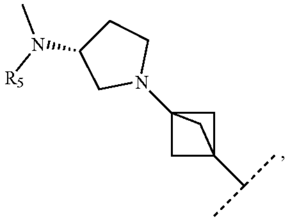,
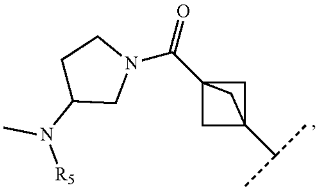,
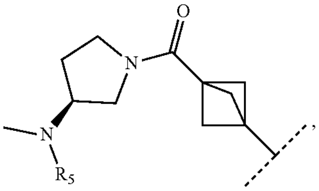,
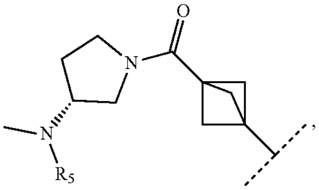,
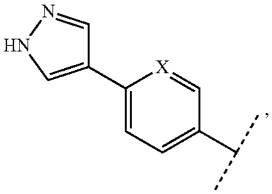,
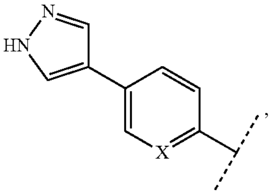,
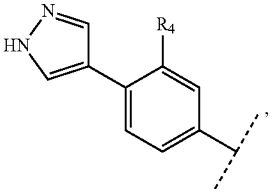,
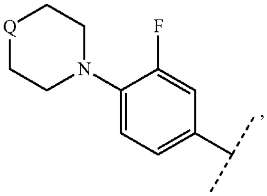,
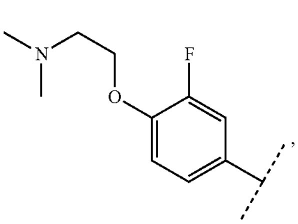,
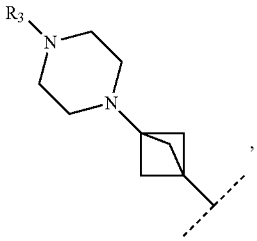,
-continued
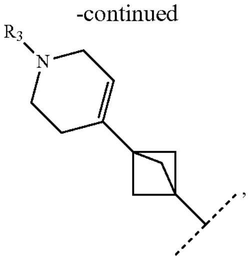,
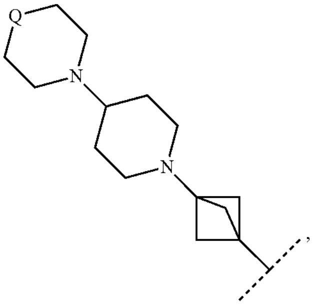,
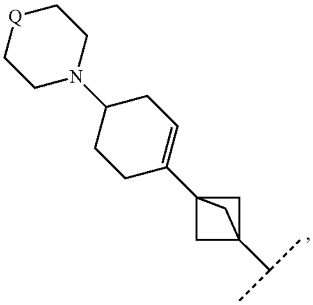,
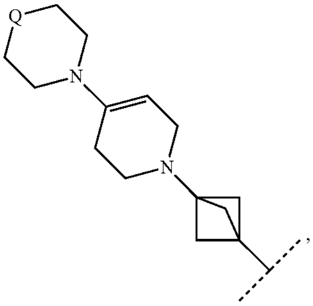,
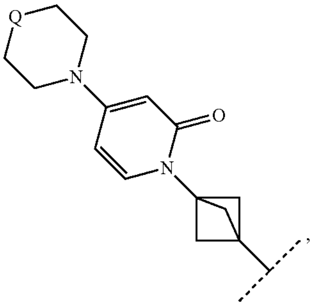,
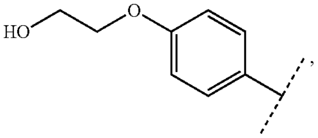,
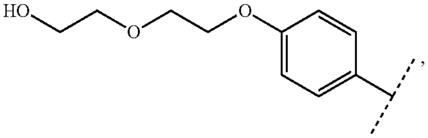, -continued
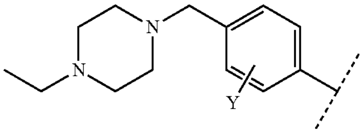,
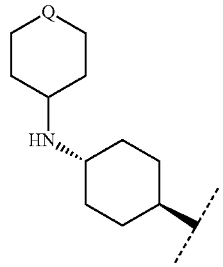,
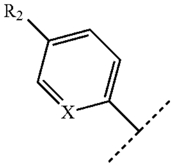,
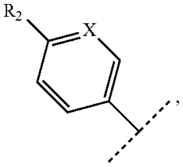,
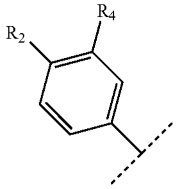,
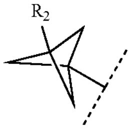,
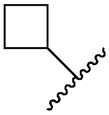
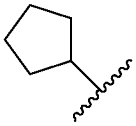
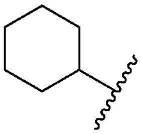
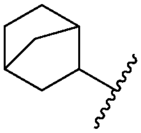
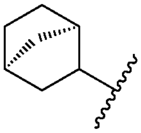
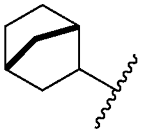
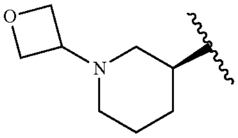
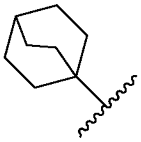
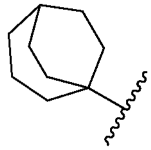
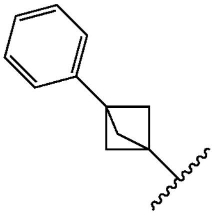
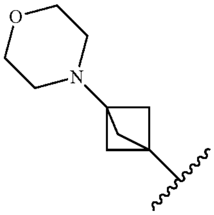
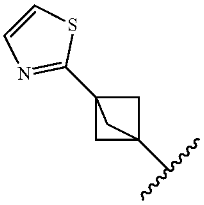
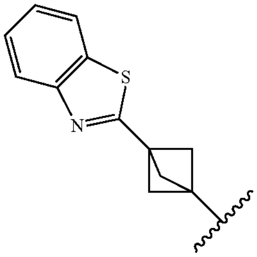
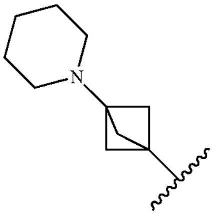
-continued
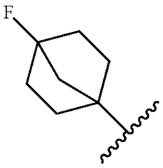
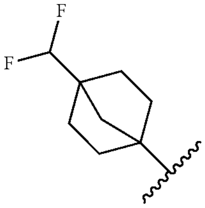
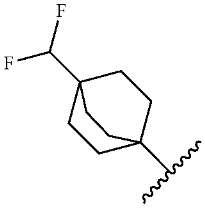
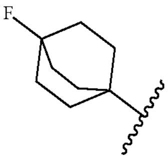
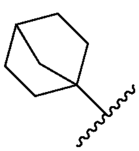
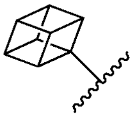
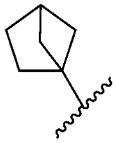
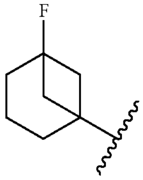
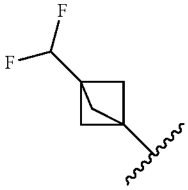
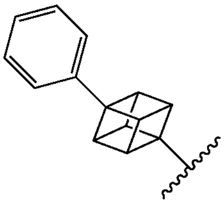
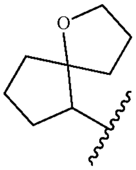
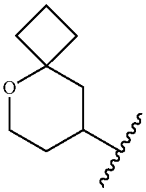
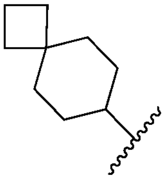
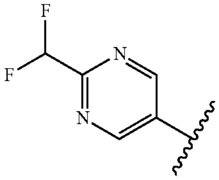
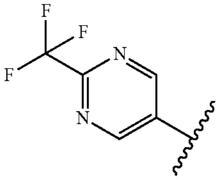
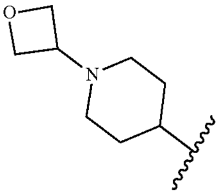
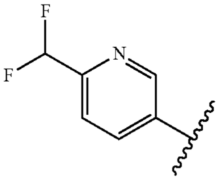

-continued
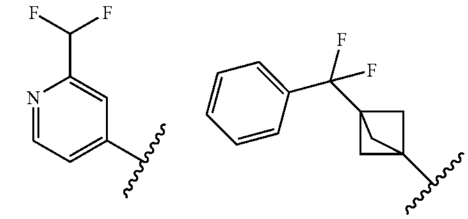
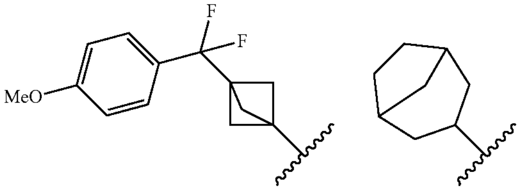
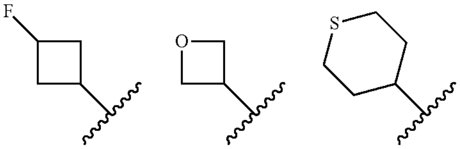
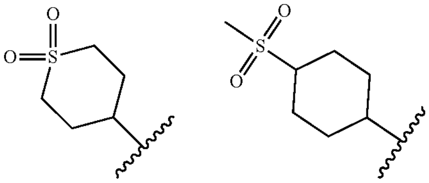
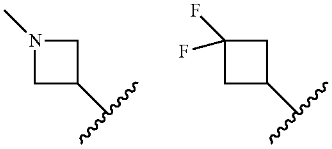
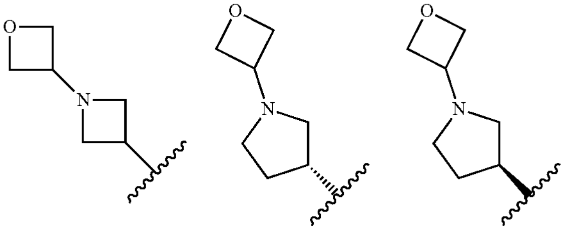
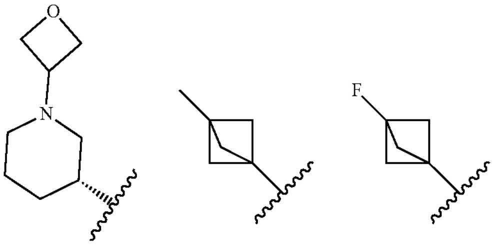
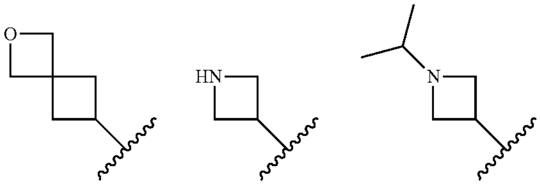
-continued
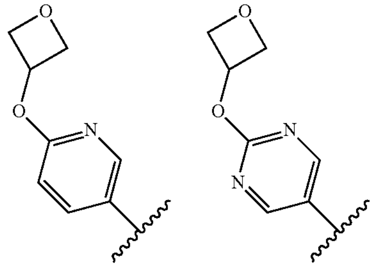
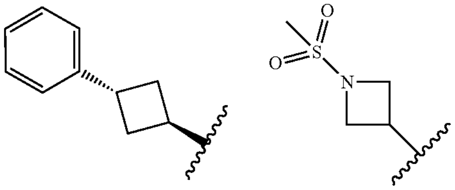
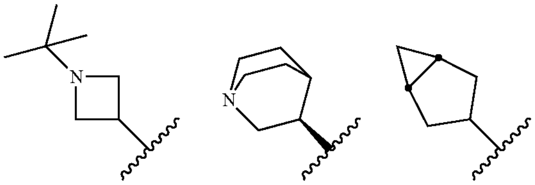
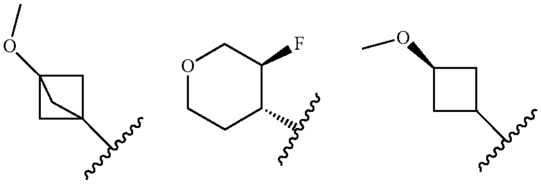
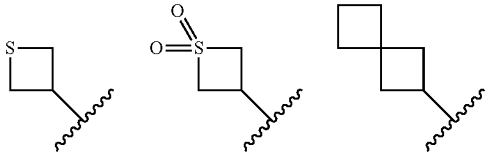
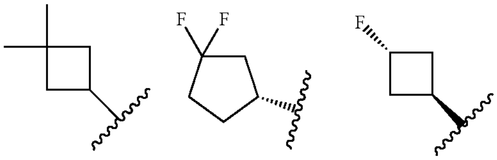
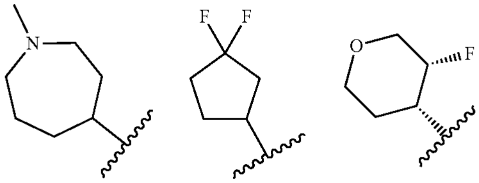
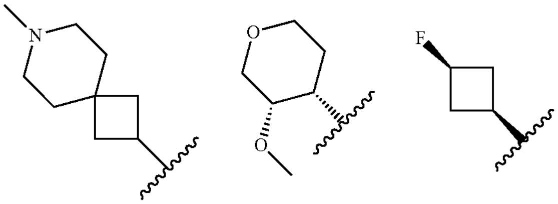
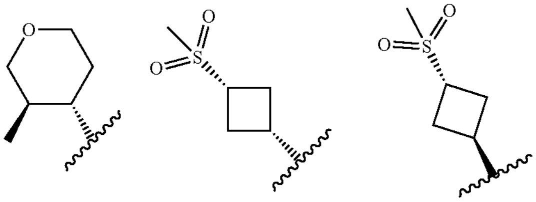

-continued
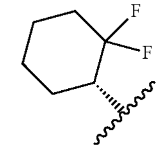
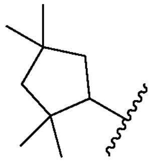
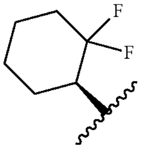
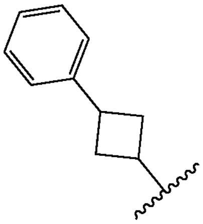
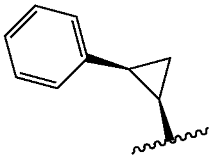
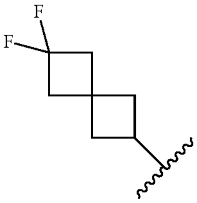
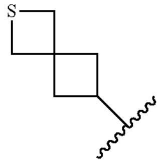
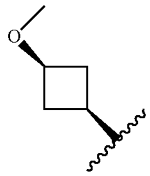
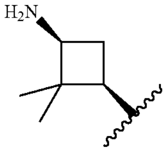
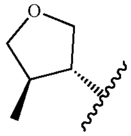
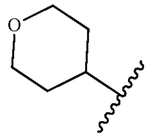
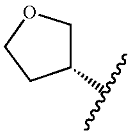
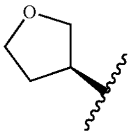
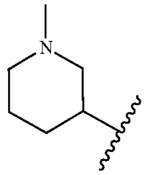
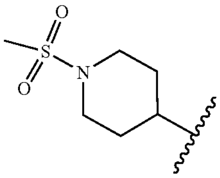
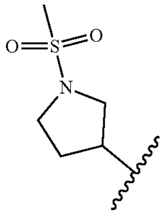
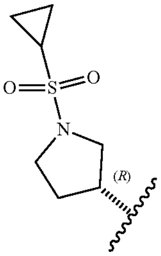
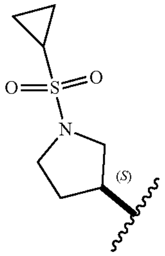
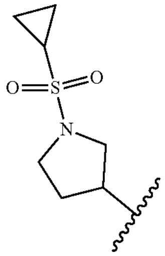
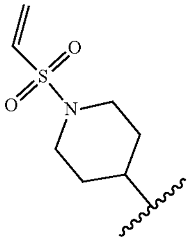
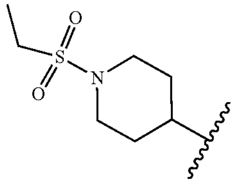
-continued
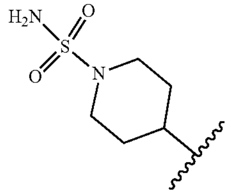
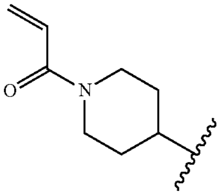
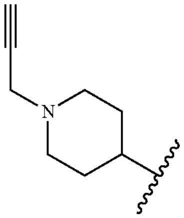
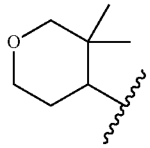
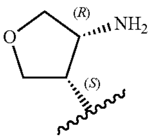
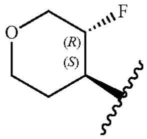
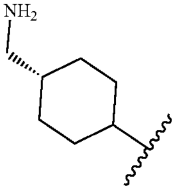
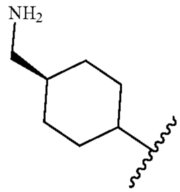
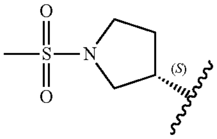
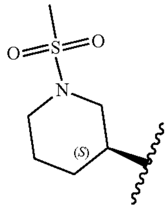
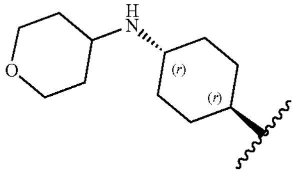
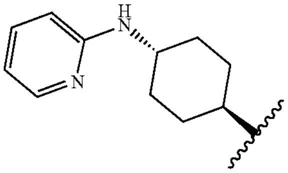
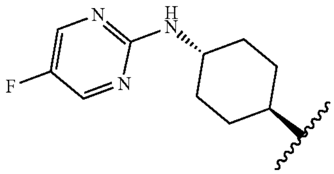
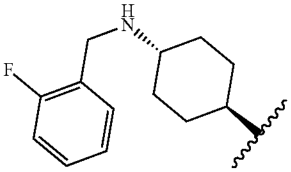
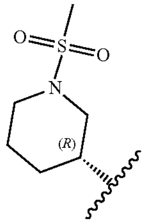

-continued
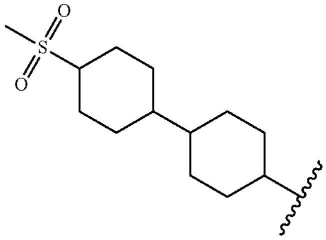
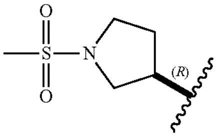
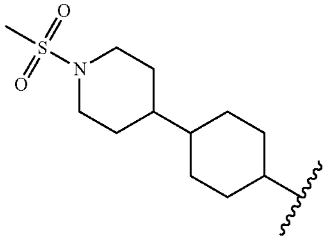
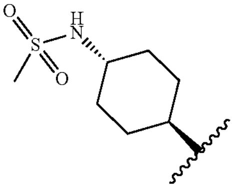
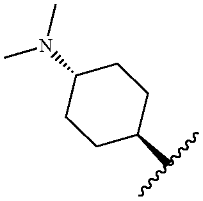
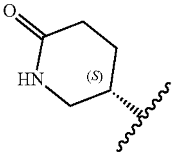
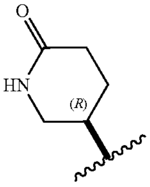
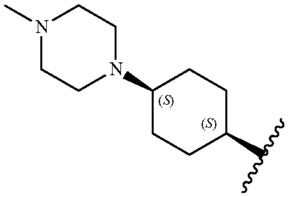
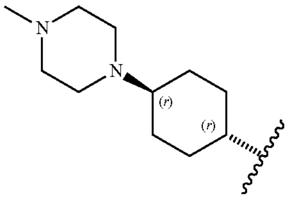
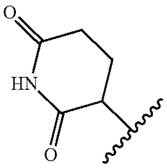
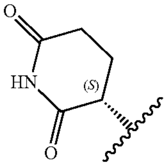
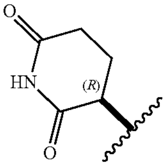
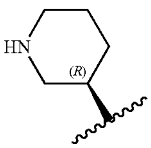
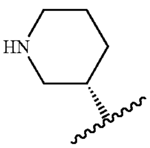
-continued
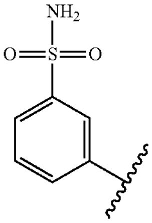
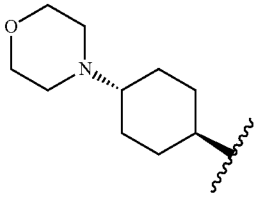
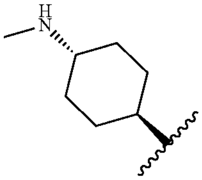
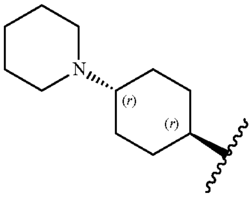
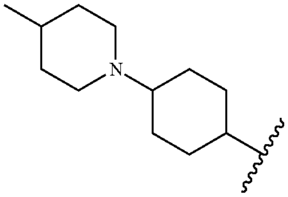
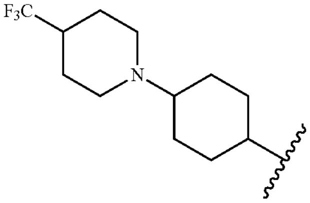
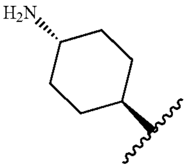
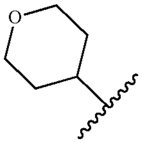
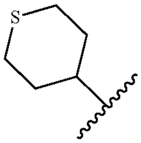
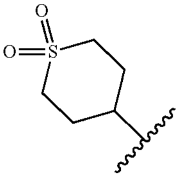
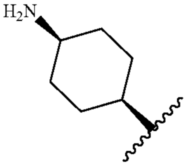
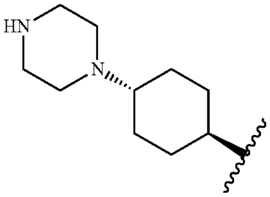
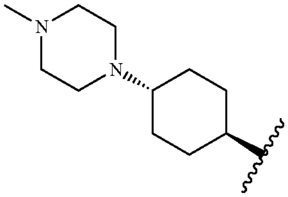
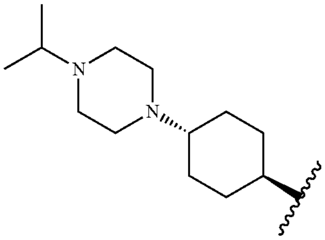
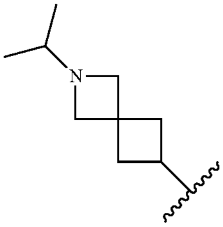

-continued
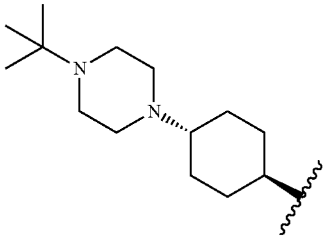
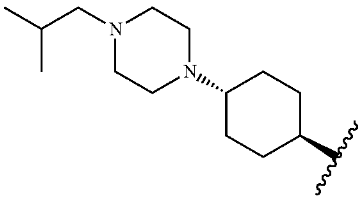
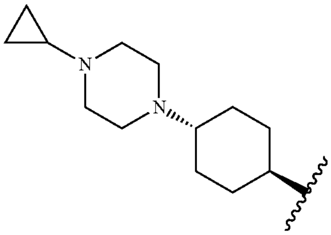
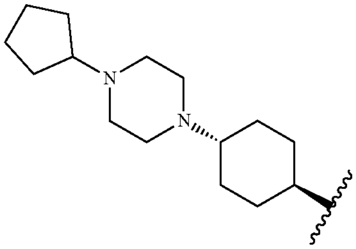
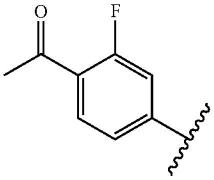
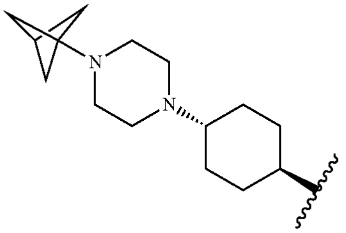
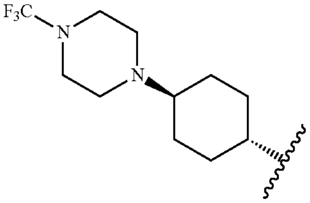
-continued
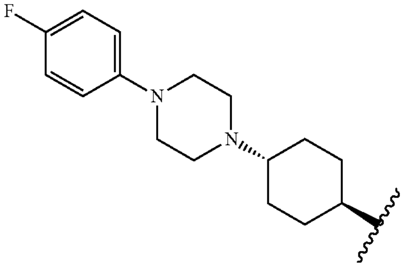
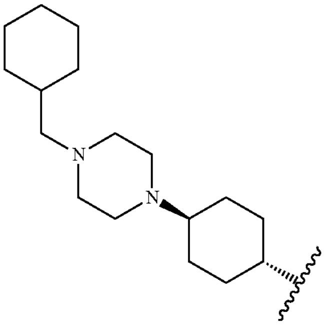
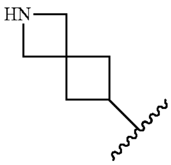
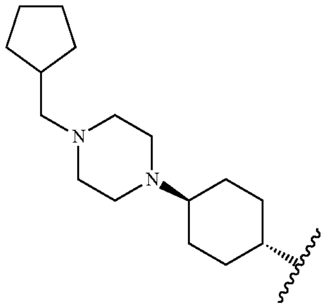
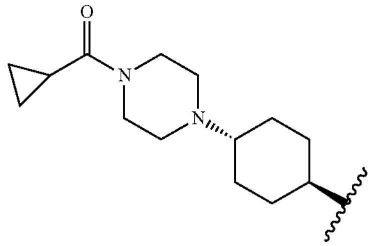
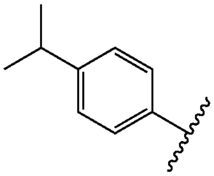
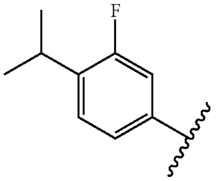
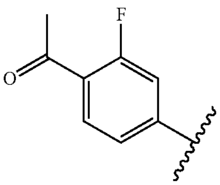
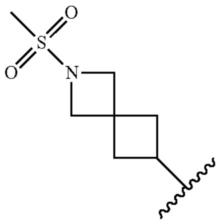

-continued
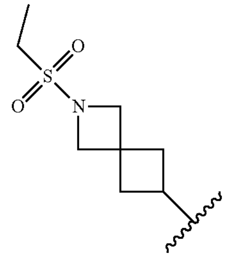
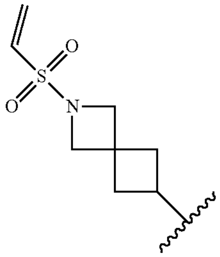
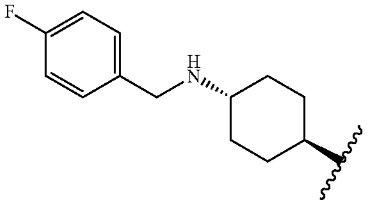
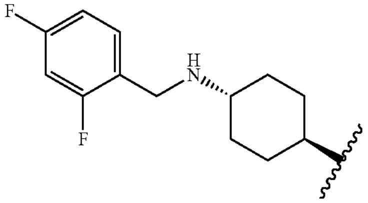
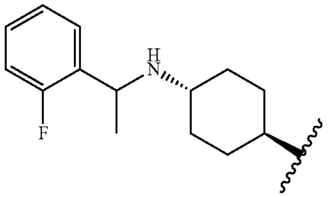
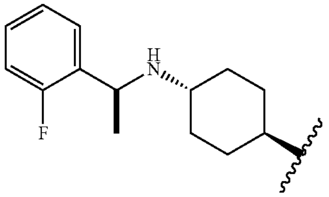
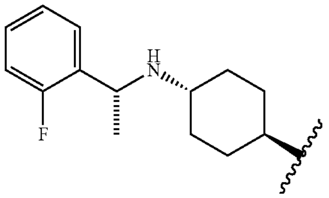
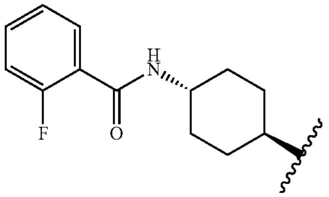
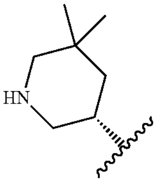
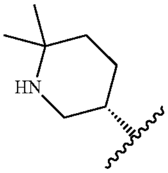
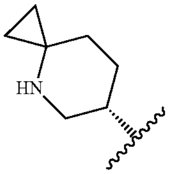
-continued
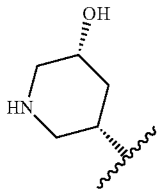
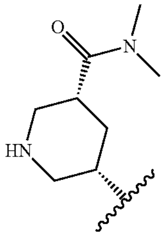
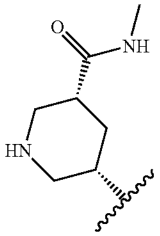
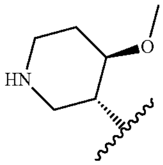
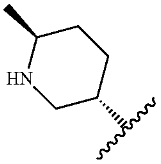
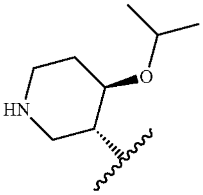
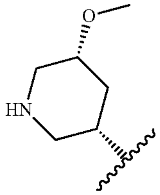
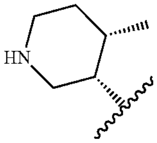
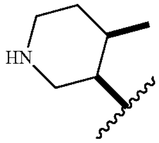
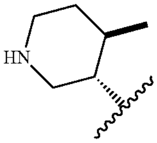
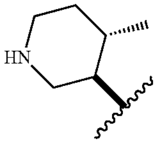
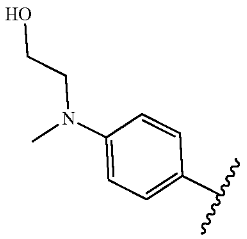
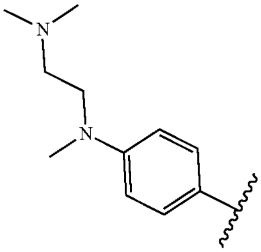
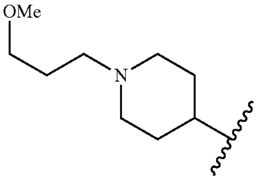
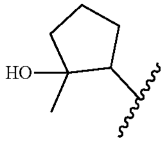
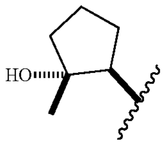
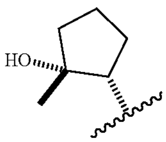
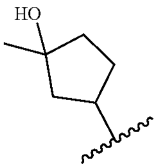
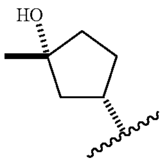
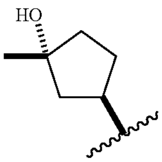

-continued
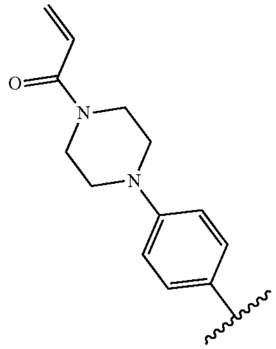
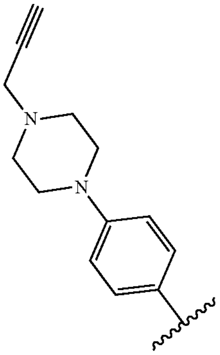
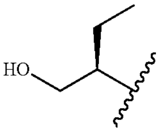
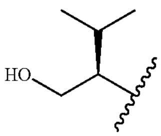
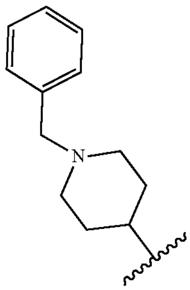
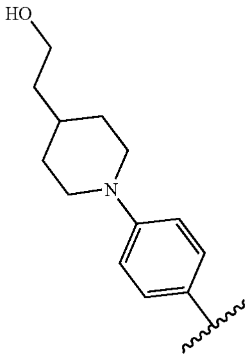
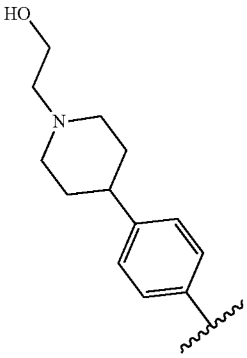
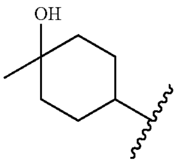
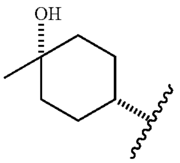
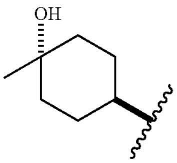
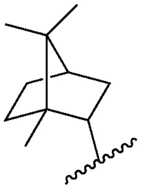
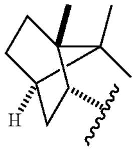
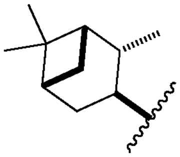
-continued
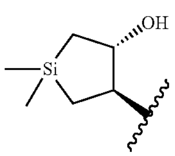
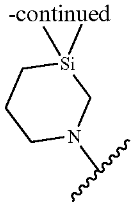
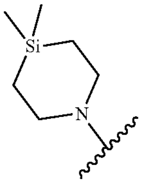
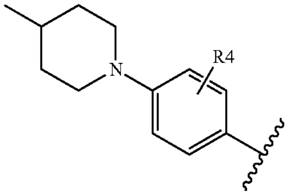
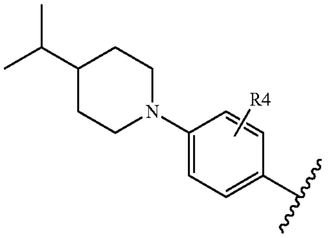
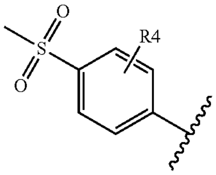
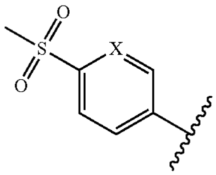
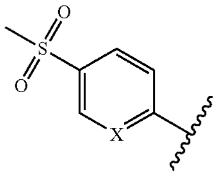
or
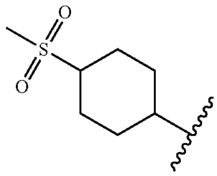
where $R_3$ is H, Me, $CH_2CH_2OH$, isopropyl, isobutyl, or bicyclo[1.1.1]pentane;
$R_4$ is H, Me, OMe, $OF_3$, or $OHF_2$;
$R_5$ is H or Me;
X is OC—H, N, or OC—F;
Y is H, N, F, Me, OMe, $OF_3$, or $CHF_2$;
Q is O or S;
n is 1, 2, or 3; and
$R_2$ is:
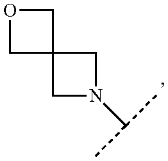
,
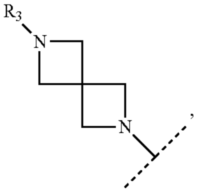
,
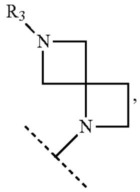
,
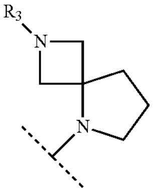
,
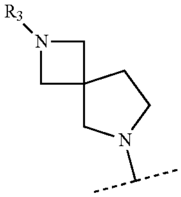
, -continued
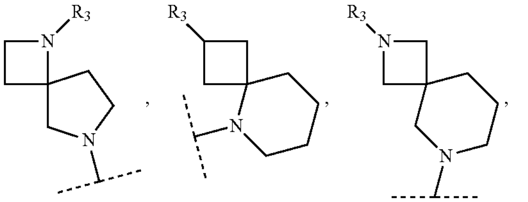
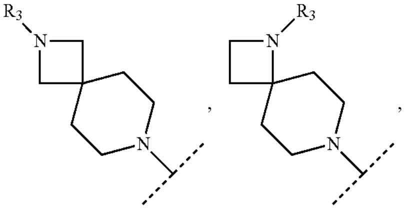
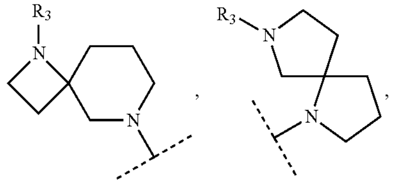
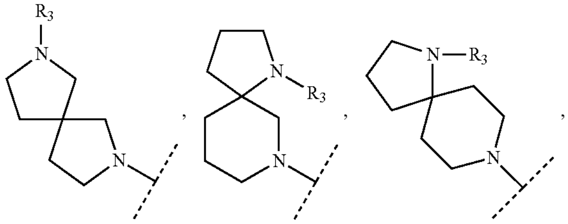
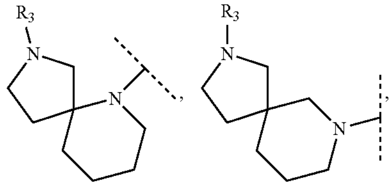
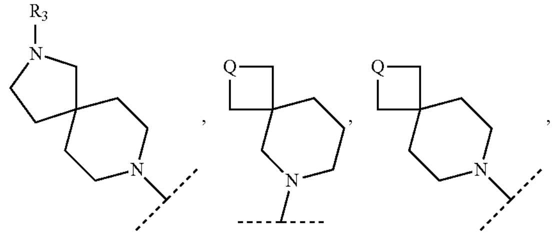
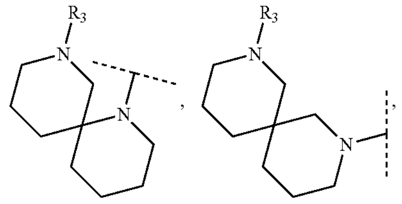
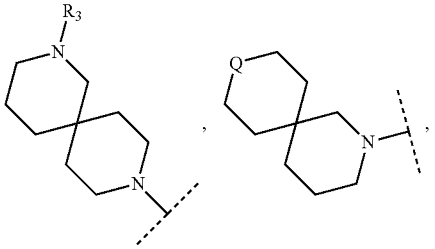
-continued
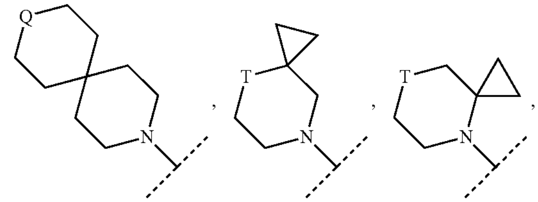
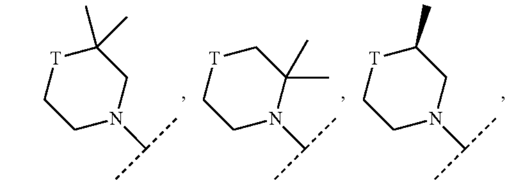
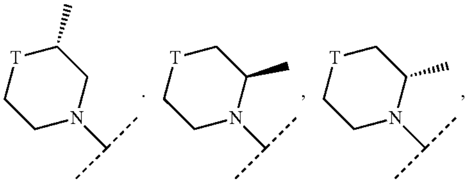
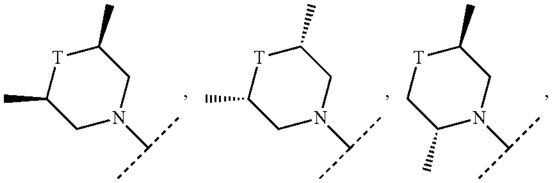
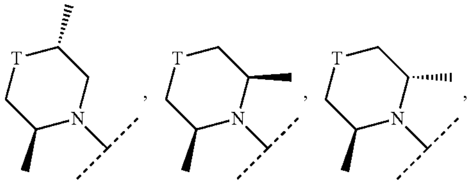
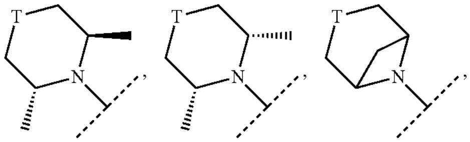
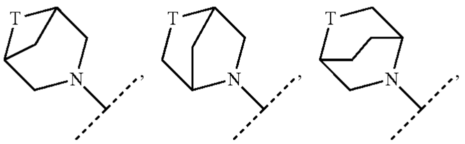
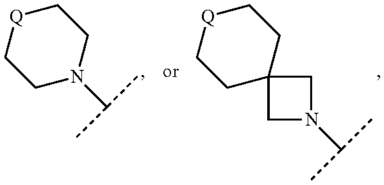
where T is O, NH, NMe, N-isopropyl, or N-isobutyl. In one aspect,
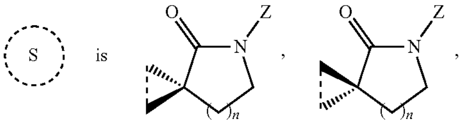

-continued

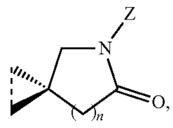

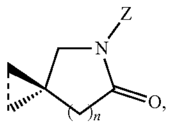

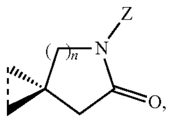

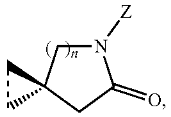

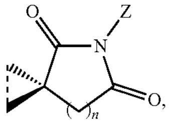

or

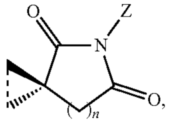

bonded in a spiro-manner,

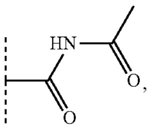

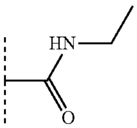

,

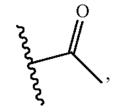

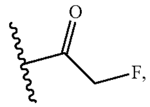

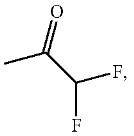

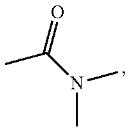

CN;

where Z is H, Me, or $CH_2CH_2OH$, $CH_2CH_2CN$, $CH_2CH_2F$, $COCH_3$, COCH═CH; and n is 0, 1, 2, or 3. In another aspect, R is

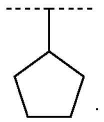

In another aspect, $R_1$ is:

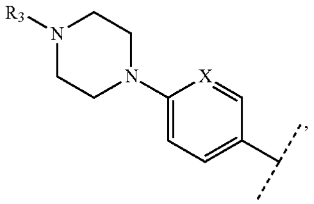

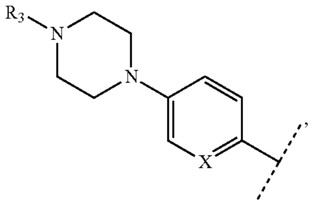

-continued

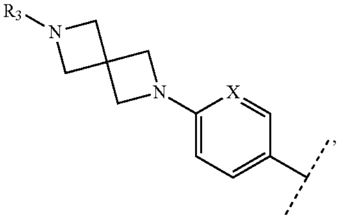

or

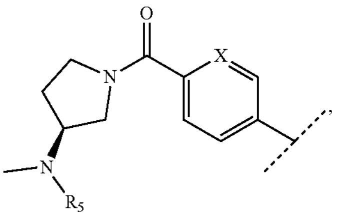

where $R_3$ is H, Me, $CH_2CH_2OH$, isopropyl, isobutyl, or bicyclo[1.1.1]pentane; $R_5$ is H or Me; and X is C—H, N, or C—F. In another aspect, the compound comprises Formula I:

(I)

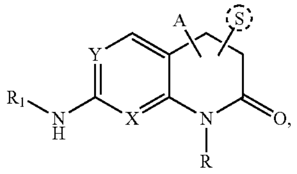

wherein A is none; and X and Y are independently, C or N. In another aspect

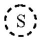

is:

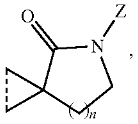

bonded in a spiro-manner; Z is H, Me, or $CH_2CH_2OH$; and n is 0, 1, 2, or 3. In another aspect, R is

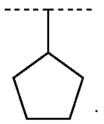

In another aspect, $R_1$ is:

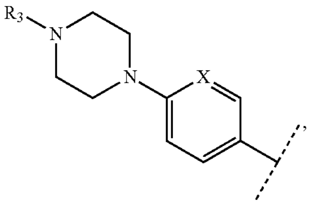

-continued

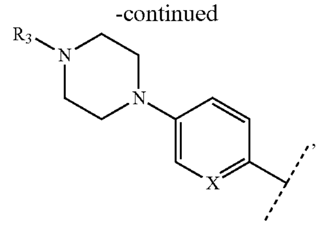

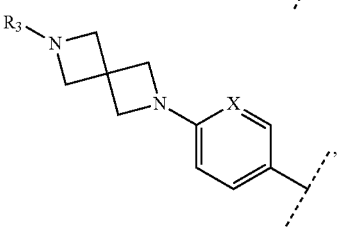

or

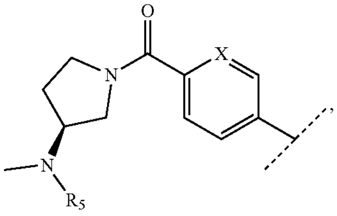

where $R_3$ is H, Me, $CH_2CH_2OH$, isopropyl, isobutyl, or bicyclo[1.1.1]pentane; $R_5$ is H or Me; and X is C—H, N, or C—F.

Another embodiment described herein is a compound or a pharmaceutically acceptable salt thereof comprising Formulae III, IV, V, or VI:

(III)

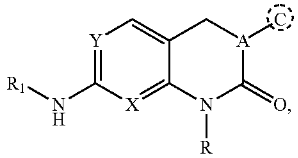

(IV)

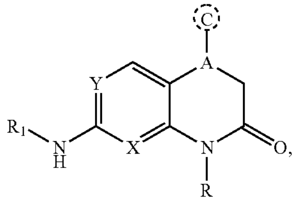

(V)

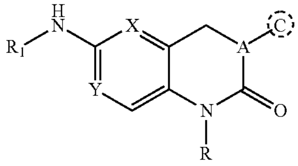

or (VI)

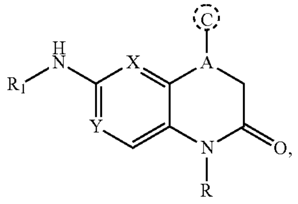

wherein, A is C or N; X and Y are independently N, C, or C—F;

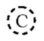 is

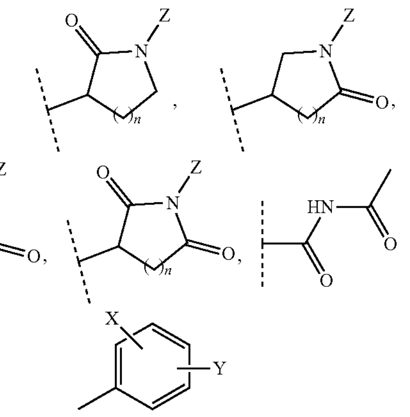

X=Y=H; X=Cl, F, Me, OMe, Y=H; X=Y=Cl, F, Me, OMe, where Z is H, Me, or $CH_2CH_2OH$; and n is 0, 1, 2, or 3;

R is $(CH_2)_n$,

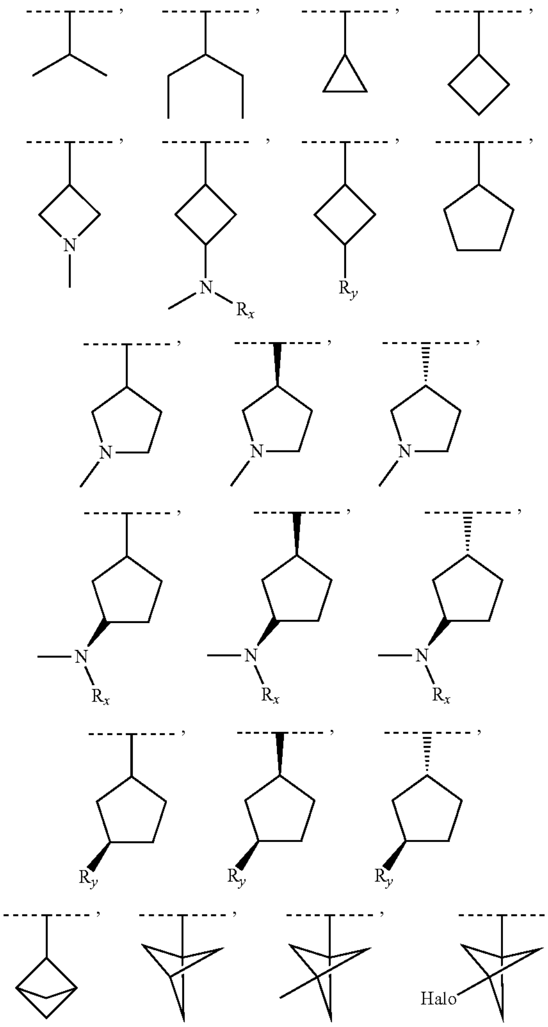

-continued
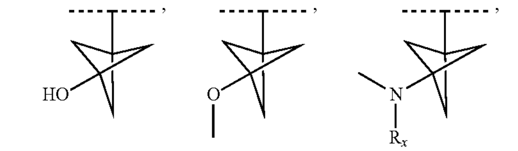
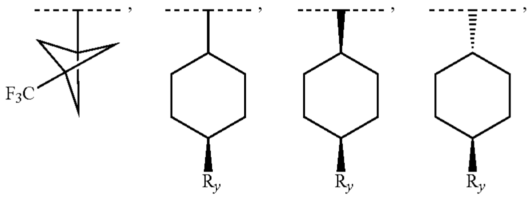
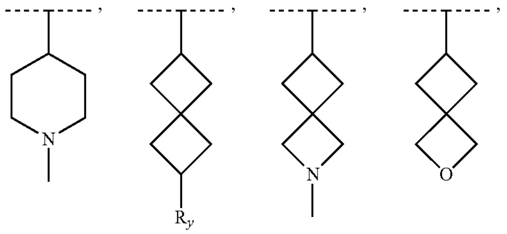
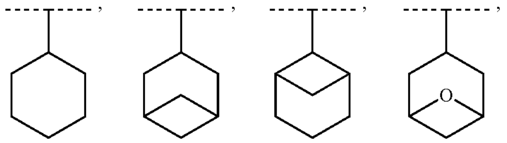
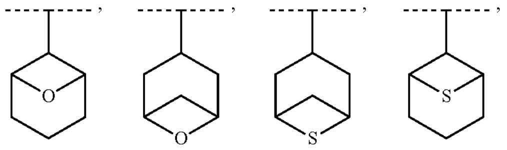
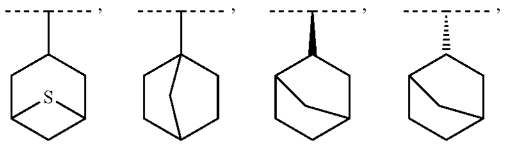
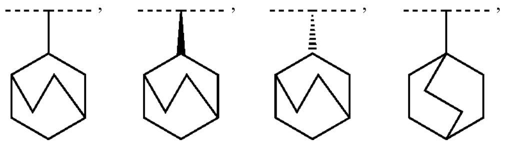
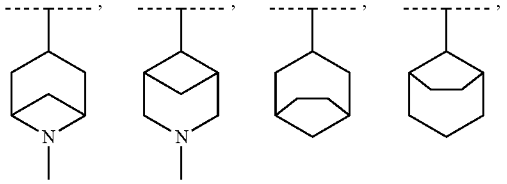
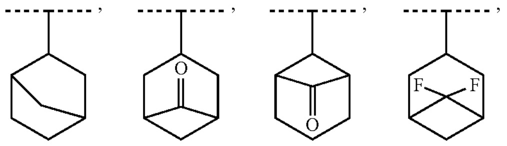
-continued
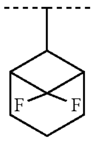,
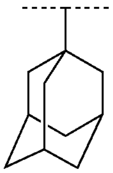,
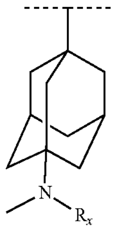, or
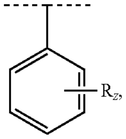
Where $R_x$ is H or Me, $R_y$ is Me, OH, or OMe; $R_z$ is H, Me, OMe, OH, N, F, or $CF_3$; and n is 1 to 11; and
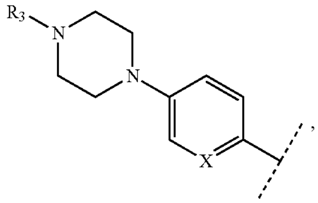
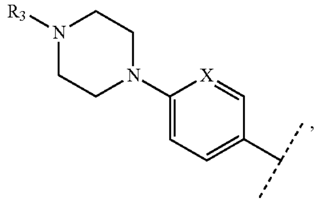
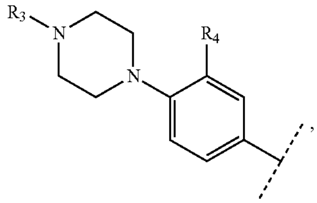
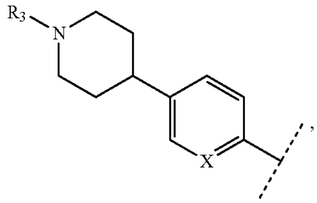
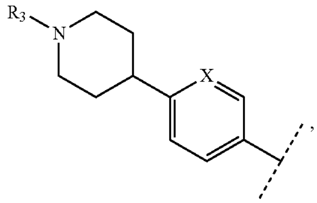
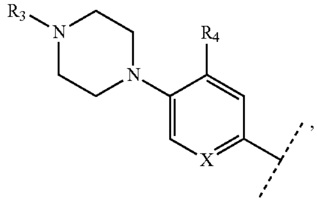

-continued
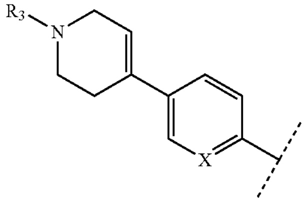
,
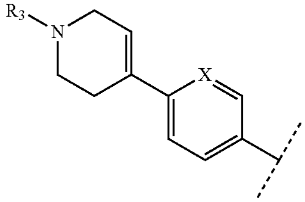
,
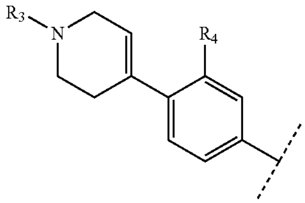
,
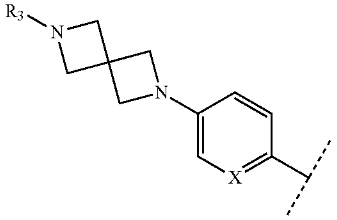
,
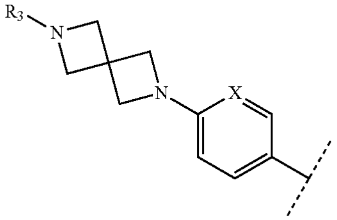
,
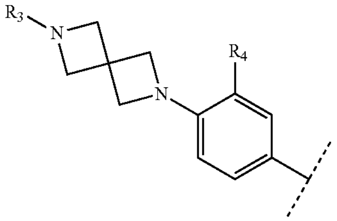
,
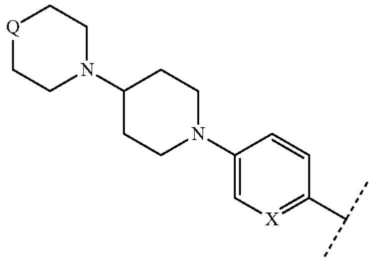
,
-continued
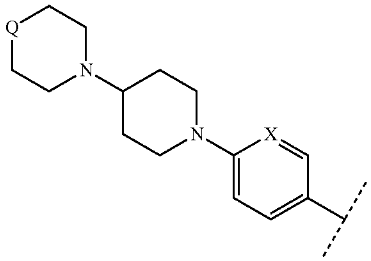
,
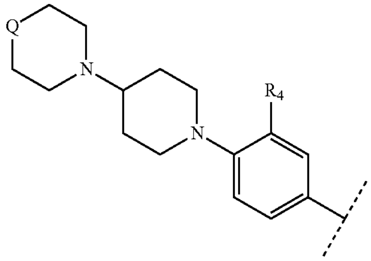
,
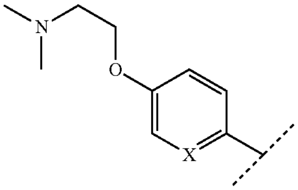
,
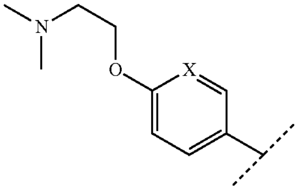
,
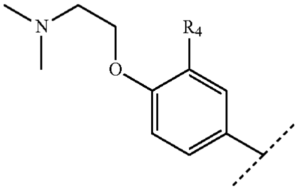
,
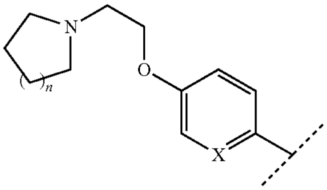
,
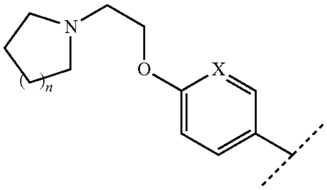
,
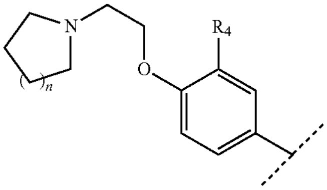
, -continued
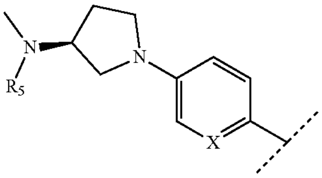
,
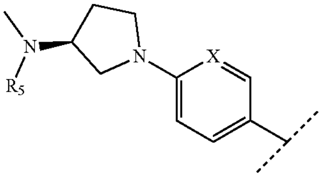
,
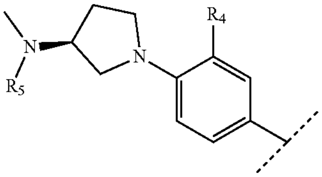
,
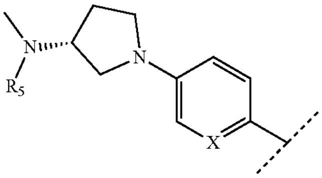
,
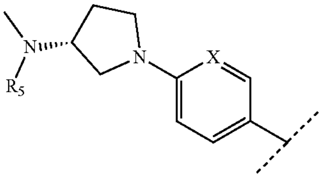
,
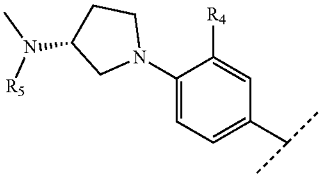
,
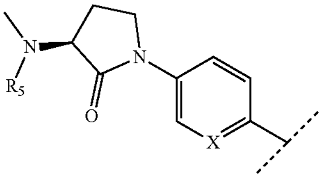
,
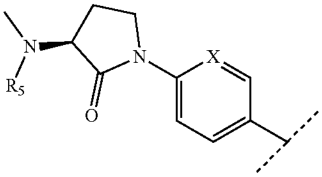
,
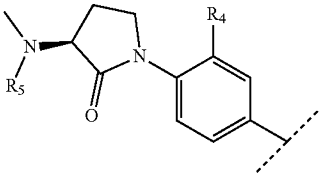
,
-continued
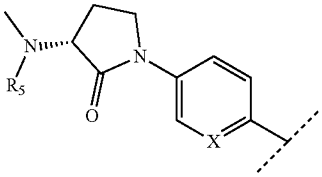
,
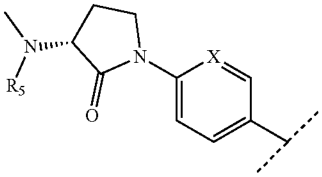
,
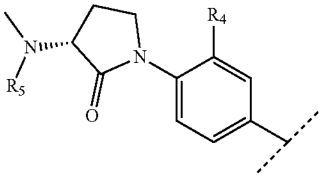
,
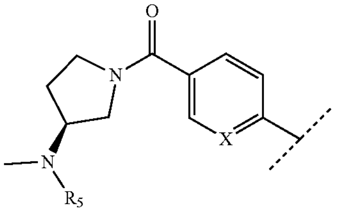
,
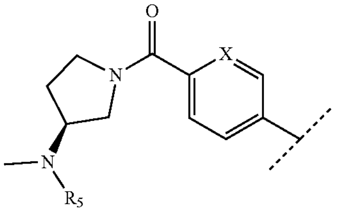
,
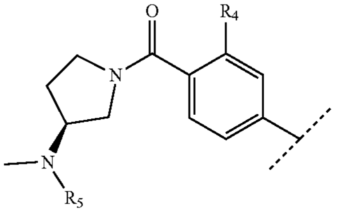
,
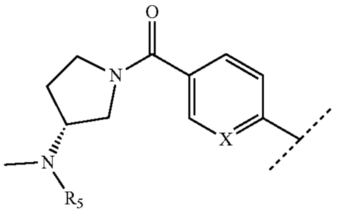
,
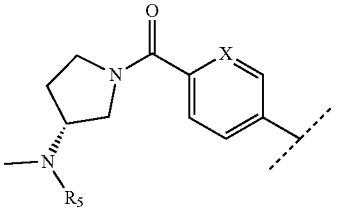
, -continued
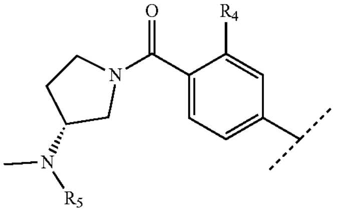
,
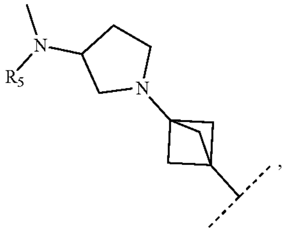
,
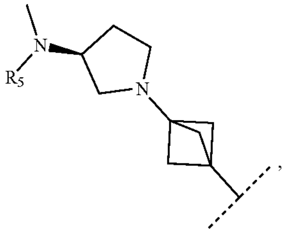
,
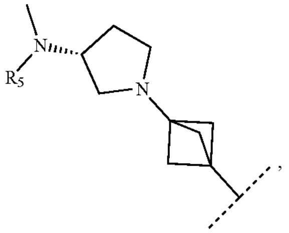
,
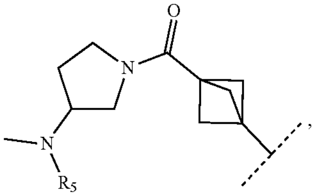
,
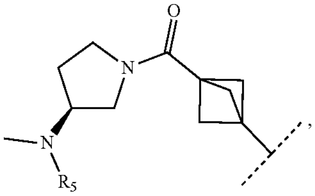
,
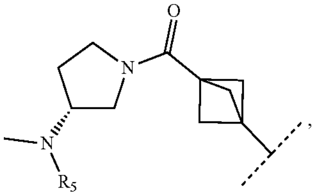
,
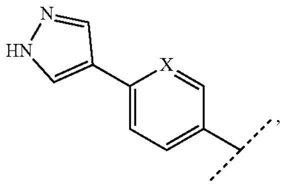
,
-continued
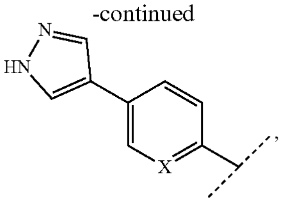
,
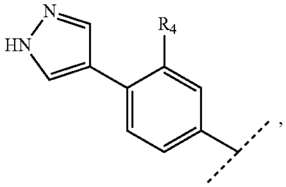
,
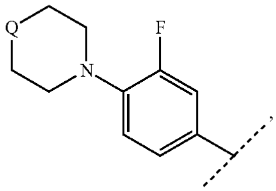
,
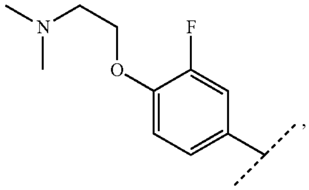
,
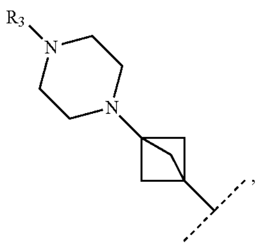
,
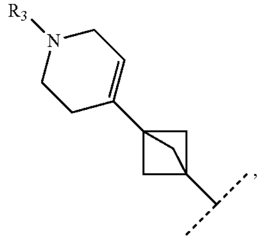
,
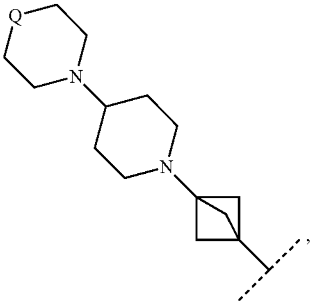
,
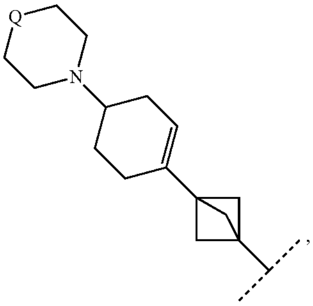
,
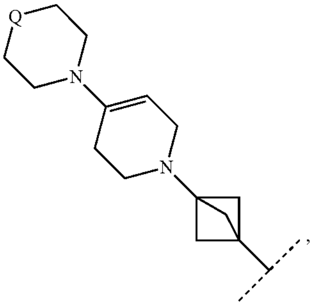
, -continued
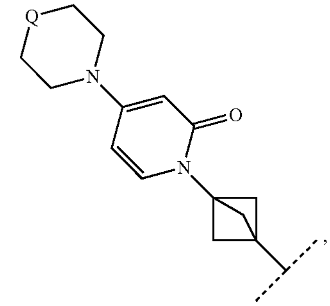,
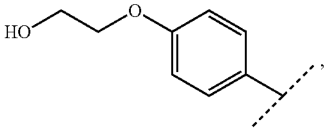,
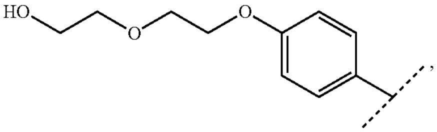,
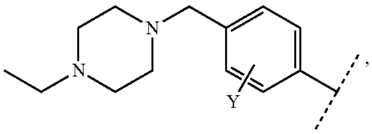,
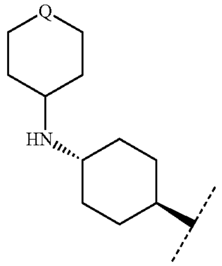, 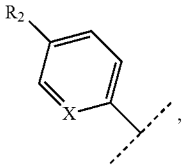,
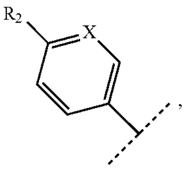, 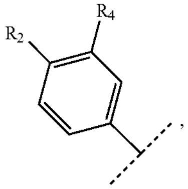, or
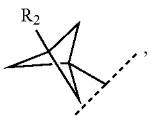,
where $R_3$ is H, Me, $CH_2CH_2OH$, isopropyl, isobutyl, or bicyclo[1.1.1]pentane;
$R_4$ is H, Me, OMe, $CF_3$, or $CHF_2$;
$R_5$ is H or Me;
X is C—H, N, or C—F;
Y is H, N, F, Me, OMe, $CF_3$, or $CHF_2$;
Q is O or S;
n is 1, 2, or 3; and
$R_2$ is:
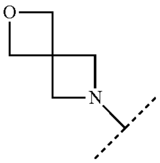, 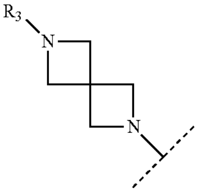,
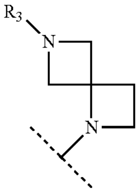, 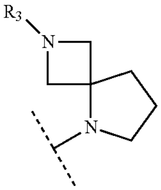, 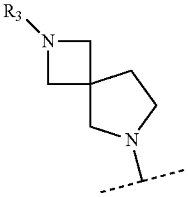,
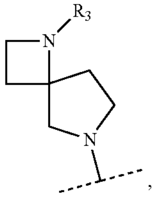, 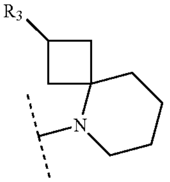, 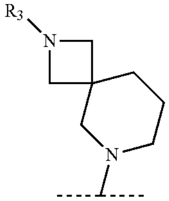,
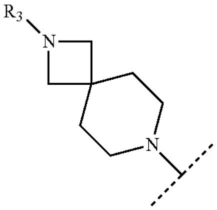, 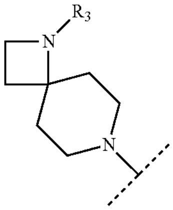,
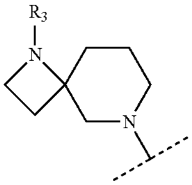, 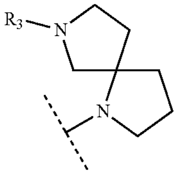,
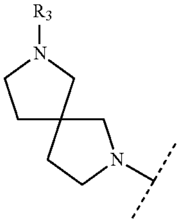, 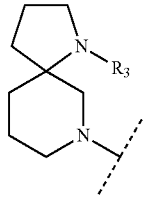, 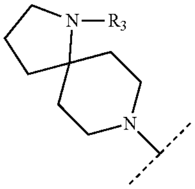,
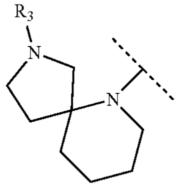, 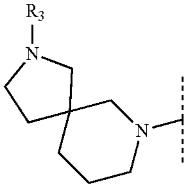,
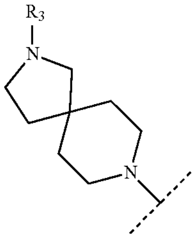, 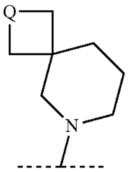, -continued
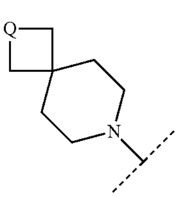, 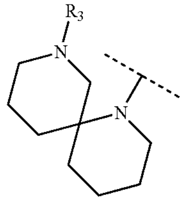,
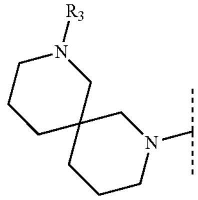, 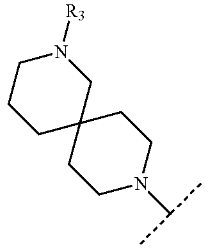,
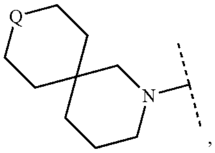, 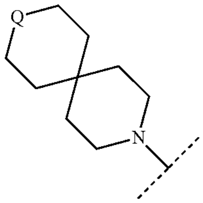,
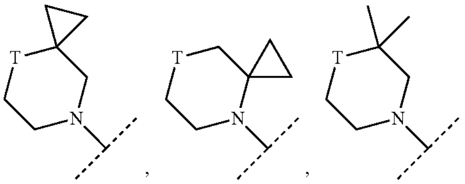
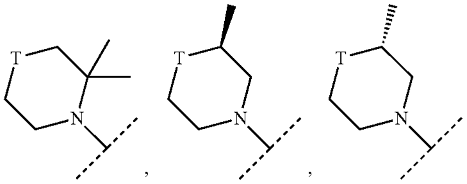
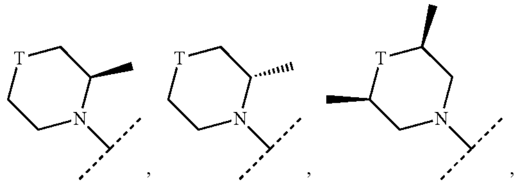
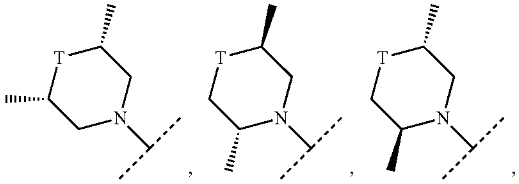
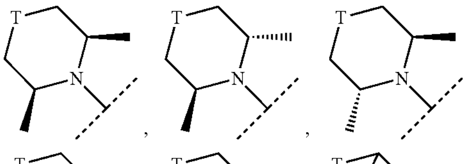
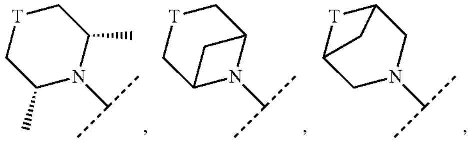
-continued
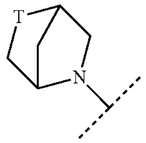, 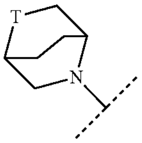, 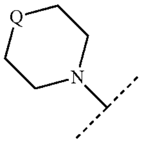, or
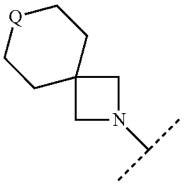,
where T is O, NH, NMe, N-isopropyl, or N-isobutyl. In one aspect, the compound comprises Formula (III):
(III)
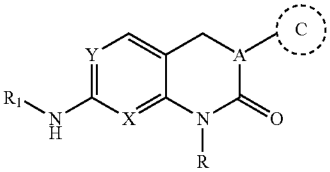,
wherein: A is C or N; X and Y are independently N, C, or C—F. In another aspect,
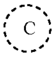 is: 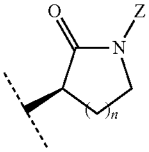, 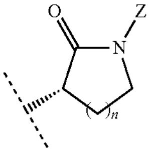,
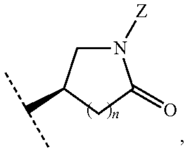, 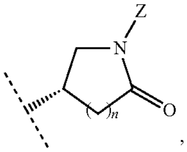,
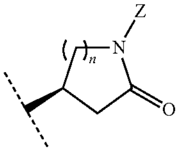, 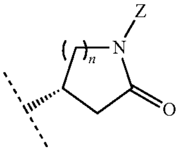,
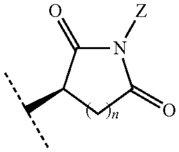, 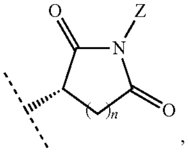,
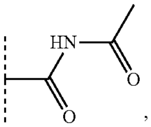, or 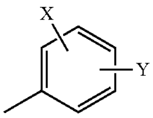
X=Y=H; X=Cl, F, Me, OMe, Y=H; X=Y=Cl, F, Me, OMe, where Z is H, Me, or $CH_2CH_2OH$; and n is 0, 1, 2, or 3. In another aspect, R is

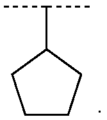
In another aspect, $R_1$ is:
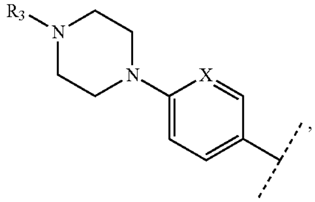,
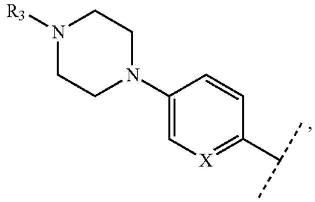,
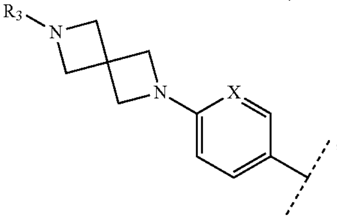, or
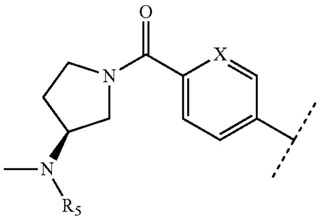,
where $R_3$ is H, Me, $CH_2CH_2OH$, isopropyl, isobutyl, or bicyclo[1.1.1]pentane; $R_5$ is H or Me; and X is C—H, N, or C—F. In another aspect, the compound comprises Formula (III):
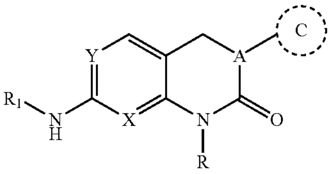
(III)
wherein: A is C; X and Y are independently N;
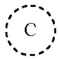 is: 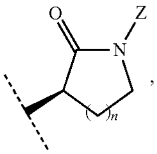, 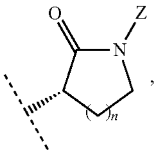,
-continued
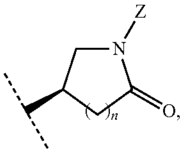, 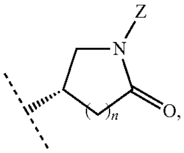, 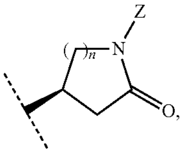,
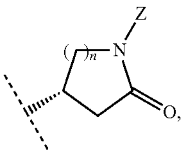, 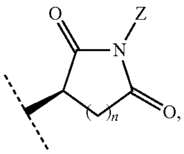, 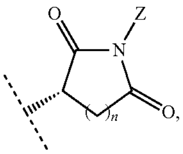,
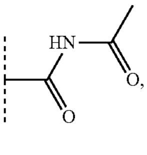, 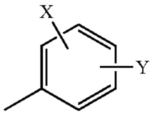
X═Y═H; X═Cl, F, Me, OMe, Y═H; X═Y═Cl, F, Me, OMe, where Z is H, Me, or $CH_2CH_2OH$; and n is 0, 1, 2, or 3;
R is
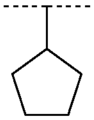;
and
$R_1$ is:
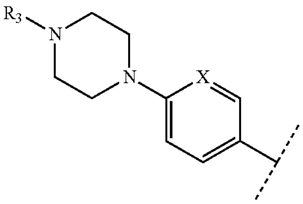,
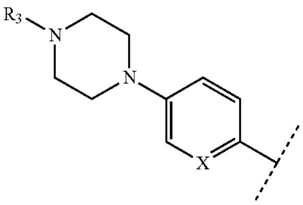,
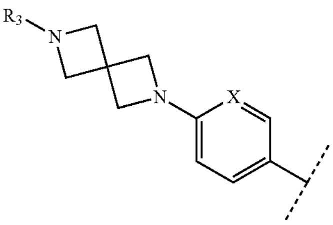, or -continued
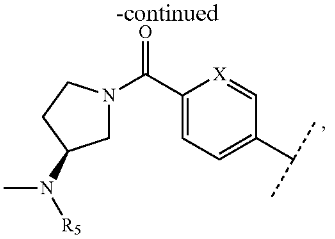
where $R_3$ is H, Me, $CH_2CH_2OH$, isopropyl, isobutyl, or bicyclo[1.1.1]pentane; $R_5$ is H or Me; and X is C—H, N, or C—F.
Another embodiment described herein is a compound or a pharmaceutically acceptable salt thereof comprising Formulae VII-XVIII:
(VII)
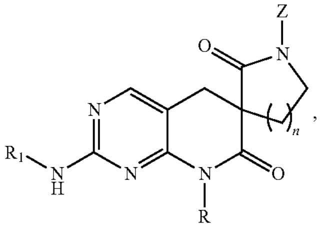
(VIII)
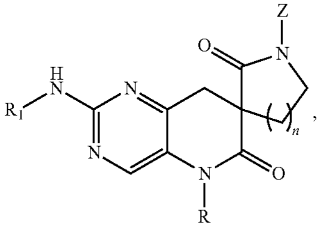
(IX)
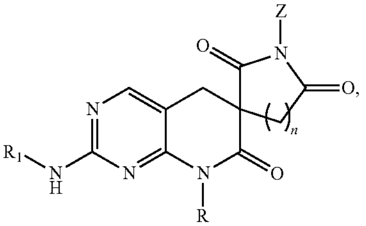
(X)
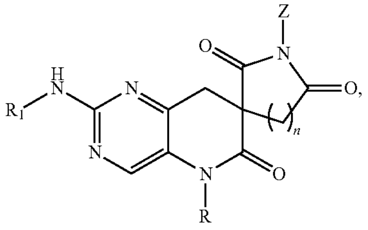
(XI)
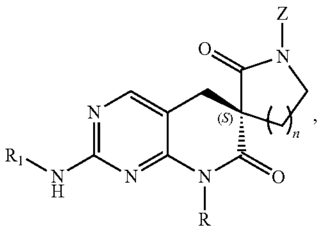
-continued
(XII)
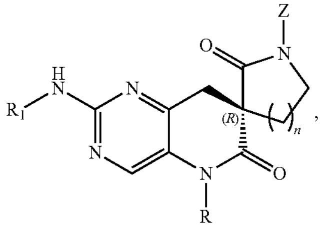
(XIII)
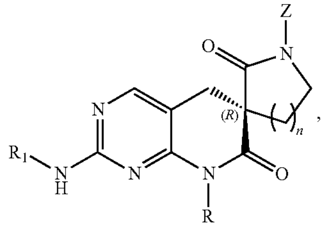
(XIV)
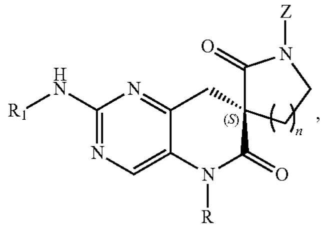
(XV)
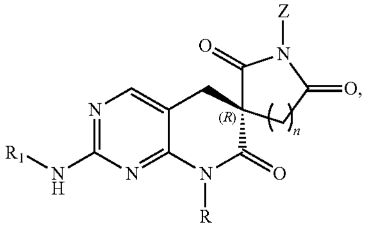
(XVI)
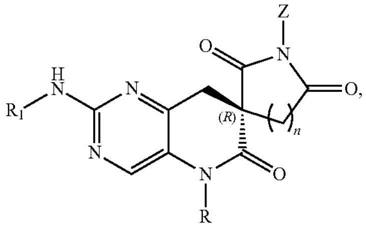
(XVII)
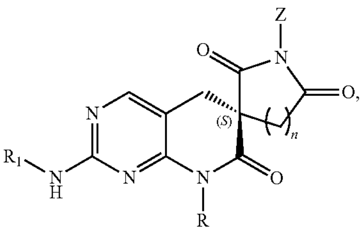
or -continued
(XVIII)
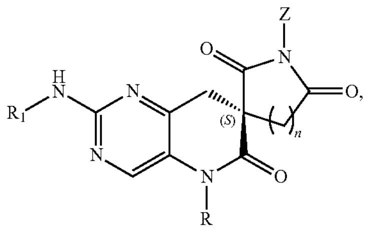
wherein Z is H, Me, or $CH_2CH_2OH$; and n is 0, 1, 2, or 3; R is $(CH_2)_n$,
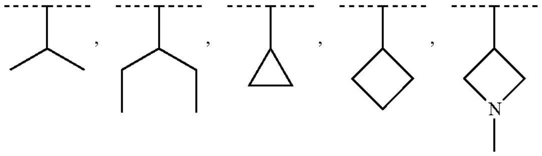,
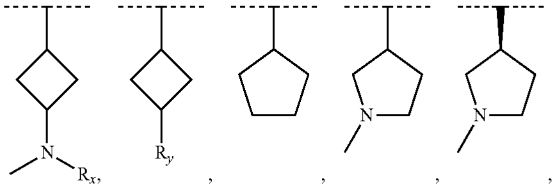,
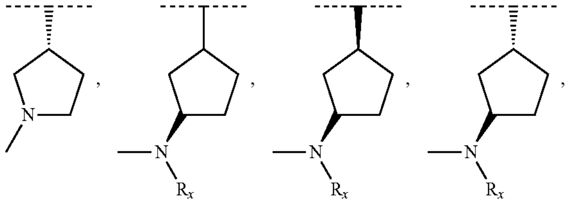,
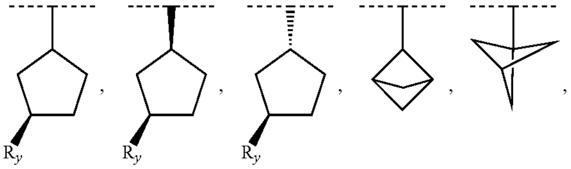,
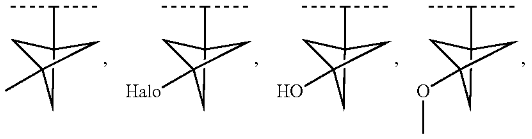,
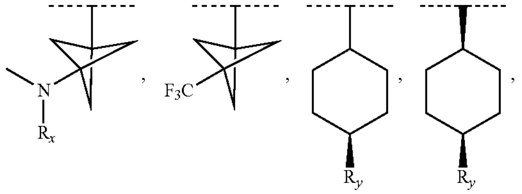,
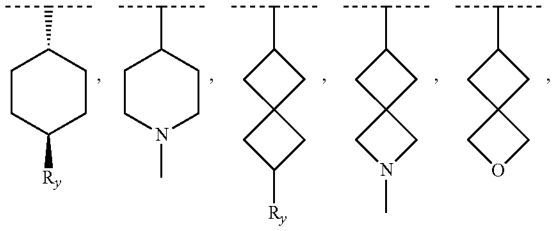,
-continued
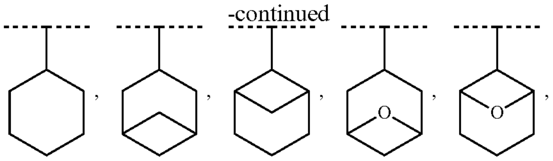,
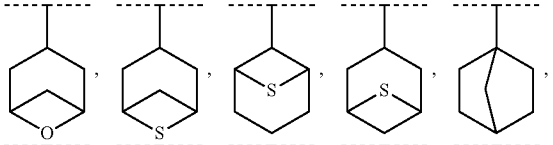,
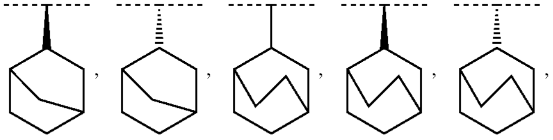,
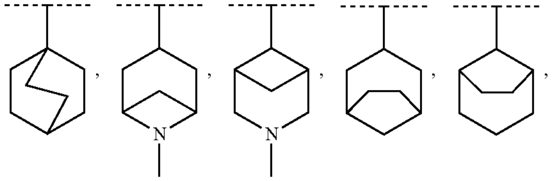,
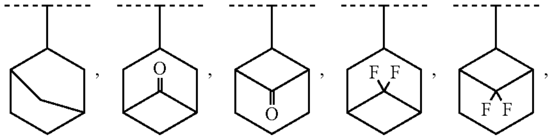,
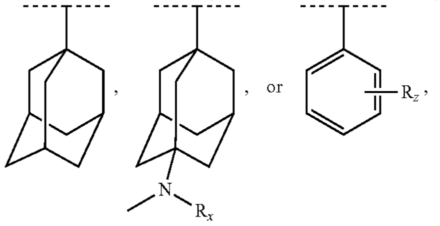,
where $R_x$ is H or Me, $R_y$ is Me, OH, or OMe; $R_z$ is H, Me, OMe, OH, N, F, or $CF_3$; and n is 1 to 11; and $R_1$ is:
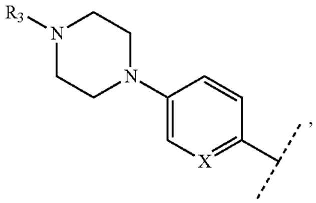,
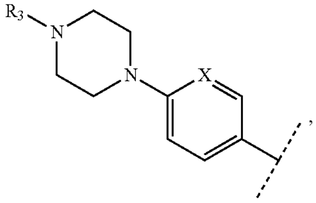,
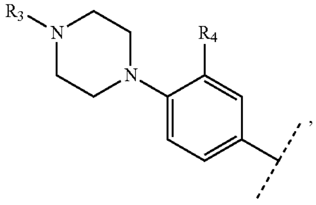, -continued
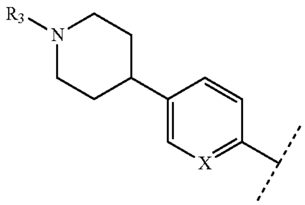
,
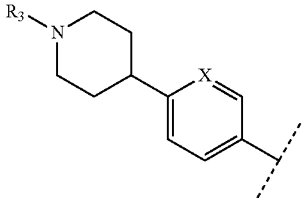
,
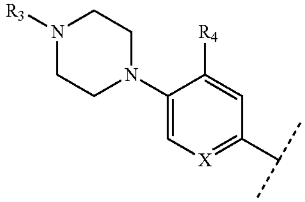
,
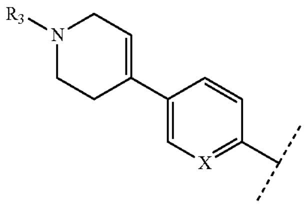
,
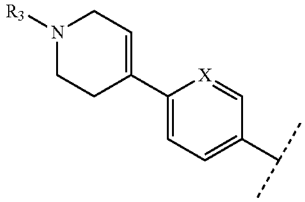
,
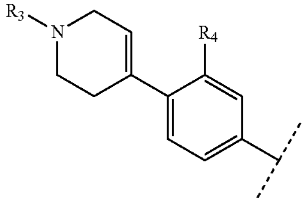
,
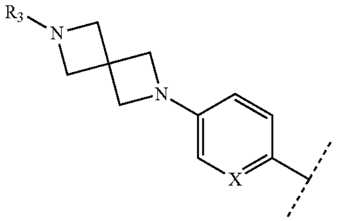
,
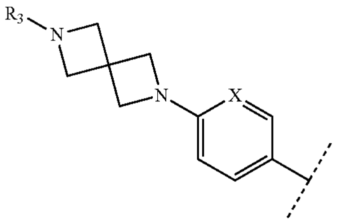
,
-continued
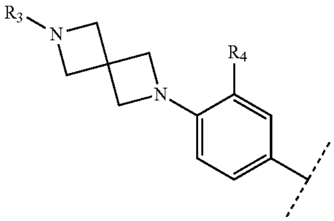
,
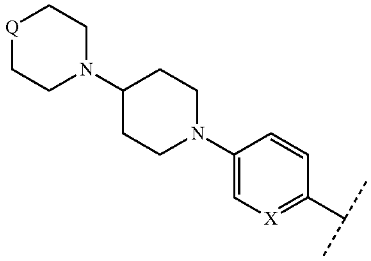
,
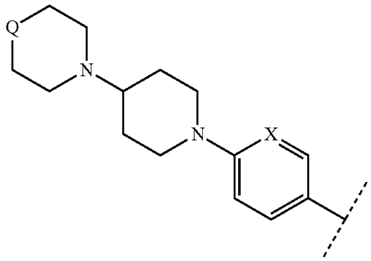
,
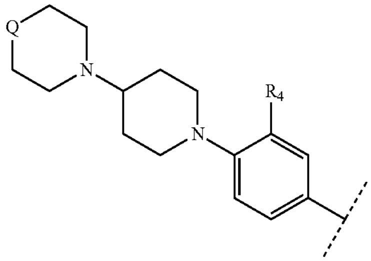
,
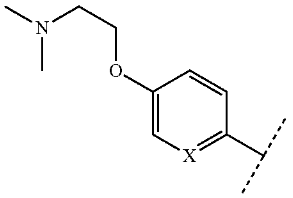
,
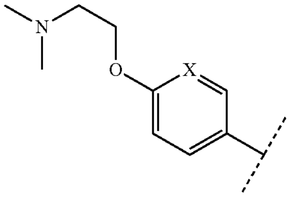
,
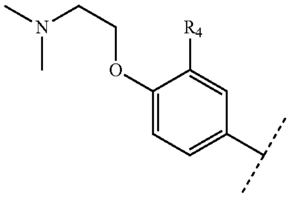
, -continued
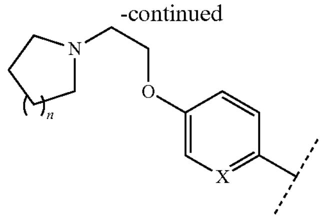
,
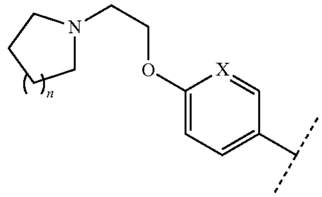
,
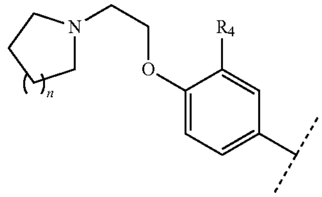
,
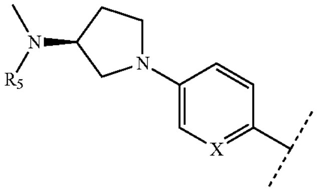
,
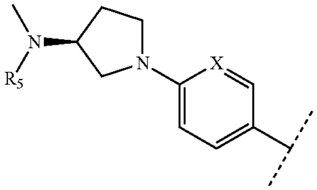
,
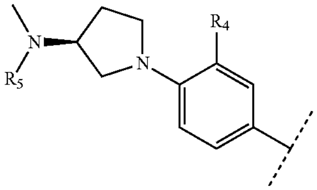
,
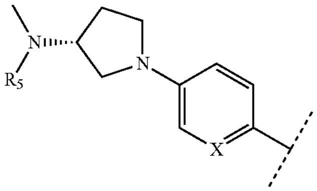
,
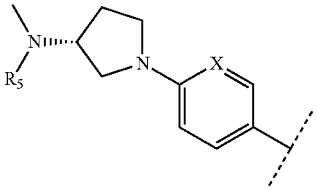
,
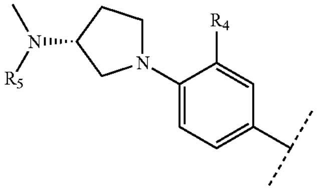
,
-continued
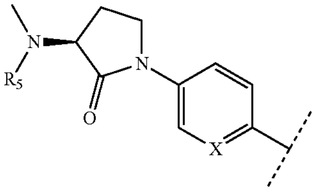
,
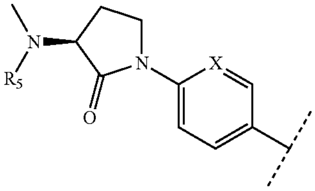
,
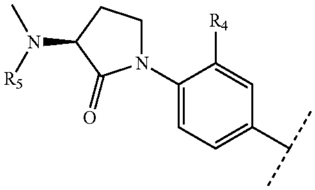
,
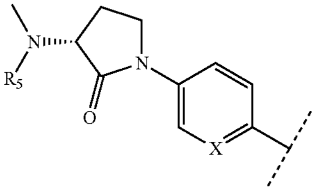
,
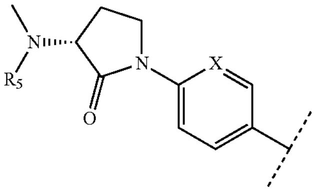
,
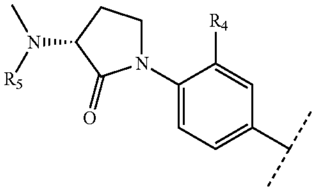
,
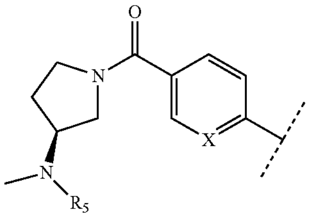
,
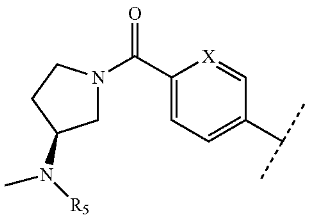
, -continued
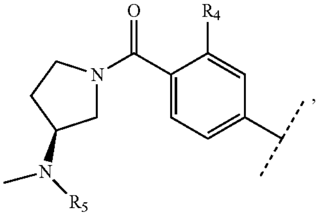
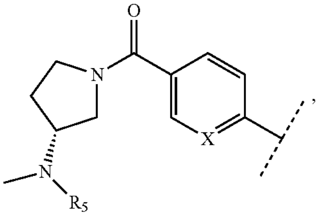
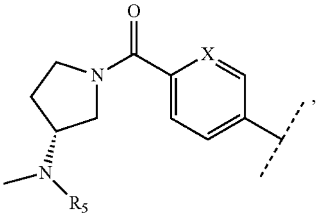
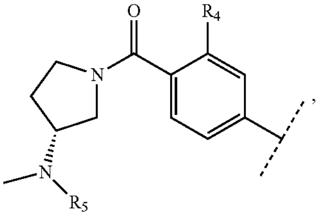
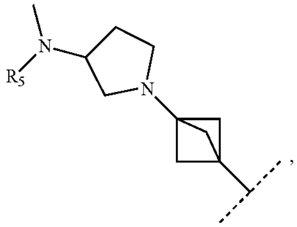
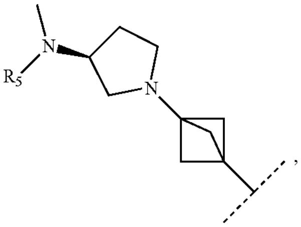
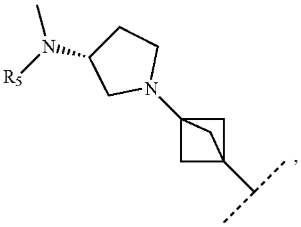
-continued
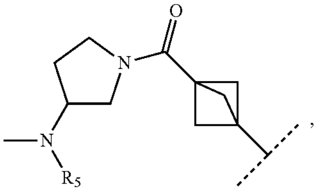
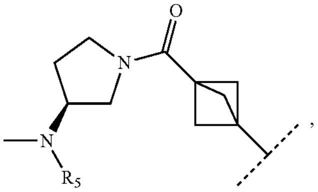
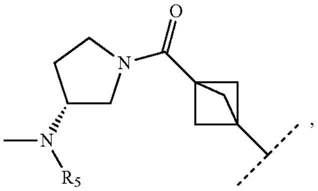
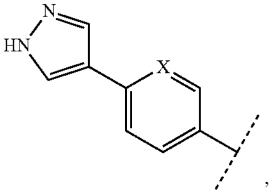
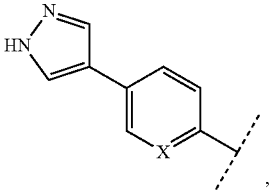
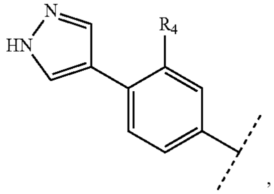
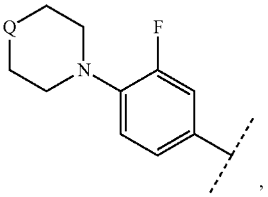
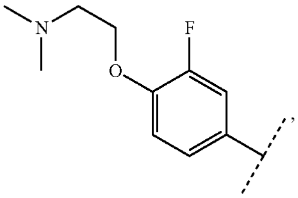
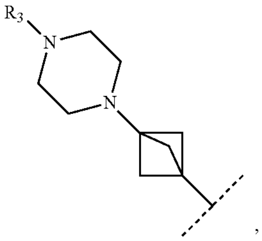
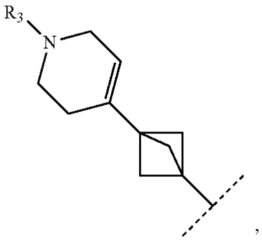
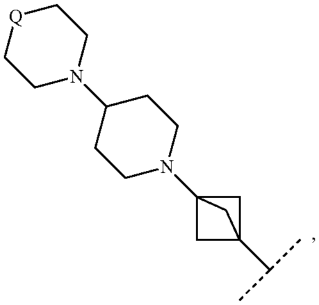

-continued
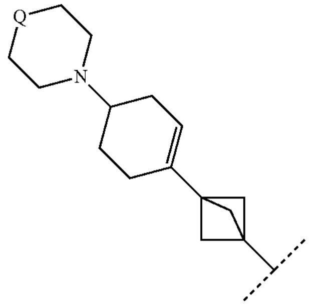,
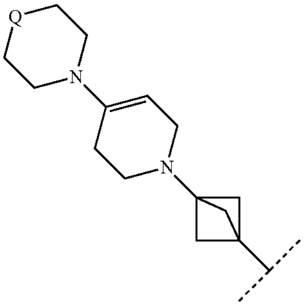,
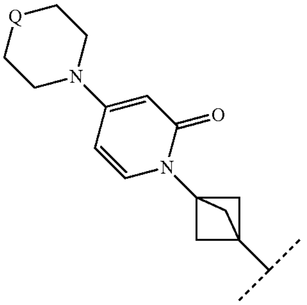,
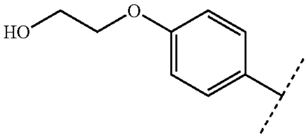,
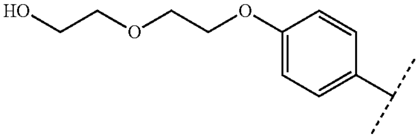,
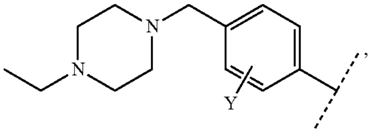,
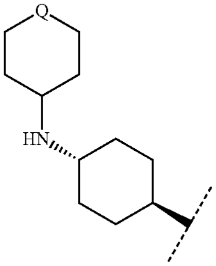, 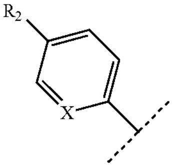,
-continued
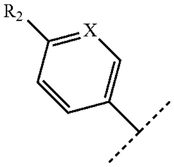, 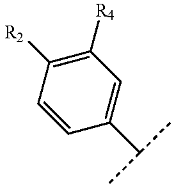, or
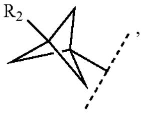,
where $R_3$ is H, Me, $CH_2CH_2OH$, isopropyl, isobutyl, or bicyclo[1.1.1]pentane;
$R_4$ is H, Me, OMe, $OF_3$, or $OHF_2$;
$R_5$ is H or Me;
X is OC—H, N, or OC—F;
Y is H, N, F, Me, OMe, $OF_3$, or $CHF_2$;
o is O or S;
n is 1, 2, or 3; and
$R_2$ is:
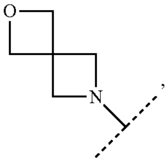, 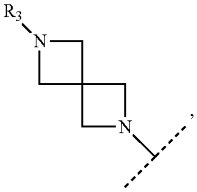,
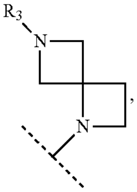, 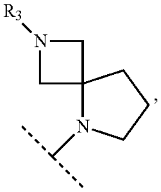, 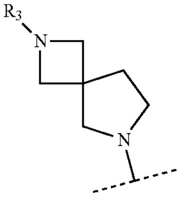,
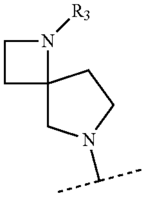, 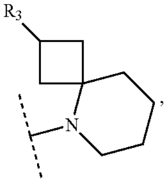, 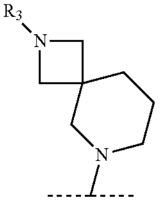,
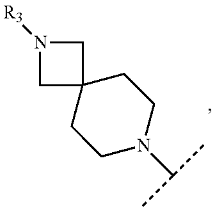, 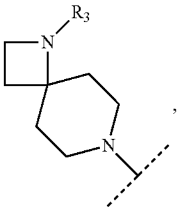,
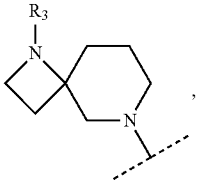, 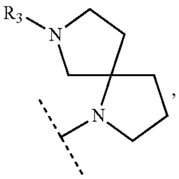, -continued
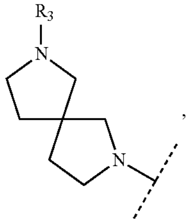, 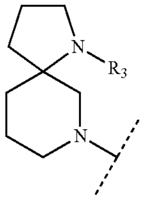, 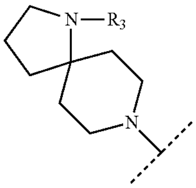,
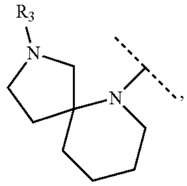, 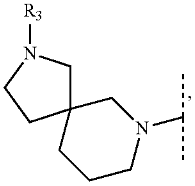,
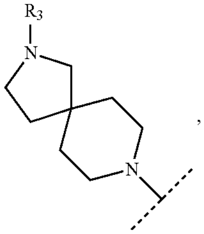, 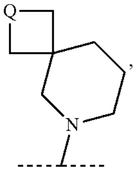, 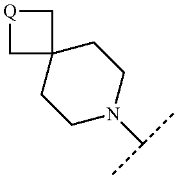,
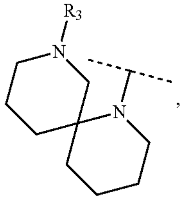, 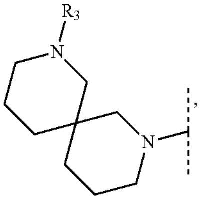,
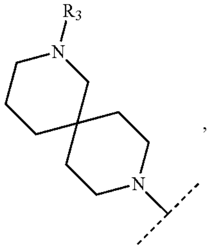, 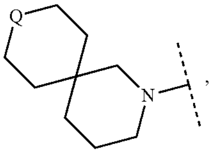,
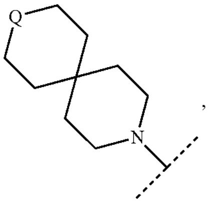, 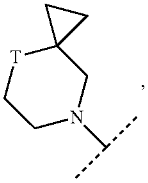, 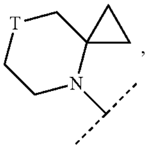,
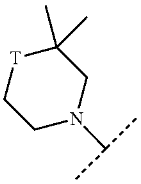, 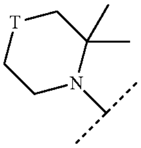, 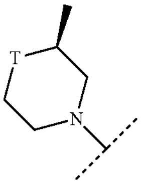,
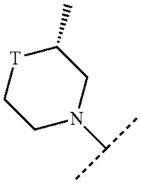, 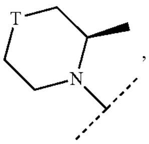, 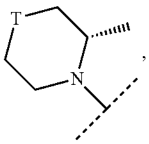,
-continued
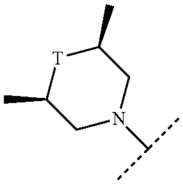, 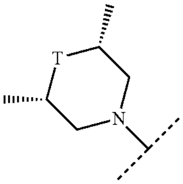, 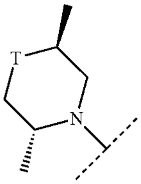,
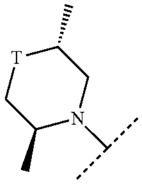, 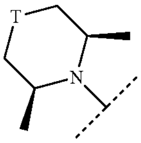, 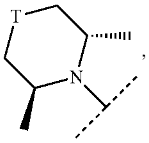,
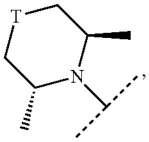, 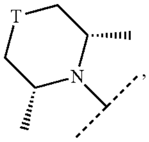, 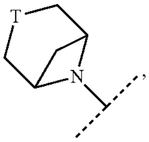,
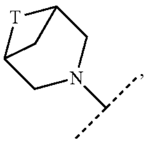, 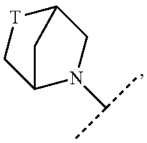, 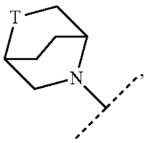,
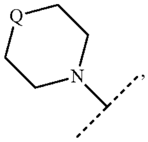 or 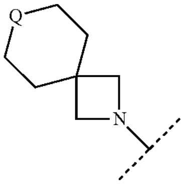,
where T is O, NH, NMe, N-isopropyl, or N-isobutyl. In one aspect, the compound comprises Formulae (VII), (XI), or (XIII):
(VII)
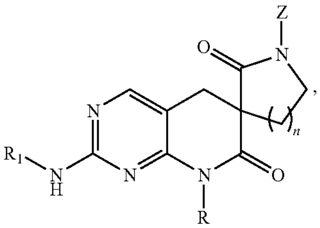
(XI)
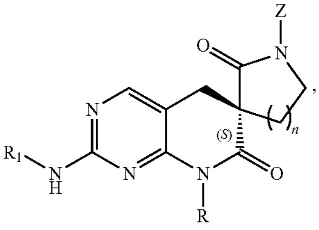, or -continued
(XIII)
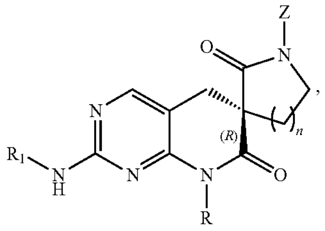
another aspect, R is
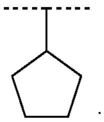
In another aspect, $R_1$ is:
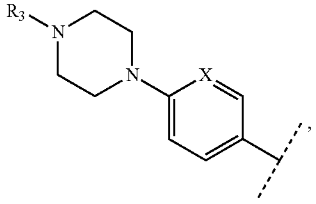
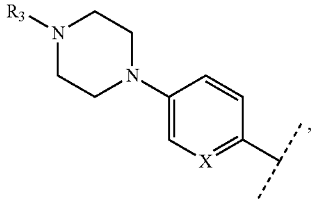
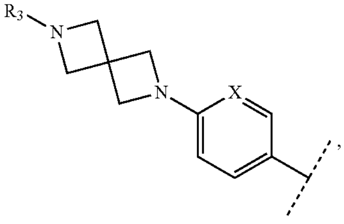
or
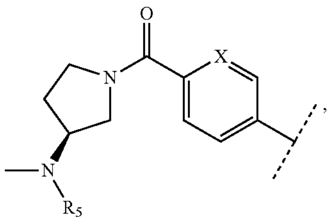
where $R_3$ is H, Me, $CH_2CH_2OH$, isopropyl, isobutyl, or bicyclo[1.1.1]pentane; $R_5$ is H or Me; and X is C—H, N, or C—F.
Another embodiment described herein is a compound selected from D1-D48 or pharmaceutically acceptable salts thereof:
(D1)
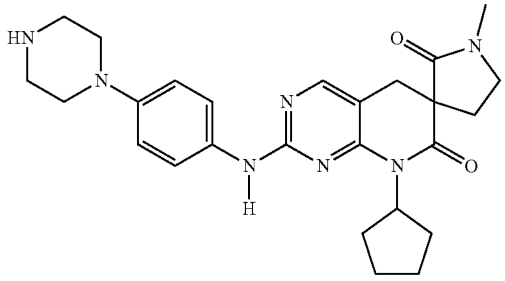
(D2)
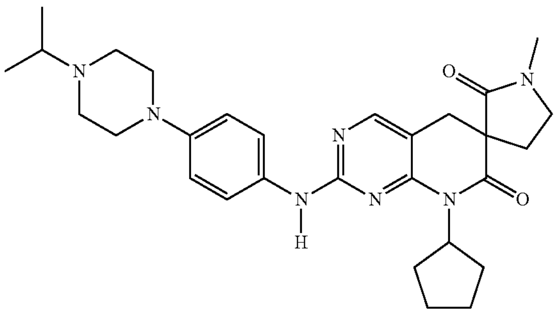
(D3)
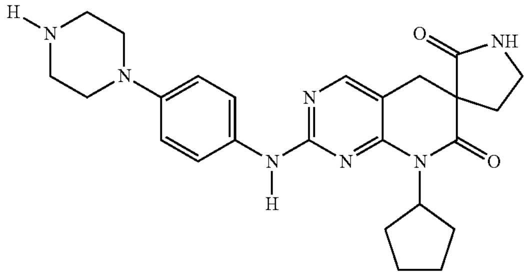
(D4)
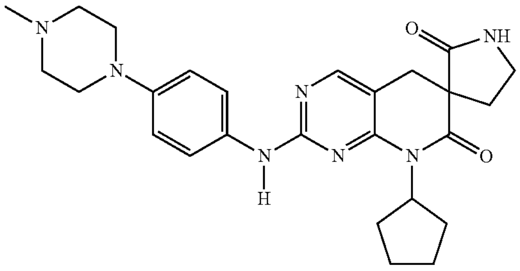
(D5)
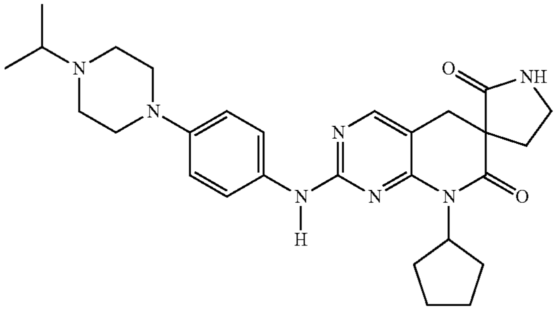

-continued
(D6)
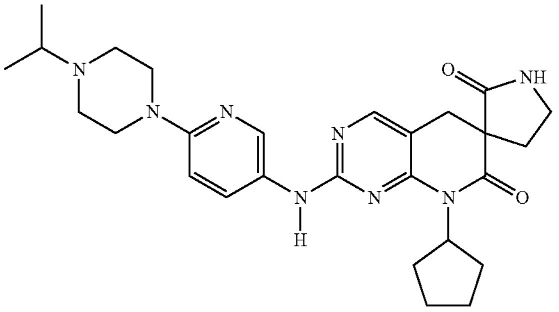
(D7)
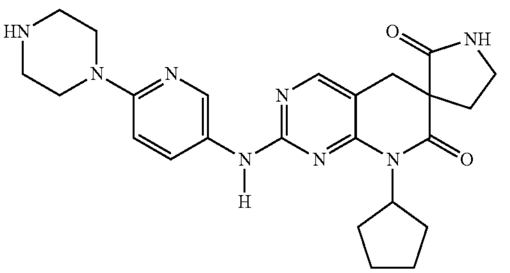
(D8)
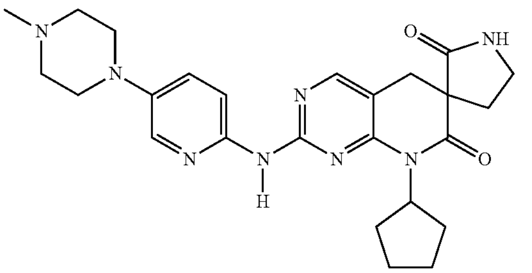
(D9)
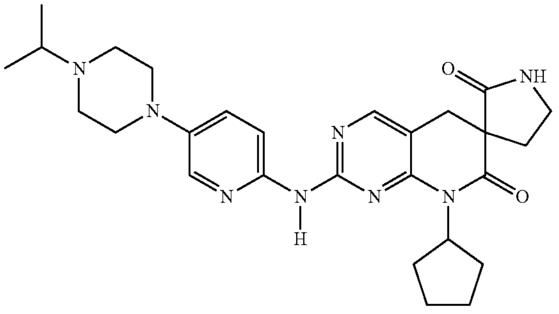
(D10)
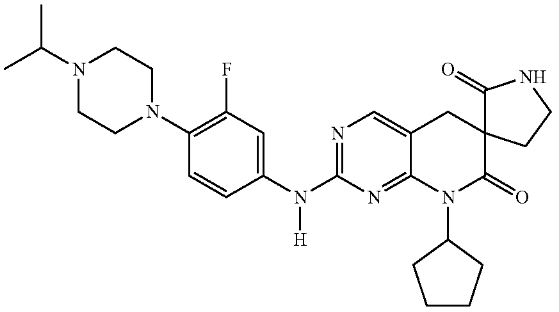
-continued
(D11)
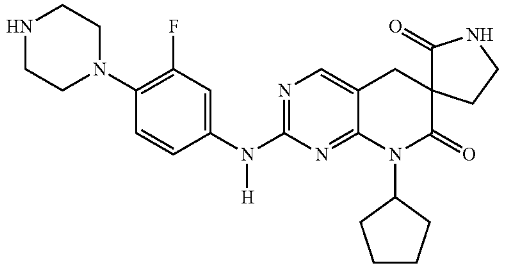
(D12)
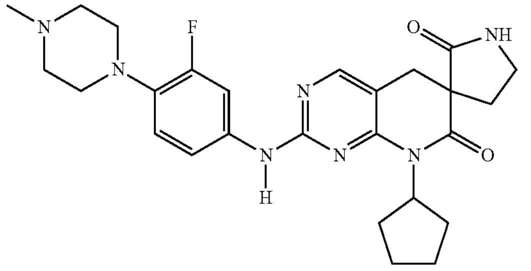
(D13)
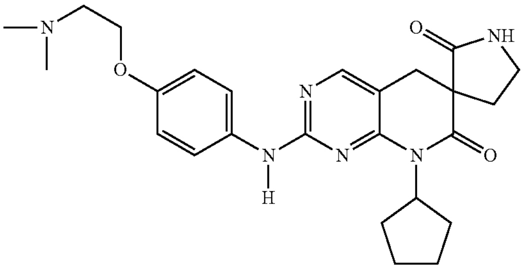
(D14)
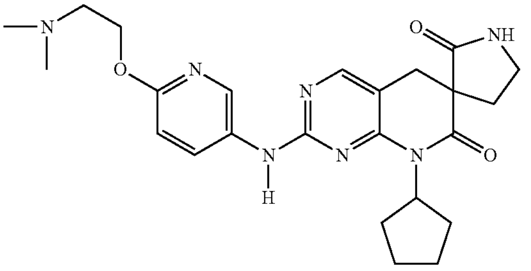
(D15)
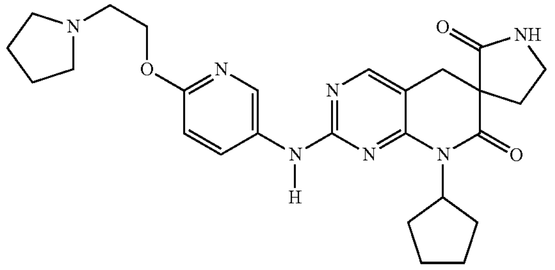

-continued
(D16)
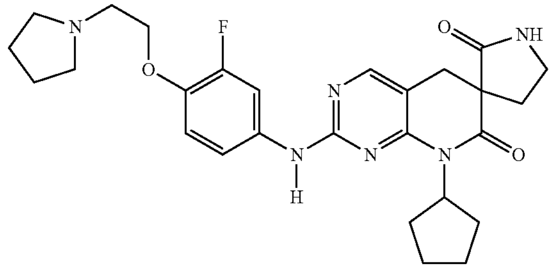
(D17)
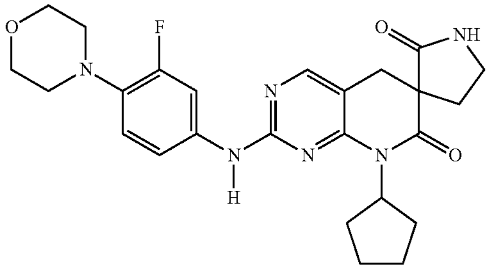
(D18)
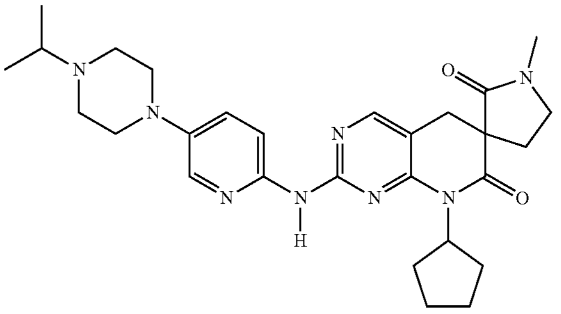
(D19)
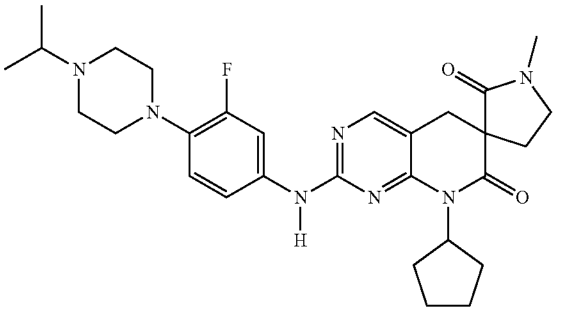
(D20)
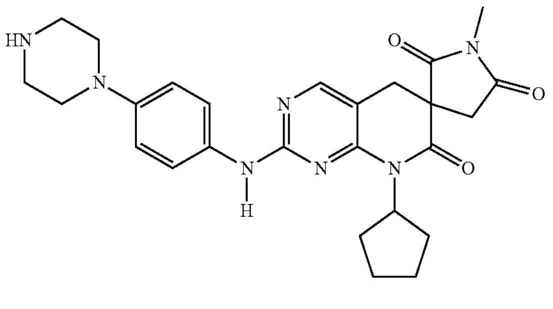
-continued
(D21)
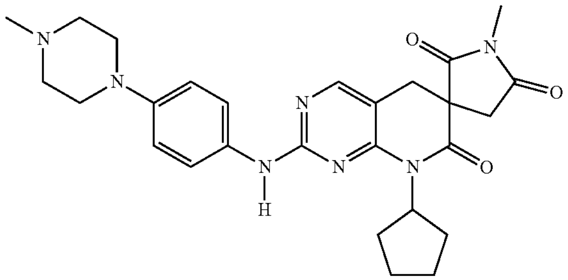
(D22)
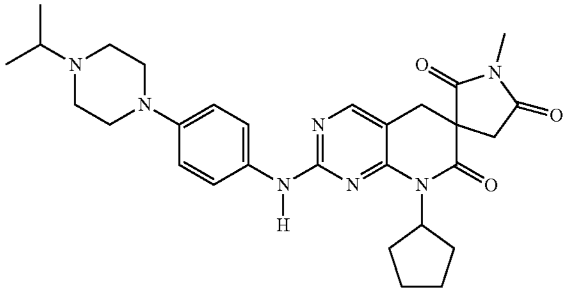
(D23)
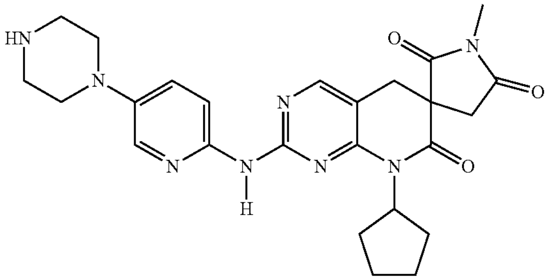
(D24)
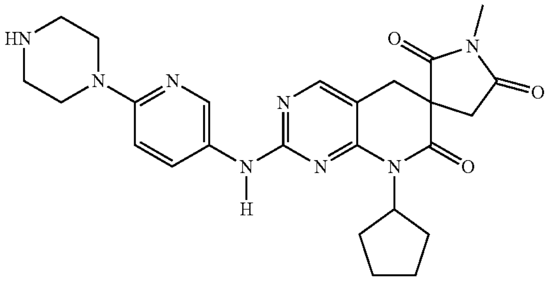
(D25)
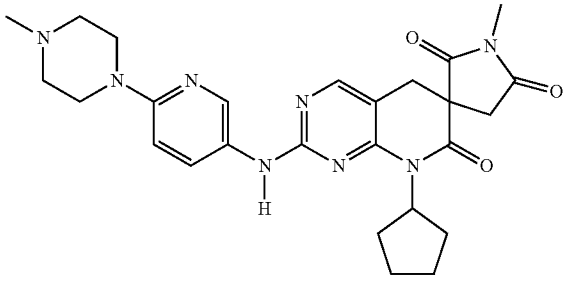

-continued
(D26)
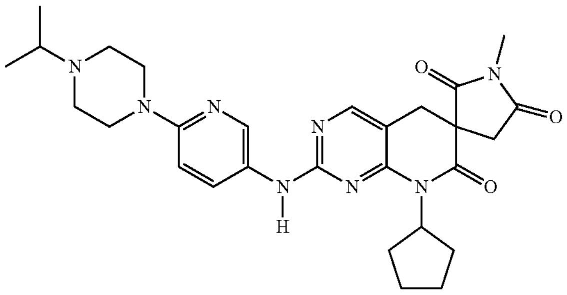
(D27)
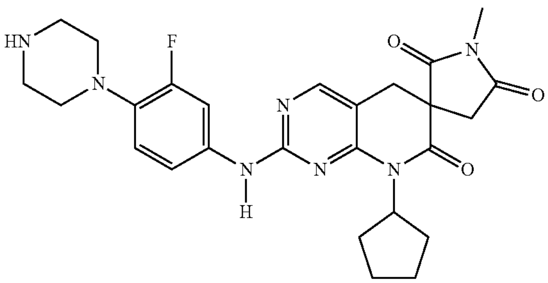
(D28)
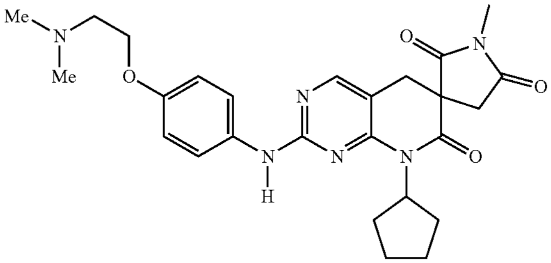
(D29)
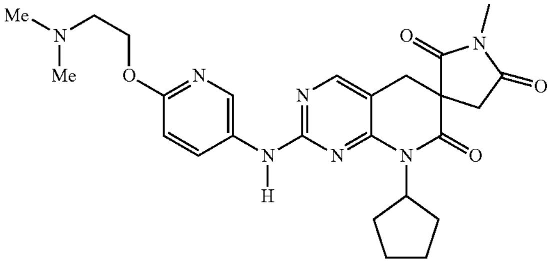
(D30)
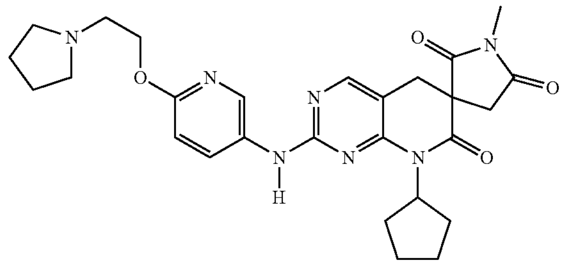
-continued
(D31)
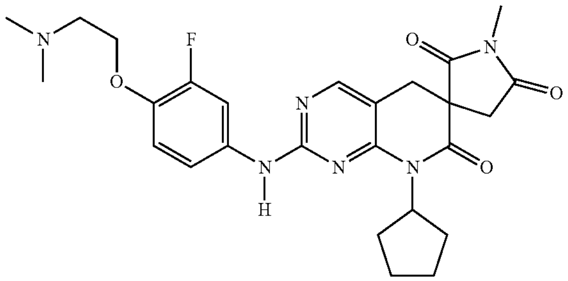
(D32)
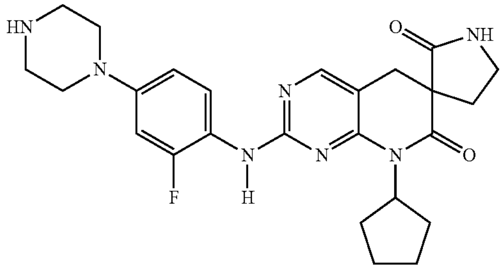
(D33)
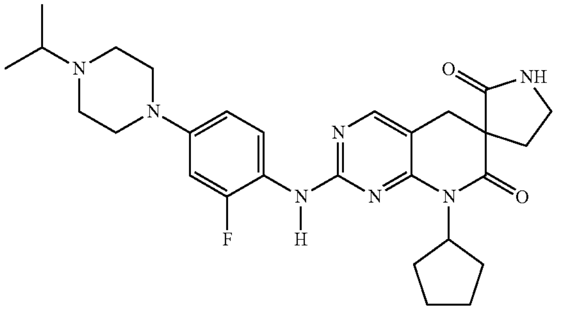
(D34)
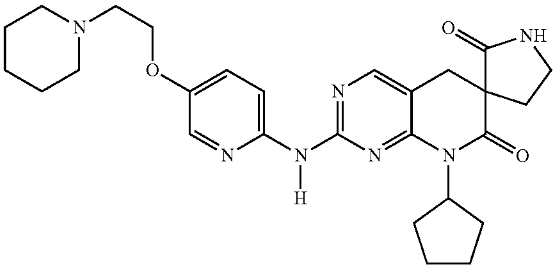
(D35)
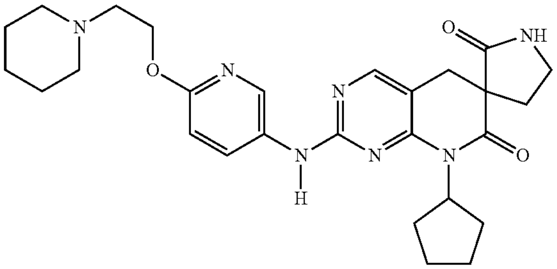

-continued
(D36)
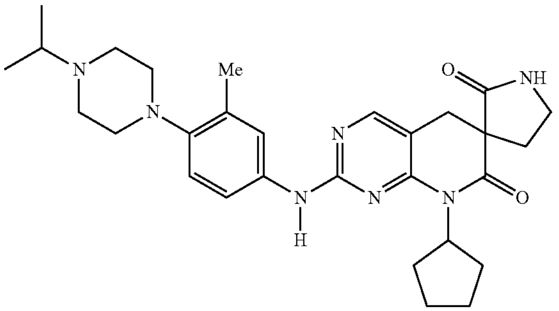
(D37)
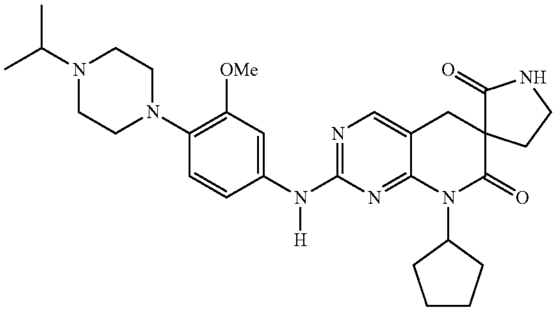
(D38)
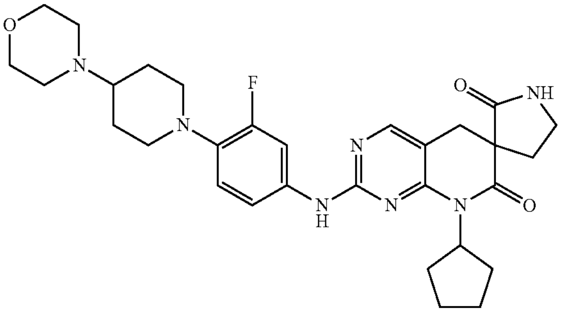
(D39)
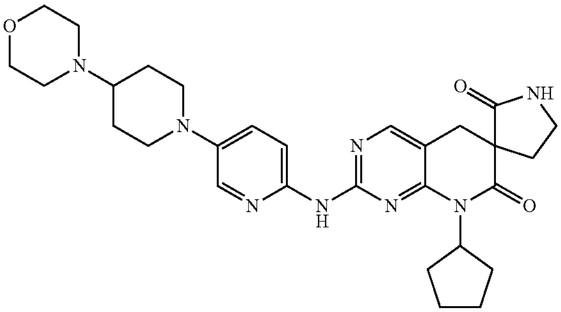
(D40)
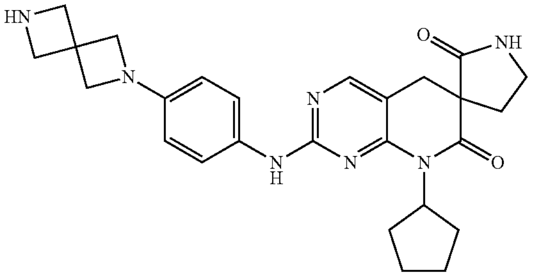
-continued
(D41)
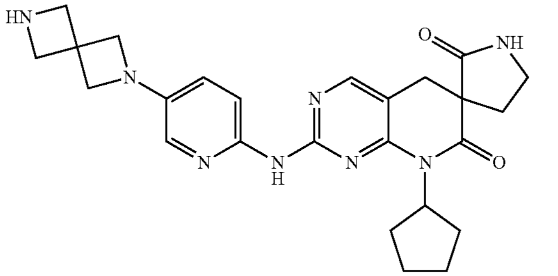
(D42)
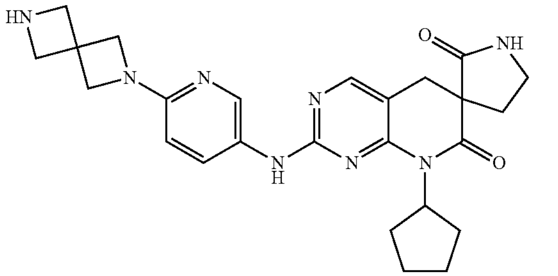
(D43)
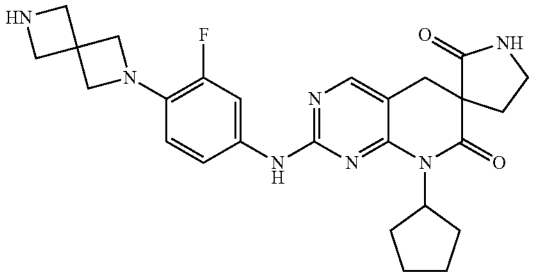
(D44)
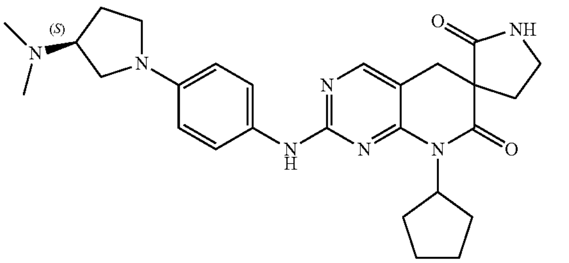
(D45)
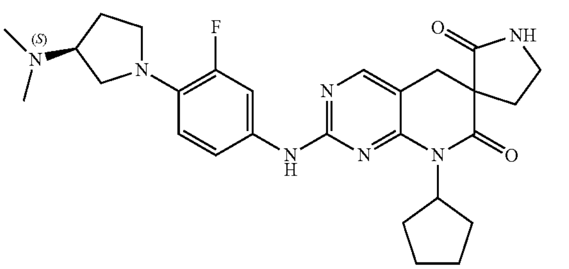

-continued (D46)

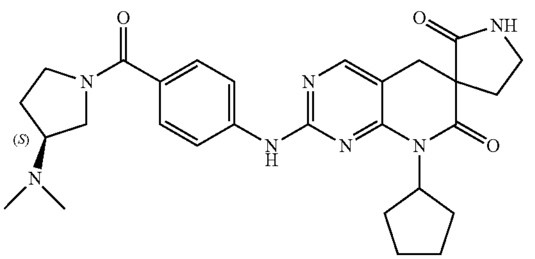

(D47)

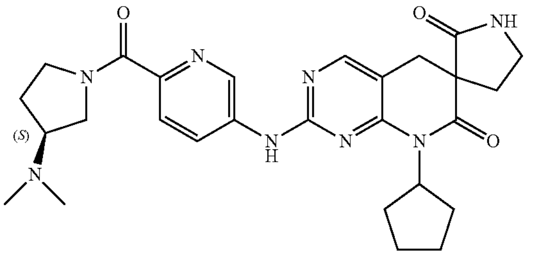

(D48)

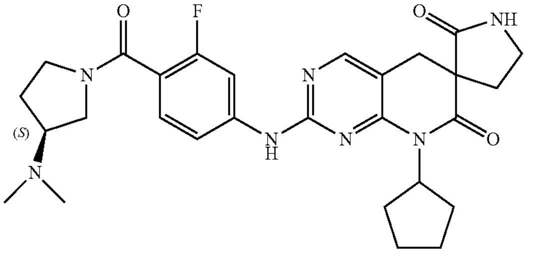

Another embodiment described herein is a pharmaceutical composition comprising one or more of Compounds D1-D48 or a pharmaceutically acceptable salt thereof and one or more pharmaceutically acceptable excipients.

Another embodiment described herein is a method of treating cancer or providing a chemotherapeutic protective effect comprising administering an effective amount of one or more of Compounds D1-D48 to a subject in need thereof.

Another embodiment described herein is a compound selected from:

8-cyclopentyl-1'-methyl-2-((4-(piperazin-1-yl)phenyl)amino)-5,8-dihydro-7H-spiro[pyrido[2,3-d]pyrimidine-6,3'-pyrrolidine]-2',7-dione (D1);

8-cyclopentyl-2-((4-(4-isopropylpiperazin-1-yl)phenyl)amino)-1'-methyl-5,8-dihydro-7H-spiro[pyrido[2,3-d]pyrimidine-6,3'-pyrrolidine]-2',7-dione (D2);

8-cyclopentyl-2-((4-(piperazin-1-yl)phenyl)amino)-5,8-dihydro-7H-spiro[pyrido[2,3-d]pyrimidine-6,3'-pyrrolidine]-2',7-dione (D3);

8-cyclopentyl-2-((4-(4-methylpiperazin-1-yl)phenyl)amino)-5,8-dihydro-7H-spiro[pyrido[2,3-d]pyrimidine-6,3'-pyrrolidine]-2',7-dione (D4);

8-cyclopentyl-2-((4-(4-isopropylpiperazin-1-yl)phenyl)amino)-5,8-dihydro-7H-spiro[pyrido[2,3-d]pyrimidine-6,3'-pyrrolidine]-2',7-dione (D5);

8-cyclopentyl-2-((6-(4-isopropylpiperazin-1-yl)pyridin-3-yl)amino)-5,8-dihydro-7H-spiro[pyrido[2,3-d]pyrimidine-6,3'-pyrrolidine]-2',7-dione (D6);

8-cyclopentyl-2-((6-(piperazin-1-yl)pyridin-2-yl)amino)-5,8-dihydro-7H-spiro[pyrido[2,3-d]pyrimidine-6,3'-pyrrolidine]-2',7-dione (D7);

8-cyclopentyl-2-((5-(4-methylpiperazin-1-yl)pyridin-3-yl)amino)-5,8-dihydro-7H-spiro[pyrido[2,3-d]pyrimidine-6,3'-pyrrolidine]-2',7-dione (D8);

8-cyclopentyl-2-((5-(4-isopropylpiperazin-1-yl)pyridin-2-yl)amino)-5,8-dihydro-7H-spiro[pyrido[2,3-d]pyrimidine-6,3'-pyrrolidine]-2',7-dione (D9);

8-cyclopentyl-2-((3-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (D10);

8-cyclopentyl-2-((3-fluoro-4-(piperazin-1-yl)phenyl)amino)-5,8-dihydro-7H-spiro[pyrido[2,3-d]pyrimidine-6,3'-pyrrolidine]-2',7-dione (D11);

8-cyclopentyl-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (D12);

8-cyclopentyl-2-((4-(2-(dimethylamino)ethoxy)phenyl)amino)-5,8-dihydro-7H-spiro[pyrido[2,3-d]pyrimidine-6,3'-pyrrolidine]-2',7-dione (D13);

8-cyclopentyl-2-((6-(2-(dimethylamino)ethoxy)pyridin-3-yl)amino)-5,8-dihydro-7H-spiro[pyrido[2,3-d]pyrimidine-6,3'-pyrrolidine]-2',7-dione (D14);

8-cyclopentyl-2-((6-(2-(pyrrolidin-1-yl)ethoxy)pyridin-3-yl)amino)-5,8-dihydro-7H-spiro[pyrido[2,3-d]pyrimidine-6,3'-pyrrolidine]-2',7-dione (D15);

8-cyclopentyl-2-((3-fluoro-4-(2-(pyrrolidin-1-yl)ethoxy)phenyl)amino)-5,8-dihydro-7H-spiro[pyrido[2,3-d]pyrimidine-6,3'-pyrrolidine]-2',7-dione (D16);

8-cyclopentyl-2-((3-fluoro-4-morpholinophenyl)amino)-5,8-dihydro-7H-spiro[pyrido[2,3-d]pyrimidine-6,3'-pyrrolidine]-2',7-dione (D17);

8-cyclopentyl-2-((5-(4-isopropylpiperazin-1-yl)pyridin-2-yl)amino)-1'-methyl-5,8-dihydro-7H-spiro[pyrido[2,3-d]pyrimidine-6,3'-pyrrolidine]-2',7-dione (D18);

8-cyclopentyl-2-((3-fluoro-4-(4-methylpiperazin-1-yl)phenyl)amino)-1'-methyl-5,8-dihydro-7H-spiro[pyrido[2,3-d]pyrimidine-6,3'-pyrrolidine]-2',7-dione (D19);

8-cyclopentyl-1'-methyl-2-((4-(piperazin-1-yl)phenyl)amino)-5,8-dihydro-7H-spiro[pyrido[2,3-d]pyrimidine-6,3'-pyrrolidine]-2',5',7-trione (D20);

8-cyclopentyl-1'-methyl-2-((4-(4-methylpiperazin-1-yl)phenyl)amino)-5,8-dihydro-7H-spiro[pyrido[2,3-d]pyrimidine-6,3'-pyrrolidine]-2',5',7-trione (D21);

8-cyclopentyl-2-((4-(4-isopropylpiperazin-1-yl)phenyl)amino)-1'-methyl-5,8-dihydro-7H-spiro[pyrido[2,3-d]pyrimidine-6,3'-pyrrolidine]-2',5',7-trione (D22);

8-cyclopentyl-1'-methyl-2-((5-(piperazin-1-yl)pyridin-2-yl)amino)-5,8-dihydro-7H-spiro[pyrido[2,3-d]pyrimidine-6,3'-pyrrolidine]-2',5',7-trione (D23);

8-cyclopentyl-1'-methyl-2-((6-(piperazin-1-yl)pyridin-3-yl)amino)-5,8-dihydro-7H-spiro[pyrido[2,3-d]pyrimidine-6,3'-pyrrolidine]-2',5',7-trione (D24);

8-cyclopentyl-1'-methyl-2-((6-(4-methylpiperazin-1-yl)pyridin-3-yl)amino)-5,8-dihydro-7H-spiro[pyrido[2,3-d]pyrimidine-6,3'-pyrrolidine]-2',5',7-trione (D25);

8-cyclopentyl-2-((6-(4-isopropylpiperazin-1-yl)pyridin-3-yl)amino)-1'-methyl-5,8-dihydro-7H-spiro[pyrido[2,3-d]pyrimidine-6,3'-pyrrolidine]-2',5',7-trione (D26);

8-cyclopentyl-2-((3-fluoro-4-(piperazin-1-yl)phenyl)amino)-1'-methyl-5,8-dihydro-7H-spiro[pyrido[2,3-d]pyrimidine-6,3'-pyrrolidine]-2',5',7-trione (D27);

8-cyclopentyl-2-((4-(2-(dimethylamino)ethoxy)phenyl)amino)-1'-methyl-5,8-dihydro-7H-spiro[pyrido[2,3-d]pyrimidine-6,3'-pyrrolidine]-2',5',7-trione (D28);

8-cyclopentyl-2-((6-(2-(dimethylamino)ethoxy)pyridin-3-yl)amino)-1'-methyl-5,8-dihydro-7H-spiro[pyrido[2,3-d]pyrimidine-6,3'-pyrrolidine]-2',5',7-trione (D29);

8-cyclopentyl-1'-methyl-2-((6-(2-(pyrrolidin-1-yl)ethoxy)pyridin-3-yl)amino)-5,8-dihydro-7H-spiro[pyrido[2,3-d]pyrimidine-6,3'-pyrrolidine]-2',5',7-trione (D30);

8-cyclopentyl-2-((4-(2-(dimethylamino)ethoxy)-3-fluorophenyl)amino)-1'-methyl-5,8-dihydro-7H-spiro[pyrido[2,3-d]pyrimidine-6,3'-pyrrolidine]-2',5',7-trione (D31);

8-cyclopentyl-2-((2-fluoro-4-(piperazin-1-yl)phenyl)amino)-5,8-dihydro-7H-spiro[pyrido[2,3-d]pyrimidine-6,3'-pyrrolidine]-2',7-dione (D32);

8-cyclopentyl-2-((2-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (D33);

8-cyclopentyl-2-((5-(2-(piperidin-1-yl)ethoxy)pyridin-2-yl)amino)-5,8-dihydro-7H-spiro[pyrido[2,3-d]pyrimidine-6,3'-pyrrolidine]-2',7-dione (D34);

8-cyclopentyl-2-((6-(2-(piperidin-1-yl)ethoxy)pyridin-3-yl)amino)-5,8-dihydro-7H-spiro[pyrido[2,3-d]pyrimidine-6,3'-pyrrolidine]-2',7-dione (D35);

8-cyclopentyl-2-((4-(4-isopropylpiperazin-1-yl)-3-methylphenyl)amino)-5,8-dihydro-7H-spiro[pyrido[2,3-d]pyrimidine-6,3'-pyrrolidine]-2',7-dione (D36);

8-cyclopentyl-2-((4-(4-isopropylpiperazin-1-yl)-3-methoxyphenyl)amino)-5,8-dihydro-7H-spiro[pyrido[2,3-d]pyrimidine-6,3'-pyrrolidine]-2',7-dione (D37);

8-cyclopentyl-2-((3-fluoro-4-(4-morpholinopiperidin-1-yl)phenyl)amino)-5,8-dihydro-7H-spiro[pyrido[2,3-d]pyrimidine-6,3'-pyrrolidine]-2',7-dione (D38);

8-cyclopentyl-2-((5-(4-morpholinopiperidin-1-yl)pyridin-2-yl)amino)-5,8-dihydro-7H-spiro[pyrido[2,3-d]pyrimidine-6,3'-pyrrolidine]-2',7-dione (D39);

2-((4-(2,6-diazaspiro[3.3]heptan-2-yl)phenyl)amino)-8-cyclopentyl-5,8-dihydro-7H-spiro[pyrido[2,3-d]pyrimidine-6,3'-pyrrolidine]-2',7-dione (D40);

2-((5-(2,6-diazaspiro[3.3]heptan-2-yl)pyridin-2-yl)amino)-8-cyclopentyl-5,8-dihydro-7H-spiro[pyrido[2,3-d]pyrimidine-6,3'-pyrrolidine]-2',7-dione (D41);

2-((6-(2,6-diazaspiro[3.3]heptan-2-yl)pyridin-3-yl)amino)-8-cyclopentyl-5,8-dihydro-7H-spiro[pyrido[2,3-d]pyrimidine-6,3'-pyrrolidine]-2',7-dione (D42);

8-cyclopentyl-2-((3-fluoro-4-(2,6-diazaspiro[3.3]heptan-2-yl)phenyl)amino)-5,8-dihydro-7H-spiro[pyrido[2,3-d]pyrimidine-6,3'-pyrrolidine]-2',7-dione (D43);

8-cyclopentyl-2-((4-((S)-3-(dimethylamino)pyrrolidin-1-yl)phenyl)amino)-5,8-dihydro-7H-spiro[pyrido[2,3-d]pyrimidine-6,3'-pyrrolidine]-2',7-dione (D44);

8-cyclopentyl-2-((4-((S)-3-(dimethylamino)pyrrolidin-1-yl)-3-fluorophenyl)amino)-5,8-dihydro-7H-spiro[pyrido[2,3-d]pyrimidine-6,3'-pyrrolidine]-2',7-dione (D45);

8-cyclopentyl-2-((4-((S)-3-(dimethylamino)pyrrolidine-1-carbonyl)phenyl)amino)-5,8-dihydro-7H-spiro[pyrido[2,3-d]pyrimidine-6,3'-pyrrolidine]-2',7-dione (D46);

8-cyclopentyl-2-((6-((S)-3-(dimethylamino)pyrrolidine-1-carbonyl)pyridin-3-yl)amino)-5,8-dihydro-7H-spiro[pyrido[2,3-d]pyrimidine-6,3'-pyrrolidine]-2',7-dione (D47);

8-cyclopentyl-2-((4-((S)-3-(dimethylamino)pyrrolidine-1-carbonyl)-3-fluorophenyl)amino)-5,8-dihydro-7H-spiro[pyrido[2,3-d]pyrimidine-6,3'-pyrrolidine]-2',7-dione (D48); or pharmaceutically acceptable salts thereof.

Another embodiment described herein is a compound selected from Compounds D49-D203 or pharmaceutically acceptable salts thereof:

(D49)

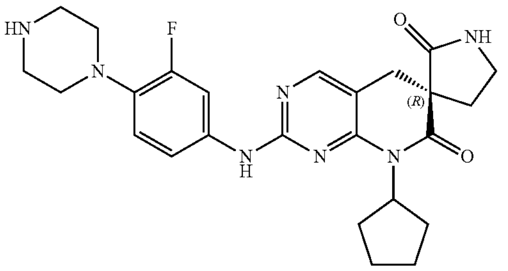

Enantiomer I (E1) of D11

(D50)

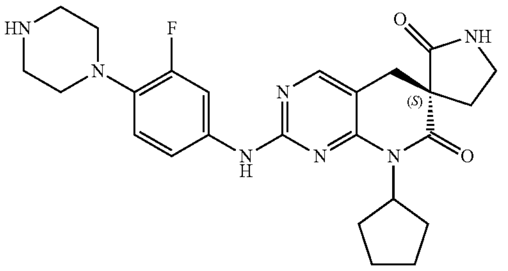

Enantiomer II (E2) of D11

(D51)

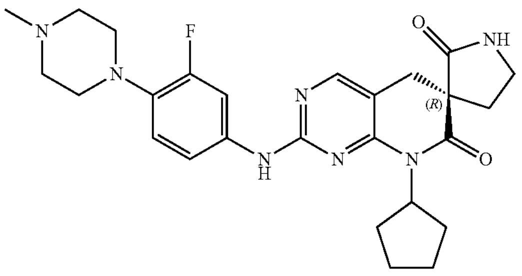

Enantiomer I (E1) of D12

(D52)

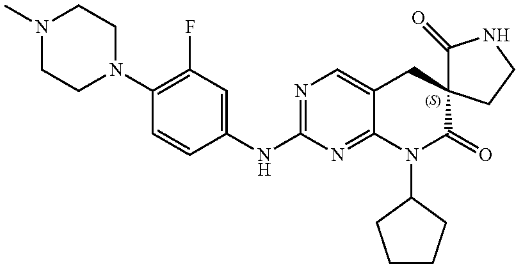

Enantiomer II (E2) of D12

-continued
(D53)
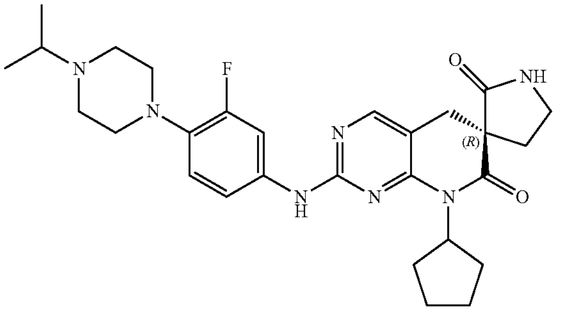
Enantiomer I (E1) of D10
(D54)
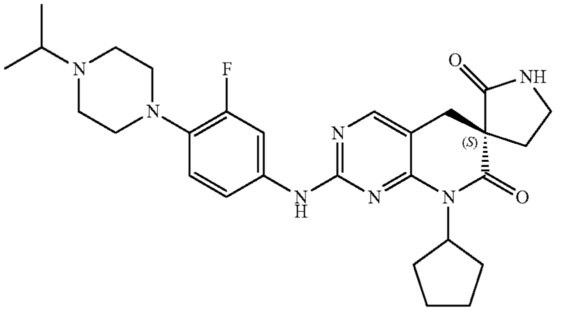
Enantiomer II (E2) of D10
(D55)
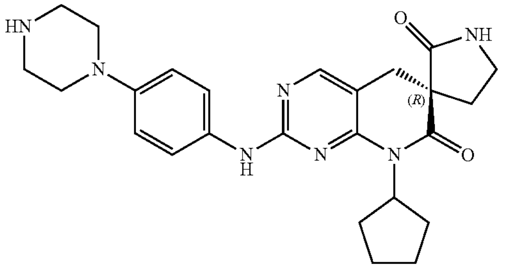
Enantiomer I (E1) of D3
(D56)
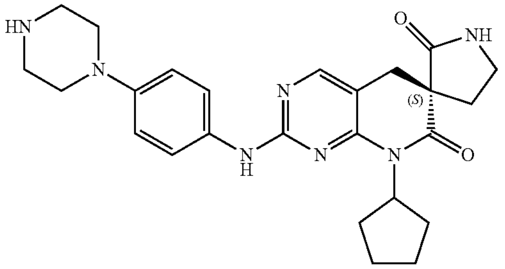
Enantiomer II (E2) of D3
-continued
(D57)
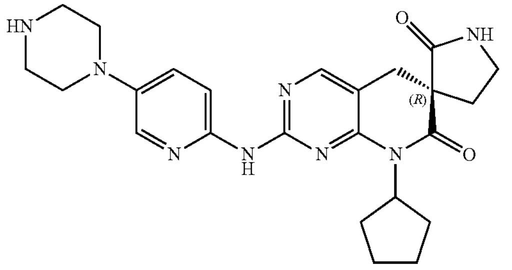
Enantiomer I (E1)
(D58)
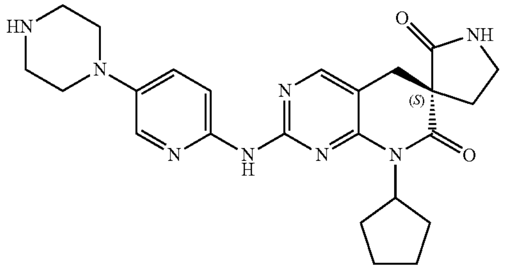
Enantiomer II (E2)
(D59)
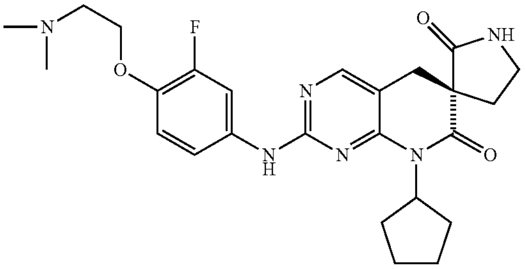
(D60)
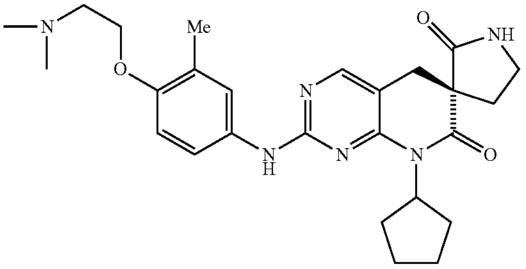
(D61)
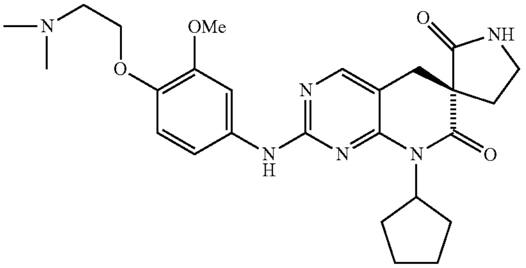

-continued
(D62)
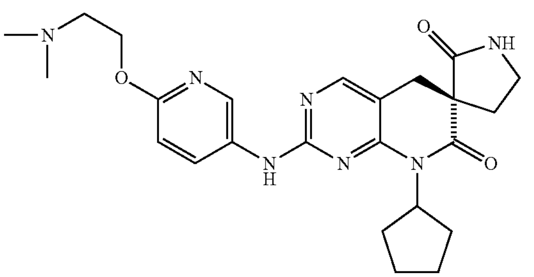
(D63)
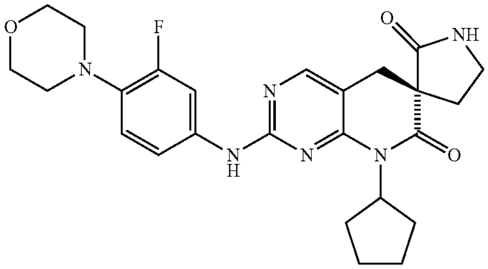
(D64)
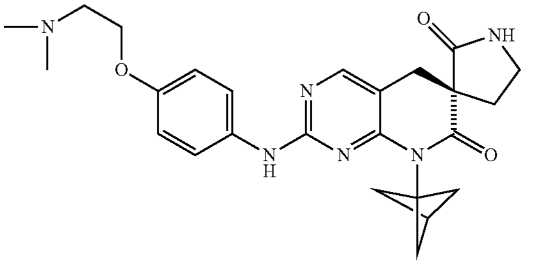
(D65)
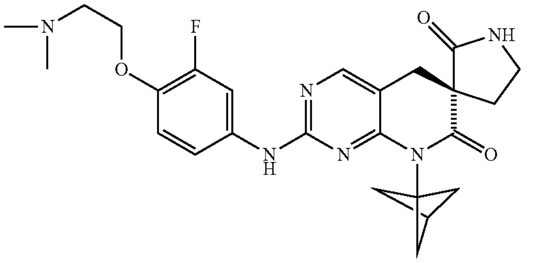
(D66)
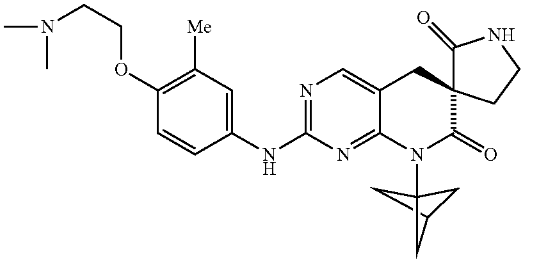
-continued
(D67)
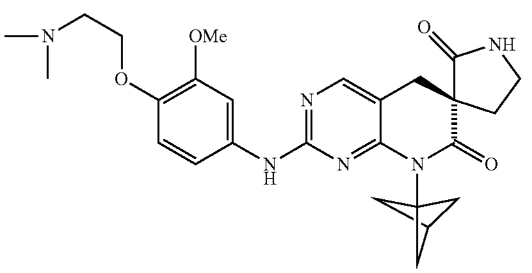
(D68)
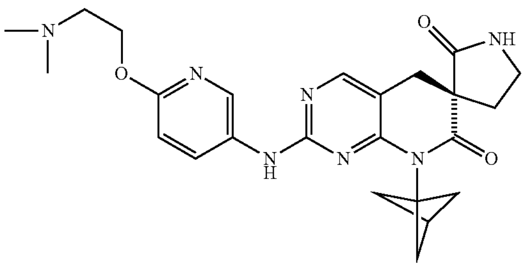
(D69)
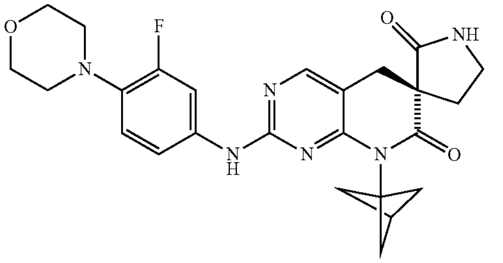
(D70)
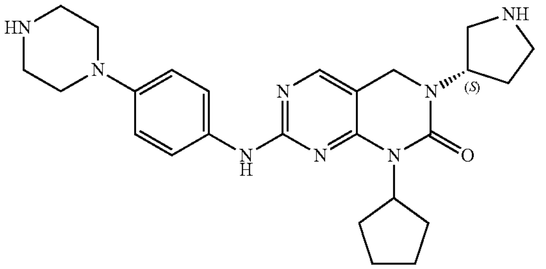
(D71)
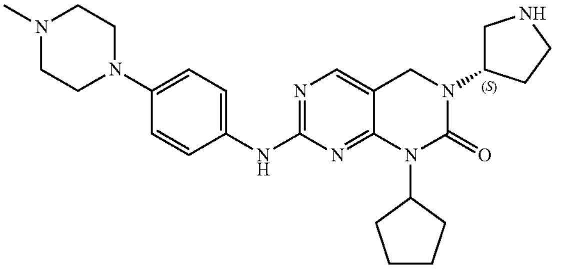

-continued
(D72)
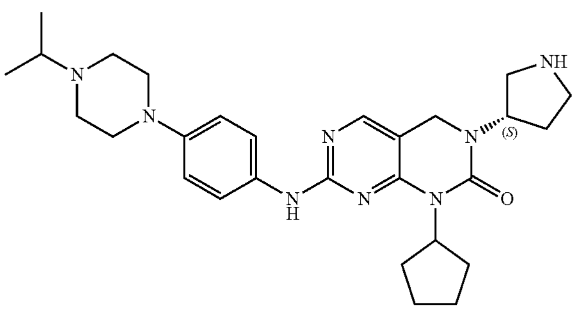
(D73)
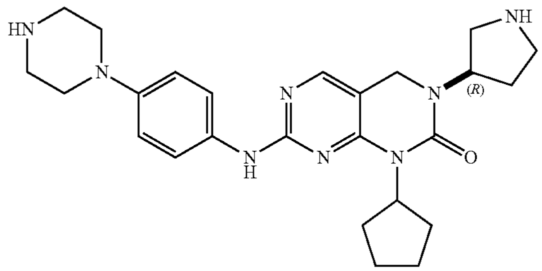
(D74)
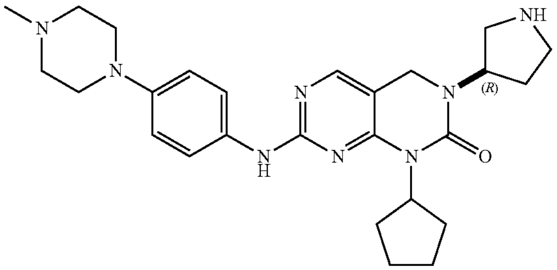
(D75)
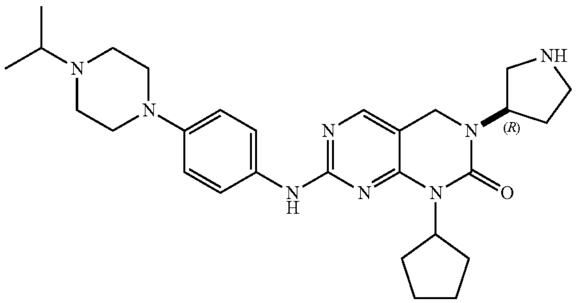
(D76)
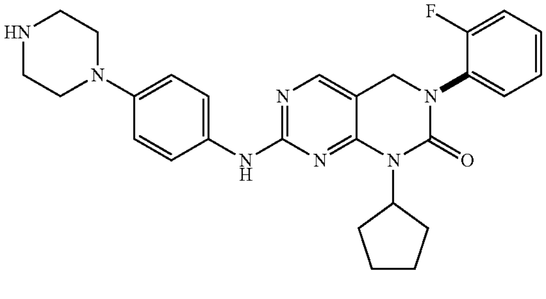
-continued
(D77)
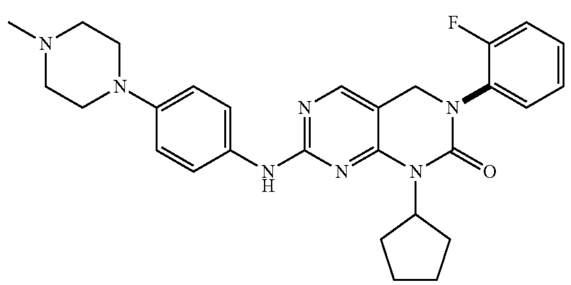
(D78)
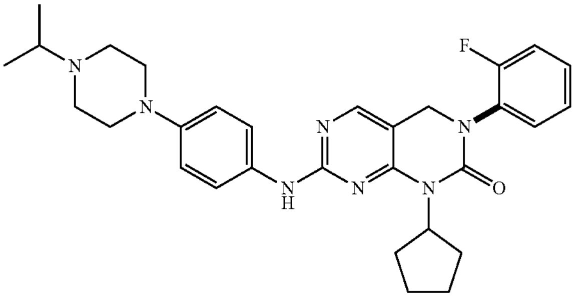
(D79)
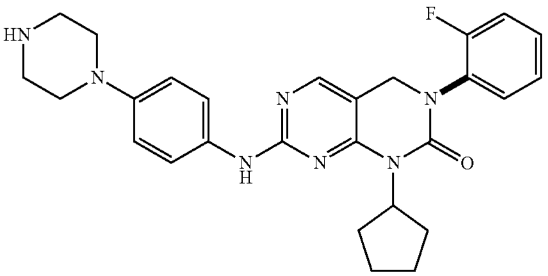
(D80)
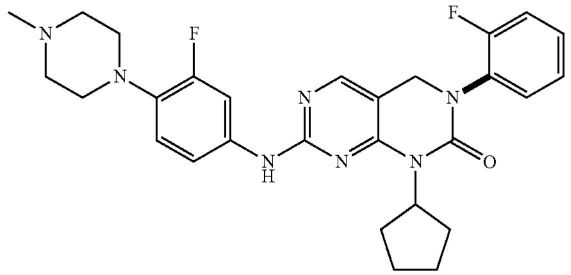
(D81)
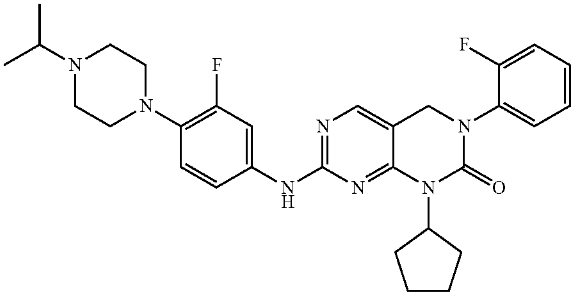

-continued
(D82)
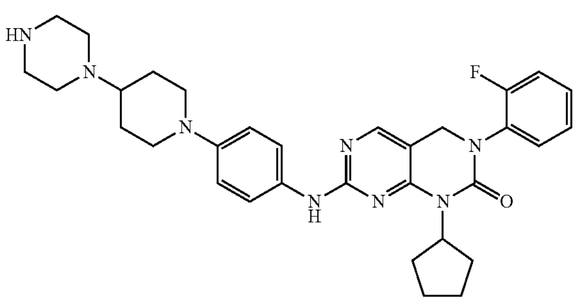
(D83)
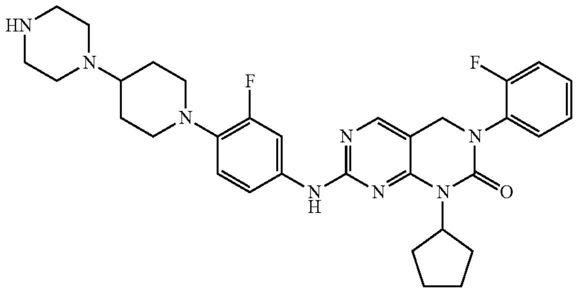
(D84)
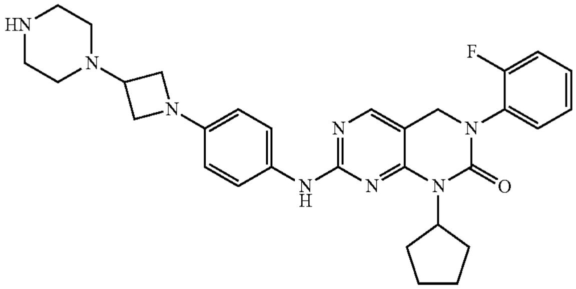
(D85)
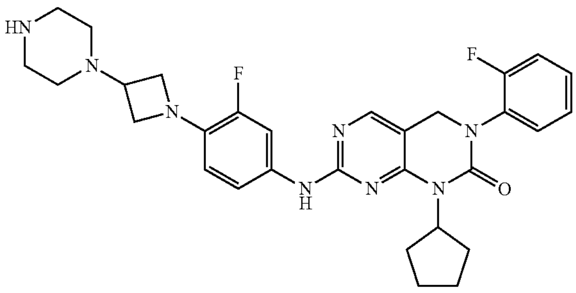
(D86)
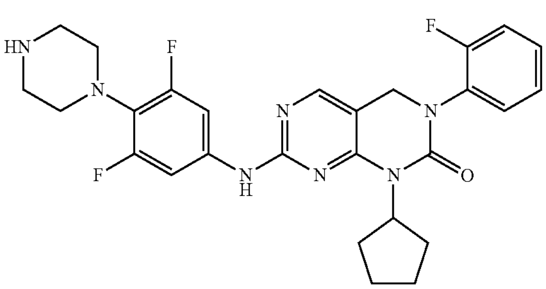
-continued
(D87)
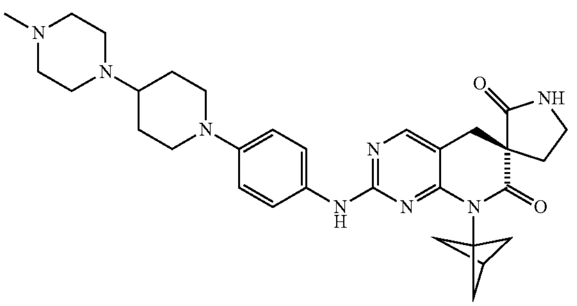
(D88)
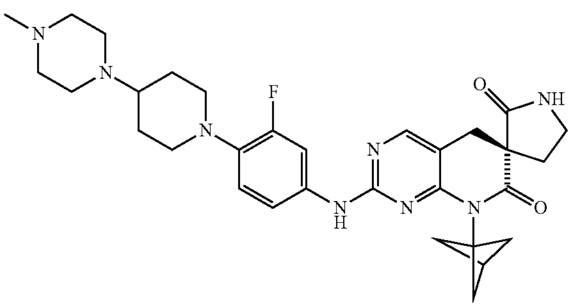
(D89)
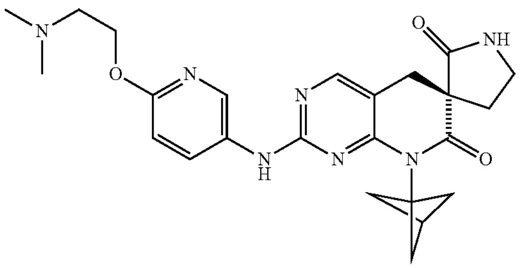
(D90)
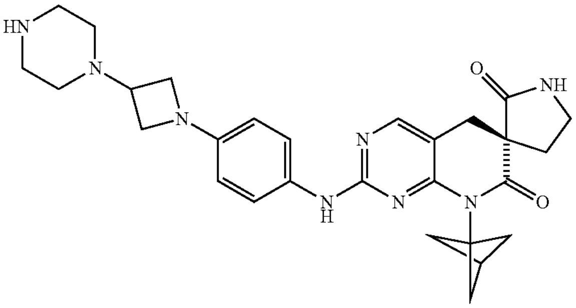
(D91)
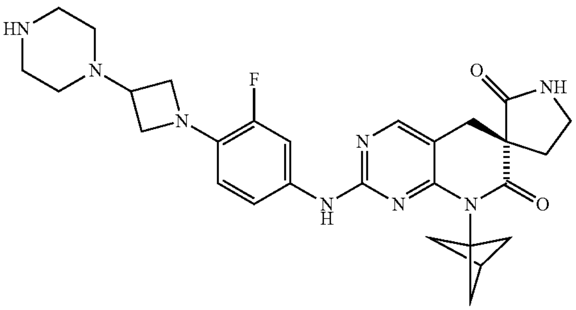

-continued
(D92)
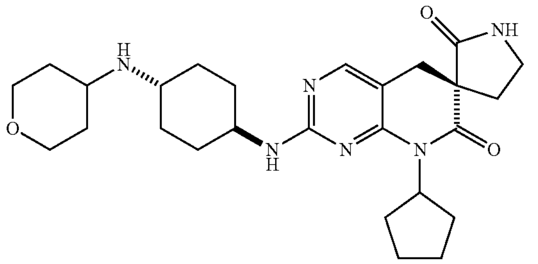
(D93)
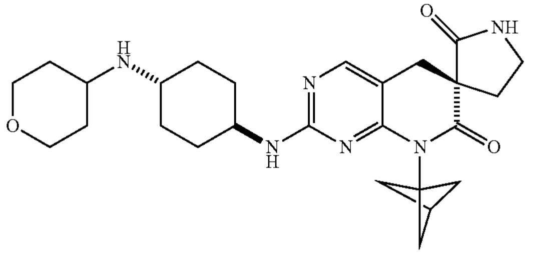
(D94)
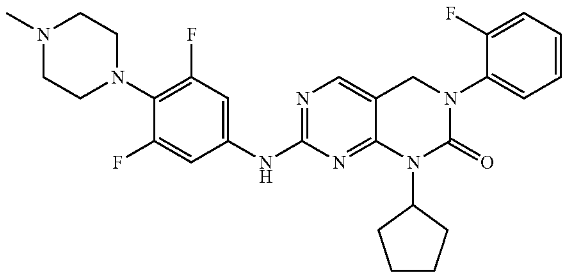
(D95)
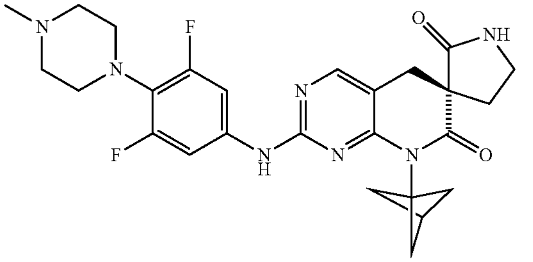
(D-96)
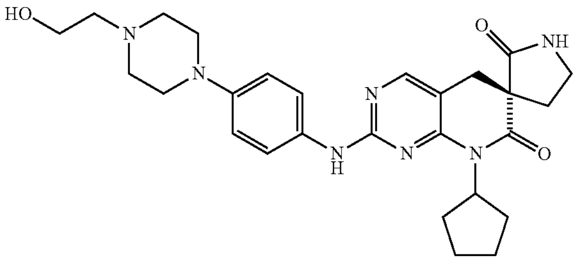
-continued
(D97)
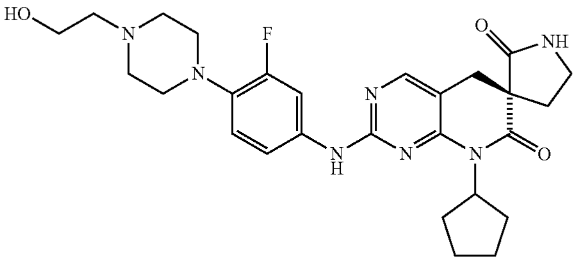
(D98)
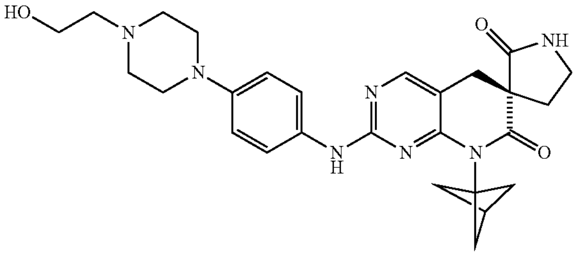
(D99)
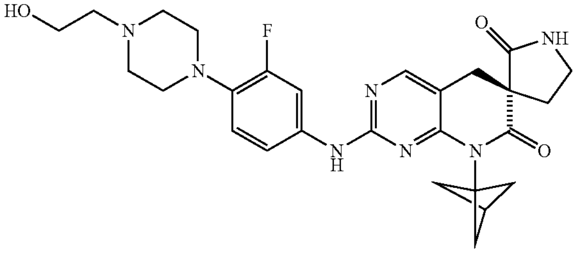
(D100)
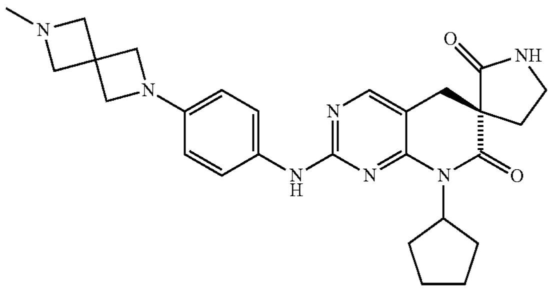
(D101)
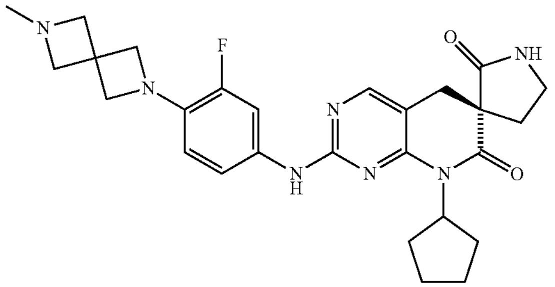

-continued
(D102)
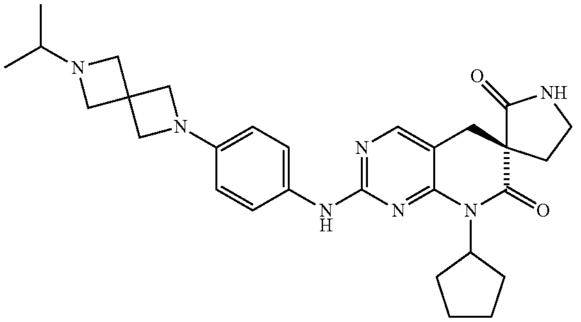
(D103)
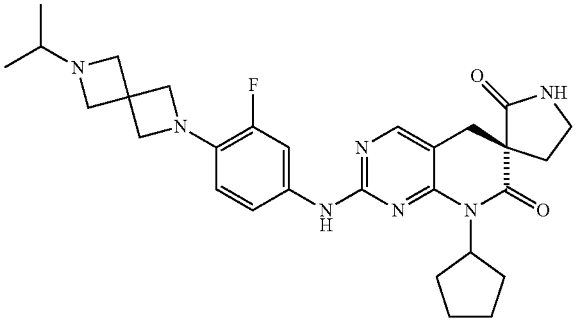
(D104)
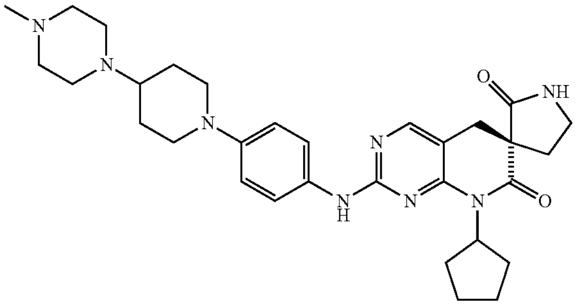
(D105)
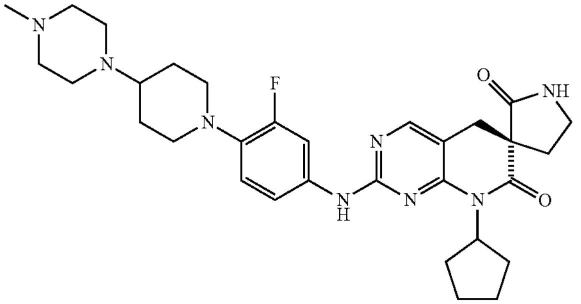
-continued
(D106)
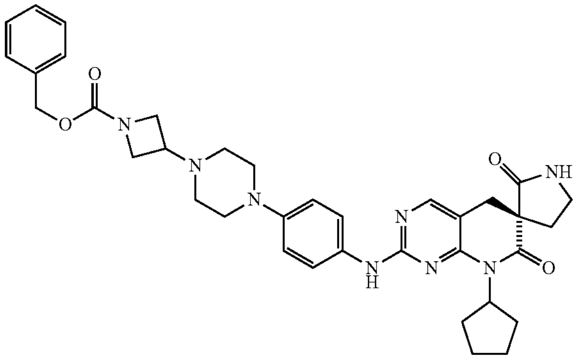
(D107)
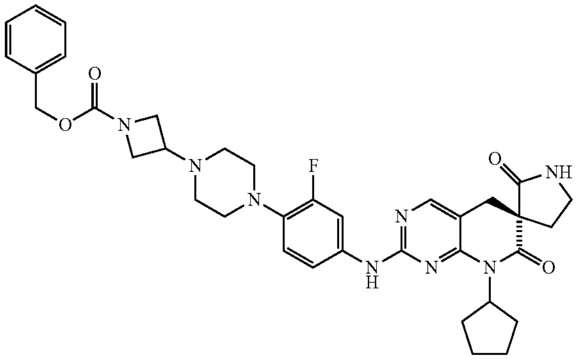
(D108)
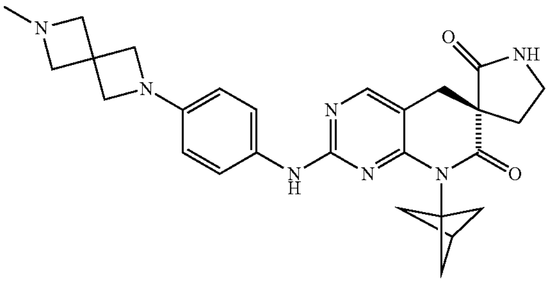
(D109)
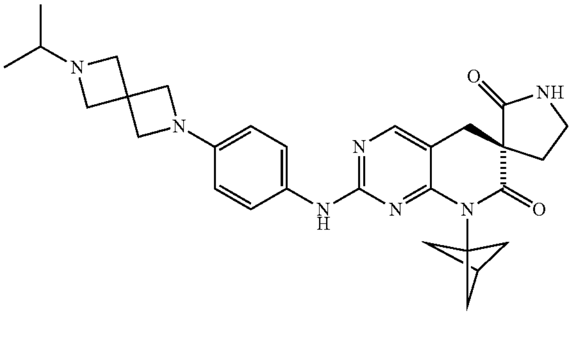

-continued
(D110)
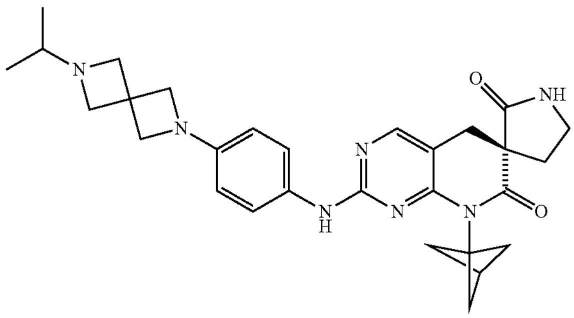
(D111)
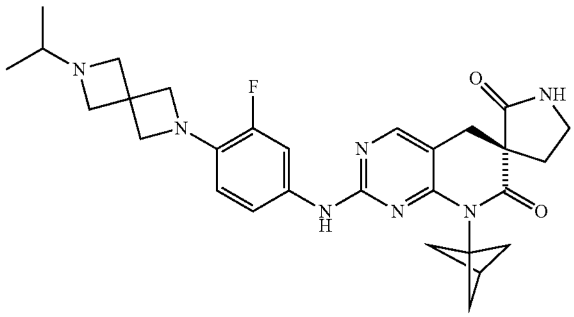
(D112)
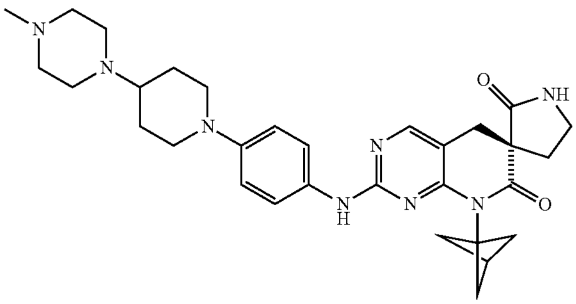
(D113)
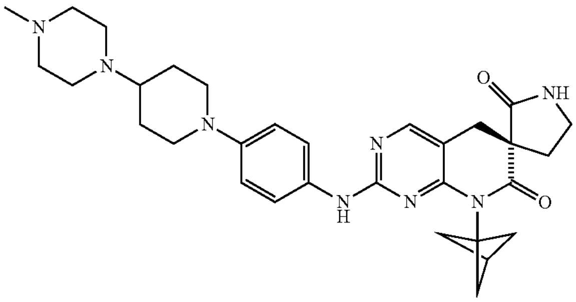
(D114)
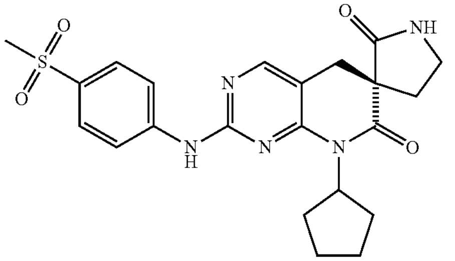
-continued
(D115)
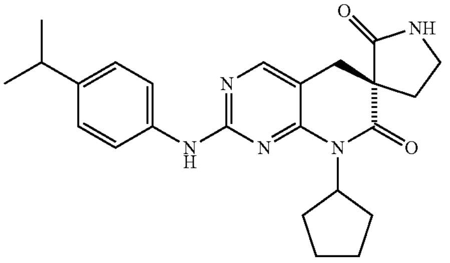
(D116)
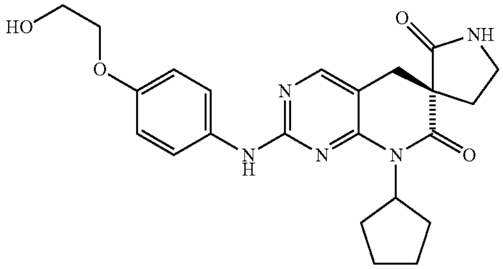
(D117)
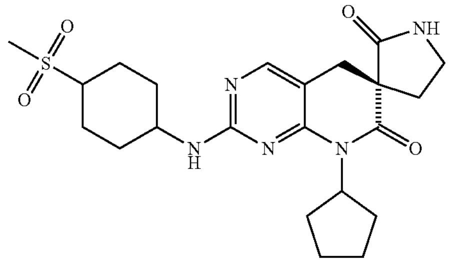
(D118)
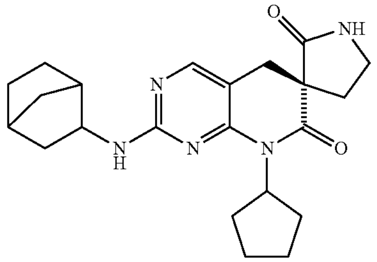
(D119)
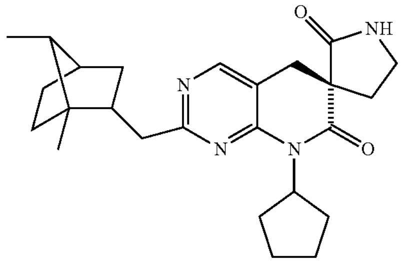
(D120)
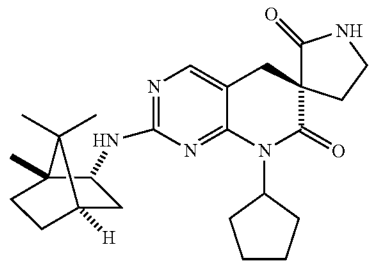

-continued
(D121)
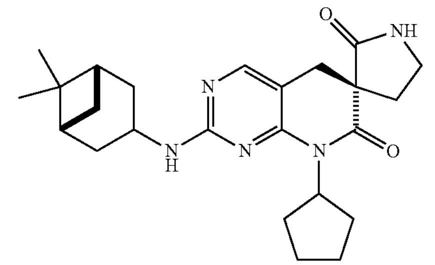
(D122)
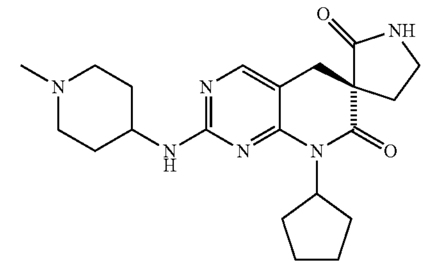
(D123)
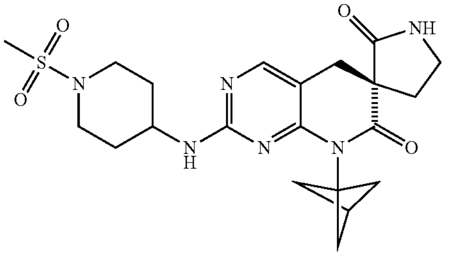
(D124)
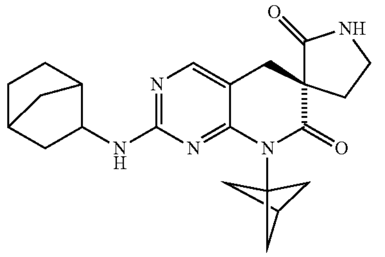
(D125)
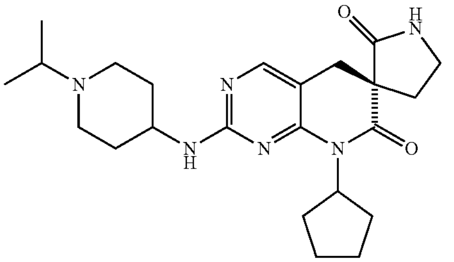
(D126)
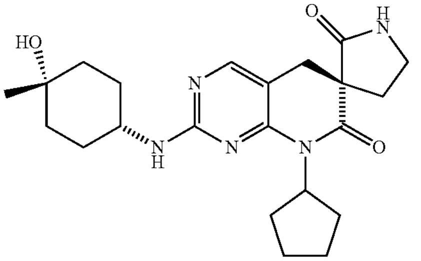
-continued
(D127)
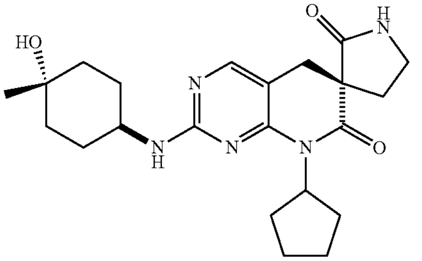
(D128)
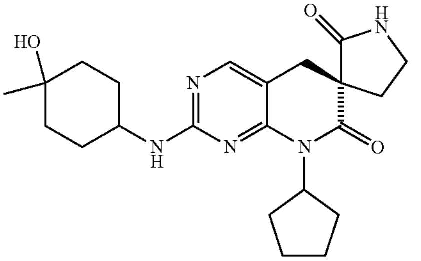
(D129)
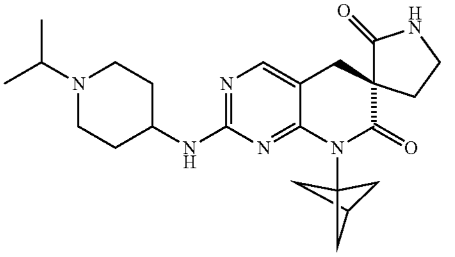
(D130)
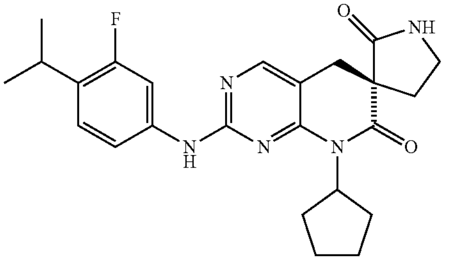
(D131)
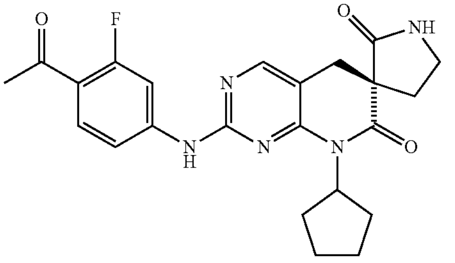
(D132)
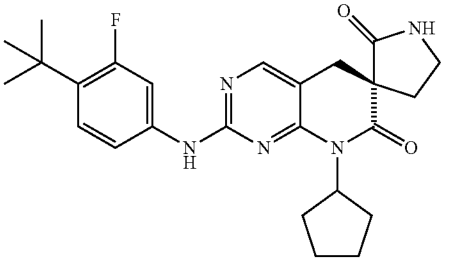

-continued
(D133)
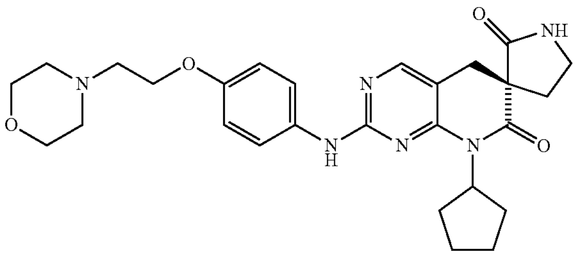
(D134)
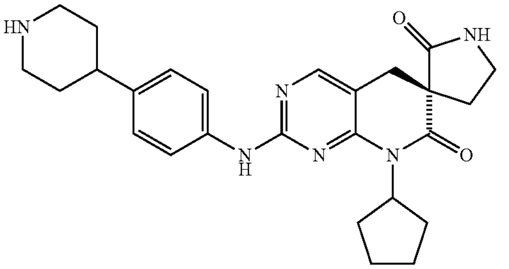
(D135)
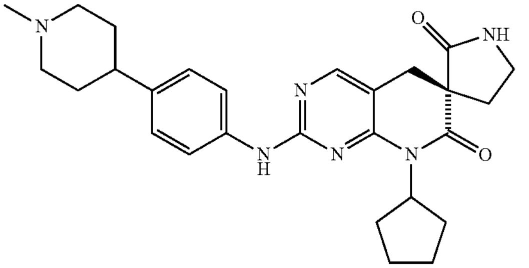
(D136)
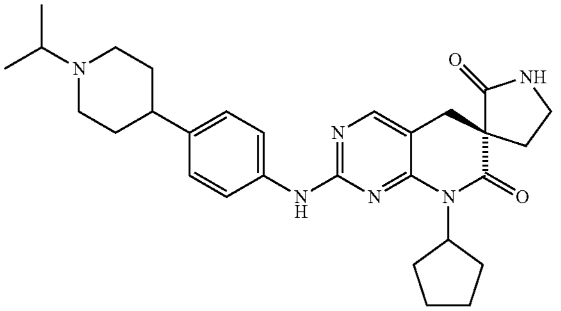
(D137)
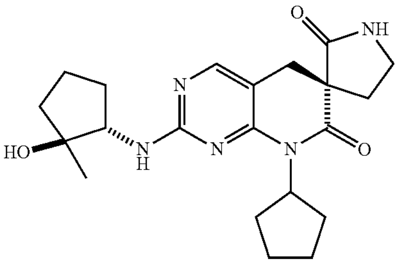
-continued
(D138)
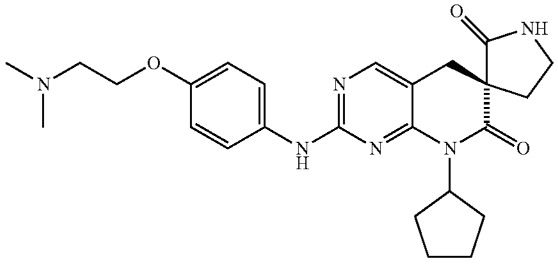
(D139)
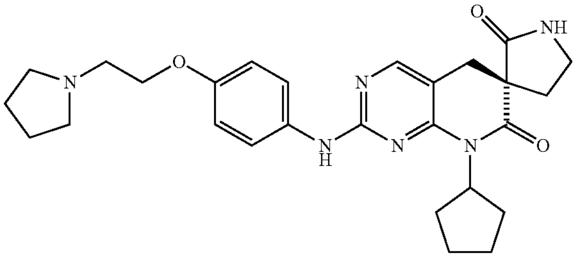
(D140)
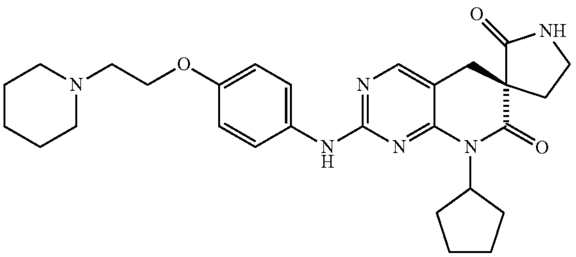
(D141)
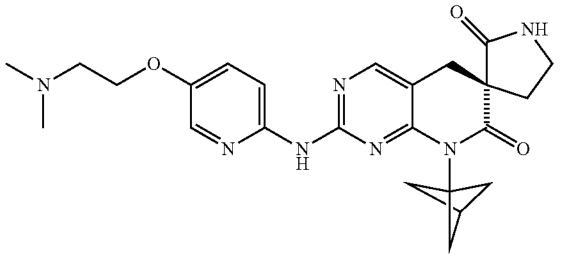
(D142)
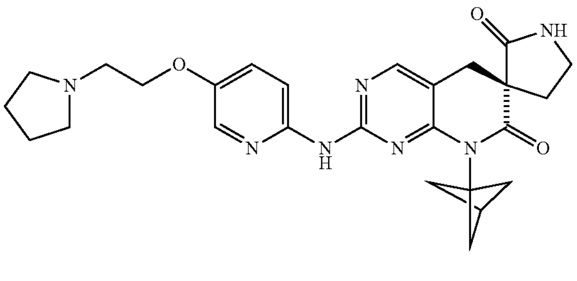

-continued
(D143)
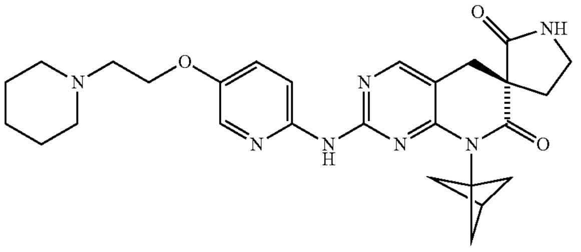
(D144)
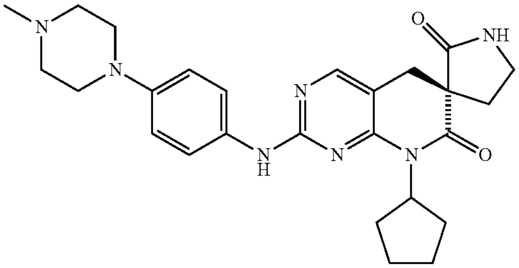
(D145)
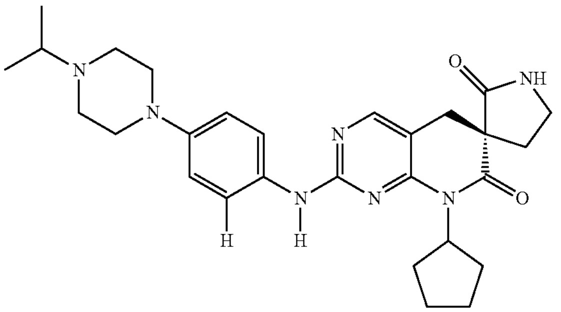
(D146)
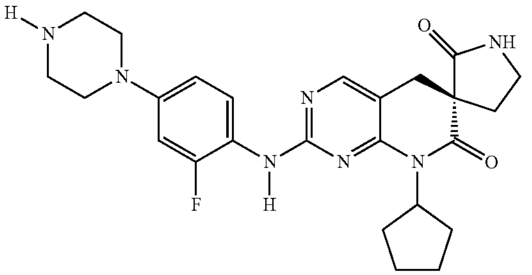
(D147)
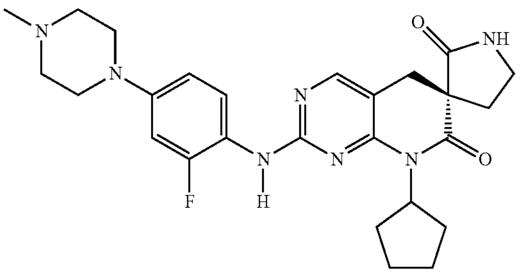
-continued
(D148)
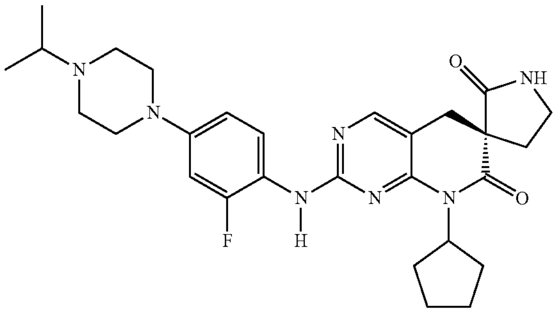
(D149)
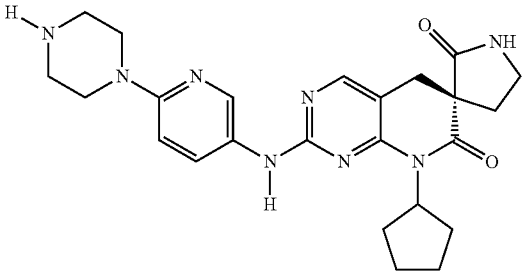
(D150)
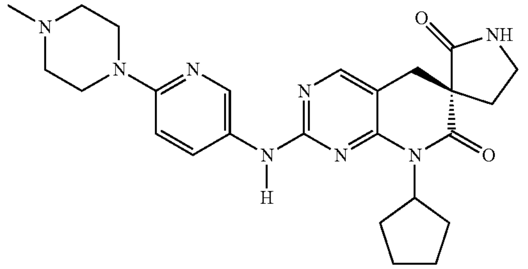
(D151)
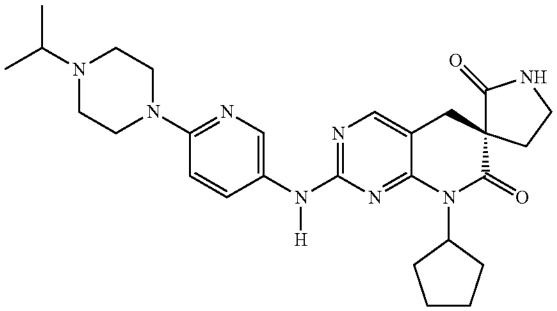
(D152)
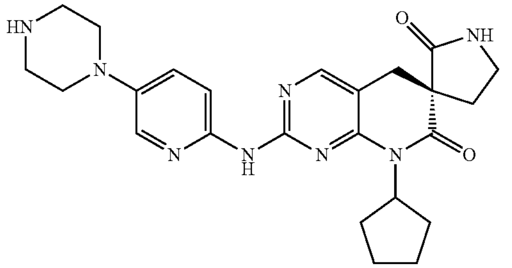

(D153)
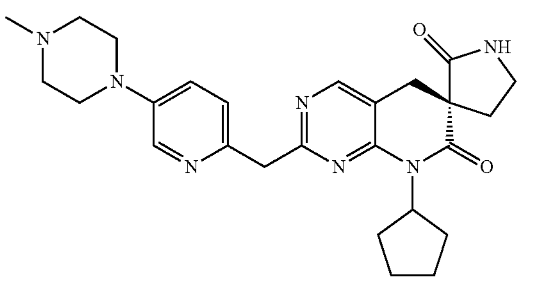
(D154)
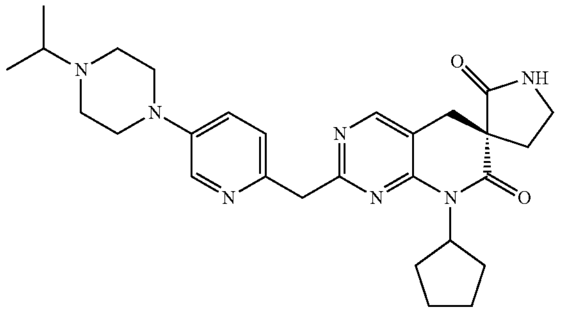
(D155)
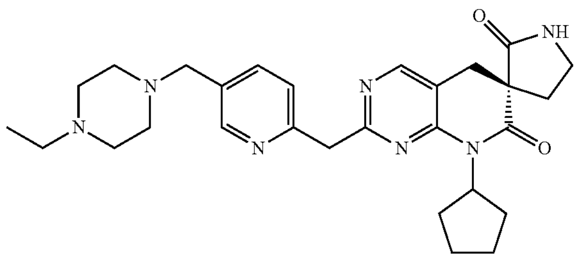
(D156)
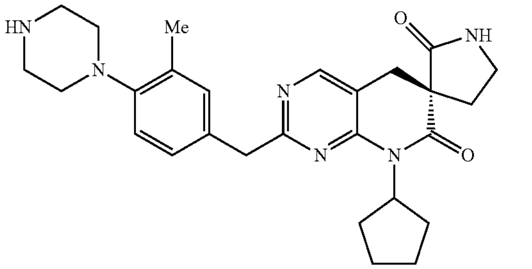
(D157)
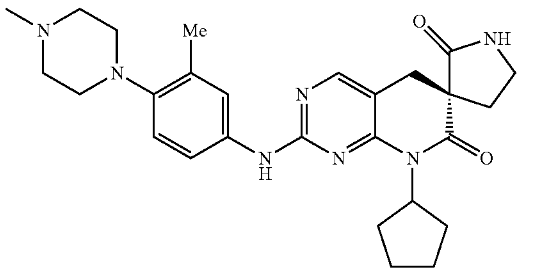
(D158)
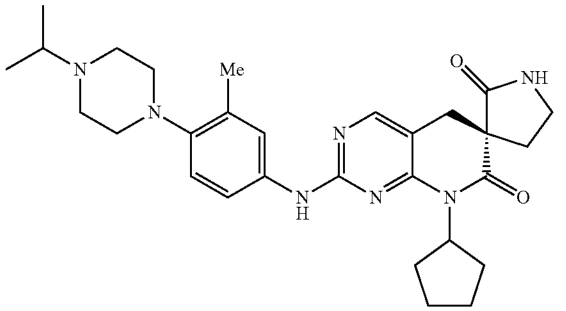
(D159)
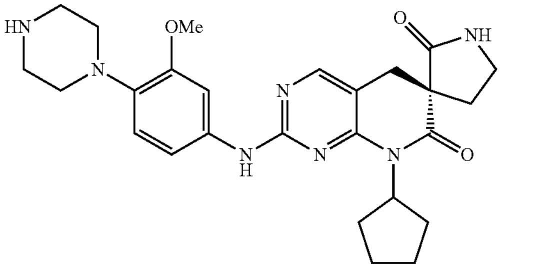
(D160)
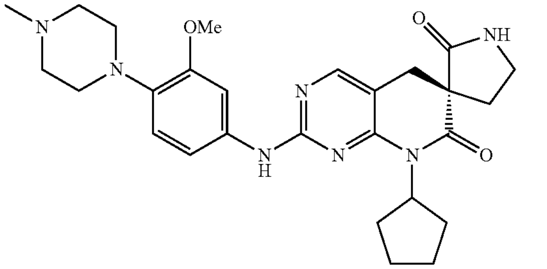
(D161)
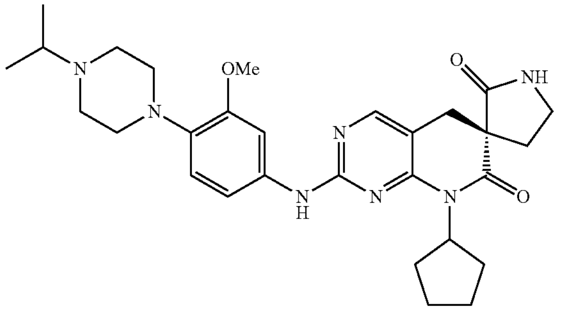
(D162)
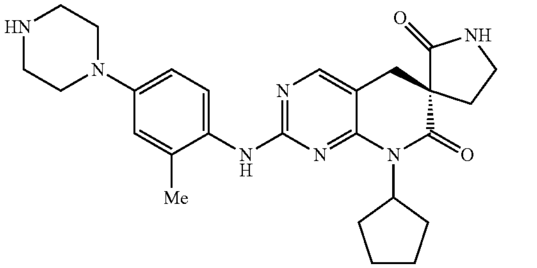

-continued
(D163)
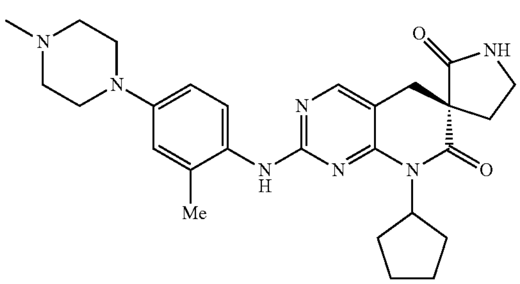
(D164)
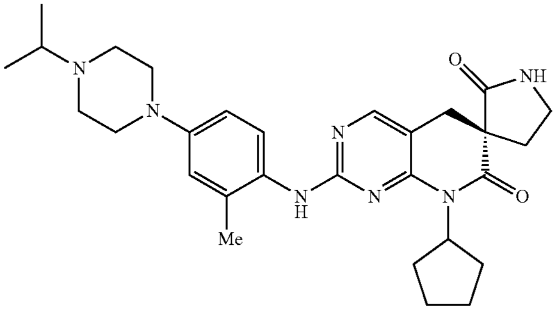
(D165)
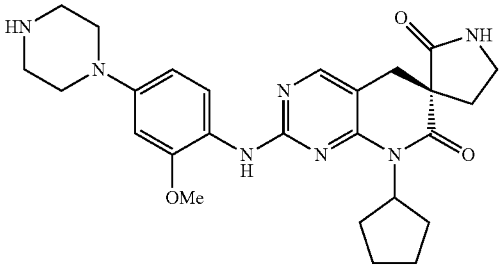
(D166)
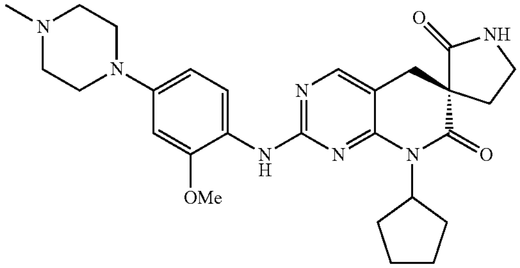
(D167)
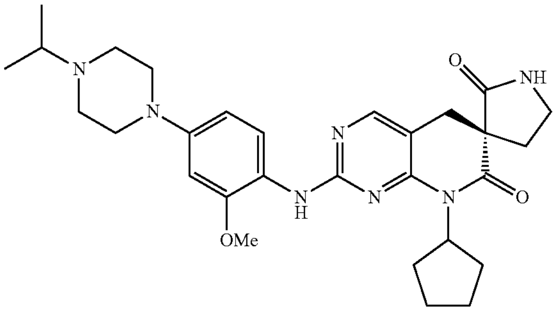
-continued
(D168)
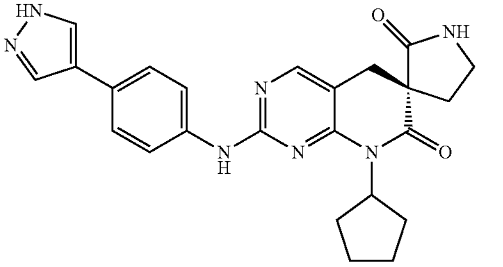
(D169)
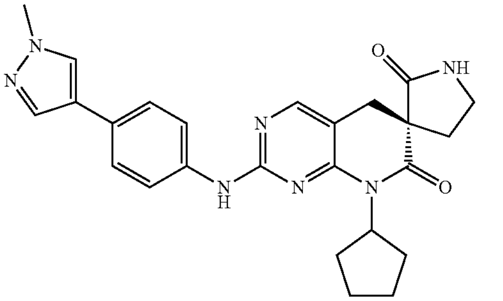
(D170)
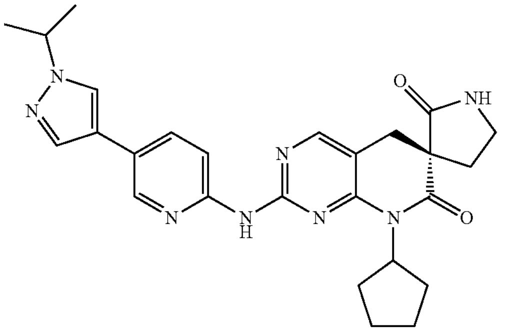
(D171)
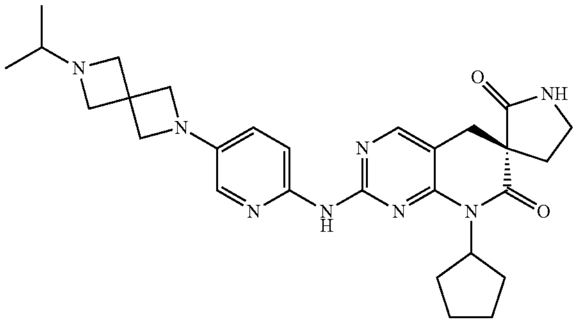
(D172)
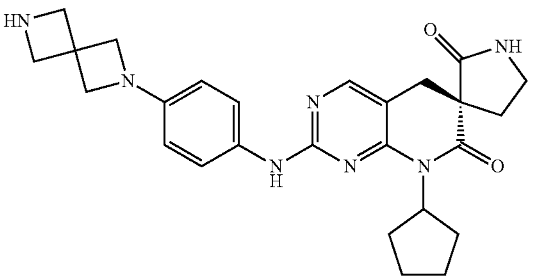

-continued
(D173)
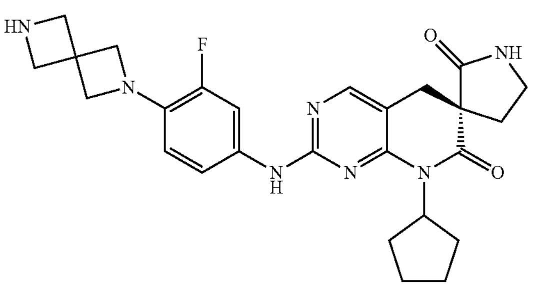
(D174)
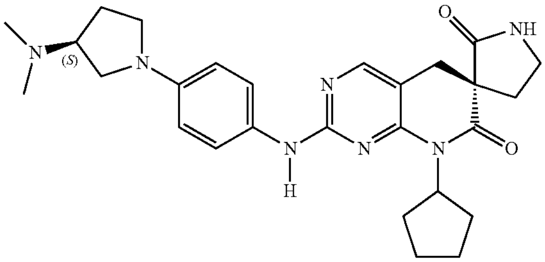
(D175)
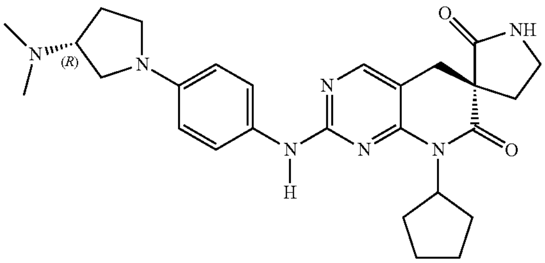
(D176)
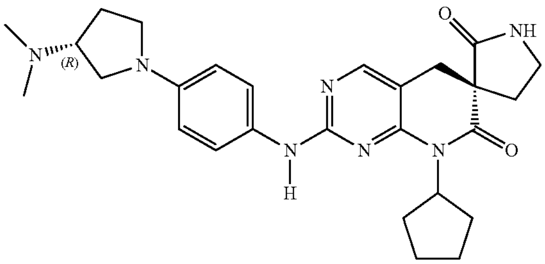
(D177)
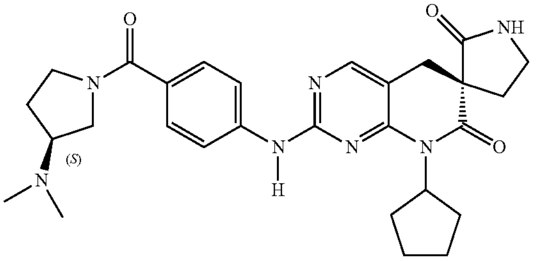
-continued
(D178)
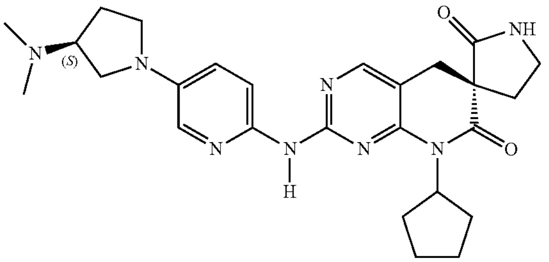
(D179)
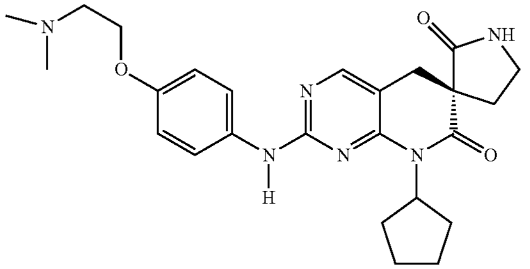
(D180)
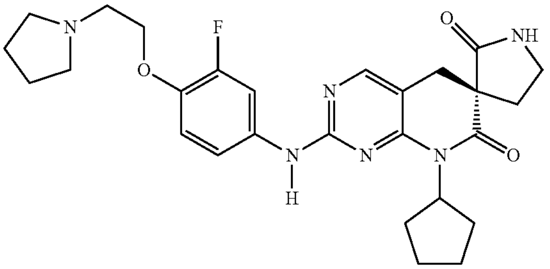
(D181)
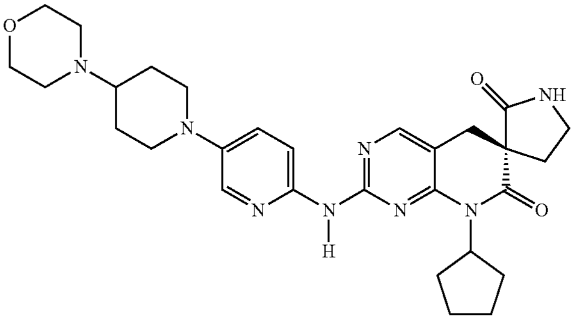
(D182)
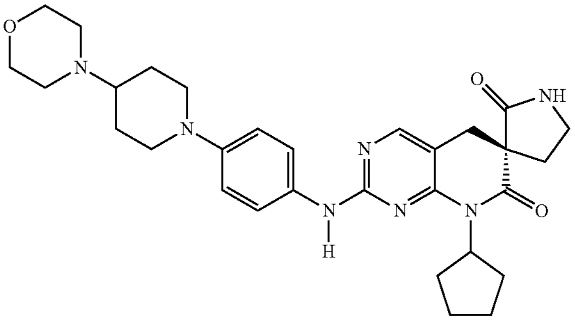

-continued
(D183)
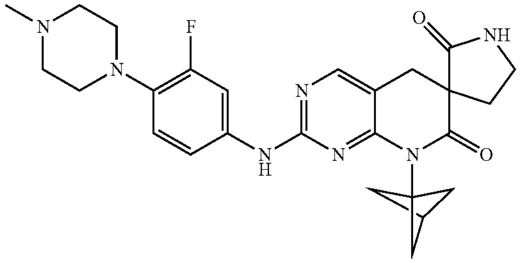
Racemic
(D184)
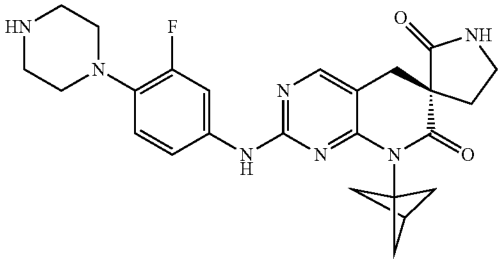
E2
(D185)
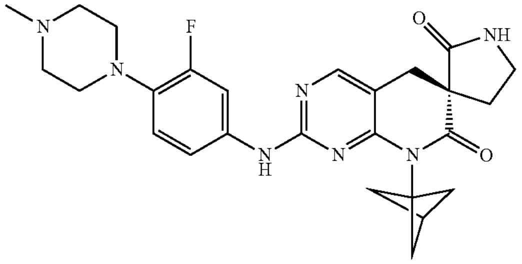
E2
(D186)
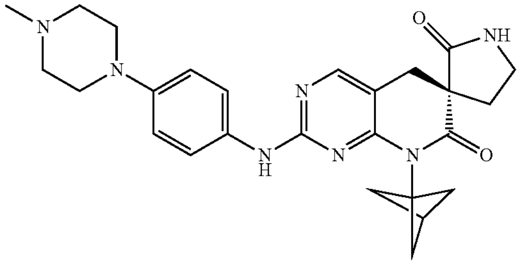
E2
-continued
(D187)
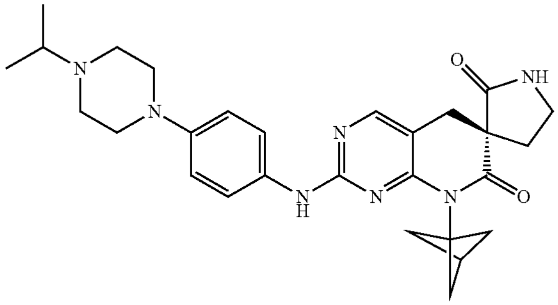
E2
(D188)
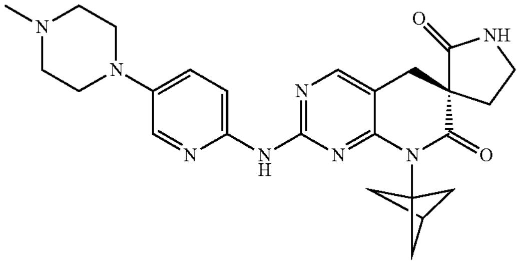
E2
(D189)
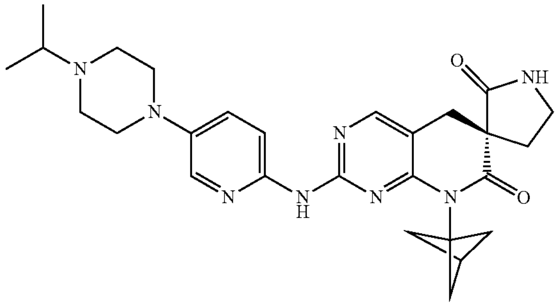
E2
(D190)
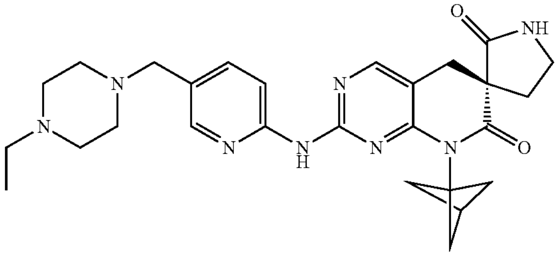
E2

-continued
(D191)
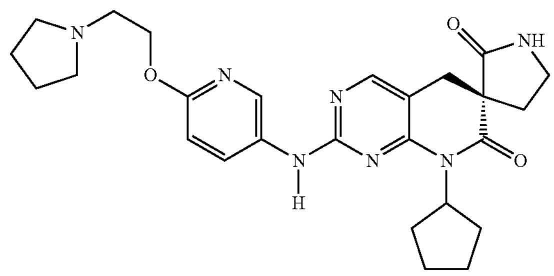
(D192)
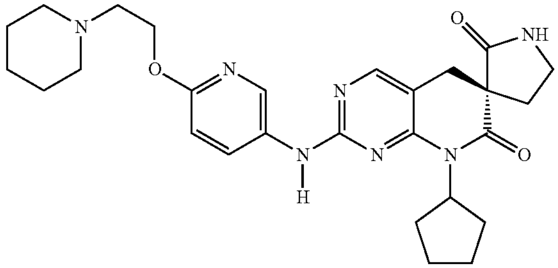
(D193)
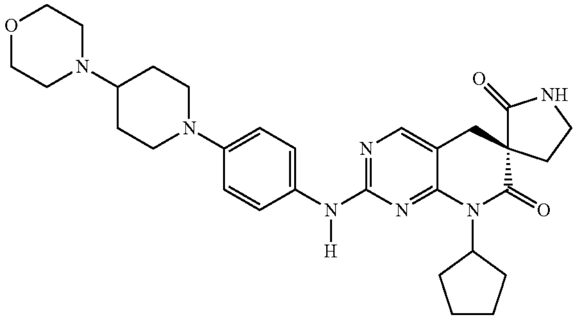
(D194)
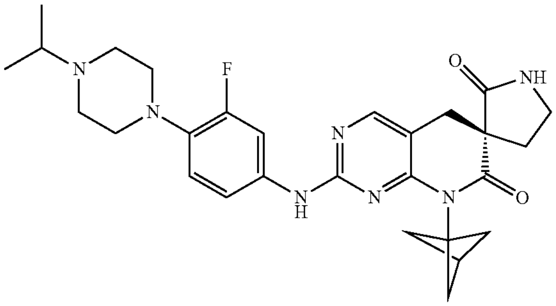
E2
-continued
(D195)
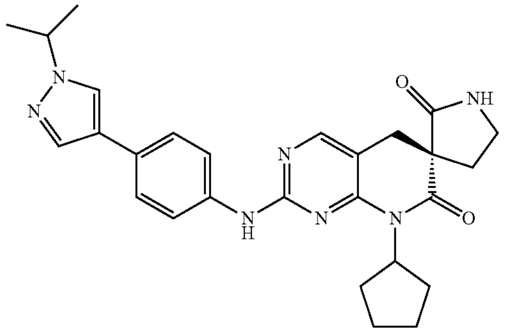
E2
(D196)
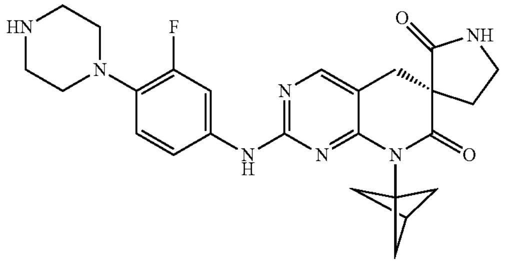
E1
(D197)
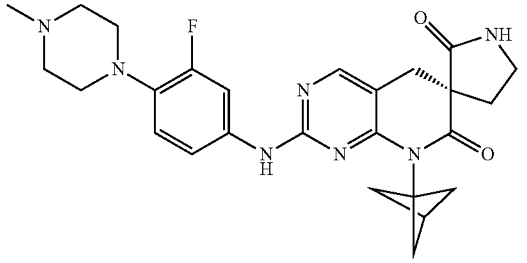
E1
(D198)
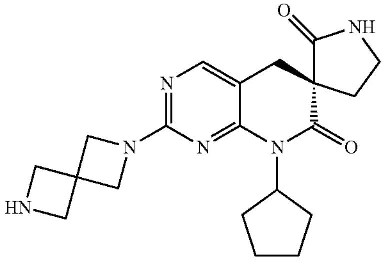

-continued (D199)

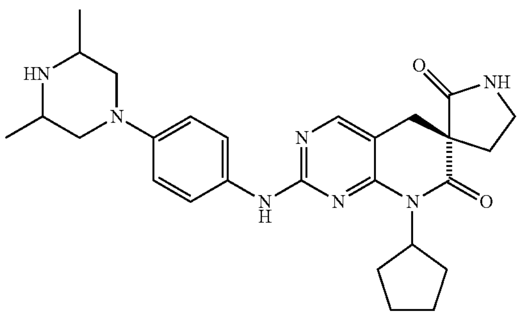

(D200)

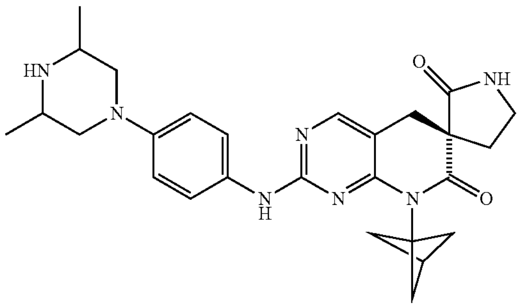

(D201)

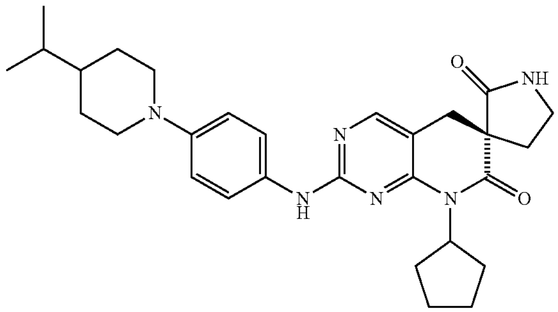

(D202)

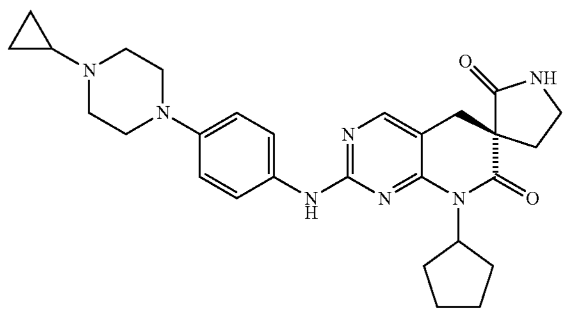

-continued (D203)

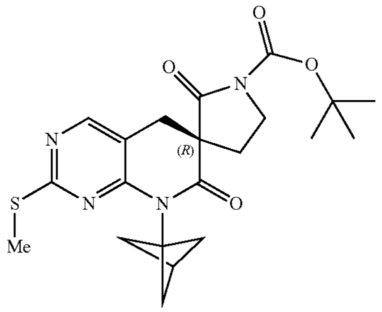

Another embodiment described herein is a pharmaceutical composition comprising one or more of Compounds D49-D203 or a pharmaceutically acceptable salt thereof and one or more pharmaceutically acceptable excipients.

Another embodiment described herein is a method of treating cancer or providing a chemotherapeutic protective effect comprising administering an effective amount of one or more of Compounds D49-D203 to a subject in need thereof.

Another embodiment described herein is a compound selected from:

(R)-8-cyclopentyl-2-((3-fluoro-4-(piperazin-1-yl)phenyl)amino)-5,8-dihydro-7H-spiro[pyrido[2,3-d]pyrimidine-6,3'-pyrrolidine]-2',7-dione (D49);

(S)-8-cyclopentyl-2-((3-fluoro-4-(piperazin-1-yl)phenyl)amino)-5,8-dihydro-7H-spiro[pyrido[2,3-d]pyrimidine-6,3'-pyrrolidine]-2',7-dione (D50);

(R)-8-cyclopentyl-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (D51);

(S)-8-cyclopentyl-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (D52);

(R)-8-cyclopentyl-2-((3-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (D53);

(S)-8-cyclopentyl-2-((3-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (D54);

(R)-8-cyclopentyl-2-((4-(piperazin-1-yl)phenyl)amino)-5,8-dihydro-7H-spiro[pyrido[2,3-d]pyrimidine-6,3'-pyrrolidine]-2',7-dione (D55);

(S)-8-cyclopentyl-2-((4-(piperazin-1-yl)phenyl)amino)-5,8-dihydro-7H-spiro[pyrido[2,3-d]pyrimidine-6,3'-pyrrolidine]-2',7-dione (D56);

(RS)-8-cyclopentyl-2-((5-(piperazin-1-yl)pyridin-2-yl)amino)-5,8-dihydro-7H-spiro[pyrido[2,3-d]pyrimidine-6,3'-pyrrolidine]-2',7-dione (D57);

(S)-8-cyclopentyl-2-((5-(piperazin-1-yl)pyridin-2-yl)amino)-5,8-dihydro-7H-spiro[pyrido[2,3-d]pyrimidine-6,3'-pyrrolidine]-2',7-dione (D58);

(S)-8-cyclopentyl-2-((4-(2-(dimethylamino)ethoxy)-3-fluorophenyl)amino)-5,8-dihydro-7H-spiro[pyrido[2,3-d]pyrimidine-6,3'-pyrrolidine]-2',7-dione (D59);

(S)-8-cyclopentyl-2-((4-(2-(dimethylamino)ethoxy)-3-methylphenyl)amino)-5,8-dihydro-7H-spiro[pyrido[2,3-d]pyrimidine-6,3'-pyrrolidine]-2',7-dione (D60);

(S)-8-cyclopentyl-2-((4-(2-(dimethylamino)ethoxy)-3-methoxyphenyl)amino)-5,8-dihydro-7H-spiro[pyrido[2,3-d]pyrimidine-6,3'-pyrrolidine]-2',7-dione (D61);

(S)-8-cyclopentyl-2-((6-(2-(dimethylamino)ethoxy)pyridin-3-yl)amino)-5,8-dihydro-7H-spiro[pyrido[2,3-d]pyrimidine-6,3'-pyrrolidine]-2',7-dione (D62);

(S)-8-cyclopentyl-2-((3-fluoro-4-morpholinophenyl)amino)-5,8-dihydro-7H-spiro[pyrido[2,3-d]pyrimidine-6,3'-pyrrolidine]-2',7-dione (D63);

(S)-8-(bicyclo[1.1.1]pentan-1-yl)-2-((4-(2-(dimethylamino)ethoxy)phenyl)amino)-5,8-dihydro-7H-spiro[pyrido[2,3-d]pyrimidine-6,3'-pyrrolidine]-2',7-dione (D64);

(S)-8-(bicyclo[1.1.1]pentan-1-yl)-2-((4-(2-(dimethylamino)ethoxy)-3-fluorophenyl)amino)-5,8-dihydro-7H-spiro[pyrido[2,3-d]pyrimidine-6,3'-pyrrolidine]-2',7-dione (D65);

(S)-8-(bicyclo[1.1.1]pentan-1-yl)-2-((4-(2-(dimethylamino)ethoxy)-3-methylphenyl)amino)-5,8-dihydro-7H-spiro[pyrido[2,3-d]pyrimidine-6,3'-pyrrolidine]-2',7-dione (D66);

(S)-8-(bicyclo[1.1.1]pentan-1-yl)-2-((4-(2-(dimethylamino)ethoxy)-3-methoxyphenyl)amino)-5,8-dihydro-7H-spiro[pyrido[2,3-d]pyrimidine-6,3'-pyrrolidine]-2',7-dione (D67);

(S)-8-(bicyclo[1.1.1]pentan-1-yl)-2-((6-(2-(dimethylamino)ethoxy)pyridin-3-yl)amino)-5,8-dihydro-7H-spiro[pyrido[2,3-d]pyrimidine-6,3'-pyrrolidine]-2',7-dione (D68);

(S)-8-(bicyclo[1.1.1]pentan-1-yl)-2-((3-fluoro-4-morpholinophenyl)amino)-5,8-dihydro-7H-spiro[pyrido[2,3-d]pyrimidine-6,3'-pyrrolidine]-2',7-dione (D69);

(S)-1-cyclopentyl-7-((4-(piperazin-1-yl)phenyl)amino)-3-(pyrrolidin-3-yl)-3,4-dihydropyrimido[4,5-d]pyrimidin-2(1H)-one (D70);

(S)-1-cyclopentyl-7-((4-(4-methylpiperazin-1-yl)phenyl)amino)-3-(pyrrolidin-3-yl)-3,4-dihydropyrimido[4,5-d]pyrimidin-2(1H)-one (D71);

(S)-1-cyclopentyl-7-((4-(4-isopropylpiperazin-1-yl)phenyl)amino)-3-(pyrrolidin-3-yl)-3,4-dihydropyrimido[4,5-d]pyrimidin-2(1H)-one (D72);

(R)-1-cyclopentyl-7-((4-(piperazin-1-yl)phenyl)amino)-3-(pyrrolidin-3-yl)-3,4-dihydropyrimido[4,5-d]pyrimidin-2(1H)-one (D73);

(R)-1-cyclopentyl-7-((4-(4-methylpiperazin-1-yl)phenyl)amino)-3-(pyrrolidin-3-yl)-3,4-dihydropyrimido[4,5-d]pyrimidin-2(1H)-one (D74);

(R)-1-cyclopentyl-7-((4-(4-isopropylpiperazin-1-yl)phenyl)amino)-3-(pyrrolidin-3-yl)-3,4-dihydropyrimido[4,5-d]pyrimidin-2(1H)-one (D75);

1-cyclopentyl-3-(2-fluorophenyl)-7-((4-(piperazin-1-yl)phenyl)amino)-3,4-dihydropyrimido[4,5-d]pyrimidin-2(1H)-one (D76);

1-cyclopentyl-3-(2-fluorophenyl)-7-((4-(4-methylpiperazin-1-yl)phenyl)amino)-3,4-dihydropyrimido[4,5-d]pyrimidin-2(1H)-one (D77);

1-cyclopentyl-3-(2-fluorophenyl)-7-((4-(4-isopropylpiperazin-1-yl)phenyl)amino)-3,4-dihydropyrimido[4,5-d]pyrimidin-2(1H)-one (D78);

1-cyclopentyl-7-((3-fluoro-4-(piperazin-1-yl)phenyl)amino)-3-(2-fluorophenyl)-3,4-dihydropyrimido[4,5-d]pyrimidin-2(1H)-one (D79);

1-cyclopentyl-7-((3-fluoro-4-(4-methylpiperazin-1-yl)phenyl)amino)-3-(2-fluorophenyl)-3,4-dihydropyrimido[4,5-d]pyrimidin-2(1H)-one (D80);

1-cyclopentyl-7-((3-fluoro-4-(4-isopropylpiperazin-1-yl)phenyl)amino)-3-(2-fluorophenyl)-3,4-dihydropyrimido[4,5-d]pyrimidin-2(1H)-one (D81);

1-cyclopentyl-3-(2-fluorophenyl)-7-((4-(4-(piperazin-1-yl)piperidin-1-yl)phenyl)amino)-3,4-dihydropyrimido[4,5-d]pyrimidin-2(1H)-one (D82);

1-cyclopentyl-7-((3-fluoro-4-(4-(piperazin-1-yl)piperidin-1-yl)phenyl)amino)-3-(2-fluorophenyl)-3,4-dihydropyrimido[4,5-d]pyrimidin-2(1H)-one (D83);

1-cyclopentyl-3-(2-fluorophenyl)-7-((4-(3-(piperazin-1-yl)azetidin-1-yl)phenyl)amino)-3,4-dihydropyrimido[4,5-d]pyrimidin-2(1H)-one (D84);

1-cyclopentyl-7-((3-fluoro-4-(3-(piperazin-1-yl)azetidin-1-yl)phenyl)amino)-3-(2-fluorophenyl)-3,4-dihydropyrimido[4,5-d]pyrimidin-2(1H)-one (D85);

1-cyclopentyl-7-((3,5-difluoro-4-(piperazin-1-yl)phenyl)amino)-3-(2-fluorophenyl)-3,4-dihydropyrimido[4,5-d]pyrimidin-2(1H)-one (D86);

(S)-8-(bicyclo[1.1.1]pentan-1-yl)-2-((4-(4-(4-methylpiperazin-1-yl)piperidin-1-yl)phenyl)amino)-5,8-dihydro-7H-spiro[pyrido[2,3-d]pyrimidine-6,3'-pyrrolidine]-2',7-dione (D87);

(S)-8-(bicyclo[1.1.1]pentan-1-yl)-2-((3-fluoro-4-(4-(4-methylpiperazin-1-yl)piperidin-1-yl)phenyl)amino)-5,8-dihydro-7H-spiro[pyrido[2,3-d]pyrimidine-6,3'-pyrrolidine]-2',7-dione (D88);

(S)-8-(bicyclo[1.1.1]pentan-1-yl)-2-((6-(2-(dimethylamino)ethoxy)pyridin-3-yl)amino)-5,8-dihydro-7H-spiro[pyrido[2,3-d]pyrimidine-6,3'-pyrrolidine]-2',7-dione (D89);

(S)-8-(bicyclo[1.1.1]pentan-1-yl)-2-((4-(3-(piperazin-1-yl)azetidin-1-yl)phenyl)amino)-5,8-dihydro-7H-spiro[pyrido[2,3-d]pyrimidine-6,3'-pyrrolidine]-2',7-dione (D90);

(S)-8-(bicyclo[1.1.1]pentan-1-yl)-2-((3-fluoro-4-(3-(piperazin-1-yl)azetidin-1-yl)phenyl)amino)-5,8-dihydro-7H-spiro[pyrido[2,3-d]pyrimidine-6,3'-pyrrolidine]-2',7-dione (D91);

(S)-8-cyclopentyl-2-(((1r,4S)-4-((tetrahydro-2H-pyran-4-yl)amino)cyclohexyl)amino)-5,8-dihydro-7H-spiro[pyrido[2,3-d]pyrimidine-6,3'-pyrrolidine]-2',7-dione (D92);

(S)-8-(bicyclo[1.1.1]pentan-1-yl)-2-(((1r,4S)-4-((tetrahydro-2H-pyran-4-yl)amino)cyclohexyl)amino)-5,8-dihydro-7H-spiro[pyrido[2,3-d]pyrimidine-6,3'-pyrrolidine]-2',7-dione (D93);

1-cyclopentyl-7-((3,5-difluoro-4-(4-methylpiperazin-1-yl)phenyl)amino)-3-(2-fluorophenyl)-3,4-dihydropyrimido[4,5-d]pyrimidin-2(1H)-one (D94);

(S)-8-(bicyclo[1.1.1]pentan-1-yl)-2-((3,5-difluoro-4-(4-methylpiperazin-1-yl)phenyl)amino)-5,8-dihydro-7H-spiro[pyrido[2,3-d]pyrimidine-6,3'-pyrrolidine]-2',7-dione (D95);

(S)-8-cyclopentyl-2-((4-(4-(2-hydroxyethyl)piperazin-1-yl)phenyl)amino)-5,8-dihydro-7H-spiro[pyrido[2,3-d]pyrimidine-6,3'-pyrrolidine]-2',7-dione (D96);

(S)-8-cyclopentyl-2-((3-fluoro-4-(4-(2-hydroxyethyl)piperazin-1-yl)phenyl)amino)-5,8-dihydro-7H-spiro[pyrido[2,3-d]pyrimidine-6,3'-pyrrolidine]-2',7-dione (D97);

(S)-8-(bicyclo[1.1.1]pentan-1-yl)-2-((4-(4-(2-hydroxyethyl)piperazin-1-yl)phenyl)amino)-5,8-dihydro-7H-spiro[pyrido[2,3-d]pyrimidine-6,3'-pyrrolidine]-2',7-dione (D98);

(S)-8-(bicyclo[1.1.1]pentan-1-yl)-2-((3-fluoro-4-(4-(2-hydroxyethyl)piperazin-1-yl)phenyl)amino)-5,8-dihydro-7H-spiro[pyrido[2,3-d]pyrimidine-6,3'-pyrrolidine]-2',7-dione (D99);

(S)-8-cyclopentyl-2-((4-(6-methyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (D100);

(S)-8-cyclopentyl-2-((3-fluoro-4-(6-methyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (D101);

(S)-8-cyclopentyl-2-((4-(6-isopropyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (D102);

(S)-8-cyclopentyl-2-((3-fluoro-4-(6-isopropyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (D103);

(S)-8-cyclopentyl-2-((4-(4-(4-methylpiperazin-1-yl)piperidin-1-yl)phenyl)amino)-5,8-dihydro-7H-spiro[pyrido[2,3-d]pyrimidine-6,3'-pyrrolidine]-2',7-dione (D104);

(S)-8-cyclopentyl-2-((3-fluoro-4-(4-(4-methylpiperazin-1-yl)piperidin-1-yl)phenyl)amino)-5,8-dihydro-7H-spiro[pyrido[2,3-d]pyrimidine-6,3'-pyrrolidine]-2',7-dione (D105);

benzyl(S)-3-(4-(4-((8-cyclopentyl-2',7-dioxo-7,8-dihydro-5H-spiro[pyrido[2,3-d]pyrimidine-6,3'-pyrrolidin]-2-yl)amino)phenyl)piperazin-1-yl)azetidine-1-carboxylate (D106);

benzyl(S)-3-(4-(4-((8-cyclopentyl-2',7-dioxo-7,8-dihydro-5H-spiro[pyrido[2,3-d]pyrimidine-6,3'-pyrrolidin]-2-yl)amino)-2-fluorophenyl)piperazin-1-yl)azetidine-1-carboxylate (D107);

(S)-8-(bicyclo[1.1.1]pentan-1-yl)-2-((4-(6-methyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (D108);

(S)-8-(bicyclo[1.1.1]pentan-1-yl)-2-((3-fluoro-4-(6-methyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (D109);

(S)-8-(bicyclo[1.1.1]pentan-1-yl)-2-((4-(6-isopropyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (D110);

(S)-8-(bicyclo[1.1.1]pentan-1-yl)-2-((3-fluoro-4-(6-isopropyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (D111);

(S)-8-(bicyclo[1.1.1]pentan-1-yl)-2-((4-(4-(4-methylpiperazin-1-yl)piperidin-1-yl)phenyl)amino)-5,8-dihydro-7H-spiro[pyrido[2,3-d]pyrimidine-6,3'-pyrrolidine]-2',7-dione (D112);

(S)-8-(bicyclo[1.1.1]pentan-1-yl)-2-((3-fluoro-4-(4-(4-methylpiperazin-1-yl)piperidin-1-yl)phenyl)amino)-5,8-dihydro-7H-spiro[pyrido[2,3-d]pyrimidine-6,3'-pyrrolidine]-2',7-dione (D113);

(S)-8-cyclopentyl-2-((4-(methylsulfonyl)phenyl)amino)-5,8-dihydro-7H-spiro[pyrido[2,3-d]pyrimidine-6,3'-pyrrolidine]-2',7-dione (D114);

(S)-8-cyclopentyl-2-((4-isopropylphenyl)amino)-5,8-dihydro-7H-spiro[pyrido[2,3-d]pyrimidine-6,3'-pyrrolidine]-2',7-dione (D115);

(S)-8-cyclopentyl-2-((4-(2-hydroxyethoxy)phenyl)amino)-5,8-dihydro-7H-spiro[pyrido[2,3-d]pyrimidine-6,3'-pyrrolidine]-2',7-dione (D116);

(S)-8-cyclopentyl-2-((1-(methylsulfonyl)piperidin-4-yl)amino)-5,8-dihydro-7H-spiro[pyrido[2,3-d]pyrimidine-6,3'-pyrrolidine]-2',7-dione (D117);

(6S)-2-(bicyclo[2.2.1]heptan-2-ylamino)-8-cyclopentyl-5,8-dihydro-7H-spiro[pyrido[2,3-d]pyrimidine-6,3'-pyrrolidine]-2',7-dione (D118);

(S)-8-cyclopentyl-2-(((1S,2S,4R)-1,7,7-trimethylbicyclo[2.2.1]heptan-2-yl)amino)-5,8-dihydro-7H-spiro[pyrido[2,3-d]pyrimidine-6,3'-pyrrolidine]-2',7-dione (D119);

(S)-8-cyclopentyl-2-(((1R,2S,4R)-1,7,7-trimethylbicyclo[2.2.1]heptan-2-yl)amino)-5,8-dihydro-7H-spiro[pyrido[2,3-d]pyrimidine-6,3'-pyrrolidine]-2',7-dione (D120);

(S)-8-cyclopentyl-2-(((1S,2S,3S,5R)-2,6,6-trimethylbicyclo[3.1.1]heptan-3-yl)amino)-5,8-dihydro-7H-spiro[pyrido[2,3-d]pyrimidine-6,3'-pyrrolidine]-2',7-dione (D121);

(S)-8-cyclopentyl-2-((1-methylpiperidin-4-yl)amino)-5,8-dihydro-7H-spiro[pyrido[2,3-d]pyrimidine-6,3'-pyrrolidine]-2',7-dione (D122);

(S)-8-(bicyclo[1.1.1]pentan-1-yl)-2-((1-(methylsulfonyl)piperidin-4-yl)amino)-5,8-dihydro-7H-spiro[pyrido[2,3-d]pyrimidine-6,3'-pyrrolidine]-2',7-dione (D123);

(6S)-8-(bicyclo[1.1.1]pentan-1-yl)-2-(bicyclo[2.2.1]heptan-2-ylamino)-5,8-dihydro-7H-spiro[pyrido[2,3-d]pyrimidine-6,3'-pyrrolidine]-2',7-dione (D124);

(S)-8-cyclopentyl-2-((1-isopropylpiperidin-4-yl)amino)-5,8-dihydro-7H-spiro[pyrido[2,3-d]pyrimidine-6,3'-pyrrolidine]-2',7-dione (D125);

(S)-8-cyclopentyl-2-(((1s,4R)-4-hydroxy-4-methylcyclohexyl)amino)-5,8-dihydro-7H-spiro[pyrido[2,3-d]pyrimidine-6,3'-pyrrolidine]-2',7-dione (D126);

(S)-8-cyclopentyl-2-(((1r,4S)-4-hydroxy-4-methylcyclohexyl)amino)-5,8-dihydro-7H-spiro[pyrido[2,3-d]pyrimidine-6,3'-pyrrolidine]-2',7-dione (D127);

(S)-8-cyclopentyl-2-((4-hydroxy-4-methylcyclohexyl)amino)-5,8-dihydro-7H-spiro[pyrido[2,3-d]pyrimidine-6,3'-pyrrolidine]-2',7-dione (D128);

(S)-8-(bicyclo[1.1.1]pentan-1-yl)-2-((1-isopropylpiperidin-4-yl)amino)-5,8-dihydro-7H-spiro[pyrido[2,3-d]pyrimidine-6,3'-pyrrolidine]-2',7-dione (D129);

(S)-8-cyclopentyl-2-((3-fluoro-4-isopropylphenyl)amino)-5,8-dihydro-7H-spiro[pyrido[2,3-d]pyrimidine-6,3'-pyrrolidine]-2',7-dione (D130);

(S)-2-((4-acetyl-3-fluorophenyl)amino)-8-cyclopentyl-5,8-dihydro-7H-spiro[pyrido[2,3-d]pyrimidine-6,3'-pyrrolidine]-2',7-dione (D131);

(S)-2-((4-(tert-butyl)-3-fluorophenyl)amino)-8-cyclopentyl-5,8-dihydro-7H-spiro[pyrido[2,3-d]pyrimidine-6,3'-pyrrolidine]-2',7-dione (D132);

(S)-8-cyclopentyl-2-((4-(2-morpholinoethoxy)phenyl)amino)-5,8-dihydro-7H-spiro[pyrido[2,3-d]pyrimidine-6,3'-pyrrolidine]-2',7-dione (D133);

(S)-8-cyclopentyl-2-((4-(piperidin-4-yl)phenyl)amino)-5,8-dihydro-7H-spiro[pyrido[2,3-d]pyrimidine-6,3'-pyrrolidine]-2',7-dione (D134);

(S)-8-cyclopentyl-2-((4-(1-methylpiperidin-4-yl)phenyl)amino)-5,8-dihydro-7H-spiro[pyrido[2,3-d]pyrimidine-6,3'-pyrrolidine]-2',7-dione (D135);

(S)-8-cyclopentyl-2-((4-(1-isopropylpiperidin-4-yl)phenyl)amino)-5,8-dihydro-7H-spiro[pyrido[2,3-d]pyrimidine-6,3'-pyrrolidine]-2',7-dione (D136);

(S)-8-cyclopentyl-2-(((1S,2S)-2-hydroxy-2-methylcyclopentyl)amino)-5,8-dihydro-7H-spiro[pyrido[2,3-d]pyrimidine-6,3'-pyrrolidine]-2',7-dione (D137);

(S)-8-cyclopentyl-2-((5-(2-(dimethylamino)ethoxy)pyridin-2-yl)amino)-5,8-dihydro-7H-spiro[pyrido[2,3-d]pyrimidine-6,3'-pyrrolidine]-2',7-dione (D138);

(S)-8-cyclopentyl-2-((5-(2-(pyrrolidin-1-yl)ethoxy)pyridin-2-yl)amino)-5,8-dihydro-7H-spiro[pyrido[2,3-d]pyrimidine-6,3'-pyrrolidine]-2',7-dione (D139);

(S)-8-cyclopentyl-2-((5-(2-(piperidin-1-yl)ethoxy)pyridin-2-yl)amino)-5,8-dihydro-7H-spiro[pyrido[2,3-d]pyrimidine-6,3'-pyrrolidine]-2',7-dione (D140);

(S)-8-(bicyclo[1.1.1]pentan-1-yl)-2-((5-(2-(dimethylamino)ethoxy)pyridin-2-yl)amino)-5,8-dihydro-7H-spiro[pyrido[2,3-d]pyrimidine-6,3'-pyrrolidine]-2',7-dione (D141);

(S)-8-(bicyclo[1.1.1]pentan-1-yl)-2-((5-(2-(pyrrolidin-1-yl)ethoxy)pyridin-2-yl)amino)-5,8-dihydro-7H-spiro[pyrido[2,3-d]pyrimidine-6,3'-pyrrolidine]-2',7-dione (D142);

(S)-8-(bicyclo[1.1.1]pentan-1-yl)-2-((5-(2-(piperidin-1-yl)ethoxy)pyridin-2-yl)amino)-5,8-dihydro-7H-spiro[pyrido[2,3-d]pyrimidine-6,3'-pyrrolidine]-2',7-dione (D143);
(S)-8-cyclopentyl-2-((4-(4-methylpiperazin-1-yl)phenyl)amino)-5,8-dihydro-7H-spiro[pyrido[2,3-d]pyrimidine-6,3'-pyrrolidine]-2',7-dione (D144);
(S)-8-cyclopentyl-2-((4-(4-isopropylpiperazin-1-yl)phenyl)amino)-5,8-dihydro-7H-spiro[pyrido[2,3-d]pyrimidine-6,3'-pyrrolidine]-2',7-dione (D145);
(S)-8-cyclopentyl-2-((2-fluoro-4-(piperazin-1-yl)phenyl)amino)-5,8-dihydro-7H-spiro[pyrido[2,3-d]pyrimidine-6,3'-pyrrolidine]-2',7-dione (D146);
(S)-8-cyclopentyl-2-((2-fluoro-4-(4-methylpiperazin-1-yl)phenyl)amino)-5,8-dihydro-7H-spiro[pyrido[2,3-d]pyrimidine-6,3'-pyrrolidine]-2',7-dione (D147);
(S)-8-cyclopentyl-2-((2-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (D148);
(S)-8-cyclopentyl-2-((6-(piperazin-1-yl)pyridin-3-yl)amino)-5,8-dihydro-7H-spiro[pyrido[2,3-d]pyrimidine-6,3'-pyrrolidine]-2',7-dione (D149);
(S)-8-cyclopentyl-2-((6-(4-methylpiperazin-1-yl)pyridin-3-yl)amino)-5,8-dihydro-7H-spiro[pyrido[2,3-d]pyrimidine-6,3'-pyrrolidine]-2',7-dione (D150);
(S)-8-cyclopentyl-2-((6-(4-isopropylpiperazin-1-yl)pyridin-3-yl)amino)-5,8-dihydro-7H-spiro[pyrido[2,3-d]pyrimidine-6,3'-pyrrolidine]-2',7-dione (D151);
(S)-8-cyclopentyl-2-((5-(piperazin-1-yl)pyridin-2-yl)amino)-5,8-dihydro-7H-spiro[pyrido[2,3-d]pyrimidine-6,3'-pyrrolidine]-2',7-dione (D152);
(S)-8-cyclopentyl-2-((5-(4-methylpiperazin-1-yl)pyridin-2-yl)amino)-5,8-dihydro-7H-spiro[pyrido[2,3-d]pyrimidine-6,3'-pyrrolidine]-2',7-dione (D153);
(S)-8-cyclopentyl-2-((5-(4-isopropylpiperazin-1-yl)pyridin-2-yl)amino)-5,8-dihydro-7H-spiro[pyrido[2,3-d]pyrimidine-6,3'-pyrrolidine]-2',7-dione (D154);
(S)-8-cyclopentyl-2-((5-((4-ethylpiperazin-1-yl)methyl)pyridin-2-yl)amino)-5,8-dihydro-7H-spiro[pyrido[2,3-d]pyrimidine-6,3'-pyrrolidine]-2',7-dione (D155);
(S)-8-cyclopentyl-2-((3-methyl-4-(piperazin-1-yl)phenyl)amino)-5,8-dihydro-7H-spiro[pyrido[2,3-d]pyrimidine-6,3'-pyrrolidine]-2',7-dione (D156);
(S)-8-cyclopentyl-2-((3-methyl-4-(4-methylpiperazin-1-yl)phenyl)amino)-5,8-dihydro-7H-spiro[pyrido[2,3-d]pyrimidine-6,3'-pyrrolidine]-2',7-dione (D157);
(S)-8-cyclopentyl-2-((4-(4-isopropylpiperazin-1-yl)-3-methylphenyl)amino)-5,8-dihydro-7H-spiro[pyrido[2,3-d]pyrimidine-6,3'-pyrrolidine]-2',7-dione (D158);
(S)-8-cyclopentyl-2-((3-methoxy-4-(piperazin-1-yl)phenyl)amino)-5,8-dihydro-7H-spiro[pyrido[2,3-d]pyrimidine-6,3'-pyrrolidine]-2',7-dione (D159);
(S)-8-cyclopentyl-2-((3-methoxy-4-(4-methylpiperazin-1-yl)phenyl)amino)-5,8-dihydro-7H-spiro[pyrido[2,3-d]pyrimidine-6,3'-pyrrolidine]-2',7-dione (D160);
(S)-8-cyclopentyl-2-((4-(4-isopropylpiperazin-1-yl)-3-methoxyphenyl)amino)-5,8-dihydro-7H-spiro[pyrido[2,3-d]pyrimidine-6,3'-pyrrolidine]-2',7-dione (D161);
(S)-8-cyclopentyl-2-((2-methyl-4-(piperazin-1-yl)phenyl)amino)-5,8-dihydro-7H-spiro[pyrido[2,3-d]pyrimidine-6,3'-pyrrolidine]-2',7-dione (D162);
(S)-8-cyclopentyl-2-((2-methyl-4-(4-methylpiperazin-1-yl)phenyl)amino)-5,8-dihydro-7H-spiro[pyrido[2,3-d]pyrimidine-6,3'-pyrrolidine]-2',7-dione (D163);
(S)-8-cyclopentyl-2-((4-(4-isopropylpiperazin-1-yl)-2-methylphenyl)amino)-5,8-dihydro-7H-spiro[pyrido[2,3-d]pyrimidine-6,3'-pyrrolidine]-2',7-dione (D164);
(S)-8-cyclopentyl-2-((2-methoxy-4-(piperazin-1-yl)phenyl)amino)-5,8-dihydro-7H-spiro[pyrido[2,3-d]pyrimidine-6,3'-pyrrolidine]-2',7-dione (D165);
(S)-8-cyclopentyl-2-((2-methoxy-4-(4-methylpiperazin-1-yl)phenyl)amino)-5,8-dihydro-7H-spiro[pyrido[2,3-d]pyrimidine-6,3'-pyrrolidine]-2',7-dione (D166);
(S)-8-cyclopentyl-2-((4-(4-isopropylpiperazin-1-yl)-2-methoxyphenyl)amino)-5,8-dihydro-7H-spiro[pyrido[2,3-d]pyrimidine-6,3'-pyrrolidine]-2',7-dione (D167);
(S)-2-((4-(1H-pyrazol-4-yl)phenyl)amino)-8-cyclopentyl-5,8-dihydro-7H-spiro[pyrido[2,3-d]pyrimidine-6,3'-pyrrolidine]-2',7-dione (D168);
(S)-8-cyclopentyl-2-((4-(1-methyl-1H-pyrazol-4-yl)phenyl)amino)-5,8-dihydro-7H-spiro[pyrido[2,3-d]pyrimidine-6,3'-pyrrolidine]-2',7-dione (D169);
(S)-8-cyclopentyl-2-((5-(1-isopropyl-1H-pyrazol-4-yl)pyridin-2-yl)amino)-5,8-dihydro-7H-spiro[pyrido[2,3-d]pyrimidine-6,3'-pyrrolidine]-2',7-dione (D170);
(S)-8-cyclopentyl-2-((5-(6-isopropyl-2,6-diazaspiro[3.3]heptan-2-yl)pyridin-2-yl)amino)-5,8-dihydro-7H-spiro[pyrido[2,3-d]pyrimidine-6,3'-pyrrolidine]-2',7-dione (D171);
(S)-2-((4-(2,6-diazaspiro[3.3]heptan-2-yl)phenyl)amino)-8-cyclopentyl-5,8-dihydro-7H-spiro[pyrido[2,3-d]pyrimidine-6,3'-pyrrolidine]-2',7-dione (D172);
(S)-8-cyclopentyl-2-((3-fluoro-4-(2,6-diazaspiro[3.3]heptan-2-yl)phenyl)amino)-5,8-dihydro-7H-spiro[pyrido[2,3-d]pyrimidine-6,3'-pyrrolidine]-2',7-dione (D173);
(S)-8-cyclopentyl-2-((4-((S)-3-(dimethylamino)pyrrolidin-1-yl)phenyl)amino)-5,8-dihydro-7H-spiro[pyrido[2,3-d]pyrimidine-6,3'-pyrrolidine]-2',7-dione (D174);
(S)-8-cyclopentyl-2-((6-((R)-3-(dimethylamino)pyrrolidin-1-yl)pyridin-3-yl)amino)-5,8-dihydro-7H-spiro[pyrido[2,3-d]pyrimidine-6,3'-pyrrolidine]-2',7-dione (D175);
(S)-8-cyclopentyl-2-((4-((R)-3-(dimethylamino)pyrrolidin-1-yl)-3-fluorophenyl)amino)-5,8-dihydro-7H-spiro[pyrido[2,3-d]pyrimidine-6,3'-pyrrolidine]-2',7-dione (D176);
(S)-8-cyclopentyl-2-((4-((S)-3-(dimethylamino)pyrrolidine-1-carbonyl)phenyl)amino)-5,8-dihydro-7H-spiro[pyrido[2,3-d]pyrimidine-6,3'-pyrrolidine]-2',7-dione (D177);
(S)-8-cyclopentyl-2-((5-((S)-3-(dimethylamino)pyrrolidin-1-yl)pyridin-2-yl)amino)-5,8-dihydro-7H-spiro[pyrido[2,3-d]pyrimidine-6,3'-pyrrolidine]-2',7-dione (D178);
(S)-8-cyclopentyl-2-((4-(2-(dimethylamino)ethoxy)phenyl)amino)-5,8-dihydro-7H-spiro[pyrido[2,3-d]pyrimidine-6,3'-pyrrolidine]-2',7-dione (D179);
(S)-8-cyclopentyl-2-((3-fluoro-4-(2-(pyrrolidin-1-yl)ethoxy)phenyl)amino)-5,8-dihydro-7H-spiro[pyrido[2,3-d]pyrimidine-6,3'-pyrrolidine]-2',7-dione (D180);
(S)-8-cyclopentyl-2-((5-(4-morpholinopiperidin-1-yl)pyridin-2-yl)amino)-5,8-dihydro-7H-spiro[pyrido[2,3-d]pyrimidine-6,3'-pyrrolidine]-2',7-dione (D181);
(S)-8-cyclopentyl-2-((4-(4-morpholinopiperidin-1-yl)phenyl)amino)-5,8-dihydro-7H-spiro[pyrido[2,3-d]pyrimidine-6,3'-pyrrolidine]-2',7-dione (D182);
8-(bicyclo[1.1.1]pentan-1-yl)-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (D183);
(S)-8-(bicyclo[1.1.1]pentan-1-yl)-2-((3-fluoro-4-(piperazin-1-yl)phenyl)amino)-5,8-dihydro-7H-spiro[pyrido[2,3-d]pyrimidine-6,3'-pyrrolidine]-2',7-dione (D184);
(S)-8-(bicyclo[1.1.1]pentan-1-yl)-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (D185);

(S)-8-(bicyclo[1.1.1]pentan-1-yl)-2-((4-(4-methylpiperazin-1-yl)phenyl)amino)-5,8-dihydro-7H-spiro[pyrido[2,3-d]pyrimidine-6,3'-pyrrolidine]-2',7-dione (D186);

(S)-8-(bicyclo[1.1.1]pentan-1-yl)-2-((4-(4-isopropylpiperazin-1-yl)phenyl)amino)-5,8-dihydro-7H-spiro[pyrido[2,3-d]pyrimidine-6,3'-pyrrolidine]-2',7-dione (D187);

(S)-8-(bicyclo[1.1.1]pentan-1-yl)-2-((5-(4-methylpiperazin-1-yl)pyridin-2-yl)amino)-5,8-dihydro-7H-spiro[pyrido[2,3-d]pyrimidine-6,3'-pyrrolidine]-2',7-dione (D188);

(S)-8-(bicyclo[1.1.1]pentan-1-yl)-2-((5-(4-isopropylpiperazin-1-yl)pyridin-2-yl)amino)-5,8-dihydro-7H-spiro[pyrido[2,3-d]pyrimidine-6,3'-pyrrolidine]-2',7-dione (D189);

(S)-8-(bicyclo[1.1.1]pentan-1-yl)-2-((5-((4-ethylpiperazin-1-yl)methyl)pyridin-2-yl)amino)-5,8-dihydro-7H-spiro[pyrido[2,3-d]pyrimidine-6,3'-pyrrolidine]-2',7-dione (D190);

(S)-8-cyclopentyl-2-((6-(2-(pyrrolidin-1-yl)ethoxy)pyridin-3-yl)amino)-5,8-dihydro-7H-spiro[pyrido[2,3-d]pyrimidine-6,3'-pyrrolidine]-2',7-dione (D191);

(S)-8-cyclopentyl-2-((6-(2-(piperidin-1-yl)ethoxy)pyridin-3-yl)amino)-5,8-dihydro-7H-spiro[pyrido[2,3-d]pyrimidine-6,3'-pyrrolidine]-2',7-dione (D192);

(S)-8-cyclopentyl-2-((6-(4-morpholinopiperidin-1-yl)pyridin-3-yl)amino)-5,8-dihydro-7H-spiro[pyrido[2,3-d]pyrimidine-6,3'-pyrrolidine]-2',7-dione (D193);

(S)-8-(bicyclo[1.1.1]pentan-1-yl)-2-((3-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (D194);

(S)-8-cyclopentyl-2-((4-(1-isopropyl-1H-pyrazol-4-yl)phenyl)amino)-5,8-dihydro-7H-spiro[pyrido[2,3-d]pyrimidine-6,3'-pyrrolidine]-2',7-dione (D195);

(R)-8-(bicyclo[1.1.1]pentan-1-yl)-2-((3-fluoro-4-(piperazin-1-yl)phenyl)amino)-5,8-dihydro-7H-spiro[pyrido[2,3-d]pyrimidine-6,3'-pyrrolidine]-2',7-dione (D196);

(R)-8-(bicyclo[1.1.1]pentan-1-yl)-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (D197);

(S)-8-cyclopentyl-2-(2,6-diazaspiro[3.3]heptan-2-yl)-5,8-dihydro-7H-spiro[pyrido[2,3-d]pyrimidine-6,3'-pyrrolidine]-2',7-dione (D198);

(6S)-8-cyclopentyl-2-((4-(3,5-dimethylpiperazin-1-yl)phenyl)amino)-5,8-dihydro-7H-spiro[pyrido[2,3-d]pyrimidine-6,3'-pyrrolidine]-2',7-dione (D199);

(6S)-8-(bicyclo[1.1.1]pentan-1-yl)-2-((4-(3,5-dimethylpiperazin-1-yl)phenyl)amino)-5,8-dihydro-7H-spiro[pyrido[2,3-d]pyrimidine-6,3'-pyrrolidine]-2',7-dione (D200);

(S)-8-cyclopentyl-2-((4-(4-isopropylpiperidin-1-yl)phenyl)amino)-5,8-dihydro-7H-spiro[pyrido[2,3-d]pyrimidine-6,3'-pyrrolidine]-2',7-dione (D201);

(S)-8-cyclopentyl-2-((4-(4-cyclopropylpiperazin-1-yl)phenyl)amino)-5,8-dihydro-7H-spiro[pyrido[2,3-d]pyrimidine-6,3'-pyrrolidine]-2',7-dione (D202);

tert-butyl (R)-8-(bicyclo[1.1.1]pentan-1-yl)-2-(methylthio)-2',7-dioxo-7,8-dihydro-5H-spiro[pyrido[2,3-d]pyrimidine-6,3'-pyrrolidine]-1'-carboxylate (D203); or pharmaceutically acceptable salts thereof.

DETAILED DESCRIPTION

Figure 1:
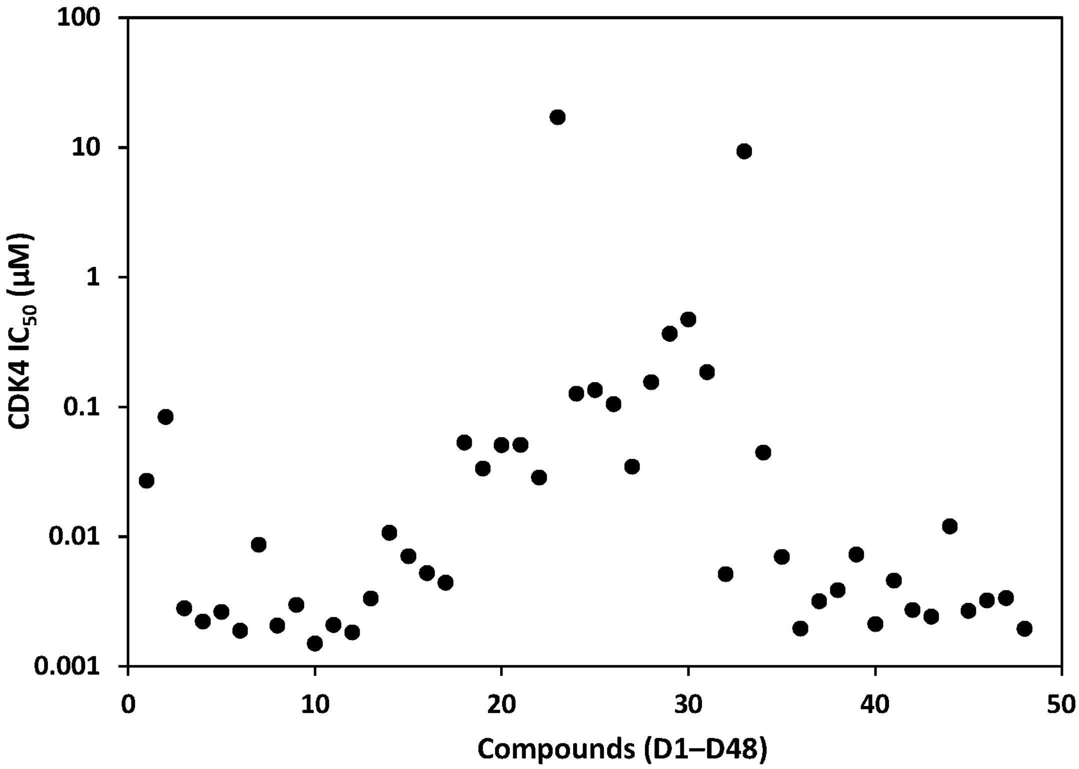
FIG. 1 shows CDK4 inhibition data for Compounds D1-D48. The plotted data is shown in Table 2.

Described herein are compounds that are useful for treating uncontrolled cell proliferative diseases, including, but not limited to, proliferative diseases such as cancer, restenosis, or rheumatoid arthritis. These compounds are useful for treating inflammation and inflammatory diseases. In addition, these compounds have utility as antiinfective agents. Moreover, these compounds have utility as chemoprotective agents through their ability to inhibit the cell cycle progression of normal untransformed cells. Many of the compounds described herein display unexpected improvements in selectivity for the serine/threonine kinases CDK4, CDK6, CDK9, and other CDKs. The synthesis of these compounds is described herein. These compounds can be administered to patients by a variety of methods including orally or intravenously.

Throughout the specification and claims, a given chemical formula or chemical name shall encompass all optical stereoisomers, as well as racemic mixtures where such isomers or mixtures exist, unless the specific isomer or diastereomer is noted. In addition, the disclosed compounds encompass all pharmaceutically acceptable salts, esters, amides, isotopes, prodrugs, solvates, or crystalline forms thereof.

The term "alkyl" as used herein means a straight or branched hydrocarbon radical having from 1 to 10 carbon atoms and includes, for example, methyl, ethyl, n-propyl, isopropyl, n-butyl, sec-butyl, isobutyl, tert-butyl, n-pentyl, iso-pentyl, n-hexyl, and the like.

The term "alkenyl" as used means straight and branched hydrocarbon radicals having from 2 to 8 carbon atoms and at least one double bond and includes, but is not limited to, ethenyl, 3-buten-1-yl, 2-ethenylbutyl, 3-hexen-1-yl, and the like. The term "alkenyl" includes cycloalkenyl, and heteroalkenyl in which 1 to 3 heteroatoms selected from O, S, N, or substituted nitrogen may replace carbon atoms.

The term "alkynyl" as used means straight and branched hydrocarbon radicals having from 2 to 8 carbon atoms and at least one triple bond and includes, but is not limited to, ethynyl, 3-butyn-1-yl, propynyl, 2-butyn-1-yl, 3-pentyn-1-yl, and the like.

The term "cycloalkyl" as used means a monocyclic or polycyclic hydrocarbyl group having from 3 to 8 carbon atoms, for instance, cyclopropyl, cycloheptyl, cyclooctyl, cyclodecyl, cyclobutyl, adamantyl, norpinanyl, decalinyl, norbornyl, cyclohexyl, and cyclopentyl. Such groups can be substituted with groups such as hydroxy, keto, amino, alkyl, and dialkylamino, and the like. Also included are rings in which 1 to 3 heteroatoms replace carbons. Such groups are termed "heterocyclyl," which means a cycloalkyl group also bearing at least one heteroatom selected from O, S, N, or substituted nitrogen. Examples of such groups include, but are not limited to, oxiranyl, pyrrolidinyl, piperidyl, tetrahydropyran, and morpholine.

The term "alkoxy" as used herein means a straight or branched chain alkyl groups having 1-10 carbon atoms and linked through oxygen. Examples of such groups include, but are not limited to, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, and 3-methylpentoxy. In addition, alkoxy refers to polyethers such as $—O—(CH_2)_2O—CH_3$, and the like.

The alkyl, alkenyl, alkoxy, and alkynyl groups described herein are optionally substituted, preferably by 1 to 3 groups selected from $NR4R_5$, phenyl, substituted phenyl, thio $C_1$-$C_6$ alkyl, $C_1$-$C_6$ alkoxy, hydroxy, carboxy, $C_1$-$C_6$ alkoxycarbonyl, halo, nitrile, cycloalkyl, and a 5- or 6-membered carbocyclic ring or heterocyclic ring having 1 or 2 heteroatoms selected from nitrogen, substituted nitrogen, oxygen, and sulfur. "Substituted nitrogen" means nitrogen bearing $C_1$-$C_6$ alkyl or $(CH_2)_pPh$ where p is 1, 2, or 3. Perhalo and polyhalo substitution is also included.

Examples of substituted alkyl groups include, but are not limited to, 2-aminoethyl, 2-hydroxyethyl, pentachloroethyl, trifluoromethyl, 2-diethylaminoethyl, 2-dimethylaminopropyl, ethoxycarbonylmethyl, 3-phenylbutyl, methanylsulfanylmethyl, methoxymethyl, 3-hydroxypentyl, 2-carboxybutyl, 4-chlorobutyl, 3-cyclopropylpropyl, pentafluoroethyl, 3-morpholinopropyl, piperazinylmethyl, and 2-(4-methylpiperazinyl)ethyl.

Examples of substituted alkynyl groups include, but are not limited to, 2-methoxyethynyl, 2-ethylsulfanylethynyl, 4-(1-piperazinyl)-3-(butynyl), 3-phenyl-5-hexynyl, 3-diethylamino-3-butynyl, 4-chloro-3-butynyl, 4-cyclobutyl-4-hexenyl, and the like.

Typical substituted alkoxy groups include aminomethoxy, trifluoromethoxy, 2-diethylaminoethoxy, 2-ethoxycarbonylethoxy, 3-hydroxypropoxy, 6-carboxhexyloxy, and the like.

Further, examples of substituted alkyl, alkenyl, and alkynyl groups include, but are not limited to, dimethylaminomethyl, carboxymethyl, 4-dimethylamino-3-buten-1-yl, 5-ethylmethylamino-3-pentyn-1-yl, 4-morpholinobutyl, 4-tetrahydropyrinidylbutyl, 3-imidazolidin-1-ylpropyl, 4-tetrahydrothiazol-3-yl-butyl, phenylmethyl, 3-chlorophenylmethyl, and the like.

The term "anion" as used herein means a negatively charged counterion such as chloride, bromide, trifluoroacetate, and triethylammonium.

The term "acyl" as used herein means an alkyl or aryl (Ar) group having from 1-10 carbon atoms bonded through a carbonyl group, i.e., R—C(O)—. For example, acyl includes, but is not limited to, a $C_1$-$C_6$ alkanoyl, including substituted alkanoyl, wherein the alkyl portion can be substituted by an amine, amide, carboxylic, or heterocyclic group. Typical acyl groups include acetyl, benzoyl, and the like.

The term "aryl" as used herein refers to an aromatic monocyclic hydrocarbon ring system or a polycyclic ring system where at least one of the rings in the ring system is an aromatic hydrocarbon ring and any other aromatic rings in the ring system include only hydrocarbons. In some embodiments, a monocyclic aryl group can have from 6 to 14 carbon atoms and a polycyclic aryl group can have from 8 to 14 carbon atoms. The aryl group can be covalently attached to the defined chemical structure at any carbon atom(s) that result in a stable structure. In some embodiments, an aryl group can have only aromatic carbocyclic rings, e.g., phenyl, 1-naphthyl, 2-naphthyl, anthracenyl, phenanthrenyl groups, and the like. In other embodiments, an aryl group can be a polycyclic ring system in which at least one aromatic carbocyclic ring is fused (i.e., having a bond in common with) to one or more cycloalkyl or cycloheteroalkyl rings. Examples of such aryl groups include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like.

The terms "halogen" or "halo" as used herein means fluorine, bromine, chlorine, and iodine.

The term "haloalkyl" refers to an alkyl group having one or more halogen substituents. In some embodiments, a haloalkyl group can have 1 to 10 carbon atoms (e.g., from 1 to 8 carbon atoms). Examples of haloalkyl groups include $CF_3$, $C_2F_5$, $CHF_2$, $CH_2F$, $CCl_3$, $CHCl_2$, $CH_2Cl$, $C_2Cl_5$, and the like. Perhaloalkyl groups, i.e., alkyl groups wherein all of the hydrogen atoms are replaced with halogen atoms (e.g., $CF_3$ and $C_2F_5$), are included within the definition of "haloalkyl." For example, a $C_{1-10}$ haloalkyl group can have the formula $—C_iH_{2+}1—jX_j$, wherein X is F, Cl, Br, or I, i is an integer in the range of 1 to 10, and j is an integer in the range of 0 to 21, provided that j is less than or equal to 2i+1.

The term "heteroaryl" as used herein refers to an aromatic monocyclic ring system containing at least one ring heteroatom selected from O, N, and S or a polycyclic ring system where at least one of the rings in the ring system is aromatic and contains at least one ring heteroatom. A heteroaryl group, as a whole, can have from 5 to 14 ring atoms and contain 1-5 ring heteroatoms. In some embodiments, heteroaryl groups can include monocyclic heteroaryl rings fused to one or more aromatic carbocyclic rings, non-aromatic carbocyclic rings, or non-aromatic cycloheteroalkyl rings. The heteroaryl group can be covalently attached to the defined chemical structure at any heteroatom or carbon atom that results in a stable structure. Generally, heteroaryl rings do not contain O—O, S—S, or S—O bonds. However, one or more N or S atoms in a heteroaryl group can be oxidized (e.g., pyridine N-oxide, thiophene S-oxide, thiophene S,S-dioxide). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyrdazinyl, thienothiazolyl, thienooxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like.

The term "lower alkenyl" as used herein refers to alkenyl groups which contains 2 to 6 carbon atoms. An alkenyl group is a hydrocarbyl group containing at least one carbon-carbon double bond. As defined herein, it may be unsubstituted or substituted with the substituents described herein. The carbon-carbon double bonds may be between any two carbon atoms of the alkenyl group. It is preferred that it contains 1 or 2 carbon-carbon double bonds and more preferably one carbon-carbon double bond. The alkenyl group may be straight chained or branched. Examples include but are not limited to ethenyl, 1-propenyl, 2-propenyl, 1-butenyl, 2-butenyl, 2-methyl-1-propenyl, 1,3-butadienyl, and the like.

The term "lower alkynyl" as used herein, refers to an alkynyl group containing 2-6 carbon atoms. An alkynyl group is a hydrocarbyl group containing at least one carbon-carbon triple bond. The carbon-carbon triple bond may be between any two carbon atom of the alkynyl group. In an embodiment, the alkynyl group contains 1 or 2 carbon-carbon triple bonds and more preferably one carbon-carbon triple bond. The alkynyl group may be straight chained or branched. Examples include but are not limited to ethynyl, 1-propynyl, 2-propynyl, 1-butynyl, 2-butynyl and the like.

The term "carbalkoxy" as used herein refers to an alkoxy-carbonyl group, where the attachment to the main chain is through the carbonyl group, e.g., —C(O)—. Examples include but are not limited to methoxy carbonyl, ethoxy carbonyl, and the like.

The term "oxo" as used herein refers to a double-bonded oxygen (i.e., =O). It is also to be understood that the terminology C(O) refers to a —C=O group, whether it be ketone, aldehyde or acid or acid derivative. Similarly, S(O) refers to a —S=O group.

The term "cycloalkyl" as used herein refers to a non-aromatic carbocyclic group including cyclized alkyl, alkenyl, and alkynyl groups. A cycloalkyl group can be monocyclic (e.g., cyclohexyl) or polycyclic (e.g., containing fused, bridged, and/or spiro ring systems), wherein the carbon atoms are located inside or outside of the ring system. A cycloalkyl group, as a whole, can have from 3 to 14 ring atoms (e.g., from 3 to 8 carbon atoms for a monocyclic cycloalkyl group and from 7 to 14 carbon atoms for a polycyclic cycloalkyl group). Any suitable ring position of the cycloalkyl group can be covalently linked to the defined chemical structure. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcaryl, adamantyl, and spiro[4.5]decanyl groups, as well as their homologs, isomers, and the like.

The term "heteroatom" as used herein refers to an atom of any element other than carbon or hydrogen and includes, for example, nitrogen, oxygen, sulfur, phosphorus, and selenium.

The term "cycloheteroalkyl" as used herein refers to a non-aromatic cycloalkyl group that contains at least one (e.g., one, two, three, four, or five) ring heteroatom selected from O, N, and S, and optionally contains one or more (e.g., one, two, or three) double or triple bonds. A cycloheteroalkyl group, as a whole, can have from 3 to 14 ring atoms and contains from 1 to 5 ring heteroatoms (e.g., from 3-6 ring atoms for a monocyclic cycloheteroalkyl group and from 7 to 14 ring atoms for a polycyclic cycloheteroalkyl group). The cycloheteroalkyl group can be covalently attached to the defined chemical structure at any heteroatom(s) or carbon atom(s) that results in a stable structure. One or more N or S atoms in a cycloheteroalkyl ring may be oxidized (e.g., morpholine N-oxide, thiomorpholine S-oxide, thiomorpholine S,S-dioxide). Cycloheteroalkyl groups can also contain one or more oxo groups, such as phthalimidyl, piperidonyl, oxazolidinonyl, 2,4(1H,3H)-dioxo-pyrimidinyl, pyridin-2(1H)-onyl, and the like. Examples of cycloheteroalkyl groups include, among others, morpholinyl, thiomorpholinyl, pyranyl, imidazolidinyl, imidazolinyl, oxazolidinyl, pyrazolidinyl, pyrazolinyl, pyrrolidinyl, pyrrolinyl, tetrahydrofuranyl, tetrahydrothienyl, piperidinyl, piperazinyl, azetidine, and the like.

The compounds described herein may contain chiral centers and therefore may exist in different enantiomeric and diastereomeric forms. One embodiment described herein encompasses all optical isomers or stereoisomers of the compounds described herein both as racemic mixtures and as individual enantiomers or diastereoisomers, or mixtures thereof, and to all pharmaceutical compositions o methods of treatment described herein that contain or employ them, respectively. Individual isomers can be obtained by known methods, such as optical resolution, optically selective reaction, or chiral chromatographic separation in the preparation of the final product or its intermediate.

The compounds described herein can exist in unsolvated forms as well as solvated forms, including hydrated forms. In general, the solvated forms, including hydrated forms, are equivalent to unsolvated forms and are intended to be encompassed within the scope described herein.

Compounds described herein also includes isotopically labelled compounds, which are identical to those described herein, but for the fact that one or more atoms are replaced by an atom having an atomic mass or mass number different from the atomic mass or mass number usually found in nature. Examples of isotopes that can be incorporated into compounds described herein include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively.

Compounds described herein, prodrugs thereof, and pharmaceutically acceptable salts of said compounds or of said prodrugs which contain the aforementioned isotopes and/or other isotopes of other atoms are within the scope described herein. Certain isotopically labelled compounds described herein, for example those into which radioactive isotopes such as $^{3}H$ and $^{14}C$ are incorporated, are useful in drug and/or substrate tissue distribution assays. Tritiated, i.e., $^{3}H$, and carbon-14 i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds described herein and prodrugs thereof can generally be prepared by carrying out the procedures disclosed in the Schemes and/or in the Examples and Preparations below, by substituting a readily available isotopically labelled reagent for a non-isotopically labelled reagent.

The term "cancer" as used herein includes, but is not limited to, the following cancers: cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidernoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia.

The term "treating," as used herein refers to reversing, alleviating, inhibiting the progress of, or preventing the disorder or condition to which such term applies, or ameliorating one or more symptoms of such condition or disorder. The term "treatment," as used herein, refers to the act of treating, as "treating" is defined immediately above.

The phrase "pharmaceutically acceptable" refers to molecular entities and compositions that are physiologically tolerable and do not typically produce a toxic, allergic, or similar untoward reaction, such as gastric upset, dizziness and the like, when administered to a human. Preferably, as used herein, the term "pharmaceutically acceptable" means approved by a regulatory agency of the Federal or a state government or listed in the U.S. or European Pharmacopeia or other generally recognized pharmacopeia for use in animals, and more particularly in humans.

The compounds described herein are capable of further forming pharmaceutically acceptable formulations comprising salts, including acid addition or base salts, solvents, or N-oxides of any compound described herein.

The term "salts" refers to the relatively non-toxic, inorganic, or organic acid addition salts of compounds described herein. These salts can be prepared in situ during the final isolation and purification of the compounds or by separately reacting the purified compound in its free base form with a suitable organic or inorganic acid and isolating the salt thus formed. In so far as the compounds described herein are basic compounds, they are all capable of forming a wide variety of different salts with various inorganic and organic acids. Although such salts must be pharmaceutically acceptable for administration to animals, it is often desirable in practice to initially isolate the base compound from the reaction mixture as a pharmaceutically unacceptable salt and then simply convert to the free base compound by treatment with an alkaline reagent and thereafter convert the free base to a pharmaceutically acceptable acid addition salt. The acid addition salts of the basic compounds are prepared by contacting the free base form with a sufficient amount of the desired acid to produce the salt in the conventional manner. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of this disclosure.

Pharmaceutically acceptable base addition salts are formed with metals or amines, such as alkali and alkaline earth metal hydroxides, or of organic amines. Examples of metals used as cations are sodium, potassium, magnesium, calcium, and the like. Examples of suitable amines are N,N'-dibenzylethylenediamine, chloroprocaine, choline, diethanolamine, ethylenediamine, N-methylglucamine, and procaine.

The base addition salts of acidic compounds are prepared by contacting the free acid form with a sufficient amount of the desired base to produce the salt in the conventional manner. The free acid form may be regenerated by contacting the salt form with an acid and isolating the free acid in a conventional manner. The free acid forms differ from their respective salt forms somewhat in certain physical properties such as solubility in polar solvents, but otherwise the salts are equivalent to their respective free acid for purposes described herein.

Salts may be prepared from inorganic acids sulfate, pyrosulfate, bisulfate, sulfite, bisulfite, nitrate, phosphate, monohydrogenphosphate, dihydrogenphosphate, metaphosphate, pyrophosphate, chloride, bromide, iodide such as hydrochloric, nitric, phosphoric, sulfuric, hydrobromic, hydriodic, phosphorus, and the like. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, laurylsulphonate and isethionate salts, and the like. Salts may also be prepared from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. and the like. Representative salts include acetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Pharmaceutically acceptable salts may include cations based on the alkali and alkaline earth metals, such as sodium, lithium, potassium, calcium, magnesium and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. Also contemplated are the salts of amino acids such as arginate, gluconate, galacturonate, and the like. See Berge et al., *J. Pharm. Sci.* 66: 1-19 (1977) which is incorporated herein by reference.

The term "pharmaceutically acceptable salts, esters, amides, and prodrugs" as used herein refers to those carboxylate salts, amino acid addition salts, esters, amides, and prodrugs of the compounds described herein which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds described herein.

Examples of pharmaceutically acceptable, non-toxic esters of the compounds described herein include $C_1$-$C_6$ alkyl esters wherein the alkyl group is a straight or branched chain. Acceptable esters also include $C_5$-$C_7$ cycloalkyl esters as well as arylalkyl esters such as, but not limited to benzyl. $C_1$-$C_4$ alkyl esters are preferred. Esters of the compounds described herein may be prepared according to conventional methods "March's Advanced Organic Chemistry, $5^{th}$ Edition," Smith and March, John Wiley & Sons (2001).

Examples of pharmaceutically acceptable, non-toxic amides of the compounds described herein include amides derived from ammonia, primary $C_1$-$C_6$ alkyl amines and secondary $C_1$-$C_6$ dialkyl amines wherein the alkyl groups are straight or branched chain. In the case of secondary amines the amine may also be in the form of a 5- or 6-membered heterocycle containing one nitrogen atom. Amides derived from ammonia, $C_1$-$C_3$ alkyl primary amines and $C_1$-$C_2$ dialkyl secondary amines are preferred. Amides of the compounds described herein may be prepared according to conventional methods such as "March's Advanced Organic Chemistry, $5^{th}$ Edition," Smith and March, John Wiley & Sons (2001).

The phrase "room temperature," "RT," or "ambient temperature" indicate a temperature of about 25° C.±10%.

The term "prodrug" as used herein refers to compounds that are rapidly transformed in vivo to yield the parent compound of the above formulae, for example, by hydrolysis in blood. A thorough discussion is provided in Higuchi, "Pro-drugs as Novel Delivery Systems," ACS Symposium Series 14 (1975), and in Roche, Edward, ed., Bioreversible Carriers in Drug Design, American Pharmaceutical Association, Pergamon Press (1987), both of which are hereby incorporated by reference.

The term "excipient" as used herein refers to a diluent, adjuvant, or vehicle with which the compound is administered. Such pharmaceutical excipients can be sterile liquids, such as water and oils, including those of petroleum, animal, vegetable or synthetic origin, such as peanut oil, soybean oil, mineral oil, sesame oil and the like. Water for injection, aqueous saline solutions, aqueous dextrose, or lactated Ringer's solution are preferably employed as excipients, particularly for injectable solutions. Suitable pharmaceutical excipients are described in "Remington's Pharmaceutical Sciences" by E. W. Martin.

The phrase "therapeutically effective amount" as used herein means an amount sufficient to reduce by at least about 10 percent, preferably by at least 50 percent, more preferably by at least 90 percent, and most preferably prevent, a clinically significant deficit in the activity, function and response of the host. Alternatively, a therapeutically effective amount is sufficient to cause an improvement in a clinically significant condition/symptom in the host.

The term "analog" as used herein refers to a small organic compound, a nucleotide, a protein, or a polypeptide that possesses similar or identical activity or function(s) as the compound, nucleotide, protein or polypeptide or compound having the desired activity and therapeutic effect (e.g., inhibition of tumor growth), but need not necessarily comprise a sequence or structure that is similar or identical to the sequence or structure of the preferred embodiment.

The term "derivative" as used herein refers to either a compound, a protein or polypeptide that comprises an amino acid sequence of a parent protein or polypeptide that has been altered by the introduction of amino acid residue substitutions, deletions or additions, or a nucleic acid or nucleotide that has been modified by either introduction of nucleotide substitutions or deletions, additions or mutations. The derivative nucleic acid, nucleotide, protein, or polypeptide possesses a similar or identical function as the parent polypeptide.

The phrases "substantial portion" or "significant portion" as used herein mean at least 80%. In alternative embodiments, the portion may be at least 85%, 90%, 95%, 99%, or greater.

The phrase "selective CDK inhibitor" used in the context of the compounds described herein indicates an ability to inhibit CDK4 activity, CDK6 activity, CDK9 activity or other CDK activities at an $IC_{50}$ molar concentration at least about 2000 times less than the $IC_{50}$ molar concentration necessary to inhibit to the same degree as CDK2 activity in a standard phosphorylation assay.

The phrase "induces G1-arrest" mean that a compound described herein induces a quiescent state in a substantial portion of a cell population at the G1 phase of the cell cycle.

The phrase "hematological deficiency" mean reduced hematological cell lineage counts or the insufficient production of blood cells (i.e., myelodysplasia) and/or lymphocytes (i.e., lymphopenia, the reduction in the number of circulating lymphocytes, such as B- and T-cells). Hematological deficiency can be observed, for example, as myelosuppression in form of anemia, reduction in platelet count (i.e., thrombocytopenia), reduction in white blood cell count (i.e., leukopenia), or the reduction in granulocytes (e.g., neutropenia).

The phrase "synchronous reentry into the cell cycle" mean that CDK4/6-replication dependent healthy cells, for example HSPCs, in G1-arrest due to the effect of a compound described herein reenter the cell-cycle within relatively the same collective timeframe or at relatively the same rate upon dissipation of the compound's effect. Comparatively, by "asynchronous reentry into the cell cycle" is meant that the healthy cells, for example HSPCs, in G1 arrest due to the effect of a CDK4/6 inhibitor compound within relatively different collective timeframes or at relatively different rates upon dissipation of the compound's effect such as pablociclib or ribociclib.

The phrases "off-cycle" or "drug holiday" mean a time period during which the subject is not administered or exposed to a chemotherapeutic. For example, in a treatment regime wherein the subject is administered the chemotherapeutic in a repeated 21 day cycle, and is not administered the chemotherapeutic at the start of the next 21-day cycle due to hematologic deficiencies, the delayed period of non-administration is considered the "off-cycle" or "drug holiday." Off-target and drug holiday may also refer to an interruption in a treatment regime wherein the subject is not administered the chemotherapeutic for a time due to a deleterious side effect, for example, myelosuppression or other hematological deficiencies.

The phrase "CDK4/6-replication independent cancer" refers to a cancer that does not significantly require the activity of CDK4/6 for replication. Cancers of such type are often, but not always, characterized by (e.g., has cells that exhibit) an increased level of CDK2 activity or by reduced expression of retinoblastoma tumor suppressor protein or retinoblastoma family member protein(s), such as, but not limited to p107 and p130. The increased level of CDK2 activity or reduced or deficient expression of retinoblastoma tumor suppressor protein or retinoblastoma family member protein(s) can be increased or reduced, for example, compared to normal cells. In some embodiments, the increased level of CDK2 activity can be associated with (e.g., can result from or be observed along with) MYC proto-oncogene amplification or overexpression. In some embodiments, the increased level of CDK2 activity can be associated with overexpression of Cyclin E1, Cyclin E2, or Cyclin A.

The phrase "long-term hematological toxicity" is meant hematological toxicity affecting a subject for a period lasting more than one or more weeks, months, or years following administration of a chemotherapeutic agent. Long-term hematological toxicity can result in bone marrow disorders that can cause the ineffective production of blood cells (i.e., myelodysplasia) and/or lymphocytes (i.e., lymphopenia, the reduction in the number of circulating lymphocytes, such as B- and T-cells). Hematological toxicity can be observed, for example, as anemia, reduction in platelet count (i.e., thrombocytopenia) or reduction in white blood cell count (i.e., neutropenia). In some cases, myelodysplasia can result in the development of leukemia. Long-term toxicity related to chemotherapeutic agents can also damage other self-renewing cells in a subject, in addition to hematological cells. Thus, long-term toxicity can also lead to graying and frailty.

Biological Activity

The compounds described herein are inhibitors of cyclin dependent kinases. For example, compounds described herein are inhibitors of cyclin dependent kinases, and in particular cyclin dependent kinases comprising CDK1, CDK2, CDK3, CDK4, CDK5, CDK6, CDK7, CDK8, CDK9, CDK9, CDK10, CDK11, CDK12, CDK13, or other CDKs. In one aspect, the compounds described herein are inhibitors of CDK4, CDK6, and/or CDK9.

Compounds described herein also have activity against glycogen synthase kinase-3 (GSK-3). As a consequence of their activity in modulating or inhibiting CDK and glycogen synthase kinase, they are expected to be useful in providing a means of arresting, or recovering control of, the cell cycle in abnormally dividing cells. It is therefore anticipated that the compounds will prove useful in treating or preventing proliferative disorders such as cancers. It is also envisaged that the compounds described herein will be useful in treating conditions such as viral infections, type II or non-insulin dependent diabetes mellitus, autoimmune diseases, head trauma, stroke, epilepsy, neurodegenerative diseases such as Alzheimer's, motor neuron disease, progressive supranuclear palsy, corticobasal degeneration and Pick's disease for example autoimmune diseases and neurodegenerative diseases.

One sub-group of disease states and conditions where it is envisaged that the compounds described herein will be useful consists of viral infections, autoimmune diseases and neurodegenerative diseases.

CDKs play a role in the regulation of the cell cycle, apoptosis, transcription, differentiation, and CNS function. Therefore, CDK inhibitors could be useful in the treatment of diseases in which there is a disorder of proliferation, apoptosis, or differentiation such as cancer. In particular, RB-ve tumours may be particularly sensitive to CDK inhibitors. These include tumours harbouring mutations in ras, Raf, Growth Factor Receptors or over-expression of Growth Factor Receptors. Furthermore, tumours with hypermethylated promoter regions of CDK inhibitors as well as tumours over-expressing cyclin partners of the cyclin dependent kinases may also display sensitivity. RB-ve tumours may also be sensitive to CDK inhibitors.

Examples of cancers which may be inhibited include, but are not limited to, a carcinoma, for example a carcinoma of the bladder, breast, colon (e.g., colorectal carcinomas such as colon adenocarcinoma and colon adenoma), kidney, epidermis, liver, lung, for example adenocarcinoma, small cell lung cancer and non-small cell lung carcinomas, oesophagus, gall bladder, ovary, pancreas e.g., exocrine pancreatic carcinoma, stomach, cervix, thyroid, nose, head and neck, prostate, or skin, for example squamous cell carcinoma; a hematopoietic tumour of lymphoid lineage, for example leukemia, acute lymphocytic leukemia, chronic lymphocytic leukaemia, B-cell lymphoma (such as diffuse large B cell lymphoma), T-cell lymphoma, multiple myeloma, Hodgkin's lymphoma, non-Hodgkin's lymphoma, hairy cell lymphoma, or Burkett's lymphoma; a hematopoietic tumour of myeloid lineage, for example acute and chronic myelogenous leukemias, myelodysplastic syndrome, or promyelocytic leukemia; thyroid follicular cancer; a tumour of mesenchymal origin, for example fibrosarcoma or habdomyosarcoma; a tumour of the central or peripheral nervous system, for example astrocytoma, neuroblastoma, glioma or schwannoma; melanoma; seminoma; teratocarcinoma; osteosarcoma; xeroderma pigmentosum; keratoctanthoma; thyroid follicular cancer; or Kaposi's sarcoma.

The cancers may be cancers which are sensitive to inhibition of any one or more cyclin dependent kinases comprising CDK1, CDK2, CDK3, CDK4, CDK5, CDK6, CDK7, CDK8, CDK9, CDK9, CDK10, CDK11, CDK12, CDK13, or other CDKs for example, one or more CDK kinases selected from CDK4, CDK6, and/or CDK9. Whether or not a particular cancer is one which is sensitive to inhibition by a cyclin dependent kinase inhibitor may be determined by means of a cell growth assay.

CDKs are also known to play a role in apoptosis, proliferation, differentiation and transcription and therefore CDK inhibitors could also be useful in the treatment of the following diseases other than cancer; viral infections, for example herpes virus, pox virus, Epstein-Barr virus, Sindbis virus, adenovirus, HIV, HPV, HCV and HCMV; prevention of AIDS development in HIV-infected individuals; chronic inflammatory diseases, for example systemic lupus erythematosus, autoimmune mediated glomerulonephritis, rheumatoid arthritis, psoriasis, inflammatory bowel disease, and autoimmune diabetes mellitus; cardiovascular diseases for example cardiac hypertrophy, restenosis, atherosclerosis; neurodegenerative disorders, for example Alzheimer's disease, AIDS-related dementia, Parkinson's disease, amyotrophic lateral sclerosis, retinitis pigmentosa, spinal muscular atrophy and cerebellar degeneration; glomerulonephritis; myelodysplastic syndromes, ischemic injury associated myocardial infarctions, stroke and reperfusion injury, arrhythmia, atherosclerosis, toxin-induced or alcohol related liver diseases, haematological diseases, for example, chronic anemia and aplastic anemia; degenerative diseases of the musculoskeletal system, for example, osteoporosis and arthritis, aspirin-sensitive rhinosinusitis, cystic fibrosis, multiple sclerosis, kidney diseases, ophthalmic diseases including age related macular degeneration, uveitis, and cancer pain.

It has also been discovered that some cyclin-dependent kinase inhibitors can be used in combination with other anticancer agents. For example, the cyclin-dependent kinase inhibitor flavopiridol has been used with other anticancer agents in combination therapy. Thus, in the pharmaceutical compositions, uses or methods described herein for treating a disease or condition comprising abnormal cell growth, the disease or condition comprising abnormal cell growth in one embodiment is a cancer.

One group of cancers includes human breast cancers (e.g., primary breast tumours, node-negative breast cancer, invasive duct adenocarcinomas of the breast, non-endometrioid breast cancers); and mantle cell lymphomas. In addition, other cancers are colorectal and endometrial cancers. Another sub-set of cancers includes hematopoietic tumours of lymphoid lineage, for example leukemia, chronic lymphocytic leukaemia, mantle cell lymphoma, and B-cell lymphoma (such as diffuse large B cell lymphoma). One particular cancer is chronic lymphocytic leukaemia. Another particular cancer is mantle cell lymphoma. Another particular cancer is diffuse large B cell lymphoma. Another sub-set of cancers includes breast cancer, ovarian cancer, colon cancer, prostate cancer, oesophageal cancer, squamous cancer, and non-small cell lung carcinomas. Another sub-set of cancers includes breast cancer, pancreatic cancer, colorectal cancer, lung cancer, and melanoma.

A further sub-set of cancers, namely cancers wherein compounds having CDK4 inhibitory activity may be of particular therapeutic benefit, comprises retinoblastomas, small cell lung carcinomas, non-small lung carcinomas, sarcomas, gliomas, pancreatic cancers, head, neck and breast cancers and mantle cell lymphomas.

Another sub-set of cancers wherein compounds having CDK4 inhibitory activity may be of particular therapeutic benefit comprises small cell lung cancer, non-small cell lung cancer, pancreatic cancer, breast cancer, glioblastoma multiforme, T cell acute lymphoblastic leukaemia and mantle cell lymphoma. A further subset of cancers which the compounds described herein may be useful in the treatment of includes sarcomas, leukemias, glioma, familial melanoma and melanoma.

One embodiment described herein is a method of treating a disorder or condition selected from the group consisting of cell proliferative disorders, such as cancer, vascular smooth muscle proliferation associated with atherosclerosis, post-surgical vascular stenosis, restenosis, and endometriosis; infections, including viral infections such as DNA viruses like herpes and RNA viruses like HIV, and fungal infections; autoimmune diseases such as psoriasis, inflammation like rheumatoid arthritis, lupus, type 1 diabetes, diabetic nephropathy, multiple sclerosis, and glomerulonephritis, organ transplant rejection, including host versus graft disease, in a mammal, including human, comprising administering to said mammal an amount of a compound described herein, or a pharmaceutically acceptable salt thereof, that is effective in treating such disorder or condition.

Another embodiment described herein provides compounds that are useful for treating abnormal cell proliferation such a cancer. One aspect is a method of treating the abnormal cell proliferation disorders such as a cancer selected from the group consisting of cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia, comprising administering a therapeutically effective amount of a compound described herein, or a pharmaceutically acceptable salt thereof, to a subject in need of such treatment.

A further embodiment described herein is a method of treating subjects suffering from diseases caused by vascular smooth muscle cell proliferation. Compounds within the scope of this disclosure effectively inhibit vascular smooth muscle cell proliferation and migration. The method comprises administering to a subject in need of treatment an amount of a compound described herein, or a pharmaceutically acceptable salt thereof, sufficient to inhibit vascular smooth muscle proliferation, and/or migration.

Another embodiment described herein is a method of treating a subject suffering from gout comprising administering to said subject in need of treatment an amount of a compound described herein, or a pharmaceutically acceptable salt thereof, sufficient to treat the condition.

Another embodiment is a method of treating a subject suffering from kidney disease, such as polycystic kidney disease, comprising administering to said subject in need of treatment an amount of a compound described herein, or a pharmaceutically acceptable salt thereof, sufficient to treat the condition.

Because of their inhibitory activity against CDKs and other kinases, the compounds described herein are also useful research tools for studying the mechanism of action of those kinases, both in vitro and in vivo.

The above-identified methods of treatment are preferably carried out by administering a therapeutically effective amount of a compound described herein (set forth below) to a subject in need of treatment. Compounds described herein are potent inhibitors of cyclin-dependent kinases. The compounds are readily synthesized and can be administered by a variety of routes, including orally and parenterally, and have little or no toxicity. The compounds described herein are members of the class of compounds described herein.

Another embodiment described herein is a pharmaceutical composition comprising a therapeutically effective amount of a compound described herein, or a pharmaceutically acceptable salt thereof, and one or more pharmaceutically acceptable excipients.

The compounds described herein are selective inhibitors of CDK4, CDK6, or CDK9, which is to say that they inhibit CDK4, CDK6, or CDK9 more potently than they inhibit tyrosine kinases and other serine-threonine kinases including other cyclin-dependent kinases such as CDK2. Despite their selectivity for CDK4, CDK6, or CDK9 inhibition, compounds described herein may inhibit other kinases, albeit at higher concentrations than those at which they inhibit CDK4, CDK6, or CDK9.

Preferred embodiments of this disclosure are compounds described herein inhibit CDK4, CDK6, or CDK9 at least about 100-fold more potently than they inhibit CDK2.

A preferred embodiment of this disclosure provides a method of inhibiting CDK4, CDK6, or CDK9 at a lower dose than is necessary to inhibit CDK2 comprising administration of a compound described herein in an effective amount that selectively inhibits CDK4, CDK6, or CDK9 over CDK2.

The compounds described herein have useful pharmaceutical and medicinal properties. Many of the compounds described herein exhibit significant selective CDK4, CDK6, or CDK9 inhibitory activity and therefore are of value in the treatment of a wide variety of clinical conditions in which CDK4, CDK6, or CDK9 kinase is abnormally elevated, or activated or present in normal amounts and activities, but where inhibition of the CDKs is desirable to treat a cellular proliferative disorder. Such disorders include, but are not limited to those enumerated in the paragraphs below.

The compounds described herein are useful for treating cancer (for example, leukemia and cancer of the lung, breast, prostate, and skin such as melanoma) and other proliferative diseases including but not limited to psoriasis, HSV, HIV, restenosis, and atherosclerosis. To utilize a compound of this disclosure to treat cancer, a patient in need of such treatment, such as one having cancer or another proliferative disease, is administered a therapeutically effective amount of a pharmaceutically acceptable composition comprising at least one compound of this disclosure.

Methods of Diagnosis

Prior to administration of a compound described herein, a patient may be screened to determine whether a disease or condition from which the patient is or may be suffering is one which would be susceptible to treatment with a compound having activity against cyclin dependent kinases. For example, a biological sample taken from a patient may be analysed to determine whether a condition or disease, such as cancer, that the patient is or may be suffering from is one which is characterised by a genetic abnormality or abnormal protein expression which leads to over-activation of CDKs or to sensitisation of a pathway to normal CDK activity. Examples of such abnormalities that result in activation or sensitisation of the CDK2 signal include up-regulation of cyclin E or loss of p21 or p27, or presence of $CDCl_4$ variants. Harwell et al., *J. Biol. Chem.* 279(13): 12695-12705 (2004); Rajagopalan et al., *Nature* 428(6978): 77-81 (2004). Tumours with mutants of $CDCl_4$ or up-regulation, in particular over-expression, of cyclin E or loss of p21 or p27 may be particularly sensitive to CDK inhibitors. The term up-regulation includes elevated expression or over-expression, including gene amplification (i.e., multiple gene copies) and increased expression by a transcriptional effect, and hyperactivity and activation, including activation by mutations.

Thus, the patient may be subjected to a diagnostic test to detect a marker characteristic of up-regulation of cyclin E, or loss of p21 or p27, or presence of $CDCl_4$ variants. The term diagnosis includes screening. Markers include genetic markers such as the measurement of DNA composition to identify mutations of $CDCl_4$. The term marker also includes markers which are characteristic of up regulation of cyclin E, including enzyme activity, enzyme levels, enzyme state (e.g., phosphorylated or not) and mRNA levels of the aforementioned proteins. Tumours with upregulation of cyclin E, or loss of p21 or p27 may be particularly sensitive to CDK inhibitors. Tumours may preferentially be screened for upregulation of cyclin E, or loss of p21 or p27 prior to treatment. Thus, the patient may be subjected to a diagnostic test to detect a marker characteristic of up-regulation of cyclin E, or loss of p21 or p27.

The diagnostic tests are typically conducted on a biological sample selected from tumour biopsy samples, blood samples (isolation and enrichment of shed tumour cells), stool biopsies, sputum, chromosome analysis, pleural fluid, peritoneal fluid, or urine.

It has been found that there were mutations present in $CDCl_4$ (also known as Fbw7 or Archipelago) in human colorectal cancers and endometrial cancers. Rajagopalan et al., *Nature* 428(6978): 77-81 (2004); Spruck et al, Cancer Res. 62(16): 4535-4539 (2002). Identification of individual carrying a mutation in $CDCl_4$ may mean that the patient would be particularly suitable for treatment with a CDK inhibitor. Tumours may preferentially be screened for presence of a $CDCl_4$ variant prior to treatment. The screening process will typically involve direct sequencing, oligonucleotide microarray analysis, or a mutant specific antibody.

Methods of identification and analysis of mutations and up-regulation of proteins are well known to a person skilled in the art. Screening methods could include, but are not limited to, standard methods such as reverse-transcriptase polymerase chain reaction (RT-PCR) or in-situ hybridization.

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel et al., *Current Protocols in Molecular Biology*, John Wiley & Sons Inc. (2004); Innis, M. A. et al., eds. *PCR Protocols: a guide to methods and applications*, Academic Press, San Diego (1990). Reactions and manipulations involving nucleic acid techniques are also described in Sambrook et al., 3$^{rd}$ ed, *Molecular Cloning: A Laboratory Manual*, Cold Spring Harbor Laboratory Press (2001).

An example of an in-situ hybridization technique for assessing mRNA expression would be fluorescence in-situ hybridization (FISH). Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labeled, for example, with radioisotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel et al. *Current Protocols in Molecular Biology,* 2004, John Wiley & Sons Inc and Fluorescence In Situ Hybridization: Technical Overview by John M. S. Bartlett in *Molecular Diagnosis of Cancer, Methods and Protocols,* 2$^{nd}$ ed, 77-88 (2004).

Alternatively, the protein products expressed from the mRNAs may be assayed by immunohistochemistry of tumour samples, solid phase immunoassay with microtiter plates, Western blotting, 2-dimensional SDS-polyacrylamide gel electrophoresis, ELISA, flow cytometry and other methods known in the art for detection of specific proteins. Detection methods would include the use of site specific antibodies. The skilled person will recognize that all such well-known techniques for detection of upregulation of cyclin E, or loss of p21 or p27, or detection of $CDCl_4$ variants could be applicable in the present case.

Therefore, all of these techniques could also be used to identify tumours particularly suitable for treatment with the compounds described herein.

Tumours with mutants of $CDCl_4$ or up-regulation, in particular over-expression, of cyclin E or loss of p21 or p27 may be particularly sensitive to CDK inhibitors. Tumours may preferentially be screened for up-regulation, in particular over-expression, of cyclin E or loss of p21 or p27 or for $CDCl_4$ variants prior to treatment. See Harwell et al., *J. Biol. Chem.* 279(13): 12695-12705 (2004); Rajagopalan et al., *Nature* 428(6978): 77-81 (2004).

Patients with mantle cell lymphoma (MCL) could be selected for treatment with a compound described herein using diagnostic tests outlined herein. MCL is a distinct clinicopathologic entity of non-Hodgkin's lymphoma, characterized by proliferation of small to medium-sized lymphocytes with co-expression of CD5 and CD20, an aggressive and incurable clinical course, and frequent t(11;14)(q13;q32) translocation. Over-expression of cyclin D1 mRNA, found in mantle cell lymphoma (MCL), is a critical diagnostic marker. Yatabe et al., Blood 95(7): 2253-2261 (2000) proposed that cyclin D1-positivity should be included as one of the standard criteria for MCL, and that innovative therapies for this incurable disease should be explored on the basis of the new criteria. Jones et al., *J. Mol. Diagn.* 6(2): 84-89 (2004) developed a real-time, quantitative, reverse transcription PCR assay for cyclin D1 (CCND1) expression to aid in the diagnosis of mantle cell lymphoma (MCL). Howe et al., *Clin. Chem.* 50(1): 80-87 (2004) used real-time quantitative RT-PCR to evaluate cyclin D1 mRNA expression and found that quantitative RT-PCR for cyclin D1 mRNA normalized to CD 19 mRNA can be used in the diagnosis of MCL in blood, marrow, and tissue. Alternatively, patients with breast cancer could be selected for treatment with a CDK inhibitor using diagnostic tests outline above. Tumour cells commonly overexpress cyclin E and it has been shown that cyclin E is over-expressed in breast cancer. Harwell et al., Cancer Res. 60: 481-489 (2000). Breast cancer, in particular, may be treated with a CDK inhibitor as described herein.

In addition, the cancer may be analysed for INK4a and RB loss of function, and cyclin D1 or CDK4 overexpression or CDK4 mutation. RB loss and mutations inactivating p16NK4a function or hypermethylation of p16INK4a occur in many tumour types. Rb is inactivated in 100% retinoblastomas and in 90% of small cell lung carcinomas. Cyclin D1 is amplified in 40% of head and neck, over-expressed in 50% of breast cancers and 90% of mantle cell lymphomas. p16 is deleted in 60% of non-small lung carcinomas and in 40% of pancreatic cancers. CDK4 is amplified in 20% of sarcomas and in 10% of gliomas. Events resulting in RB or p16NK4a inactivation through mutation, deletion, or epigenetic silencing, or in the overexpression of cyclin D1 or Cdk4 can be identified by the techniques outlined herein. Tumours with up-regulation, in particular over-expression of cyclin D or CDK4 or loss of INK4a or RB may be particularly sensitive to CDK inhibitors. Thus, the patient may be subjected to a diagnostic test to detect a marker characteristic of over-expression of cyclin D or CDK4 or loss of INK4a or RB.

Cancers that experience INK4a and RB loss of function and cyclin D1 or CDK4 overexpression, include small cell lung cancer, non-small cell lung cancer, pancreatic cancer, breast cancer, glioblastoma multiforme, T cell ALL and mantle cell lymphoma. Therefore patients with small cell lung cancer, non-small cell lung cancer, pancreatic cancer, breast cancer, glioblastoma multiforme, T cell ALL or mantle cell lymphoma could be selected for treatment with a CDK inhibitor using diagnostic tests outlined above and may in particular be treated with a CDK inhibitor as provided herein.

Patients with specific cancers caused by aberrations in the D-Cyclin-CDK4/6-INK4-Rb pathway could be identified by using the techniques described herein and then treated with a CDK4 inhibitor as provided. Examples of abnormalities that activate or sensitise tumours to CDK4 signal include, receptor activation e.g., Her-2/Neu in breast cancer, ras mutations for example in pancreatic, colorectal or lung cancer, raf mutations for example in melanoma, p16 mutations for example in melanoma, p16 deletions for example in lung cancer, p16 methylation for example in lung cancer or cyclin D overexpression for example in breast cancer. Thus, a patient could be selected for treatment with a compound described herein using diagnostic tests as outlined herein to identify up-regulation of the D-Cyclin-CDK4/6-INK4-Rb pathway for example by overexpression of cyclin D, mutation of CDK4, mutation or depletion of pRb, deletion of p16-INK4, mutation, deletion or methylation of p16, or by activating events upstream of the CDK4/6 kinase e.g., Ras mutations or Raf mutations or hyperactive or over-expressed receptors such as Her-2/Neu.

The compounds described herein are particularly advantageous in that they are selective inhibitors of CDK4 over other cyclin dependent kinases. Compounds of this class have been previously described, but the compounds described herein have increased potency and selectivity of CDK4 over other cyclin dependent kinases. See e.g., U.S. Pat. Nos. 6,936,612; 8,685,980; 8,324,225; and U.S. Pat. Pub. No. US 20160220569.

The inhibition of protein kinase activity by the compounds described herein may be measured using a number of assays available in the art. Examples of such assays are described in the Exemplification section below.

Pharmaceutical Compositions

The language "effective amount" of the compound is that amount necessary or sufficient to treat or prevent a protein kinase-associated disorder, e.g., prevent the various morphological and somatic symptoms of a protein kinase-associated disorder, and/or a disease or condition described herein. In an example, an effective amount of the compound described herein is the amount sufficient to treat a protein kinase-associated disorder in a subject. The effective amount can vary depending on such factors as the size and weight of the subject, the type of illness, or the particular compound described herein. For example, the choice of the compound described herein can affect what constitutes an "effective amount." One of ordinary skill in the art would be able to study the factors contained herein and make the determination regarding the effective amount of the compounds described herein without undue experimentation.

The regimen of administration can affect what constitutes an effective amount. The compound described herein can be administered to the subject either prior to or after the onset of a protein kinase-associated disorder. Further, several divided dosages as well as staggered dosages, can be administered daily or sequentially, or the dose can be continuously infused, or can be a bolus injection. Further, the dosages of the compound(s) described herein can be proportionally increased or decreased as indicated by the exigencies of the therapeutic or prophylactic situation.

Compounds described herein may be used in the treatment of states, disorders or diseases as described herein, or for the manufacture of pharmaceutical compositions for use in the treatment of these diseases. Methods of use of the compounds described herein in the treatment of these diseases, or pharmaceutical preparations having the compounds described herein for the treatment of these diseases.

The language "pharmaceutical composition" includes preparations suitable for administration to mammals, e.g., humans. When the compounds described herein are administered as pharmaceuticals to mammals, e.g., humans, they can be given per se or as a pharmaceutical composition containing, for example, 0.1% to 99.5% (preferably, 1% to 90%) of active ingredient in combination with a pharmaceutically acceptable excipient.

The phrase "pharmaceutically acceptable excipient" includes any pharmaceutically acceptable material, composition, or vehicle, suitable for administering the compounds described herein to mammals. The excipient includes liquid or solid filler, diluent, excipient, solvent or encapsulating material, involved in carrying or transporting the subject agent from one organ, or portion of the body, to another organ, or portion of the body. Each excipient must be "acceptable" in the sense of being compatible with the other ingredients of the formulation and not injurious to the patient. Some examples of materials which can serve as pharmaceutically acceptable excipients include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers, or lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, α-tocopherol, and the like; and metal chelating agents, such as citric acid, ethylenediamine tetraacetic acid (EDTA), sorbitol, tartaric acid, phosphoric acid, and the like.

Formulations described herein include those suitable for oral, nasal, topical, buccal, sublingual, rectal, vaginal, and/or parenteral administration. The formulations may conveniently be presented in unit dosage form and may be prepared by any methods well known in the art of pharmacy. The amount of active ingredient that can be combined with an excipient material to produce a single dosage form will generally be that amount of the compound that produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound as described herein with the excipient and, optionally, one or more accessory ingredients. In general, the formulations are prepared by uniformly and intimately bringing into association a compound described herein with liquid excipients, or finely divided solid excipients, or both, and then, if necessary, shaping the product.

Formulations described herein suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound described herein as an active ingredient. A compound described herein may also be administered as a bolus, electuary, or paste.

In solid dosage forms described herein for oral administration (capsules, tablets, pills, dragees, powders, granules and the like), the active ingredient is mixed with one or more pharmaceutically acceptable excipients, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof, and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions described herein, such as dragees, capsules, pills and granules, may optionally be scored or prepared with coatings and shells, such as enteric coatings and other coatings well known in the pharmaceutical-formulating art. They may also be formulated to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions that can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner Examples of embedding compositions that can be used include polymeric substances and waxes. The active ingredient can also be in micro-encapsulated form, if appropriate, with one or more of the above-described excipients.

Liquid dosage forms for oral administration of the compounds described herein include pharmaceutically acceptable emulsions, microemulsions, solutions, suspensions, syrups, or elixirs. In addition to the active ingredient, the liquid dosage forms may contain inert diluent commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying agents, suspending agents, sweetening, flavoring, coloring, perfuming, preservative agents, or combinations thereof.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions described herein for rectal or vaginal administration may be presented as a suppository, which may be prepared by mixing one or more compounds described herein with one or more suitable nonirritating excipients or excipients comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations described herein which are suitable for vaginal administration also include pessaries, tampons, creams, gels, pastes, foams or spray formulations containing such excipients as are known in the art to be appropriate.

Dosage forms for the topical or transdermal administration of a compound described herein include powders, sprays, ointments, pastes, creams, lotions, gels, solutions, patches and inhalants. The active compound may be mixed under sterile conditions with a pharmaceutically acceptable excipient, and with any preservatives, buffers, or propellants that may be required.

The ointments, pastes, creams, and gels may contain, in addition to an active compound described herein, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound described herein, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound described herein to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this disclosure.

Pharmaceutical compositions described herein suitable for parenteral administration comprise one or more compounds described herein in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous excipients that may be employed in the pharmaceutical compositions described herein include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents, dispersing agents, or combinations thereof. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution, which in turn, may depend upon crystal size and crystalline form. Alternatively, delayed absorption of a parenterally administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissue.

The preparations described herein may be given orally, parenterally, topically, or rectally. They are of course given by forms suitable for each administration route. For example, they are administered in tablets or capsule form, by injection, inhalation, eye lotion, ointment, suppository, etc., administration by injection, infusion or inhalation; topical by lotion or ointment; and rectal by suppositories. Oral and/or IV administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, and intrasternal injection or infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

The subject treated is typically a human subject, although it is to be understood the methods described herein are effective with respect to other animals, such as mammals and vertebrate species. More particularly, the term subject can include animals used in assays such as those used in preclinical testing including but not limited to mice, rats, monkeys, dogs, pigs and rabbits; as well as domesticated swine (pigs and hogs), ruminants, equine, poultry, felines, bovines, murines, canines, and the like.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds described herein, which may be used in a suitable hydrated form, and/or the pharmaceutical compositions described herein, are formulated into pharmaceutically acceptable dosage forms by conventional methods known to those of skill in the art.

Actual dosage levels of the active ingredients in the pharmaceutical compositions described herein may be varied to obtain an amount of the active ingredient that is effective to achieve the desired therapeutic response for a particular patient, composition, and mode of administration, without being toxic to the patient.

The selected dosage level will depend upon a variety of factors including the activity of the particular compound described herein employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds described herein employed in the pharmaceutical composition at levels lower than that required in order to achieve the desired therapeutic effect and gradually increase the dosage until the desired effect is achieved.

In general, a suitable daily dose of a compound described herein will be that amount of the compound that is the lowest dose effective to produce a therapeutic effect. Such an effective dose will generally depend upon the factors described herein. Generally, intravenous and subcutaneous doses of the compounds described herein for a patient, when used for the indicated analgesic effects, will range from about 0.0001 to about 200 mg per kilogram of body weight per day, more preferably from about 0.01 to about 50 mg per kg per day, and still more preferably from about 1.0 to about 200 mg per kg per day. An effective amount is that amount treats a protein kinase-associated disorder.

When used in the context of a dosage amount, e.g., $mg/m^2$, the numerical weight refers to the weight of a compound described herein, exclusive of any salt, counterion, and so on.

Therefore, to obtain the equivalent of 100 $mg/m^2$ of a compound described herein, it would be necessary to utilize more than 100 $mg/m^2$ of its salt, due to the additional weight of the salt.

If desired, the effective daily dose of the active compound may be administered as two, three, four, five, six or more sub-doses administered separately at appropriate intervals throughout the day, optionally, in unit dosage forms.

While it is possible for a compound described herein to be administered alone, it is preferable to administer the compound as a pharmaceutical composition.

Synthetic Procedures

The compounds described herein are prepared from commonly available compounds using procedures known to those skilled in the art, including any one or more of the following conditions without limitation:

Within the scope of this disclosure, only a readily removable group that is not a constituent of the particular desired end product of the compounds described herein is designated a "protecting group," unless the context indicates otherwise. The protection of functional groups by such protecting groups, the protecting groups themselves, and their cleavage reactions are described for example in standard reference works, such as e.g., Science of Synthesis: Houben-Weyl Methods of Molecular Transformation. Georg Thieme Verlag, Stuttgart, Germany (2005); McOmie, "Protective Groups in Organic Chemistry," Plenum Press, London and New York (1973); Greene and Wuts, "Protective Groups in Organic Synthesis," Third edition, Wiley, New York (1999); Gross and Meienhofer, eds., "The Peptides"; Vol. 3 Academic Press, London and New York (1981). A characteristic of protecting groups is that they can be removed readily (i.e., without the occurrence of undesired secondary reactions) for example by solvolysis, reduction, photolysis or alternatively under physiological conditions (e.g., by enzymatic cleavage).

Salts of the compounds described herein having at least one salt-forming group may be prepared in a manner known per se. For example, salts of the compounds described herein having acid groups may be formed, for example, by treating the compounds with metal compounds, such as alkali metal salts of suitable organic carboxylic acids, e.g., the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of the compounds described herein are obtained in customary manner, e.g., by treating the compounds with an acid or a suitable anion exchange reagent. Internal salts of the compounds described herein containing acid and basic salt-forming groups, e.g., a free carboxy group and a free amino group, may be formed, e.g., by the neutralisation of salts, such as acid addition salts, to the isoelectric point, e.g., with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable as described herein can be separated in a manner known per se into the individual isomers; diastereoisomers can be separated, for example, by partitioning between polyphasic solvent mixtures, recrystallisation and/or chromatographic separation, for example over silica gel or by, e.g., medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials. Intermediates and final products can be worked up and/or purified according to standard methods, e.g., using chromatographic methods, distribution methods, (re-) crystallization, and the like.

General Process Conditions

The following applies in general to all processes mentioned throughout this disclosure. The process steps to synthesize the compounds described herein can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g., in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80° C. to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described in Science of Synthesis: Houben-Weyl Methods of Molecular Transformation. Georg Thieme Verlag, Stuttgart, Germany 2005.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of those solvents, for example aqueous solutions, unless otherwise indicated in the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

Other embodiments are forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process as described herein is produced under the process conditions and processed further in situ.

Prodrugs

Also described are pharmaceutical compositions containing, and methods of treating protein kinase-associated disorders through administering, pharmaceutically acceptable prodrugs of compounds of the compounds described herein. For example, compounds described herein having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds described herein. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews* 19: 115 (1996). Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described herein, are also encompassed. Prodrugs of this type are described by TenBrink et al., *J. Med. Chem.,* 39: 10 (1996). Free amines can also be derivatized as amides, sulfonamides, or phosphonamides. All of these prodrug moieties may incorporate groups including but not limited to ether, amine, or carboxylic acid functionalities.

Any reference to a compound described herein is therefore to be understood as referring also to the corresponding pro-drugs of the compound described herein, as appropriate and expedient.

Combinations

The compounds described herein may also be used in combination with other agents, e.g., an additional protein kinase inhibitor that is or is not a compound described herein, for treatment of a protein kinase-associated disorder in a subject.

By the term "combination" is meant either a fixed combination in one dosage unit form, or a kit of parts for the combined administration where a compound described herein and a combination partner may be administered independently at the same time or separately within time intervals that especially allow that the combination partners show a cooperative, e.g., synergistic, effect, or any combination thereof.

The compounds described herein may be administered, simultaneously or sequentially, with an antiinflammatory, antiproliferative, chemotherapeutic agent, immunosuppressant, anti-cancer, cytotoxic agent or kinase inhibitor other than a compound described herein or salt thereof. Further examples of agents that may be administered in combination with the compounds described herein include, but are not limited to, a PTK inhibitor, cyclosporin A, CTLA4-Ig, antibodies selected from anti-ICAM-3, anti-IL-2 receptor, anti-CD45RB, anti-CD2, anti-CD3, anti-CD4, anti-CD80, anti-CD86, and monoclonal antibody OKT3, agents blocking the interaction between CD40 and gp39, fusion proteins constructed from CD40 and gp39, inhibitors of NF-kappa B function, non-steroidal antiinflammatory drugs, steroids, gold compounds, antiproliferative agents, FK506, mycophenolate mofetil, cytotoxic drugs, TNF-α inhibitors, anti-TNF antibodies or soluble TNF receptor, rapamycin, leflunomide, cyclooxygenase-2 inhibitors, paclitaxel, cisplatin, carboplatin, doxorubicin, carminomycin, daunorubicin, aminopterin, methotrexate, methopterin, mitomycin C, ecteinascidin 743, porfiromycin, 5-fluorouracil, 6-mercaptopurine, gemcitabine, cytosine arabinoside, podophyllotoxin, etoposide, etoposide phosphate, teniposide, melphalan, vinblastine, vincristine, leurosidine, epothilone, vindesine, leurosine, or derivatives thereof.

The compound described herein and any additional agent may be formulated in separate dosage forms. Alternatively, to decrease the number of dosage forms administered to a patient, the compound described herein and any additional agent may be formulated together in any combination. For example, the compound described herein inhibitor may be formulated in one dosage form and the additional agent may be formulated together in another dosage form. Any separate dosage forms may be administered at the same time or different times.

Alternatively, a composition described herein comprises an additional agent as described herein. Each component may be present in individual compositions, combination compositions, or in a single composition.

Chemotherapeutic Agents

As contemplated herein, the compounds described herein are orally or intravenously administered to a subject undergoing an anti-cancer therapeutic treatment regimen, for example a chemotherapeutic treatment regimen, prior to the subject receiving the anti-cancer therapy. As used herein the term "chemotherapy" or "chemotherapeutic agent" refers to treatment with a cytostatic or cytotoxic agent (i.e., a compound) to reduce or eliminate the growth or proliferation of undesirable cells, for example cancer cells. Thus, as used herein, "chemotherapy" or "chemotherapeutic agent" refers to a cytotoxic or cytostatic agent used to treat a proliferative disorder, for example cancer. The cytotoxic effect of the agent can be, but is not required to be, the result of one or more of nucleic acid intercalation or binding, DNA or RNA alkylation, inhibition of RNA or DNA synthesis, the inhibition of another nucleic acid-related activity (e.g., protein synthesis), or any other cytotoxic effect. In one embodiment, the chemotherapeutic agent is selected from etoposide, carboplatin, cisplatin, and topotecan, or a combination thereof. In one embodiment, the chemotherapeutic agent is topotecan. In one embodiment, the chemotherapeutic agent is cisplatin. In one embodiment, the chemotherapeutic agent is carboplatin. In one embodiment, the chemotherapeutic agent is etoposide.

Thus, a "cytotoxic agent" can be any one or any combination of compounds also described as "antineoplastic" agents or "chemotherapeutic agents." Such compounds include, but are not limited to, DNA damaging compounds and other chemicals that can kill cells. "DNA damaging chemotherapeutic agents" include, but are not limited to, alkylating agents, DNA intercalators, protein synthesis inhibitors, inhibitors of DNA or RNA synthesis, DNA base analogs, topoisomerase inhibitors, and telomerase inhibitors or telomeric DNA binding compounds. For example, alkylating agents include alkyl sulfonates, such as busulfan, improsulfan, and piposulfan; aziridines, such as a benzodizepin, carboquone, meturedepa, and uredepa; ethyleneimines and methylmelamine, such as altretamine, triethylenemelamine, triethylenephosphoramide, triethylenethiophosphoramide, and trimethylolmelamine; nitrogen mustards such as chlorambucil, chlornaphazine, cyclophosphamide, estramustine, iphosphamide, mechlorethamine, mechlorethamine oxide hydrochloride, melphalan, novembichine, phenesterine, prednimustine, trofosfamide, and uracil mustard; and nitroso ureas, such as carmustine, chlorozotocin, fotemustine, lomustine, nimustine, and ranimustine.

Antibiotics used in the treatment of cancer include dactinomycin, daunorubicin, doxorubicin, idarubicin, bleomycin sulfate, mytomycin, plicamycin, and streptozocin. Chemotherapeutic antimetabolites include mercaptopurine, thioguanine, cladribine, fludarabine phosphate, fluorouracil (5-FU), floxuridine, cytarabine, pentostatin, methotrexate, and azathioprine, acyclovir, adenine β-1-D-arabinoside, amethopterin, aminopterin, 2-aminopurine, aphidicolin, 8-azaguanine, azaserine, 6-azauracil, 2'-azido-2'-deoxynucleosides, 5-bromodeoxycytidine, cytosine β-1-D-arabinoside, diazooxonorleucine, dideoxynucleosides, 5-fluorodeoxycytidine, 5-fluorodeoxyuridine, and hydroxyurea.

Chemotherapeutic protein synthesis inhibitors include abrin, aurintricarboxylic acid, chloramphenicol, colicin E3, cycloheximide, diphtheria toxin, edeine A, emetine, erythromycin, ethionine, fluoride, 5-fluorotryptophan, fusidic acid, guanylyl methylene diphosphonate and guanylyl imidodiphosphate, kanamycin, kasugamycin, kirromycin, and O-methyl threonine. Additional protein synthesis inhibitors include modeccin, neomycin, norvaline, pactamycin, paromomycine, puromycin, ricin, shiga toxin, showdomycin, sparsomycin, spectinomycin, streptomycin, tetracycline, thiostrepton, and trimethoprim. Inhibitors of DNA synthesis, include alkylating agents such as dimethyl sulfate, mitomycin C, nitrogen and sulfur mustards; intercalating agents, such as acridine dyes, actinomycins, adriamycin, anthracenes, benzopyrene, ethidium bromide, propidium diiodide-intertwining; and other agents, such as distamycin and netropsin. Topoisomerase inhibitors, such as coumermycin, nalidixic acid, novobiocin, and oxolinic acid; inhibitors of cell division, including colcemide, colchicine, vinblastine, and vincristine; and RNA synthesis inhibitors including actinomycin D, α-amanitine and other fungal amatoxins, cordycepin (3'-deoxyadenosine), dichlororibofuranosyl benzimidazole, rifampicine, streptovaricin, and streptolydigin also can be used as the DNA damaging compound.

Current chemotherapeutic agents whose toxic effects can be mitigated by the presently disclosed dosages of the compounds described herein include, but are not limited to, adriamycin, 5-fluorouracil (5FU), 6-mercaptopurine, gemcitabine, melphalan, chlorambucil, mitomycin, irinotecan, mitoxantrone, etoposide, camptothecin, topotecan, irinotecan, exatecan, lurtotecan, actinomycin-D, mitomycin, cisplatin, hydrogen peroxide, carboplatin, procarbazine, mechlorethamine, cyclophosphamide, ifosfamide, melphalan, chlorambucil, busulfan, nitrosurea, dactinomycin, daunorubicin, doxorubicin, bleomycin, plicomycin, tamoxifen, taxol, transplatinum, vinblastine, vinblastin, carmustine, cytarabine, mechlorethamine, chlorambucil, streptozocin, lomustine, temozolomide, thiotepa, altretamine, oxaliplatin, campothecin, topotecan, and methotrexate, and the like, and similar acting-type agents. In one embodiment, the DNA damaging chemotherapeutic agent is selected from the group consisting of cisplatin, carboplatin, camptothecin, doxorubicin, and etoposide. In one embodiment, the DNA damaging chemotherapeutic agent is topotecan. In one embodiment, the DNA-damaging chemotherapeutic agent is etoposide. In one embodiment, the DNA damaging chemotherapeutic agent is carboplatin. In one embodiment, the DNA damaging chemotherapeutic agent is a combination of etoposide and carboplatin.

In certain alternative embodiments, compounds described herein in a dosage described herein is also used for an anti-cancer or anti-proliferative effect in combination with a chemotherapeutic to treat a CDK4/6 replication independent, such as an Rb-negative cancer or proliferative disorder. Compounds described herein, under certain conditions, may provide an additive or synergistic effect to the chemotherapeutic, resulting in a greater anti-cancer effect than seen with the use of the chemotherapeutic alone. In one embodiment, the compounds described herein can be combined with one or more of the chemotherapeutic compounds described herein. In one embodiment, the compounds described herein can be combined with a chemotherapeutic selected from, but not limited to, tamoxifen, midazolam, letrozole, bortezomib, anastrozole, goserelin, an mTOR inhibitor, a PI3 kinase inhibitor, a dual mTOR-PI3K inhibitor, a Bruton's tyrosine kinase (BTK) inhibitor, a spleen tyrosine kinase (Syk) inhibitor, a MEK inhibitor, a RAS inhibitor, an ALK inhibitor, an HSP inhibitor (for example, an HSP70 or an HSP 90 inhibitor, or a combination thereof), a BCL-2 inhibitor, an apoptotic inducing compound, an AKT inhibitor, including but not limited to, MK-2206, GSK690693, Perifosine, (KRX-0401), GDC-0068, Triciribine, AZD5363, Honokiol, PF-04691502, and Miltefosine, a PD-1 inhibitor including but not limited to, nivolumab, CT-011, MK-3475, BMS936558, and AMP-514 or a FLT-3 inhibitor, including but not limited to, P406, dovitinib, quizartinib (AC220), amuvatinib (MP-470), tandutinib (MLN518), ENMD-2076, and KW-2449, or combinations thereof. Examples of mTOR inhibitors include but are not limited to rapamycin and its analogs, everolimus (Afinitor), temsirolimus, ridaforolimus, sirolimus, and deforolimus.

PI3k inhibitors that may be used in this disclosure are well known. Examples of PI3 kinase inhibitors include but are not limited to wortmannin, demethoxyviridin, perifosine, idelalisib, Pictilisib, Palomid 529, ZSTK474, PWT33597, CUDC-907, and AEZS-136, duvelisib, GS-9820, GDC-0032 (2-[4-[2-(2-Isopropyl-5-methyl-1,2,4-triazol-3-yl)-5,6-dihydroimidazo[1,2-d][1,4]benzoxazepin-9-yl]pyrazol-1-yl]-2-methylpropanamide), MLN-1117 ((2R)-1-Phenoxy-2-butanyl hydrogen (S)-methylphosphonate; or Methyl(oxo){[(2R)-1-phenoxy-2-butanyl]oxy}phosphonium)), BYL-719 ((2S)—N1-[4-Methyl-5-[2-(2,2,2-trifluoro-1,1-dimethylethyl)-4-pyridinyl]-2-thiazolyl]-1,2-pyrrolidinedicarboxamide), GSK2126458 (2,4-Difluoro-N-{2-(methyloxy)-5-[4-(4-pyridazinyl)-6-quinolinyl]-3-pyridinyl}benzenesulfonamide), TGX-221 ((±)-7-Methyl-2-(morpholin-4-yl)-9-(1-phenylaminoethyl)-pyrido[1,2-a]-pyrimidin-4-one), GSK2636771 (2-Methyl-1-(2-methyl-3-(trifluoromethyl)benzyl)-6-morpholino-1H-benzo[d]imidazole-4-carboxylic acid dihydrochloride), KIN-193 ((R)-2-((1-(7-methyl-2-morpholino-4-oxo-4H-pyrido[1,2-a]pyrimidin-9-yl)ethyl)amino)benzoic acid), TGR-1202/RP5264, GS-9820 ((S)-1-(4-((2-(2-aminopyrimidin-5-yl)-7-methyl-4-mohydroxypropan-1-one), GS-1101 (5-fluoro-3-phenyl-2-([S)]-1-[9H-purin-6-ylamino]-propyl)-3H-quinazolin-4-one), AMG-319, GSK-2269557, SAR245409 (N-(4-(N-(3-((3,5-dimethoxyphenyl)amino)quinoxalin-2-yl)sulfamoyl)phenyl)-3-methoxy-4 methylbenzamide), BAY80-6946 (2-amino-N-(7-methoxy-8-(3-morpholinopropoxy)-2,3-dihydroimidazo[1,2-c]quinaz), AS 252424 (5-[1-[5-(4-Fluoro-2-hydroxy-phenyl)-furan-2-yl]-meth-(Z)-ylidene]-thiazolidine-2,4-dione), CZ 24832 (5-(2-amino-8-fluoro-[1,2,4]triazolo[1,5-a]pyridin-6-yl)-N-tert-butylpyridine-3-sulfonamide), buparlisib (5-[2,6-Di(4-morpholinyl)-4-pyrimidinyl]-4-(trifluoromethyl)-2-pyridinamine), GDC-0941 (2-(1H-Indazol-4-yl)-6-[[4-(methylsulfonyl)-1-piperazinyl]methyl]-4-(4-morpholinyl)thieno[3,2-d]pyrimidine), GDC-0980 ((S)-1-(4-((2-(2-aminopyrimidin-5-yl)-7-methyl-4-morpholinothieno[3,2-d]pyrimidin-6 yl)methyl)piperazin-1-yl)-2-hydroxypropan-1-one (also known as RG7422)), SF1126 ((8S,14S,17S)-14-(carboxymethyl)-8-(3-guanidinopropyl)-17-(hydroxymethyl)-3,6,9,12,15-pentaoxo-1-(4-(4-oxo-8-phenyl-4H-chromen-2-yl)morpholino-4-ium)-2-oxa-7,10,13,16-tetraazaoctadecan-18-oate), PF-05212384 (N-[4-[[4-(Dimethylamino)-1-piperidinyl]carbonyl]phenyl]-N'-[4-(4,6-di-4-morpholinyl-1,3,5-triazin-2-yl)phenyl]urea), LY3023414, BEZ235 (2-Methyl-2-{4-[3-methyl-2-oxo-8-(quinolin-3-yl)-2,3-dihydro-1H-imidazo[4,5-c]quinolin-1-yl]phenyl}propanenitrile), XL-765 (N-(3-(N-(3-(3,5-dimethoxyphenylamino)quinoxalin-2-yl)sulfamoyl)phenyl)-3-methoxy-4-methylbenzamide), and GSK1059615 (5-[[4-(4-Pyridinyl)-6-quinolinyl]methylene]-2,4-thiazolidenedione), PX886 ([(3 aR,6E,9S,9aR,10R,1-1aS)-6-[[bis(prop-2-enyl)amino]methylidene]-5-hydroxy-9-(methoxymethyl)-9a,1-1a-dimethyl-1,4,7-trioxo-2,3,3a,9,10,11-hexahydroindeno[4,5h]isochromen-10-yl]acetate (also known as sonolisib)). In one embodiment, the compounds described herein are combined in a single dosage form with the Plk3 inhibitor.

BTK inhibitors for use as described herein are well known. Examples of BTK inhibitors include ibrutinib (also known as PCI-32765)(Imbruvica™)(1-[(3R)-3-[4-amino-3-(4-phenoxy-phenyl)pyrazolo[3,4-d]pyrimidin-1-yl]piperidin-1-yl]prop-2-en-1-one), dianilinopyrimidine-based inhibitors such as AVL-101 and AVL-291/292 (N-(3-((5-fluoro-2-((4-(2-methoxyethoxy)phenyl)amino)pyrimidin-4-yl)amino)phenyl)acrylamide) (Avila Therapeutics) (see US Patent Publication No 20110117073), Dasatinib ([N-(2-chloro-6-methylphenyl)-2-(6-(4-(2-hydroxyethyl)piperazin-1-yl)-2-methylpyrimidin-4-ylamino)thiazole-5-carboxamide], LFM-A13 (alpha-cyano-beta-hydroxy-beta-methyl-N-(2,5-ibromophenyl) propenamide), GDC-0834 ([R—N-(3-(6-(4-(1,4-dimethyl-3-oxopiperazin-2-yl)phenylamino)-4-methyl-5-oxo-4,5-dihydropyrazin-2-yl)-2-methylphenyl)-4,5,6,7-tetrahydrobenzo[b]thiophene-2-carboxamide], CGI-560 4-(tert-butyl)-N-(3-(8-(phenylamino)imidazo[1,2-a]pyrazin-6-yl)phenyl)benzamide, CGI-1746 (4-(tert-butyl)-N-(2-methyl-3-(4-methyl-6-((4-(morpholine-4-carbonyl)phenyl)amino)-5-oxo-4,5-dihydropyrazin-2-yl)phenyl)benzamide), CNX-774 (4-(4-((4-((3-acrylamidophenyl)amino)-5-fluoropyrimidin-2-yl)amino)phenoxy)-N-methylpicolinamide), CTA056 (7-benzyl-1-(3-(piperidin-1-yl)propyl)-2-(4-(pyridin-4-yl)phenyl)-1H-imidazo[4,5-g]quinoxalin-6(5H)-one), GDC-0834 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), GDC-0837 ((R)—N-(3-(6-((4-(1,4-dimethyl-3-oxopiperazin-2-yl)phenyl)amino)-4-methyl-5-oxo-4,5-dihydropyrazin-2-yl)-2-methylphenyl)-4,5,6,7-tetrahydrobenzo[b]thiophene-2-carboxamide), HM-71224, ACP-196, ONO-4059 (Ono Pharmaceuticals), PRT062607 (4-((3-(2H-1,2,3-triazol-2-yl)phenyl)amino)-2-(((1R,2S)-2-aminocyclohexyl)amino)pyrimidine-5-carboxamide hydrochloride), QL-47 (1-(1-acryloylindolin-6-yl)-9-(1-methyl-1H-pyrazol-4-yl)benzo[h][1,6]naphthyridin-2(1H)-one), and RN486 (6-cyclopropyl-8-fluoro-2-(2-hydroxymethyl-3-{1-methyl-5-[5-(4-methyl-piperazin-1-yl)-pyridin-2-ylamino]-6-oxo-1,6-dihydro-pyridin-3-yl}-phenyl)-2H-isoquinolin-1-one), and other molecules capable of inhibiting BTK activity, for example those BTK inhibitors disclosed in Akinleye et al, *J. Hemat. Oncol.* 6: 59 (2013), the entirety of which is incorporated herein by reference. In one embodiment, the compounds described herein are combined in a single dosage form with the BTK inhibitor.

Syk inhibitors for use as described herein are well known, and include, for example, cerdulatinib (4-(cyclopropylamino)-2-((4-(4-(ethylsulfonyl)piperazin-1-yl)phenyl)amino)pyrimidine-5-carboxamide), entospletinib (6-(1H-indazol-6-yl)-N-(4-morpholinophenyl)imidazo[1,2-a]pyrazin-8-amine), fostamatinib ([6-({5-Fluoro-2-[(3,4,5-trimethoxyphenyl)amino]-4-pyrimidinyl}amino)-2,2-dimethyl-3-oxo-2,3-dihydro-4H-pyrido[3,2-b][1,4]oxazin-4-yl]methyl dihydrogen phosphate), fostamatinib disodium salt (sodium(6-((5-fluoro-2-((3,4,5-trimethoxyphenyl)amino)pyrimidin-4-yl)amino)-2,2-dimethyl-3-oxo-2H-pyrido[3,2-b][1,4]oxazin-4(3H)-yl)methyl phosphate), BAY 61-3606 (2-(7-(3,4-Dimethoxyphenyl)-imidazo[1,2-c]pyrimidin-5-ylamino)-nicotinamide HCl), R09021 (6-[(1R,2S)-2-Amino-cyclohexylamino]-4-(5,6-dimethyl-pyridin-2-ylamino)-pyridazine-3-carboxylic acid amide), imatinib (Gleevac; 4-[(4-methylpiperazin-1-yl)methyl]-N-(4-methyl-3-{[4-(pyridin-3-yl)pyrimidin-2-yl]amino}phenyl)benzamide), staurosporine, GSK143 (2-(((3R,4R)-3-aminotetrahydro-2H-pyran-4-yl)amino)-4-(p-tolylamino)pyrimidine-5-carboxamide), PP2 (1-(tert-butyl)-3-(4-chlorophenyl)-1H-pyrazolo[3,4-d]pyrimidin-4-amine), PRT-060318 (2-(((1R,2S)-2-aminocyclohexyl)amino)-4-(m-tolylamino) pyrimidine-5-carboxamide), PRT-062607 (4-((3-(2H-1,2,3-triazol-2-yl)phenyl)amino)-2-(((1R,2S)-2-aminocyclohexyl)amino)pyrimidine-5-carboxamide hydrochloride), R112 (3,3'-((5-fluoropyrimidine-2,4-diyl) bis(azanediyl))diphenol), R348 (3-Ethyl-4-methylpyridine), R406 (6-((5-fluoro-2-((3,4,5-trimethoxyphenyl)amino)pyrimidin-4-yl)amino)-2,2-dimethyl-2H-pyrido[3,2-b][1,4] oxazin-3(4H)-one), YM193306, 7-azaindole, piceatannol, ER-27319, Compound D, PRT060318, luteolin, apigenin, quercetin, fisetin, myricetin, or morin. See Singh et al. *J. Med. Chem.* 55: 3614-3643 (2012). In one embodiment, the compounds described herein are combined in a single dosage form with the Syk inhibitor.

MEK inhibitors for use as described herein are well known, and include, for example, tametinib/GSK1 120212 (N-(3-{3-Cyclopropyl-5-[(2-fluoro-4-iodophenyl)amino]-6,8-dimethyl-2,4,7-trioxo-3,4,6,7-tetrahydropyrido[4,3-d]pyrimidin-1(2H-yl)}phenyl)acetamide), selumetinob (6-(4-bromo-2-chloroanilin)-7-fluoro-N-(2-hydroxyethoxy)-3-methylbenzimidazole-5-carboxamide), pimasertib/AS703026/MSC 1935369 ((S)—N-(2,3-dihydroxypropyl)-3-((2-fluoro-4-iodophenyl)amino)isonicotinamide), XL-518/GDC-0973 (1-({3,4-difluoro-2-[(2-fluoro-4-iodophenyl)amino]phenyl}carbonyl)-3-[(2S)-piperidin-2-yl] azetidin-3-ol), refametinib/BAY869766/RDEAI 19 (N-(3,4-difluoro-2-(2-fluoro-4-iodophenylamino)-6-methoxyphenyl)-1-(2,3-dihydroxypropyl)cyclopropane-1-sulfonamide), PD-0325901 (N-[(2R)-2,3-Dihydroxypropoxy]-3,4-difluoro-2-[(2-fluoro-4-iodophenyl)amino]-benzamide), TAK733 ((R)-3-(2,3-Dihydroxypropyl)-6-fluoro-5-(2-fluoro-4-iodophenylamin)-8-methylpyrido[2,3-d]pyrimidine-4,7(3H,8H)-dione), MEK162/ARRY438162 (5-[(4-Bromo-2-fluorophenyl) amino]-4-fluoro-N-(2-hydroxyethoxy)-1-methyl-1H-benzimidazole-6-carboxamide), R05126766 (3-[[3-Fluoro-2-(methylsulfamoylamino)-4-pyridyl]methyl]-4-methyl-7-pyrimidin-2-yloxychromen-2-one), WX-554, R04987655/CH4987655 (3,4-difluoro-2-((2-fluoro-4-iodophenyl) amino)-N-(2-hydroxyethoxy)-5-((3-oxo-1,2-oxazinan-2yl) methyl)benzamide), or AZD8330 (2-((2-fluoro-4-iodophenyl)amino)-N-(2 hydroxyethoxy)-1,5-dimethyl-6-oxo-1,6-dihydropyridine-3-carboxamide). In one embodiment, the compounds described herein are combined in a single dosage form with the MEK inhibitor.

Raf inhibitors for use as described herein are well known, and include, for example, Vemurafinib (N-[3-[[5-(4-Chlorophenyl)-1H-pyrrolo[2,3-b]pyridin-3-yl]carbonyl]-2,4-difluorophenyl]-1-propanesulfonamide), sorafenib tosylate (4-[4-[[4-chloro-3-(trifluoromethyl)phenyl]carbamoylamino] phenoxy]-N-methylpyridine-2-carboxamide; 4-methylbenzenesulfonate), AZ628 (3-(2-cyanopropan-2-yl)-N-(4-methyl-3-(3-methyl-4-oxo-3,4-dihydroquinazolin-6-ylamino)phenyl)benzamide), NVP-BHG712 (4-methyl-3-(1-methyl-6-(pyridin-3-yl)-1H-pyrazolo[3,4-d]pyrimidin-4-ylamino)-N-(3-(trifluoromethyl)phenyl)benzamide), RAF-265 (1-methyl-5-[2-[5-(trifluoromethyl)-1H-imidazol-2-yl] pyridin-4-yl]oxy-N-[4-(trifluoromethyl)phenyl] benzimidazol-2-amine), 2-Bromoaldisine (2-Bromo-6,7-dihydro-1H,5H-pyrrolo[2,3-c]azepine-4,8-dione), Raf Kinase Inhibitor IV (2-chloro-5-(2-phenyl-5-(pyridin-4-yl)-1H-imidazol-4-yl)phenol), and Sorafenib N-Oxide (4-[4-[[[[4-Chloro-3 (trifluoroMethyl)phenyl]aMino]carbonyl] aMino]phenoxy]-N-Methyl-2pyridinecarboxaMide 1-Oxide). In one embodiment, the compounds described herein are combined in a single dosage form with the Raf inhibitor. In one embodiment, the at least one additional chemotherapeutic agent combined or alternated with the compounds described herein is a protein cell death-1 (PD-1) inhibitor. PD-1 inhibitors are known in the art, and include, for example, nivolumab (BMS), pembrolizumab (Merck), pidilizumab (CureTech/Teva), AMP-244 (Amplimmune/GSK), BMS-936559 (BMS), and MED14736 (Roche/Genentech). In one embodiment, the compounds described herein are combined in a single dosage form with the PD-1 inhibitor.

In one embodiment, the at least one additional chemotherapeutic agent combined or alternated with a selected compound disclosed herein is a B-cell lymphoma 2 (Bcl-2) protein inhibitor. BCL-2 inhibitors are known in the art, and include, for example, ABT-199 (4-[4-[[2-(4-Chlorophenyl)-4,4-dimethylcyclohex-1-en-1-yl]methyl]piperazin-1-yl]-N-[[3-nitro-4-[[(tetrahydro-2H-pyran-4-yl)methyl]amino]phenyl]sulfonyl]-2-[(1H-pyrrolo[2,3-b]pyridin-5-yl)oxy] benzamide), ABT-737 (4-[4-[[2-(4-chlorophenyl)phenyl] methyl]piperazin-1-yl]-N-[4-[[(2R)-4-(dimethylamino)-1-phenylsulfanylbutan-2-yl]amino]-3-nitrophenyl] sulfonylbenzamide), ABT-263 ((R)-4-(4-((4'-chloro-4,4-dimethyl-3,4,5,6-tetrahydro-[1,1'-biphenyl]-2-yl)methyl) piperazin-1-yl)-N-((4-((4-morpholino-1-(phenylthio)butan-2-yl)amino)-3((trifluoromethyl)sulfonyl)phenyl)sulfonyl) benzamide), GX15-070 (obatoclax mesylate, (2Z)-2-[(5Z)-5-[(3,5-dimethyl-1H-pyrrol-2-yl)methylidene]-4-methoxypyrrol-2-ylidene]indole; methanesulfonic acid))), 2-methoxy-antimycin A3, YC137 (4-(4,9-dioxo-4,9-dihydronaphtho[2,3-d]thiazol-2-ylamino)-phenyl ester), pogosin, ethyl 2-amino-6-bromo-4-(1-cyano-2-ethoxy-2-oxoethyl)-4H-chromene-3-carboxylate, Nilotinib-d3, TW-37 (N-[4-[[2-(1,1-Dimethylethyl)phenyl]sulfonyl]phenyl]-2,3,4-trihydroxy-5-[[2-(1-methylethyl)phenyl]methyl] benzamide), Apogossypolone (ApoG2), or G3139 (Oblimersen). In one embodiment, the compounds described herein are administered in the dosage described herein and combined in a single dosage form with the at least one BCL-2 inhibitor.

Examples of RAS inhibitors include but are not limited to Reolysin and siG12D LODER. Examples of ALK inhibitors include but are not limited to Crizotinib, AP26113, and LDK378. HSP inhibitors include but are not limited to Geldanamycin or 17-N-Allylamino-17-demethoxygeldanamycin (17AAG), and Radicicol.

In one embodiment described herein, the compounds described herein are administered in the dosage described herein in combination with a topoisomerase inhibitor. In one aspect, an advantageous treatment of select Rb-negative cancers is disclosed using the compounds described herein a in combination with a topoisomerase inhibitor. In one embodiment, the topoisomerase inhibitor is a topoisomerase I inhibitor or a topoisomerase I and II dual inhibitor. In one embodiment, the topoisomerase inhibitor is a topoisomerase II inhibitor.

In one embodiment, the topoisomerase inhibitor is selected from a topoisomerase I inhibitor. Known topoisomerase I inhibitors useful as described herein include (S)-10-[(dimethylamino)methyl]-4-ethyl-4,9-dihydroxy-1H-pyrano[3',4':6,7]indolizino[1,2-b]quinoline-3,14(4H,12H)-dione monohydrochloride (topotecan), (S)-4-ethyl-4-hydroxy-1H-pyrano[3',4':6,7]indolizino[1,2-b]quinoline-3,14-(4H,12H)-dione (camptothecin), (1 S,9 S)-1-Amino-9-ethyl-5-fluoro-1,2,3,9,12,15-hexahydro-9-hydroxy-4-methyl-10H,13H-benzo(de)pyrano(3',4':6,7)indolizino(1,2-b)quinoline-10,13-dione (exatecan), (7-(4-methylpiperazinomethylene)-10,11-ethylenedioxy-20(S)-camptothecin (lurtotecan), or (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate (irinotecan), (R)-5-ethyl-9,10-difluoro-5-hydroxy-4,5-dihydrooxepino[3',4':6,7]indolizino[1,2-b]quinoline-3,15(1H,13H)-dione (diflomotecan), (4S)-11-((E)-((1-Dimethylethoxy)imino)methyl)-4-ethyl-4-hydroxy-1,12-dihydro-14H-pyrano(3',4':6,7)indolizino(1,2-b)quinoline-3,14(4H)-dione (gimatecan), (S)-8-ethyl-8-hydroxy-15-((4-methylpiperazin-1-yl)methyl)-11,14-dihydro-2H-[1,4]dioxino[2,3-g]pyrano[3',4':6,7]indolizino[1,2-b]quinoline-9,12(3H,8H)-dione (lurtotecan), (4S)-4-Ethyl-4-hydroxy-11-[2-[(1-methylethyl)amino]ethyl]-1H-pyrano[3',4':6,7]indolizino[1,2-b]quinoline-3,14(4H,12H)-dione (belotecan), 6-((1,3-dihydroxypropan-2-yl)amino)-2,10-dihydroxy-12-((2R,3R,4S,5S,6R)-3,4,5-trihydroxy-6-(hydroxymethyl)tetrahydro-2H-pyran-2-yl)-12,13-dihydro-5H-indolo[2,3-a]pyrrolo[3,4-c]carbazole-5,7(6H)-dione (edotecarin), 8,9-dimethoxy-5-(2-N,N-dimethylamino-ethyl)-2,3-methylenedioxy-5H-dibenzo(c,h)(1,6)naphthyridin-6-one (topovale), benzo[6,7]indolizino[1,2-b]quinolin-11(13H)-one (rosettacin), (S)-4-ethyl-4-hydroxy-11-(2-(trimethylsilyl)ethyl)-1H-pyrano[3',4':6,7]indolizino[1,2-b]quinoline-3,14(4H, 12H)-dione (cositecan), tetrakis{(4S)-9-[([1,4'-bipiperidinyl]-1'-carbonyl)oxy]-4,11-diethyl-3,14-dioxo-3,4,12,14-tetrahydro-1H-pyrano[3',4':6,7]indolizino[1,2-b]quinolin-4-yl}N,N',N',N'''-{{methanetetrayltetrakis[methylenepoly(oxyethylene)oxy(1-oxoethylene)]}}tetraglycinate tetrahydrochloride (etirinotecan pegol), 10-hydroxy-camptothecin (HOCPT), 9-nitrocamptothecin (rubitecan), SN38 (7-ethyl-10-hydroxycamptothecin), and 10-hydroxy-9-nitrocamptothecin (CPT109), (R)-9-chloro-5-ethyl-5-hydroxy-10-methyl-12-((4-methylpiperidin-1-yl)methyl)-4,5-dihydrooxepino[3',4':6,7]indolizino[1,2-b]quinoline-3,15(1H, 13H)-dione (elmotecan).

In a particular embodiment, the topoisomerase inhibitor is the topoisomerase I inhibitor (S)-10-[(dimethylamino)methyl]-4-ethyl-4,9-dihydroxy-1H pyrano[3',4':6,7]indolizino[1,2-b]quinoline-3,14(4H,12H)-dione monohydrochloride (topotecan hydrochloride). In one non-limiting example, the compounds described herein are administered in the dosage described herein in combination with a topoisomerase I inhibitor selected from the group consisting of (S)-10-[(dimethylamino)methyl]-4-ethyl-4,9-dihydroxy-1H-pyrano[3',4':6,7]indolizino[1,2-b]quinoline-3,14(4H, 12H)-dione monohydrochloride (topotecan), (S)-4-ethyl-4-hydroxy-1H-pyrano[3',4':6,7]indolizino[1,2-b]quinoline-3,14-(4H, 12H)-dione (camptothecin), (1S,9S)-1-Amino-9-ethyl-5-fluoro-1,2,3,9,12,15-hexahydro-9-hydroxy-4-methyl-10H,13H-benzo(de)pyrano(3',4':6,7)indolizino(1,2-b)quinoline-10,13-dione (exatecan), (7-(4-methylpiperazinomethylene)-10,11-ethylenedioxy-20(S)-camptothecin (lurtotecan), or (S)-4,11-diethyl-3,4,12,14-tetrahydro-4-hydroxy-3,14-dioxo1H-pyrano[3',4':6,7]-indolizino[1,2-b]quinolin-9-yl-[1,4'bipiperidine]-1'-carboxylate (irinotecan). In one embodiment, the topoisomerase I inhibitor is topotecan.

PROTACS

In addition to inhibiting the catalytic function of CDK proteins, another strategy also focuses on their level of expression. Thus the present disclosure also contemplates the use of the novel compounds described herein as Proteolysis Targeting Chimeras or "PROTACS" useful for the suppression of CDK proteins. PROTACS are bivalent inhibitors where the first moiety binds a protein targeted for ubiquitination and the second moiety for binding E3 ubiquitin ligase, thus inducing proximity that leads to ubiquitination of targets and subsequent proteolysis of the target protein in the proteasome. Thus the compounds described herein may readily be made into these chimeras for selective degradation and disruption in the cell. Thus the present disclosure contemplates bivalent compounds or PROTACs, comprising a CDK ligand (or targeting moiety) conjugated to a degradation tag.

As used herein, the term "CDK ligand" encompasses a wide variety of molecules associated with or binding to a CDK protein, including but not limited to CDK1, CDK2, CDK4, CDK6, CDK7 and CDK9. The CDK ligand may be a CDK inhibitor, capable of interfering with the enzymatic activity of the CDK proteins. CDK inhibitors include, but are not limited to, abemaciclib, palbociclib, ribociclib, trilaciclib (GIT28), GIT38 and SHR6390. As used herein, an "inhibitor" may refer to an agent that restrains, retards, or otherwise inhibits enzyme activity. Inhibitors can refer to a drug, compound, or agent that prevents or reduces the expression, transcription, or translation of a gene or protein.

CDK-Replication Dependent Cells and Cyclin-Dependent Kinase Inhibitors

Tissue-specific stem cells and subsets of other resident proliferating cells are capable of self-renewal, meaning that they are capable of replacing themselves throughout the adult mammalian lifespan through regulated replication. Additionally, stem cells divide asymmetrically to produce "progeny" or "progenitor" cells that in turn produce various components of a given organ. For example, in the hematopoietic system, the hematopoietic stem cells give rise to progenitor cells which in turn give rise to all the differentiated components of blood (e.g., white blood cells, red blood cells, and platelets).

Certain proliferating cells, such as HSPCs, require the enzymatic activity of the proliferative kinases cyclin-dependent kinase 4 (CDK4) and/or cyclin-dependent kinase 6 (CDK6) for cellular replication. In contrast, the majority of proliferating cells in adult mammals (e.g., the more differentiated blood-forming cells in the bone marrow) do not require the activity of CDK4 and/or CDK6 (i.e., CDK4/6). These differentiated cells can proliferate in the absence of CDK4/6 activity by using other proliferative kinases, such as cyclin-dependent kinase 2 (CDK2) or cyclin-dependent kinase 1 (CDK1).

The compounds described herein show a marked selectivity for the inhibition of CDK4 and/or CDK6 in comparison to other CDKs, for example CDK2. For example, the compounds described herein provide for a dose-dependent G1-arresting effect on a subject's CDK4/6-replication dependent healthy cells, for example HSPCs or renal epithelial cells, and the methods provided for herein are sufficient to afford chemoprotection to targeted CDK4/6-replication dependent healthy cells during chemotherapeutic agent exposure, for example, during the time period that a DNA-damaging chemotherapeutic agent is capable of DNA-damaging effects on CDK4/6-replication dependent healthy cells in the subject, while allowing for the synchronous and rapid reentry into the cell-cycle by these cells shortly after the chemotherapeutic agent dissipates due to the time-limited CDK4/6 inhibitory effect provided by the compound compared to, e.g., ribociclib, palbociclib, or abemaciclib.

In some embodiments, a CDK4/6-replication dependent healthy cell is a hematopoietic stem progenitor cell. Hematopoietic stem and progenitor cells include, but are not limited to, long term hematopoietic stem cells (LT-HSCs), short term hematopoietic stem cells (ST-HSCs), multipotent progenitors (MPPs), common myeloid progenitors (CMPs), common lymphoid progenitors (CLPs), granulocyte-monocyte progenitors (GMPs), and megakaryocyte-erythroid progenitors (MEPs). Administration of the compounds described herein provides temporary, transient pharmacologic quiescence of hematopoietic stem and/or hematopoietic progenitor cells in the subject.

In some embodiments, the CDK4/6-replication dependent healthy cell may be a cell in a non-hematopoietic tissue, such as, but not limited to, the liver, kidney, pancreas, brain, lung, adrenals, intestine, gut, stomach, skin, auditory system, bone, bladder, ovaries, uterus, testicles, gallbladder, thyroid, heart, pancreatic islets, blood vessels, and the like. In some embodiments, the CDK4/6-replication dependent healthy cell is a renal cell, and in particular a renal epithelial cell, for example, a renal proximal tubule epithelial cell. In some embodiments, a CDK4/6-replication dependent healthy cell is a hematopoietic stem progenitor cell. In some embodiments, the CDK4/6-replication dependent healthy cell may be a cell in a non-hematopoietic tissue, such as, but not limited to, the liver, kidney, pancreas, brain, lung, adrenals, intestine, gut, stomach, skin, auditory system, bone, bladder, ovaries, uterus, testicles, gallbladder, thyroid, heart, pancreatic islets, blood vessels, and the like.

Likewise, the compounds described herein provides for a dose-dependent mitigating effect on CDK4/6-replication dependent healthy cells that have been exposed to toxic levels of chemotherapeutic agents, allowing for repair of DNA damage associated with chemotherapeutic agent exposure and synchronous, rapid reentry into the cell-cycle following dissipation of the CDK4/6 inhibitory effect compared to, e.g., ribociclib, palbociclib, or abemaciclib. In one embodiment, the use of the compounds described herein results in the G1-arresting effect on the subject's CDK4/6-replication dependent healthy cells dissipating following administration of the compounds described herein so that the subject's healthy cells return to or approach their pre-administration baseline cell-cycle activity within less than about 24 hours, 30 hours, 36 hours, or 40 hours, of administration. In one embodiment, the G1-arresting effect dissipates such that the subject's CDK4/6-replication dependent healthy cells return to their pre-administration baseline cell-cycle activity within less than about 24 hours, 30 hours, 36 hours, or 40 hours.

In one embodiment, the use of the compounds described herein results in the G1-arresting effect dissipating such that the subject's CDK4/6-dependent healthy cells return to or approach their pre-administration baseline cell-cycle activity within less than about 24 hours, 30 hours, 36 hours, or 40 hours of the chemotherapeutic agent effect. In one embodiment, the G1-arresting effect dissipates such that the subject's CDK4/6-replication dependent cells return to their pre-administration baseline cell-cycle activity within less than about 24 hours, 30 hours, 36 hours, or 40 hours, or within about 48 hours of the cessation of the chemotherapeutic agent administration. In one embodiment, the CDK4/6-replication dependent healthy cells are HSPCs. In one embodiment, the CDK4/6-dependent healthy cells are renal epithelial cells.

In one embodiment, the use of the compounds described herein results in the G1-arresting effect dissipating so that the subject's CDK4/6-replication dependent healthy cells return to or approach their pre-administration baseline cell-cycle activity within less than about 24 hours, 30 hours, 36 hours, 40 hours, or within less than about 48 hours from the point in which the CDK4/6 inhibitor's concentration level in the subject's blood drops below a therapeutic effective concentration.

In one embodiment, the compounds described herein are used to protect renal epithelium cells during exposure to a chemotherapeutic agent, for example, a DNA damaging chemotherapeutic agent, wherein the renal epithelial cells are transiently prevented from entering S-phase in response to chemotherapeutic agent induced renal tubular epithelium damage for no more than about 24 hours, about 30 hours, about 36 hours, about 40 hours, or about 48 hours from the point in which the compounds described herein concentration level in the subject's blood drops below a therapeutic effective concentration or biological effective concentration, from the cessation of the chemotherapeutic agent effect, or from administration of the compounds described herein.

The compounds described herein may be synchronous in their off-effect, that is, upon dissipation of the G1 arresting effect, CDK4/6-replication dependent healthy cells exposed to the compounds described herein in the concentrations described herein reenter the cell-cycle in a similarly timed fashion. CDK4/6-replication dependent healthy cells that reenter the cell-cycle do so such that the normal proportion of cells in G1 and S are reestablished quickly and efficiently, within less than about 24 hours, 30 hours, 36 hours, 40 hours, or within about 48 hours of the from the point in which the compounds described herein concentration level in the subject's blood drops below a therapeutic effective concentration. This advantageously allows for a larger number of healthy cells to begin replicating upon dissipation of the G1 arrest compared with asynchronous CDK4/6 inhibitors such as ribociclib, palbociclib, or abemaciclib.

In addition, synchronous cell-cycle reentry following G1 arrest using the compounds described herein in concentrations and dosages described herein provides for the ability to time the administration of hematopoietic growth factors to assist in the reconstitution of hematopoietic cell lines to maximize the growth factor effect. In one embodiment described herein, the compounds described herein can be administered in a concerted regimen with a blood growth factor agent. As such, in one embodiment, the use of the compounds described herein and methods described herein are combined with the use of hematopoietic growth factors including, but not limited to, granulocyte colony stimulating factor (G-CSF, for example, sold as Neupogen (filgrastin), Neulasta (peg-filgrastin), or lenograstin), granulocyte-macrophage colony stimulating factor (GM-CSF, for example sold as molgramostim and sargramostim (Leukine)), M-CSF (macrophage colony stimulating factor), thrombopoietin (megakaryocyte growth development factor (MGDF), for example sold as Romiplostim and Eltrombopag) interleukin (IL)-12, interleukin-3, interleukin-11 (adipogenesis inhibiting factor or oprelvekin), SCF (stem cell factor, steel factor, kit-ligand, or KL) and erythropoietin (EPO), and their derivatives (sold as for example epoetin-α as Darbopoetin, Epocept, Nanokine, Epofit, Epogin, Eprex and Procrit; epoetin-β sold as for example NeoRecormon, Recormon and Micera), epoetin-delta (sold as for example Dynepo), epoetin-omega (sold as for example Epomax), epoetin zeta (sold as for example Silapo and Reacrit) as well as for example Epocept, EPOTrust, Erypro Safe, Repoeitin, Vintor, Epofit, Erykine, Wepox, Espogen, Relipoeitin, Shanpoietin, Zyrop and EPIAO). In one embodiment, the compounds described herein are administered prior to administration of the hematopoietic growth factor. In one embodiment, the hematopoietic growth factor administration is timed so that the compounds described herein inhibitory effect on HSPCs has dissipated.

CDK 4/6-Replication Independent Proliferative Disorders

One aspect described herein is a dosing regimen comprising the administration of the compounds described herein that provides a specific PK and/or PD blood profile followed by the administration of a chemotherapeutic agent for the treatment of the CDK 4/6-replication independent cellular proliferation disorder. The subject treated as described herein may be undergoing therapeutic chemotherapy for the treatment of a proliferative disorder that is CDK4/6 replication independent.

CDK 4/6-replication independent cellular proliferation disorders, for example as seen in certain types of cancer, can be characterized by one or a combination of increased activity of cyclin-dependent kinase 1 (CDK1), increased activity of cyclin-dependent kinase 2 (CDK2), loss, deficiency, or absence of retinoblastoma tumor suppressor protein (Rb)(Rb-null), high levels of MYC expression, increased cyclin E1, E2, and increased cyclin A. The cancer may be characterized by reduced expression of the retinoblastoma tumor suppressor protein or a retinoblastoma family member protein or proteins (such as, but not limited to p107 and p130). In one embodiment, the subject is undergoing chemotherapeutic treatment for the treatment of an Rb-null or Rb-deficient cancer, including but not limited to small cell lung cancer, triple-negative breast cancer, HPV-positive head and neck cancer, retinoblastoma, Rb-negative bladder cancer, Rb negative prostate cancer, osteosarcoma, or cervical cancer. Administration of the compounds described herein may allow for a higher dose of a chemotherapeutic agent to be used to treat the disease than the standard dose that would be safely used in the absence of administration of the compounds described herein.

The host or subject, including a human, may be undergoing chemotherapeutic treatment of a non-malignant proliferative disorder, or other abnormal cellular proliferation, such as a tumor, multiple sclerosis, lupus, or arthritis.

Proliferative disorders that are treated with chemotherapy include cancerous and non-cancer diseases. In a typical embodiment, the proliferative disorder is a CDK4/6-replication independent disorder. The compounds described herein are effective in protecting healthy CDK4/6-replication dependent cells, for example HSPCs, during chemotherapeutic treatment of a broad range of tumor types, including but not limited to the following: breast, prostate, ovarian, skin, lung, colorectal, brain (i.e., glioma) and renal. Preferably, the compounds described herein should not compromise the efficacy of the chemotherapeutic agent or arrest G1 arrest the cancer cells. Many cancers do not depend on the activities of CDK4/6 for proliferation as they can use the proliferative kinases promiscuously (e.g., can use CDK 1/2/4/or 6) or lack the function of the retinoblastoma tumor suppressor protein (Rb), which is inactivated by the CDKs. The potential sensitivity of certain tumors to CDK4/6 inhibition can be deduced based on tumor type and molecular genetics using standard techniques. Cancers that are not typically affected by the inhibition of CDK4/6 are those that can be characterized by one or more of the group including, but not limited to, increased activity of CDK1 or CDK2, loss, deficiency, or absence of retinoblastoma tumor suppressor protein (Rb), high levels of MYC expression, increased cyclin E (e.g., E1 or E2) and increased cyclin A, or expression of a Rb-inactivating protein (such as HPV-encoded E7). Such cancers can include, but are not limited to, small cell lung cancer, retinoblastoma, HPV positive malignancies like cervical cancer and certain head and neck cancers, MYC amplified tumors such as Burkitts' Lymphoma, and triple negative breast cancer; certain classes of sarcoma, certain classes of non-small cell lung carcinoma, certain classes of melanoma, certain classes of pancreatic cancer, certain classes of leukemia, certain classes of lymphoma, certain classes of brain cancer, certain classes of colon cancer, certain classes of prostate cancer, certain classes of ovarian cancer, certain classes of uterine cancer, certain classes of thyroid and other endocrine tissue cancers, certain classes of salivary cancers, certain classes of thymic carcinomas, certain classes of kidney cancers, certain classes of bladder cancers, and certain classes of testicular cancers.

The loss or absence of retinoblastoma (Rb) tumor suppressor protein (Rb-null) can be determined through any of the standard assays known to one of ordinary skill in the art, including but not limited to Western Blot, ELISA (enzyme linked immunoadsorbent assay), IHC (immunohistochemistry), and FACS (fluorescent activated cell sorting). The selection of the assay will depend upon the tissue, cell line or surrogate tissue sample that is utilized e.g., for example Western Blot and ELISA may be used with any or all types of tissues, cell lines or surrogate tissues, whereas the IHC method would be more appropriate wherein the tissue utilized in the methods described herein was a tumor biopsy. FACs analysis would be most applicable to samples that were single cell suspensions such as cell lines and isolated peripheral blood mononuclear cells. See e.g., US 20070212736.

Alternatively, molecular genetic testing may be used for determination of retinoblastoma gene status. Molecular genetic testing for retinoblastoma includes the following as described in Lohmann and Gallie "Retinoblastoma. Gene Reviews" (2010) or Parsam et al., *J. Genetics* 88(4): 517-527 (2009).

Increased activity of CDK1 or CDK2, high levels of MYC expression, increased cyclin E and increased cyclin A can be determined through any of the standard assays known to one of ordinary skill in the art, including but not limited to Western Blot, ELISA (enzyme linked immunoadsorbent assay), IHC (immunohistochemistry), and FACS (fluorescent activated cell sorting). The selection of the assay will depend upon the tissue, cell line, or surrogate tissue sample that is utilized e.g., for example Western Blot and ELISA may be used with any or all types of tissues, cell lines, or surrogate tissues, whereas the IHC method would be more appropriate wherein the tissue utilized in the methods described herein was a tumor biopsy. FACs analysis would be most applicable to samples that were single cell suspensions such as cell lines and isolated peripheral blood mononuclear cells.

In some embodiments, the cancer is selected from a small cell lung cancer, retinoblastoma, and triple negative (ER/PR/Her2 negative) or "basal-like" breast cancer, which almost always have inactivate retinoblastoma tumor suppressor proteins (Rb), and therefore do not require CDK4/6 activity to proliferate. Triple negative (basal-like) breast cancer is also almost always genetically or functionally Rb-null. Also, certain virally induced cancers (e.g., cervical cancer and subsets of Head and Neck cancer) express a viral protein (E7) which inactivates Rb making these tumors functionally Rb-null. Some lung cancers are also believed to be caused by HPV. In one particular embodiment, the cancer is small cell lung cancer, and the patient is treated with a DNA-damaging agent selected from the group consisting of etoposide, carboplatin, and cisplatin, or a combination thereof.

The compounds described herein can also be used in protecting healthy CDK4/6-replication dependent cells during chemotherapeutic treatments of abnormal tissues in non-cancer proliferative diseases, including but not limited to: psoriasis, lupus, arthritis (notably rheumatoid arthritis), hemangiomatosis in infants, multiple sclerosis, myelodegenerative disease, neurofibromatosis, ganglioneuromatosis, keloid formation, Paget's Disease of the bone, fibrocystic disease of the breast, Peyronie's and Duputren's fibrosis, restenosis, and cirrhosis. Further, the compounds described herein can be used to ameliorate the effects of chemotherapeutic agents in the event of accidental exposure or overdose (e.g., methotrexate overdose).

Chemoprotective Regimes

In certain embodiments, the compounds described herein or pharmaceutically acceptable compositions, salts, isotopic analogs, or prodrugs thereof, are administered at a dose described herein so that the protection afforded by the compound is short term and transient in nature, allowing a significant portion of the cells to synchronously renter the cell-cycle quickly following the cessation of the chemotherapeutic agent's effect, for example within less than about 24, 30, 36, or 40 hours. Cells that are quiescent within the G1 phase of the cell cycle are more resistant to the damaging effect of chemotherapeutic agents than proliferating cells.

The compounds described herein can be administered to the subject prior to treatment with a chemotherapeutic agent, during treatment with a chemotherapeutic agent, after exposure to a chemotherapeutic agent, or a combination thereof. The compounds described herein are typically administered in a manner that allows the drug facile access to the blood stream, for example via intravenous injection. In one embodiment, the compound is administered to the subject less than about 24 hours, 20 hours, 16 hours, 12 hours, 8 hours, or 4 hours, 2.5 hours, 2 hours, 1 hour, ½ hour or less prior to treatment with the chemotherapeutic agent. In an alternative embodiment, the compound is administered to the subject less than about 48 hours, 40 hours, 36 hours, or 32 hours or less prior to treatment with the chemotherapeutic agent.

Typically, the compound described herein is administered to the subject prior to treatment with the chemotherapeutic agent such that the compound reaches peak serum levels before or during treatment with the chemotherapeutic agent. In one embodiment, are administered to the subject about 30 minutes prior to administration of the chemotherapeutic agent. In one embodiment, the compounds described herein are administered to the subject over about a 30 minute period and then the subject is administered a chemotherapeutic agent. In one embodiment, the Compound is administered concomitantly, or closely thereto, with the chemotherapeutic agent exposure. If desired, the compound can be administered multiple times during the chemotherapeutic agent treatment to maximize inhibition, especially when the chemotherapeutic drug is administered over a long period or has a long half-life. In an alternative embodiment, the compounds described herein can be administered following exposure to the chemotherapeutic agent if desired to mitigate healthy cell damage associated with chemotherapeutic agent exposure. In certain embodiments, the compound is administered up to about ½ hour, up to about 1 hour, up to about 2 hours, up to about 4 hours, up to about 8 hours, Up to about 10 hours, up to about 12 hours, up to about 14 hours, up to about 16 hours, or up to about 20 hours or greater following the chemotherapeutic agent exposure. In a particular embodiment, the compound is administered up to between about 12 hours and 20 hours following exposure to the chemotherapeutic agent.

Importantly, at the dosing ranges provided herein, the compounds described herein can be used in a multi-day chemotherapeutic regimen without concomitant accumulation in the subject. Accordingly, the PK and/or PD levels provided herein are not significantly altered, that is, by no more than about 10%, across a multi-day dosing regimen. Because of this, the compounds described herein are ideal chemoprotectants in chemotherapeutic treatment regimens that require multi-day chemotherapeutic agent administration, for example as seen in small cell lung cancer, triple negative breast cancer, bladder cancer, and HPV-positive head and neck and cervical cancer.

In one aspect, the use of the compounds described herein at the PK and PD parameters described herein allows for a chemo-protective regimen for use during standard chemotherapeutic dosing schedules or regimens common in many anti-cancer treatments. For example, the compounds described herein can be administered so that CDK4/6-replication dependent healthy cells are G1 arrested during chemotherapeutic agent exposure wherein, due to the rapid dissipation of the G1-arresting effect of the compounds, a significant number of healthy cells reenter the cell-cycle and are capable of replicating shortly after chemotherapeutic agent exposure, for example, within less than about 24, 30, 40, or 48 hours, and continue to replicate until administration of the compounds described herein in anticipation of the next chemotherapeutic treatment. In one embodiment, the compounds described herein are administered to allow for the cycling of the CDK4/6-replication dependent healthy cells between G1-arrest and reentry into the cell-cycle to accommodate a repeated-dosing chemotherapeutic treatment regimen, for example including but not limited to a treatment regimen wherein the chemotherapeutic agent is administered: on day 1-3 every 21 days; on days 1-3 every 28 days; on day 1 every 3 weeks; on day 1, day 8, and day 15 every 28 days, on day 1 and day 8 every 28 days; on days 1 and 8 every 21 days; on days 1-5 every 21 days; 1 day a week for 6-8 weeks; on days 1, 22, and 43; days 1 and 2 weekly; days 1-4 and 22-25; 1-4; 22-25, and 43-46; and similar type-regimens, wherein the CDK4/6-replication dependent cells are G1 arrested during chemotherapeutic agent exposure. In one embodiment, the compounds described herein can be administered so that the subject's CDK4/6-replication dependent cells are G1-arrested during daily chemotherapeutic agent exposure, for example a contiguous multi-day chemotherapeutic regimen. In one embodiment, the compounds described herein can be administered so that the subject's CDK4/6-replication dependent cells are G1-arrested during chemotherapeutic agent exposure, for example a contiguous multi-day regimen, but a significant portion of healthy cells reenter the cell-cycle and replicate during the off periods before starting the next cycle of chemotherapeutic agent exposure, for example cycle 2, cycle 3, cycle 4, etc. In one embodiment, the compounds described herein are administered so that a subject's CDK4/6-replication dependent cells' G1-arrest is provided during a daily chemotherapeutic agent treatment regimen, for example, a contiguous multi-day treatment regimen, and the arrested cells are capable of reentering the cell-cycle shortly after the multi-day regimen ends.

In one embodiment, the subject has small cell lung cancer and the compounds described herein are administered intravenously over about a 30 minute period about 30 minutes prior to administration of either etoposide or carboplatin on day 1, and etoposide on days 2 and 3 during a 21-day treatment cycle, wherein the subject is administered both etoposide and carboplatin on day 1 and etoposide on day 2 and 3 during a 21-day cycle first line treatment protocol. In one embodiment, the dose of etoposide administered is 100 $mg/m^2$ administered intravenously over about 60 minutes daily on days 1, 2, and 3 of each 21-day cycle. In one embodiment, the dose of carboplatin administered to the subject is calculated using the Calvert formula with a target AUC of 5 (maximum dose of 750 mg) administered intravenously over 30 minutes on day 1 of each 21-day cycle.

In one embodiment, the subject has small cell lung cancer and the compounds described herein are administered intravenously over about a 30 minute period about 30 minutes prior to administration of topotecan during a 21-day treatment cycle, wherein the subject is administered topotecan on days 1, 2, 3, 4, and 5 during a 21-day cycle second or third line treatment protocol. In one embodiment, the dose of topotecan administered is 1.5 $mg/m^2$ administered intravenously over about 30 minutes daily on days 1, 2, 3, 4, and 5 of each 21-day cycle. In one embodiment, the dose of topotecan administered is 1.25 $mg/m^2$ administered intravenously over about 30 minutes daily on days 1, 2, 3, 4, and 5 of each 21-day cycle. In one embodiment, the dose of topotecan administered is 0.75 $mg/m^2$ administered intravenously over about 30 minutes daily on days 1, 2, 3, 4, and 5 of each 21-day cycle.

In one embodiment, the subject has small cell lung cancer and the compounds described herein are administered intravenously over about a 30 minute period about 30 minutes prior to administration of topotecan during a 21-day treatment cycle, wherein the subject is administered topotecan on days 1, 2, and 3 during a 21-day cycle second or third line treatment protocol. In one embodiment, the dose of topotecan administered is 1.25 $mg/m^2$ administered intravenously over about 30 minutes daily on days 1, 2, and 3 of each 21-day cycle.

Administration of the compounds described herein in the doses described herein can result in reduced anemia, reduced lymphopenia, reduced thrombocytopenia, or reduced neutropenia compared to that typically expected after, common after, or associated with treatment with chemotherapeutic agents in the absence of administration of the compounds described herein. The use of the compounds described herein results in a faster recovery from bone marrow suppression associated with long-term use of CDK4/6 inhibitors, such as myelosuppression, anemia, lymphopenia, thrombocytopenia, or neutropenia, following the cessation of use of the compounds described herein. In some embodiments, the use of the compounds described herein results in reduced or limited bone marrow suppression associated with long-term use of CDK4/6 inhibitors, such as myelosuppression, anemia, lymphopenia, thrombocytopenia, or neutropenia.

In one embodiment, the compounds described herein, at the concentrations and doses described herein, is used in a CDK4/6-replication dependent healthy cell cycling strategy wherein a subject is exposed to regular, repeated chemotherapeutic treatments, wherein the healthy cells are G1-arrested when chemotherapeutic agent exposed and allowed to reenter the cell-cycle before the subject's next chemotherapeutic treatment. Such cycling allows CDK4/6-replication dependent cells to regenerate damaged blood cell lineages between regular, repeated treatments, for example those associated with standard chemotherapeutic treatments for cancer, and reduces the risk associated with long term CDK4/6 inhibition. This cycling between a state of G1-arrest and a state of replication is not feasible in limited time-spaced, repeated chemotherapeutic agent exposures using longer acting CDK4/6 inhibitors such as ribociclib, palbociclib, or abemaciclib, as the lingering G1-arresting effects of the compound prohibit significant and meaningful reentry into the cell-cycle before the next chemotherapeutic agent exposure or delay the healthy cells from entering the cell cycle and reconstituting damaged tissues or cells following treatment cessation.

The compounds described herein can be administered to a subject on any chemotherapeutic treatment schedule and in any dose consistent with the prescribed course of treatment. The compounds described herein can be administered prior to, during, or following the administration of the chemotherapeutic agent. In one embodiment, the compounds described herein can be administered to the subject during the time period ranging from 24 hours prior to chemotherapeutic treatment until 24 hours following exposure. This time period, however, can be extended to time earlier that 24 hour prior to exposure to the agent (e.g., based upon the time it takes the chemotherapeutic agent used to achieve suitable plasma concentrations and/or the compound's plasma half-life). Further, the time period can be extended longer than 24 hours following exposure to the chemotherapeutic agent so long as later administration of the compounds described herein leads to at least some protective effect. Such post-exposure treatment can be especially useful in cases of accidental exposure or overdose. In an alternative embodiment, the compounds described herein can be administered to the subject during the time period ranging from 48 hours prior to chemotherapeutic treatment until 48 hours following exposure.

In some embodiments, the compounds described herein can be administered to the subject at a time period prior to the administration of the chemotherapeutic agent, so that plasma levels of the compounds described herein are peaking at the time of administration of the chemotherapeutic agent. If convenient, the compounds described herein can be administered at the same time as the chemotherapeutic agent, in order to simplify the treatment regimen. In some embodiments, the chemoprotectant and chemotherapeutic can be provided in a single formulation.

In some embodiments, the compounds described herein can be administered to the subject such that the chemotherapeutic agent can be administered either at higher doses (increased chemotherapeutic dose intensity) or more frequently (increased chemotherapeutic dose density) or at a dose that achieves equivalent AUC therapeutic levels as seen when the chemotherapeutic agent is administered alone.

Dose-dense chemotherapy is a chemotherapy treatment plan in which drugs are given with less time between treatments than in a standard chemotherapy treatment plan. Chemotherapy dose intensity represents unit dose of chemotherapy administered per unit time. Dose intensity can be increased or decreased through altering dose administered, time interval of administration, or both. Myelosuppression continues to represent the major dose-limiting toxicity of cancer chemotherapy, resulting in considerable morbidity and mortality along with frequent reductions in chemotherapy dose intensity, which may compromise disease control and survival. The compounds and their use as described herein represent a way of increasing chemotherapy dose density and/or dose intensity while mitigating adverse events such as, but not limited to, myelosuppression.

If desired, multiple doses of the compounds described herein can be administered to the subject. Alternatively, the subject can be given a single dose of the compounds described herein. For example, the compounds described herein can be administered so that CDK4/6-replication dependent healthy cells are G1 arrested during chemotherapeutic agent exposure wherein, due to the rapid dissipation of the G1-arresting effect of the compounds, a significant number of healthy cells reenter the cell-cycle and are capable of replicating shortly after chemotherapeutic agent exposure, for example, within about 24-48 hours or less, and continue to replicate until administration of the CDK4/6-inhibitor in anticipation of the next chemotherapeutic treatment. In one embodiment, the compounds described herein are administered to allow for the cycling of the CDK4/6-replication dependent healthy cells between G1-arrest and reentry into the cell-cycle to accommodate a repeated-dosing chemotherapeutic treatment regimen, for example, including but not limited to a treatment regimen wherein the chemotherapeutic agent is administered: on day 1-3 every 21 days; on days 1-3 every 28 days; on day 1 every 3 weeks; on day 1, day 8, and day 15 every 28 days, on day 1 and day 8 every 28 days; on days 1 and 8 every 21 days; on days 1-5 every 21 days; 1 day a week for 6-8 weeks; on days 1, 22, and 43; days 1 and 2 weekly; days 1-4 and 22-25; 1-4; 22-25, and 43-46; and similar type-regimens, wherein the CDK4/6-replication dependent cells are G1 arrested during chemotherapeutic agent exposure and a significant portion of the cells reenter the cell-cycle in between chemotherapeutic agent exposure.

As contemplated herein, the compounds described herein can be used as a chemoprotectant in conjunction with a number of standard of care chemotherapeutic treatment regimens used to provide chemoprotection to a subject's CDK4/6-replication dependent healthy cells during a CDK4/6-replication independent cancer treatment protocol. In alternative embodiments, for example, the compounds described herein can be administered to provide chemoprotection in a small cell lung cancer therapy protocol such as, but not limited to: cisplatin 60 $mg/m^2$ IV on day 1 plus etoposide 120 $mg/m^2$ IV on days 1-3 every 21 d for 4 cycles; cisplatin 80 $mg/m^2$ IV on day 1 plus etoposide 100 $mg/m^2$ IV on days 1-3 every 28 d for 4 cycles; cisplatin 60-80 $mg/m^2$ IV on day 1 plus etoposide 80-120 $mg/m^2$ IV on days 1-3 every 21-28 d (maximum of 4 cycles); carboplatin AUC 5-6 min-mg/mL IV on day 1 plus etoposide 80-100 $mg/m^2$ IV on days 1-3 every 28 d (maximum of 4 cycles); Cisplatin 60-80 $mg/m^2$ IV on day 1 plus etoposide 80-120 $mg/m^2$ IV on days 1-3 every 21-28 d; carboplatin AUC 5-6 min-mg/mL IV on day 1 plus etoposide 80-100 $mg/m^2$ IV on days 1-3 every 28 d (maximum 6 cycles); cisplatin 60 $mg/m^2$ IV on day 1 plus irinotecan 60 $mg/m^2$ IV on days 1, 8, and 15 every 28 d (maximum 6 cycles); cisplatin 30 $mg/m^2$ IV on days 1 and 8 or 80 $mg/m^2$ IV on day 1 plus irinotecan 65 $mg/m^2$ IV on days 1 and 8 every 21 d (maximum 6 cycles); carboplatin AUC 5 min-mg/mL IV on day 1 plus irinotecan 50 $mg/m^2$ IV on days 1, 8, and 15 every 28 d (maximum 6 cycles); carboplatin AUC 4-5 IV on day 1 plus irinotecan 150-200 $mg/m^2$ IV on day 1 every 21 d (maximum 6 cycles); cyclophosphamide 800-1000 $mg/m^2$ IV on day 1 plus doxorubicin 40-50 $mg/m^2$ IV on day 1 plus vincristine 1-1.4 $mg/m^2$ IV on day 1 every 21-28 d (maximum 6 cycles); Etoposide 50 $mg/m^2$ P0 daily for 3 wk every 4 wk; topotecan 2.3 $mg/m^2$ PO on days 1-5 every 21 d; topotecan 1.5 $mg/m^2$ IV on days 1-5 every 21 d; carboplatin AUC 5 min-mg/mL IV on day 1 plus irinotecan 50 $mg/m^2$ IV on days 1, 8, and 15 every 28 d; carboplatin AUC 4-5 IV on day 1 plus irinotecan 150-200 $mg/m^2$ IV on day 1 every 21 d; cisplatin 30 $mg/m^2$ IV on days 1, 8, and 15 plus irinotecan 60 $mg/m^2$ IV on days 1, 8, and 15 every 28 d; cisplatin 60 $mg/m^2$ IV on day 1 plus irinotecan 60 $mg/m^2$ IV on days 1, 8, and 15 every 28 d; cisplatin 30 $mg/m^2$ IV on days 1 and 8 or 80 $mg/m^2$ IV on day 1 plus irinotecan 65 $mg/m^2$ IV on days 1 and 8 every 21 d; paclitaxel 80 $mg/m^2$ IV weekly for 6 wk every 8 wk; paclitaxel 175 $mg/m^2$ IV on day 1 every 3 wk; etoposide 50 $mg/m^2$ PO daily for 3 wk every 4 wk; topotecan 2.3 $mg/m^2$ PO on days 1-5 every 21 d; topotecan 1.5 $mg/m^2$ IV on days 1-5 every 21 d; carboplatin AUC 5 min-mg/mL IV on day 1 plus irinotecan 50 $mg/m^2$ IV on days 1, 8, and 15 every 28 d; carboplatin AUC 4-5 IV on day 1 plus irinotecan 150-200 $mg/m^2$ IV on day 1 every 21 d; cisplatin 30 $mg/m^2$ IV on days 1, 8, and 15 plus irinotecan 60 $mg/m^2$ IV on days 1, 8, and 15 every 28 d; cisplatin 60 $mg/m^2$ IV on day 1 plus irinotecan 60 $mg/m^2$ IV on days 1, 8, and 15 every 28 d; cisplatin 30 $mg/m^2$ IV on days 1 and 8 or 80 $mg/m^2$ IV on day 1 plus irinotecan 65 $mg/m^2$ IV on days 1 and 8 every 21 d; paclitaxel 80 $mg/m^2$ IV weekly for 6 wk every 8 wk; and paclitaxel 175 $mg/m^2$ IV on day 1 every 3 wk. In alternative embodiments, the compounds described herein are administered to provide chemoprotection in a small cell lung cancer therapy protocol such as, but not limited to: topotecan 2.0 $mg/m^2$ PO on days 1-5 every 21 d; topotecan 1.5-2.3 $mg/m^2$ PO on days 1-5 every 21 d; etoposide 100 $mg/m^2$ intravenously (IV) on days 1 through 3 plus cisplatin 50 $mg/m^2$ IV on days 1 and 2 (treatment cycles administered every 3 weeks to a maximum of six cycles); etoposide 100 $mg/m^2$ intravenously (IV) on days 1 through 3 plus carboplatin 300 $mg/m^2$ IV on day 1 (treatment cycles administered every 3 weeks to a maximum of six cycles); carboplatin (300 $mg/m^2$ IV on day 1) and escalating doses of etoposide starting with 80 $mg/m^2$ IV on days 1-3; carboplatin 125 $mg/m^2$/day combined with etoposide 200 $mg/m^2$/day administered for 3 days; etoposide 80-200 $mg/m^2$ intravenously (IV) on days 1 through 3 plus carboplatin 125-450 $mg/m^2$ IV on day 1 (treatment cycles administered every 21-28 days); carboplatin AUC 5-6 min-mg/mL IV on day 1 plus etoposide 80-200 $mg/m^2$ IV on days 1-3 every 28 d (maximum of 4 cycles).

In one embodiment, the compounds described herein are administered in a dosage describe herein to a subject with small cell lung cancer on days 1, 2, and 3 of a treatment protocol wherein the DNA damaging agent selected from the group consisting of carboplatin, etoposide, and cisplatin, or a combination thereof, is administered on days 1, 2, and 3 every 21 days.

In one embodiment, the compounds described herein are used to provide chemoprotection to a subject's CDK4/6-replication dependent healthy cells during a CDK4/6-replication independent head and neck cancer treatment protocol. In one embodiment, the compounds described herein are administered to provide chemoprotection in a CDK4/6-replication independent head and neck cancer therapy protocol such as, but not limited to: cisplatin 100 $mg/m^2$ IV on days 1, 22, and 43 or 40-50 $mg/m^2$ IV weekly for 6-7 wk; cetuximab 400 $mg/m^2$ IV loading dose 1 wk before the start of radiation therapy, then 250 $mg/m^2$ weekly (premedicate with dexamethasone, diphenhydramine, and ranitidine); cisplatin 20 $mg/m^2$ IV on day 2 weekly for up to 7 wk plus paclitaxel 30 $mg/m^2$ IV on day 1 weekly for up to 7 wk; cisplatin 20 $mg/m^2$/day IV on days 1-4 and 22-25 plus 5-FU 1000 $mg/m^2$/day by continuous IV infusion on days 1-4 and 22-25; 5-FU 800 $mg/m^2$ by continuous IV infusion on days 1-5 given on the days of radiation plus hydroxyurea 1 g PO q1-2 h (11 doses per cycle); chemotherapy and radiation given every other week for a total of 13 wk; carboplatin 70 $mg/m^2$/day IV on days 1-4, 22-25, and 43-46 plus 5-FU 600

$mg/m^2$/day by continuous IV infusion on days 1-4, 22-25, and 43-46; carboplatin AUC 1.5 IV on day 1 weekly plus paclitaxel 45 $mg/m^2$ IV on day 1 weekly; cisplatin 100 $mg/m^2$ IV on days 1, 22, and 43 or 40-50 $mg/m^2$ IV weekly for 6-7 wk; docetaxel 75 $mg/m^2$ IV on day 1 plus cisplatin 100 $mg/m^2$ IV on day 1 plus 5-FU 100 $mg/m^2$/day by continuous IV infusion on days 1-4 every 3 wk for 3 cycles, then 3-8 wk later, carboplatin AUC 1.5 IV weekly for up to 7 wk during radiation therapy; docetaxel 75 $mg/m^2$ IV on day 1 plus cisplatin 75 $mg/m^2$ IV on day 1 plus 5-FU 750 $mg/m^2$/day by continuous IV infusion on days 1-4 every 3 wk for 4 cycles; cisplatin 100 $mg/m^2$ IV on day 1 every 3 wk for 6 cycles plus 5-FU 1000 $mg/m^2$/day by continuous IV infusion on days 1-4 every 3 wk for 6 cycles plus cetuximab 400 $mg/m^2$ IV loading dose on day 1, then 250 $mg/m^2$ IV weekly until disease progression (premedicate with dexamethasone, diphenhydramine, and ranitidine); carboplatin AUC 5 min-mg/mL IV on day 1 every 3 wk for 6 cycles plus 5-FU 1000 $mg/m^2$/day by continuous IV infusion on days 1-4 every 3 wk for 6 cycles plus cetuximab 400 $mg/m^2$ IV loading dose on day 1, then 250 $mg/m^2$ IV weekly until disease progression (premedicate with dexamethasone, diphenhydramine, and ranitidine); cisplatin 75 $mg/m^2$ IV on day 1 plus docetaxel 75 $mg/m^2$ IV on day 1 every 3 wk; cisplatin 75 $mg/m^2$ IV on day 1 plus paclitaxel 175 $mg/m^2$ IV on day 1 every 3 wk; carboplatin AUC 6 IV on day 1 plus docetaxel 65 $mg/m^2$ IV on day 1 every 3 wk; carboplatin AUC 6 IV on day 1 plus paclitaxel 200 $mg/m^2$ IV on day 1 every 3 wk; cisplatin 75-100 $mg/m^2$ IV on day 1 every 3-4 wk plus cetuximab 400 $mg/m^2$ IV loading dose on day 1, then 250 $mg/m^2$ IV weekly (premedicate with dexamethasone, diphenhydramine, and ranitidine); cisplatin 100 $mg/m^2$ IV on day 1 plus 5-FU 1000 $mg/m^2$/day by continuous IV infusion on days 1-4 every 3 wk; methotrexate 40 $mg/m^2$ IV weekly (3 wk equals 1 cycle); paclitaxel 200 $mg/m^2$ IV every 3 wk; docetaxel 75 $mg/m^2$ IV every 3 wk; cetuximab 400 $mg/m^2$ IV loading dose on day 1, then 250 $mg/m^2$ IV weekly until disease progression (premedicate with dexamethasone, diphenhydramine, and ranitidine); cisplatin 100 $mg/m^2$ IV on day 1 every 3 wk for 6 cycles plus 5-FU 1000 $mg/m^2$/day by continuous IV infusion on days 1-4 every 3 wk for 6 cycles plus cetuximab 400 $mg/m^2$ IV loading dose on day 1, then 250 $mg/m^2$ IV weekly (premedicate with dexamethasone, diphenhydramine, and ranitidine); carboplatin AUC 5 min-mg/mL IV on day 1 every 3 wk for 6 cycles plus 5-FU 1000 $mg/m^2$/day by continuous IV infusion on days 1-4 every 3 wk for 6 cycles plus cetuximab 400 $mg/m^2$ IV loading dose on day 1, then 250 $mg/m^2$ IV weekly (premedicate with dexamethasone, diphenhydramine, and ranitidine); cisplatin 75 $mg/m^2$ IV on day 1 plus docetaxel 75 $mg/m^2$ IV on day 1 every 3 wk; cisplatin 75 $mg/m^2$ IV on day 1 plus paclitaxel 175 $mg/m^2$ IV on day 1 every 3 wk; carboplatin AUC 6 IV on day 1 plus docetaxel 65 $mg/m^2$ IV on day 1 every 3 wk; carboplatin AUC 6 IV on day 1 plus paclitaxel 200 $mg/m^2$ IV on day 1 every 3 wk; cisplatin 75-100 $mg/m^2$ IV on day 1 every 3-4 wk plus cetuximab 400 $mg/m^2$ IV loading dose on day 1, then 250 $mg/m^2$ IV weekly (premedicate with dexamethasone, diphenhydramine, and ranitidine); cisplatin 100 $mg/m^2$ IV on day 1 plus 5-FU 1000 $mg/m^2$/day by continuous IV infusion on days 1-4 every 3 wk; methotrexate 40 $mg/m^2$ IV weekly (3 wk equals 1 cycle); paclitaxel 200 $mg/m^2$ IV every 3 wk; docetaxel 75 $mg/m^2$ IV every 3 wk; cetuximab 400 $mg/m^2$ IV loading dose on day 1, then 250 $mg/m^2$ IV weekly until disease progression (premedicate with dexamethasone, diphenhydramine, and ranitidine); cisplatin 100 $mg/m^2$ IV on days 1, 22, and 43 with radiation, then cisplatin 80 $mg/m^2$ IV on day 1 plus 5-FU 1000 $mg/m^2$/day by continuous IV infusion on days 1-4 every 4 wk for 3 cycles; cisplatin 75 $mg/m^2$ IV on day 1 plus docetaxel 75 $mg/m^2$ IV on day 1 every 3 wk; cisplatin 75 $mg/m^2$ IV on day 1 plus paclitaxel 175 $mg/m^2$ IV on day 1 every 3 wk; carboplatin AUC 6 IV on day 1 plus docetaxel 65 $mg/m^2$ IV on day 1 every 3 wk; carboplatin AUC 6 IV on day 1 plus paclitaxel 200 $mg/m^2$ IV on day 1 every 3 wk; cisplatin 100 $mg/m^2$ IV on day 1 plus 5-FU 1000 $mg/m^2$/day by continuous IV infusion on days 1-4 every 3 wk; cisplatin 50-70 $mg/m^2$ IV on day 1 plus gemcitabine 1000 $mg/m^2$ IV on days 1, 8, and 15 every 4 wk; gemcitabine 1000 $mg/m^2$ IV on days 1, 8, and 15 every 4 wk or gemcitabine 1250 $mg/m^2$ IV on days 1 and 8 every 3 wk; methotrexate 40 $mg/m^2$ IV weekly (3 wk equals 1 cycle); paclitaxel 200 $mg/m^2$ IV every 3 wk; docetaxel 75 $mg/m^2$ IV every 3 wk; cisplatin 75 $mg/m^2$ IV on day 1 plus docetaxel 75 $mg/m^2$ IV on day 1 every 3 wk; cisplatin 75 $mg/m^2$ IV on day 1 plus paclitaxel 175 $mg/m^2$ IV on day 1 every 3 wk; carboplatin AUC 6 IV on day 1 plus docetaxel 65 $mg/m^2$ IV on day 1 every 3 wk; carboplatin AUC 6 IV on day 1 plus paclitaxel 200 $mg/m^2$ IV on day 1 every 3 wk; cisplatin 100 $mg/m^2$ IV on day 1 plus 5-FU 1000 $mg/m^2$/day by continuous IV infusion on days 1-4 every 3 wk; cisplatin 50-70 $mg/m^2$ IV on day 1 plus gemcitabine 1000 $mg/m^2$ IV on days 1, 8, and 15 every 4 wk; gemcitabine 1000 $mg/m^2$ IV on days 1, 8, and 15 every 4 wk or gemcitabine 1250 $mg/m^2$ IV on days 1 and 8 every 3 wk; methotrexate 40 $mg/m^2$ IV weekly (3 wk equals 1 cycle); paclitaxel 200 $mg/m^2$ IV every 3 wk; and docetaxel 75 $mg/m^2$ IV every 3 wk.

In one embodiment, the compounds described herein are used to provide chemoprotection to a subject's CDK4/6-replication dependent healthy cells during a CDK4/6-replication independent triple negative breast cancer treatment protocol. In one embodiment, the compounds described herein are administered to provide a blood plasma concentration described herein to provide chemoprotection in a CDK4/6-replication independent triple negative breast cancer therapy protocol such as, but not limited to: dose-dense doxorubicin (adriamycin) and cyclophosphamide (cytoxan) every two weeks for four cycles followed by dose-dense paclitaxel (Taxol) every two weeks for four cycles; adriamycin/paclitaxel/cyclophosphomide every three weeks for a total of four cycles; adriamycin/paclitaxel/cyclophosphomide every two weeks for a total of four cycles; adriamycin/cyclophosphomide followed by paclitaxel (Taxol) every three weeks for four cycles each; and adriamycin/cyclophosphomide followed by paclitaxel (Taxol) every two weeks for four cycles each.

In one embodiment, the compounds described herein are used to provide chemoprotection to a subject's CDK4/6-replication dependent healthy cells during a CDK4/6-replication independent bladder cancer treatment protocol. In one embodiment, the compounds described herein are administered to provide a blood plasma concentration described herein to provide chemoprotection in a CDK4/6-replication independent bladder cancer therapy protocol such as, but not limited to: postoperative adjuvant intravesical chemotherapy for non-muscle invasive bladder cancer, first-line chemotherapy for muscle-invasive bladder cancer, and second-line chemotherapy for muscle invasive bladder cancer. Non-limiting examples of postoperative chemotherapy for bladder cancer include one dose or mitomycin (40 mg), epirubicin (80 mg), thiotepa (30 mg), or doxorubicin (50 mg). Non-limiting examples of first-line chemotherapy for bladder cancer include: gemcitabine 1000 $mg/m^2$ on days 1, 8, and 15 plus cisplatin 70 $mg/m^2$ on day 1 or 2 repeating cycle every 28 days for a total of four cycles; dosing methotrexate 30 mg/$m^2$ IV on days 1, 15, and 22 plus vinblastine 3 mg/$m^2$ IV on days 2, 15, and 22 plus doxorubicin 30 mg/$m^2$ IV on day 2 plus cisplatin 70 mg/$m^2$ IV on day 2, repeat cycle every 28 d for a total of 3 cycles; and dose-dense regimens of the above administered along with doses of growth factor stimulants.

In one embodiment, the compounds described herein are used to provide chemoprotection to a subject's CDK4/6-replication dependent healthy cells during a CDK4/6-replication independent retinoblastoma treatment protocol. In one embodiment, the compounds described herein are administered to provide a blood plasma concentration described herein to provide chemoprotection in a CDK4/6-replication independent retinoblastoma therapy protocol such as, but not limited to the administration of carboplatin, vincristine, or etoposide in conjunction with surgery, radiotherapy, cryotherapy, thermotherapy, or other local therapy techniques.

In one embodiment, the compounds described herein are used to provide chemoprotection to a subject's CDK4/6-replication dependent healthy cells during a CDK4/6-replication independent cervical cancer treatment protocol. In one embodiment, the compounds described herein are administered to provide a blood plasma concentration described herein to provide chemoprotection in a CDK4/6-replication independent cervical cancer therapy protocol such as, but not limited to the administration of cisplatin 40 mg/$m^2$ IV once weekly, cisplatin 50-75 mg/$m^2$ IV on day 1 plus 5-fluorouracil (5-FU) 1000 mg/$m^2$ continuous IV infusion on days 2-5 and days 30-33, cisplatin 50-75 mg/$m^2$ IV on day 1 plus 5-FU 1000 mg/$m^2$ IV infusion over 24 hour on days 1-4 every 3 weeks for 3-4 cycles, bevacizumab 15 mg/kg IV over 30-90 minutes plus cisplatin on day 1 or 2 plus paclitaxel on day 1 every 3 weeks, bevacizumab plus paclitaxel on day 1 plus topotecan on days 1-3 every 3 weeks, paclitaxel followed by cisplatin on day 1 every 3 weeks, topotecan on days 1-3 followed by cisplatin on day 1 every 3 weeks, and paclitaxel on day 1 every 3 weeks. In another embodiment, the cervical cancer therapy protocol is as above in addition to radiation, surgery, or another procedure.

Triple-negative breast cancer (TNBC) is defined as the absence of staining for estrogen receptor, progesterone receptor, and HER2/neu. TNBC is insensitive to some of the most effective therapies available for breast cancer treatment including HER2-directed therapy such as trastuzumab and endocrine therapies such as tamoxifen or the aromatase inhibitors. Combination cytotoxic chemotherapy administered in a dose-dense or metronomic schedule remains the standard therapy for early-stage TNBC. Platinum agents have recently emerged as drugs of interest for the treatment of TNBC with carboplatin added to paclitaxel and adriamycin plus cyclophosphamide chemotherapy in the neoadjuvant setting. The poly (ADP-ribose) polymerase (PARP) inhibitors are emerging as promising therapeutics for the treatment of TNBC. PARPs are a family of enzymes involved in multiple cellular processes, including DNA repair.

As a nonlimiting illustration, the subject is exposed to chemotherapeutic agent at least 5 times a week, at least 4 times a week, at least 3 times a week, at least 2 times a week, at least 1 time a week, at least 3 times a month, at least 2 times a month, or at least 1 time a month, wherein the subject's CDK4/6-replication dependent healthy cells are G1 arrested during treatment and allowed to cycle in between chemotherapeutic agent exposure, for example during a treatment break. In one embodiment, the subject is undergoing 5 times a week chemotherapeutic treatment, wherein the subject's CDK4/6-replication dependent healthy cells are G1 arrested during the chemotherapeutic agent exposure and allowed to reenter the cell-cycle during the 2 day break, for example, over the weekend.

In one embodiment, using the compounds described herein at the dosage described herein, the subject's CDK4/6-replicaton dependent healthy cells are arrested during the entirety of the chemotherapeutic agent exposure time-period, for example, during a contiguous multi-day regimens, the cells are arrested over the time period that is required to complete the contiguous multi-day course, and then allowed to recycle at the end of the contiguous multi-day course. In one embodiment, using the compounds described herein at the dosage described herein, the subject's CDK4/6-replication dependent healthy cells are arrested during the entirety of the chemotherapeutic regimen, for example, in a daily chemotherapeutic exposure for three weeks, and rapidly reenter the cell-cycle following the completion of the therapeutic regimen.

In one embodiment, the subject has been exposed to a chemotherapeutic agent, and, using the compounds described herein at the dosage described herein, the subject's CDK4/6-replication dependent healthy cells are placed in G1 arrest following exposure in order to mitigate, for example, DNA damage. In one embodiment, the compounds described herein at the dosage described herein is administered at least ½ hour, at least 1 hour, at least 2 hours, at least 3 hours, at least 4 hours, at least 5 hours, at least 6 hours, at least 7 hours, at least 8 hours, at least 10 hours, at least 12 hours, at least 14 hours, at least 16 hours, at least 18 hours, at least 20 hours or more post chemotherapeutic agent exposure.

In some embodiments, the CDK4/6-replication dependent healthy cells can be arrested for longer periods to allow for intensified chemotherapeutic treatment, for example, over a period of hours, days, and/or weeks, through multiple, time separated administrations of a CDK4/6 inhibitor described herein. Because of the rapid and synchronous reentry into the cell cycle by CDK4/6-replication dependent healthy cells, for example HSPCs, upon dissipation of the CDK4/6 inhibitors intra-cellular effects, the cells are capable of reconstituting the cell lineages faster than CDK4/6 inhibitors with longer G1 arresting profiles, for example, ribociclib, palbociclib, or abemaciclib.

The reduction in chemotoxicity afforded by the compounds described herein at the dosage described herein can allow for dose intensification (e.g., more therapy can be given in a fixed period of time) in medically related chemotherapies, which will translate to better efficacy. Therefore, the presently disclosed methods can result in chemotherapy regimens that are less toxic and more effective.

The use of the compounds described herein at the dosage described herein can induce selective G1 arrest in CDK4/6-dependent cells (e.g., as measured in a cell-based in vitro assay). In one embodiment, the compounds described herein at the dosage described herein is capable of increasing the percentage of CDK4/6-dependent cells in the G1 phase, while decreasing the percentage of CDK4/6-dependent cells in the G2/M phase and S phase. In one embodiment, the compounds described herein at the dosage described herein induces substantially pure (i.e., "clean") G1 cell cycle arrest in the CDK4/6-dependent cells (e.g., wherein treatment with the compounds described herein induces cell cycle arrest such that the majority of cells are arrested in G1 as defined by standard methods (e.g., propidium iodide (PI) staining or others) with the population of cells in the G2/M and S phases combined being less than about 30%, about 25%, about 20%, about 15%, about 10%, about 5%, about 3% or less of the total cell population. Methods of assessing the cell phase of a population of cells are known in the art (see, for example, in U.S. Patent Application Publication No. 20020224522) and include cytometric analysis, microscopic analysis, gradient centrifugation, elutriation, fluorescence techniques including immunofluorescence, and combinations thereof. Cytometric techniques include exposing the cell to a labeling agent or stain, such as DNA-binding dyes, e.g., PI, and analyzing cellular DNA content by flow cytometry. Immunofluorescence techniques include detection of specific cell cycle indicators such as, for example, thymidine analogs (e.g., 5-bromo-2-deoxyuridine (BrdU) or an iododeoxyuridine), with fluorescent antibodies.

In some embodiments, the use of the compounds described herein at the dosage described herein results in reduced or substantially free off-target effects, particularly related to inhibition of kinases other than CDK4 and or CDK6 such as CDK2, as the compounds described herein at the dosage described herein is a poor inhibitor (e.g., >1 μM $IC_{50}$) of CDK2. Furthermore, because of the high selectivity for CDK4/6, the use of the compounds described herein should not induce cell cycle arrest in CDK4/6-independent cells. In addition, because of the short transient nature of the G1-arrest effect, the CDK4/6-replication dependent cells more quickly reenter the cell-cycle than, comparatively, use of palbociclib provides, resulting in the reduced risk of, in one embodiment, hematological toxicity development during long term treatment regimens due to the ability of HSPCs to replicate between chemotherapeutic treatments.

In some embodiments, the use of the compounds described herein at the dosage described herein reduces the risk of undesirable off-target effects including, but not limited to, long term toxicity, anti-oxidant effects, and estrogenic effects. Anti-oxidant effects can be determined by standard assays known in the art. For example, a compound with no significant anti-oxidant effects is a compound that does not significantly scavenge free-radicals, such as oxygen radicals. The anti-oxidant effects of a compound can be compared to a compound with known anti-oxidant activity, such as genistein. Thus, a compound with no significant anti-oxidant activity can be one that has less than about 2, 3, 5, 10, 30, or 100-fold anti-oxidant activity relative to genistein. Estrogenic activities can also be determined via known assays. For instance, a non-estrogenic compound is one that does not significantly bind and activate the estrogen receptor.

A compound that is substantially free of estrogenic effects can be one that has less than about 2, 3, 5, 10, 20, or 100-fold estrogenic activity relative to a compound with estrogenic activity, e.g., genistein.

Dosing Profiles

One embodiment described herein is the particular dosing and blood profile ranges of the CDK4/6 inhibitor compounds described herein, and methods using said dosages, for treating a subject undergoing DNA-damaging chemotherapeutic therapy for the treatment of a CDK 4/6-replication independent cellular proliferation disorder.

As contemplated herein and for purposes of the disclosed ranges herein, all ranges described herein include any and all numerical values occurring within the identified ranges. For example, a range of 1 to 10, as contemplated herein, would include the numerical values 1, 2, 3, 4, 5, 6, 7, 8, 9, 10, as well as fractions thereof.

The term "AUC" (amount-time/volume) as used herein means the area under the plasma concentration-time curve.

The term "$AUC_{inf}$" (amount-time/volume) as used herein means the area under the plasma concentration-time curve from time zero to infinity.

The term "$AUC_t$" (amount-time/volume) as used herein means the area under the plasma concentration time curve from time zero to time t.

The term "$AUC_\tau$" (amount-time/volume) as used herein means the area under the plasma concentration-time curve during a dosage interval (τ).

The term "$AUC_{last}$" (amount-time/volume) as used herein means the area under the plasma concentration-time curve from time zero to time of the last measurable concentration.

The term "$C_{max}$" (amount/volume) as used herein means the maximum (peak) plasma drug concentration.

The term "CL" (volume/time or volume/time/kg) as used herein means the apparent total body clearance of the drug from plasma.

The term "CL/F" (volume/time or volume/time/kg) as used herein means the apparent total clearance of the drug from plasma after administration.

The term "κ" ($time^{-1}$) as used herein means first-order rate constant.

The term "$\kappa_{12}$" ($time^{-1}$) as used herein means the transfer rate constant (first-order) from the central (1) to the peripheral (2) compartment.

The term "$\kappa_{21}$" ($time^{-1}$) as used herein means the transfer rate constant (first-order) from the peripheral (2) to the central (1) compartment.

The term "$\kappa_{31}$" ($time^{-1}$) as used herein means the transfer rate constant (first-order) from the deep peripheral (3) to the central (1) compartment.

The term "$\kappa_Z$" ($time^{-1}$) as used herein means the terminal disposition rate constant/terminal rate constant.

The term "$MRT_{inf}$" (time) as used herein means mean residence time.

The term "$T_{max}$" (time) as used herein means time to reach maximum (peak) plasma concentration following drug administration.

The term "T½" (time) as used herein means the elimination half-life as used in one or non-compartmental models.

The term "T½β" (time) as used herein means the terminal elimination half-life as used in two-compartmental models.

The term "T½γ" (time) as used herein means the terminal or elimination half-life as used in three compartmental models.

The term "$V_{ss}$" (volume or volume/kg) as used herein means the apparent volume of distribution at steady state.

In one embodiment, the compounds described herein are orally or intravenously administered to a subject prior to administration of a chemotherapeutic agent so that a single dose of the compounds described herein provides a specific PK and/or PD blood profile as described herein. In one embodiment, the dose administered to the subject is between about 180 and about 215 $mg/m^2$. In one embodiment, the dose is between about 180 and about 280 $mg/m^2$. In one embodiment, the dose administered is between about 170 to about 215 $mg/m^2$. In one embodiment, the dose administered is between about 170 to about 280 $mg/m^2$. For example, the dose is about 170, 175, 180, 185, 190, 195, 200, 205, 210, 215, 220, 225, 230, 235, 240, 245, 250, 255, 260, 265, 270, 275, or 280 $mg/m^2$. In one embodiment, the dose is about 190 $mg/m^2$.

In one embodiment, the dose is about 200 $mg/m^2$. In one embodiment, the dose is about 240 $mg/m^2$. In one embodiment, the dose administered provides for a mean $AUC_{last}$ measured at 24.5 hours or a mean $C_{max}$ as described below.

In another embodiment, the compounds described herein are orally or intravenously administered to a subject prior to administration of a chemotherapeutic agent so that a single dose of the compounds described herein provides a blood plasma level profile dosage-corrected mean $C_{max}$ ((ng/mL)/(mg/$m^2$)) of between about 1 (ng/mL)/(mg/$m^2$) and 20 (ng/mL)/(mg/$m^2$), between about 2.5 (ng/mL)/(mg/$m^2$) and 15 (ng/mL)/(mg/$m^2$), or of between about 4 (ng/mL)/(mg/$m^2$) and 12 (ng/mL)/(mg/$m^2$). In one embodiment, the dosage-corrected mean $C_{max}$((ng/mL)/(mg/$m^2$) is about 1, 2, 3, 4, 5, 6, 7, 8, 9, 10, 11, 12, 13, 14, 15, 16, 17, 18, 19, or 20 ((ng/mL)/(mg/$m^2$). In one embodiment, the dosage-corrected mean $C_{max}$ ((ng/mL)/(mg/$m^2$)) is about 8.0 (ng/mL)/(mg/$m^2$)±3.5 (ng/mL)/(mg/$m^2$), about 8.5 (ng/mL)/(mg/$m^2$)±2.5 (ng/mL)/(mg/$m^2$), about 9.5 (ng/mL)/(mg/$m^2$) ±2.0 (ng/mL)/(mg/$m^2$), or about 10.2 (ng/mL)/(mg/$m^2$)±1.5 (ng/mL)/(mg/$m^2$). In one embodiment, the dosage-corrected mean $C_{max}$ is about 6.0±20%. The dosage corrected mean $C_{max}$ is mean $C_{max}$ divided by the number of milligrams/$m^2$ of the compounds described herein in the formulation. In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$.

Another embodiment is a method of treating a subject undergoing chemotherapy for the treatment of an CDK 4/6-replication independent cellular proliferation disorder by providing an intravenously administered formulation of the compounds described herein wherein a single-dose provides a blood plasma level profile dosage-corrected mean $C_{max}$ ((ng/mL)/(mg/$m^2$)) of between about 4.6 (ng/mL)/(mg/$m^2$) and about 17.1 (ng/mL)/(mg/$m^2$) or about 1.8 (ng/mL)/(mg/$m^2$) to about 16.8 (ng/mL)/(mg/$m^2$). In one embodiment, the dosage-corrected mean $C_{max}$ ((ng/mL)/(mg/$m^2$)) is about at least 8.5 (ng/mL)/(mg/$m^2$) or about at least 3.8 (ng/mL)/(mg/$m^2$).

In another embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a dosage-corrected mean $C_{max}$ (ng/mL)/(mg/$m^2$) of between of between about 1 (ng/mL)/(mg/$m^2$) and 20 (ng/mL)/(mg/$m^2$), between about 2.5 (ng/mL)/(mg/$m^2$) and 15 (ng/mL)/(mg/$m^2$), or of between about 4 (ng/mL)/(mg/$m^2$) and 14 (ng/mL)/(mg/$m^2$). In one embodiment, the dosage-corrected mean $C_{max}$ ((ng/mL)/(mg/$m^2$) is about 1, 2, 3, 4, 5, 6, 7, 8, 9, 10, 11, 12, 13, 14, 15, 16, 17, 18, 19, or 20 ((ng/mL)/(mg/$m^2$). In one embodiment, the dosage-corrected mean $C_{max}$ ((ng/mL)/(mg/$m^2$)) is about 9.5 (ng/mL)/(mg/$m^2$)±1.5 (ng/mL)/(mg/$m^2$). In an alternative embodiment the dosage-corrected mean $C_{max}$ is about 9.5 (ng/mL)/(mg/$m^2$)±1.9 (ng/mL)/(mg/$m^2$) or 9.5 (ng/mL)/(mg/$m^2$)±about 20%. In one embodiment, the mean dose-corrected $C_{max}$ ((ng/mL)/(mg/$m^2$)) is about 10.45 (ng/mL)/(mg/$m^2$)±about 20%. In one embodiment, the dosage-corrected mean $C_{max}$ is about 6.0 ((ng/mL)/(mg/$m^2$))±20%. In one embodiment, the dosage-corrected mean $C_{max}$ is about 6.5 ((ng/mL)/(mg/$m^2$))±20%. In one embodiment, the compounds described herein are administered on days 1 and 2 of the treatment regime. In one embodiment, the compounds described herein are administered on days 1, 2, and 3 of the treatment regime. In one embodiment, the compounds described herein are administered on days 1, 2, 3, and 4 of the treatment regime. In one embodiment, the compounds described herein are administered on days 1, 2, 3, 4, and 5 of the treatment regime.

In another embodiment, the compounds described herein are orally or intravenously administered to a subject prior to administration of a chemotherapeutic agent so that a single dose of the compounds described herein provides a blood plasma level profile dosage-corrected with a mean $C_{max}$ (ng/mL) of between about 1000 ng/mL and about 3500 ng/mL, or between about 1400 ng/mL and about 3100 ng/mL, or between about 1700 ng/mL and about 2500 ng/mL, or between about 1900 ng/mL and about 2150 ng/mL. In one embodiment, the mean $C_{max}$ (ng/mL) is about 1000, 1100, 1200, 1300, 1400, 1500, 1600, 1700, 1800, 1900, 2000, 2100, 2200, 2300, 2400, 2500, 2600, 2700, 2800, 2900, 3000, 3100, 3200, 3300, 3400, or 3500 (ng/mL). In one embodiment, the mean $C_{max}$ (ng/mL) is about 2030 ng/mL±555 ng/mL. In one embodiment, the mean $C_{max}$ (ng/mL) is about 1900 ng/mL, about 1950 ng/mL, about 1975 ng/mL, about 2000 ng/mL, about 2025 ng/mL, about 2030 ng/mL, about 2040 ng/mL, about 2050 ng/mL, about 2075 ng/mL, or about 2100 ng/mL. In one embodiment, the maximum mean concentration occurs at the end of the infusion period of the formulation. In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$.

In another embodiment, the compounds described herein are orally or intravenously administered to a subject prior to administration of a chemotherapeutic agent so that a single dose of the compounds described herein provides a blood plasma level profile dosage-corrected a mean $C_{max}$ (ng/mL) of between about 885 ng/mL and about 3280 ng/mL, or between about 355 ng/mL and about 3360 ng/mL. In one embodiment, the mean $C_{max}$ (ng/mL) is about at least 1705 ng/mL. In one embodiment, the $C_{max}$ (ng/mL) is about at least 752 ng/mL.

In another embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a mean $C_{max}$ (ng/mL) of between about 1000 ng/mL and 3500 ng/mL. In one embodiment, the mean $C_{max}$ (ng/mL) is between about 1400 ng/mL and about 3100 ng/mL. In one embodiment, the mean $C_{max}$ (ng/mL) of about 1000, 1100, 1200, 1300, 1400, 1450, 1500, 1550, 1600, 1650, 1700, 1750, 1800, 1850, 1900, 1950, 2000, 2050, 2100, 2150, 2200, 2250, 2300, 2400, 2450, 2500, 2600, 2650, 2700, 2750, 2800, 2850, 2900, 2950, 3000, 3050, 3100, 3200, 3300, 3400, 3500 (ng/mL). In one embodiment, the mean $C_{max}$ (ng/mL) is about 2030 ng/mL±555 ng/mL. In an alternative embodiment, the mean $C_{max}$ is about 2030 ng/mL±406 ng/mL or about 2030 ng/mL about 20%. In an alternative embodiment, the mean $C_{max}$ is about 2230 ng/mL±about 20%. In one embodiment, the mean $C_{max}$ is at least about 1020 ng/mL. In one embodiment, the maximum mean concentration occurs at the end of the infusion period of the compounds described herein. In one embodiment, the compounds described herein are administered on days 1 and 2 of the treatment regime. In one embodiment, the compounds described herein are administered on days 1, 2, and 3 of the treatment regime. In one embodiment, the compounds described herein are administered on days 1, 2, 3, and 4 of the treatment regime. In one embodiment, the compounds described herein are administered on days 1, 2, 3, 4, and 5 of the treatment regime.

In another embodiment, provided is a method of treating a subject undergoing chemotherapy for the treatment of a CDK 4/6-replication independent cellular proliferation disorder by providing an intravenous administered formulation of the compounds described herein wherein a single-dose provides a blood plasma level profile with a mean $T_{max}$ (h) of between about 0.10 hrs and about 1.0 hrs, of between about 0.20 hrs and about 0.6 hrs, or of between about 0.30 hrs and about 0.5 hrs. In one embodiment, the $T_{max}$ (h) is about 0.10, 0.15, 0.20, 0.25, 0.30, 0.35, 0.40, 0.45, 0.50, 0.55, 0.60, 0.65, 0.70, 0.85, 0.90, 0.95, or 1.0 (h). In one embodiment, the mean $T_{max}$ (h) is about 0.417 hrs 0.129 hrs. In one embodiment, the mean $T_{max}$ (h) is about 0.3 hrs, about 0.35 hrs, about 0.375 hrs, about 0.40 hrs, about 0.415 hrs, about 0.425 hrs, about 0.45 hrs, about 0.475 hrs, or about 0.5 hrs. In one embodiment, the single dose is between about 170 mg/m$^2$ and 280 mg/m$^2$ or 170 mg/m$^2$ and 215 mg/m$^2$. In one embodiment, the single dose is about 190 mg/m$^2$. In one embodiment, the single dose is about 200 mg/m$^2$. In one embodiment, the single dose is about 240 mg/m$^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a $T_{max}$ (h) as described herein.

Another embodiment is a method of treating a subject undergoing chemotherapy for the treatment of a CDK 4/6-replication independent cellular proliferation disorder by providing an intravenous administered formulation of the compounds described herein wherein a single-dose provides a blood plasma level profile with a mean $T_{max}$ (h) of between about 0.25 hrs and about 0.48 hrs. In one embodiment, the mean $T_{max}$ (h) is about at least 0.47 hrs.

In another embodiment, the compounds described herein are orally or intravenously administered to a subject prior to administration of a chemotherapeutic agent so that a single dose of the compounds described herein provides a blood plasma level profile mean $AUC_{inf}$ (h·ng/mL) measured over 24.5 hours after administration of between about 2000 h·ng/mL to about 4500 h·ng/mL, of between about 2300 h·ng/mL to about 4000 h·ng/mL, of between about 2500 h·ng/mL to about 3500 h·ng/mL, or of between about 2700 h·ng/mL to about 3200 h·ng/mL. In one embodiment, the mean $AUC_{inf}$ (h·ng/mL) is about 2000, 2100, 2200, 2300, 2400, 2500, 2600, 2700, 2800, 2900, 3000, 3100, 3200, 3300, 3400, 3500, 3600, 3700, 3800, 3900, or 4000 (h·ng/mL). In one embodiment, the mean $AUC_{inf}$ (h·ng/mL) measured over 24.5 hours after administration is about 3050 h·ng/mL±513 h·ng/mL. In one embodiment, the mean $AUC_{inf}$(h·ng/mL) measured over 24.5 hours after administration is about 2500 h·ng/mL, is about 2750 h·ng/mL, about 2900 h·ng/mL, about 3000 h·ng/mL, about 3050 h·ng/mL, about 3100 h·ng/mL, about 3250 h·ng/mL, about 3300 h·ng/mL. In one embodiment, the mean $AUC_{inf}$ (h·ng/mL) measured over 72.5 hours after administration is between about 2000 h·ng/mL to about 4500 h·ng/mL, of between about 2300 h·ng/mL to about 4000 h·ng/mL, of between about 2500 h·ng/mL to about 3500 h·ng/mL, or of between about 2700 h·ng/mL to about 3200 h·ng/mL. In one embodiment, the mean $AUC_{inf}$ (h·ng/mL) measured over 72.5 hours after administration is about 2000, 2100, 2200, 2300, 2400, 2500, 2600, 2700, 2800, 2900, 3000, 3100, 3200, 3300, 3400, 3500, 3600, 3700, 3800, 3900, or 4000 (h·ng/mL). In one embodiment, the mean $AUC_{inf}$(h·ng/mL) measured over 72.5 hours after administration is about 3160 h·ng/mL±522 h·ng/mL. In one embodiment, the mean $AUC_{inf}$ (h·ng/mL) measured over 72.5 hours after administration is about 2500 h·ng/mL, is about 2600 h·ng/mL, about 2900 h·ng/mL, about 3000 h·ng/mL, about 3050 h·ng/mL, about 3100 h·ng/mL, about 3250 h·ng/mL, about 3300 h·ng/mL, about 3500 h·ng/mL, about 3600 h·ng/mL, about 3700 h·ng/mL, or about 3800 h·ng/mL. In one embodiment, the single dose is between about 170 mg/m$^2$ and 280 mg/m$^2$ or 170 mg/m$^2$ and 215 mg/m$^2$. In one embodiment, the single dose is about 190 mg/m$^2$. In one embodiment, the single dose is about 200 mg/m$^2$. In one embodiment, the single dose is about 240 mg/m$^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a $AUC_{inf}$ (h·ng/mL) as described herein.

In another embodiment, the compounds described herein are orally or intravenously administered to a subject prior to administration of a chemotherapeutic agent so that a single dose of the compounds described herein provides a blood plasma level profile with a mean $AUC_{inf}$ (h·ng/mL) measured over 24.5 hours after administration of between about 2379 h·ng/mL to about 3762 h·ng/mL or about 1530 h·ng/mL to about 3300 h·ng/mL. In one embodiment, the mean $AUC_{inf}$ h·ng/mL measured over 24.5 hours after administration is about at least 2991 h·ng/mL or about at least 2140 h·ng/mL. In one embodiment, the mean $AUC_{inf}$ h·ng/mL measured over 72.5 hours after administration of between about 2379 h·ng/mL to about 3762 h·ng/mL or about 1530 h·ng/mL to about 3300 h·ng/mL. In one embodiment, the mean $AUC_{inf}$ h·ng/mL measured over 72.5 hours after administration is about at least 2991 h·ng/mL or about at least 2140 h·ng/mL.

In another embodiment, the compounds described herein are orally or intravenously administered to a subject prior to administration of a chemotherapeutic agent so that a single dose of the compounds described herein provides a blood plasma level profile with a mean $AUC_t$(ng·hr/mL) measured over 24.5 hours after administration of between about 2000 h·ng/mL to about 4500 h·ng/mL, between about 2600 h·ng/mL to about 3700 h·ng/mL, between about 2800 h·ng/mL to about 3500 h·ng/mL, or between about 3000 h·ng/mL to about 3200 h·ng/mL. In one embodiment, the mean $AUC_t$ (ng·hr/mL) measured over 24.5 hours after administration is about 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, or 4500 (h·ng/mL). In one embodiment, the mean $AUC_t$(ng·hr/mL) measured over 24.5 hours after administration is about 2830 (ng·hr/mL)±474 (ng·hr/mL). In one embodiment, the mean $AUC_t$(ng·hr/mL) measured over 72.5 hours after administration is between about 2000 h·ng/mL to about 4500 h·ng/mL, between about 2600 h·ng/mL to about 3700 h·ng/mL, between about 2800 h·ng/mL to about 3500 h·ng/mL, or between about 3000 h·ng/mL to about 3200 h·ng/mL. In one embodiment, the mean $AUC_t$(ng·hr/mL) measured over about 72.5 hours after administration is about 2000, 2100, 2200, 2300, 2400, 2500, 2600, 2700, 2800, 2900, 3000, 3100, 3200, 3300, 3400, 3500, 3600, 3700, 3800, 3900, 4000, 4100, 4200, 4300, 4400, or 4500 (ng·hr/mL). In one embodiment, the mean $AUC_t$(ng·hr/mL) measured over 72.5 hours after administration is about 3110 (ng·hr/mL)±515 (ng·hr/mL). In one embodiment, the mean $AUC_t$(ng·hr/mL) measured over 72.5 hours after administration is about 3000 (ng·hr/mL), is about 3050 (ng·hr/mL), is about 3100 (ng·hr/mL), is about 3110 (ng·hr/mL), is about 3150 (ng·hr/mL), is about 3200 (ng·hr/mL), or is about 3250 (ng·hr/mL). In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$.

In another embodiment, the compounds described herein are orally or intravenously administered to a subject prior to administration of a chemotherapeutic agent so that a single dose of the compounds described herein provides a blood plasma level profile with a mean $AUC_t$ (ng·hr/mL) of between about 2360 h·ng/mL to about 3750 h·ng/mL or about 1530 h·ng/mL to about 3300 h·ng/mL. In one embodiment, the mean $AUC_t$(ng·hr/mL) is about at least 2991 h·ng/mL or about at least 2140 h·ng/mL.

In another embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a mean $AUC_t$(ng·hr/mL) measured over about 24.5 hours after administration of between about 2300 h·ng/mL to about 4000 h·ng/mL. In one embodiment, the mean $AUC_t$ (ng·hr/mL) measured over about 24.5 hours after administration is about 2300, 2400, 2500, 2600, 2700, 2800, 2900, 3000, 3100, 3200, 3300, 3400, 3500, 3600, 3700, 3800, 3900, or 4000 (ng·hr/mL). In one embodiment, the mean $AUC_t$(ng·hr/mL) measured over about 24.5 hours after administration is about 2830 (ng·hr/mL)±550 (ng·hr/mL). In an alternative embodiment, the mean $AUC_t$(ng·hr/mL) measured over about 24.5 hours after administration is about 2830 (ng·hr/mL)±560 (ng·hr/mL) or about 2830 (ng·hr/mL)±about 20%. In one embodiment, the mean $AUC_t$ (ng·hr/mL) measured over about 24.5 hours after administration is about 3020 (ng·hr/mL) about 20%. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a mean $AUC_t$(ng·hr/mL) measured over about 24.5 hours after administration of at least about 2040 ng·hr/mL. In one embodiment, the mean $AUC_t$(ng·hr/mL) measured over about 72.5 hours after administration is between about 2300 h·ng/mL to about 4100 h·ng/mL. In one embodiment, the mean $AUC_t$(ng·hr/mL) measured over about 72.5 hours after administration is about 2300, 2400, 2500, 2600, 2700, 2800, 2900, 3000, 3100, 3200, 3300, 3400, 3500, 3600, 3700, 3800, 3900, 4000, or 4100 (ng·hr/mL). In an alternative embodiment, the mean $AUC_t$(ng·hr/mL) measured over about 72.5 hours after administration is about 3100 (ng·hr/mL) 620 (ng·hr/mL) or about 3100 (ng·hr/mL)±about 20%. In one embodiment, the mean $AUC_t$(ng·hr/mL) measured over about 72.5 hours after administration is about 3410 (ng·hr/mL)±about 20%. In one embodiment, the compounds described herein are administered on days 1 and 2 of the treatment regime. In one embodiment, the compounds described herein are administered on days 1, 2, and 3 of the treatment regime. In one embodiment, the compounds described herein are administered on days 1, 2, 3, and 4 of the treatment regime. In one embodiment, the compounds described herein are administered on days 1, 2, 3, 4, and 5 of the treatment regime.

In another embodiment, the compounds described herein are orally or intravenously administered to a subject prior to administration of a chemotherapeutic agent so that a single dose of the compounds described herein provides a blood plasma level profile with a dosage-corrected mean $AUC_t$ (h·ng/mL)/(mg/$m^2$) of between about 6 (h·ng/mL)/(mg/$m^2$) and 20 (h·ng/mL)/(mg/$m^2$), of between about 8 (h·ng/mL)/(mg/$m^2$) and 15 (h·ng/mL)/(mg/$m^2$), of between about 10 (h·ng/mL)/(mg/$m^2$) and 13 (h·ng/mL)/(mg/$m^2$). In one embodiment, the dosage-corrected mean $AUC_t$(h·ng/mL)/(mg/$m^2$) is about 6, 7, 8, 9, 10, 11, 12, 13, 14, 15, 16, 17, 18, 19, or 20 (h·ng/mL)/(mg/$m^2$). In one embodiment, the dosage-corrected mean $AUC_t$ (h·ng/mL)/(mg/$m^2$) is about 12.5 (h·ng/mL)/(mg/$m^2$)±2.2 (h·ng/mL)/(mg/$m^2$). In one embodiment, the dosage-corrected mean $AUC_t$(h·ng/mL)/(mg/$m^2$) is about 10.5 (h·ng/mL)/(mg/$m^2$), about 11.0 (h·ng/mL)/(mg/$m^2$), about 11.5 (h·ng/mL)/(mg/$m^2$), about 12.0 (h·ng/mL)/(mg/$m^2$), about 12.5 (h·ng/mL)/(mg/$m^2$), or about 13.0 (h·ng/mL)/(mg/$m^2$). The dosage corrected mean $AUC_t$ is mean $AUC_t$ divided by the number of milligrams/$m^2$ of the compounds described herein in the formulation. In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$.

In another embodiment, the compounds described herein are orally or intravenously administered to a subject prior to administration of a chemotherapeutic agent so that a single dose of the compounds described herein provides a blood plasma level profile with a dosage-corrected mean $AUC_t$ (h·ng/mL)/(mg/$m^2$) of between about 12.3 (h·ng/mL)/(mg/$m^2$) to about 19.5 (h·ng/mL)/(mg/$m^2$) or about 7.6 (h·ng/mL)/(mg/$m^2$) to about 16.5 (h·ng/mL)/(mg/$m^2$). In one embodiment, the dosage-corrected mean $AUC_t$(h·ng/mL)/(mg/$m^2$) is about at least 15.6 (h·ng/mL)/(mg/$m^2$) or about at least 10.7 (h·ng/mL)/(mg/$m^2$).

In another embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a dosage-corrected mean $AUC_t$(h·ng/mL)/(mg/$m^2$) of between about 6 (h·ng/mL)/(mg/$m^2$) and 20 (h·ng/mL)/(mg/$m^2$). In one embodiment, the dosage-corrected mean $AUC_t$(h·ng/mL)/(mg/$m^2$) is about 15.0 (h·ng/mL)/(mg/$m^2$)±3.0 (h·ng/mL)/(mg/$m^2$) or about 15.0 (h·ng/mL)/(mg/$m^2$)±about 20%. In one embodiment, the dosage-corrected mean $AUC_t$ (h·ng/mL)/(mg/$m^2$) is at least about 8.35

(h·ng/mL)/(mg/$m^2$). In one embodiment, the dosage-corrected mean $AUC_t$(h·ng/mL)/(mg/$m^2$) is about 16.5 (h·ng/mL)/(mg/$m^2$)±about 20%. In one embodiment, the dosage-corrected mean $AUC_t$(h·ng/mL)/(mg/$m^2$) is at least about 10.0 (h·ng/mL)/(m g/$m^2$). The dosage corrected $AUC_t$ is $AUC_t$ divided by the number of milligrams/$m^2$ of the compounds described herein in the formulation. In one embodiment, the compounds described herein are administered on days 1 and 2 of the treatment regime. In one embodiment, the compounds described herein are administered on days 1, 2, and 3 of the treatment regime. In one embodiment, the compounds described herein are administered on days 1, 2, 3, and 4 of the treatment regime. In one embodiment, the compounds described herein are administered on days 1, 2, 3, 4, and 5 of the treatment regime.

In another embodiment, the compounds described herein are orally or intravenously administered to a subject prior to administration of a chemotherapeutic agent so that a single dose of the compounds described herein provides a blood plasma level profile with a dosage-corrected mean $AUC_{inf}$ (h·ng/mL)/(mg/$m^2$) of between about 6 (h·ng/mL)/(mg/$m^2$) and 20 (h·ng/mL)/(mg/$m^2$), of between about 8 (h·ng/mL)/(mg/$m^2$) and 15 (h·ng/mL)/(mg/$m^2$), of between about 10 (h·ng/mL)/(mg/$m^2$) and 13 (h·ng/mL)/(mg/$m^2$). In one embodiment, the dosage-corrected mean $AUC_{inf}$ (h·ng/mL)/(mg/$m^2$) is about 6, 7, 8, 9, 10, 11, 12, 13, 14, 15, 16, 17, 18, 19, or 20 (h·ng/mL)/(mg/$m^2$). In one embodiment, the dosage-corrected mean $AUC_{inf}$ (h·ng/mL)/(mg/$m^2$) is about 12.7 (h·ng/mL)/(mg/$m^2$)±2.5 (h·ng/mL)/(mg/$m^2$). In one embodiment, the dosage-corrected mean $AUC_{inf}$ (h·ng/mL)/(mg/$m^2$) is about 10.5 (h·ng/mL)/(mg/$m^2$), about 11.0 (h·ng/mL)/(mg/$m^2$), about 11.5 (h·ng/mL)/(mg/$m^2$), about 12.0 (h·ng/mL)/(mg/$m^2$), about 12.5 (h·ng/mL)/(mg/$m^2$), about 13.0 (h·ng/mL)/(mg/$m^2$), or about 13.5 (h·ng/mL)/(mg/$m^2$). The dosage corrected mean $AUC_{inf}$ is mean $AUC_{inf}$ divided by the number of milligrams/$m^2$ of the compounds described herein in the formulation. In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$.

In another embodiment, the compounds described herein are orally or intravenously administered to a subject prior to administration of a chemotherapeutic agent so that a single dose of the compounds described herein provides a blood plasma level profile with a dosage-corrected mean $AUC_{inf}$ (h·ng/mL)/(mg/$m^2$) measured over 24.5 hours after administration of between about 12.4 (h·ng/mL)/(mg/$m^2$) to about 19.6 (h·ng/mL)/(mg/$m^2$) or about 7.6 (h·ng/mL)/(mg/$m^2$) to about 16.5 (h·ng/mL)/(mg/$m^2$). In one embodiment, the mean $AUC_{inf}$ (h·ng/mL)/(mg/$m^2$) measured over 24.5 hours after administration is about at least 15. (h·ng/mL)/(mg/$m^2$) or about at least 10.7 (h·ng/mL)/(mg/$m^2$). In one embodiment, the mean $AUC_{inf}$ (h·ng/mL)/(mg/$m^2$) measured over 72.5 hours after administration of between about 12.4 (h·ng/mL)/(mg/$m^2$) to about 19.6 (h·ng/mL)/(mg/$m^2$) or about 7.6 (h·ng/mL)/(mg/$m^2$) to about 16.5 (h·ng/mL)/(mg/$m^2$). In one embodiment, the mean $AUC_{inf}$ (h·ng/mL)/(mg/$m^2$) measured over 72.5 hours after administration is about at least 15.6 h-(h·ng/mL)/(mg/$m^2$) or about at least 10.7 (h·ng/mL)/(mg/$m^2$).

In another embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a dosage-corrected mean $AUC_t$ (h·ng/mL)/(mg/$m^2$) of between about 6 (h·ng/mL)/(mg/$m^2$) and 20 (h·ng/mL)/(mg/$m^2$). In one embodiment, the dosage-corrected mean $AUC_t$ (h·ng/mL)/(mg/$m^2$) is 6, 7, 8, 9, 10, 11, 12, 13, 14, 15, 16, 17, 18, 19, or 20 (h·ng/mL)(mg/$m^2$). In one embodiment, the dosage-corrected mean $AUC_t$(h·ng/mL)/(mg/$m^2$) is about 15.0 (h·ng/mL)/(mg/$m^2$)±3.0 (h·ng/mL)/(mg/$m^2$) or about 15.0 (h·ng/mL)/(mg/$m^2$)±about 20%. In one embodiment, the dosage-corrected mean $AUC_t$(h·ng/mL)/(mg/$m^2$) is about 8.35 (h·ng/mL)/(mg/$m^2$)±about 20%. In one embodiment, the dosage-corrected mean $AUC_t$ (h·ng/mL)/(mg/$m^2$) is about 16.5 (h·ng/mL)/(mg/$m^2$)±about 20%. In one embodiment, the dosage-corrected mean $AUC_t$(h·ng/mL)/(mg/$m^2$) is at least about 10.0 (h·ng/mL)/(mg/$m^2$). The dosage corrected $AUC_t$ is $AUC_t$ divided by the number of milligrams/$m^2$ of the compounds described herein in the formulation. In one embodiment, the compounds described herein are administered on days 1 and 2 of the treatment regime. In one embodiment, the compounds described herein are administered on days 1, 2, and 3 of the treatment regime. In one embodiment, the compounds described herein are administered on days 1, 2, 3, and 4 of the treatment regime. In one embodiment, the compounds described herein are administered on days 1, 2, 3, 4, and 5 of the treatment regime.

In another embodiment, the compounds described herein are orally or intravenously administered to a subject prior to administration of a chemotherapeutic agent so that a single dose of the compounds described herein provides a blood plasma level profile with a with a mean CL (L/h/$m^2$) measured over 24.5 hours after administration of between about 45 L/h/$m^2$ and about 85 L/h/$m^2$. In one embodiment, the mean CL (L/h/$m^2$) measured over 24.5 hours after administration is 45, 50, 55, 60, 65, 70, 75, 80, or 85 (L/h/$m^2$). In one embodiment, the mean CL (L/h/$m^2$) measured over 24.5 hours after administration is about 65 (L/h/$m^2$)±15 (L/h/$m^2$). In one embodiment, the mean CL (L/h/$m^2$) measured over 24.5 hours after administration is about 64.4 (L/h/$m^2$)±10.6 (L/h/$m^2$). In one embodiment, the mean CL (L/h/$m^2$) measured over 72.5 hours after administration is between about 45 (L/h/$m^2$) to about 80 (L/h/$m^2$). In one embodiment, the mean CL (L/h/$m^2$) measured over 72.5 hours after administration is about 60 (L/h/$m^2$)±15 (L/h/$m^2$). In one embodiment, the mean CL (L/h/$m^2$) measured over 72.5 hours after administration is about 62.1 (L/h/$m^2$)±10.3 (L/h/$m^2$). In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a CL (L/h/$m^2$) as described herein.

In another embodiment, provided is a method of treating a subject undergoing chemotherapy for the treatment of a CDK 4/6-replication independent cellular proliferation disorder by providing an intravenous administered formulation of the compounds described herein wherein a single-dose provides a blood plasma level profile with a mean $V_{ss}$ ($L/m^2$) measured over 24.5 hours after final administration of between about 320 ($L/m^2$) and about 630 ($L/m^2$). In one embodiment, the mean $V_{ss}$ ($L/m^2$) measured over 24.5 hours is 320, 370, 400, 420, 470, 500, 520, 570, 600, or 630 ($L/m^2$). In one embodiment, the mean $V_{ss}$ ($L/m^2$) measured over 24.5 hours is about 425 ($L/m^2$)±150 ($L/m^2$). In one embodiment, the mean $V_{ss}$ ($L/m^2$) measured over 24.5 hours in about 421 ($L/m^2$)±101 ($L/m^2$). In one embodiment, the mean $V_{ss}$ ($L/m^2$) measured over 72.5 hours after final administration of between about 390 ($L/m^2$) and about 825 ($L/m^2$). In one embodiment, the mean $V_{ss}$ ($L/m^2$) measured over 72.5 hours after final administration is 400, 450, 500, 550, 600, 650, 700, 750, 800, or 825 ($L/m^2$). In one embodiment, the mean $V_{ss}$ ($L/m^2$) measured over 72.5 hours after final administration is about 550 ($L/m^2$)±175 ($L/m^2$). In one embodiment, the mean $V_{ss}$ ($L/m^2$) measured over 72.5 hours after final administration is about 547 ($L/m^2$)±147 ($L/m^2$). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a $V_{ss}$ ($L/m^2$) as described herein.

In another embodiment, the compounds described herein are orally or intravenously administered to a subject prior to administration of a chemotherapeutic agent so that a single dose of the compounds described herein provides a blood plasma level profile with a mean MRTs (h) measured over 24.5 hours of between about 4.75 (h) and about 9.25 (h). In one embodiment, the mean $MRT_{inf}$ (h) measured over 24.5 hours is 4.75, 5.25, 5.75, 6.25, 6.75, 7.25, 7.75, 8.25, 8.75, or 9.25 (h). In one embodiment, the mean $MRT_{inf}$ (h) measured over 24.5 hours is about 6.5 (h)±1.75 (h). In one embodiment, the mean $MRT_{inf}$(h) measured over 24.5 hours is about 6.59 (h)±1.33 (h). In one embodiment, the mean $MRT_{inf}$(h) measured over 72.5 hours is between about 6 (h) and about 13 (h). In one embodiment, the mean $MRT_{inf}$ (h) measured over 72.5 hours is about 9 (h)±2.5 (h). In one embodiment, the mean $MRT_{inf}$(h) measured over 72.5 hours is about 8.86 (h)±2.12 (h). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a $V_e$s ($L/m^2$) as described herein.

In another embodiment, the compounds described herein are orally or intravenously administered to a subject prior to administration of a chemotherapeutic agent so that a single dose of the compounds described herein provides a blood plasma level profile with a mean λz (1/h) measured over 24.5 hours of between about 0.07 and 0.15. In one embodiment, the mean λz (1/h) measured over 24.5 hours is 0.07, 0.08, 0.09, 0.10, 0.11, 0.12, 0.13, 0.14, or 0.15 (1/h). In one embodiment, the mean λz (1/h) measured over 24.5 hours is about 0.09±0.025. In one embodiment, the λz mean (1/h) measured over 24.5 hours is about 0.0899±0.0157. In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a λz (1/h) measured over 24.5 hours as described herein.

In another embodiment, the compounds described herein are orally or intravenously administered to a subject prior to administration of a chemotherapeutic agent so that a single dose of the compounds described herein provides a blood plasma level profile with a mean t½ (h) measured over 24.5 hours of between about 5 h and 9.5 h. In one embodiment, the mean t½ (h) measured over 24.5 hours is 5, 5.5, 6, 6.5, 7, 7.5, 8, 8.5, 9, or 9.5 h. In one embodiment, the mean t½ (h) measured over 24.5 hours is about 8±1.5 (h). In one embodiment, the mean t½ (h) measured over 24.5 hours is about 7.87±1.14 (h). In one embodiment, the mean t½β (h) measured over 72.5 hours is between about 5.5 (h) and about 9 (h). In one embodiment, the mean t½β (h) measured over 24.5 hours is 5, 5.5, 6, 6.5, 7, 7.5, 8, 8.5, or 9 h. In one embodiment, the mean t½β (h) measured over 72.5 hours is about 8 (h)±1.5 (h). In one embodiment, the mean t½β (h) measured over 72.5 hours is about 7.87 (h)±1.14 (h). In one embodiment, the mean t½γ (h) measured over 72.5 hours is between about 15 (h) and about 22 (h). In one embodiment, the mean t½γ (h) measured over 72.5 hours is 15, 16, 17, 18, 19, 20, 21, or 22 (h). In one embodiment, the mean t½γ (h) measured over 72.5 hours is about 18 (h)±2.25 (h). In one embodiment, the mean t½γ (h) measured over 72.5 hours is about 18.0 (h)±1.92 (h). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a t½ (h), t½β (h), and/or t½γ (h) measured over 24.5 hours and/or 72.5 hours as described herein.

In another embodiment, the compounds described herein are orally or intravenously administered to a subject prior to administration of a chemotherapeutic agent so that a single dose of the compounds described herein provides a blood plasma level profile with a mean t½ (h) of between about 11.9 h and 17.3 h.

In one embodiment, the compounds described herein are orally or intravenously administered to a subject prior to administration of a chemotherapeutic agent so that a single dose of the compounds described herein provides a blood plasma level profile with a mean concentration (ng/mL) at 24.5 hours after the end of administration of between about 5 (ng/mL) and about 35 (ng/mL). In one embodiment, the mean concentration at 24.5 hours after the end of administration is 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 (ng/mL). In one embodiment, the mean concentration at 24.5 hours after the end of administration is about 19 (ng/mL)±5.24 (ng/mL). In one embodiment, the mean concentration at 24.5 hours after the end of administration is about 20 (ng/mL)±7.5 (ng/mL). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean concentration (ng/mL) at 24.5 hours after the end of administration as described herein.

In another embodiment, the compounds described herein are orally or intravenously administered to a subject prior to administration of a chemotherapeutic agent so that a single dose of the compounds described herein provides a blood plasma level profile with a mean concentration (ng/mL) at 72.5 hours after the end of administration of between about 0.7 (ng/mL) and about 3 (ng/mL). In one embodiment, the mean concentration at 72.5 hours after the end of administration is about 0.7, 0.9, 1.0, 1.2, 1.4, 1.6, 1.8, 2.0, 2.2, 2.4, 2.6, 2.8, or 3 (ng/mL). In one embodiment, the mean concentration at 72.5 hours after the end of administration is about 2.25 (ng/mL)±1.5 (ng/mL). In one embodiment, the mean concentration at 72.5 hours after the end of administration is about 1.79 (ng/mL)±0.731 (ng/mL). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean concentration (ng/mL) at 72.5 hours after the end of administration as described herein.

In another embodiment, the compounds described herein are orally or intravenously administered to a subject prior to administration of a chemotherapeutic agent so that a single dose of the compounds described herein provides a primary pharmacokinetic blood plasma level profile with a mean $\alpha$ (1/h) of between about 1 (1/h) and 15 (1/h). In one embodiment, a single-dose provides a primary pharmacokinetic blood plasma level profile with a mean $\alpha$ (1/h) of 1, 2, 3, 4, 5, 6, 7, 8, 9, 10, 11, 12, 13, 14, 15 (1/h). In one embodiment, a single-dose provides a primary pharmacokinetic blood plasma level profile with a mean $\alpha$ (1/h) of about 11 (1/h)±9 (1/h). In one embodiment, a single-dose provides a primary pharmacokinetic blood plasma level profile with a mean $\alpha$ (1/h) of about 11.3 (1/h)±7.06 (1/h). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean $\alpha$ (1/h) as described herein.

In another embodiment, the compounds described herein are orally or intravenously administered to a subject prior to administration of a chemotherapeutic agent so that a single dose of the compounds described herein provides a primary pharmacokinetic blood plasma level profile with a mean $\beta$ (1/h) of about 0.4 (1/h)±0.3 (1/h). In one embodiment, provided is a primary pharmacokinetic blood plasma level profile with a mean $\beta$ (1/h) of about 0.362 (1/h)±0.110 (1/h). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean $\beta$ (1/h) as described herein.

In another embodiment, the compounds described herein are orally or intravenously administered to a subject prior to administration of a chemotherapeutic agent so that a single dose of the compounds described herein provides a primary pharmacokinetic blood plasma level profile with a mean $\gamma$ (1/h) of about 0.05 (1/h)±0.01 (1/h). In one embodiment, provided is a primary pharmacokinetic blood plasma level profile with a mean $\gamma$ (1/h) of about 0.0497 (1/h)±0.00442 (1/h). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean $\gamma$ (1/h) as described herein.

In another embodiment, the compounds described herein are orally or intravenously administered to a subject prior to administration of a chemotherapeutic agent so that a single dose of the compounds described herein provides a 3-compartment primary pharmacokinetic blood plasma level profile with a mean K21 (1/h) of about 1 (1/h)±0.6. In one embodiment, a single-dose provides a 3-compartment primary pharmacokinetic blood plasma level profile with a mean K21 (1/h) of about 0.993 (1/h)±0.439. In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean K21 (1/h) as described herein.

In another embodiment, the compounds described herein are orally or intravenously administered to a subject prior to administration of a chemotherapeutic agent so that a single dose of the compounds described herein provides a 3-compartment primary pharmacokinetic blood plasma level profile with a mean K31 (1/h) of about 0.08 (1/h)±0.03 (1/h). In one embodiment, a single-dose provides a 3-compartment primary pharmacokinetic blood plasma level profile with a mean K31 (1/h) of about 0.0750 (1/h)±0.0160 (1/h). In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean K31 (1/h) as described herein.

In another embodiment, the compounds described herein are orally or intravenously administered to a subject prior to administration of a chemotherapeutic agent so that a single dose of the compounds described herein provides a 3-compartment primary pharmacokinetic blood plasma level profile with a mean V1 (L/$m^2$) of about 25±15. In one embodiment, a single-dose provides a 3-compartment primary pharmacokinetic blood plasma level profile with a mean V1 (L/$m^2$) of about 25.6±9.51. In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean V1 (L/$m^2$) as described herein.

In another embodiment, the compounds described herein are orally or intravenously administered to a subject prior to administration of a chemotherapeutic agent so that a single dose of the compounds described herein provides a 3-compartment primary pharmacokinetic blood plasma level profile with a mean $C_{max}$ (ng/mL) of about 2000 (ng/mL)±650 (ng/mL). In one embodiment, a single-dose provides a 3-compartment primary pharmacokinetic blood plasma level profile with a mean $C_{max}$ (ng/mL) of about 2020 (ng/mL) ±505 (ng/mL). In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean $C_{max}$(ng/mL) as described herein.

In another embodiment, the compounds described herein are orally or intravenously administered to a subject prior to administration of a chemotherapeutic agent so that a single dose of the compounds described herein provides a primary pharmacokinetic blood plasma level profile with a mean t½α of about 0.1 (h)±0.05 (h). In one embodiment, a single-dose provides a primary pharmacokinetic blood plasma level profile with a mean t % a of about 0.0776 (h)±0.0329 (h). In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$. In one embodiment, the single dose is about 190 mg/$m^2$. In one embodiment, the single dose is about 200 mg/$m^2$. In one embodiment, the single dose is about 240 mg/$m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean t½α (h) as described herein.

In another embodiment, the compounds described herein are orally or intravenously administered to a subject prior to administration of a chemotherapeutic agent so that a single dose of the compounds described herein provides a 2-compartment primary pharmacokinetic blood plasma level profile with a mean t½β of about 2 (h)±0.75 (h). In one embodiment, a single-dose provides a 2-compartment primary pharmacokinetic blood plasma level profile with a mean t½β of about 2.03 (h)±0.444 (h). In one embodiment, the single dose is between about 170 mg/$m^2$ and 280 mg/$m^2$ or 170 mg/$m^2$ and 215 mg/$m^2$. In one embodiment, the single dose is about 190 mg/$m^2$. In one embodiment, the single dose is about 200 mg/$m^2$. In one embodiment, the single dose is about 240 mg/$m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean t½β (h) as described herein.

In another embodiment, the compounds described herein are orally or intravenously administered to a subject prior to administration of a chemotherapeutic agent so that a single dose of the compounds described herein provides a 3-compartment primary pharmacokinetic blood plasma level profile with a mean t½γ of about 15 (h)±3 (h). In one embodiment, a single-dose provides a 3-compartment primary pharmacokinetic blood plasma level profile with a mean t½γ of about 14.0 (h)±1.35 (h). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean t½γ (h) as described herein.

In another embodiment, the compounds described herein are orally or intravenously administered to a subject prior to administration of a chemotherapeutic agent so that a single dose of the compounds described herein provides a 3-compartment primary pharmacokinetic blood plasma level profile with a mean AUC (h·ng/mL) of about 3200 (h·ng/mL) ±750 (h·ng/mL). In one embodiment, a single-dose provides a 3-compartment primary pharmacokinetic blood plasma level profile with a mean AUC (h·ng/mL) of about 3220 (h·ng/mL)±559 (h·ng/mL). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean AUC (h·ng/mL) as described herein.

In another embodiment, the compounds described herein are orally or intravenously administered to a subject prior to administration of a chemotherapeutic agent so that a single dose of the compounds described herein provides a 3-compartment primary pharmacokinetic blood plasma level profile with a mean CL ($L/h/m^2$) of about 60 ($L/h/m^2$)±15 ($L/h/m^2$). In one embodiment, a 3-compartment primary pharmacokinetic blood plasma level profile with a mean CL ($L/h/m^2$) of about 61.1 ($L/h/m^2$)±10.6 ($L/h/m^2$). In one embodiment, the single dose is between about 170 $mg/m^2$ and 240 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean CL ($L/h/m^2$) as described herein.

In another embodiment, the compounds described herein are orally or intravenously administered to a subject prior to administration of a chemotherapeutic agent so that a single dose of the compounds described herein provides a 3-compartment primary pharmacokinetic blood plasma level profile with a mean $V_{ss}$ ($L/m^2$) of about 500 ($L/m^2$)±200 ($L/m^2$). In one embodiment, a 3-compartment primary pharmacokinetic blood plasma level profile with a mean $V_{ss}$ ($L/m^2$) of about 508 ($L/m^2$)±131 ($L/m^2$). In one embodiment, the single dose is between about 170 $mg/m^2$ and 280 $mg/m^2$ or 170 $mg/m^2$ and 215 $mg/m^2$. In one embodiment, the single dose is about 190 $mg/m^2$. In one embodiment, the single dose is about 200 $mg/m^2$. In one embodiment, the single dose is about 240 $mg/m^2$. In one embodiment, the compounds described herein are administered to a subject prior to administration of a chemotherapeutic agent in a multi-day chemotherapeutic treatment regime, for example, 2 days, 3 days, 4 days, or 5 days, wherein the compounds described herein, following administration on any day of the multi-day chemotherapeutic treatment regime, for example day 2, 3, 4, or 5, provides a blood plasma level profile of the compounds described herein with a with a mean $V_{ss}$ ($L/m^2$) as described herein.

In another embodiment, the compounds described herein at the dosages described about is administered daily for more than 1, more than 2, more than 3, more than 4, more than 5, more than 6, more than 7, more than 8, more than 9, more than 10, more than 11, more than 12, more than 13, more than 14, more than 15, more than 16, more than 17, more than 18, more than 19, more than 20, more than 21, more than 22, more than 23, more than 24, more than 25 more than 26, more than 27, or more than 28 days. In one embodiment, provided is a method of treating a subject undergoing chemotherapy for the treatment of a CDK 4/6-replication independent cellular proliferation disorder by providing an intravenous administered formulation of the compounds described herein at a dosage described herein daily for 1, 2, 3, 4, 5, 6, 7, 8, 9, 10, 11, 12, 13, 14, 15, 16, 17, 18, 19, 20, 21, 22, 23, 24, 25, 26, 27, or 28 days or more.

In another embodiment, provided is a method of treating a subject undergoing chemotherapy for the treatment of a CDK 4/6-replication independent cellular proliferation disorder by providing an intravenous administered formulation of the compounds described herein wherein a single-dose of the compounds described herein followed by a single-dose of Topotecan at 1.5 $mg/m^2$ provides a mean $C_{max}$ (ng/mL) of Topotecan between about 30 ng/mL to about 150 ng/mL. In one embodiment, the mean $C_{max}$ (ng/mL) of Topotecan at 1.5 $mg/m^2$ is about 30 ng/mL, about 40 ng/mL, about 50 ng/mL, about 60 ng/mL, about 70 ng/mL, about 80 ng/mL, about 90 ng/mL, about 100 ng/mL. about 110 ng/mL, about 120 ng/mL, about 130 ng/mL, about 140 ng/mL or about 150 ng/mL. In one embodiment, a single-dose of the compounds described herein followed by a single-dose of Topotecan at 1.25 $mg/m^2$ provides a mean $C_{max}$ (ng/mL) of Topotecan between about 20 ng/mL and 120 ng/mL. In one embodiment, the mean $C_{max}$ (ng/mL) of Topotecan at 1.25 $mg/m^2$ is about 20 ng/mL, about 30 ng/mL, about 40 ng/mL, about 50 ng/mL, about 60 ng/mL, about 70 ng/mL, about 80 ng/mL, about 90 ng/mL, about 100 ng/mL, about 110 ng/mL, or about 120 ng/mL. In one embodiment, a single-dose of the compounds described herein followed by a single-dose of Topotecan at 0.75 $mg/m^2$ provides a mean $C_{max}$ (ng/mL) of Topotecan between about 10 ng/mL and 70 ng/mL. In one embodiment, the mean $C_{max}$ (ng/mL) of Topotecan at 0.75 $mg/m^2$ is about 10 ng/mL, about 15 ng/mL, about 20 ng/mL, about 25 ng/mL, about 30 ng/mL, about 35 ng/mL, about 40 ng/mL, about 45 ng/mL, about 50 ng/mL, about 55 ng/mL, about 60 ng/mL, about 65 ng/mL, or about 70 ng/mL.

In another embodiment, provided is a method of treating a subject undergoing chemotherapy for the treatment of a CDK 4/6-replication independent cellular proliferation disorder by providing an intravenous administered formulation of the compounds described herein wherein a single-dose of the compounds described herein followed by a single-dose of Topotecan at 1.5 $mg/m^2$ provides a mean $C_{max}$ (ng/mL) of Topotecan between about 40.2 ng/mL and about 122 ng/mL. In one embodiment, a single-dose of the compounds described herein followed by a single-dose of Topotecan at 1.25 $mg/m^2$ provides a mean $C_{max}$ (ng/mL) of Topotecan between about 33.1 ng/mL and 104 ng/mL. In one embodiment, a single-dose of the compounds described herein followed by a single-dose of Topotecan at 0.75 $mg/m^2$ provides a mean $C_{max}$ (ng/mL) of Topotecan between about 17.9 ng/mL and 38.5 ng/mL.

In another embodiment, provided is a method of treating a subject undergoing chemotherapy for the treatment of a CDK 4/6-replication independent cellular proliferation disorder by providing an intravenous administered formulation of the compounds described herein wherein a single-dose of the compounds described herein followed by a single-dose of Topotecan at 1.5 $mg/m^2$ provides a mean AUC, (h·ng/mL) of Topotecan between about 100 h·ng/mL and about 300 h·ng/mL. In one embodiment, the mean AUC, (h·ng/mL) of Topotecan at 1.5 $mg/m^2$ is about 100 h·ng/mL, about 110 h·ng/mL, about 120 h·ng/mL, about 130 h·ng/mL, about 140 h·ng/mL, about 150 h·ng/mL, about 160 h·ng/mL, about 170 h·ng/mL, about 180 h·ng/mL, about 190 h·ng/mL, about 200 h·ng/mL, about 220 h·ng/mL, about 240 h·ng/mL, about 260 h·ng/mL, about 280 h·ng/mL, or about 300 h·ng/mL. In one embodiment, a single-dose of the compounds described herein followed by a single-dose of Topotecan at 1.25 $mg/m^2$ provides a mean AUC, (h·ng/mL) of Topotecan between about 80 h·ng/mL and about 300 h·ng/mL. In one embodiment, the mean AUC, (h·ng/mL) of Topotecan at 1.25 $mg/m^2$ is about 80 h·ng/mL, about 90 h·ng/mL, about 100 h·ng/mL, about 110 h·ng/mL, about 120 h·ng/mL, about 130 h·ng/mL, about 140 h·ng/mL, about 150 h·ng/mL, about 160 h·ng/mL, about 170 h·ng/mL, about 180 h·ng/mL, about 190 h·ng/mL, about 200 h·ng/mL, about 220 h·ng/mL, about 240 h·ng/mL, about 260 h·ng/mL, about 280 h·ng/mL, or about 300 h·ng/mL. In one embodiment, a single-dose of the compounds described herein followed by a single-dose of Topotecan at 0.75 $mg/m^2$ provides a mean AUC, (h·ng/mL) of Topotecan between about 50 h·ng/mL and about 200 h·ng/mL. In one embodiment, the mean AUC, (h·ng/mL) of Topotecan at 0.75 $mg/m^2$ is about 50 h·ng/mL, about 60 h·ng/mL, 70 h·ng/mL, about 80 h·ng/mL, about 90 h·ng/mL, about 100 h·ng/mL, about 110 h·ng/mL, about 120 h·ng/mL, about 130 h·ng/mL, about 140 h·ng/mL, about 150 h·ng/mL, about 160 h·ng/mL, about 170 h·ng/mL, about 180 h·ng/mL, about 190 h·ng/mL, or about 200 h·ng/mL.

In another embodiment, provided is a method of treating a subject undergoing chemotherapy for the treatment of a CDK 4/6-replication independent cellular proliferation disorder by providing an intravenous administered formulation of the compounds described herein wherein a single-dose of the compounds described herein followed by a single-dose of Topotecan at 1.5 $mg/m^2$ provides a mean AUC, (h·ng/mL) of Topotecan between about 132 h·ng/mL and about 181 h·ng/mL. In one embodiment, a single-dose of the compounds described herein followed by a single-dose of Topotecan at 1.25 $mg/m^2$ provides a mean AUC, (h·ng/mL) of Topotecan between about 121 h·ng/mL and about 254 h·ng/mL. In one embodiment, a single-dose of the compounds described herein followed by a single-dose of Topotecan at 0.75 $mg/m^2$ provides a mean AUC, (h·ng/mL) of Topotecan between about 74.4 h·ng/mL and about 120 h·ng/mL.

As provided herein, the compounds described herein can be administered wherein any one or more of the described PK or PD blood profile parameters described herein is reached to treat a subject undergoing chemotherapy for the treatment of any CDK-replication independent cellular proliferation disorder.

In another embodiment, provided is a method of treating a subject having a CDK-replication dependent cellular proliferation disorder by providing an intravenous administered formulation of the compounds described herein in a dosage providing a blood plasma profile as described herein.

In another embodiment, provided is method of treating a subject having a CDK-replication independent cellular proliferation disorder by providing an intravenous administered formulation of the compounds described herein in a dosage providing a combination of two or more blood plasma parameters at levels described herein. Non-limiting examples of parameters that can be provided in combinations of two or more at levels described herein include: mean $C_{max}$, mean dosage-corrected $C_{max}$, mean $T_{max}$, mean $AUC_{inf}$, dosage-corrected mean $AUC_{inf}$, mean $AUC_t$, dosage-corrected mean $AUC_t$, and mean t½.

Another embodiment described herein is a kit for dispensing a pharmaceutical dosage form comprising any of the compounds described herein, the kit comprising: (a) at least one dosage form comprising a compound described herein; (b) at least one moisture proof dispensing receptacle comprising blister or strip packs, an aluminum blister, a transparent or opaque polymer blister with pouch, polypropylene tubes, colored blister materials, tubes, bottles, and bottles optionally containing a child-resistant feature, optionally comprising a desiccant, such as a molecular sieve or silica gel; and optionally (c) an insert comprising instructions or prescribing information for the compound 1 comprised by the oral pharmaceutical composition; or (d) directions for administration or any contraindications.

Another embodiment is a kit comprising one or more pre-filled syringes comprising a solution or suspension of one or more compounds described herein. In one embodiment, such a kit comprises a pre-filled syringe comprising compounds described herein in a blister pack or a sealed sleeve. The blister pack or sleeve may be sterile on the inside. In one aspect, pre-filled syringes as described herein may be placed inside such blister packs or sleeves prior to undergoing sterilization, for example terminal sterilization.

Such a kit may further comprise one or more needles for administration of the compounds described herein. Such kits may further comprise instructions for use, a drug label, contraindications, warnings, or other relevant information. One embodiment described herein is a carton or package comprising one or more pre-filled syringes comprising one or more compounds as described herein contained within a blister pack, a needle, and optionally instructions for administration, a drug label, contraindications, warnings, or other relevant information.

A terminal sterilization process may be used to sterilize the syringe and such a process may use a known process such as an ethylene oxide or a hydrogen peroxide ($H_2O_2$) sterilization process. Needles to be used with the syringe may be sterilised by the same method, as may kits described herein. In one aspect, a package is exposed to the sterilising gas until the outside of the syringe is sterile. Following such a process, the outer surface of the syringe may remain sterile (whilst in its blister pack) for up to 6 months, 9 months, 12 months, 15 months, 18 months, 24 months or longer. Thus, in one embodiment, a pre-filed syringe as described herein (in its blister pack) may have a shelf life of up to 6 months, 9 months, 12 months, 15 months, 18 months, 24 months, or even longer. In one embodiment, less than one syringe in a million has detectable microbial presence on the outside of the syringe after 18 months of storage. In one aspect, the pre-filled syringe has been sterilised using ethylene oxide with a Sterility Assurance Level of at least $10^{-6}$. In another aspect, the pre-filled syringe has been sterilised using hydrogen peroxide with a Sterility Assurance Level of at least $10^{-6}$. Significant amounts of the sterilising gas should not enter the variable volume chamber of the syringe. The term "significant amounts" As used herein, refers to an amount of gas that would cause unacceptable modification of the compound solution or suspension within the variable volume chamber. In one embodiment, the pre-filled syringe has been sterilised using ethylene oxide, but the outer surface of the syringe has ≤1 ppm, preferably 50.2 ppm ethylene oxide residue. In one embodiment, the pre-filled syringe has been sterilised using hydrogen peroxide, but the outer surface of the syringe has 51 ppm, preferably 50.2 ppm hydrogen peroxide residue. In another embodiment, the pre-filled syringe has been sterilised using ethylene oxide, and the total ethylene oxide residue found on the outside of the syringe and inside of the blister pack is 50.1 mg. In another embodiment, the pre-filled syringe has been sterilised using hydrogen peroxide, and the total hydrogen peroxide residue found on the outside of the syringe and inside of the blister pack is 50.1 mg.

Another aspect is a kit of parts. For liquid and suspension compositions, and when the administration device is simply a hypodermic syringe, the kit may comprise the syringe, a needle and a container comprising the compounds described herein for use with the syringe. In case of a dry composition, the container may have one chamber containing the dry compound, and a second chamber comprising a reconstitution solution. In one embodiment, the injection device is a hypodermic syringe adapted so the separate container with compound can engage with the injection device such that in use the liquid or suspension or reconstituted dry composition in the container is in fluid connection with the outlet of the injection device. Examples of administration devices include but are not limited to hypodermic syringes and pen injector devices. Particularly preferred injection devices are the pen injectors, in which case the container is a cartridge, preferably a disposable cartridge.

Another embodiment comprises a kit comprising a needle and a container containing the compounds described herein and optionally further containing a reconstitution solution, the container being adapted for use with the needle. In one aspect, the container is a pre-filled syringe. In another aspect, the container is dual chambered syringe. Another embodiment is a cartridge containing a composition of the compounds described herein for use with a pen injector device. The cartridge may contain a single dose or plurality of doses of drug delivery system.

In another embodiment composition comprises a compound described herein and one or more excipients, and also other biologically active agents, either in their free form or as drugs or combined with other drug delivery systems such as pegylated drugs or hydrogel linked drugs. In one aspect, such additional one or more biologically active agents is a free form drug or a second drug delivery system. In another embodiment, one or more compounds described herein are simultaneously administered, with each compound having either separate or related biological activities or targets.

In an alternative embodiment, the compound is combined with a second biologically active compound in such way that the composition is administered to a subject in need thereof first, followed by the administration of the second compound. Alternatively, the compounds described herein are administered to a subject in need thereof after another compound has been administered to the same subject.

It will be apparent to one of ordinary skill in the relevant art that suitable modifications and adaptations to the compositions, formulations, methods, processes, and applications described herein can be made without departing from the scope of any embodiments or aspects thereof.

The compositions, methods, and experiments provided are exemplary and are not intended to limit the scope of any of the specified embodiments. All of the various embodiments, aspects, and options disclosed herein can be combined in any variations or iterations. The scope of the compositions, formulations, methods, and processes described herein include all actual or potential combinations of embodiments, aspects, options, examples, and preferences herein described. The exemplary compositions and formulations described herein may omit any component, substitute any component disclosed herein, or include any component disclosed elsewhere herein. The ratios of the mass of any component of any of the compositions or formulations disclosed herein to the mass of any other component in the formulation or to the total mass of the other components in the formulation are hereby disclosed as if they were expressly disclosed. Should the meaning of any terms in any of the patents or publications incorporated by reference conflict with the meaning of the terms used in this disclosure, the meanings of the terms or phrases in this disclosure are controlling. All patents and publications cited herein are incorporated by reference herein for the specific teachings thereof.

The present disclosure includes duplicates. Duplicates are intended to be supplementary and additive.

EXAMPLES

Example 1

Synthesis of $R_1$ Groups

The following amines were purchased from commercial sources:

1

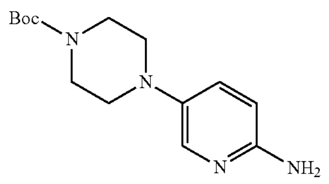

-continued

2

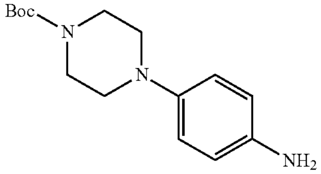

3

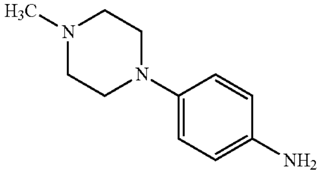

4

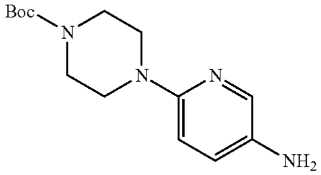

5

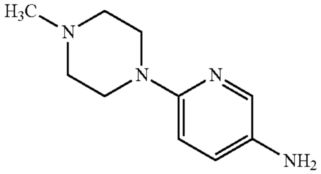

6

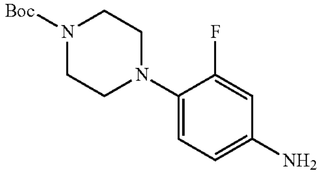

7

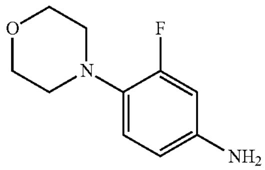

8

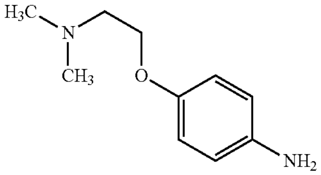

9

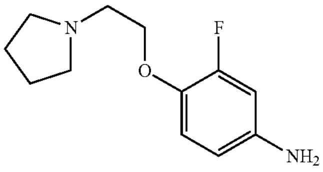

The following amines were synthesized using reported methods.

10

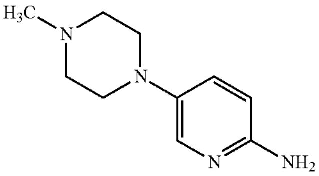

Compound 10 was synthesized using the procedure reported in Int. Pat. App. Publication No. WO 2009156284.

11

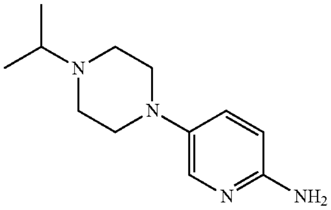

Compound 11 was synthesized using the reported procedures reported in Int. Pat. App. Publication No. WO 2011112995 and U.S. Pat. No. 7,713,994.

12

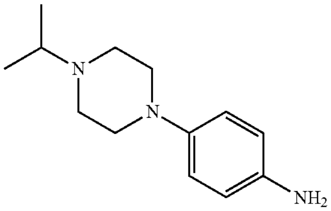

Compound 12 was synthesized using the procedure reported in Int. Pat. App. Publication No. WO 2007131991.

13

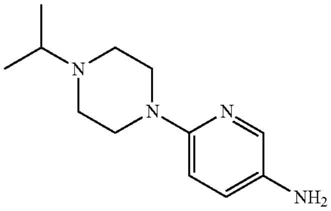

Compound 13 was synthesized using the procedure reported by Li et al., *ACS Med. Chem. Lett.,* 4(7): 647-650 (2013).

14

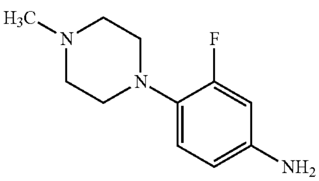

Compound 14 was synthesized using the procedures reported in Int. Pat. App. Publication No. WO 2014012360 and Tsou et al., *J. Med. Chem.* 51(12): 3507-3525 (2008).

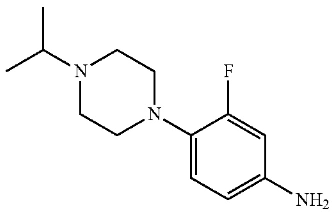

Compound 15 was synthesized using the procedures reported in Int. Pat. App. Publication No. WO 2014012360 and Tsou et al., J. Med. Chem. 51(12): 3507-3525 (2008).

Synthesis of 2-fluoro-4-(4-methylpiperazin-1-yl)aniline (16)

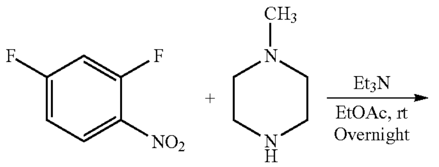

16a

16b

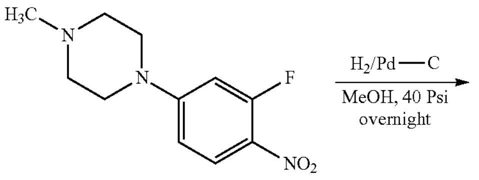

16c

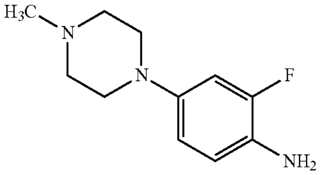

16

Step 1: Synthesis of 16c: To a solution of 16a (1.4 g, 13.9 mmol) and $Et_3N$ (1.4 g, 13.9 mmol) in EtOAc (15 mL) was added 1,3-difluoro-4-nitrobenzene 16a (2 g, 12.6 mmol) dropwise with stirring and the mixture was stirred at RT overnight. The reaction mixture was diluted with EtOAc (100 mL), washed with brine, dried over anhydrous $Na_2SO_4$ and concentrated in vacuo to give the title compound 16c as a yellow solid (3.0 g, quantitative). This product is used as such in the next step.

Step 2: Synthesis of 16: To a solution of Compound 16c (3 g, 12.9 mmol) in methanol (100 mL) was added catalytic amount of 10% Pd/C-50% wet (2 g). The mixture was hydrogenated on a Parr apparatus at 35-40 psi for 3 h at RT. The reaction mixture was filtered through a pad of Celite and the filtrate was concentrated under reduced pressure to afford 16 as a solid (2.4 g, 78% yield). MS(ESI) m/z 210.2 $[M+H]^+$. $^1H$ NMR (600 MHz, DMSO-$d_6$) δ 6.71 (dd, J=10.7, 2.5 Hz, 1H), 6.65-6.61 (m, 2H), 4.53 (s, 2H), 2.80 (s, 4H), 2.52-2.49 (m, 2H), 2.23 (s, 3H).

Synthesis of 2-fluoro-4-(4-isopropylpiperazin-1-yl)aniline hydrochloride (17)

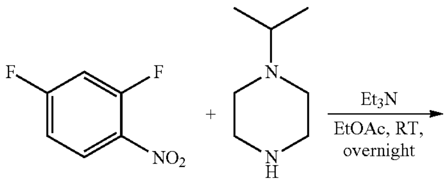

16a

17a

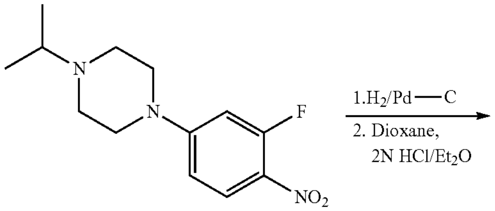

17b

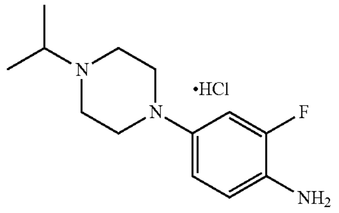

17

Step 1: Synthesis of 17b: Prepared according to the procedure described for compound 16c (quantitative yield).

Step 1: Synthesis of 17: 30 g (112 mmol) of 17b was hydrogenated following the procedure described for the preparation of compound 16. The resultant crude amine was dissolved in dioxane and treated with 2 N HCl in $Et_2O$. After stirring for 1 h at RT, the solid is filtered and dried to give 12 g (34%) of 17 as white solid. MS(ESI) m/z 238.2 $[M+H]^+$. $^1H$ NMR (600 MHz, Chloroform-d) δ 6.74 (dt, J=10.2, 1.6 Hz, 1H), 6.63 (dd, J=6.9, 1.6 Hz, 2H), 3.78 (s, 2H), 2.93 (s, 4H), 2.67 (s, 3H), 1.09 (d, J=6.6 Hz, 6H).

Synthesis of 6-(2-(dimethylamino)ethoxy)pyridin-3-amine (18)

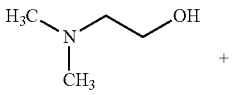

18a

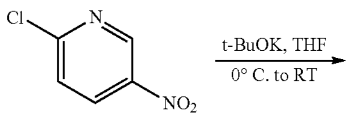

18b

-continued

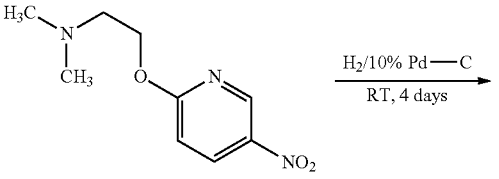

18c

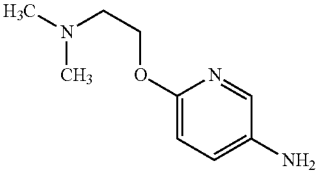

•HCl

18

Step 1: Synthesis of 18c: To a solution of 2-(dimethylamino)ethanol 18a (18.55 g, 208 mmol) in THF (200 mL) was added potassium tert-butoxide (18.6 g, 166.6 mmol) portion wise at 0° C. After stirring at room temperature for 1.5 h, 2-chloro-5-nitropyridine 18b (29.8 g, 187.2 mmol) was added in portion wise 0° C. The reaction was warmed to room temperature and stirred for 16 h. The reaction mixture was concentrated under reduced pressure, diluted with water (250 mL), and then extracted with Dichloromethane (3×250 mL). The organic extracts were combined, washed with water, brine, dried over ($Na_2SO_4$) and concentrated to afford crude material which was further purified by column chromatography on silica gel using 0-7% methanol/methylene chloride to give 2-(5-nitropyridin-2-yloxy)-N,N-dimethylethanamine 18 as a light-yellow solid (20 g, 58%, purity 80%). MS(ESI) m/z 212.2 $(M+H)^+$.

Step 1: Synthesis of 18: To a solution of Compound 18c (20 g, 96.1 mmol) in a 1:2 mixture (200 mL) of ethanol and ethyl acetate, catalytic amount of 10% palladium on carbon-50% $H_2O$ (10 g) was added carefully under an argon atmosphere. The flask was flushed three times with hydrogen (standard hydrogenation procedure) and then stirred at room temperature under a hydrogen atmosphere (balloon of $H_2$ was connected) for 4 days. The reaction mixture was filtered through a pad of Celite and washed with EtOAc. The filtrate was concentrated under reduced pressure to afford the crude product (15 g) as a brown oil. Purification by column chromatography on silica gel using 0-20% percent methanol/methylene chloride (containing 0.25% $NH_3$ in MeOH) gave 2-(dimethylamino)ethoxy]pyridin-3-amine 18 as a syrup (5.3 g, 31%). MS(ESI) m/z 182.2 $[M+H]^+$. $^1H$ NMR (600 MHz, DMSO-$d_6$) δ 11.01 (s, 2H), 8.31 (d, J=2.5 Hz, 1H), 7.86 (dd, J=8.8, 2.6 Hz, 1H), 7.03 (d, J=8.8 Hz, 1H), 4.72-4.60 (m, 2H), 3.56-3.46 (m, 2H), 2.82 (d, J=4.0 Hz, 6H).

LC-MS of this compound showed two peaks. 6-[2-(dimethylamino)ethoxy]pyridin-3-amine was converted to di-Boc derivative using standard reaction conditions. Purification by column chromatography on silica gel using 0-4% percent methanol/methylene chloride and then di de-Boc with methanolic hydrochloride gave ~3 g of 6[2-(dimethylamino)ethoxy]pyridin-3-amine hydrochloride salt 18.

Synthesis of 6-(2-(pyrrolidin-1-yl)ethoxy)pyridin-3-amine (19)

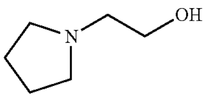

+

19a

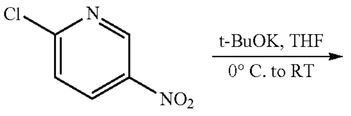

18b

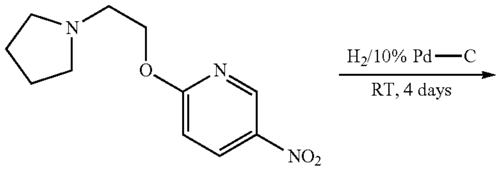

19b

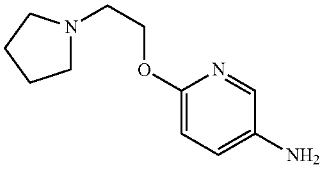

19

Step 1: Synthesis of 19b: Prepared according to the procedure described for compound 18c (16 g, 32% yield). MS(ESI) m/z 238.2 $[M+H]^+$.

Step 1: Synthesis of 19: Prepared according to the procedure described for compound of 18 (4 g, 29% yield). MS(ESI) m/z 208.2 $[M+H]^+$. $^1H$ NMR (600 MHz, Chloroform-d) δ 7.63 (d, J=2.9 Hz, 1H), 7.02 (dd, J=8.7, 3.0 Hz, 1H), 6.63 (d, J=8.7 Hz, 1H), 4.36 (t, J=5.9 Hz, 2H), 3.35 (s, 2H), 2.88 (t, J=5.9 Hz, 2H), 2.68-2.53 (m, 4H), 1.81 (p, J=3.2 Hz, 4H).

Synthesis of 6-(2-(piperidin-1-yl)ethoxy)pyridin-3-amine (20)

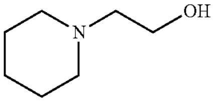

+

20a

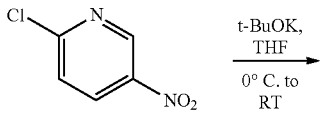

18b

-continued

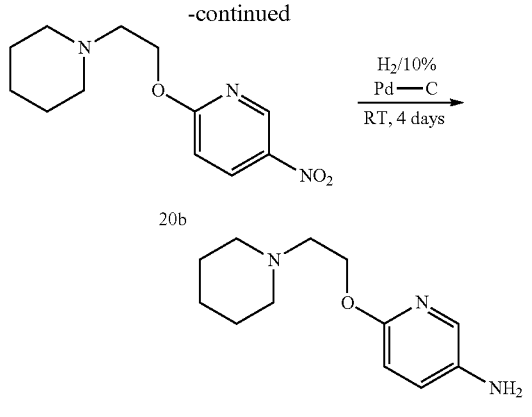

20b

20

Step 1: Synthesis of 20b: Prepared according to the procedure described for compound 18c (18 g, 34% yield). MS(ESI) m/z 252.2 $[M+H]^+$ Step 1: Synthesis of 20: Prepared according to the procedure described for compound 18c (8 g, 51% yield). MS(ESI) m/z 222.2 $[M+H]^+$. $^1H$ NMR (600 MHz, Chloroform-d) δ 7.64 (d, J=2.9 Hz, 1H), 7.01 (dd, J=8.7, 2.9 Hz, 1H), 6.61 (d, J=8.7 Hz, 1H), 4.34 (t, J=6.1 Hz, 2H), 3.36 (s, 2H), 2.73 (t, J=6.1 Hz, 2H), 2.49 (s, 4H), 1.60 (p, J=5.6 Hz, 4H), 1.49-1.38 (m, 2H).

Synthesis of 5-(2-(dimethylamino)ethoxy)pyridin-2-amine (21)

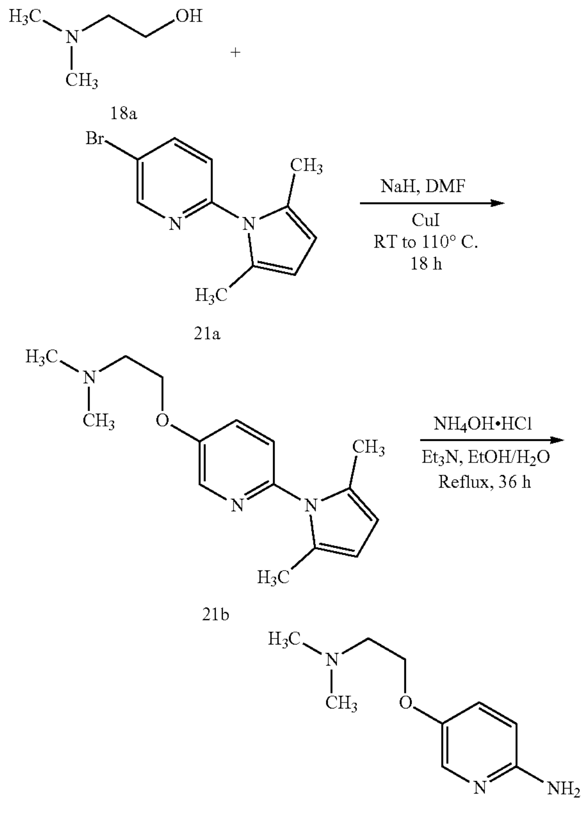

18a

21a

21b

21

Step 1: Synthesis of 21b: To a solution of 2-(dimethylamino)ethanol 18a (68.8 g, 772 mmol) in DMF (400 mL) was added sodium hydride (60% dispersion in mineral oil) (18.5 g, 454.1 mmol) portion wise at 0° C. The mixture was stirred at room temperature for 1.5 h, cooled to 0° C. again, CuI (7.35 g, 38.6 mmol) and 2-(2,5-dimethyl-1H-pyrrol-1-yl)-5-bromo-pyridine 21a (55 g, 219.0 mmol) were added. The reaction mixture was stirred at 110° C. for overnight. The Reaction mixture was cooled to RT and the solids were filtered over Celite and the filtrate was diluted with water (1.5 lit.) and extracted five times (4×200 mL) with dichloromethane. The combined organic phases were washed with 10% aqueous $NH_4OH$ solution, dried with $Na_2SO_4$ and concentrated under reduced pressure to yield the crude product which was purified by flash chromatography (silica gel, 0-5% methanol/dichloromethane) to afford the desired product 21 b (45 g, 64%, purity: 70-80%). MS(ESI) m/z 260.3 $[M+H]^+$.

Step 2: Synthesis of 21: A mixture of 21b (45 g, 179.2 mmol), hydroxylamine hydrochloride (78.17 g, 1.12 mol), triethylamine (47.11 mL, 335.3 mmol), ethanol (350 mL) and water (150 mL) was refluxed for 36 h. The solution was cooled to RT and the solvent was removed under reduced pressure. The pH was adjusted to 9-10 with 6 M NaOH solution and the resulting mixture was extracted (4×200 mL) with dichloromethane. The combined organic phases were dried over $Na_2SO_4$, filtered and the solvent was removed in vacuo. The oily residue was purified by column chromatography on silica gel (gradient elution: dichloromethane/methanol) to give 5-(2-(dimethylamino)ethoxy)pyridin-2-amine 21 (6 g, 19%). MS(ESI) m/z 182.2 $[M+H]^+$. $^1H$ NMR (600 MHz, Chloroform-d) δ 7.79 (d, J=2.9 Hz, 1H), 7.12 (dd, J=8.8, 3.0 Hz, 1H), 6.47 (d, J=8.8 Hz, 1H), 4.21 (bs, 2H), 4.01 (t, J=5.7 Hz, 2H), 2.70 (t, J=5.7 Hz, 2H), 2.33 (s, 6H).

Synthesis of 5-(2-(pyrrolidin-1-yl)ethoxy)pyridin-2-amine (22)

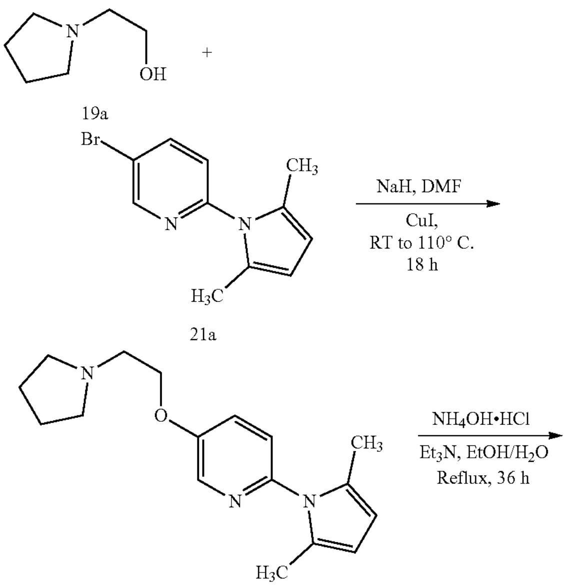

19a

21a

22a

-continued

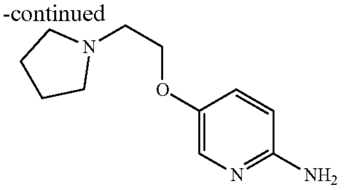

22

Step 1: Synthesis of 22a: Prepared according to the procedure described for compound 21b (2 g, 67%).

Step 2: Synthesis of 22: Prepared according to the procedure described for compound 21 (6 g, 33% yield). MS(ESI) m/z 208.2 $[M+H]^+$. $^1H$ NMR (600 MHz, Chloroform-d) δ 7.79 (d, J=2.9 Hz, 1H), 7.12 (dd, J=8.8, 2.9 Hz, 1H), 6.47 (d, J=8.8 Hz, 1H), 4.23 (s, 2H), 4.05 (t, J=5.9 Hz, 2H), 2.86 (t, J=5.9 Hz, 2H), 2.66-2.57 (m, 4H), 1.81 (p, J=3.1 Hz, 4H).

Synthesis of 5-(2-(piperidin-1-yl)ethoxy)pyridin-2-amine (23)

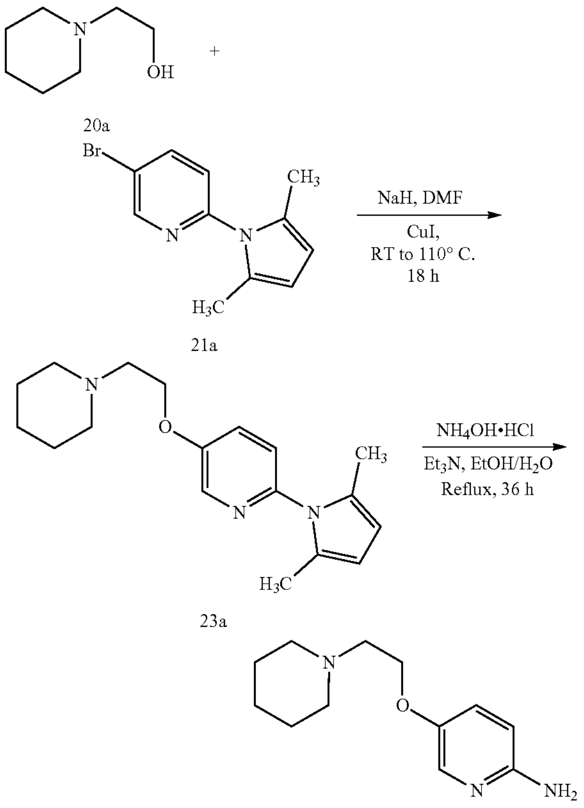

20a

21a

23a

23

Step 1: Synthesis of 23a: Prepared according to the procedure described for compound 21b (45 g, 81% yield).

Step 1: Synthesis of 23: Prepared according to the procedure described for compound 21 (8.5 g, 38% yield). MS(ESI) m/z 222.2 $[M+H]^+$. $^1H$ NMR (600 MHz, Chloroform-d) δ 7.78 (d, J=2.9 Hz, 1H), 7.10 (dd, J=8.8, 2.9 Hz, 1H), 6.46 (d, J=8.8 Hz, 1H), 4.25 (s, 2H), 4.04 (t, J=6.0 Hz, 2H), 2.72 (t, J=6.0 Hz, 2H), 2.48 (s, 4H), 1.60 (p, J=5.6 Hz, 4H), 1.50-1.38 (m, 2H).

Synthesis of tert-butyl 6-amino-3',6'-dihydro-[3,4'-bipyridine]-1'(2'H)-carboxylate (24)

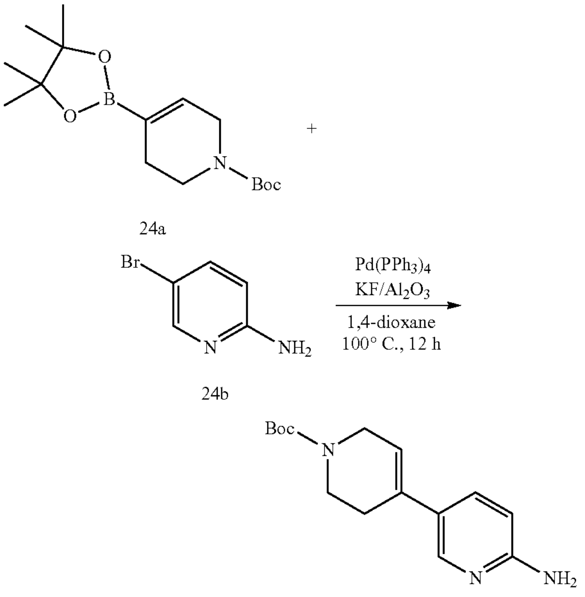

24a

24b

24

Step 1: Synthesis of 24: To a mixture of 5-bromo-2-aminopyridine 24b (100 g, 0.578 mol) and 4-(4,4,5,5-tetramethyl-[1,3,2]dioxaborolan-2-yl)-3,6-dihydro-2H-pyridine-1-carboxylic acid tertbutylester 24a (121.3 g, 0.578 mol) in 1,4-dioxane (2 L) were added $Pd(PPh_3)_4$ (10 g) and $KF/Al_2O_3$ (200 g, 1:1 ratio) The mixture was degassed for 0.5 h and then heated at 100° C. for 12 h under argon. The reaction mixture was concentrated, and the crude was diluted with EtOAc (2 L), filtered through a pad of Celite, and the filter cake was rinsed with EtOAc (2×250 mL). The combined filtrates were dried over $Na_2SO_4$, filtered, and concentrated in vacuo. Purification by $SiO_2$ column chromatography (EtOAc/n-hexanes) provided 24 (35 g, 22% yield) as a brownish solid. MS(ESI) m/z 276.2 $[M+H]^+$. $^1H$ NMR (600 MHz, Chloroform-d) δ 8.08 (s, 1H), 7.47 (dd, J=8.6, 2.3 Hz, 1H), 6.48 (d, J=8.6 Hz, 1H), 5.90 (s, 1H), 4.54 (s, 2H), 4.05 (s, 2H), 3.68-3.53 (m, 2H), 2.45 (s, 2H), 1.49 (s, 9H).

Synthesis of 1'-isopropyl-1',2',3',6'-tetrahydro-[3,4'-bipyridin]-6-amine (25)

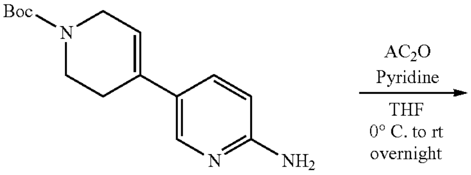

24

-continued

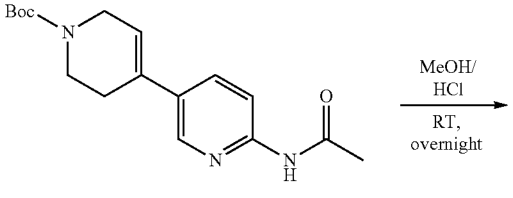

25a

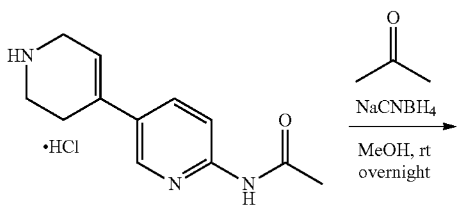

25b

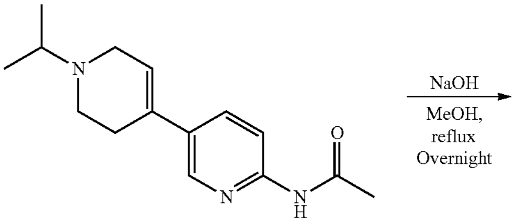

25c

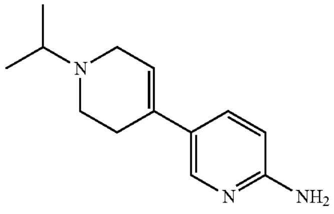

25

Step 1: Synthesis of 25a: To a solution of tert-butyl 6-amino-3',6'-dihydro-[3,4'-bipyridine]-1'(2'H)-carboxylate 24 (10 g, 36.2 mmol) and 5 mL pyridine in THF (100 mL) was added acetic anhydride (4.4 g, 43.6 mmol) dropwise at 0° C. The mixture was stirred at room temperature for overnight. The solvent was removed, reaction mixture partitioned between water (50 mL) and dichloromethane (100 mL). The two layers were separated, and the aqueous layer further extracted with dichloromethane (2×100 mL). The organic extracts were combined, washed with brine, dried over sodium sulfate, and concentrated to give the crude material as a brown syrup. Purification by column chromatography on silica gel using 0-3% methanol/methylene chloride yielded 25a as a light-yellow solid (9.1 g, purity 80%). MS(ESI) m/z 318.2 $[M+H]^+$.

Step 2: Synthesis of 25b: tert-butyl 6-acetamido-3',6'-dihydro-[3,4'-bipyridine]-1'(2'H)-carboxylate 25a (9.12 g, 14.3 mmol) was dissolved in 3 N methanolic hydrochloride (200 mL) and stirred for overnight. The reaction mixture was concentrated to afford crude N-(1',2',3',6'-tetrahydro-[3,4'-bipyridin]-6-yl)acetamide hydrochloride salt, 25b (8.2 g).

Step 3: Synthesis of 25c: A solution of N-(1',2',3',6'-tetrahydro-[3,4'-bipyridin]-6-yl) acetamide hydrochloride 25b (4.0 g, 15.8 mmol) in 50 mL of methanol was added to a mixture of acetone (2 mL) and sodium cyanoborohydride (3.92 g, 63.2 mmol) and the resultant mixture was stirred at room temperature for overnight. The reaction mixture was concentrated and evaporated to dryness. The residue was partitioned between dichloromethane (100 mL) and saturated sodium bicarbonate (50 mL). The layers were separated, and the aqueous layer was extracted with methylene chloride (4×100 mL). The organic phases were combined and washed with brine, dried ($Na_2SO4$) and concentrated. The residue was purified by column chromatography (dichloromethane:methanol=95:5, v/v) to afford of 25c as a light-yellow syrup (2.1 g, 53% yield).

Step 4: Synthesis of 25: To a solution of compound 25c (1.8 g, 6.9 mmol) in MeOH (100 mL), NaOH (2.78 g, 69 mmol) was added and the resultant mixture was stirred at reflux temperature for 18 h. The standard work-up and chromatography purification (see Preston et al., Dalton Transactions, 45(19): 8050-8060 (2016)) afforded compound 25 (0.888 g, 60%) as a light-yellow solid. MS(ESI) m/z 218.2 $[M+H]^+$. $^1H$ NMR (600 MHz, DMSO-$d_6$) δ 7.95 (s, 1H), 7.46 (d, J=8.6 Hz, 1H), 6.40 (d, J=8.6 Hz, 1H), 5.93 (s, 1H), 5.89 (s, 2H), 3.09 (s, 2H), 2.77-2.65 (m, 1H), 2.65-2.54 (m, 2H), 2.35 (s, 2H), 1.01 (d, J=6.4 Hz, 6H).

Synthesis of tert-butyl 6-(4-amino-2-fluorophenyl)-2,6-diazaspiro[3.3]heptane-2-carboxylate (26)

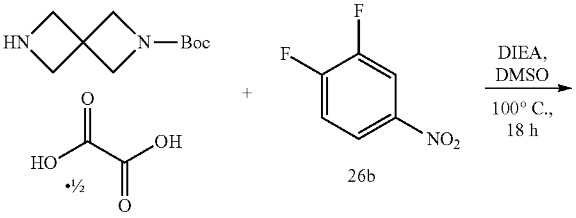

26a

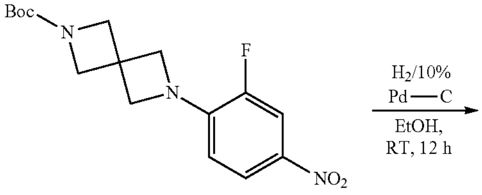

26c

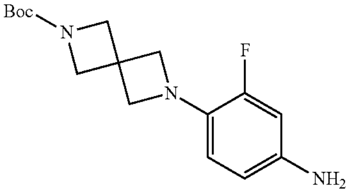

26

Step 1: Synthesis of 26c: To a mixture of tert-butyl 2,6-diazaspiro[3.3]heptane-2-carboxylate hemioxalate 26a (1.5 g, 6.17 mmol) and DIEA (3.3 mL, 19 mmol) in DMSO (15 mL) was added 1,3-difluoro-4-nitrobenzene 26b (1 g, 6.3 mmol) dropwise over a period of 5 minutes. The resultant reaction mixture was stirred at 100° C. for 18 h and then cooled to room temperature. The reaction mixture was and then poured into $H_2O$ (100 mL) and extracted with EtOAc (3×50 mL). The combined organic layer was washed with water (2×25 mL), brine (1×25 mL), dried ($Na_2SO_4$) and concentrated to afford the product 26c as a yellow solid (~1.8 g) which was used as such for the next step.

Step 2: Synthesis of 26: The Parr-hydrogenator flask (500 mL) was charged with nitro compound 26c (1.8 g, 5.6 mmol) and ethanol (100 mL). A 10% Pd—C(1 g, 50% $H_2O$) was introduced carefully under argon. The resultant mixture was hydrogenated at ~33 Psi 12 h at RT. The reaction mixture was filtered through pad of Celite and washed with EtOAc. The filtrate was concentrated under reduced pressure to afford the title product 26 as a gray solid (1.36 g 72% yield). MS(ESI) m/z 308.2 $[M+H]^+$. $^1H$ NMR (600 MHz, Chloroform-d) δ 6.43-6.29 (m, 3H), 4.07 (s, 4H), 3.92 (d, J=1.5 Hz, 4H), 1.44 (s, 9H).

Synthesis of tert-butyl 6-(5-aminopyridin-2-yl)-2,6-diazaspiro[3.3]heptane-2-carboxylate (27)

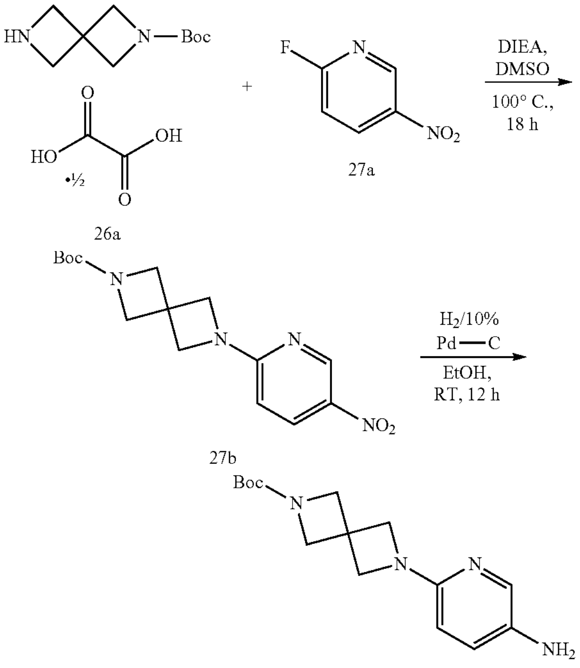

26a 27a 27b 27

Step 1: Synthesis of 27b: Prepared according to the procedure described for compound 26c.

Step 2: Synthesis of 27: Prepared according to the procedure described for compound 26 (1.36 g, 76% yield). MS(ESI) m/z 291.2 $[M+H]^+$. $^1H$ NMR (600 MHz, Chloroform-d) δ 7.73 (d, J=2.6 Hz, 1H), 6.97 (dd, J=8.6, 2.7 Hz, 1H), 6.24 (d, J=8.6 Hz, 1H), 4.08 (s, 4H), 4.02 (s, 4H), 1.44 (s, 9H).

Synthesis of tert-butyl 6-(4-aminophenyl)-2,6-diazaspiro[3.3]heptane-2-carboxylate (28)

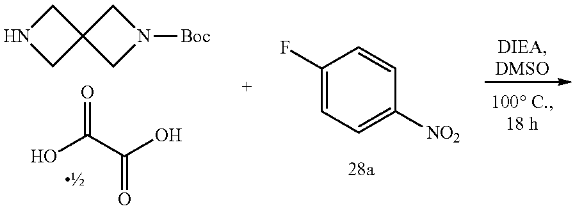

26a 28a

-continued

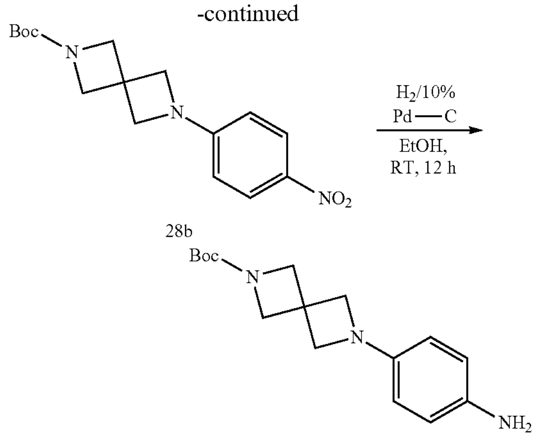

28b 28

Step 1: Synthesis of 28b: Prepared according to the procedure described for compound 26c.

Step 2: Synthesis of 28: Prepared according to the procedure described for compound 26 (7.12 g, 98% yield). MS(ESI) m/z 290.2 $[M+H]^+$. $^1H$ NMR (600 MHz, Chloroform-d) δ 6.63 (d, J=8.5 Hz, 2H), 6.35 (d, J=8.5 Hz, 2H), 3.33 (S, 2H), 4.06 (s, 4H), 1.44 (s, 9H).

Synthesis of tert-butyl 4-(4-amino-3-fluorophenyl) piperazine-1-carboxylate (29)

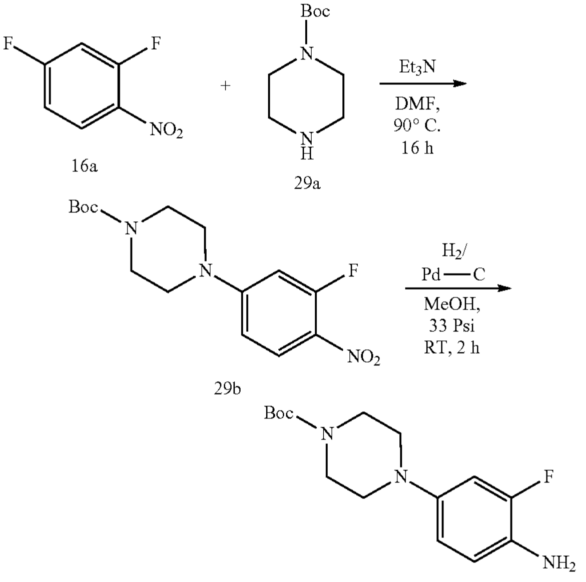

16a 29a 29b 29

Step 1: Synthesis of 29b: (Ref: US 20090093497): A mixture of 2,4-difluoro-nitro-benzene 16a (20 g, 126 mmol), piperazine-1-carboxylic acid tert-butyl ester 29a (23.4 g, 126 mmol), and triethylamine (63 mL, 378 mmol) in anhydrous DMF (200 mL) was stirred at 90° C. for 16 h. The reaction mixture was partitioned between water and ethyl acetate, layers were separated, and the aqueous layer was extracted with ethyl acetate twice. Organic layers were collected, combined, washed with brine, dried over sodium sulfate, filtered, and concentrated. The residue was purified by silica-gel column with ethyl acetate and hexanes as eluting solvents to give the product 29b as a light-yellow solid (25.1 g, 62% yield). MS(ESI) m/z 326.1 $[M+H]^+$.

Synthesis of 29: (Ref: WO 2015038417): The solution of compound 29b (25 g, 89.2 mmol) in Methanol (300 mL) in the presence of 10% palladium on carbon (12.5 g, 50% wet) was shaken under the hydrogen with a pressure of 33 psi at room temperature for 12 hr. The reaction mixture was filtered through a plug of Celite and the filtration pad was washed with methanol. The organic layer was collected, concentrated, and dried to give compound 29 (26 g, 99%) as a light red gummy material, which was used as such without further purification. MS(ESI) m/z 296.2 $[M+H]^+$. $^1$H NMR (600 MHz, Chloroform-d) δ 6.74-6.70 (m, 1H), 6.66-6.63 (m, 1H), 6.59-6.55 (m, 1H), 3.56 (t, J=5.1 Hz, 4H), 2.96 (d, J=5.6 Hz, 4H), 1.48 (s, 9H).

Synthesis of (S)-1-(4-amino-2-fluorophenyl)-N,N-dimethylpyrrolidin-3-amine (30)

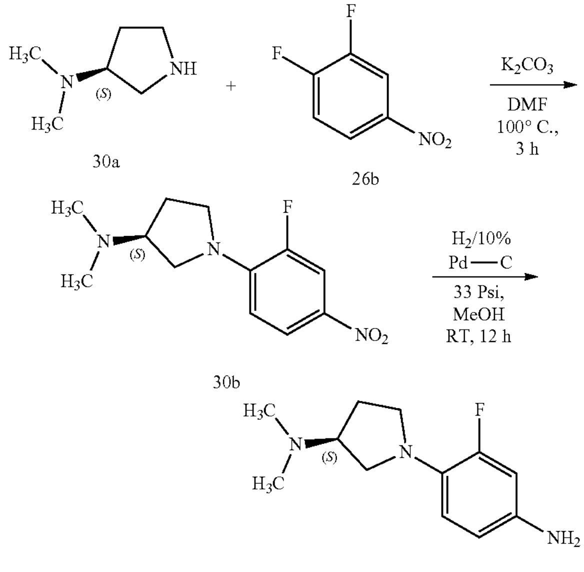

30a 26b 30b 30

Step 1: Synthesis of 30b: (Ref: WO 2015038417): To a stirred mixture of compound 30a (2.0 g, 16.9 mmol) in DMF (50 mL) at room temperature were added 26b (3.0 g, 18.9 mmol) and $K_2CO_3$ (13.1 g, 94.5 mmol). The resulting mixture was stirred at 110° C. for 16 h. After cooling down to room temperature, the reaction mixture was diluted with water (200 mL) and extracted with EtOAc (3×150 mL). The organic layer was washed with brine solution (50 mL), dried ($Na_2SO_4$), and concentrated to provide crude residue. The crude was triturated with n-hexane and filtered to give compound 30b as a yellow solid (3.8 g, 80% yield). MS(ESI) m/z 254.2 $[M+H]^+$.

Step 2: Synthesis of 30: (Ref: WO 2015038417): The solution of compound 30b (3.75 g 15 mmol) in Methanol (200 mL) in the presence of 10% palladium on carbon (2 g, 50% $H_2O$) was shaken under the hydrogen with a pressure of 33 psi at room temperature for 12 hr. The reaction mixture was filtered through a plug of Celite and the filtration pad was washed with methanol. The organic layer was collected, concentrated, and dried to give compound 30 (3.2 g, 96%) as a light red solid, which was directly used in the next step reaction without further purification. MS(ESI) m/z 224.2 $[M+H]^+$. $^1$H NMR (600 MHz, Chloroform-d) δ 6.62-6.52 (m, 1H), 6.49-6.34 (m, 2H), 3.49-3.31 (m, 4H), 3.31-3.18 (m, 1H), 3.18-3.09 (m, 1H), 2.83 (p, J=7.6 Hz, 1H), 2.28 (s, 6H), 2.21-2.07 (m, 1H), 1.92-1.80 (m, 1H).

Synthesis of (S)-6-(3-(dimethylamino)pyrrolidin-1-yl)pyridin-3-amine (31)

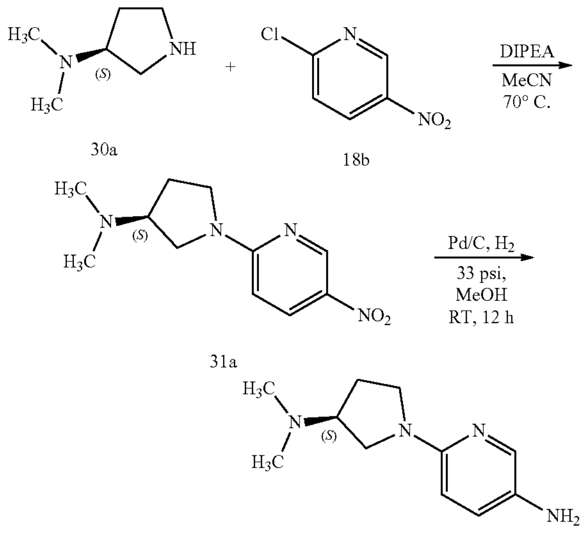

30a 18b 31a 31

Step 1: Synthesis of 31a: (Ref: WO 20050261307): To a stirred mixture of compound 30a (1.5 g, 12.5 mmol) in MeCN (25 mL) at room temperature, nitro compound 18b (1.8 g, 11.4 mmol) and diisopropylethylamine (4 mL, 23 mmol) were added and stirred at 70° C. for overnight. The reaction mixture was concentrated under reduced pressure and the residue was dissolved in EtOAc (150 mL) and then washed with $H_2O$ (2×30 mL), brine, dried over sodium sulfate and concentrated to give 31a as yellow solid (2.3 g, 85% yield). MS(ESI) m/z 237.2 $[M+H]^+$.

Step 2: Synthesis of 31: Prepared according to the procedure described for compound 30 (1.85 g, 92%). MS(ESI) m/z 207.2 $[M+H]^+$. $^1$H NMR (600 MHz, DMSO-$d_6$) δ 7.60 (d, J=2.6 Hz, 1H), 7.34 (s, 2H), 7.01 (dd, J=8.7, 2.7 Hz, 1H), 6.40 (d, J=8.8 Hz, 1H), 3.85 (q, J=7.4 Hz, 1H), 3.69 (dd, J=10.6, 7.6 Hz, 1H), 3.55-3.47 (m, 2H), 3.24 (q, J=8.5 Hz, 2H), 2.73 (s, 6H), 2.38-2.30 (m, 1H), 2.29-2.20 (m, 1H).

Synthesis of (S)-5-(3-(dimethylamino)pyrrolidin-1-yl)pyridin-2-amine (32)

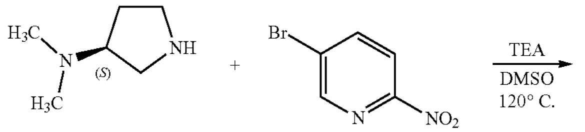

30a 32a

-continued

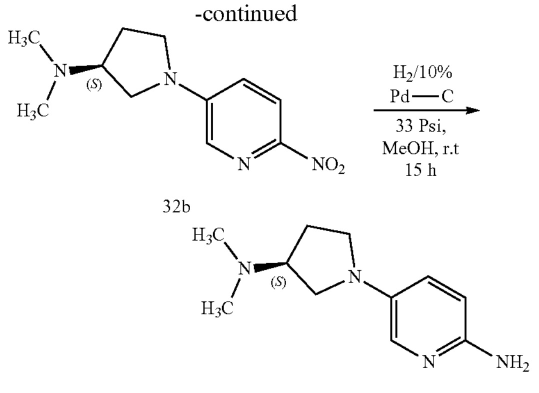

32b

32

Step 1: Synthesis of 32b: (Ref: WO 20180072707): To a stirred mixture of compound 30a (1.5 g, 12.5 mmol) and nitro compound 32a (1.8 g, 11.4 mmol) in DMSO (15 mL) was added triethylamine (4 mL, 23 mmol) at room temperature and stirred at 120° C. for overnight. The reaction mixture was diluted with water (200 mL) and extracted with EtOAc (3×150 mL). The organic layer was washed with brine solution (50 mL), dried ($Na_2SO_4$), and concentrated to provide crude residue. The crude residue was further purified by silica-gel column using 0-20% MeOH in DCM to give 32b as yellow solid (3.3 g, 80% yield). MS(ESI) m/z 237.2 $[M+H]^+$.

Step 2: Synthesis of 32: Prepared according to the procedure described for compound 30 (2.8 g, quantitative yield). MS(ESI) m/z 207.2 $[M+H]^+$. $^1$H NMR (600 MHz, Chloroform-d) δ 7.48 (d, J=2.9 Hz, 1H), 6.84 (dd, J=8.8, 3.0 Hz, 1H), 6.50 (d, J=8.7 Hz, 1H), 3.43-3.37 (m, 1H), 3.37-3.30 (m, 1H), 3.30-3.24 (m, 1H), 3.10 (t, J=8.2 Hz, 1H), 2.91-2.84 (m, 1H), 2.31 (s, 6H), 2.23-2.15 (m, 1H), 1.97-1.88 (m, 1H).

Synthesis of (S)-1-(4-aminophenyl)-N,N-dimethylpyrrolidin-3-amine (33)

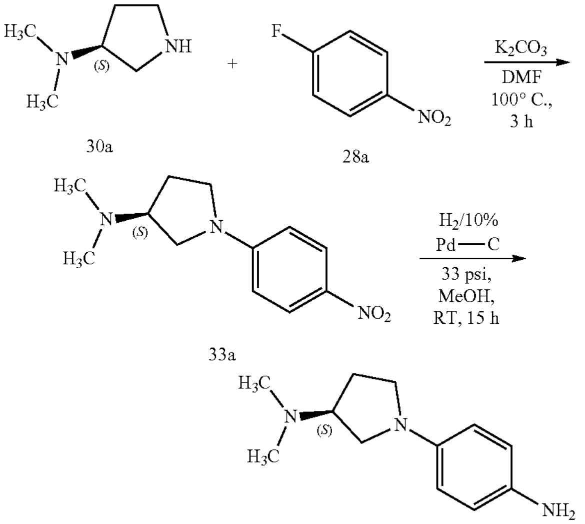

30a

28a

33a

33

Step 1: Synthesis of 33a: Prepared according to the procedure described for compound 30b. (3.8 g, 81% yield) as yellow solid. MS(ESI) m/z 236.2 $[M+H]^+$.

Step 1: Synthesis of 33: Prepared according to the procedure described for compound 30 (3.23 g, 99% yield). MS(ESI) m/z 206.2 $[M+H]^+$. $^1$H NMR (600 MHz, Chloroform-d) δ 6.67 (d, J=8.6 Hz, 2H), 6.45 (d, J=8.6 Hz, 2H), 3.41 (t, J=7.9 Hz, 1H), 3.38-3.23 (m, 2H), 3.09 (t, J=8.2 Hz, 1H), 2.89-2.80 (m, 1H), 2.30 (s, 6H), 2.22-2.13 (m, 1H), 1.97-1.84 (m, 1H).

Synthesis of 3-fluoro-4-(4-morpholinopiperidin-1-yl)aniline (34)

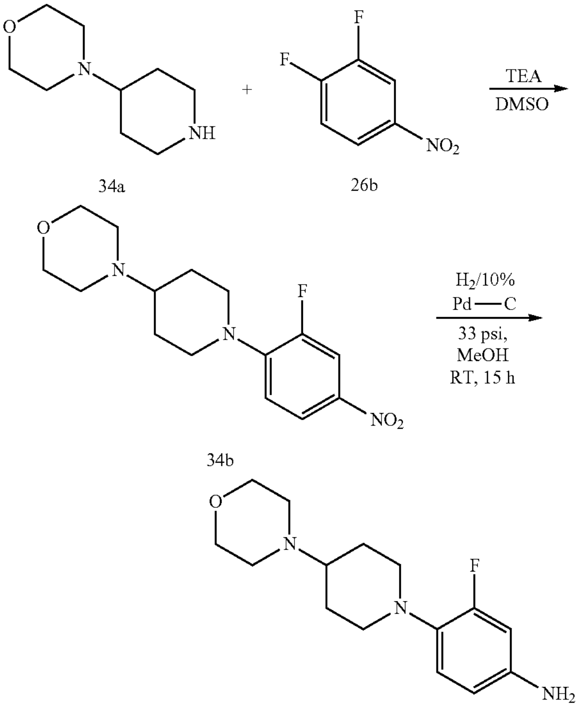

34a

26b

34b

34

Step 1: Synthesis of 34b: (Ref: WO 20160400858): To a stirred mixture of compound 34a (4.0 g, 23.5 mmol) and compound 26b (3.4 g, 21.4 mmol) in DMSO (20 mL) at room temperature was added triethylamine (9.8 mL, 71 mmol) and stirred at 120° C. for overnight. After TLC showed completion of starting material the mixture was diluted with water (100 mL) and the solid formed was filtered and dried under vacuum to give the product 34b (6.3 g, 84% yield) as yellow solid which is used in the next step without further purification. MS(ESI) m/z 310.1 $[M+H]^+$.

Step 1: Synthesis of 34: (Ref: WO 2015038417): The solution of compound 34b (6.3 g, 0.4 mmol) in Methanol (mL) in the presence of 10% palladium on carbon was shaken under the hydrogen with a pressure of 50 psi at room temperature for 2 hr. The reaction mixture was filtered through a plug of Celite and the filtration pad was washed with methanol. The organic layer was collected, concentrated, and dried to give compound 34 (4.9 g, 86%) as a light red solid, which was directly used in the next step reaction without further purification. MS(ESI) m/z 280.2 $[M+H]^+$. $^1$H NMR (600 MHz, Chloroform-d) δ 6.80 (t, J=8.9 Hz, 1H), 6.49-6.34 (m, 2H), 3.77-3.69 (m, 3H), 3.53 (s, 2H), 3.34 (d, J=11.6 Hz, 2H), 2.67-2.53 (m, 5H), 2.38-2.27 (m, 1H), 1.94-1.85 (m, 2H), 1.81-1.61 (m, 3H).

Synthesis of 6-(4-morpholinopiperidin-1-yl)pyridin-3-amine (35)

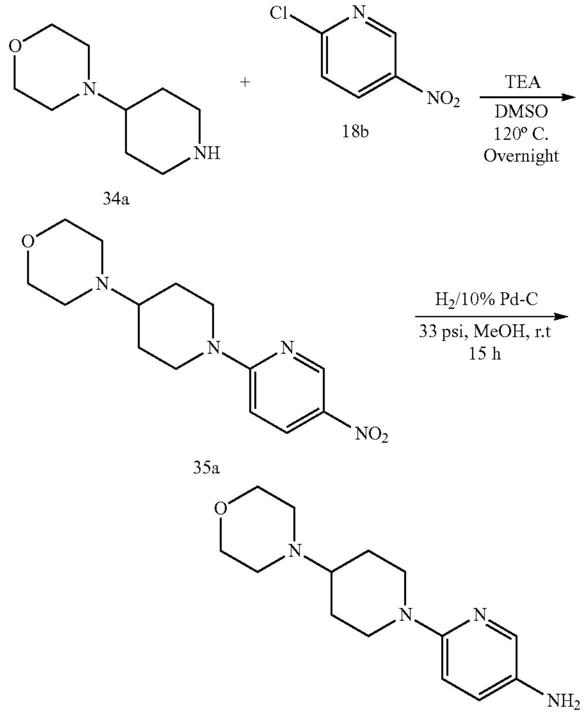

34a 18b 35a

35

Synthesis of 35a: Prepared according to the procedure described for compound 34b (3.6 g, 69% yield). MS(ESI) m/z 293.2 $[M+H]^+$.

Synthesis of 35: Prepared according to the procedure described for compound 34 (1.25 g, 40% yield). MS(ESI) m/z 263.2 $[M+H]^+$. $^1H$ NMR (600 MHz, Chloroform-d) δ 7.78 (d, J=2.7 Hz, 1H), 6.97 (dd, J=8.8, 2.9 Hz, 1H), 6.60 (d, J=8.8 Hz, 1H), 4.10 (d, J=12.8 Hz, 2H), 3.75-3.71 (m, 3H), 3.28 (s, 2H), 2.73 (td, J=12.6, 2.0 Hz, 2H), 2.64-2.51 (m, 4H), 2.41-2.30 (m, 1H), 1.92 (d, J=12.5 Hz, 2H), 1.64-1.48 (m, 2H).

Synthesis of 5-(4-morpholinopiperidin-1-yl)pyridin-2-amine (36)

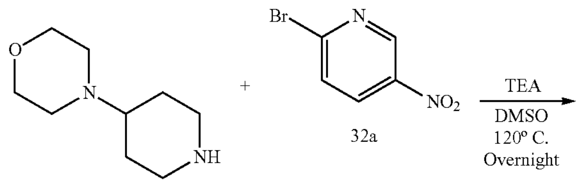

32a

34a

-continued

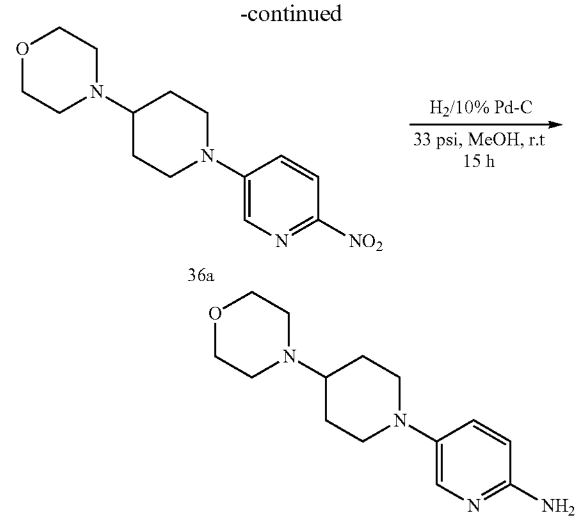

36a

36

Synthesis of 36a: Prepared according to the procedure described for compound 34b (3.5 g, 68% yield). MS(ESI) m/z 293.2 $[M+H]^+$.

Synthesis of 37: Prepared according to the procedure described for compound 34 (1.25 g, 40% yield). MS(ESI) m/z 263.2 $[M+H]^+$. $^1H$ NMR (600 MHz, Chloroform-d) δ 7.78 (d, J=2.8 Hz, 1H), 7.18 (dd, J=8.8, 2.9 Hz, 1H), 6.47 (d, J=8.8 Hz, 1H), 3.76-3.72 (m, 5H), 3.47 (d, J=12.3 Hz, 2H), 2.67-2.61 (m, 2H), 2.61-2.56 (m, 4H), 2.32-2.26 (m, 1H), 1.94 (d, J=12.5 Hz, 2H), 1.72-1.63 (m, 2H).

Synthesis of 4-(4-morpholinopiperidin-1-yl)aniline (37)

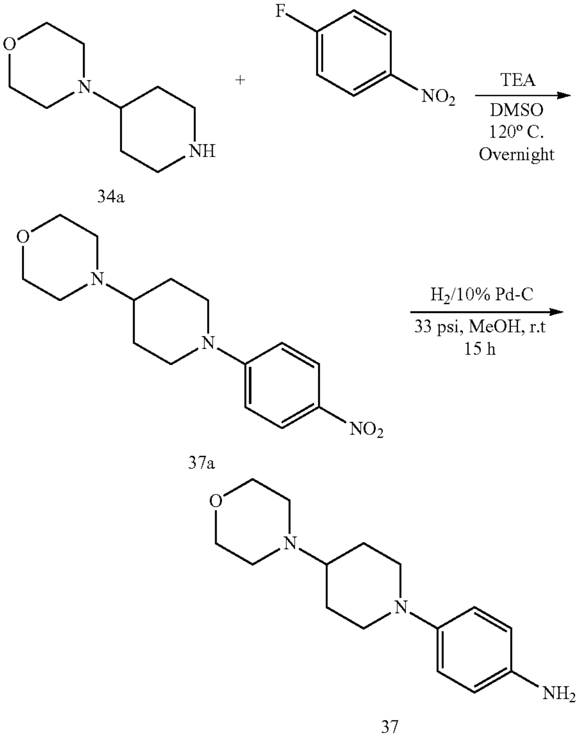

34a 37a

37

Synthesis of 37a: Prepared according to the procedure described for compound 34b (3.6 g, 70% yield). MS(ESI) m/z 292.2 $[M+H]^+$.

Synthesis of 37: Prepared according to the procedure described for compound 34 (1.25 g, 40% yield). MS(ESI) m/z 262.2 $[M+H]^+$. $^1H$ NMR (600 MHz, Chloroform-d) δ 6.86-6.78 (m, 2H), 6.70-6.58 (m, 2H), 3.77-3.68 (m, 3H), 3.52 (d, J=12.3 Hz, 2H), 3.42 (s, 2H), 2.63-2.60 (m, 1H), 2.60-2.56 (m, 4H), 2.34-2.24 (m, 1H), 1.96-1.88 (m, 2H), 1.77-1.62 (m, 3H).

Synthesis of (S)-(6-aminopyridin-3-yl)(3-(dimethylamino)pyrrolidin-1-yl)methanone (38)

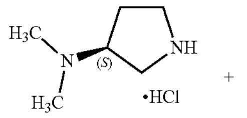

38a

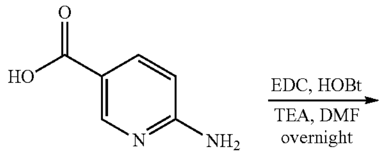

38b

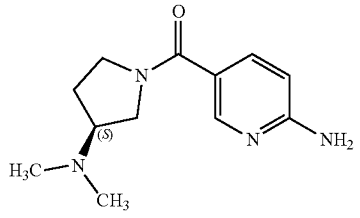

38

Synthesis of 38: (Ref: WO 2016015605): To a solution of compound 38b (1.1 g, 8.0 mmol) in DMF (25 mL) were added EDC (1.53 g, 8 mmol), HOBt (1.22 g, 8 mmol) and triethylamine (5.5 mL, 40 mmol). After stirring the mixture for 10 min, compound 38a (1.5 g, 8 mmol) was added. The resulting mixture was stirred at room temperature for overnight. The reaction mixture was concentrated in vacuo and the residue was purified by silica-gel chromatography using 0-10% MeOH in DCM to give 38 as a light-yellow solid (0.61 g, 34% yield). MS(ESI) m/z 235.2 $[M+H]^+$. $^1H$ NMR (600 MHz, Chloroform-d) δ 8.31 (s, 1H), 7.74-7.63 (m, 1H), 6.49 (d, J=8.5 Hz, 1H), 4.81 (s, 2H), 3.82-3.54 (m, 2H), 3.45-3.37 (m, 1H), 2.79-2.61 (m, 1H), 2.26 (d, J=40.6 Hz, 6H), 2.20-2.05 (m, 2H), 1.88-1.79 (m, 1H).

Synthesis of (S)-(5-aminopyridin-2-yl)(3-(dimethylamino)pyrrolidin-1-yl)methanone (39)

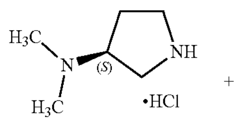

38a

-continued

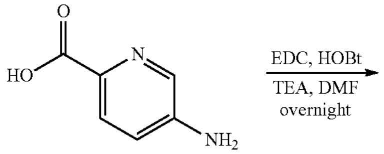

39a

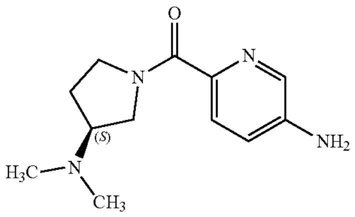

39

Synthesis of 39: Prepared according to the procedure described for compound 38 (0.95 g, 50% yield). MS(ESI) m/z 235.2 $[M+H]^+$. $^1H$ NMR (600 MHz, Chloroform-d) δ 8.00 (dd, J=11.5, 2.7 Hz, 1H), 7.75 (d, J=8.4 Hz, 1H), 7.00 (dd, J=8.5, 2.7 Hz, 1H), 4.14-4.10 (m, 0.5H), 4.05-4.00 (m, 0.5H), 3.98 (d, J=12.2 Hz, 2H), 3.91-3.83 (m, 1H), 3.65-3.59 (m, 1H), 3.45-3.38 (m, 1H), 2.76-2.67 (m, 1H), 2.30 (s, 3H), 2.26 (s, 3H), 2.16-2.08 (m, 1H), 1.87-1.74 (m, 3H).

Synthesis of (S)-(4-amino-2-fluorophenyl)(3-(dimethylamino)pyrrolidin-1-yl)methanone (40)

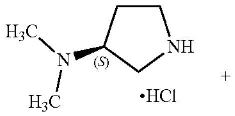

38a

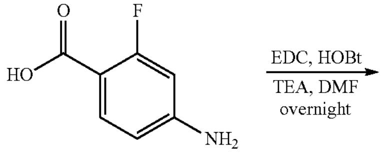

40a

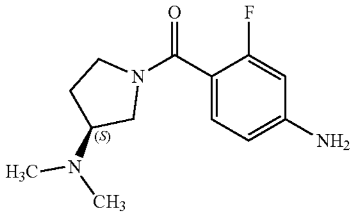

40

Synthesis of 40: Prepared according to the procedure described for compound 38 (1.0 g, 50% yield). MS(ESI) m/z 252.2 $[M+H]^+$. $^1H$ NMR (600 MHz, Chloroform-d) δ 7.22-7.15 (m, 1H), 6.46-6.40 (m, 1H), 6.35-6.28 (m, 1H), 4.15 (d, J=14.1 Hz, 2H), 3.94-3.86 (m, 0.5H), 3.84-3.75 (m, 0.5H), 3.63-3.40 (m, 2H), 3.40-3.33 (m, 0.5H), 3.33-3.24 (m, 0.5H), 2.81-2.71 (m, 0.5H), 2.72-2.64 (m, 0.5H), 2.28 (s, 3H), 2.21 (s, 3H), 2.19-2.12 (m, 0.5H), 2.10-2.02 (m, 0.5H), 1.87-1.73 (m, 1H).

Synthesis of (S)-(4-aminophenyl)(3-(dimethylamino)pyrrolidin-1-yl)methanone (41)

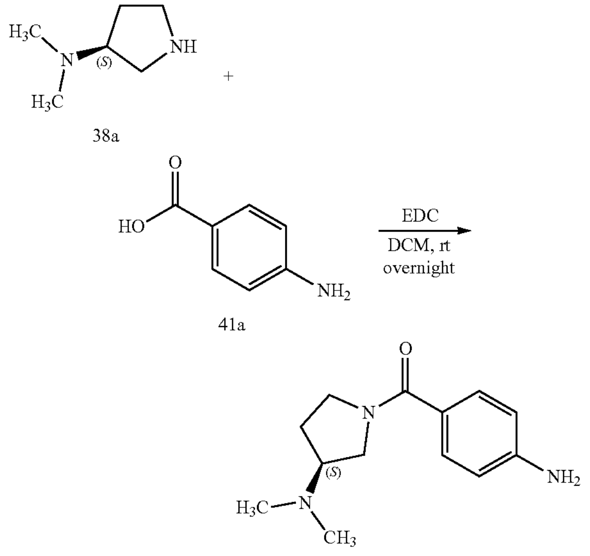

38a

41a

41

Synthesis of 41: Prepared according to the procedure described for compound 38 (0.63 g, 45% yield). MS(ESI) m/z 234.2 $[M+H]^+$. $^1H$ NMR (600 MHz, Chloroform-d) δ 7.39 (d, J=8.0 Hz, 2H), 6.64 (d, J=8.3 Hz, 2H), 3.89 (s, 3H), 3.83-3.50 (m, 3H), 3.45-3.30 (m, 1H), 2.68 (d, J=68.0 Hz, 1H), 2.26 (d, J=44.2 Hz, 6H), 1.83-1.77 (m, 1H).

Synthesis of 4-(4-isopropylpiperazin-1-yl)-3-methoxyaniline (42)

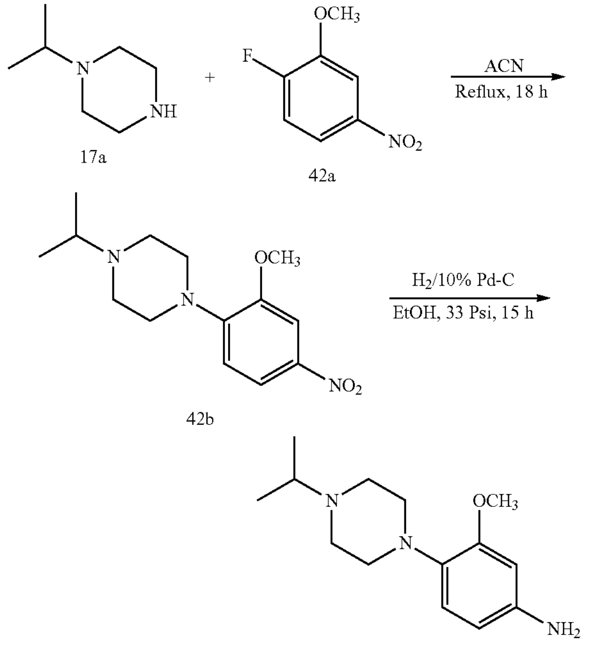

17a

42a

42b

42

Following the above scheme, the title compound 42 (4.75 g, 64% for two steps) was synthesized. MS(ESI) m/z 250.2 $[M+H]^+$. $^1H$ NMR (600 MHz, Chloroform-d) δ 6.78 (d, J=8.2 Hz, 1H), 6.31-6.15 (m, 2H), 3.81 (s, 3H), 3.48 (s, 2H), 3.01 (s, 4H), 2.81-2.65 (m, 5H), 1.10 (d, J=6.5 Hz, 6H).

Synthesis of 4-(4-isopropylpiperazin-1-yl)-3-methylaniline (43)

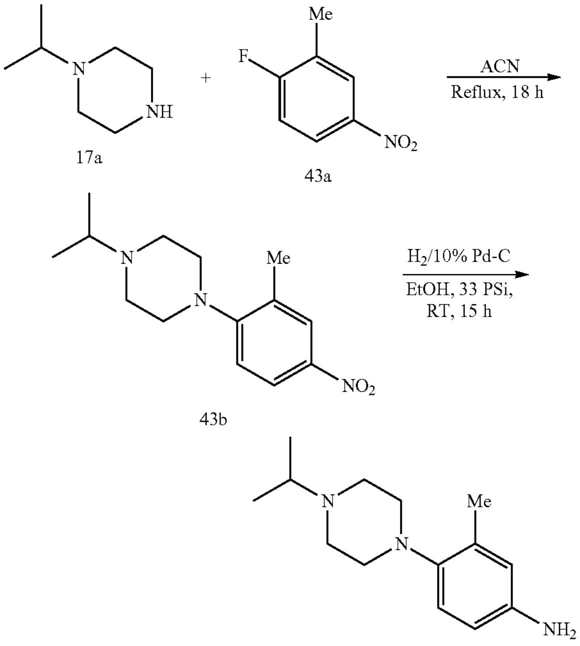

17a

43a

43b

43

Following the scheme, the title compound 43, (4.46 g, 64% for two steps), was synthesized. MS(ESI) m/z 234.3 $[M+H]^+$. $^1H$ NMR (600 MHz, Chloroform-d) δ 6.89 (d, J=8.3 Hz, 1H), 6.55 (d, J=2.6 Hz, 1H), 6.50 (dd, J=8.3, 2.7 Hz, 1H), 3.44 (s, 2H), 2.91-2.81 (m, 4H), 2.75-2.67 (m, 2H), 2.65 (s, 3H), 2.23 (s, 3H), 1.09 (d, J=6.5 Hz, 6H).

The amines 44, 45, and 46 were prepared by following the reported methods. See Walia et al., *J. Org. Chem.* 78(21): 10931-10937 (2013).

Synthesis of 5-(4-isopropylpiperazin-1-yl)-4-(trifluoromethyl)pyridin-2-amine (44)

44

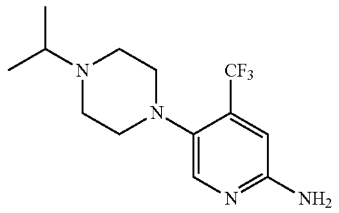

MS(ESI) m/z 289.3 $[M+H]^+$.

Synthesis of 5-(4-methylpiperazin-1-yl)-4-(trifluoromethyl)pyridin-2-amine (45)

45

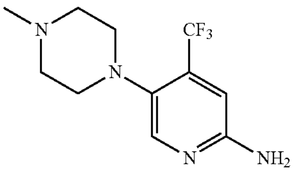

MS(ESI) m/z 261.3 $[M+H]^+$.

Synthesis of tert-butyl 4-(6-amino-4-(trifluoromethyl)pyridin-3-yl)piperazine-1-carboxylate (46)

46

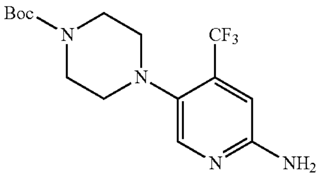

MS(ESI) m/z 347.3 $[M+H]^+$.

Synthesis of 5-(1,4-diazabicyclo[3.2.2]nonan-4-yl)pyridin-2-amine (47):

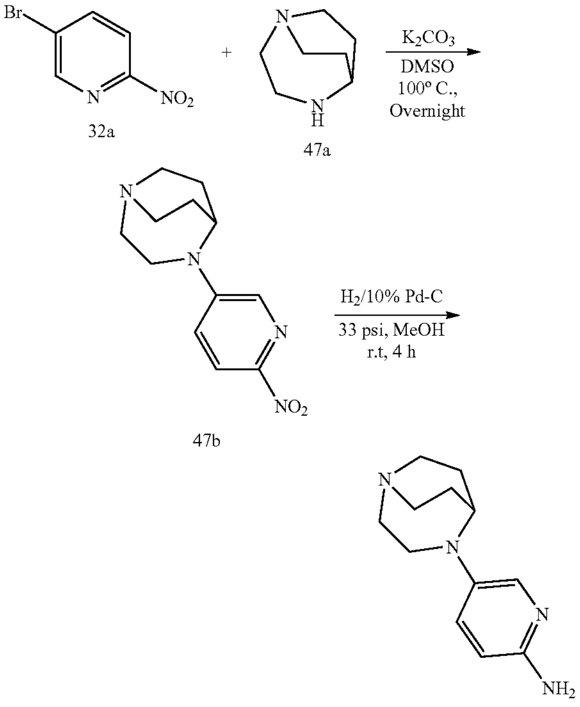

32a 47a 47b 47

Step 1: Synthesis of 47b: Prepared according to the procedure described for the preparation of compound 30b (12 g, 52% yield).

Step 2: Synthesis of 47: Prepared according to the procedure described for the preparation of compound 32 (4 g, 66% yield). MS(ESI) m/z 219.3 $[M+H]^+$.

Compounds 48 and 49 were purchased from commercial sources:

48

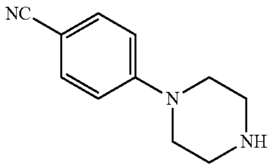

49

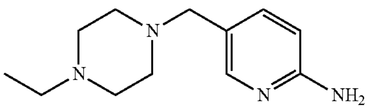

The following amines were synthesized using a reported procedure:

50

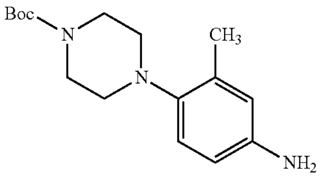

Compound 50 was synthesized using procedure reported in WO2001068643.

51

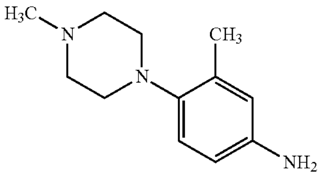

Compound 51 was synthesized using procedure reported in WO2012059932.

52

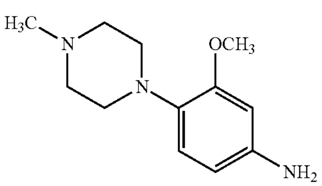

Compound 52 was synthesized using procedure reported in WO2008051547.

53

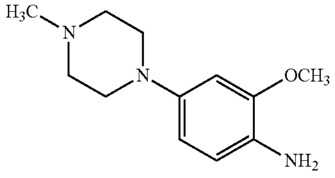

Compound 53 was synthesized using procedure reported in WO2017076355 and US20180208564

54

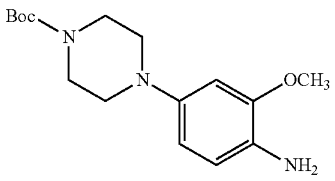

Compound 54 was synthesized using procedure reported in WO2017143842 and JMC 2019, 62, 4401-4410

55

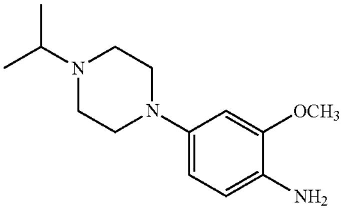

Compound 55 was synthesized using procedure reported in WO2004080980

56

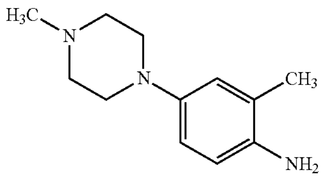

Compound 56 was synthesized using procedure reported in WO2008051547

57

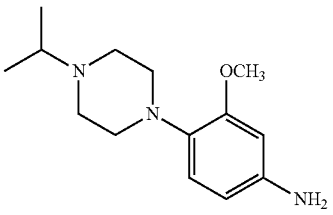

Compound 57 was synthesized using procedure reported in WO2005009443

58

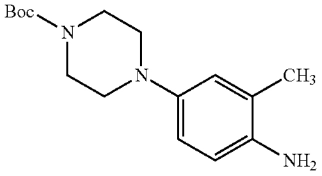

Compound 58 was synthesized using procedure reported in WO2007089768 and WO2006004200

59

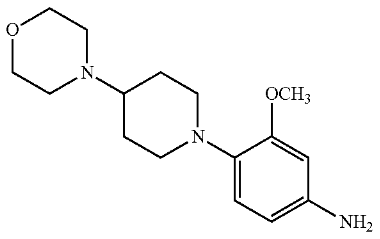

Compound 59 was synthesized using procedure reported in WO2016049211

60

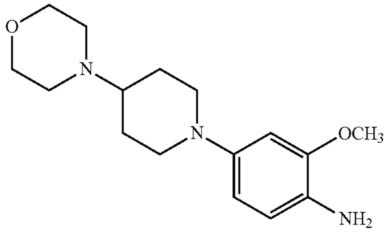

Compound 60 was synthesized using procedure reported in WO2018183112

61

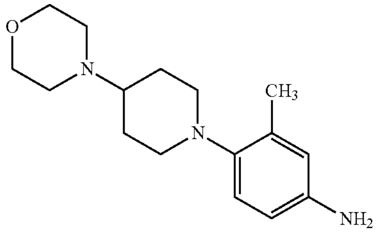

Compound 61 was synthesized using procedure reported in WO2012053606

62

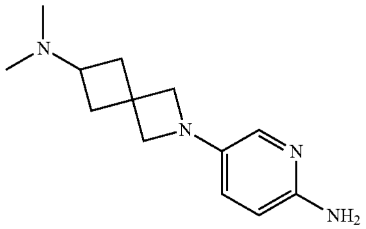

Synthesis of 62: Prepared according to the procedure described for the preparation of compound 91. MS (ESI) m/z 233.2 $[M+H]^+$.

63

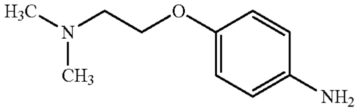

Compound 63 was synthesized using procedure reported in WO2008152013

64

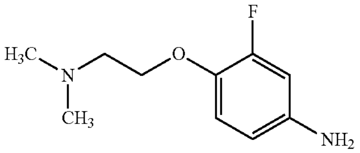

Compound 64 was synthesized using procedure reported in WO2009076140 and BMCL 2015, 23, 1044-1054

65

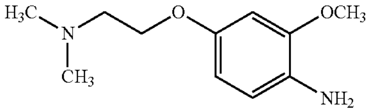

Compound 65 was synthesized using procedure reported in WO2014134308

66

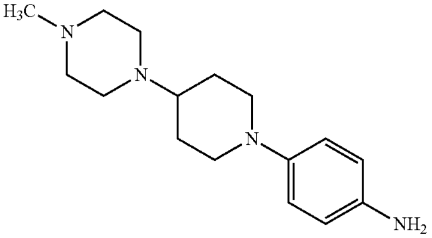

Compound 66 was synthesized using procedure reported in eJMC 2019, 163, 690-709

67

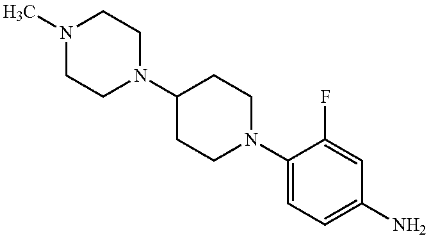

Compound 67 was synthesized using procedure reported in WO2012053605

68

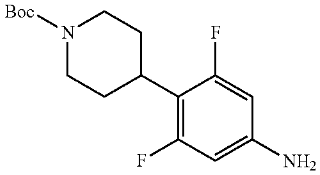

Compound 68 was synthesized using procedure reported in WO20120220572

69

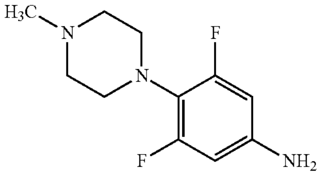

Compound 69 was synthesized using procedure reported in WO2017066428

70

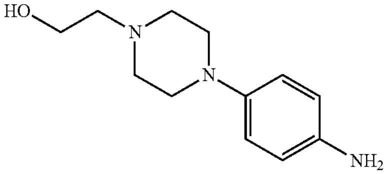

Compound 70 was synthesized using procedure reported in JMC 2005, 48, 2371-2387 and WO2003037872

71

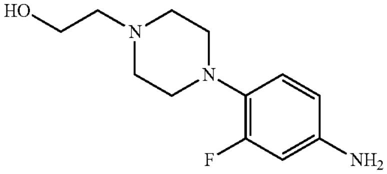

Compound 71 was synthesized using procedure reported in WO2010090764

72

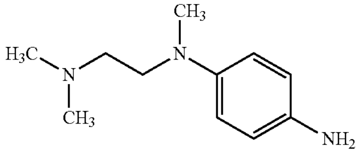

Compound 72 was synthesized using procedure reported in WO2004011438 and WO2008152013

73

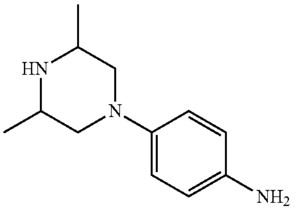

Compound 73 was synthesized using procedure reported in WO2015092431 and JMC 2008, 51, 3507-3525

74

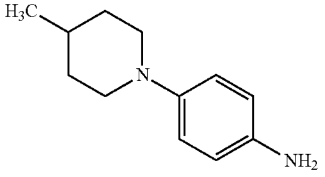

Compound 74 was synthesized using procedure reported in JMC 2012, 55, 10685-10699

75

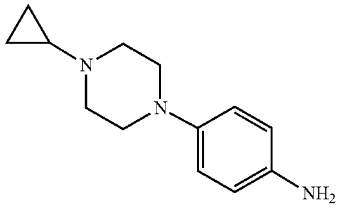

Compound 75 was synthesized using procedure reported in WO2017211216

76

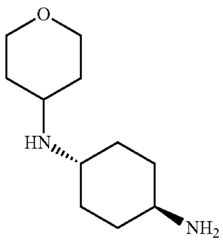

Compound 76 was synthesized using procedure reported in WO2012058392

77

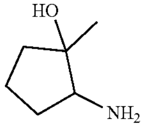

Compound 77 was synthesized using procedure reported in JMC 2016, 59, 750-755

78

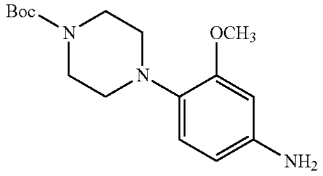

Compound 78 was synthesized using procedure reported in Part in WO2009079597 and WO2002010146

Synthesis of 4-4-(isopropylpiperazin-1-yl)-2-methylaniline (79)

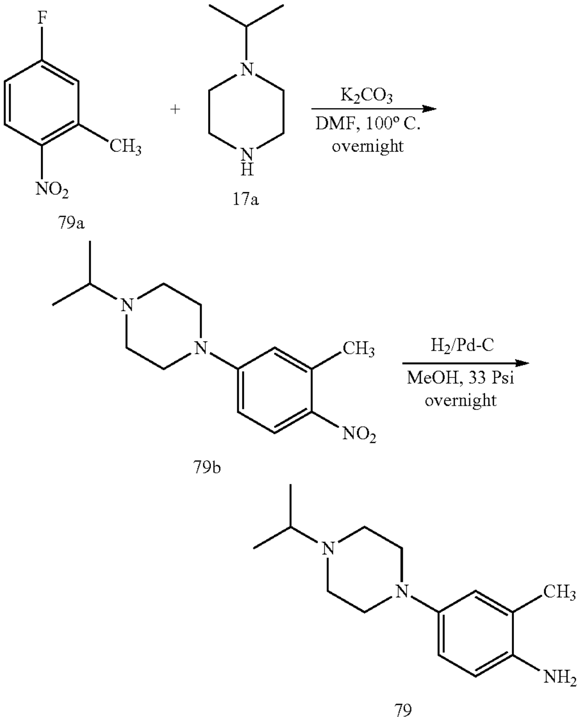

Step 1: Synthesis of 79b: (Part in WO2009079597) To a stirred mixture of compound 79a (3.6 g, 23.4 mmol) in DMF (25 mL) at room temperature were added 17a (3.0 g, 23.4 mmol) and $K_2CO_3$ (9.7 g, 70.2 mmol). The resulting mixture was stirred at 100° C. for overnight. After cooling to room temperature, the reaction mixture was diluted with water (200 mL) and the solid obtained was filtered, washed with water (3×25 mL), and dried under vacuum to give compound 79b as a yellow solid (5.1 g, 75% yield). MS (ESI) m/z 264.2 $[M+H]^+$. This product was used as such in the next step.

Step 2: Synthesis of 79: (Part in WO2002010146) To a solution of compound 79b (4.5 g, 17.1 mmol) in methanol (200 mL) was added a 10% Pd/C-50% wet (2.3 g). The mixture was hydrogenated on a par apparatus at 33 psi for overnight at RT. The reaction mixture was filtered through a pad of Celite and the filtrate was concentrated to afford 79 as a solid (3.5 g, 88% yield). MS (ESI) m/z 233.2 $[M+H]^+$. $^1H$ NMR (600 MHz, Chloroform-d) δ 6.73 (d, J=2.8 Hz, 1H), 6.70 (dd, J=8.4, 2.8 Hz, 1H), 6.62 (d, J=8.4 Hz, 1H), 3.09-3.03 (m, 4H), 2.74-2.66 (m, 5H), 2.17 (s, 2H), 2.16 (s, 3H), 1.09 (d, J=6.5 Hz, 6H).

Synthesis of 5-(1-methyl-1H-pyrazol-4-yl)pyridine-2-amine (80)

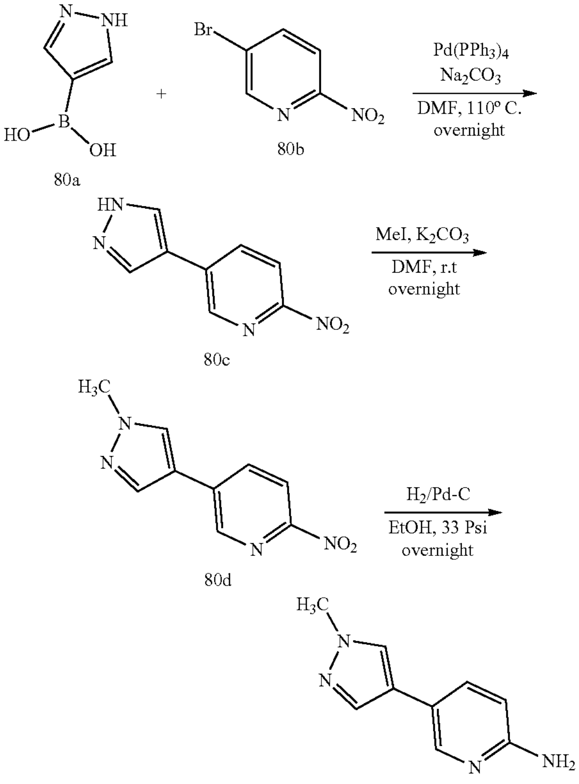

80a 80b 80c 80d 80

Step 1: Synthesis of 80c: (Part in WO2012082817) To a mixture of compound 80a (5.0 g, 45 mmol) and compound 80b (9.1 g, 45 mmol) in DMF (100 mL) was added 2M $Na_2CO_3$ solution (10 mL) and the reaction mixture was degassed for 5 min and then tetrakis(triphenylphosphine) palladium(0) (0.52 g, 0.45 mmol) was added at room temperature under Argon. The resulting mixture was stirred at 110° C. for overnight. Reaction mixture was cooled and poured onto $H_2O$ (1000 mL). The solid obtained was filtered and washed with methanol to give compound 80c as a solid (2.1 g, 25% yield). MS (ESI) m/z 191.2 $[M+H]^+$ Step 2: Synthesis of 80d: (Part in WO2018124001) To a stirred mixture of compound 80c (1.0 g, 5.3 mmol) in DMF (20 mL) at room temperature were added MeI (1.5 g, 10.5 mmol) and $K_2CO_3$ (2.2 g, 16 mmol). The resulting mixture was stirred at room temperature for overnight. Reaction mixture was cooled and poured onto $H_2O$ (200 mL). The solid obtained was filtered and dried to give compound 80d as a solid (0.75 g, 75% yield). MS (ESI) m/z 205.1 $[M+H]^+$.

Step 3: Synthesis of 80: (Part in WO2002010146) Following the standard hydrogenation conditions and isolation techniques gave 80 as a solid (240 mg, 38% yield). MS (ESI) m/z 175.1 $[M+H]^+$.

Synthesis of 5-(1-isopropyl-1H-pyrazol-4-yl)pyridine-2-amine (81)

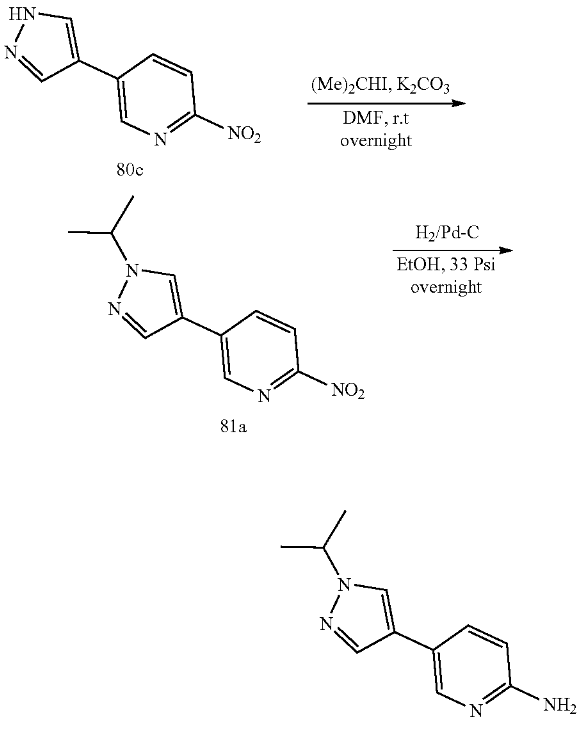

80c 81a 81

Step 1: Synthesis of 81b: (Part in WO2018124001) To a stirred mixture of compound 80c (1.0 g, 5.3 mmol) in DMF (20 mL) at room temperature were added $(Me)_2CHI$ (1.8 g, 10.5 mmol) and $K_2CO_3$ (2.2 g, 16 mmol). The resulting mixture was stirred at room temperature for overnight. The reaction mixture was diluted with water (100 mL) and extracted with EtOAc (3×100 mL). The organic layer was washed with brine solution (50 mL), dried ($Na_2SO_4$), and concentrated to provide crude residue. The crude residue was further purified by silica-gel column using 0-20% MeOH in DCM to give 81b as a solid (0.9 g, 75% yield). MS (ESI) m/z 233.1 $[M+H]^+$.

Step 2: Synthesis of 81: (Part in WO2002010146) Following the standard hydrogenation conditions and isolation techniques gave 81 as a solid (670 mg, 86% yield). MS (ESI) m/z 203.2 $[M+H]^+$. 5 H NMR (600 MHz, Chloroform-d) δ 8.22 (dd, J=2.4, 0.8 Hz, 1H), 7.69-7.66 (m, 1H), 7.58 (d, J=0.8 Hz, 1H), 7.54 (dd, J=8.4, 2.4 Hz, 1H), 7.27 (s, 1H), 6.53 (dd, J=8.5, 0.9 Hz, 1H), 4.62-4.47 (m, 1H), 4.41 (s, 2H), 1.81 (s, 1H), 1.54 (d, J=6.7 Hz, 6H).

Synthesis of 5-(1H-pyrazol-4-yl)pyridin-2-amine (82)

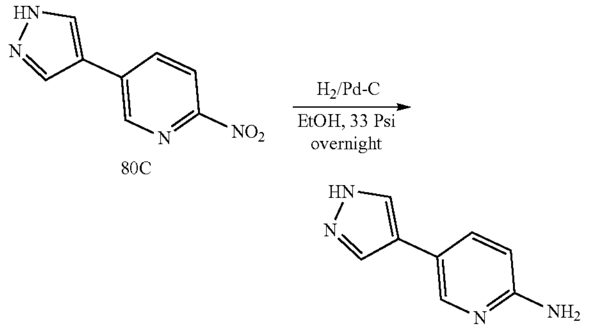

80C

81

Step 1: Synthesis of 82: (Part in WO2002010146) To a solution of compound 80c (1.1 g, 3.8 mmol) in ethanol (100 mL) was added catalytic amount of 10% Pd/C-50% wet (600 mg). The mixture was hydrogenated on a par apparatus at 33 psi for overnight at RT. Following standard isolation techniques gave 81 as a solid (660 mg, 76% yield). MS (ESI) m/z 161.2 $[M+H]^+$.

Synthesis of tert-butyl-4-(6-aminophenyl)-1H-pyrazole-1carboxylate (82)

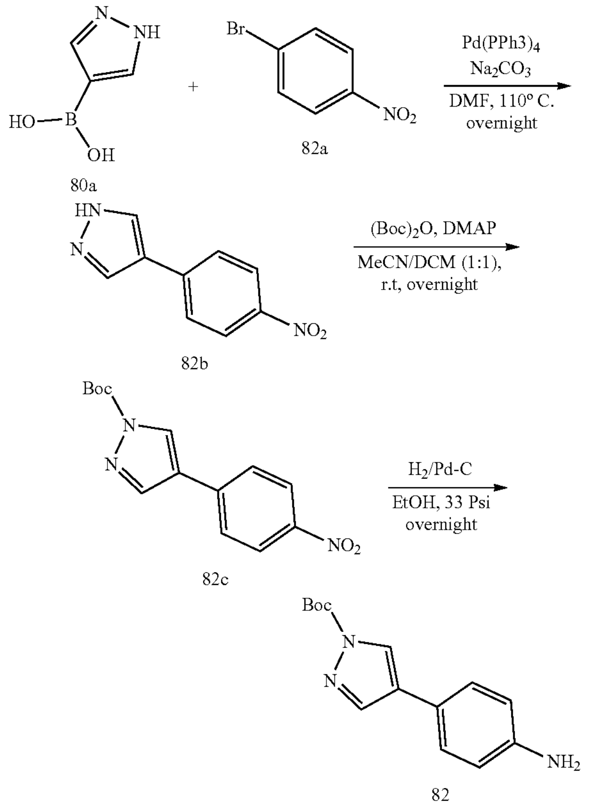

80a

82a

82b

82c

82

Step 1: Synthesis of 82b: (Part in WO2012082817) The procedure used for making 80c was used to isolate 82b as a solid (3.7 g, 44% yield). MS (ESI) m/z 190.1 $[M+H]^+$.

Step 2: Synthesis of 82c: (Part in WO2018005193) To a stirred mixture of compound 82b (1.0 g, 5.3 mmol) in MeCN/DCM (1:1) (50 mL) at room temperature were added $(Boc)_2O$ (5.8 g, 27 mmol) and DMAP (324 mg, 2.7 mmol). The resulting mixture was stirred at room temperature for overnight. The work-up and column chromatography gave 82c as a solid (1.1 g, 66% yield). MS (ESI) m/z 291.1 $[M+H]^+$.

Step 3: Synthesis of 82: (Part in WO2002010146) The hydrogenation of 82c (1.1 g, 0.8 mmol) in ethanol (100 mL) using catalytic amount of 10% Pd/C-50% wet (600 mg) gave 82 as a solid (950 mg, 96% yield). MS (ESI) m/z 260.1 $[M+H]^+$. δ $^1$H NMR (600 MHz, Chloroform-d) δ 8.17 (d, J=0.9 Hz, 1H), 7.91 (d, J=0.9 Hz, 1H), 7.32 (d, J=8.5 Hz, 2H), 6.71 (d, J=8.5 Hz, 2H), 1.67 (s, 9H).

Synthesis of tert-butyl-4-(1-methyl-1H-pyrazol-4-yl) aniline (83)

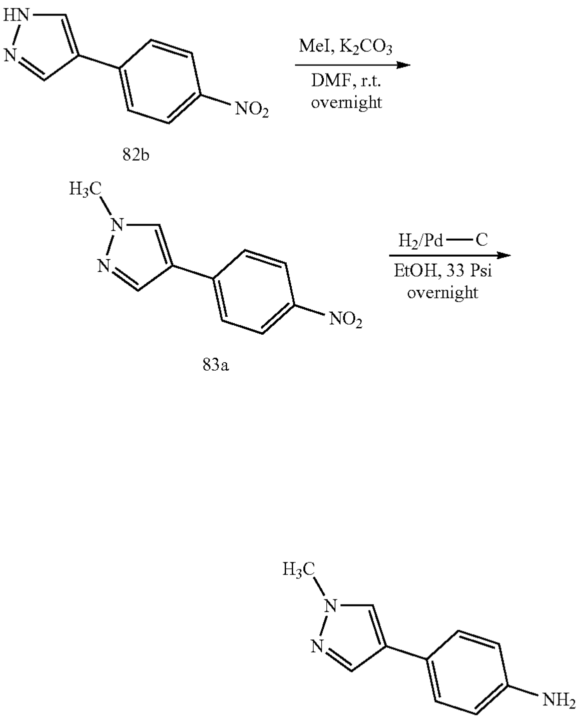

82b

83a

83

Step 1: Synthesis of 83a: (Part in WO2018124001) To a stirred mixture of compound 82b (1.0 g, 5.3 mmol) in DMF (20 mL) at room temperature were added MeI (1.5 g, 10.5 mmol) and $K_2CO_3$ (2.2 g, 16 mmol). The resulting mixture was stirred at room temperature for overnight. The work-up and purification gave 83a as a solid (0.8 g, 73% yield). MS (ESI) m/z 204.1 $[M+H]^+$.

Step 2: Synthesis of 83: (Part in WO2002010146) Following the standard hydrogenation technique and isolation procedure gave 83 as a gray solid (660 mg, 97% yield). MS (ESI) m/z 174.1 $[M+H]^+$. 5 $^1$H NMR (600 MHz, Chloroform-d) δ 7.66 (s, 1H), 7.49 (s, 1H), 7.28-7.25 (m, 2H), 6.69 (d, J=8.4 Hz, 2H), 3.91 (s, 3H), 3.66 (s, 2H).

Synthesis of 4-(1-isopropyl-1H-pyrazol-4-yl)aniline (84)

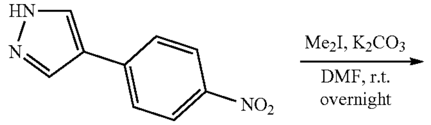

82b

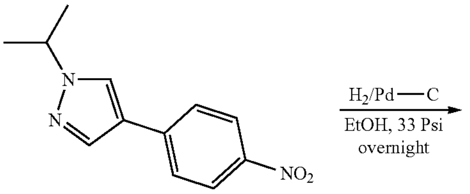

84a

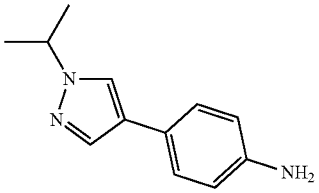

84

Step 1: Synthesis of 84a: (Part in WO2018124001) The procedure described for 81a was employed to isolate 84a as a solid (0.9 g, 75% yield). MS (ESI) m/z 233.2 $[M+H]^+$.

Step 2: Synthesis of 84: (Part in WO2002010146) (750 mg, 96% yield). Following the standard hydrogenation technique and isolation procedure gave 84 as a gray solid MS (ESI) m/z 203.1 $[M+H]^+$. $^1$H NMR (600 MHz, Chloroform-d) δ 7.68 (s, 1H), 7.55 (s, 1H), 7.27 (dd, J=8.9, 6.9 Hz, 2H), 6.72-6.66 (m, 2H), 4.55-4.46 (m, 1H), 1.53 (d, J=6.7 Hz, 6H).

Synthesis of 4-(2-(dimethylamino)ethoxy)-3-methoxyaniline (85)

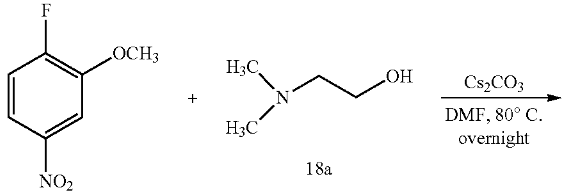

42a 18a

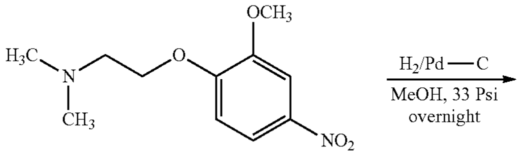

85a

-continued

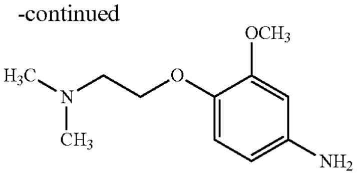

85

Step 1: Synthesis of 85a: (Part in 2009076140) To a stirred mixture of compound 42a (5.0 g, 29 mmol) in DMF (50 mL) at room temperature were added 18a (3.9 g, 44 mmol) and $Cs_2CO_3$ (29 g, 188 mmol). The resulting mixture was stirred at 80° C. for overnight. Reaction mixture was cooled, diluted with water (200 mL) and extracted with EtOAc (3×200 mL). The organic layer was washed with brine solution (100 mL), dried ($Na_2SO_4$), and concentrated to provide crude residue. The crude residue was further purified by silica-gel column using 0-20% MeOH in DCM to give 85a as a solid (5.0 g, 71% yield). MS (ESI) m/z 241.1 $[M+H]^+$.

Step 2: Synthesis of 85: (Part in WO2002010146) To a solution of compound 85a (5.0 g, 21 mmol) in methanol (200 mL) was added catalytic amount of 10% Pd/C-50% wet (2.5 g). The mixture was hydrogenated on a par apparatus at 40 psi for overnight at RT. The reaction mixture was filtered and concentrated to afford 85 as a solid (3.9 g, 89% yield). MS (ESI) m/z 211.2 [M+H]+. $^1$H NMR (600 MHz, DMSO-$d_6$) δ 7.95 (s, 1H), 6.64 (d, J=8.4 Hz, 1H), 6.26 (d, J=2.6 Hz, 1H), 6.04 (dd, J=8.4, 2.5 Hz, 1H), 3.84 (t, J=6.1 Hz, 2H), 3.67 (s, 3H), 2.55-2.48 (m, 3H), 2.19 (s, 6H).

Synthesis of 4-(2-(dimethylamino)ethoxy)-3-methylaniline (86)

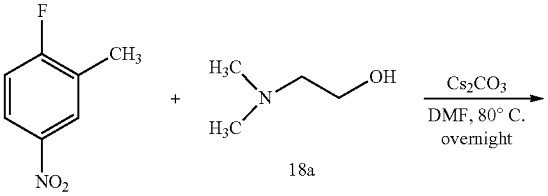

43a 18a

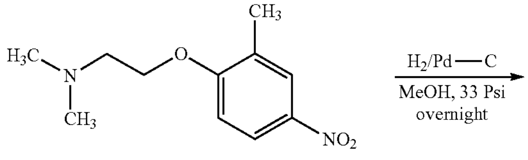

86a

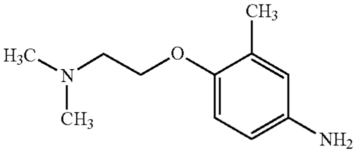

86

Step 1: Synthesis of 86a: (Part in 2009076140) The procedure to make 85a was used to isolate 86a as a solid (7.0 g, 97% yield). MS (ESI) 225.1 m/z $[M+H]^+$.

Step 2: Synthesis of 86: (Part in WO2002010146) The standard hydrogenation technique and isolation procedure was used to isolate 86 as a solid (6.0 g, 99% yield). MS (ESI) m/z 195.2 $[M+H]^+$. δ $^1H$ NMR (600 MHz, DMSO-$d_6$) δ 7.95 (s, 1H), 6.62 (s, 1H), 6.38 (s, 1H), 6.33 (s, 1H), 3.86 (s, 2H), 2.21 (s, 6H), 2.03 (s, 3H).

Synthesis of (R)-5-(3-(dimethylamino)pyrrolidin-1-yl)pyridin-2-amine (87)

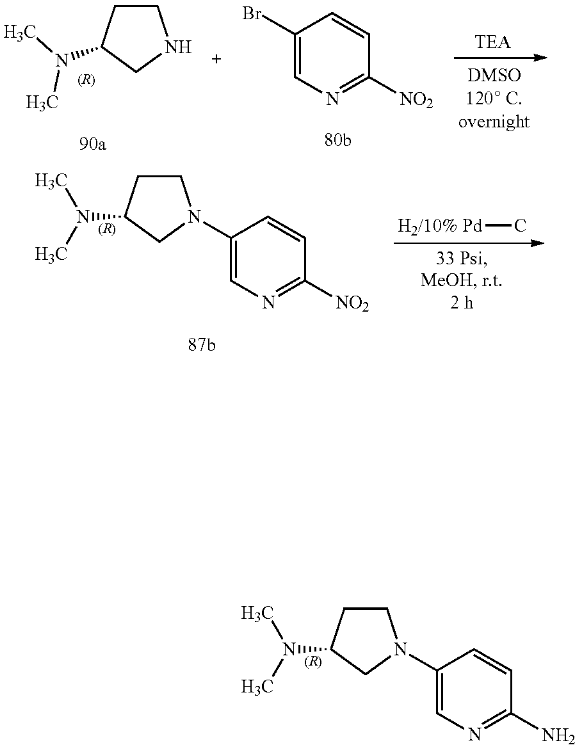

87

Step 1: Synthesis of 87b: (Part in Ref: WO 20180072707 A1): To a stirred mixture of compound 90a (5.0 g, 44 mmol) and bromo compound 80b (8.4 g, 42 mmol) in DMSO (25 mL) was added triethylamine (31 mL, 220 mmol) at room temperature and stirred at 120° C. for overnight. The reaction mixture was cooled and diluted with water (300 mL) and extracted with EtOAc (3×150 mL). The organic layer was washed with brine solution (100 mL), dried ($Na_2SO_4$), and concentrated to provide crude residue. The crude residue was further purified by silica-gel column using 0-20% MeOH in DCM to give 87bc as yellow solid (8.0 g, 78% yield). MS (ESI) m/z 237.2 $[M+H]^+$.

Step 2: Synthesis of 87: (Part in WO 2015038417 A1) Hydrogenation of 87b by following standard hydrogenation technique and isolation method afforded 90 as a solid (6.8 g, 97% yield). MS (ESI) m/z 207.2 $[M+H]^+$. $^1H$ NMR (600 MHz, Chloroform-d) δ 7.48 (d, J=3.0 Hz, 1H), 6.84 (dd, J=8.8, 3.0 Hz, 1H), 6.50 (d, J=8.7 Hz, 1H), 3.42-3.36 (m, 1H), 3.32 (dd, J=8.8, 2.7 Hz, 1H), 3.30-3.23 (m, 1H), 3.10 (t, J=8.2 Hz, 1H), 2.90-2.84 (m, 1H), 2.31 (s, 6H), 2.23-2.15 (m, 1H), 1.96-1.87 (m, 1H).

Synthesis of 4-(2-(dimethylamino)ethoxy)-2-methylaniline (88)

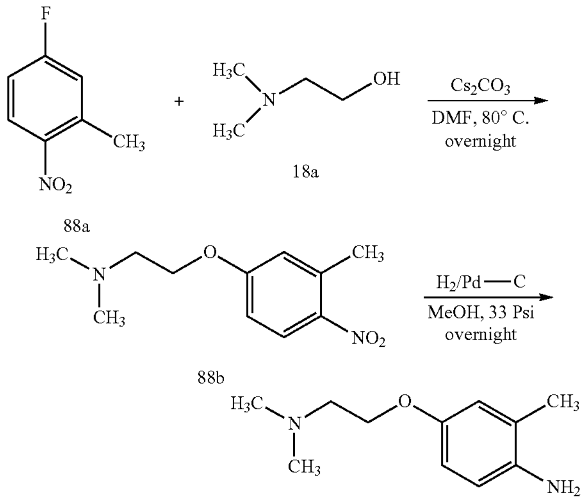

88

Step 1: Synthesis of 88b: (Part in WO2014134308) The procedure to make 85b was used to isolate 88b as a solid (4.1 g, 57% yield). MS (ESI) m/z 225.2 $[M+H]^+$.

Step 2: Synthesis of 88: (Part in WO2002010146) Hydrogenation and then filtered through a pad of Celite and the filtrate was concentrated under reduced pressure to afford 91 as a solid (3.0 g, 83% yield). MS (ESI) m/z 195.1$[M+H]^+$. $^1H$ NMR (600 MHz, Chloroform-d) δ 6.69 (d, J=2.8 Hz, 1H), 6.63 (d, J=2.8 Hz, 1H), 6.61 (s, 1H), 3.99 (t, J=5.8 Hz, 2H), 2.68 (t, J=5.8 Hz, 2H), 2.32 (s, 6H), 2.15 (s, 3H)

Synthesis of 4-(2-(dimethylamino)ethoxy)-2-fluoroaniline (89)

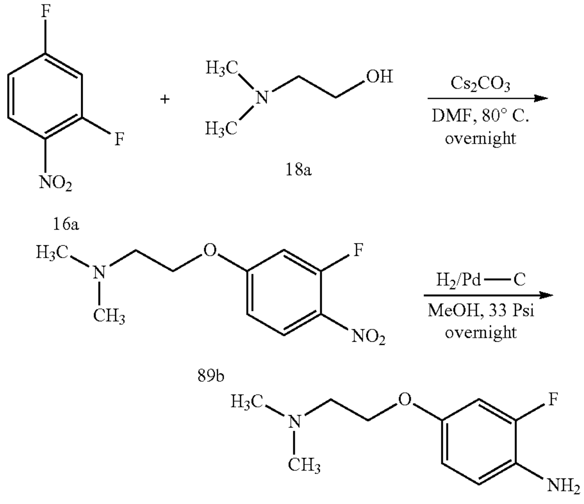

89

Step 1: Synthesis of 89b: (Part in WO2009076140) The procedure to make 85a was used to isolate 89bas a solid (6.3 g, 44% yield). MS (ESI) 229.1 m/z $[M+H]^+$.

Step 2: Synthesis of 89: (Part in WO2002010146) Standard hydrogenation of 89b was followed. The reaction mixture was filtered through a pad of Celite and the filtrate was concentrated under reduced pressure to afford 89 as a solid (5.1 g, 94% yield). MS (ESI) m/z 199.1 $[M+H]^+$. $^1H$ NMR (600 MHz, Chloroform-d) δ 6.62 (dd, J=8.5, 5.7 Hz, 1H), 6.57 (dd, J=10.2, 2.7 Hz, 1H), 6.51 (td, J=8.5, 2.7 Hz, 1H), 4.07 (t, J=5.7 Hz, 2H), 2.76 (t, J=5.7 Hz, 2H), 2.35 (s, 6H).

Synthesis of 4-(6-methyl-2,6-diazaspiro[3,3]heptan-2-yl)amine (90)

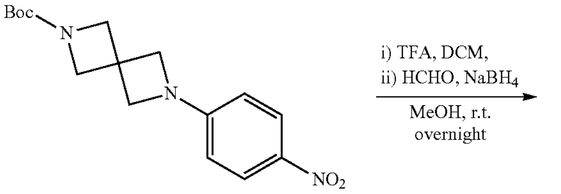

28b

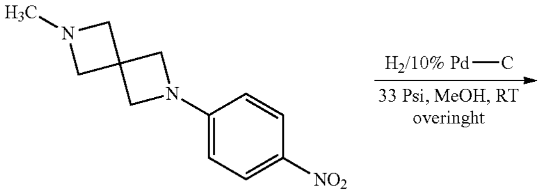

90a

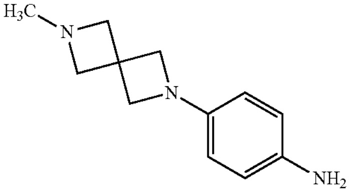

90

Step 2: Synthesis of 90a: To compound 28b (1.5 g, 5 mmol) was added 25% TFA in DCM (100 mL) and stirred at room temperature for 1 h. After completion of the reaction, removed solvent under vacuum and used as such for the next step. The crude reaction mixture and formaldehyde (2 mL, 25 mmol, 37% aqueous solution) were added to methanol (30 mL), stirred at room temperature for 1 h, then sodium borohydride (946 mg, 25 mmol) was added to the reaction mixture in portions and reaction was continued for overnight. After the reaction is completed, removed solvents under vacuum and the crude residue was purified by silica-gel column using 0-20% MeOH in DCM to give 90a as liquid (701 mg, 60% yield). MS (ESI) 234.1 m/z Step 3: Synthesis of 90: (WO2002010146) To a solution of compound 97c (0.7 g, 3 mmol) in methanol (100 mL) was added catalytic amount of 10% Pd/C-50% wet (0.4 g). The mixture was hydrogenated on a par apparatus at 40 psi for overnight. The reaction mixture was filtered through a pad of Celite and the filtrate was concentrated under reduced pressure to afford 90 as a solid (560 mg, 93% yield). MS (ESI) m/z 204.1 $^1H$ NMR (600 MHz, Chloroform-d) δ 6.62 (d, J=8.6 Hz, 2H), 6.35 (d, J=8.6 Hz, 2H), 3.84 (s, 3H), 3.39 (s, 4H), 2.33 (s, 4H).

Synthesis of 3-fluoro-4-(6-methyl-2,6-diazaspiro[3,3]heptan-2-yl)amine (91)

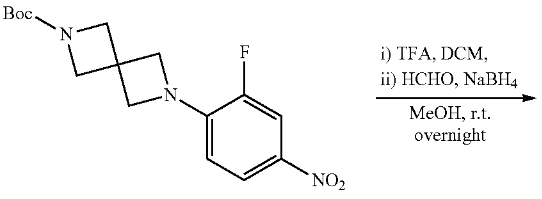

26C

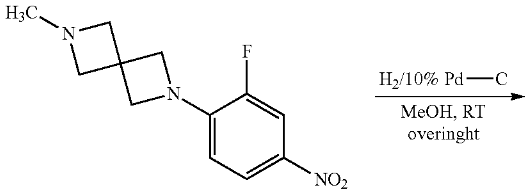

91a

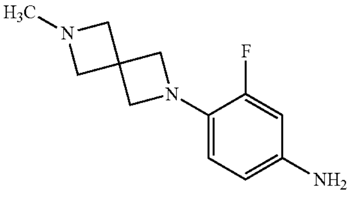

91

Step 2: Synthesis of 91a: The procedure described for making 90a was used to isolate 91 (601 mg, 48% yield). MS (ESI) m/z 252.1 (VP-HB5-227A)

Synthesis of 3-fluoro-4-(6-isopropyl-2,6-diazaspiro[3,3]heptan-2-yl)amine (92)

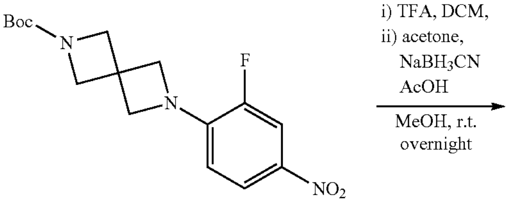

26c

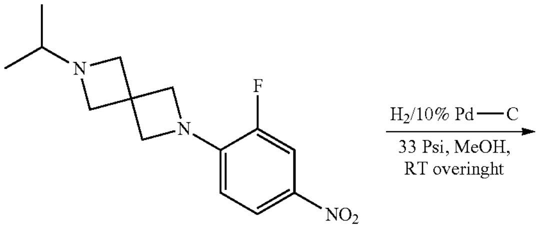

92a

-continued

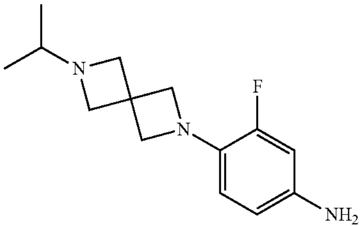

92

-continued

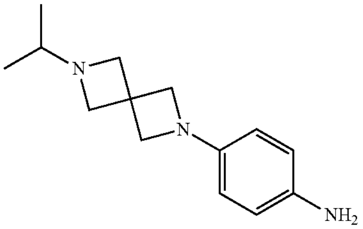

93

Step 1: Synthesis of 92a: To compound 26c (1.7 g, 5.1 mmol) was added 25% TFA in DCM (100 mL) and stirred at room temperature for 1 h. After completion of the reaction, removed solvent under vacuum and used as such for the next step. The crude reaction mixture, acetic acid (2.5 mL) and acetone (2.5 mL, 51 mmol, 37% aqueous solution) were added to methanol (30 mL), stirred at room temperature for 1 h, then sodium cyanoborohydride (3.2 g, 51 mmol) was added to the reaction mixture in portions and reaction was continued for overnight. After the reaction is completed, removed solvents under vacuum and the crude residue was purified by silica-gel column using 0-20% MeOH in DCM to give 92a as liquid (0.85 g, 61% yield). MS (ESI) m/z 280.1

Step 2: Synthesis of 92: (WO2002010146) To a solution of compound 92a (0.85 g, 3 mmol) in methanol (100 mL) was added catalytic amount of 10% Pd/C-50% wet (0.5 g). The mixture was hydrogenated on a par apparatus at 40 psi for overnight. The reaction mixture was filtered through a pad of Celite and the filtrate was concentrated under reduced pressure to afford 92 as a solid (0.71 g, 93% yield). MS (ESI) m/z 250.2 $[M+H]^+$. $^1H$ NMR (600 MHz, Chloroform-d) δ 6.42-6.30 (m, 3H), 3.90 (s, 4H), 3.33 (s, 4H), 0.93 (d, J=6.2 Hz, 6H).

Synthesis of 4-(6-isopropyl-2,6-diazaspiro[3,3]heptan-2-yl)amine (93)

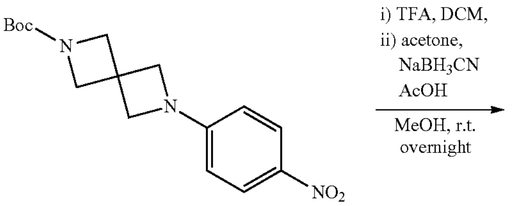

28b

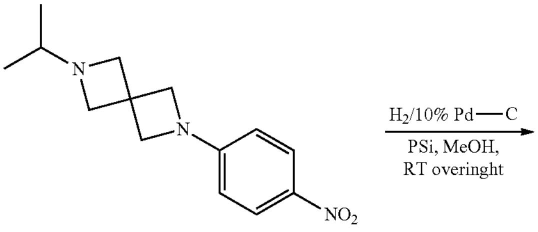

93a

Step 1: Synthesis of 93a: To compound 28b (1.5 g, 5 mmol) was added 25% TFA in DCM (100 mL) and stirred at room temperature for 1 h. After completion of the reaction, removed solvent under vacuum and used as such for the next step. The crude reaction mixture, acetic acid (2.5 mL) and acetone (2.5 mL, 50 mmol, 37% aqueous solution) were added to methanol (30 mL), stirred at room temperature for 1 h, then sodium cyanoborohydride (3.1 g, 50 mmol) was added to the reaction mixture in portions and reaction was continued for overnight. After the reaction is completed, removed solvents under vacuum and the crude residue was purified by silica-gel column using 0-20% MeOH in DCM to give 93a as liquid (0.86 g, 66% yield). MS (ESI) m/z 262.1

Step 2: Synthesis of 93: (WO2002010146) To a solution of compound 93a (0.86 g, 3.3 mmol) in methanol (100 mL) was added catalytic amount of 10% Pd/C-50% wet (0.5 g). The mixture was hydrogenated on a par apparatus at 40 psi for overnight. The reaction mixture was filtered through a pad of Celite and the filtrate was concentrated under reduced pressure to afford 93 as a solid (0.74 g, 97% yield). MS (ESI) m/z 232.2 $[M+H]^+$. $^1H$ NMR (600 MHz, Chloroform-d) δ 6.63 (d, J=8.6 Hz, 2H), 6.35 (d, J=8.6 Hz, 2H), 3.84 (s, 4H), 3.32 (s, 4H), 2.24 (dt, J=12.4, 6.2 Hz, 1H), 0.93 (d, J=6.2 Hz, 6H).

Synthesis of 4-(4-isopropylpiperidin-1yl)aniline (94)

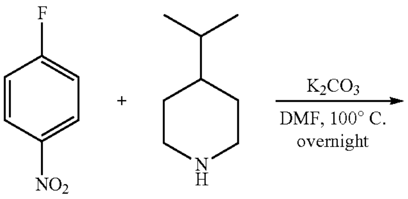

28a 94a

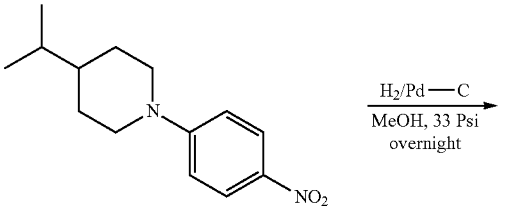

94b

-continued

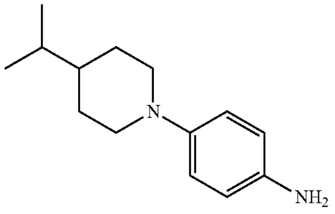

94

Step 1: Synthesis of 94: (Part in WO2009079597) To a stirred mixture of compound 28a (1.1 g, 8 mmol) in DMF (25 mL) at room temperature were added 101a (1.0 g, 8 mmol) and $K_2CO_3$ (3.3 g, 24 mmol). The resulting mixture was stirred at 80° C. for overnight. Reaction mixture was cooled and diluted with water (200 mL) and the solid obtained was filtered and washed with water (3×25 mL) and dried under vacuum to give compound 94a as a yellow solid (1.7 g, 87% yield). MS (ESI) m/z 249.1 $[M+H]^+$. This product is used as such in the next step.

Step 2: Synthesis of 94: (WO2002010146) The standard hydrogenation technique and isolation procedure afforded 94 as a solid (1.3 g, 87% yield). MS (ESI) m/z 219.2 $[M+H]^+$. $^1H$ NMR (600 MHz, Chloroform-d) δ 6.83 (d, J=8.7 Hz, 2H), 6.64 (d, J=8.7 Hz, 2H), 3.52-3.44 (m, 2H), 2.58-2.46 (m, 2H), 1.80-1.70 (m, 2H), 1.54-1.37 (m, 3H), 1.09 (dddd, J=15.5, 11.9, 6.8, 3.7 Hz, 1H), 0.91 (d, J=6.8 Hz, 6H).

The following amines were purchased from commercial sources:

95

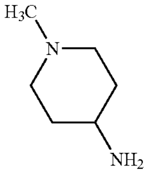

96

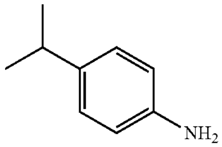

97

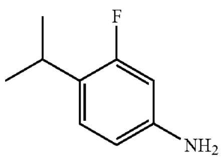

98

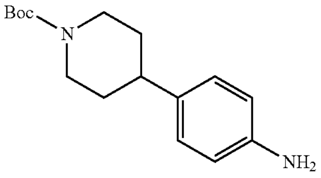

-continued

99

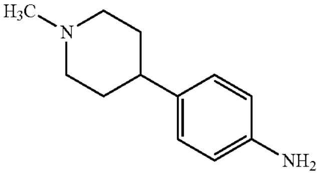

100

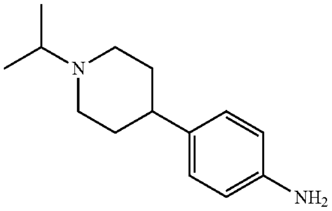

101

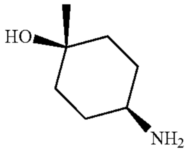

102

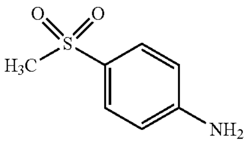

103

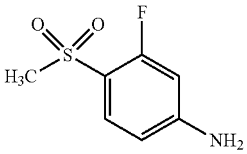

104

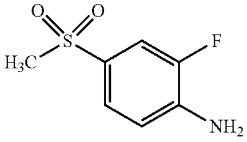

105

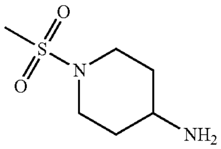

106

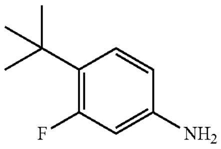

-continued

107

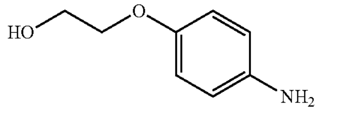

108

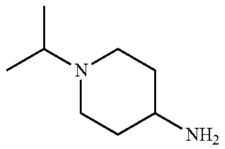

109

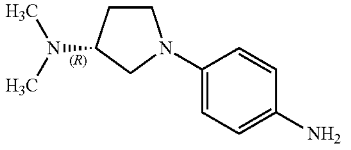

Synthesis of 109: Prepared according to the procedure described for the preparation of compound 33. MS (ESI) m/z 206.2 $[M+H]^+$.

110

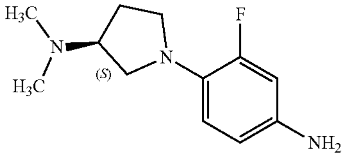

Synthesis of 110: Prepared according to the procedure described for the preparation of compound 30. MS (ESI) m/z 224.2 $[M+H]^+$.

Some of the amines that are not mentioned here are commercially available and might have used to make the final target molecules.

111

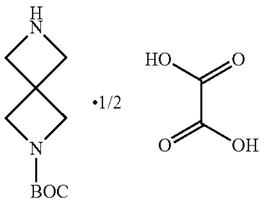

Procured from a commercial source.

Example 2

General Synthesis and Schemes

General Methods. General reaction conditions are described in International Pat. App. Publication No. WO 2018009625, which is incorporated by reference for such teachings. The reactions were generally carried out under a dry argon atmosphere using anhydrous solvents (Sigma-Aldrich, St. Louis, MO). All common chemicals were purchased from commercial sources. The purification of the molecules was carried out using Combi Flash Rf from Teledyne ISCO, regular silica gel columns, and C18 columns. Chiral HPLC columns (Chiral Technologies) and lyophilization techniques (VirTis Genesis 25 L Pilot Lyophilizer) were used wherever necessary to isolate the desired products. The isolated target products are excellent powder/fluffy material and possess the purity, in general, of >97%. $^1H$ NMR spectra were recorded on a 600 MHz Fourier Transform Brucker Spectrometer. Spectra were obtained from samples prepared in 5 mm diameter tubes in $CDC_3$, $CD_3OD$ or DMSO-$d_6$. The spin multiplicities are indicated by the symbols, s (singlet), d (doublet), t (Triplet), m (multiplet) and, br (broad). Coupling constants (J) are reported in Hz. MS spectra were obtained using electrospray ionization (ESI) on an Agilent Technologies' 6120 quadrupole LCMS system.

The compounds described herein may be synthesized by many methods available to those skilled in the art of organic chemistry. Maffrand et al., *Heterocycles* 16(1): 35-37 (1981). General synthetic schemes for preparing compounds described herein are described below. These schemes are illustrative and are not meant to limit the possible techniques one skilled in the art may use to prepare the compounds disclosed herein. Different methods to prepare the compounds described herein will be evident to those skilled in the art. Additionally, the various steps in the synthesis may be performed in an alternate sequence in order to give the desired compound or compounds. Examples of compounds described herein prepared by methods described in the general schemes are shown below.

Preparation of homochiral examples may be carried out by techniques known to one having ordinary skill in the art. For example, homochiral compounds may be prepared by separation of racemic products by chiral phase preparative HPLC. Alternatively, the example compounds may be prepared by methods known to give enantiomerically enriched products such as asymmetric synthesis and enantioselective synthesis. These include, but are not limited to, the incorporation of chiral auxiliary functionalities into racemic intermediates that serve to control the diastereoselective of transformations, providing enantio-enriched products upon cleavage of the chiral auxiliary. The compounds described herein can be prepared in a number of ways known to one skilled in the art of organic synthesis. The compounds described herein can be synthesized using the methods described below, together with synthetic methods known in the art of synthetic organic chemistry, or by variations thereon as appreciated by those skilled in the art. Preferred methods include, but are not limited to, those described below. The reactions are performed in a solvent or solvent mixture appropriate to the reagents and materials employed and suitable for the transformations being affected. It will be understood by those skilled in the art of organic synthesis that the functionality present on the molecule should be consistent with the transformations proposed. This will sometimes require a judgment to modify the order of the synthetic steps or to select one process scheme over another in order to obtain a desired compound described herein. It will also be recognized that another major consideration in the planning of any synthetic route in this field is the judicious choice of the protecting group used for protection of the reactive functional groups present in the compounds described herein. An authoritative account describing the many alternatives to the trained practitioner is Greene et al., *Protective Groups in Organic Synthesis,* $4^{th}$ ed., Wiley-Interscience (2006).

General Scheme for Compounds

Scheme T

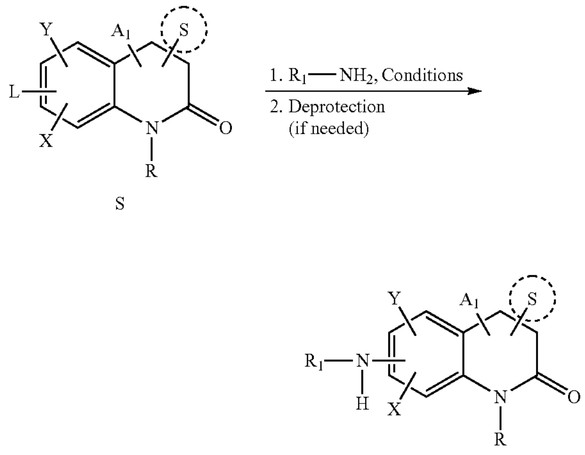

S

T $A_1$ = None, —Me, carbonyl, or gem-difluoro

Scheme T can be followed to make the final target molecules. The synthesis of variously substituted starting materials (S) can be made using one or more of the schemes shown below. It may be modified the proposed synthetic plan to affect the desired transformation. $R_1NH_2$ can be obtained from the commercial source, or it can be made using the standard reactions (Scheme A) that are appreciated by those skilled in the art. Group L may be changed to L1 (e.g., SMe to SOMe/$SO_2Me$) before reacting with $R_1NH_2$ in the sequence.

General Scheme for Making $R_1NH_2$

Scheme A

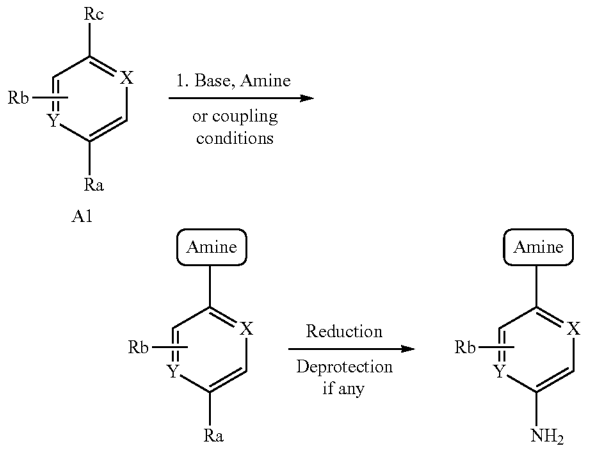

A1

A2

A3

Ra = $NO_2$, Masked amine or Amine
Rb = F, Me, OMe, $CF_3$, $CHF_2$
X = Y = Independently C or N
Rc = Halogen (Cl, Br, F), —$CO_2H$ The $R_1NH_2$ required for making the final targets would be synthesized via a sequence shown in the scheme A. The appropriately substituted A1 can give the intermediate or the final amine A2 via a reaction(s) such as displacement of halogen atom or amide bond formation reactions that are appreciated by those skilled in the art. The desired A3 ($R_1NH_2$) can be obtained from A2 by reduction of a nitro group or de-masking the amine as needed.

General Schemes to Make Building Blocks and Final Target Molecules

Scheme G

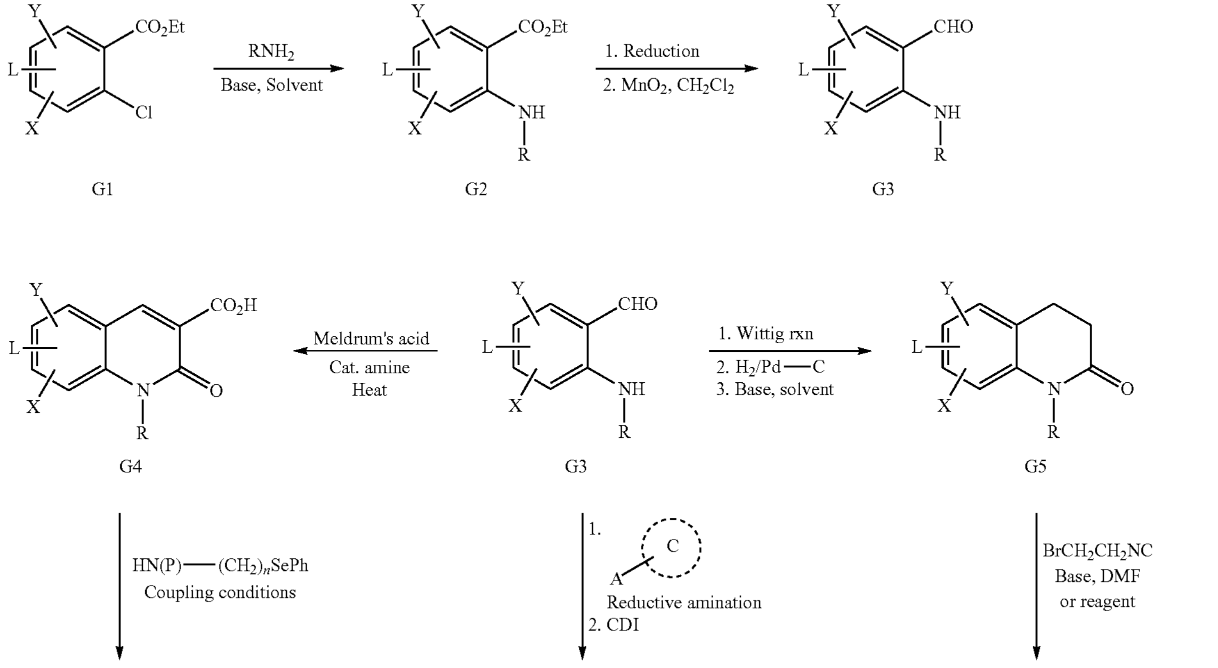

G1

G2

G3

G4

G3

G5

-continued

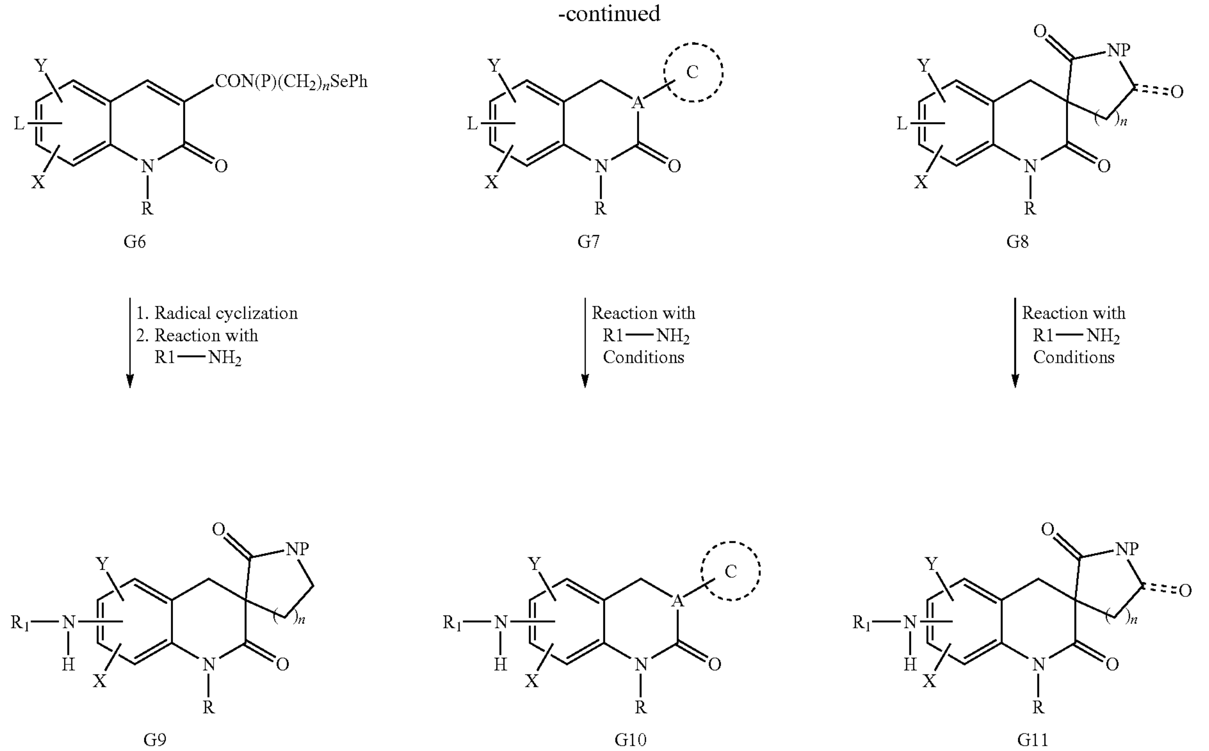

As shown in Scheme G, compounds depicted in the general claim may be synthesized from a readily available starting material. The required intermediates and the target molecules can be made using standard synthetic organic chemistry procedures. The reported standard reaction conditions on a substrate can be extended to perform the reactions on analogous substrates to effect the transformation. The proposed routes or slightly modified schemes may be performed.

Representative Schemes

Scheme 1

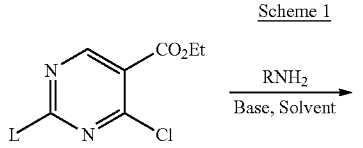

1A

-continued

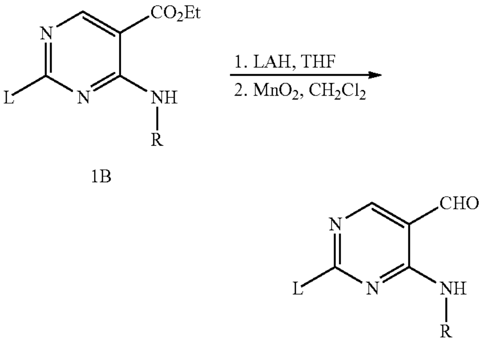

1B

1C

L = Cl, SMe

Scheme 1 shows that conversation of commercially available ester 1A to a known aldehyde 1C using the reported procedure. See Reddy et al., *J. Med. Chem.* 57(3): 578-599 (2014).

Scheme 2

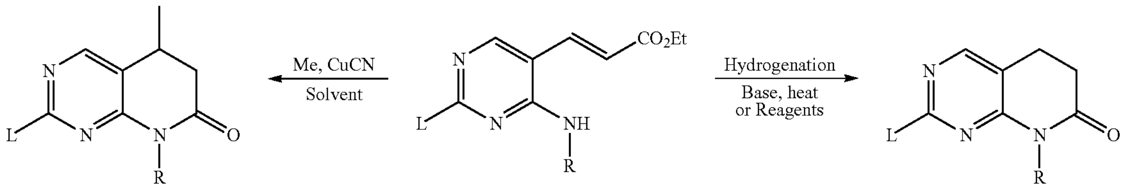

2E 2C 2C

-continued

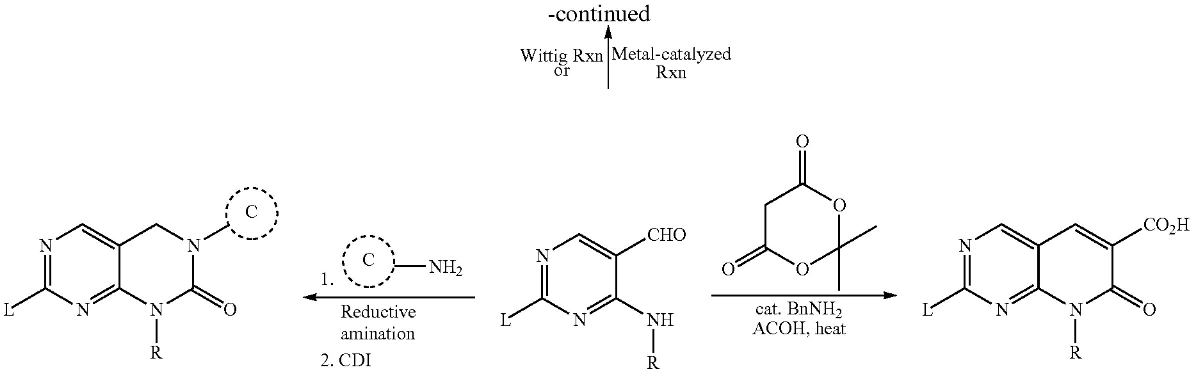

2B 1C 2A

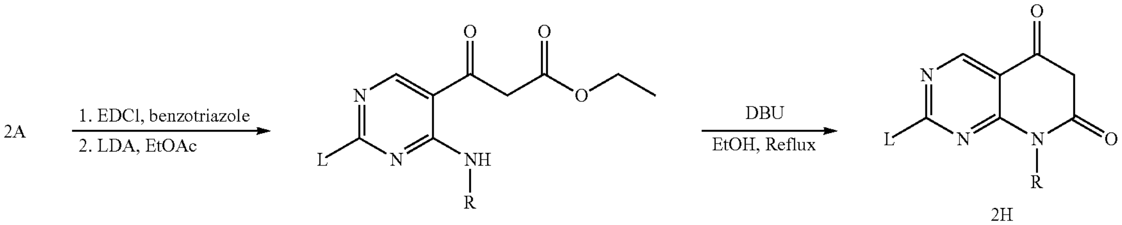

2D 2H

L = Cl, SMe

Scheme 2 shows the synthesis of crucial building blocks starting from the aldehyde 1C. Acid 2A can be made via condensation reaction using Meldrum's acid and an aldehyde 1C. See e.g., WO 2008032162. The bicyclic compound 2B can be prepared from aldehyde 1C via reductive amination with the corresponding amine followed by a reaction with 1,1'-carbonyldiimidazole (CDI). See e.g., WO 2000024744. The compounds 2D, 2E, and 2H were made by following the literature reports or analogs procedure. See US 20090270389; Sakamoto et al., *Bioorg. Med. Chem. Lett.* 25(7): 1431-1435 (2015).

Scheme 3

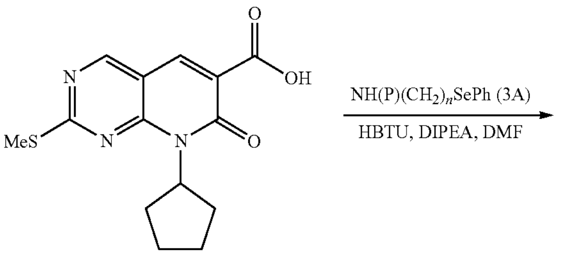

2A

-continued

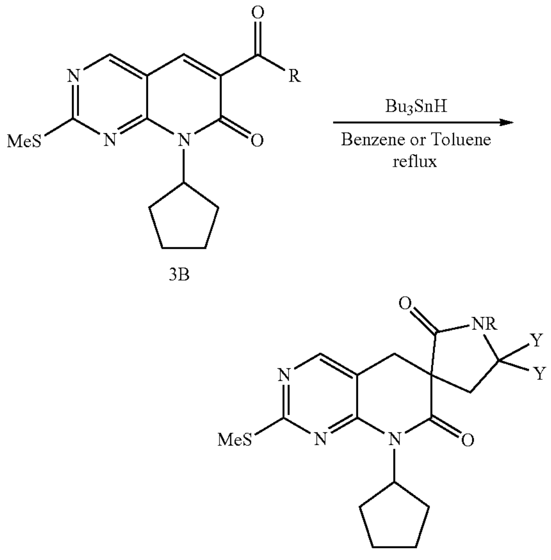

3B

3C

Y = Y = H; Y = Y = Carbonyl

R = N (P)$CH_2CH_2$SePh
P = H, BOC, Me, PMB, Bn
MOM, SEM, Any protective group
R = N(P)CO—$CH_2$SePh
n = 1

Scheme 3 describes the method used to synthesize Spiro compound 3C. An appropriately substituted selenide 3A (made from the corresponding chloro compound (see Kyei et al., *Tetrahedron Lett.* 45(48): 8931-8934 (2004)) was coupled with acid 2A under amide bond forming reaction conditions (see WO 2010020675 and WO 2012069680) to afford the penultimate compound 3B to perform the radical cyclization to get the Spiro compound 3C. For the reaction conditions of radical cyclization, see Kyei et al., *Tetrahedron Lett.* 45(48): 8931-8934 (2004).

Scheme 4

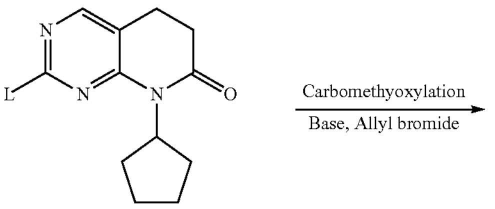

2D

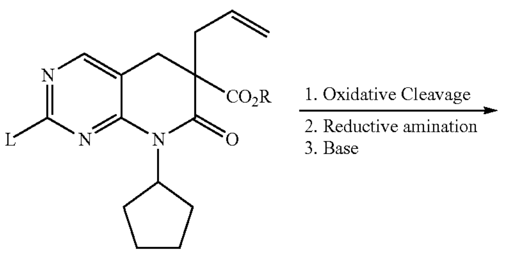

4A

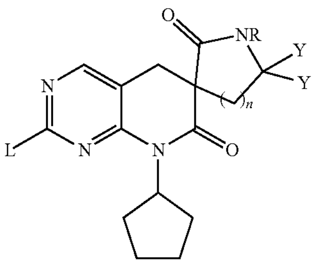

4B

X = Cl, SMe

Scheme 5

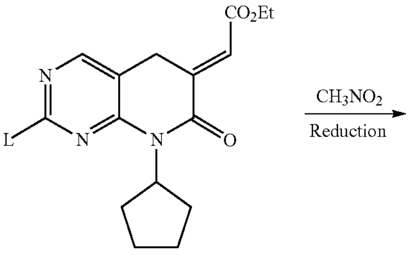

5A

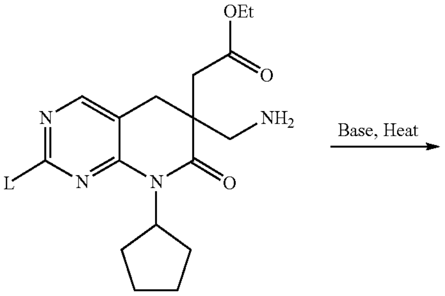

5B

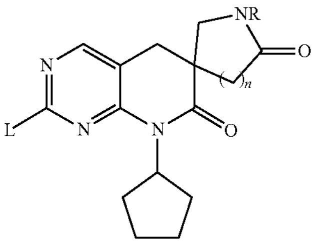

5C

X = Cl, SMe

Scheme 4 describes the alternative synthetic sequence to make the tricyclic spiro lactam, 4B. Scheme 4 starts with a critical amide 2D to give olefin ester 4A via two-step sequence carboalkyloxyation followed by alkylation with allyl halide or vice versa. The compound 4A can be converted to an aldehyde via oxidative cleavage followed by reductive amination See Crosignani et al., *J. Med. Chem.* 51(7): 2227-2243(2008); WO 2006125784.

Scheme 5 describes the synthesis of spiro compound 5C that has a different orientation. Compound 5A can be obtained from 2D via a two-step protocol can be converted to 5B using nitromethane and the reduction of the nitro group of the resultant substrate. The Spiro compound 5C can be obtained from 5B using a procedure known in the art (base and heating). See e.g., Crosignani et al., *J. Med. Chem.* 51(7): 2227-2243 (2008).

Scheme 6

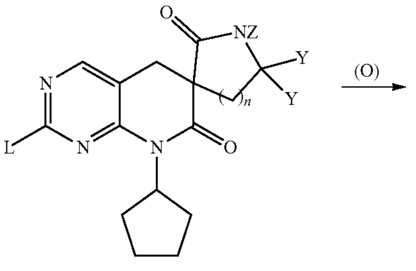

5C

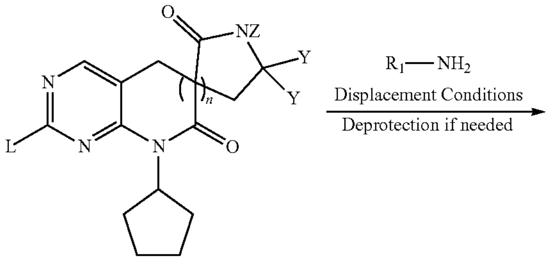

6A

-continued

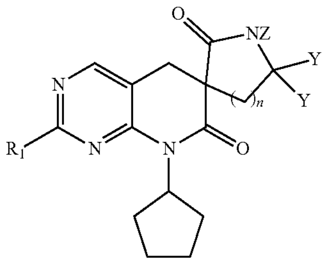

6B
Final Target Molecules

Y = Y = H, Y = Y = Carbonyl
$L_1$ = SOMe, $SO_2Me$
Z = H, Me, Bn, PMB

Scheme 6 describes the synthesis of the target molecules. The reactive spiro sulfoxide or sulfone compound 6A can react with counter partner $R_1$—$NH_2$ under a variety of reaction conditions that are disclosed under the experimental section. See e.g., US 20090270389; WO 2018005865; WO 2010065721; CN 201510800951.

Scheme E

A.

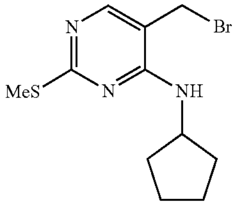

E1

+

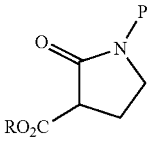

E2

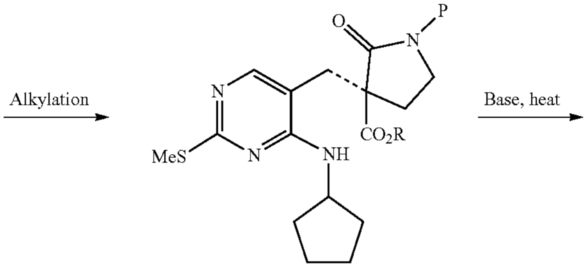

E3
R = H, amide coupling
R = Me/Et

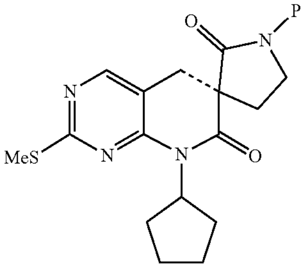

E4

-continued

B.

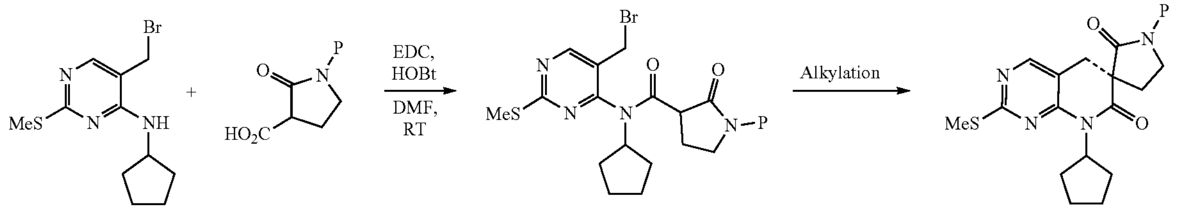

E1 E2 E5 E5

C.

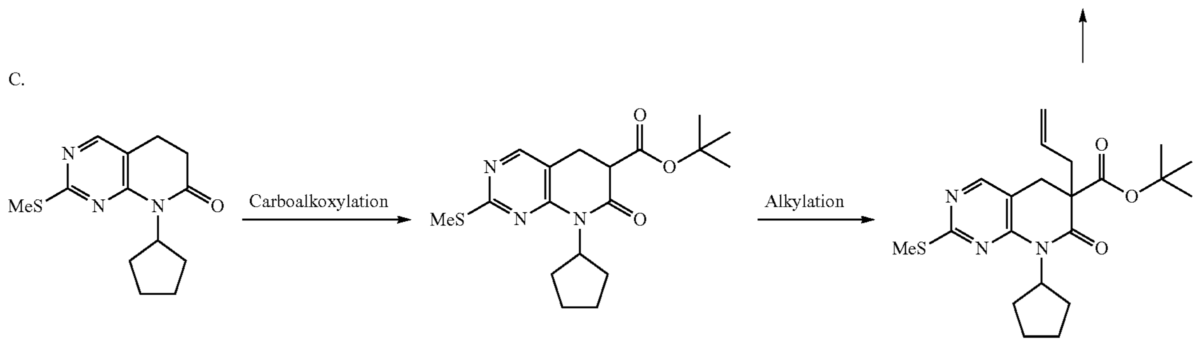

E7 E8 E9

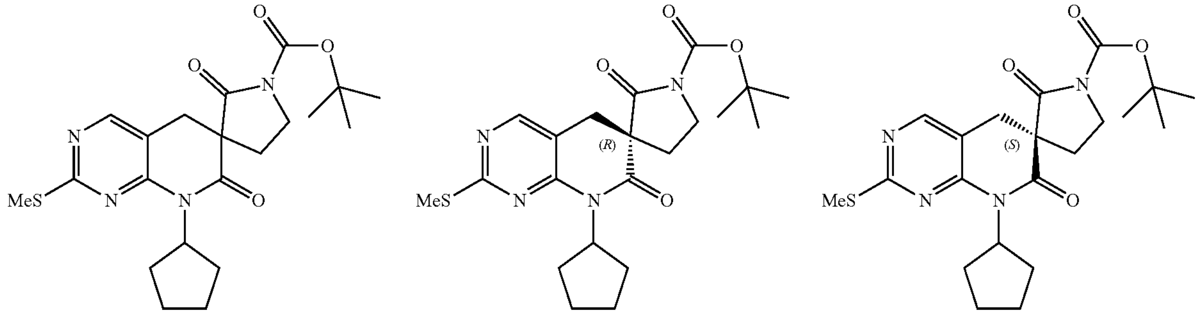

E10 E11 E12

In Scheme E, the starting materials can be selected depending on the kind of reaction intended to be performed and the final target molecule. For example, Bromo compound E1 (can be obtained from the aldehyde 1C via two steps sequence) can react with compound E2 (obtained from to N-protected pyrrolidone; see Moody et al., *Tetrahedron Lett.* 53(15): 1897-1899 (2012)) to obtain E3 via intermolecular alkylation reaction that is well known to those skilled in the art of synthetic organic chemistry. This reaction either it can be done under based mediated conditions to get the racemic version or chose to do asymmetric or enantioselective alkylation to obtain the desired enantiopure substrate. See Lee et al., *Arch. Pharm. Res.* 37(10): 1264-1270 (2013); Park et al., *Adv. Synth Catal.* 353(18): 3313-3318 (2011). It will provide a substrate ester, an amine group in the proximity to form a six-membered lactone, E3 and then a base treatment reaction will provide spiro compound, E4. The same target spiro compound can be made in an alternative way; E1 can be coupled with E2 (R=H) using the standard amide bond forming reaction conditions (see WO 2010020675) and then perform the intramolecular alkylation using either enantioselective or normal reaction conditions. In both cases, the target spiro compound E4 can be obtained. Alternatively, the Spiro compound, E4 can be made starting from E7 by performing known reactions sequentially, carboalkoxylation, alkylation, and then oxidative cleavage of the olefin to realize the aldehyde that upon reductive amination with an appropriate amine will provide the Spiro lactam E4 in the protected form.

The protective group can be removed or can be retained on the substrate until the last step was performed, where you need to realize the free amide. The scheme will allow making the target spiro lactams E10, E11, and E12. The key to arriving at that stage will depend on choosing the right sequence, reagents, and catalysts. Many literature reports describe the synthesis of Spiro compounds, for example: Benabdallah et al., *Curr. Med. Chem.* 25(31): 3748-3767 (2018); Rios, *Chem. Soc. Rev. Rev.* 41(3): 1060-1074 (2012); Ding et al., *Chem. Soc. Rev.* 47 (15): 5946-5996 (2018); Singh et al., Beilstein *J. Org. Chem.* 14: 1778-1805 (2018).

Scheme M
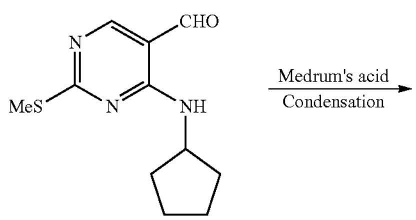
1C
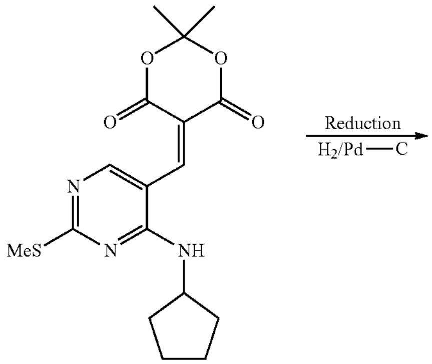
M1
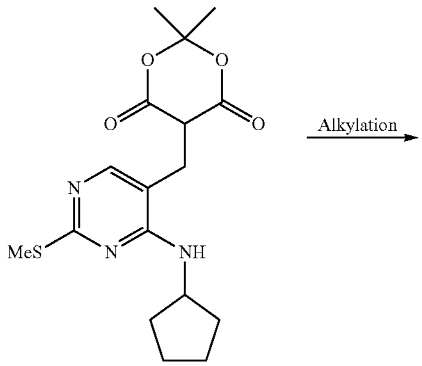
M2
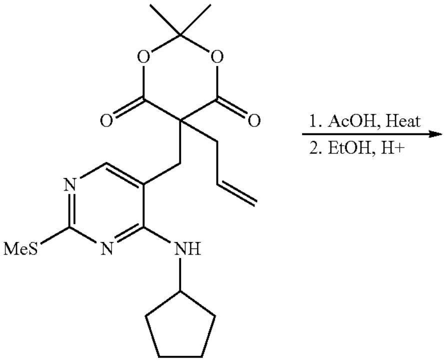
M3
-continued
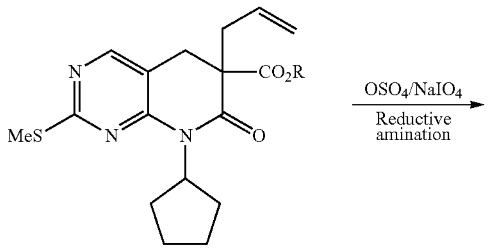
M4
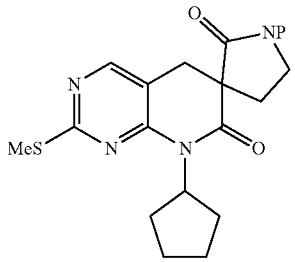
M5
M2
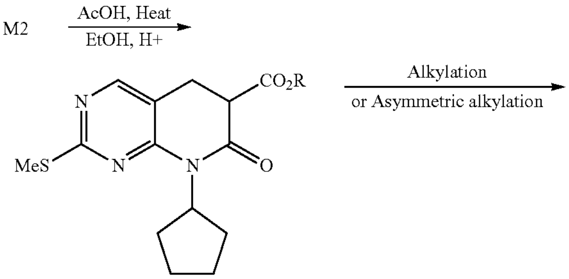
M6
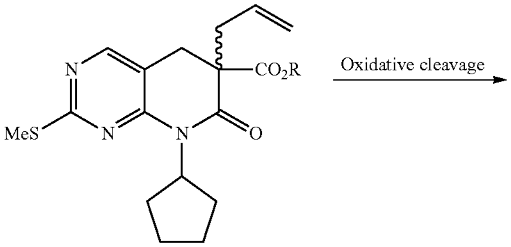
M7
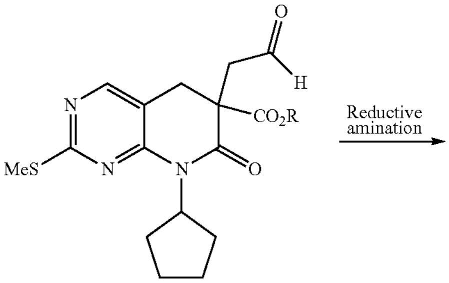
M8

-continued

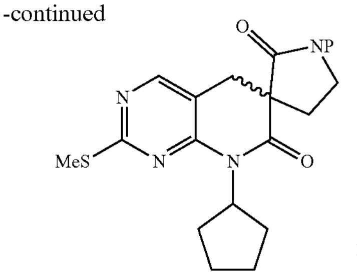

M9

Scheme M also describes an approach to make the spiro compounds in both racemic as well as in enantiopure forms. The reaction between an aldehyde 1C and Meldrum's acid gives condensed product M1, which upon reduction gives compound M2. The alkylation of M2 with an appropriate ally halide provides M3. The cyclization conditions provide allyl ester M4. The spiro compound can # be obtained from M4 via a two-step sequence. The oxidative cleavage of olefin followed by reductive amination with an appropriately protected amine (e.g., benzylamine or P-OMe benzylamine) provides M4. The compound M2 can be converted to a substrate M6, which can be used to switch to an advanced intermediate M7 using asymmetric synthesis protocol. See: Park et al., *Adv. Synth Catal.* 353(18): 3313-3318 (2011); Lee et al., *Arch. Pharm. Res.* 37(10): 1264-1270 (2013); Benabdallah et al., *Curr. Med. Chem.* 25(31): 3748-3767 (2018); Rios, *Chem. Soc. Rev. Rev.* 41(3): 1060-1074 (2012); Ding et al., *Chem. Soc. Rev.* 47 (15): 5946-5996 (2018). The compound M7 can be smoothly converted to M8 and then to the desired enantiopure spiro compound, M9. See e.g., Gonzalez-Vera et al., *J. Org. Chem.* 70(9): 3660-3666 (2005).

Example 3

General Procedures for the Synthesis of Compounds D1-D58

General Procedure A

Parts of the procedure were described in U.S. Pat. No. 7,776,869, which is incorporated by reference herein for such teachings. A mixture of amide (1 eq), corresponding amine (2 eq), TFA (10 eq.) in 2-propanol (5 mL) were heated at 100° C. in a sealed tube for 24 h. After completion, the reaction mixture was concentrated and purified using silica gel chromatography (0 to 100% Methanol in dichloromethane). The fractions containing required compound were collected and concentrated under reduced pressure. The obtained residue was dissolved and stirred in 5 mL of 30% TFA/DCM solution for 2 h at RT. The mixture was concentrated to dryness and treated with 7N $NH_3$/MeOH solution. The mixture was concentrated again and purified using a C18 column (0 to 100% $CH_3CN$ in $H_2O$ with 0.025% AcOH). The fractions containing desired compound were combined and lyophilized.

General Procedure A-M

Parts of the procedure were described in U.S. Pat. No. 7,776,869, which is incorporated by reference herein for such teachings. A mixture of amide (1 eq), corresponding amine (2 eq), TFA (10 eq.) in 2-propanol (5 mL) were heated at 118° C. in a sealed tube for 18 h. The reaction mixture was concentrated, and the residue was dissolved in 5 mL of 30% TFA/DCM solution for 2 h at RT. The mixture was concentrated to dryness and treated with 7 N $NH_3$/MeOH solution.

The mixture was concentrated again and purified using a C18 column (0 to 100% $CH_3CN$ in $H_2O$ with 0.025% AcOH). The fractions containing desired compound were combined and lyophilized.

General Procedure B

Parts of the procedure were described in Chinese Patent Application No. CN 106749259, published as CN 201510800951, both of which are incorporated by reference herein for such teachings. To a solution of corresponding amine (3 eq) in anhydrous toluene was added 1 M LiHMDS in toluene (3.6 eq) dropwise at RT. After stirring for 30 minutes, a solution of amide (1 eq) in anhydrous toluene was added dropwise and stirring was continued for 3 h. The reaction mixture is then quenched with AcOH, concentrated and purified using silica gel chromatography (0 to 100% methanol in dichloromethane). The fractions containing required compound were collected and concentrated under reduced pressure. The obtained residue was dissolved and stirred in 5 mL of 30% TFA/DCM solution for 2 h at RT. The mixture was concentrated to dryness and treated with 7 $NNH_3$/MeOH solution. The mixture was concentrated again and purified using a C18 column (0 to 100% $CH_3CN$ in $H_2O$ with 0.025% AcOH). The fractions containing desired compound were combined and lyophilized.

General Procedure C

Parts of the procedure were described in International Pat. App. Publication No. WO 2018005865, which is incorporated by reference herein for such teachings. To a stirred solution of corresponding amine (3 eq) in anhydrous THF was added LiHMDS (1.2 eq) dropwise at 0° C. After stirring for 15 minutes at RT, corresponding amide (1 eq) in anhydrous THF was added dropwise at RT and stirred for 3 h. After completion, the reaction mixture was quenched with AcOH, concentrated and purified using silica gel chromatography (0 to 100% methanol in dichloromethane). The fractions containing required compound were collected and concentrated under reduced pressure. The obtained residue was dissolved and stirred in 5 mL of 30% TFA/DCM solution for 2 h at RT. The mixture was concentrated to dryness and treated with 7 N $NH_3$/MeOH solution. The mixture was concentrated again and purified using a C18 column (0 to 100% $CH_3CN$ in $H_2O$ with 0.025% AcOH). The fractions containing desired compound were combined and lyophilized.

General Procedure D

A mixture of amide (1 eq), corresponding amine (1 eq) in toluene was heated at reflux for 24 h. After completion, the reaction mixture was concentrated and purified using silica gel chromatography (0 to 100% Methanol in dichloromethane). The fractions containing required compound were collected and concentrated under reduced pressure. The obtained residue was dissolved and stirred in 5 mL of 30% TFA/DCM solution for 2 h at RT. The mixture was concentrated to dryness and treated with 7 $NNH_3$/MeOH solution. The mixture was concentrated again and purified using a C18 column (0 to 100% $CH_3CN$ in $H_2O$ with 0.025% AcOH). The fractions containing desired compound were combined and lyophilized.

General Procedure E

Parts of the procedure were described in International Pat. App. Publication No. WO 2010065721, which is incorporated by reference herein for such teachings. A mixture of amide (1 eq), corresponding amine (1.5 eq), CSA (3 eq) in N, N-Dimethyl acetamide were heated in an RB flask at 140° C. for 1.5 h. After completion, the reaction mixture was concentrated and purified using silica gel chromatography (0 to 100% Methanol in dichloromethane). The fractions containing required compound were collected and concentrated under reduced pressure. The obtained residue was dissolved and stirred in 5 mL of 30% TFA/DCM solution for 2 h at RT. The mixture was concentrated to dryness and treated with 7 N $NH_3$/MeOH solution. The mixture was concentrated again and purified using a C18 column (0 to 100% $CH_3CN$ in $H_2O$ with 0.025% AcOH). The fractions containing desired compound were combined and lyophilized.

General Procedure F

Parts of the procedure were described in International Pat. App. Publication No. WO 2010020675, which is incorporated by reference herein for such teachings. A mixture of corresponding amine (1.5 eq), amide (1 eq), BINAP (20 mole percent) and sodium-tert-butoxide (2 eq) in dioxane was degassed and $Pd_2(dba)_3$ (10 mole percent) was added under argon. The reaction mixture was heated to 100° C. for 2 h in an oil bath. After completion, the reaction mixture was quenched with MeOH, concentrated and purified using silica gel chromatography (0 to 100% methanol in dichloromethane). The fractions containing required compound were collected and concentrated under reduced pressure. The obtained residue was dissolved and stirred in 5 mL of 30% TFA/DCM solution for 2 h at RT. The mixture was concentrated to dryness and treated with 7 N $NH_3$/MeOH solution. The mixture was concentrated again and purified using a C18 column (0 to 100% $CH_3CN$ in $H_2O$ with 0.025% AcOH). The fractions containing desired compound were combined and lyophilized.

General Procedure G

Parts of the procedure were described in International Pat. App. Publication No. WO 2016105564, which is incorporated by reference herein for such teachings. Amide (1 eq.), corresponding amine (1.5 eq), N,N-diisopropylethylamine (8 eq.), Xantphos (30 mole percent) and palladium (II) acetate (20 mole percent) were combined under argon in NMP. The reaction mixture was heated at 150° C. in a sealed vessel for 4 h. The reaction mixture was then cooled to RT, absorbed on silica gel and purified using silica gel chromatography (0 to 100% methanol/dichloromethane). The fractions containing required compound were collected and concentrated under reduced pressure. The obtained residue was dissolved and stirred in 5 mL of 30% TFA/DCM solution for 2 h at RT. The mixture was concentrated to dryness and treated with 7 N $NH_3$/MeOH solution. The mixture was concentrated again and purified using a C18 column (0 to 100% $CH_3CN$ in $H_2O$ with 0.025% AcOH). The fractions containing desired compound were combined and lyophilized.

Example 1: Compound D3

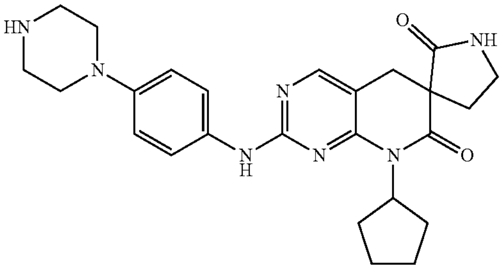 [SMILES: O=C1NCCC12Cc1cnc(Nc3ccc(N4CCNCC4)cc3)nc1N(C1CCCC1)C2=O]

Step 1: Synthesis of 8-cyclopentyl-2-(methylthio)-7-oxo-7,8-dihydropyrido[2,3-d]pyrimidine-6-carboxylic Acid (1-C)

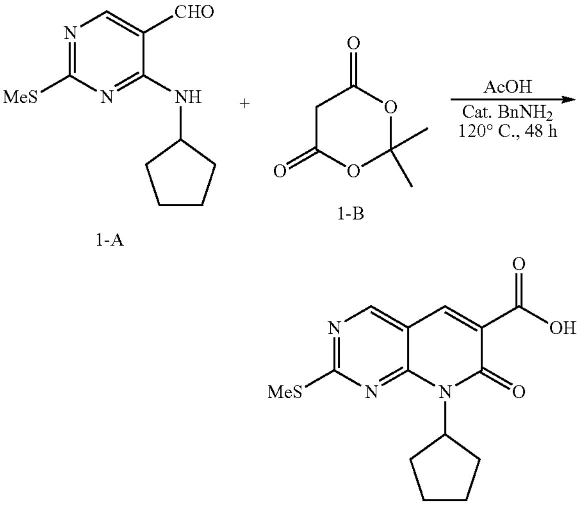

1-A 1-B

1-C (Ref: WO 2008032162): To a solution of compound 1-A (25 g, 105 mmol) and 1-B (18.2 g, 127 mmol) in acetic added (150 mL) was added benzyl amine (1.1 g, 10.5 mmol) and the resulting mixture was refluxed for 48 h. After completion, the reaction mixture was cooled to room temperature and diluted with hexane (300 mL). The solid was filtered, washed with water and dried to afford 1-C (27.2 g, 85% yield). MS(ESI) m/z 306.1 $[M+H]^+$. $^1H$ NMR (600 MHz, Chloroform-d) δ 13.85 (s, 1H), 8.86 (s, 1H), 8.81 (s, 1H), 6.07 (p, J=8.8 Hz, 1H), 2.67 (s, 3H), 2.37-2.28 (m, 2H), 2.18-2.07 (m, 2H), 2.01-1.92 (m, 2H), 1.80-1.70 (m, 2H).

Step 2: Synthesis of 2-(phenylselanyl)ethanamine (1-E)

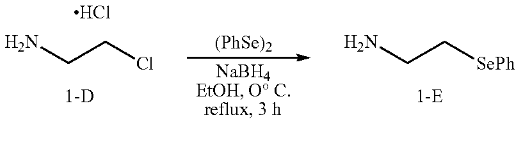

1-D 1-E (Ref: Kyei et al., *Tetrahedron Lett.* 45(48): 8931-8934 (2004)): To a stirred solution of diphenyl selenide (34 g, 312 mmol) in ethanol (300 mL) at 0° C. was added $NaBH_4$ (12.2 g, 323 mmol) portion wise. After stirring for 15 minutes at the same temperature, compound 1-D (25 g, 216 mmol) in ethanol (200 mL) was added dropwise at 0° C. The reaction mixture is stirred at 0° C. for 30 min and at reflux temperature for 2 h. After completion, the reaction mixture was quenched with brine and the solvents were removed under reduced pressure. The crude is partitioned between ethyl acetate (500 mL) and saturated $NaHCO_3$ (300 mL). After the layers were separated, the organic layer was washed with brine, dried over sodium sulfate, concentrated and purified by column chromatography (0-10% MeOH in DCM) to get compound 1-E (41 g, 93% yield) as light-yellow oil.

MS(ESI) m/z 202.1 $[M+H]^+$. $^1H$ NMR (600 MHz, Chloroform-d) δ 7.55-7.50 (m, 2H), 7.26 (m, 3H), 3.01 (m, 6H).

Step 3: Synthesis of tert-butyl 8-cyclopentyl-2-(methylthio)-2',7-dioxo-7,8-dihydro-5H-spiro[pyrido[2,3-d]pyrimidine-6,3'-pyrrolidine]-1'-carboxylate (1-H)

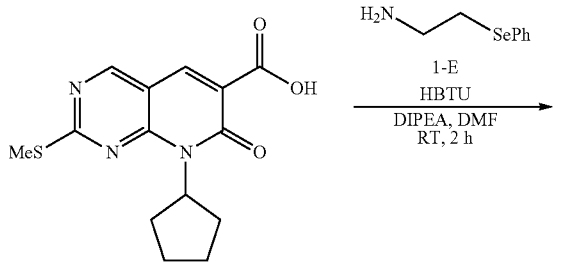

1-C

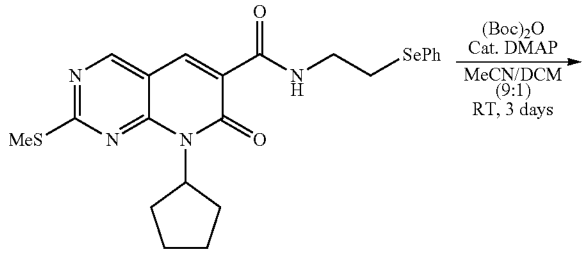

1-F

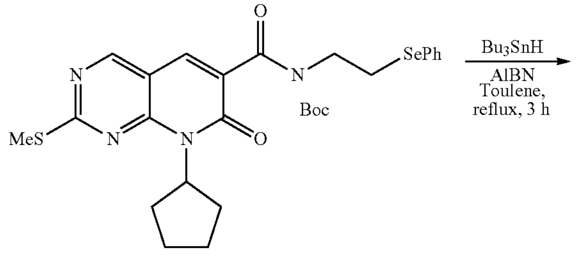

1-G

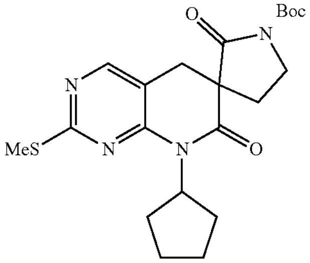

1-H

Synthesis of 1F: (WO 2010020675): To a solution of Compound 1-C (4.5 g, 14.7 mmol), HBTU (6.1 g, 16.2 mmol) and diisopropylethylamine (7.7 mL, 44.1 mmol) in DMF (20 mL) was added compound 1-E (3.5 g, 17.7 mmol) and the reaction mixture was stirred for 2 h at room temperature. After completion, the reaction mixture was diluted with ethyl acetate (200 mL) and washed sequentially with saturated aqueous sodium bicarbonate (150 mL), water (100 mL), and brine (4×100 mL). The organic phase is dried ($Na_2SO_4$) and concentrated to get the crude compound which was further purified by $SiO_2$ column chromatography (0 to 20% ethyl acetate in hexanes) to give compound 1-F (6.5 g, 90% yield) as a light-gray solid. MS(ESI) m/z 489.1 $[M+H]^+$. $^1H$ NMR (600 MHz, Chloroform-d) δ 9.72 (s, 1H), 8.75 (d, J=19.5 Hz, 2H), 7.63-7.52 (m, 2H), 7.31-7.18 (m, 3H), 6.02 (p, J=8.9 Hz, 1H), 3.77-3.70 (m, 2H), 3.19-3.11 (m, 2H), 2.64 (s, 3H), 2.38-2.29 (m, 2H), 2.16-2.06 (m, J=5.1 Hz, 2H), 1.96-1.87 (m, 2H), 1.78-1.68 (m, 2H).

Synthesis of 1-G: (WO 2012069680): To a stirred solution of compound 1-F (6.5 g, 13.3 mmol) in MeCN/DCM (9:1) was added Boc anhydride (29 g, 133 mmol) and DMAP (1.6 g, 13.3 mmol) and the reaction mixture was stirred for 3 days. After completion of the reaction, the solvents were removed under reduced pressure and purified by column chromatography (0 to 20% ethyl acetate in hexanes) to give compound 1-G (6.5 g, 83% yield) as a gummy liquid. MS(ESI) m/z 589.1 $[M+H]^+$. $^1H$ NMR (600 MHz, Chloroform-d) δ 8.60 (s, 1H), 7.67 (s, 1H), 7.59-7.55 (m, 2H), 7.30-7.23 (m, 3H), 5.93 (p, J=8.9 Hz, 1H), 4.19-4.02 (m, 2H), 3.22-3.10 (m, 2H), 2.62 (s, 3H), 2.36-2.22 (m, 2H), 2.11-1.99 (m, 2H), 1.92-1.78 (m, 2H), 1.72-1.61 (m, 2H), 1.34 (s, 9H). Note: Repeated this sequence to produce the required amount of 1-F.

Synthesis of 1-H: (Kyei et al., *Tetrahedron Lett.* 45(48): 8931-8934 (2004)). The selenide compound 1-G (30 g, 51 mmol) was dissolved in anhydrous toluene (600 mL), purged with argon and heated to 110° C. while stirring. A solution of tributyl tin hydride (30 mL, 111 mmol) and AIBN (4.2 g, 25.5 mmol) was dissolved in toluene (150 mL) and added drop-wise to the above selenide over a period of 2 h. The reaction mixture was stirred at that temperature for additional 1 h and then cooled to room temperature, diluted with EtOAc (750 mL), washed with water (2×100 mL), brine (1×100 mL), dried ($Na_2SO_4$) and then concentrated to give the crude product, which was subjected for $SiO_2$ column chromatography (0 to 100% EtOAc in n-hexanes) to afford 1-H (12.10 g, 55%) as an off-white solid. MS(ESI) m/z 433.2 $[M+H]^+$. $^1H$ NMR (600 MHz, Chloroform-d) δ 8.19 (s, 1H), 5.46-5.33 (m, 1H), 3.85-3.72 (m, 2H), 3.37 (d, J=16.0 Hz, 1H), 2.67 (d, J=16.0 Hz, 1H), 2.55 (s, 3H), 2.35-2.28 (m, 1H), 2.22-2.14 (m, 1H), 2.09-2.01 (m, 1H), 2.01-1.93 (m, 2H), 1.91-1.80 (m, 3H), 1.67-1.57 (m, 2H), 1.54 (s, 9H).

Step 4: Synthesis of tert-butyl 8-cyclopentyl-2-(methylsulfinyl)-2',7-dioxo-7,8-dihydro-5H-spiro[pyrido[2,3-d]pyrimidine-6,3'-pyrrolidine]-1'-carboxylate (1-1)

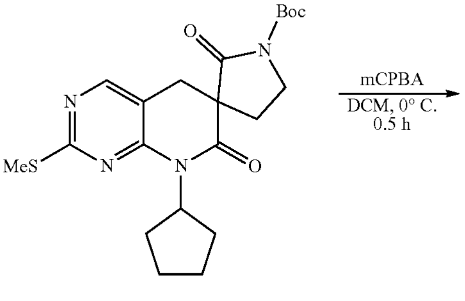

1-H

-continued

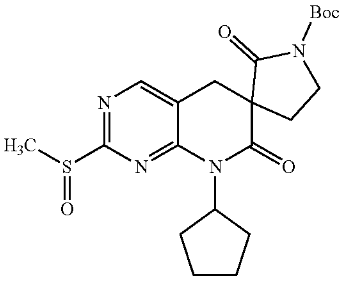

1-I

To a solution of 1-H (2.2 g, 5.1 mmol) in DCM (200 mL) at 0° C. was added mCPBA (1.26 g of ~77%, 5.6 mmol, 1.1 eq.) in one portion. The resulting mixture was stirred at the same temperature for 30 min. The reaction mixture was washed with saturated $NaHCO_3$ solution (3×30 mL), water (1×30 mL), and brine (1×30 mL) respectively. The organic layer is then dried over sodium sulfate, filtered, and concentrated under reduced pressure to give 1-1 (2 g, quantitative). MS(ESI) m/z 449.2 $(M+H)^+$. $^1$H NMR (600 MHz, Chloroform-d) δ 8.50 (d, J=13.1 Hz, 1H), 5.45 (dp, J=17.6, 9.0 Hz, 1H), 3.94-3.75 (m, 2H), 3.51-3.35 (m, 1H), 2.94 (s, 3H), 2.92-2.87 (m, 1H), 2.56 (ddd, J=13.0, 7.6, 3.7 Hz, 0.5H), 2.49 (ddd, J=13.0, 7.4, 3.7 Hz, 0.5H), 2.15-1.95 (m, 4H), 1.95-1.83 (m, 3H), 1.69 (s, 2H), 1.53 (s, 9H).

Step 5: Synthesis of 8-cyclopentyl-2-((4-(piperazin-1-yl)phenyl)amino)-5,8-dihydro-7H-spiro[pyrido[2,3-d]pyrimidine-6,3'-pyrrolidine]-2',7-dione (Compound 03)

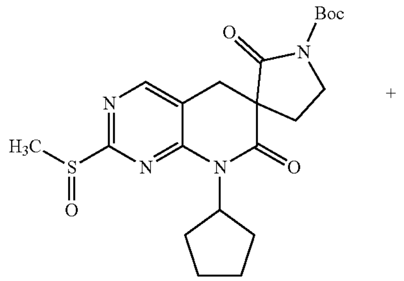

+

1-I

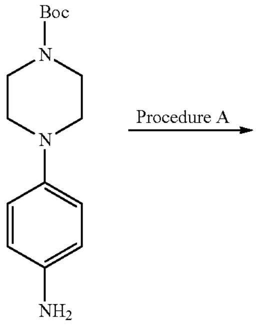

2

-continued

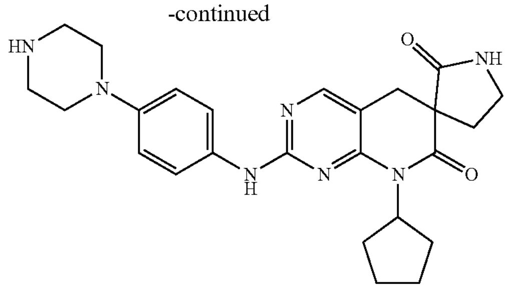

Compound D3

Compound D3 was synthesized following the general procedure A, 2 mg (4% yield). MS(ESI) m/z 462.3 $(M+H)^+$. $^1$H NMR (600 MHz, DMSO-$d_6$) δ 9.18 (s, 1H), 8.62 (s, 2H), 8.03 (s, 1H), 7.90 (s, 1H), 7.50 (d, J=8.9 Hz, 2H), 6.87 (d, J=9.0 Hz, 2H), 5.27 (p, J=8.7 Hz, 1H), 3.22-3.11 (m, 10H), 2.96 (d, J=15.8 Hz, 1H), 2.67 (d, J=15.8 Hz, 1H), 2.32 (ddd, J=12.8, 7.8, 5.0 Hz, 1H), 2.02-1.92 (m, 2H), 1.88-1.75 (m, 3H), 1.75-1.66 (m, 2H), 1.51-1.41 (m, 2H).

Example 2: Compound D4

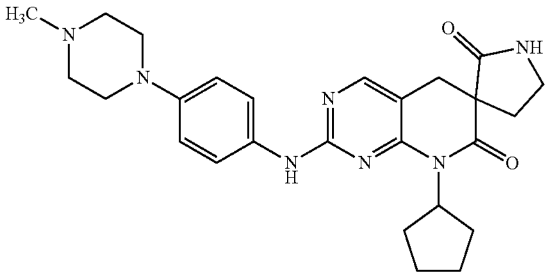 [SMILES: CN1CCN(c2ccc(Nc3ncc4c(n3)N(C3CCCC3)C(=O)C3(CCNC3=O)C4)cc2)CC1]

Synthesis of 8-cyclopentyl-2-((4-(4-methylpiperazin-1-yl)phenyl)amino)-5,8-dihydro-7H-spiro[pyrido[2,3-d]pyrimidine-6,3'-pyrrolidine]-2',7-dione (Compound D4)

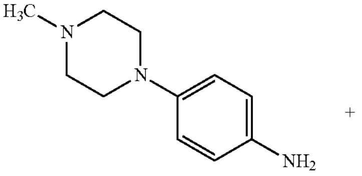

+

3

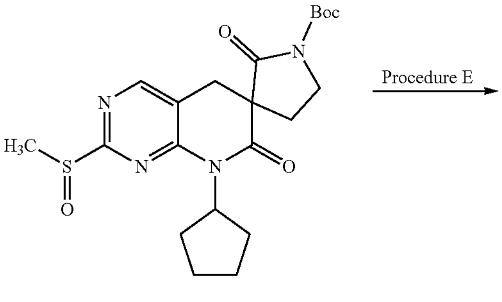

1-I

-continued

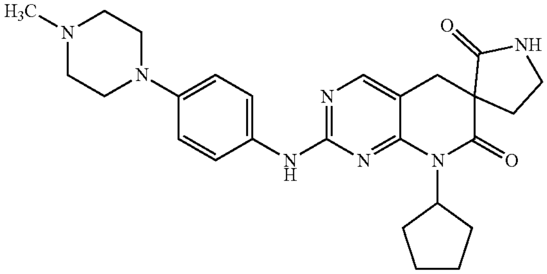

Compound D4

Compound D4 was synthesized following the general procedure E, 20 mg (38% yield). MS(ESI) m/z 476.3 $(M+H)^+$. $^1H$ NMR (600 MHz, Chloroform-d) δ 8.05 (s, 1H), 7.42 (d, J=8.9 Hz, 2H), 6.93 (d, J=8.9 Hz, 2H), 6.87 (s, 1H), 5.89 (s, 1H), 5.35 (p, J=8.8 Hz, 1H), 3.48 (q, J=7.8 Hz, 1H), 3.42-3.34 (m, 1H), 3.32 (d, J=15.6 Hz, 1H), 3.24-3.14 (m, 4H), 2.62 (s, 4H), 2.59 (d, J=15.7 Hz, 1H), 2.43-2.39 (m, 1H), 2.38 (s, 3H), 2.27-2.18 (m, 1H), 2.09-1.97 (m, 2H), 1.94-1.88 (m, 2H), 1.87-1.78 (m, 2H), 1.62-1.53 (m, 2H).

Example 3: Compound D5

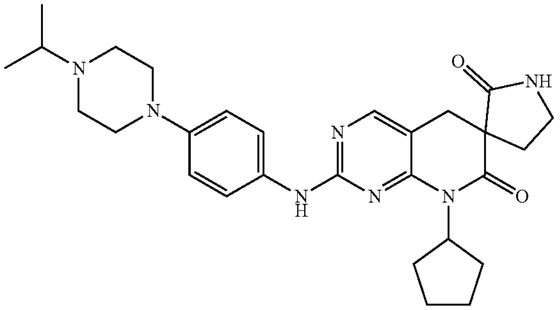

Synthesis of 8-cyclopentyl-2-((4-(4-methylpiperazin-1-yl)phenyl)amino)-5,8-dihydro-7H-spiro [pyrido[2,3-d]pyrimidine-6,3'-pyrrolidine]-2',7-dione (Compound 05)

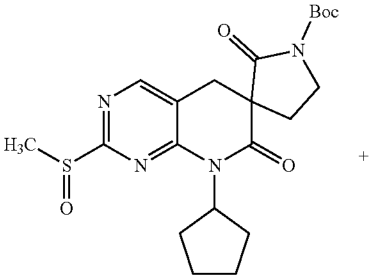

1-I

+

-continued

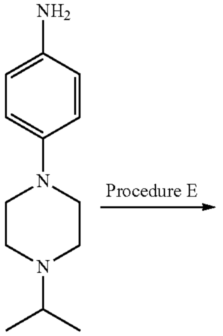

12

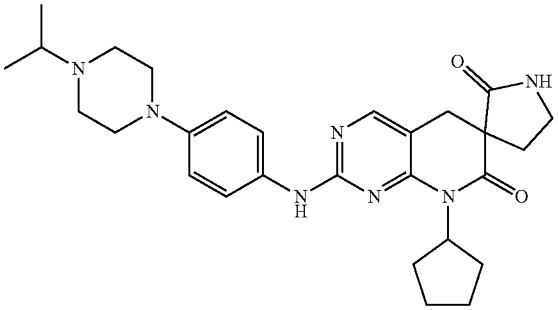 [SMILES: CC(C)N1CCN(c2ccc(Nc3ncc4c(n3)N(C3CCCC3)C(=O)C3(CCNC3=O)C4)cc2)CC1]

Compound D5

Compound D5 was synthesized following the general procedure E, 11 mg (20% yield). MS(ESI) m/z 504.3 $(M+H)^+$. $^1H$ NMR (600 MHz, Chloroform-d) δ 8.04 (s, 1H), 7.41 (d, J=8.9 Hz, 2H), 6.93 (d, J=8.9 Hz, 3H), 5.86 (s, 1H), 5.35 (p, J=8.8 Hz, 1H), 3.48 (q, J=7.8 Hz, 1H), 3.43-3.35 (m, 1H), 3.32 (d, J=15.6 Hz, 1H), 3.22-3.14 (m, 4H), 2.79-2.68 (m, 5H), 2.58 (d, J=15.6 Hz, 1H), 2.42-2.36 (m, 1H), 2.27-2.17 (m, 1H), 2.08-1.97 (m, 2H), 1.95-1.87 (m, 2H), 1.88-1.80 (m, 2H), 1.63-1.52 (m, 2H), 1.11 (d, J=6.5 Hz, 6H).

Example 4: Compound D6

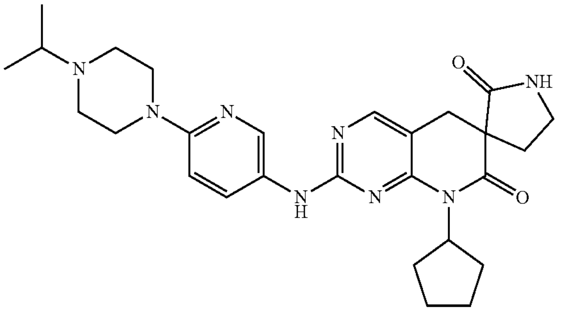

Synthesis of 8-cyclopentyl-2-((6-(4-isopropylpiperazin-1-yl)pyridin-3-yl)amino)-5,8-dihydro-7H-spiro[pyrido[2,3-d]pyrimidine-6,3'-pyrrolidine]-2',7-dione (Compound D6)

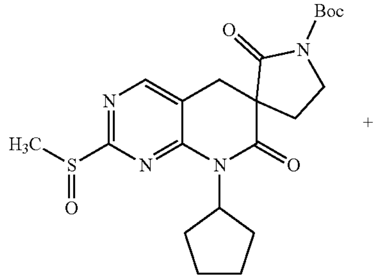

1-I

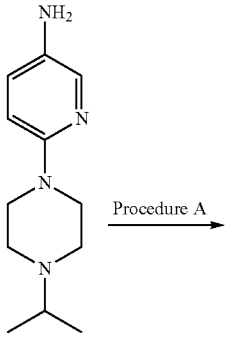

13

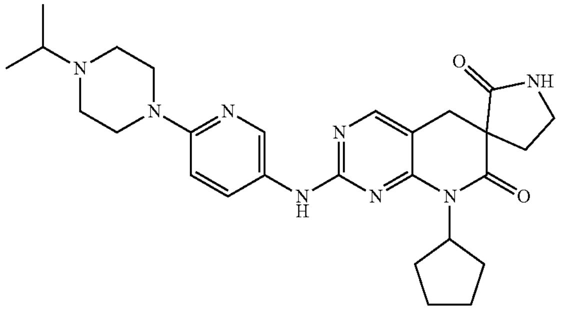

Compound D6

Compound D6 was synthesized following the general procedure A, 9 mg (16% yield). MS(ESI) m/z 505.3 $(M+H)^+$. $^1H$ NMR (600 MHz, Chloroform-d) δ 8.25 (d, J=2.4 Hz, 1H), 8.04 (s, 1H), 7.85-7.77 (m, 1H), 6.75 (s, 1H), 6.68 (d, J=9.0 Hz, 1H), 5.88 (s, 1H), 5.32 (p, J=8.7 Hz, 1H), 3.62 (s, 4H), 3.49 (q, J=7.7 Hz, 1H), 3.42-3.35 (m, 1H), 3.30 (d, J=15.6 Hz, 1H), 2.82 (s, 4H), 2.60 (d, J=15.7 Hz, 1H), 2.42 (ddd, J=13.1, 7.5, 3.1 Hz, 1H), 2.23-2.13 (m, 1H), 2.06-1.97 (m, 2H), 1.88 (s, 2H), 1.84-1.77 (m, 2H), 1.63 (s, 3H), 1.18 (d, J=4.4 Hz, 6H).

Example 5: Compound D7

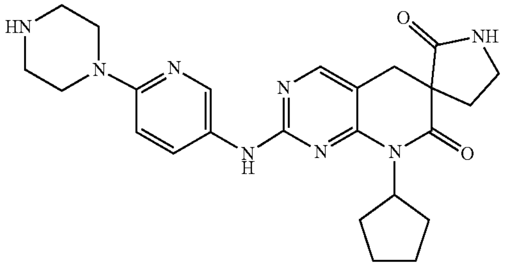 [SMILES: O=C1NCCC12Cc1cnc(Nc3ccc(N4CCNCC4)nc3)nc1N(C1CCCC1)C2=O]

Synthesis of 8-cyclopentyl-2-((6-(piperazin-1-yl)pyridin-3-yl)amino)-5,8-dihydro-7H-spiro[pyrido[2,3-d]pyrimidine-6,3'-pyrrolidine]-2',7-dione (Compound D7)

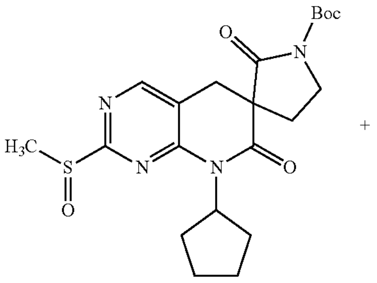

1-I

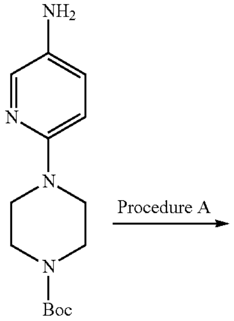

1

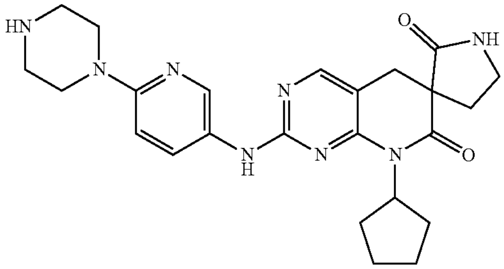

Compound D7

Compound D7 was synthesized following the general procedure A, 2 mg (6% yield). MS(ESI) m/z 463.3 $(M+H)^+$. $^1H$ NMR (600 MHz, Chloroform-d) δ 8.04 (s, 1H), 7.64 (dd, J=9.5, 2.7 Hz, 1H), 7.31 (s, 1H), 6.76 (d, J=9.5 Hz, 1H), 5.93 (s, 1H), 5.34 (p, J=8.9 Hz, 1H), 3.99-3.90 (m, 4H), 3.49 (q, J=7.7 Hz, 1H), 3.43-3.35 (m, 1H), 3.28 (d, J=15.6 Hz, 1H), 3.11-3.04 (m, 4H), 2.59 (d, J=15.6 Hz, 1H), 2.42 (ddd, J=13.0, 7.6, 3.2 Hz, 1H), 2.29-2.20 (m, 1H), 2.02-1.98 (m, 1H), 1.98-1.93 (m, 2H), 1.91-1.81 (m, 3H), 1.67-1.60 (m, 2H).

Example 6: Compound D8

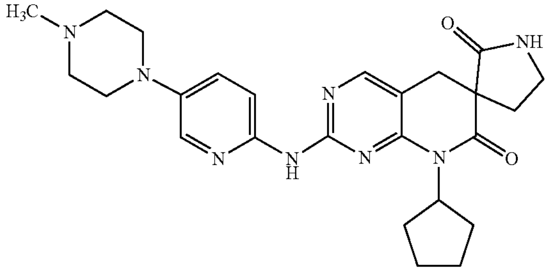 [SMILES: CN1CCN(c2ccc(Nc3ncc4c(n3)N(C3CCCC3)C(=O)C3(CCNC3=O)C4)nc2)CC1]

Synthesis of 8-cyclopentyl-2-((5-(4-methylpiperazin-1-yl)pyridin-2-yl)amino)-5,8-dihydro-7H-spiro[pyrido[2,3-d]pyrimidine-6,3'-pyrrolidine]-2',7-dione (Compound D8)

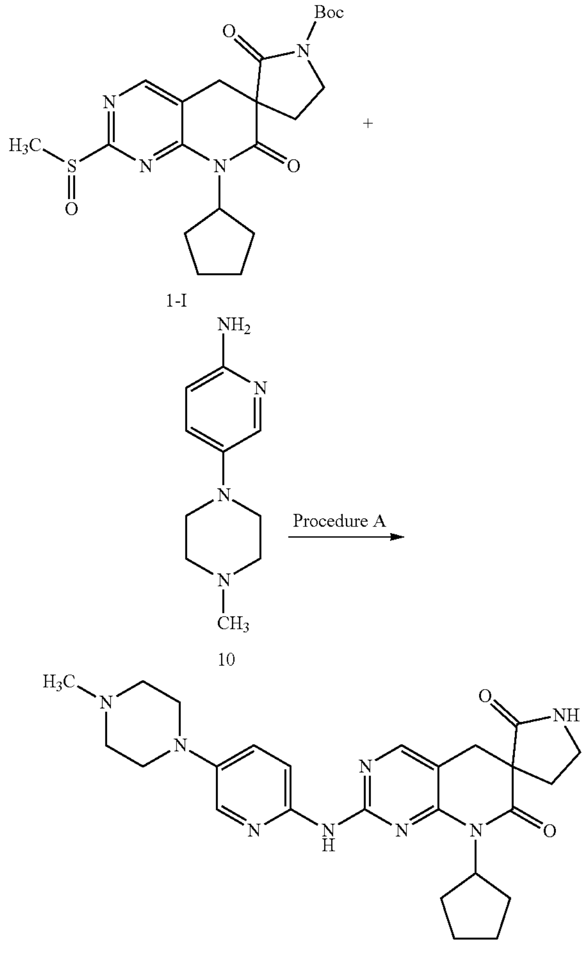

1-I

10

Compound D8

Compound 08 was synthesized following the general procedure A, 9 mg (17% yield). MS(ESI) m/z 477.3 $(M+H)^+$.

Example 7: Compound D9

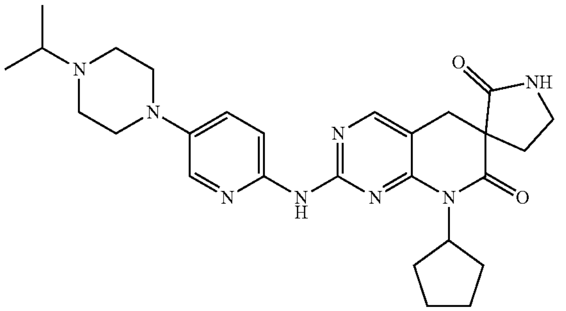 [SMILES: CC(C)N1CCN(c2ccc(Nc3ncc4c(n3)N(C3CCCC3)C(=O)C3(CCNC3=O)C4)nc2)CC1]

Synthesis of 8-cyclopentyl-2-((5-(4-isopropylpiperazin-1-yl)pyridin-2-yl)amino)-5,8-dihydro-7H-spiro[pyrido[2,3-d]pyrimidine-6,3'-pyrrolidine]-2',7-dione (Compound D9)

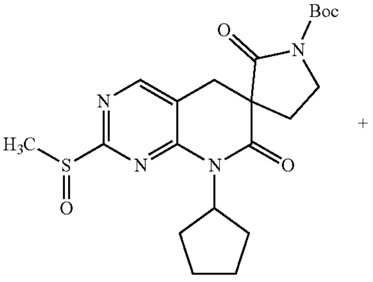

1-I

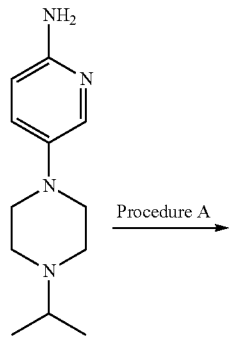

11

-continued

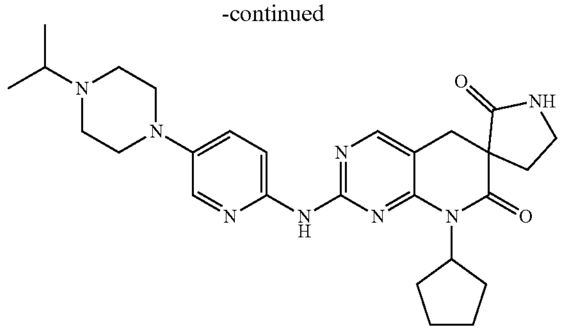

Compound D9

Compound D9 was synthesized following the general procedure A, 14 mg (25% yield). MS(ESI) m/z 505.3 $(M+H)^+$. $^1H$ NMR (600 MHz, Chloroform-d) δ 8.31 (d, J=2.5 Hz, 1H), 8.03 (s, 1H), 7.86 (dd, J=9.0, 2.6 Hz, 1H), 7.07 (s, 1H), 6.69 (d, J=9.0 Hz, 1H), 6.15 (s, 1H), 5.32 (p, J=8.7 Hz, 1H), 3.80 (s, 2H), 3.53-3.45 (m, 2H), 3.42-3.36 (m, 1H), 3.29 (d, J=15.7 Hz, 1H), 3.16 (s, 3H), 2.63 (d, J=15.7 Hz, 1H), 2.44 (ddd, J=13.0, 7.6, 3.3 Hz, 1H), 2.22-2.14 (m, 1H), 2.06-1.97 (m, 3H), 1.94-1.86 (m, 3H), 1.86-1.76 (m, 3H), 1.62-1.52 (m, 2H), 1.35 (d, J=6.6 Hz, 6H).

Example 8: Compound D10

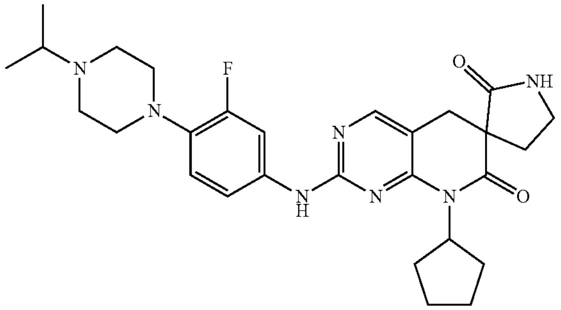

Synthesis of 8-cyclopentyl-2-((3-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (Compound D10)

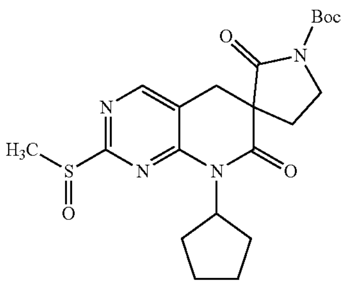

1-I

+

-continued

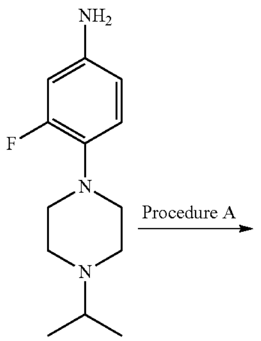

15

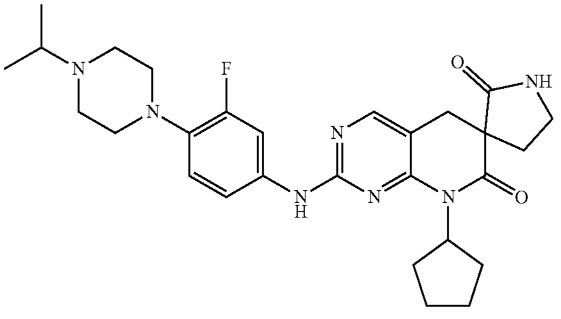 [SMILES: CC(C)N1CCN(c2ccc(Nc3ncc4c(n3)N(C3CCCC3)C(=O)C3(CCNC3=O)C4)cc2F)CC1]

Compound D10

Compound D10 was synthesized following the general procedure A, 5 mg (9% yield). MS(ESI) m/z 522.3 $(M+H)^+$. $^1H$ NMR (600 MHz, Chloroform-d) δ 8.08 (s, 1H), 7.63 (d, J=14.2 Hz, 1H), 7.08-7.04 (m, 1H), 7.01 (s, 1H), 6.93 (t, J=9.0 Hz, 1H), 5.73 (s, 1H), 5.35 (p, J=8.8 Hz, 1H), 3.50 (q, J=7.8 Hz, 1H), 3.39 (td, J=8.7, 2.5 Hz, 1H), 3.32 (d, J=15.7 Hz, 1H), 3.26 (s, 4H), 3.00 (s, 4H), 2.63 (d, J=15.7 Hz, 1H), 2.43 (ddd, J=13.0, 7.5, 2.9 Hz, 1H), 2.27-2.18 (m, 1H), 2.08-1.98 (m, 2H), 1.98-1.80 (m, 5H), 1.76 (s, 2H), 1.26 (s, 6H).

Example 9: Compound D11

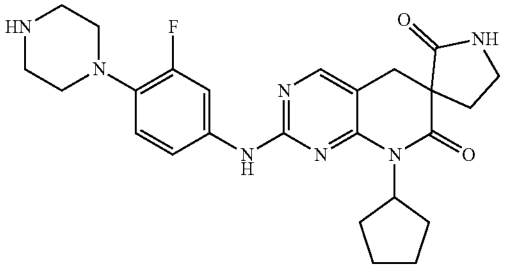 [SMILES: O=C1NCCC12Cc1cnc(Nc3ccc(N4CCNCC4)c(F)c3)nc1N(C1CCCC1)C2=O]

Synthesis of 8-cyclopentyl-2-((3-fluoro-4-(piperazin-1-yl)phenyl)amino)-5,8-dihydro-7H-spiro[pyrido[2,3-d]pyrimidine-6,3'-pyrrolidine]-2',7-dione (Compound D11)

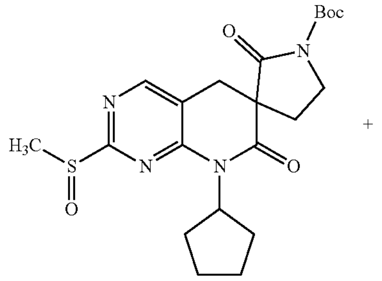

1-I

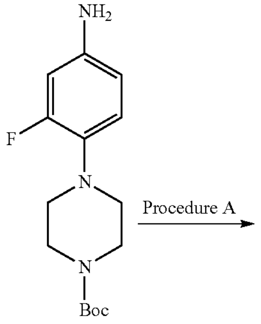

6

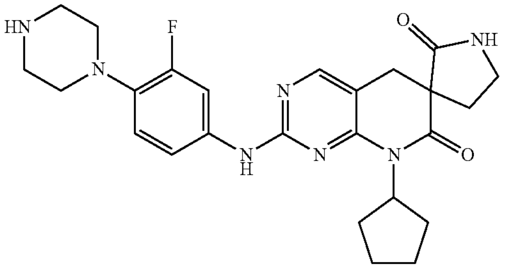

Compound D11

Compound D11 was synthesized following the general procedure A, 5 mg (10% yield). MS(ESI) m/z 480.3 $(M+H)^+$. $^1$H NMR (600 MHz, Chloroform-d) δ 8.07 (s, 1H), 7.60 (dd, J=14.7, 2.3 Hz, 1H), 7.47 (d, J=42.9 Hz, 1H), 6.93 (d, J=7.7 Hz, 1H), 6.84 (t, J=9.0 Hz, 1H), 6.58 (s, 1H), 5.35 (p, J=8.8 Hz, 1H), 3.52 (q, J=7.6 Hz, 1H), 3.45-3.37 (m, 1H), 3.24 (d, J=15.7 Hz, 1H), 3.15-3.06 (m, 4H), 3.07-2.94 (m, 4H), 2.72 (d, J=15.6 Hz, 1H), 2.60 (s, 1H), 2.19-2.12 (m, 1H), 2.12-2.07 (m, 1H), 2.04-1.97 (m, 1H), 1.97-1.91 (m, 2H), 1.91-1.81 (m, 2H), 1.65-1.55 (m, 2H).

Example 10: Compound D12

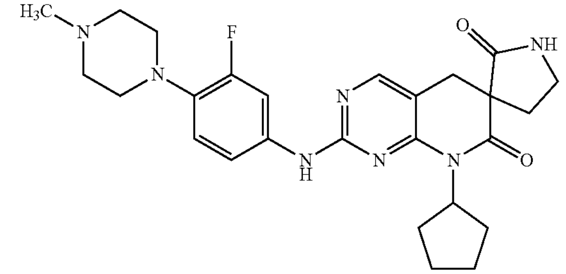

Synthesis of 8-cyclopentyl-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (Compound D12)

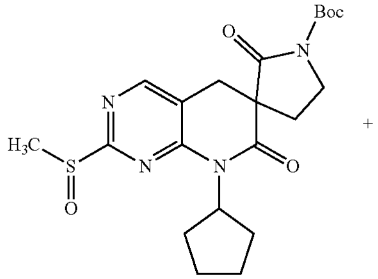

1-I

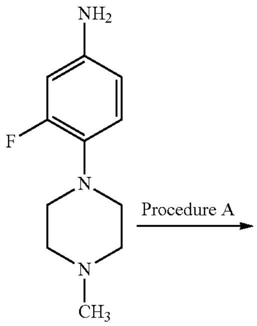

14

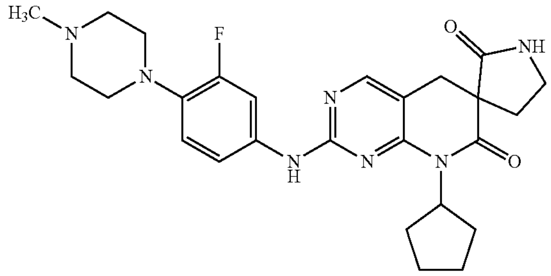 [SMILES: CN1CCN(c2ccc(Nc3ncc4c(n3)N(C3CCCC3)C(=O)C3(CCNC3=O)C4)cc2F)CC1]

Compound D12

Compound D12 was synthesized following the general procedure A, 5 mg (9% yield). MS(ESI) m/z 494.3 $(M+H)^+$. $^1$H NMR (600 MHz, Chloroform-d) δ 8.07 (s, 1H), 7.59 (dd, J=14.6, 2.4 Hz, 1H), 7.08-7.02 (m, 1H), 7.01 (s, 1H), 6.92 (t, J=9.1 Hz, 1H), 5.88 (s, 1H), 5.35 (p, J=8.8 Hz, 1H), 3.49

(d, J=9.2 Hz, 1H), 3.38 (td, J=8.7, 2.8 Hz, 1H), 3.32 (d, J=15.6 Hz, 1H), 3.10 (s, 4H), 2.69-2.57 (m, 5H), 2.42 (ddd, J=13.0, 7.5, 3.1 Hz, 1H), 2.37 (s, 3H), 2.27-2.18 (m, 1H), 2.09-1.98 (m, 2H), 1.98-1.91 (m, 2H), 1.91-1.80 (m, 2H), 1.65-1.55 (m, 2H).

Example 11: Compound D13

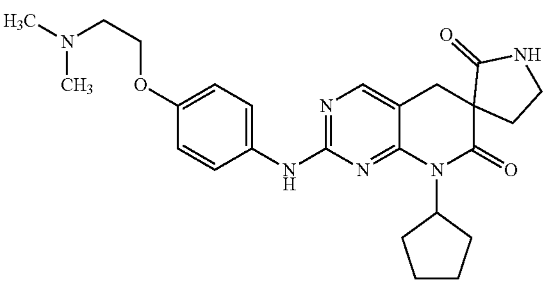

Synthesis of 8-cyclopentyl-2-((4-(2-(dimethylamino)ethoxy)phenyl)amino)-5,8-dihydro-7H-spiro[pyrido[2,3-d]pyrimidine-6,3'-pyrrolidine]-2',7-dione (Compound D13)

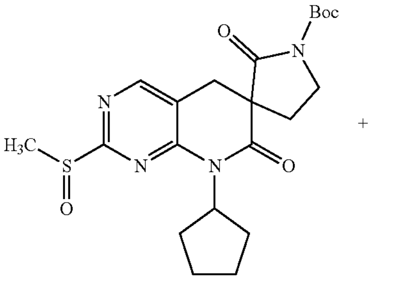

1-I

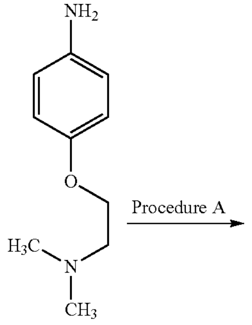

8

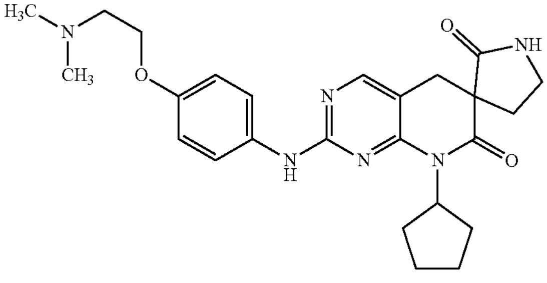 [SMILES: CN(C)CCOc1ccc(Nc2ncc3c(n2)N(C2CCCC2)C(=O)C2(CCNC2=O)C3)cc1]

Compound D13

Compound D13 was synthesized following the general procedure A, 3 mg (6% yield). MS(ESI) m/z 465.3 $(M+H)^+$. $^1H$ NMR (600 MHz, Chloroform-d) δ 8.05 (s, 1H), 7.48 (d, J=9.0 Hz, 2H), 7.01 (s, 1H), 6.88 (d, J=9.0 Hz, 2H), 5.82 (s, 1H), 5.35 (p, J=8.7 Hz, 1H), 4.41-4.30 (m, 2H), 3.49 (q, J=7.7 Hz, 1H), 3.46-3.34 (m, 3H), 3.31 (d, J=16.2 Hz, 1H), 2.87 (s, 6H), 2.62 (d, J=15.7 Hz, 1H), 2.43 (ddd, J=13.0, 7.5, 3.1 Hz, 1H), 2.26-2.16 (m, 1H), 2.08-1.97 (m, 3H), 1.92 (s, 2H), 1.89-1.79 (m, 3H).

Example 12: Compound D14

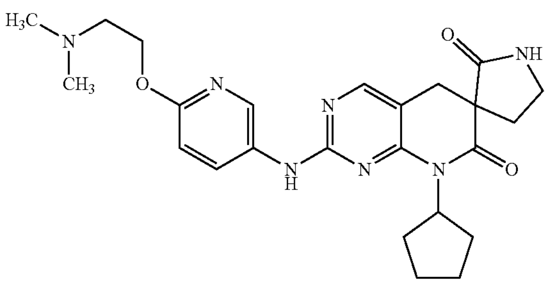 [SMILES: CN(C)CCOc1ccc(Nc2ncc3c(n2)N(C2CCCC2)C(=O)C2(CCNC2=O)C3)cn1]

Synthesis of 8-cyclopentyl-2-((6-(2-(dimethylamino)ethoxy)pyridin-3-yl)amino)-5,8-dihydro-7H-spiro[pyrido[2,3-d]pyrimidine-6,3'-pyrrolidine]-2',7-dione (Compound D14)

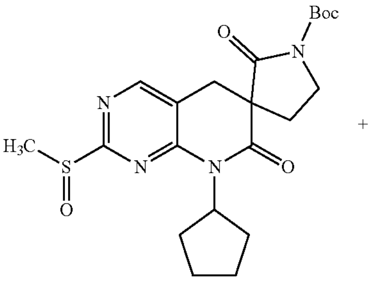

1-I

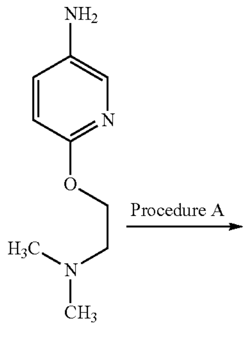

18

-continued

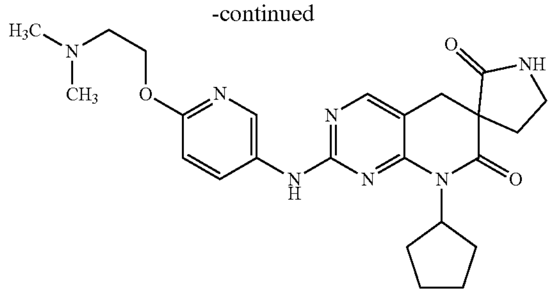

Compound D14

Compound D14 was synthesized following the general procedure A, 1 mg (2% yield). MS(ESI) m/z 466.3 $(M+H)^+$.

Example 13: Compound D15

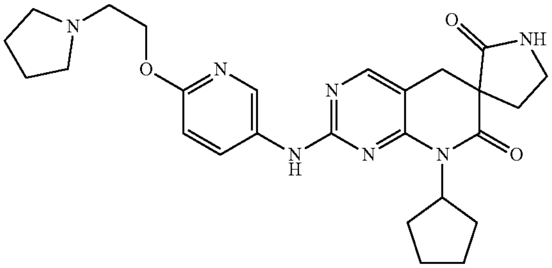 [SMILES: O=C1NCCC12Cc1cnc(Nc3ccc(OCCN4CCCC4)nc3)nc1N(C1CCCC1)C2=O]

Synthesis of 8-cyclopentyl-2-((6-(2-(pyrrolidin-1-yl) ethoxy)pyridin-3-yl)amino)-5,8-dihydro-7H-spiro [pyrido[2,3-d]pyrimidine-6,3'-pyrrolidine]-2',7-dione (Compound D15)

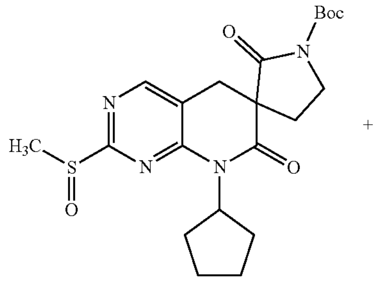

1-I

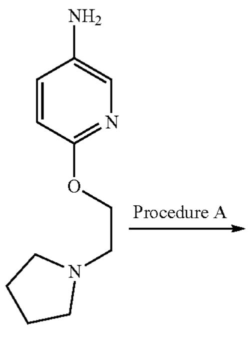

19

-continued

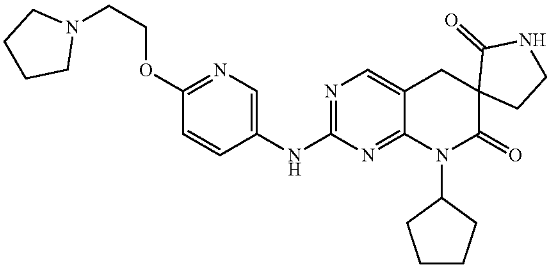

Compound D15

Compound D15 was synthesized following the general procedure A, 4 mg (6% yield). MS(ESI) m/z 492.3 $(M+H)^+$. $^1H$ NMR (600 MHz, Chloroform-d) δ 8.23 (d, J=2.7 Hz, 1H), 8.05 (s, 1H), 7.92 (dd, J=8.8, 2.7 Hz, 1H), 6.88 (s, 1H), 6.77 (d, J=8.8 Hz, 1H), 5.82 (s, 1H), 5.32 (p, J=8.8 Hz, 1H), 4.64 (s, 2H), 3.52-3.47 (m, 1H), 3.44 (s, 2H), 3.41-3.36 (m, 1H), 3.30 (d, J=15.7 Hz, 1H), 2.64 (d, J=15.7 Hz, 1H), 2.46 (ddd, J=13.0, 7.6, 3.2 Hz, 1H), 2.22-2.14 (m, 1H), 2.08 (s, 4H), 2.05-1.98 (m, 2H), 1.96-1.87 (m, 3H), 1.87-1.78 (m, 3H), 1.61-1.53 (m, 4H).

Example 14: Compound D16

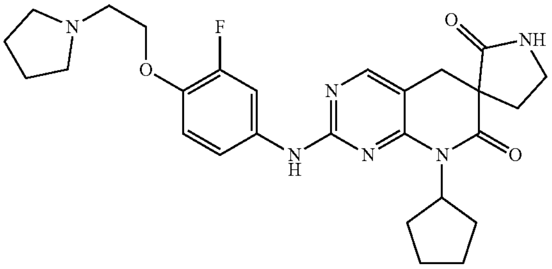

Synthesis of 8-cyclopentyl-2-((3-fluoro-4-(2-(pyrrolidin-1-yl)ethoxy)phenyl)amino)-5,8-dihydro-7H-spiro[pyrido[2,3-d]pyrimidine-6,3'-pyrrolidine]-2',7-dione (Compound D16)

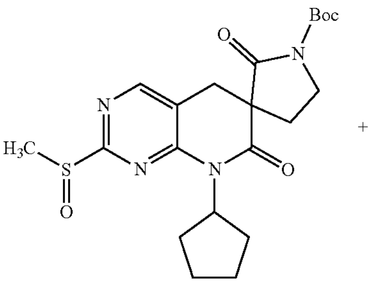

1-I

-continued

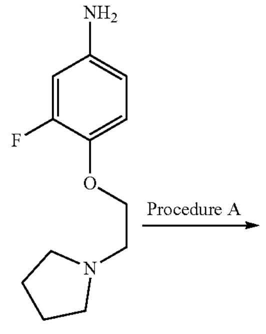

9

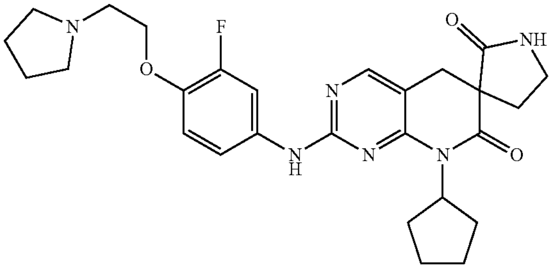 [SMILES: O=C1NCCC12Cc1cnc(Nc3ccc(OCCN4CCCC4)c(F)c3)nc1N(C1CCCC1)C2=O]

Compound D16

Compound D16 was synthesized following the general procedure A, 6 mg (11% yield). MS(ESI) m/z 509.3 $(M+H)^+$. $^1H$ NMR (600 MHz, Chloroform-d) δ 8.07 (s, 1H), 7.62 (dd, J=13.3, 2.4 Hz, 1H), 7.05 (s, 1H), 7.04 (s, 1H), 6.94 (t, J=9.0 Hz, 1H), 5.91 (s, 1H), 5.35 (p, J=8.7 Hz, 1H), 4.23 (t, J=5.6 Hz, 2H), 3.54-3.46 (m, 1H), 3.43-3.35 (m, 1H), 3.32 (d, J=15.7 Hz, 1H), 3.08 (s, 2H), 2.85 (s, 3H), 2.63 (d, J=15.7 Hz, 1H), 2.47-2.40 (m, 1H), 2.26-2.16 (m, 1H), 2.04-1.98 (m, 2H), 1.97-1.92 (m, 3H), 1.89 (s, 5H), 1.66-1.54 (m, 3H).

Example 15: Compound D17

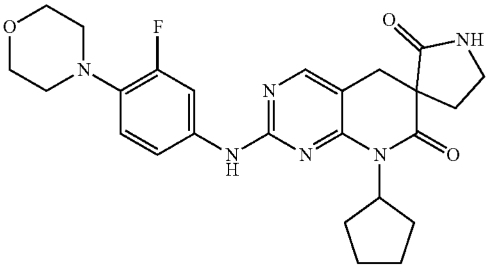

Synthesis of 8-cyclopentyl-2-((3-fluoro-4-morpholinophenyl)amino)-5,8-dihydro-7H-spiro[pyrido[2,3-d]pyrimidine-6,3'-pyrrolidine]-2',7-dione (Compound D17)

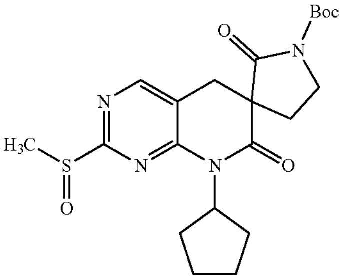

1-I

+

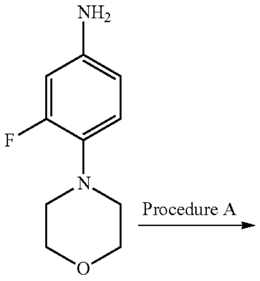

7

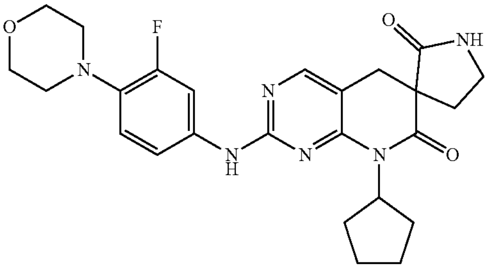 [SMILES: O=C1NCCC12Cc1cnc(Nc3ccc(N4CCOCC4)c(F)c3)nc1N(C1CCCC1)C2=O]

Compound D17

Compound D17 was synthesized following the general procedure A, 16 mg (30% yield). MS(ESI) m/z 481.3 $(M+H)^+$. $^1H$ NMR (600 MHz, Chloroform-d) δ 8.08 (s, 1H), 7.61 (dd, J=14.6, 2.4 Hz, 1H), 7.13 (s, 1H), 7.10-7.04 (m, 1H), 6.90 (t, J=9.1 Hz, 1H), 6.20 (s, 1H), 5.36 (p, J=8.8 Hz, 1H), 3.92-3.85 (m, 4H), 3.53-3.45 (m, 1H), 3.39 (td, J=8.7, 2.6 Hz, 1H), 3.32 (d, J=16.1 Hz, 1H), 3.12-3.01 (m, 4H), 2.63 (d, J=15.7 Hz, 1H), 2.43 (ddd, J=13.0, 7.6, 3.2 Hz, 1H), 2.22 (dq, J=15.6, 8.0 Hz, 1H), 2.09-1.97 (m, 3H), 1.97-1.91 (m, 2H), 1.91-1.79 (m, 3H).

Example 16: Compound D32

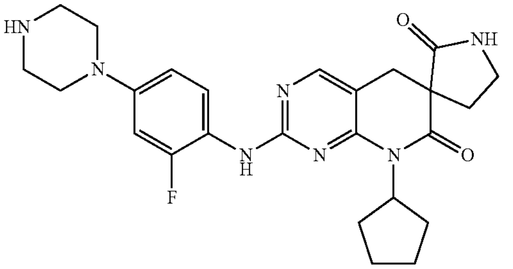

Synthesis of 8-cyclopentyl-2-((2-fluoro-4-(piperazin-1-yl)phenyl)amino)-5,8-dihydro-7H-spiro[pyrido[2,3-d]pyrimidine-6,3'-pyrrolidine]-2',7-dione (Compound D32)

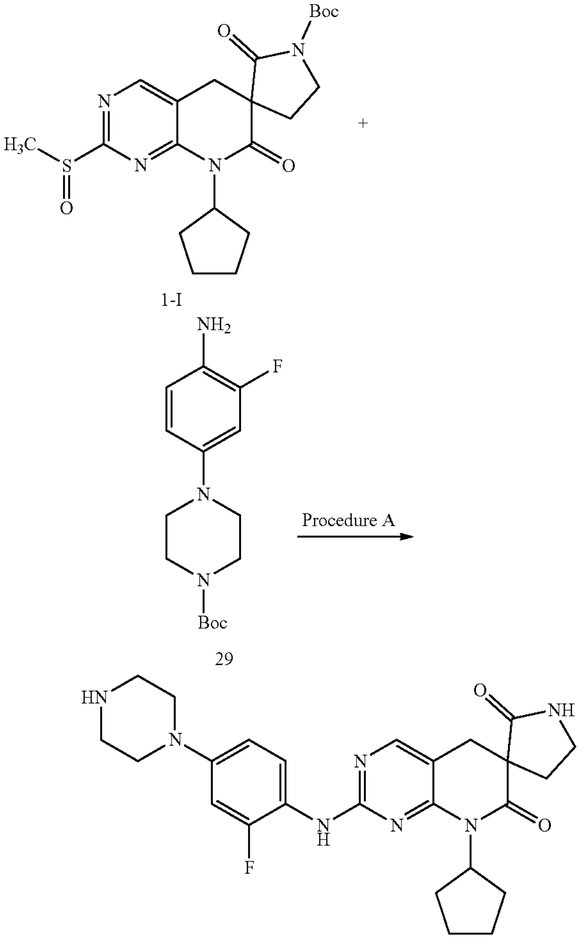

1-I

29

Compound D32

Compound D32 was synthesized following the general procedure A, 4 mg (6% yield). MS(ESI) m/z 480.3 $(M+H)^+$. $^1H$ NMR (600 MHz, DMSO-$d_6$) δ 8.67 (s, 1H), 8.03 (s, 1H), 7.96 (s, 1H), 7.32 (t, J=9.0 Hz, 1H), 6.85 (dd, J=13.7, 2.5 Hz, 1H), 6.76 (dd, J=8.8, 2.4 Hz, 1H), 5.20 (s, 1H), 3.22-3.18 (m, 5H), 3.09-3.03 (m, 4H), 3.00 (d, J=15.7 Hz, 1H), 2.70 (d, J=15.8 Hz, 1H), 2.34 (ddd, J=12.7, 7.7, 4.7 Hz, 1H), 1.98 (s, 2H), 1.93-1.87 (m, 2H), 1.63 (s, 4H), 1.40 (s, 2H).

Example 17: Compound D33

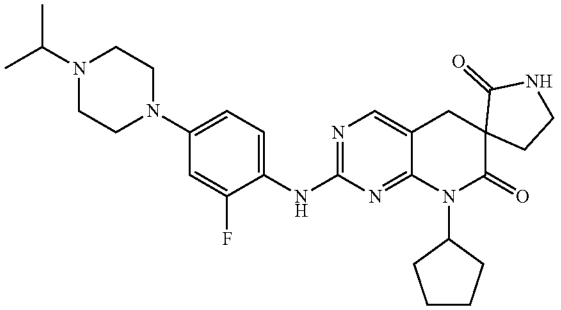

Synthesis of 8-cyclopentyl-2-((2-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (Compound D33)

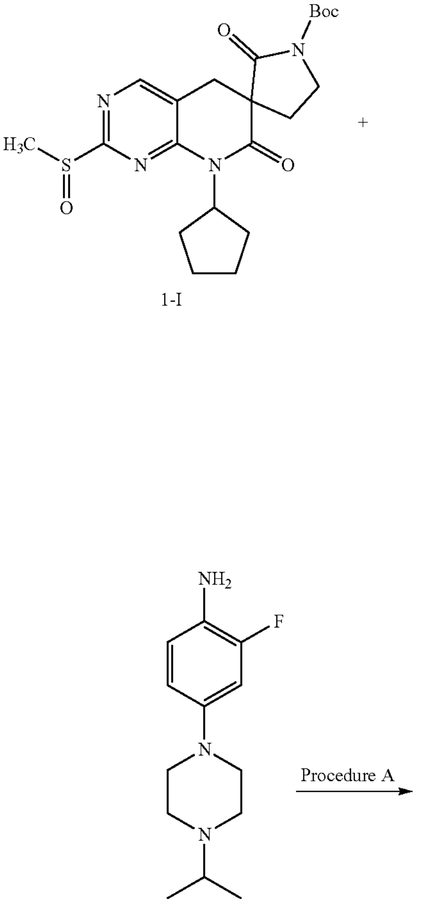

1-I 17 (free amine)

-continued

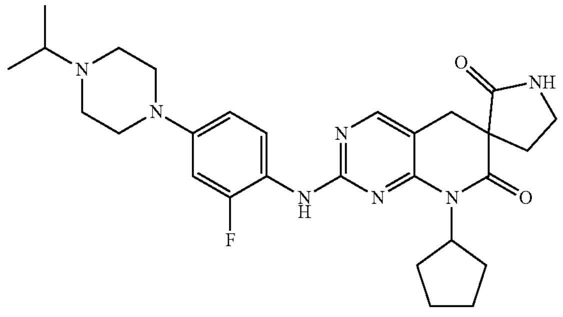

Compound D33

Compound D33 was synthesized following the general procedure A, 4 mg (6% yield). MS(ESI) m/z 522.4 $(M+H)^+$. $^1H$ NMR (600 MHz, Chloroform-d) δ 8.30 (dd, J=9.0, 6.0 Hz, 1H), 8.11 (s, 1H), 7.91 (s, 1H), 6.89 (dd, J=9.8, 2.8 Hz, 1H), 6.83 (td, J=8.6, 2.8 Hz, 1H), 5.73 (s, 1H), 5.40 (q, J=8.8 Hz, 1H), 3.51 (q, J=7.7 Hz, 1H), 3.42-3.37 (m, 1H), 3.33 (d, J=15.6 Hz, 1H), 3.01-2.89 (m, 4H), 2.74 (s, 5H), 2.63 (d, J=15.7 Hz, 1H), 2.44 (ddd, J=13.0, 7.5, 3.1 Hz, 1H), 2.31-2.22 (m, 1H), 2.17-2.09 (m, 1H), 2.07-1.98 (m, 3H), 1.94-1.83 (m, 2H), 1.70-1.61 (m, 2H), 1.11 (d, J=6.5 Hz, 6H).

Example 18: Compound D34

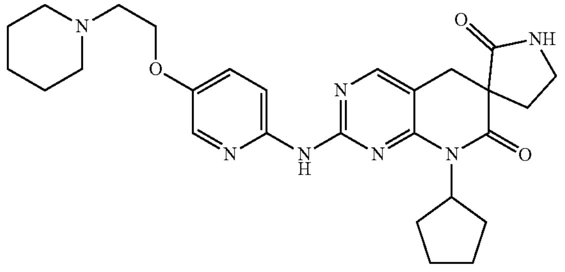 [SMILES: O=C1NCCC12Cc1cnc(Nc3ccc(OCCN4CCCCC4)cn3)nc1N(C1CCCC1)C2=O]

Synthesis of 8-cyclopentyl-2-((5-(2-(piperidin-1-yl) ethoxy)pyridin-2-yl)amino)-5,8-dihydro-7H-spiro [pyrido[2,3-d]pyrimidine-6,3'-pyrrolidine]-2',7-dione (Compound D34)

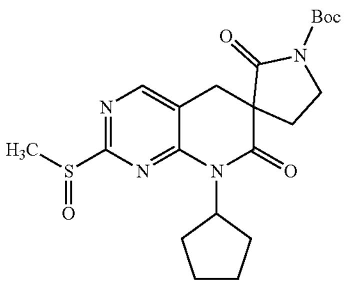

+

1-I

-continued

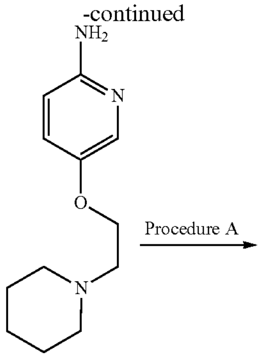

23

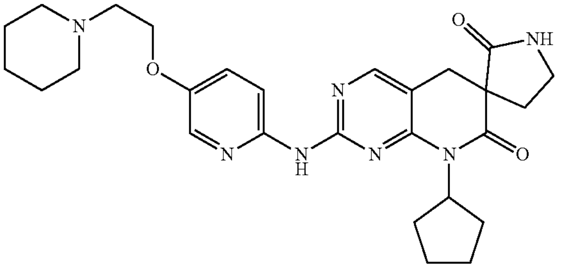

Compound D34

Compound D34 was synthesized following the general procedure A, 3 mg (6% yield). MS(ESI) m/z 506.3 $(M+H)^+$.

Example 19: Compound D35

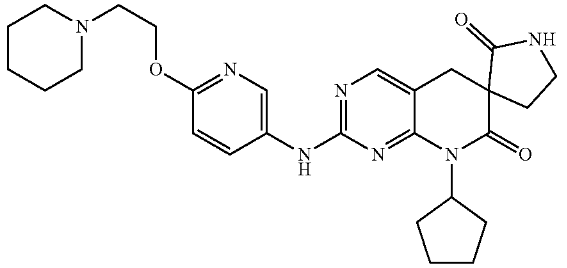 [SMILES: O=C1NCCC12Cc1cnc(Nc3ccc(OCCN4CCCCC4)nc3)nc1N(C1CCCC1)C2=O]

Synthesis of 8-cyclopentyl-2-((5-(2-(piperidin-1-yl) ethoxy)pyridin-2-yl)amino)-5,8-dihydro-7H-spiro [pyrido[2,3-d]pyrimidine-6,3'-pyrrolidine]-2',7-dione (Compound D35)

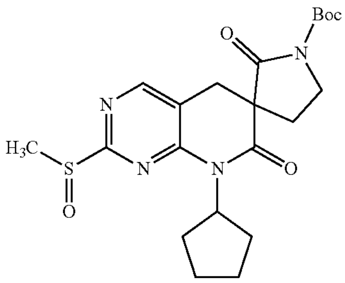

+

9

-continued

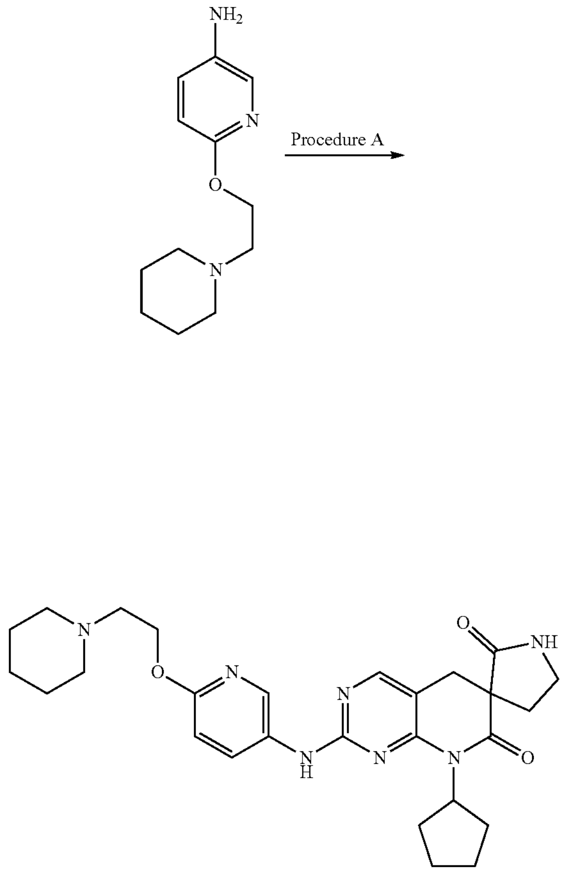

Compound D35

Compound D35 was synthesized following the general procedure A, 22 mg (39% yield). MS(ESI) m/z 506.3 $(M+H)^+$. $^1H$ NMR (600 MHz, Chloroform-d) δ 8.22 (d, J=2.6 Hz, 1H), 8.05 (s, 1H), 7.91 (dd, J=8.8, 2.5 Hz, 1H), 6.89 (s, 1H), 6.76 (d, J=8.8 Hz, 1H), 5.79 (s, 1H), 5.38-5.25 (m, 1H), 4.63 (s, 1H), 3.50 (q, J=7.8 Hz, 1H), 3.43-3.36 (m, 1H), 3.30 (d, J=15.7 Hz, 1H), 3.14 (s, 2H), 2.83 (s, 2H), 2.64 (d, J=15.7 Hz, 1H), 2.50-2.44 (m, 1H), 2.23-2.14 (m, 1H), 2.07-1.96 (m, 2H), 1.94-1.88 (m, 2H), 1.87-1.79 (m, 3H), 1.67 (s, 7H), 1.61-1.45 (m, 3H).

Example 20: Compound D36

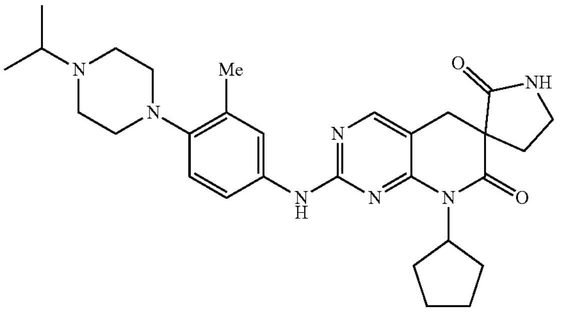 [SMILES: Cc1cc(Nc2ncc3c(n2)N(C2CCCC2)C(=O)C2(CCNC2=O)C3)ccc1N1CCN(C(C)C)CC1]

Synthesis of 8-cyclopentyl-2-((4-(4-isopropylpiperazin-1-yl)-3-methylphenyl)amino)-5,8-dihydro-7H-spiro[pyrido[2,3-d]pyrimidine-6,3'-pyrrolidine]-2',7-dione (Compound D36)

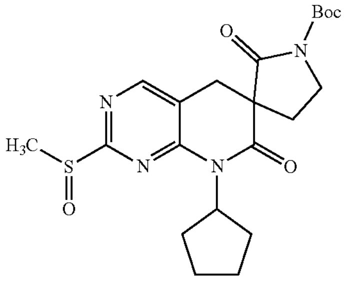

1-I

+

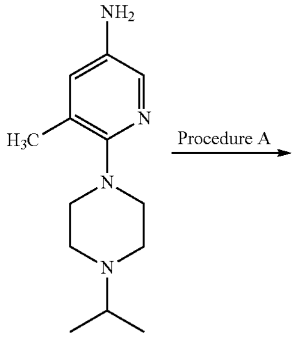

43

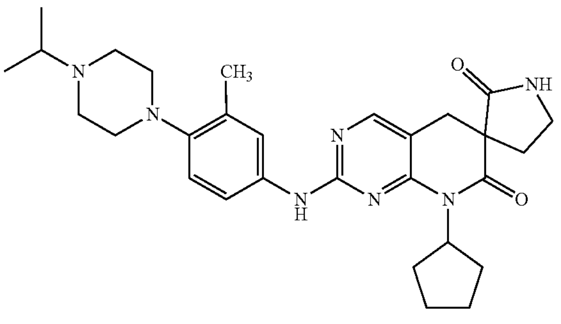

Compound D36

Compound D36 was synthesized following the general procedure A, 14 mg (25% yield). MS(ESI) m/z 518.4 $(M+H)^+$.

Example 21: Compound D37

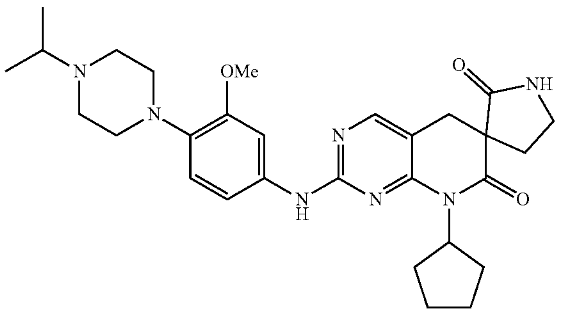

Synthesis of 8-cyclopentyl-2-((4-(4-isopropylpiperazin-1-yl)-3-methoxyphenyl)amino)-5,8-dihydro-7H-spiro[pyrido[2,3-d]pyrimidine-6,3'-pyrrolidine]-2',7-dione (Compound D37)

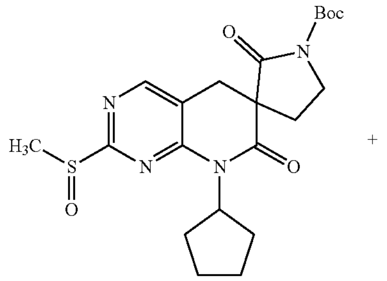

9
1-I

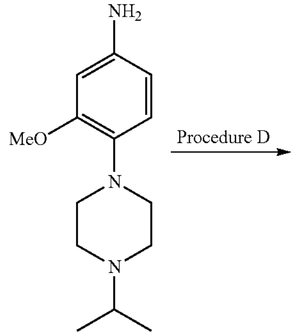

42

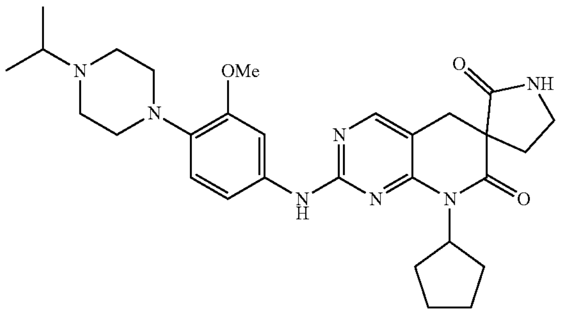 [SMILES: COc1cc(Nc2ncc3c(n2)N(C2CCCC2)C(=O)C2(CCNC2=O)C3)ccc1N1CCN(C(C)C)CC1]

Compound D37

Compound D37 was synthesized following the general procedure D, 3 mg (4% yield). MS(ESI) m/z 534.4 $(M+H)^+$. $^1H$ NMR (600 MHz, Chloroform-d) δ 8.07 (s, 1H), 7.01 (dd, J=8.5, 2.1 Hz, 1H), 6.91 (d, J=8.4 Hz, 2H), 5.69 (s, 1H), 5.41 (p, J=8.8 Hz, 1H), 3.88 (s, 3H), 3.49 (q, J=7.8 Hz, 1H), 3.41-3.36 (m, 1H), 3.32 (d, J=15.7 Hz, 1H), 3.20 (s, 4H), 2.94 (s, 3H), 2.62 (d, J=15.7 Hz, 1H), 2.45-2.39 (m, 1H), 2.24-2.16 (m, 1H), 2.07-1.98 (m, 2H), 1.93 (s, 2H), 1.89-1.78 (m, 2H), 1.58 (s, 4H), 1.27 (d, J=19.1 Hz, 6H).

Example 22: Compound D38

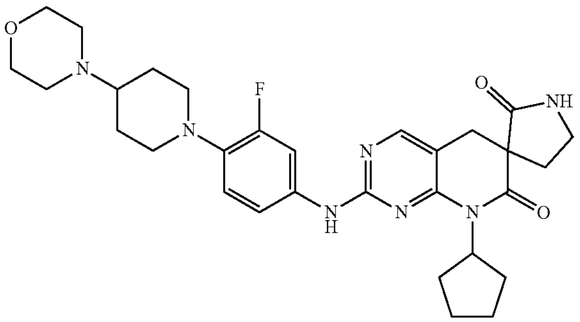

Synthesis of 8-cyclopentyl-2-((3-fluoro-4-(4-morpholinopiperidin-1-yl)phenyl)amino)-5,8-dihydro-7H-spiro[pyrido[2,3-d]pyrimidine-6,3'-pyrrolidine]-2',7-dione (Compound D38)

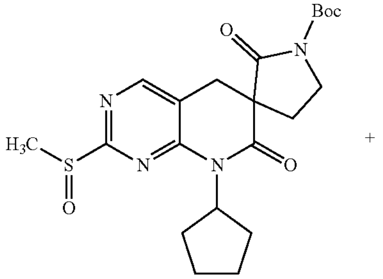

9
1-I

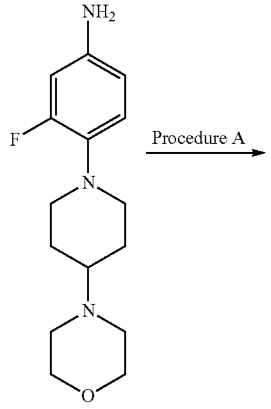

34

-continued

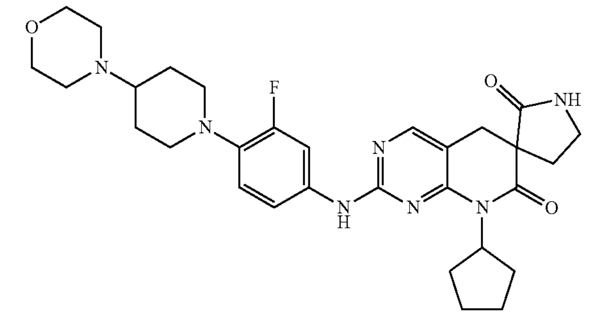 [SMILES: O=C1NCCC12Cc1cnc(Nc3ccc(N4CCC(N5CCOCC5)CC4)c(F)c3)nc1N(C1CCCC1)C2=O]

Compound D38

Compound D38 was synthesized following the general procedure A, 3 mg (5% yield). MS(ESI) m/z 564.3 $(M+H)^+$. $^1H$ NMR (600 MHz, Chloroform-d) δ 8.08 (s, 1H), 7.58 (d, J=14.4 Hz, 1H), 7.04 (d, J=6.8 Hz, 1H), 6.95-6.87 (m, 2H), 5.65 (s, 1H), 5.39-5.32 (m, 1H), 3.76 (s, 5H), 3.55-3.44 (m, 3H), 3.44-3.35 (m, 2H), 3.32 (d, J=15.8 Hz, 1H), 2.77-2.66 (m, 3H), 2.63 (d, J=15.7 Hz, 2H), 2.47-2.41 (m, 1H), 2.27-2.18 (m, 2H), 2.09-1.98 (m, 3H), 1.95 (s, 2H), 1.91-1.81 (m, 2H), 1.78 (s, 2H), 0.91-0.78 (m, 3H).

Example 23: Compound D39

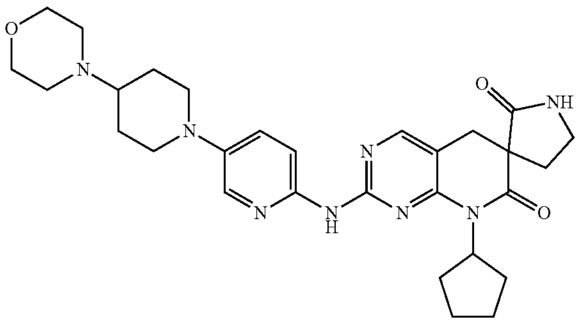

Synthesis of 8-cyclopentyl-2-((5-(4-morpholinopiperidin-1-yl)pyridin-2-yl)amino)-5,8-dihydro-7H-spiro[pyrido[2,3-d]pyrimidine-6,3'-pyrrolidine]-2',7-dione (Compound D39)

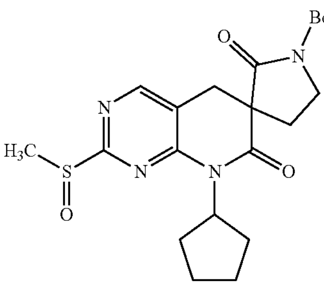

1-I

+

-continued

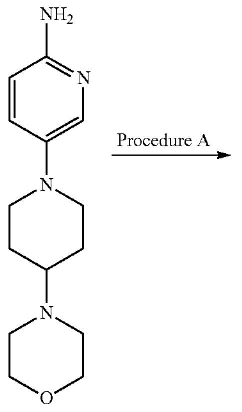

35

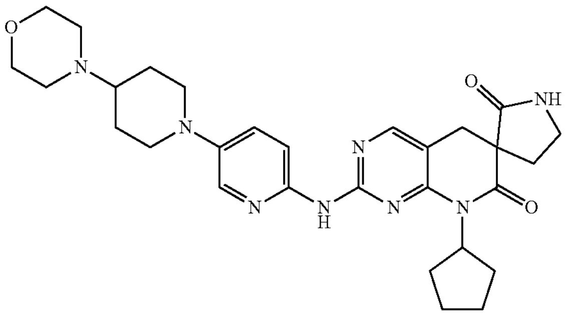 [SMILES: O=C1NCCC12Cc1cnc(Nc3ccc(N4CCC(N5CCOCC5)CC4)cn3)nc1N(C1CCCC1)C2=O]

Compound D39

Compound D39 was synthesized following the general procedure A, 3 mg (6% yield). MS(ESI) m/z 547.4 $(M+H)^+$. $^1H$ NMR (600 MHz, Chloroform-d) δ 8.06 (s, 1H), 7.46-7.40 (m, 1H), 7.29 (s, 1H), 7.03 (d, J=8.5 Hz, 1H), 6.92 (s, 1H), 5.79 (s, 1H), 5.38 (p, J=8.6 Hz, 1H), 3.54-3.45 (m, 1H), 3.42-3.35 (m, 1H), 3.33 (d, J=15.6 Hz, 1H), 2.98 (s, 4H), 2.76 (s, 4H), 2.60 (d, J=15.7 Hz, 1H), 2.40 (ddd, J=13.0, 7.5, 2.9 Hz, 1H), 2.31 (s, 3H), 2.27-2.17 (m, 1H), 2.06-1.97 (m, 2H), 1.96-1.80 (m, 4H), 1.62-1.54 (m, 3H), 1.15 (s, 5H).

Example 24: Compound D40

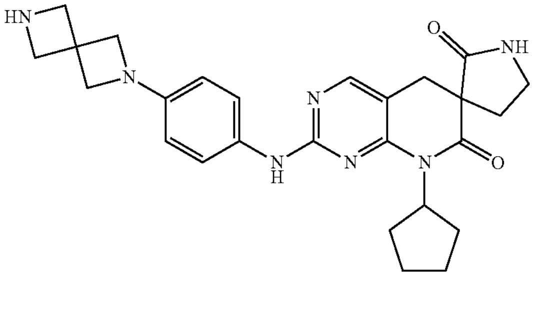 [SMILES: O=C1NCCC12Cc1cnc(Nc3ccc(N4CC5(CNC5)C4)cc3)nc1N(C1CCCC1)C2=O]

Synthesis of 2-((4-(2,6-diazaspiro[3.3]heptan-2-yl)phenyl)amino)-8-cyclopentyl-5,8-dihydro-7H-spiro[pyrido[2,3-d]pyrimidine-6,3'-pyrrolidine]-2',7-dione (Compound D40):

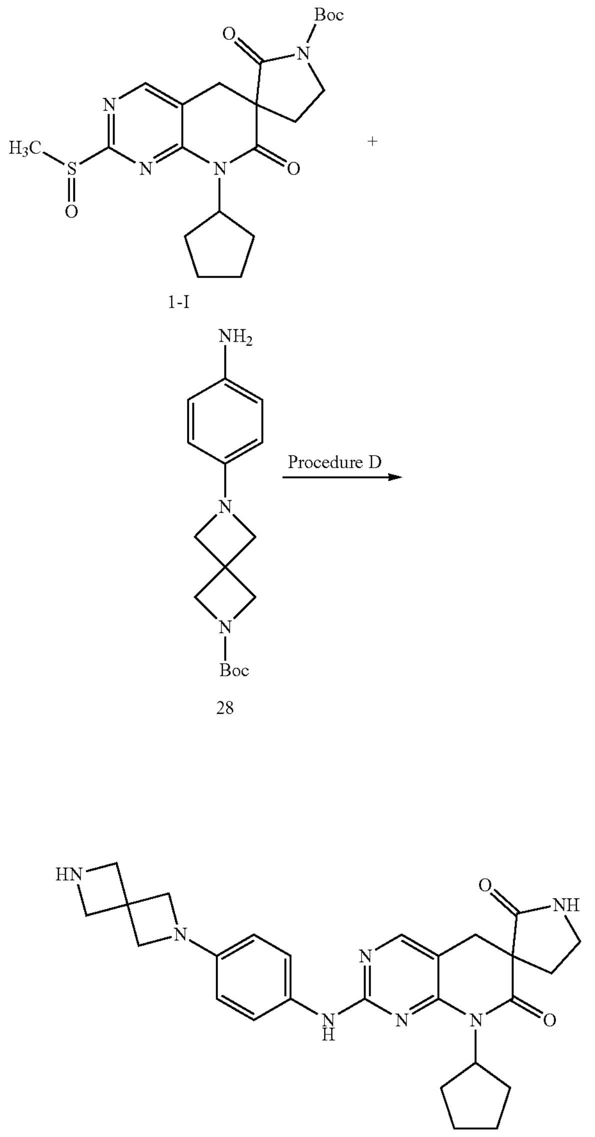

1-I

28

Compound D40

Compound D40 was synthesized following the general procedure D, 3 mg (5% yield). MS(ESI) m/z 474.4 $(M+H)^+$.

Example 25: Compound D41

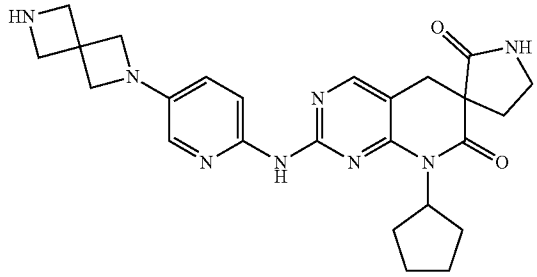 [SMILES: O=C1NCCC12Cc1cnc(Nc3ccc(N4CC5(CNC5)C4)cn3)nc1N(C1CCCC1)C2=O]

Synthesis of 2-((5-(2,6-diazaspiro[3.3]heptan-2-yl)pyridin-2-yl)amino)-8-cyclopentyl-5,8-dihydro-7H-spiro[pyrido[2,3-d]pyrimidine-6,3'-pyrrolidine]-2',7-dione (Compound D41)

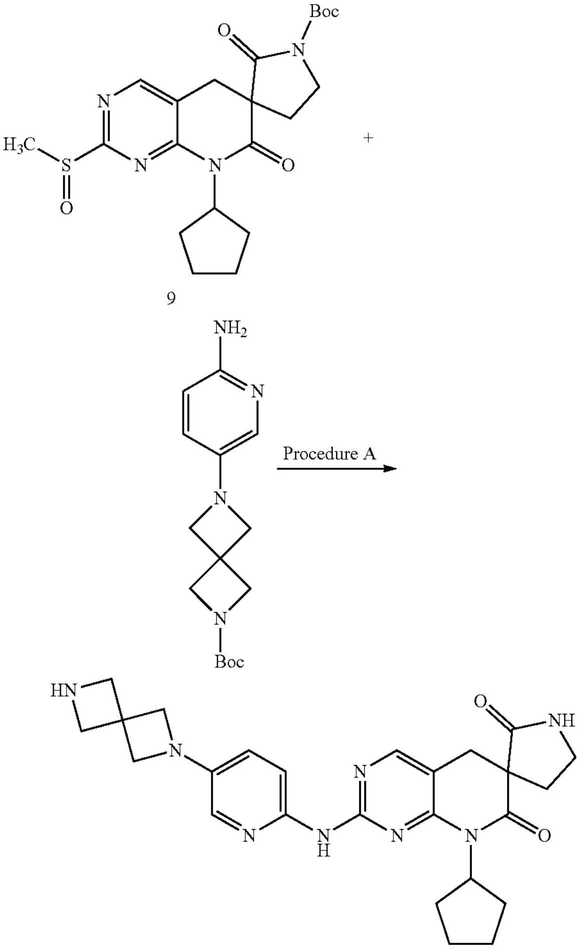

9

Compound 41

Compound D41 was synthesized following the general procedure A, 6 mg (13% yield). MS(ESI) m/z 475.4 $(M+H)^+$.

Example 26: Compound D42

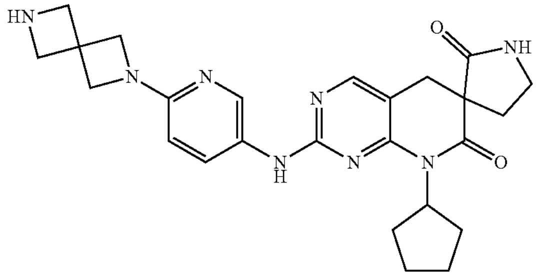 [SMILES: O=C1NCCC12Cc1cnc(Nc3ccc(N4CC5(CNC5)C4)nc3)nc1N(C1CCCC1)C2=O]

Synthesis of 2-((6-(2,6-diazaspiro[3.3]heptan-2-yl) pyridin-3-yl)amino)-8-cyclopentyl-5,8-dihydro-7H-spiro[pyrido[2,3-d]pyrimidine-6,3'-pyrrolidine]-2',7-dione (Compound D42)

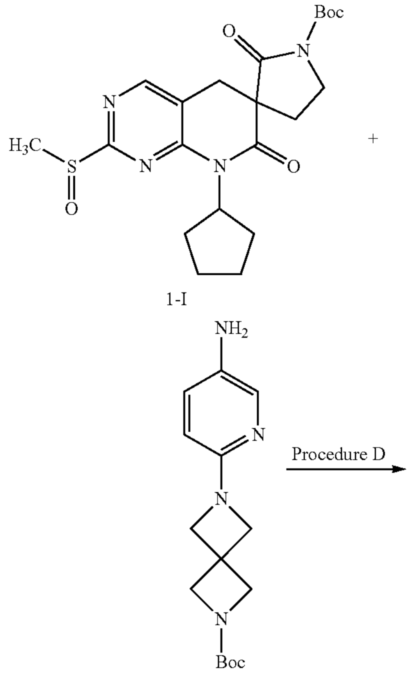

1-I

27

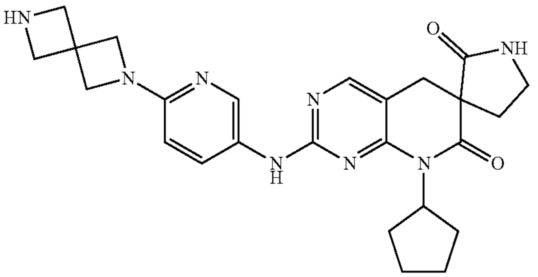

Compound D42

Compound D42 was synthesized following the general procedure D, 4 mg (8% yield). MS(ESI) m/z 475.4 $(M+H)^+$. $^1H$ NMR (600 MHz, DMSO-$d_6$) δ 9.04 (s, 1H), 8.21 (d, J=2.2 Hz, 1H), 8.00 (s, 1H), 7.90 (s, 1H), 7.72 (dd, J=8.8, 2.3 Hz, 1H), 6.34 (d, J=8.8 Hz, 1H), 5.28-5.18 (m, 1H), 3.95 (s, 3H), 3.92 (s, 3H), 3.18-3.08 (m, 4H), 2.95 (d, J=15.9 Hz, 1H), 2.65 (d, J=15.8 Hz, 1H), 2.34-2.27 (m, 1H), 1.99-1.90 (m, 2H), 1.88-1.81 (m, 1H), 1.77 (s, 2H), 1.71-1.61 (m, 2H), 1.48-1.40 (m, 2H).

Example 27: Compound D43

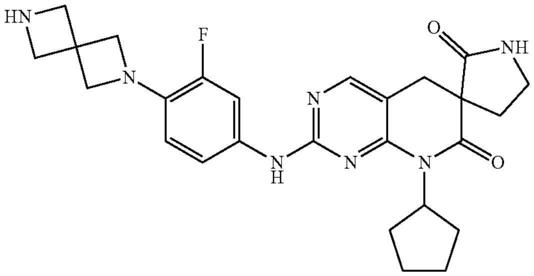 [SMILES: O=C1NCCC12Cc1cnc(Nc3ccc(N4CC5(CNC5)C4)c(F)c3)nc1N(C1CCCC1)C2=O]

Synthesis of 8-cyclopentyl-2-((3-methyl-4-(2,6-diazaspiro[3.3]heptan-2-yl)phenyl)amino)-5,8-dihydro-7H-spiro[pyrido[2,3-d]pyrimidine-6,3'-pyrrolidine]-2',7-dione (Compound D43)

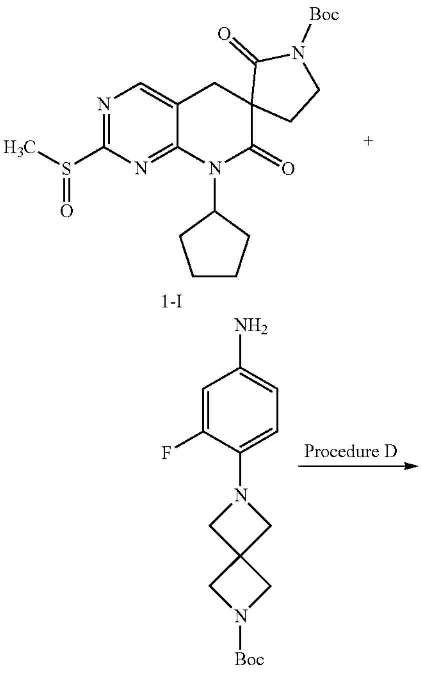

1-I

26

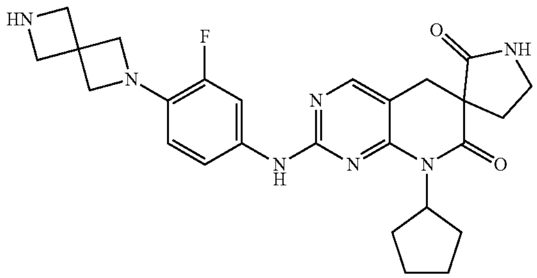

Compound D43

Compound D43 was synthesized following the general procedure D, 3 mg (6% yield). MS(ESI) m/z 492.3 $(M+H)^+$. $^1H$ NMR (600 MHz, DMSO-$d_6$) δ 9.27 (s, 1H), 8.05 (s, 1H), 7.90 (s, 1H), 7.53 (dd, J=15.2, 2.0 Hz, 1H), 7.16 (d, J=7.7

Hz, 1H), 6.45 (dd, J=10.3, 8.9 Hz, 1H), 5.30-5.21 (m, 1H), 3.95 (s, 3H), 3.92-3.89 (m, 3H), 3.19-3.12 (m, 3H), 2.96 (d, J=15.9 Hz, 1H), 2.68 (d, J=15.9 Hz, 1H), 2.58-2.53 (m, 1H), 2.35-2.30 (m, 1H), 1.97 (s, 2H), 1.88-1.77 (m, 3H), 1.71 (s, 2H), 1.52-1.41 (m, 2H).

Example 28: Compound D44

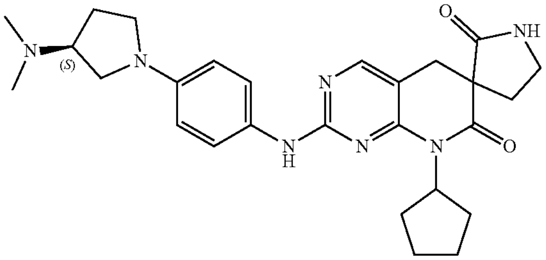

Synthesis of 8-cyclopentyl-2-((4-((S)-3-(dimethylamino)pyrrolidin-1-yl)phenyl)amino)-5,8-dihydro-7H-spiro[pyrido[2,3-d]pyrimidine-6,3'-pyrrolidine]-2',7-dione (Compound D44)

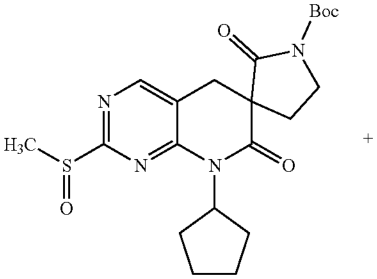

1-I

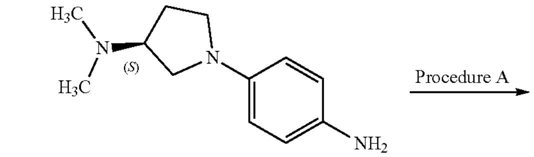

33

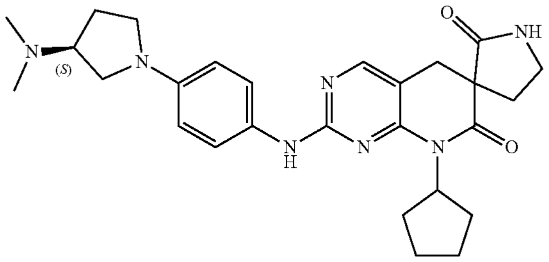

Compound D44

Compound D44 was synthesized following the general procedure A, 3 mg (6% yield). MS(ESI) m/z 490.3 $(M+H)^+$.

Example 29: Compound D45

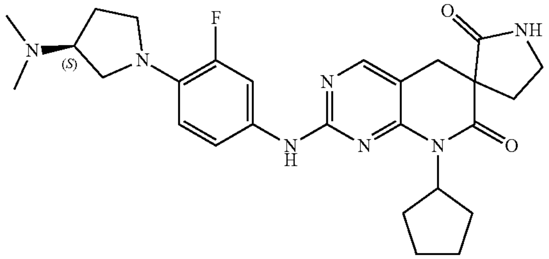

Synthesis of 8-cyclopentyl-2-((4-((S)-3-(dimethylamino)pyrrolidin-1-yl)-3-fluorophenyl)amino)-5,8-dihydro-7H-spiro[pyrido[2,3-d]pyrimidine-6,3'-pyrrolidine]-2',7-dione (Compound D45)

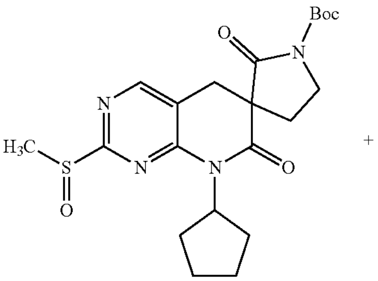

1-I

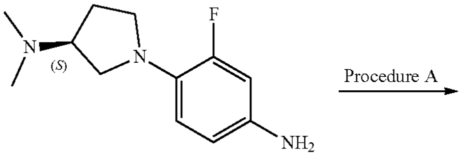

34

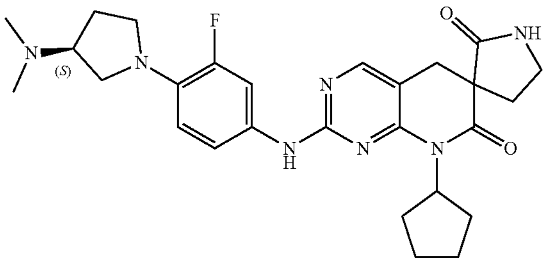

Compound D45

Compound D45 was synthesized following the general procedure A, 24 mg (43% yield). MS(ESI) m/z 508.3 $(M+H)^+$.

Example 30: Compound D46

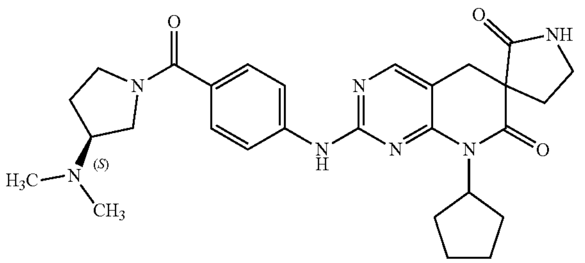

Synthesis of 8-cyclopentyl-2-((4-((S)-3-(dimethylamino)pyrrolidine-1-carbonyl)phenyl)amino)-5,8-dihydro-7H-spiro[pyrido[2,3-d]pyrimidine-6,3'-pyrrolidine]-2',7-dione (Compound D46)

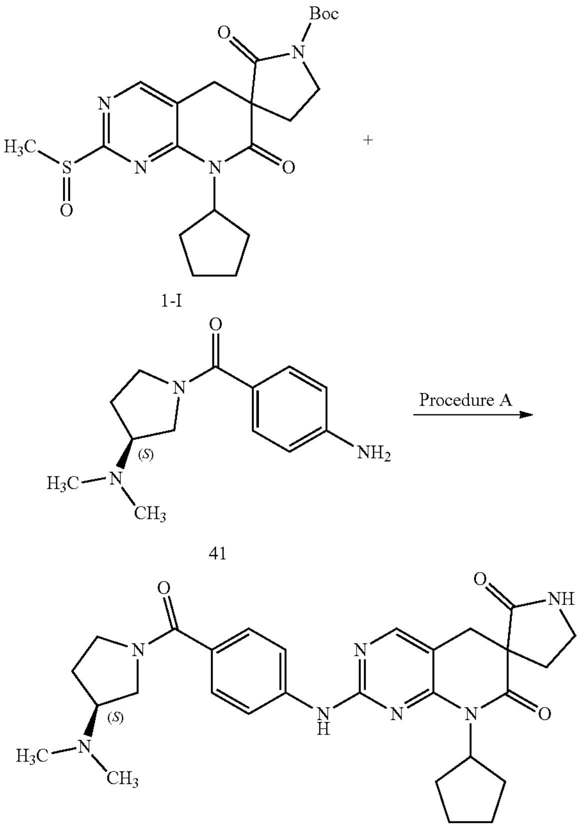

1-I

41

Compound D46

Compound D46 was synthesized following the general procedure A, 2 mg (4% yield). MS(ESI) m/z 518.4 $(M+H)^+$. $^1H$ NMR (600 MHz, Chloroform-d) δ 8.12 (s, 1H), 7.66 (d, J=8.6 Hz, 2H), 7.54 (d, J=8.5 Hz, 2H), 5.75 (s, 1H), 5.38 (p, J=8.8 Hz, 1H), 3.82 (s, 2H), 3.56-3.48 (m, 1H), 3.46-3.38 (m, 1H), 3.33 (d, J=15.7 Hz, 1H), 2.68 (d, J=15.6 Hz, 3H), 2.65-2.54 (m, 3H), 2.52-2.44 (m, 1H), 2.30 (s, 2H), 2.26-2.13 (m, 2H), 2.12-1.94 (m, 5H), 1.94-1.82 (m, 3H), 1.76-1.43 (m, 3H).

Example 31: Compound D47

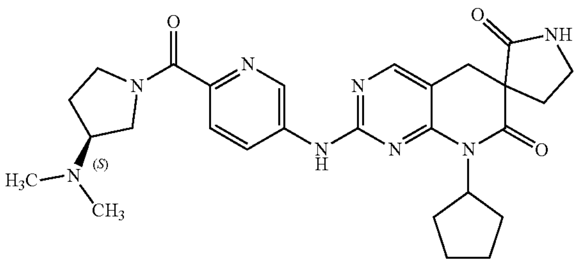

Synthesis of 8-cyclopentyl-2-((6-((S)-3-(dimethylamino)pyrrolidine-1-carbonyl)pyridin-3-yl)amino)-5,8-dihydro-7H-spiro[pyrido[2,3-d]pyrimidine-6,3'-pyrrolidine]-2',7-dione (Compound D47)

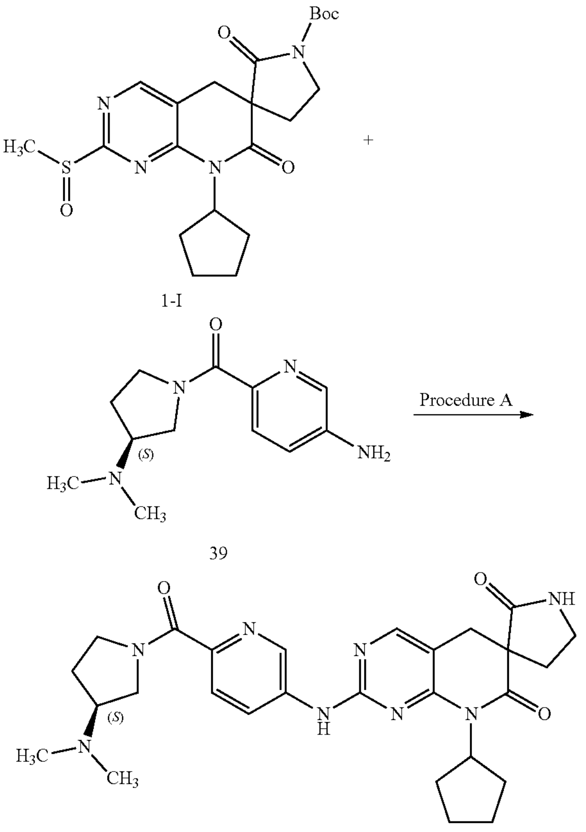

1-I

39

Compound D47

Compound D47 was synthesized following the general procedure A, 6 mg (11% yield). MS(ESI) m/z 519.4 $(M+H)^+$. $^1H$ NMR (600 MHz, Chloroform-d) δ 8.70 (d, J=10.7 Hz, 1H), 8.27 (d, J=7.0 Hz, 1H), 8.15 (s, 1H), 7.97 (dd, J=13.0, 8.7 Hz, 1H), 7.21 (s, 1H), 5.73 (d, 1H), 5.43-5.31 (m, 1H), 4.36 (s, 1H), 4.18 (s, 1H), 4.14-4.03 (m, 1H), 4.05-3.95 (m, 1H), 3.72-3.62 (m, 1H), 3.57-3.49 (m, 1H), 3.47-3.37 (m, 1H), 3.32 (d, J=15.8 Hz, 1H), 2.71 (d, J=15.7 Hz, 1H), 2.63 (s, 4H), 2.56-2.48 (m, 1H), 2.30 (s, 1H), 2.26-2.16 (m, 2H), 2.15-2.06 (m, 1H), 2.06-1.94 (m, 3H), 1.89 (s, 3H), 1.62-1.58 (m, 3H).

Example 32: Compound D48

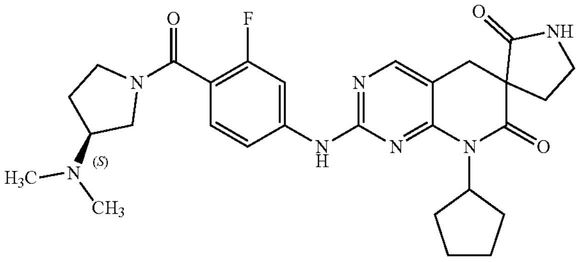

Synthesis of 8-cyclopentyl-2-((4-((S)-3-(dimethylamino)pyrrolidine-1-carbonyl)-3-fluorophenyl)amino)-5,8-dihydro-7H-spiro[pyrido[2,3-d]pyrimidine-6,3'-pyrrolidine]-2',7-dione (Compound D48)

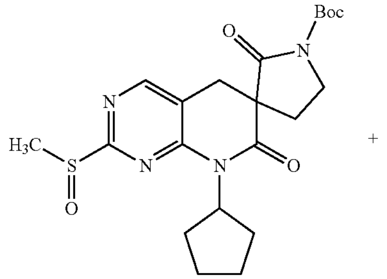

1-I

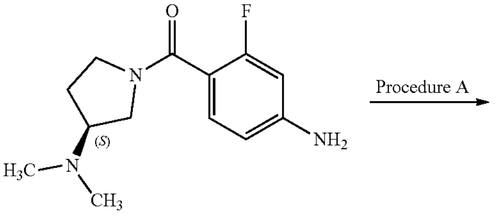

40

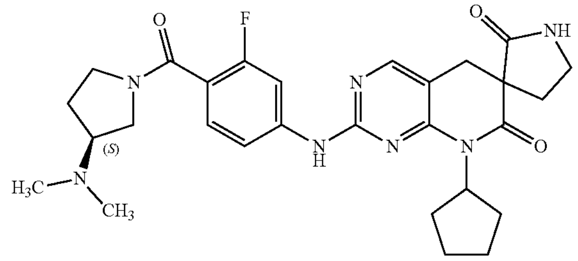

Compound D48

Compound D48 was synthesized following the general procedure A, 2 mg (3% yield). MS(ESI) m/z 536.4 $(M+H)^+$. $^1H$ NMR (600 MHz, Chloroform-d) δ 8.13 (s, 1H), 7.80 (dd, J=12.7, 4.6 Hz, 1H), 7.41-7.36 (m, 1H), 7.30 (d, J=7.1 Hz, 1H), 7.19-7.13 (m, 1H), 5.88 (s, 1H), 5.36 (p, J=8.8 Hz, 1H), 4.02-3.93 (m, 0.5H), 3.90-3.83 (m, 0.5H), 3.67-3.58 (m, 0.5H), 3.58-3.53 (m, 0.5H), 3.53-3.44 (m, 2H), 3.33 (d, J=15.7 Hz, 1H), 2.86 (s, 0.5H), 2.75 (s, 0.5H), 2.69 (d, J=15.7 Hz, 1H), 2.48 (ddd, J=11.0, 7.5, 2.9 Hz, 1H), 2.35 (s, 3H), 2.25 (s, 3H), 2.23-2.18 (m, 2H), 2.06-1.94 (m, 4H), 1.94-1.83 (m, 4H), 1.81-1.50 (m, 3H).

Example 33: Compound D1

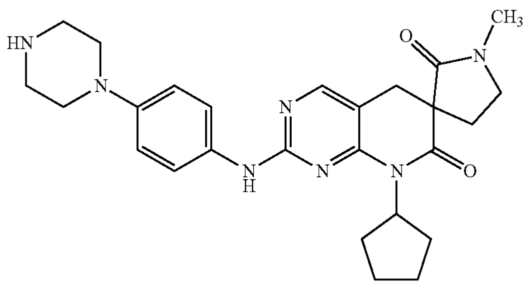 [SMILES: CN1CCC2(Cc3cnc(Nc4ccc(N5CCNCC5)cc4)nc3N(C3CCCC3)C2=O)C1=O]

Step 1: Synthesis of N-methyl-2-(phenylselanyl)ethanamine (43C)

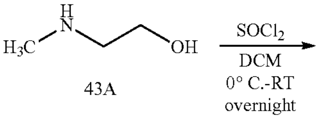

43A

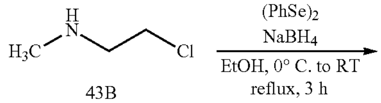

43B

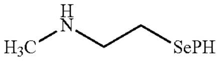

43C

Synthesis of compound 43B: (Ref: Habtemariam et al., *J. Chem. Soc., Dalton Trans.* 8: 1306-1318 (2001)): To a solution of compound 43A (23 g, 306 mmol) in 200 mL $CH_2Cl_2$ was added $SOCl_2$ (28 mL in 25 mL $CH_2Cl_2$) dropwise at 0° C. The reaction mixture was then stirred at RT for overnight. The reaction mixture was evaporated to dryness on a rotary evaporator and the resulting crude product 43B (36 g, 90% yield) was used as such for next step. $^1H$ NMR (600 MHz, Chloroform-d) 3.99 (t, J=6.2 Hz, 2H), 3.35 (t, J=6.2 Hz, 3H), 2.81 (s, 3H).

Synthesis of compound 43C: Starting from compound 43B (29 g, 223 mmol) and following the procedure described for the synthesis of compound 1-E, compound 43C was prepared, 31 g (65% yield). MS(ESI) m/z 216.1 $(M+H)^+$. $^1$HNMR: $^1H$ NMR (600 MHz, Chloroform-d) δ 7.51 (m, 2H), 7.32-7.20 (m, 3H), 3.05 (t, J=6.7 Hz, 2H), 2.85 (t, J=6.7 Hz, 2H), 2.42 (s, 3H), 2.18 (s, 1H).

Step 2: Synthesis of 8-cyclopentyl-1'-methyl-2-(methylthio)-5H-spiro [pyrido[2,3-d]pyrimidine-6,3'-pyrrolidine]-2',7(8H)-dione (43E)

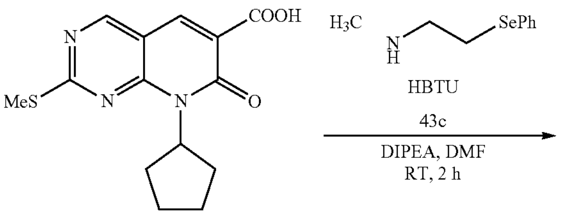

1C

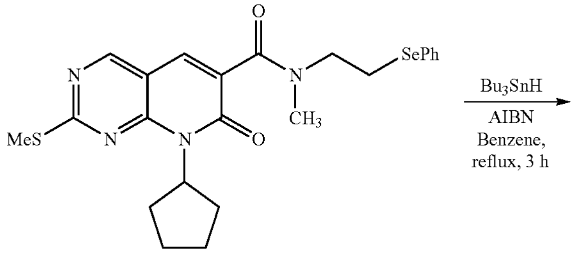

43D

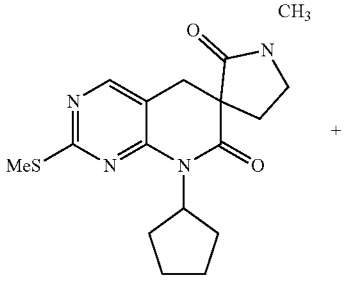

43E

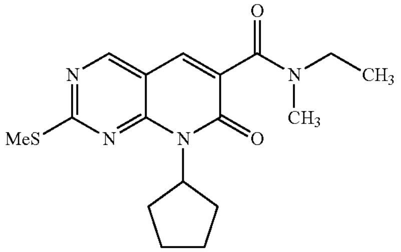

43F

Synthesis of compound 430: Prepared using the procedure described for the synthesis of compound 1-F, 5.5 g (67% yield). MS(ESI) m/z 503.1 $[M+H]^+$. $^1H$ NMR (600 MHz, Chloroform-d) δ 8.59 (s, 0.5H), 8.47 (s, 0.5H), 7.61-7.55 (m, 1H), 7.51 (s, 0.5H), 7.47 (s, 0.5H), 7.33-7.24 (m, 2H), 6.96-6.90 (m, 2H), 5.98-5.88 (m, 1H), 3.22 (t, J=7.2 Hz, 1H), 3.08 (s, 2H), 2.80 (s, 3H), 2.66 (s, 2H), 2.66 (s, 1.5H), 2.62 (s, 1.5H), 2.36-2.28 (m, 1H), 2.09-2.04 (m, 2H), 1.90-1.85 (m, 2H), 1.72-1.67 (m, 2H).

Synthesis of spiro compound 43E: Prepared using the radical cyclization procedure described for the synthesis of compound 1-H, Yield for desired spiro compound 43E: 3.5 g, (42% yield), Data for 43E: MS(ESI) m/z 347.2 $[M+H]^+$. $^1H$ NMR (600 MHz, Chloroform-d) δ 8.17 (s, 1H), 5.39 (p, J=8.8 Hz, 1H), 3.54-3.46 (m, 1H), 3.37-3.30 (m, 2H), 2.92 (s, 3H), 2.65 (d, J=16.0 Hz, 1H), 2.55 (s, 3H), 2.37-2.31 (m, 1H), 2.23-2.15 (m, 1H), 2.11-2.01 (m, 1H), 2.02-1.94 (m, 2H), 1.93-1.79 (m, 3H), 1.67-1.55 (m, 2H).

We isolated product 43F and data for Compound 43F: Yield 2.7 g, (32%). MS(ESI) m/z 347.2 $[M+H]^+$. $^1H$ NMR (600 MHz, Chloroform-d) δ 8.62 (d, J=2.1 Hz, 1H), 6.02-5.92 (m, 1H), 3.62-3.56 (m, 1H), 3.26 (q, J=7.1 Hz, 1H), 3.09 (s, 1.5H), 2.92 (s, 1.5H), 2.63 (s, 3H), 2.39-2.27 (m, 2H), 2.13-2.03 (m, 2H), 1.91-1.87 (m, 2H), 1.72-1.66 (m, 2H), 1.25 (t, J=7.2 Hz, 1.5H), 1.16 (t, J=7.1 Hz, 1.5H).

Step 3: Synthesis of 8-cyclopentyl-1'-methyl-2-(methylsulfonyl)-5H-spiro [pyrido[2,3-d]pyrimidine-6,3'-pyrrolidine]-2',7(8H)-dione (43G)

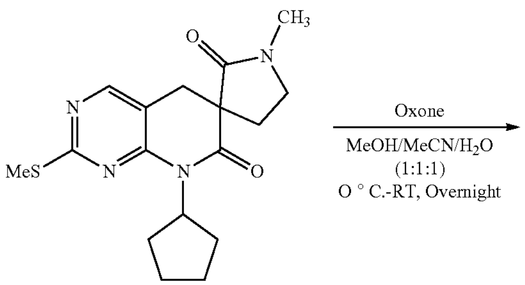

43E

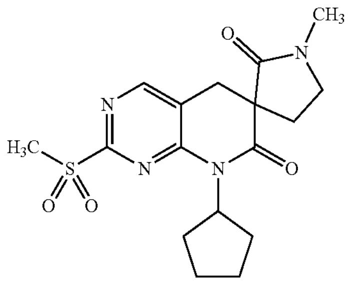

43G

Synthesis of sulfone 43G: (Ref: WO 2006066748): To a stirred solution of compound 43E (250 mg, 0.72 mmol) in 30 mL of mixture of MeOH/MeCN/$H_2O$ (1:1:1) at 0° C. was added a solution of oxone (1.1 g, 3.6 mmol) dissolved in 10 mL of $H_2O$ dropwise and the resulting mixture was stirred at RT for overnight. The solvents were removed under reduced pressure, diluted with water, and extracted with 20% MeOH in DCM (3×25 mL). The combined organic layers were dried over sodium sulfate and concentrated to get the crude compound, which was further purified by column chromatography (0 to 10% MeOH in DCM) to give sulfone 43G (220 mg, 80% yield) as a light-yellow solid. MS(ESI) m/z 379.2 $[M+H]^+$. $^1H$ NMR (600 MHz, Chloroform-d) δ 8.46 (s, 1H), 5.44 (p, J=9.2 Hz, 1H), 3.62-3.52 (m, 1H), 3.42-3.35 (m, 2H), 3.32 (s, 3H), 2.93 (d, J=16.5 Hz, 1H), 2.90 (s, 3H), 2.61-2.55 (m, 1H), 2.15-2.01 (m, 3H), 1.98-1.84 (m, 4H), 1.70-1.59 (m, 2H).

Step 4: Synthesis of 8-cyclopentyl-1'-methyl-2-((4-(piperazin-1-yl)phenyl)amino)-5,8-dihydro-7H-spiro[pyrido[2,3-d]pyrimidine-6,3'-pyrrolidine]-2',7-dione (Compound D1)

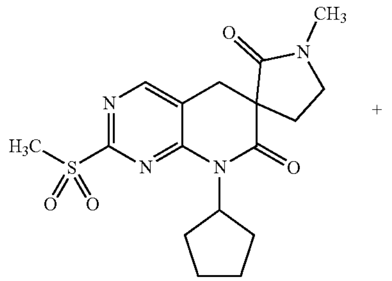

43G

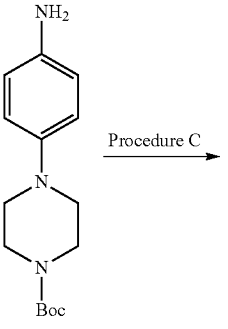

2

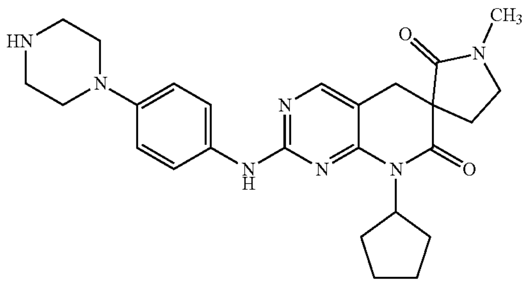

Compound D1

Compound D1 was synthesized using sulfone 43G, following the general procedure C, 7 mg (9% yield). MS(ESI) m/z 476.3 $(M+H)^+$. $^1H$ NMR (600 MHz, Chloroform-d) δ 8.03 (s, 1H), 7.44 (d, J=8.9 Hz, 2H), 6.99 (s, 1H), 6.92 (d, J=8.9 Hz, 2H), 5.33 (p, J=8.8 Hz, 1H), 3.52-3.44 (m, 1H), 3.36-3.29 (m, 2H), 3.20-3.15 (m, 4H), 3.15-3.10 (m, 4H), 2.93 (s, 3H), 2.58 (s, 1H), 2.31 (ddd, J=13.0, 7.8, 3.1 Hz, 1H), 2.25-2.16 (m, 2H), 1.93-1.77 (m, 5H), 1.62-1.52 (m, 2H).

Example 34: Compound D2

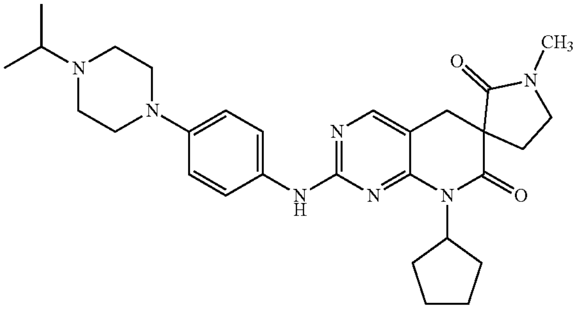

Synthesis of 8-cyclopentyl-2-((4-(4-isopropylpiperazin-1-yl)phenyl)amino)-1'-methyl-5,8-dihydro-7H-spiro[pyrido[2,3-d]pyrimidine-6,3'-pyrrolidine]-2',7-dione (Compound D2)

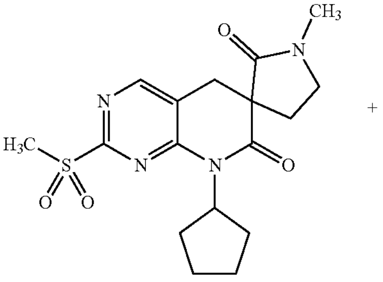

43G

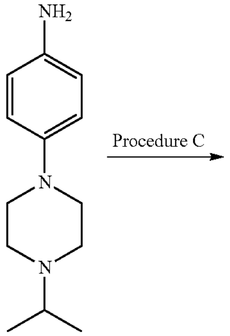

12

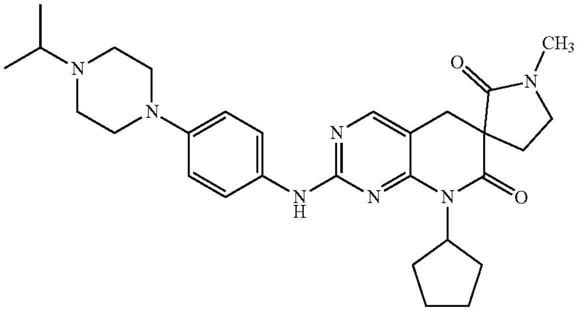 [SMILES: CC(C)N1CCN(c2ccc(Nc3ncc4c(n3)N(C3CCCC3)C(=O)C3(CCN(C)C3=O)C4)cc2)CC1]

Compound D2

Compound D2 was synthesized starting sulfone 43G, following the general procedure C, 4 mg (5% yield). MS(ESI) m/z 518.4 $(M+H)^+$.

Example 35: Compound D18

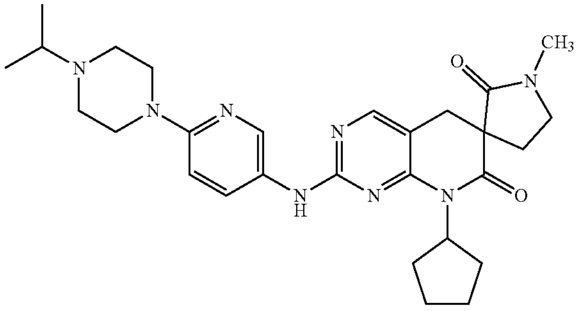 [SMILES: CC(C)N1CCN(c2ccc(Nc3ncc4c(n3)N(C3CCCC3)C(=O)C3(CCN(C)C3=O)C4)cn2)CC1]

Synthesis of 8-cyclopentyl-2-((6-(4-isopropylpiperazin-1-yl)pyridin-3-yl)amino)-1'-methyl-5,8-dihydro-7H-spiro[pyrido[2,3-d]pyrimidine-6,3'-pyrrolidine]-2',7-dione (Compound D18)

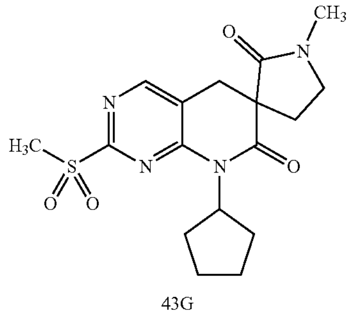

43G

+

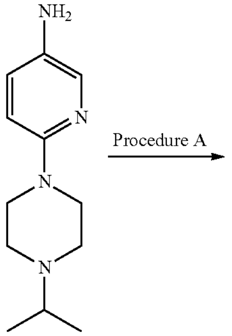

13

-continued

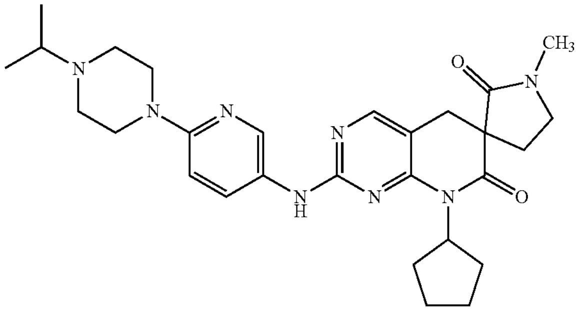

Compound D18

Compound D18 was synthesized staring from sulfone 43G, following the general procedure A, 15 mg (26% yield). MS(ESI) m/z 519.3 $(M+H)^+$. $^1H$ NMR (600 MHz, Chloroform-d) δ 8.24 (d, J=2.6 Hz, 1H), 8.02 (s, 1H), 7.81 (dd, J=9.0, 2.5 Hz, 1H), 6.75 (s, 1H), 6.67 (d, J=9.0 Hz, 1H), 5.30 (p, J=8.8 Hz, 1H), 3.63 (s, 4H), 3.51-3.44 (m, 1H), 3.36-3.31 (m, 1H), 3.30 (d, J=16.2 Hz, 1H), 2.93 (s, 3H), 2.81 (s, 4H), 2.58 (d, J=15.7 Hz, 1H), 2.36-2.29 (m, 1H), 2.23-2.13 (m, 1H), 2.07-1.98 (m, 1H), 1.93-1.84 (m, 3H), 1.84-1.76 (m, 3H), 1.59-1.51 (m, 2H), 1.18 (d, J=5.9 Hz, 6H).

Example 36: Compound D19

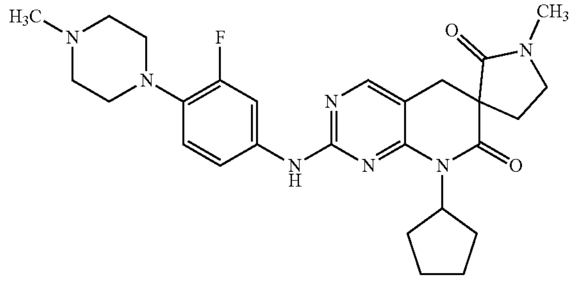 [SMILES: CN1CCN(c2ccc(Nc3ncc4c(n3)N(C3CCCC3)C(=O)C3(CCN(C)C3=O)C4)cc2F)CC1]

Synthesis of 8-cyclopentyl-2-((3-fluoro-4-(4-methylpiperazin-1-yl)phenyl)amino)-1'-methyl-5,8-dihydro-7H-spiro[pyrido[2,3-d]pyrimidine-6,3'-pyrrolidine]-2',7-dione (Compound D19)

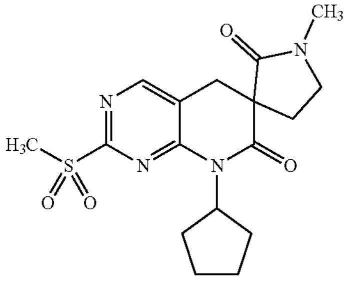

43G

+

-continued

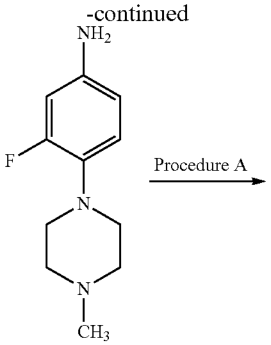

14

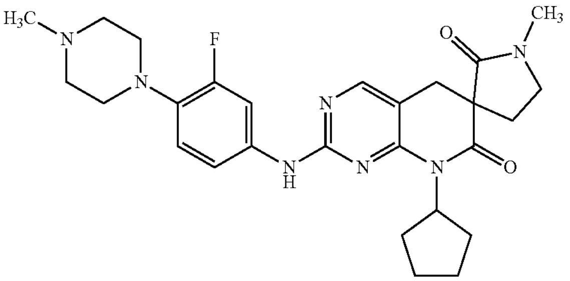

Compound D19

Compound D19 was synthesized starting from sulfone 43G, following the general procedure A, 4 mg (6% yield). MS(ESI) m/z 508.3 $(M+H)^+$. $^1H$ NMR (600 MHz, Chloroform-d) δ 8.05 (s, 1H), 7.60 (d, J=14.5 Hz, 1H), 7.10 (s, 1H), 7.05 (d, J=8.3 Hz, 1H), 6.92 (t, J=9.0 Hz, 1H), 5.34 (p, J=8.8 Hz, 1H), 3.48 (q, J=7.8 Hz, 1H), 3.38-3.32 (m, 2H), 3.30 (s, 1H), 3.14 (s, 4H), 2.93 (s, 3H), 2.72 (s, 3H), 2.60 (d, J=15.6 Hz, 1H), 2.44 (s, 3H), 2.37-2.30 (m, 1H), 2.26-2.15 (m, 1H), 2.04 (d, J=11.0 Hz, 1H), 1.92 (d, J=14.0 Hz, 3H), 1.91-1.84 (m, 4H).

Example 37: Compound D20

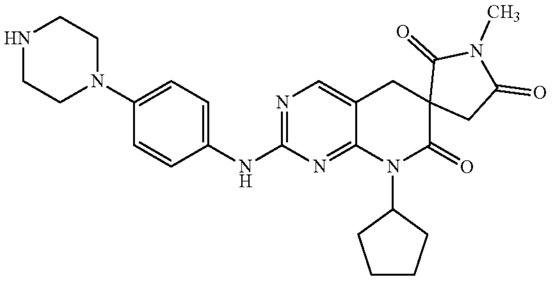 [SMILES: CN1C(=O)CC2(Cc3cnc(Nc4ccc(N5CCNCC5)cc4)nc3N(C3CCCC3)C2=O)C1=O]

Step 1: Synthesis of N-methyl-2-(phenylselanyl)acetamide (48B)

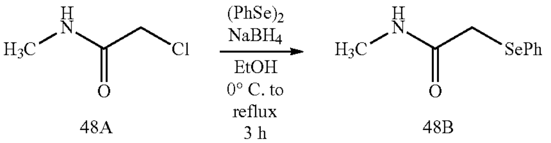

48A 48B

Synthesis of compound 48B: Prepared using the procedure described for the synthesis of compound 1-E. Yield: 29 g, 91%. MS(ESI) m/z 230.1 $(M+H)^+$. $^1H$ NMR (600 MHz, Chloroform-d) δ 7.52-7.41 (m, 2H), 7.30-7.27 (m, 3H), 6.50 (s, 1H), 3.55 (s, 2H), 2.79 (d, J=4.9 Hz, 3H).

Step 2: Synthesis of 8-cyclopentyl-1'-methyl-2-(methylthio)-5H-spiro[pyrido[2,3-d]pyrimidine-6,3'-pyrrolidine]-2',5',7(8H)-trione (48E)

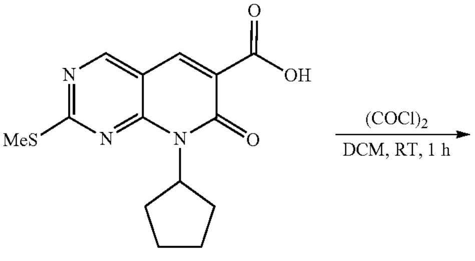

1-C

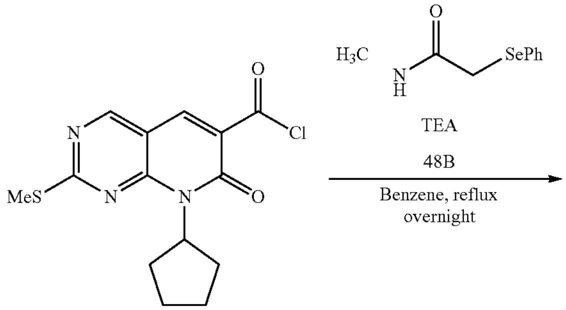

48C

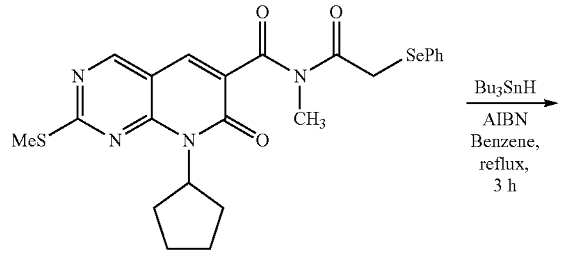

48D

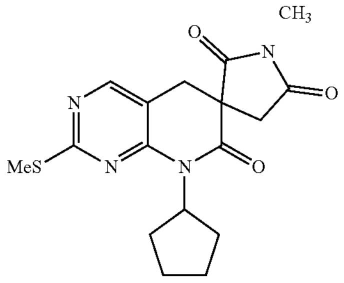

48E

Synthesis of compound 48C: (Ref: Takeuchi et al., *Tetrahedron* 45(20): 6375-6386 (1989)): To a stirred solution of Compound 1-C (10 g, 32.7 mmol) in DCM (100 mL) was added oxalyl chloride (8.4 mL, 98.1 mmol) dropwise at room temperature under argon. To this mixture was added catalytic amount of DMF (0.8 mL) and stirring is continued for 2 h. The reaction mixture was concentrated to dryness to afford acid chloride 48C.

Synthesis of compound 48D: To a solution of compound 48C in anhydrous benzene (150 mL) was added compound 48B (7.5 g, 32.7 mmol) and triethyl amine (4.6 mL, 32.7 mmol) under Argon. The reaction mixture was heated at 80° C. for 2 h. After cooling down to room temperature, the mixture was filtered, and the filtrate was evaporated under reduced pressure. Further purification by column chromatography (0 to 20% ethyl acetate in hexanes) gave compound 48D (8.6 g, 51% yield) as a gummy liquid. MS(ESI) m/z 517.1 $[M+H]^+$. $^1H$ NMR (600 MHz, Chloroform-d) δ 8.63 (s, 1H), 7.71 (s, 1H), 7.65-7.58 (m, 2H), 7.32-7.27 (m, 3H), 6.00-5.93 (m, 1H), 4.00 (s, 2H), 3.29 (s, 3H), 2.63 (s, 3H), 2.34-2.22 (m, 2H), 2.12-2.01 (m, 2H), 1.97-1.84 (m, 2H), 1.74-1.63 (m, 2H).

Synthesis of spiro compound 48E: Prepared using the procedure described for the synthesis of compound spiro compound I-H. Yield: 2.5 g, 42%. MS(ESI) m/z 361.1 $[M+H]^+$. $^1H$ NMR (600 MHz, Chloroform-d) δ 8.19 (s, 1H), 5.43 (p, J=8.8 Hz, 1H), 3.34 (d, J=16.1 Hz, 1H), 3.21 (d, J=18.1 Hz, 1H), 3.03 (s, 3H), 2.90 (d, J=16.0 Hz, 1H), 2.56 (s, 3H), 2.52 (d, J=18.1 Hz, 1H), 2.17-2.02 (m, 2H), 2.03-1.94 (m, 2H), 1.94-1.83 (m, 2H), 1.67-1.59 (m, 2H).

Step 3: Synthesis of 8-cyclopentyl-1'-methyl-2-(methylsulfinyl)-5H-spiro[pyrido[2,3-d]pyrimidine-6,3'-pyrrolidine]-2',5',7(8H)-trione (48F)

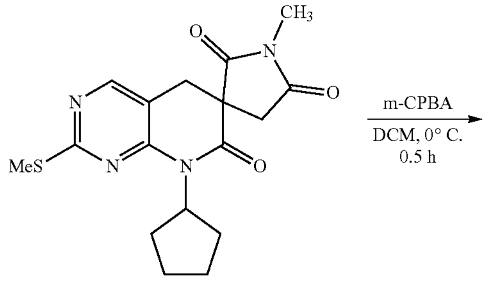

48E

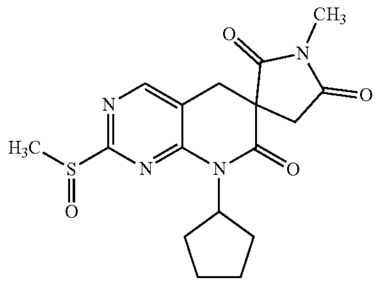

48F

Sulfoxide 48F was prepared from sulfide 48E using the procedure described for the synthesis of compound 1-I. Yield: 1.00 g (96% yield). MS(ESI) m/z 377.2 $^1H$ NMR (600 MHz, Chloroform-d) δ 8.51 (d, J=7.4 Hz, 1H), 5.57-5.42 (m, 1H), 3.48 (d, J=18.0 Hz, 0.5H), 3.43 (d, J=5.5 Hz, 0.5H), 3.40 (d, J=3.5 Hz, 0.5H), 3.36 (d, J=13.5 Hz, 0.5H), 3.14 (t, J=16.3 Hz, 1H), 3.01 (d, J=6.2 Hz, 3H), 2.97 (d, J=5.0 Hz, 3H), 2.58 (d, J=18.1 Hz, 1H), 2.15-2.07 (m, 1H), 2.07-1.97 (m, 4H), 1.97-1.87 (m, 3H).

Step 4: Synthesis of 8-cyclopentyl-1'-methyl-2-((4-(piperazin-1-yl)phenyl)amino)-5,8-dihydro-7H-spiro[pyrido[2,3-d]pyrimidine-6,3'-pyrrolidine]-2',5',7-trione (Compound D20)

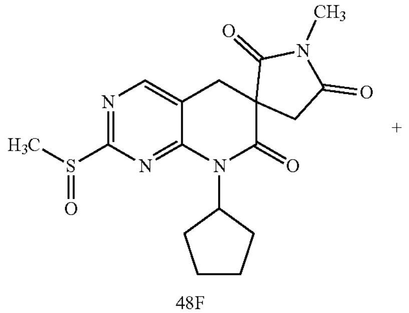

48F

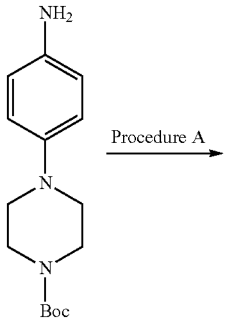

2

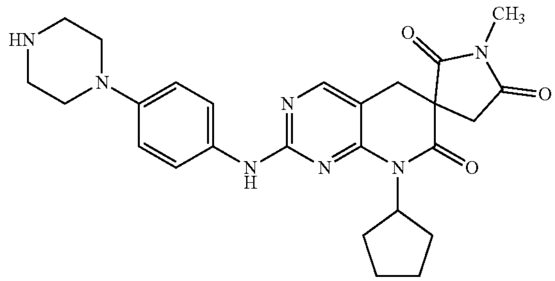

Compound D20

Compound D20 was synthesized from sulfoxide 48F, following the general procedure A, 4 mg (6% yield). MS(ESI) m/z 490.3 $(M+H)^+$. $^1H$ NMR (600 MHz, Chloroform-d) δ 8.05 (s, 1H), 7.43 (d, J=8.9 Hz, 2H), 6.99 (s, 1H), 6.93 (d, J=8.9 Hz, 2H), 5.37 (p, J=8.5 Hz, 1H), 3.33 (d, J=15.7 Hz, 1H), 3.17-3.12 (m, 4H), 3.11-3.07 (m, 4H), 3.04 (s, 3H), 2.80 (d, J=15.7 Hz, 1H), 2.54 (d, J=18.1 Hz, 1H), 2.18-2.09 (m, 1H), 2.06-1.99 (m, 1H), 1.94-1.81 (m, 5H), 1.57 (s, 2H).

Example 38: Compound D21

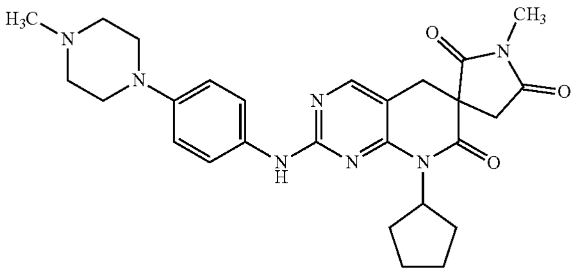 [SMILES: CN1CCN(c2ccc(Nc3ncc4c(n3)N(C3CCCC3)C(=O)C3(CC(=O)N(C)C3=O)C4)cc2)CC1]

Synthesis of 8-cyclopentyl-1'-methyl-2-((4-(4-methylpiperazin-1-yl)phenyl)amino)-5,8-dihydro-7H-spiro[pyrido[2,3-d]pyrimidine-6,3'-pyrrolidine]-2',5',7-trione (Compound D21)

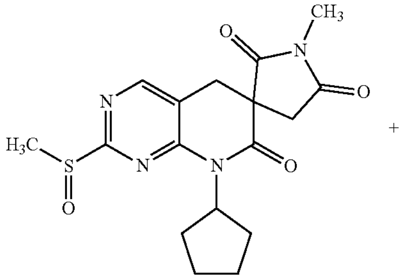

48F

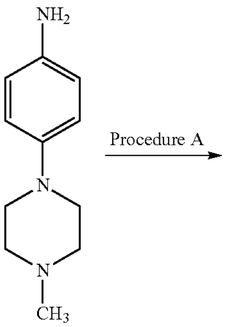

1

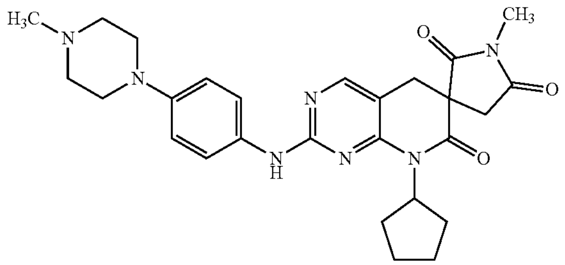

Compound D21

Compound D21 was synthesized from sulfoxide 48F, following the general procedure A, 8 mg (13% yield). MS(ESI) m/z 504.3 $(M+H)^+$. $^1H$ NMR (600 MHz, Chloroform-d) δ 8.05 (s, 1H), 7.41 (d, J=8.9 Hz, 2H), 6.93 (d, J=9.0 Hz, 2H), 6.90 (s, 1H), 5.36 (p, J=8.6 Hz, 1H), 3.33 (d, J=15.7 Hz, 1H), 3.23-3.16 (m, 4H), 3.11 (d, J=18.1 Hz, 1H), 3.04 (s, 3H), 2.79 (d, J=15.7 Hz, 1H), 2.65-2.57 (m, 4H), 2.53 (d, J=18.1 Hz, 1H), 2.37 (s, 3H), 2.19-2.09 (m, 1H), 2.08-1.98 (m, 1H), 1.95-1.80 (m, 4H), 1.62-1.52 (m, 2H).

Example 39: Compound D22

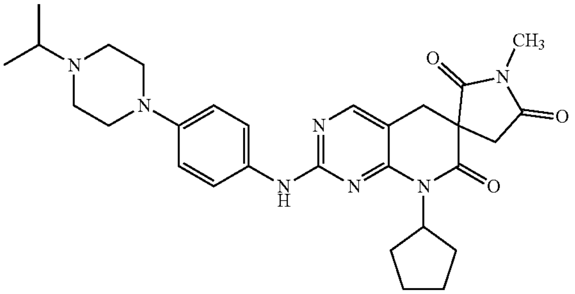 [SMILES: CC(C)N1CCN(c2ccc(Nc3ncc4c(n3)N(C3CCCC3)C(=O)C3(CC(=O)N(C)C3=O)C4)cc2)CC1]

Synthesis of 8-cyclopentyl-2-((4-(4-isopropylpiperazin-1-yl)phenyl)amino)-1'-methyl-5,8-dihydro-7H-spiro[pyrido[2,3-d]pyrimidine-6,3'-pyrrolidine]-2',5',7-trione (Compound D22)

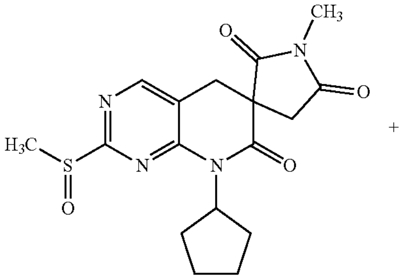

48F

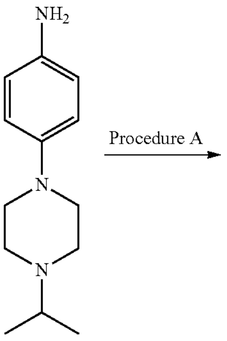

12

-continued

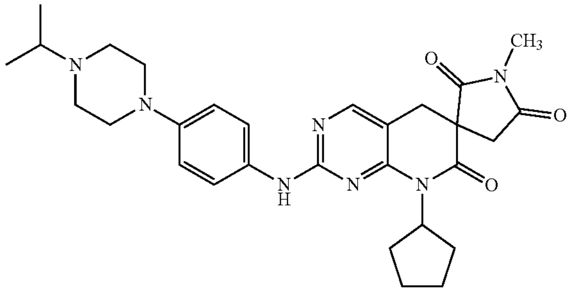

Compound D22

Compound D22 was synthesized from sulfoxide 48F and following the general procedure A, 8 mg (12% yield). MS(ESI) m/z 532.3 $(M+H)^+$. $^1H$ NMR (600 MHz, Chloroform-d) δ 8.04 (s, 1H), 7.41 (d, J=8.9 Hz, 2H), 6.99 (s, 1H), 6.93 (d, J=9.0 Hz, 2H), 5.36 (p, J=8.7 Hz, 1H), 3.32 (d, J=15.8 Hz, 1H), 3.23-3.17 (m, 4H), 3.10 (d, J=18.1 Hz, 1H), 3.04 (s, 3H), 2.79 (d, J=15.7 Hz, 1H), 2.77-2.69 (m, 5H), 2.53 (d, J=18.1 Hz, 1H), 2.18-2.09 (m, 1H), 2.04-1.99 (m, 1H), 1.93-1.80 (m, 4H), 1.62-1.53 (m, 2H), 1.11 (d, J=6.5 Hz, 6H).

Example 40: Compound D23

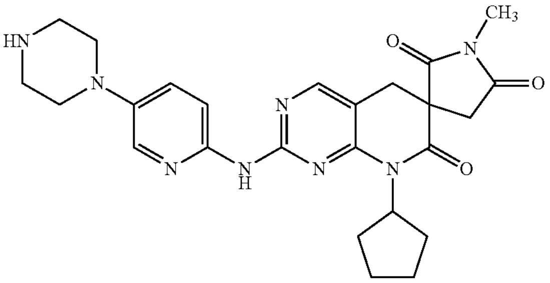 [SMILES: CN1C(=O)CC2(Cc3cnc(Nc4ccc(N5CCNCC5)cn4)nc3N(C3CCCC3)C2=O)C1=O]

Synthesis of 8-cyclopentyl-1'-methyl-2-((5-(piperazin-1-yl)pyridin-2-yl)amino)-5,8-dihydro-7H-spiro[pyrido[2,3-d]pyrimidine-6,3'-pyrrolidine]-2',5',7-trione (Compound D23)

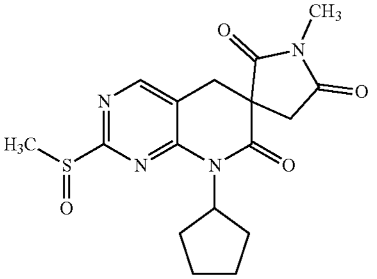

48F

+

-continued

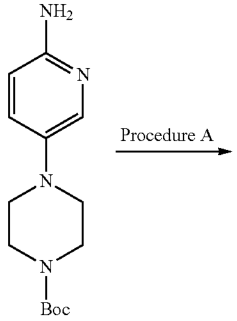

1

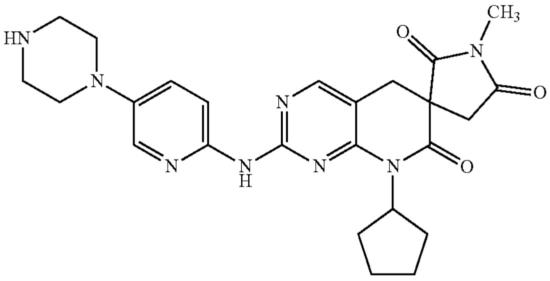

Compound D23

Compound D23 was synthesized from sulfoxide 48F and following the general procedure A, 3 mg (5% yield). MS(ESI) m/z 491.3 $(M+H)^+$. $^1H$ NMR (600 MHz, Chloroform-d) δ 8.03 (s, 1H), 7.77 (d, J=2.6 Hz, 1H), 7.28-7.27 (m, 1H), 6.53 (d, J=8.8 Hz, 1H), 5.37 (q, J=8.8 Hz, 1H), 4.02-3.92 (m, 4H), 3.31 (d, J=15.6 Hz, 1H), 3.12-3.08 (m, 4H), 3.07 (s, 1H), 3.04 (s, 3H), 2.76 (d, J=15.6 Hz, 1H), 2.53 (d, J=18.1 Hz, 1H), 2.09-2.00 (m, 2H), 1.95 (s, 3H), 1.91-1.82 (m, 3H).

Example 41: Compound D24

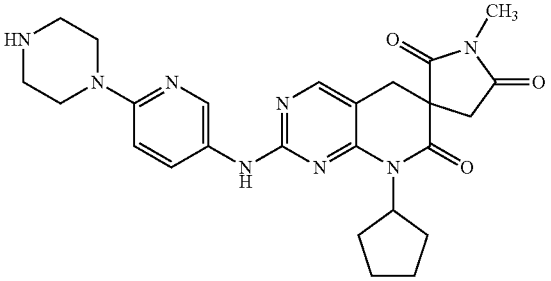 [SMILES: CN1C(=O)CC2(Cc3cnc(Nc4ccc(N5CCNCC5)nc4)nc3N(C3CCCC3)C2=O)C1=O]

Synthesis of 8-cyclopentyl-1'-methyl-2-((6-(piperazin-1-yl)pyridin-3-yl)amino)-5,8-dihydro-7H-spiro[pyrido[2,3-d]pyrimidine-6,3'-pyrrolidine]-2',5',7-trione (Compound D24)

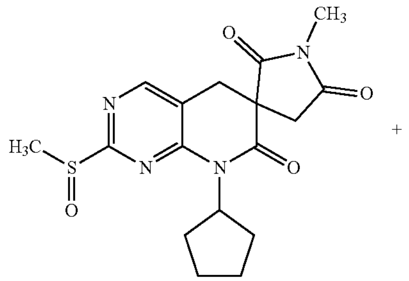

48F

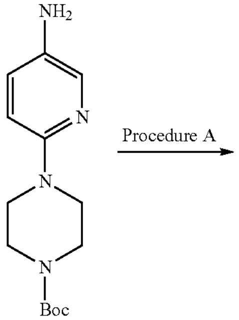

4

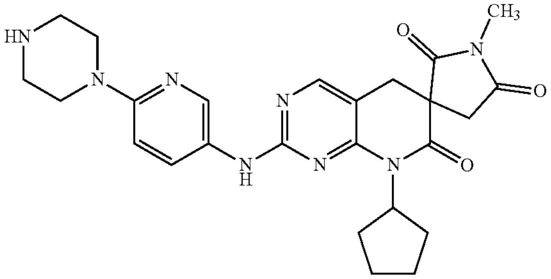

Compound D24

Compound D24 was synthesized from sulfoxide 48F and following the general procedure A, 2 mg (3% yield). MS(ESI) m/z 491.3 $(M+H)^+$. $^1H$ NMR (600 MHz, Chloroform-d) δ 8.24 (d, J=2.6 Hz, 1H), 8.03 (s, 1H), 7.77 (dd, J=9.1, 2.7 Hz, 1H), 6.76 (s, 1H), 6.67 (d, J=9.1 Hz, 1H), 5.34 (d, J=8.7 Hz, 1H), 3.51-3.45 (m, 3H), 3.31 (d, J=15.7 Hz, 1H), 3.13 (d, J=18.2 Hz, 1H), 3.04 (s, 2H), 3.03-2.99 (m, 3H), 2.81 (d, J=15.7 Hz, 1H), 2.53 (d, J=18.2 Hz, 1H), 2.09 (s, 2H), 2.05-1.99 (m, 1H), 1.86 (s, 4H), 1.30-1.24 (m, 2H), 0.91-0.78 (m, 2H).

Example 42: Compound D25

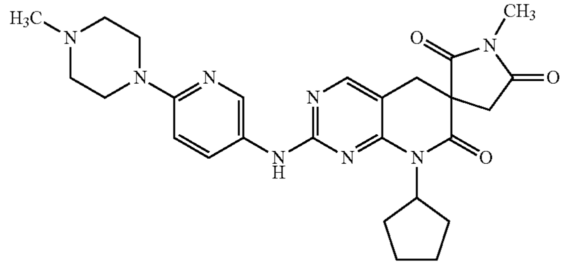 [SMILES: CN1CCN(c2ccc(Nc3ncc4c(n3)N(C3CCCC3)C(=O)C3(CC(=O)N(C)C3=O)C4)cn2)CC1]

Synthesis of 8-cyclopentyl-1'-methyl-2-((6-(4-methylpiperazin-1-yl)pyridin-3-yl)amino)-5,8-dihydro-7H-spiro[pyrido[2,3-d]pyrimidine-6,3'-pyrrolidine]-2',5',7-trione (Compound D25)

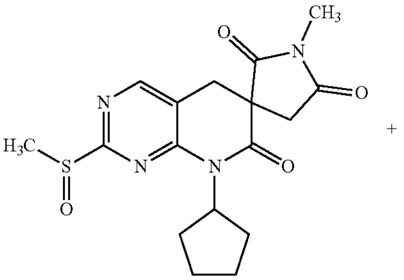

48F

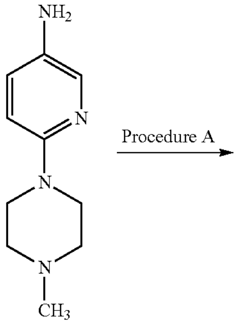

5

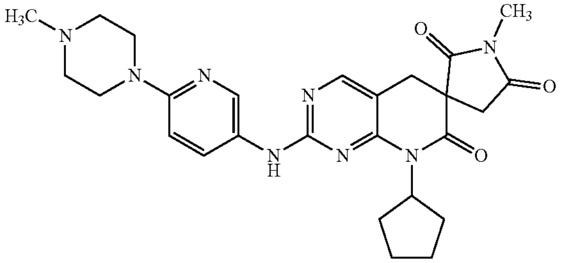

Compound D25

Compound D25 was synthesized from sulfoxide 48F and following the general procedure A, 26 mg (41% yield). MS(ESI) m/z 505.3 $(M+H)^+$. $^1H$ NMR (600 MHz, Chloroform-d) δ 8.29 (d, J=2.6 Hz, 1H), 8.04 (s, 1H), 7.83 (dd, J=9.0, 2.6 Hz, 1H), 6.91 (s, 1H), 6.70 (d, J=9.0 Hz, 1H), 5.33 (p, J=8.6 Hz, 1H), 3.73 (s, 4H), 3.31 (d, J=15.8 Hz, 1H), 3.17

(d, J=18.1 Hz, 1H), 3.03 (s, 3H), 2.95 (s, 3H), 2.83 (d, J=15.7 Hz, 1H), 2.63 (s, 3H), 2.53 (d, J=18.1 Hz, 1H), 2.14-2.08 (m, 1H), 2.06-2.00 (m, 1H), 1.93-1.80 (m, 5H), 1.62-1.53 (m, 2H).

Example 43: Compound D26

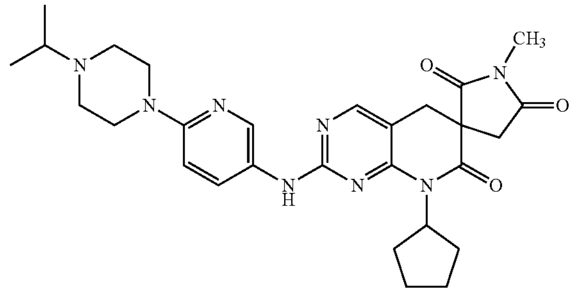 [SMILES: CC(C)N1CCN(c2ccc(Nc3ncc4c(n3)N(C3CCCC3)C(=O)C3(CC(=O)N(C)C3=O)C4)cn2)CC1]

Synthesis of 8-cyclopentyl-2-((6-(4-isopropylpiperazin-1-yl)pyridin-3-yl)amino)-1'-methyl-5,8-dihydro-7H-spiro[pyrido[2,3-d]pyrimidine-6,3'-pyrrolidine]-2',5',7-trione (Compound D26)

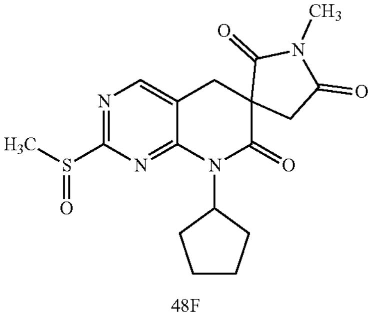

48F

+

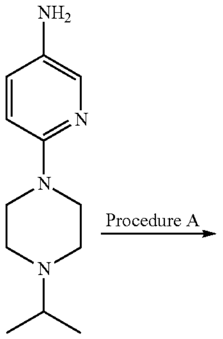

13

-continued

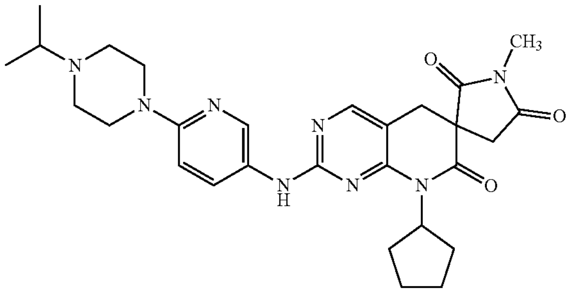

Compound D26

Compound D26 was synthesized from sulfoxide 48F and following the general procedure A, 9 mg (13% yield). MS(ESI) m/z 533.3 $(M+H)^+$. $^1$H NMR (600 MHz, Chloroform-d) δ 8.26 (d, J=2.6 Hz, 1H), 8.04 (s, 1H), 7.80 (dd, J=8.9, 2.3 Hz, 1H), 6.79 (s, 1H), 6.68 (d, J=9.0 Hz, 1H), 5.33 (p, J=8.6 Hz, 1H), 3.67 (s, 4H), 3.31 (d, J=15.7 Hz, 1H), 3.15 (d, J=18.1 Hz, 1H), 3.04 (s, 3H), 2.86 (s, 3H), 2.82 (d, J=15.7 Hz, 1H), 2.53 (d, J=18.1 Hz, 1H), 2.16-2.07 (m, 1H), 2.07-2.00 (m, 1H), 1.93-1.79 (m, 4H), 1.61-1.53 (m, 3H), 1.31-1.10 (m, 7H).

Example 44: Compound D27

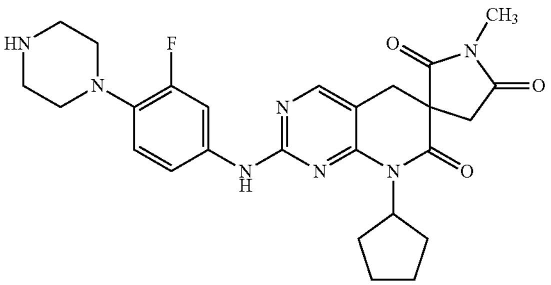 [SMILES: CN1C(=O)CC2(Cc3cnc(Nc4ccc(N5CCNCC5)c(F)c4)nc3N(C3CCCC3)C2=O)C1=O]

Synthesis of 8-cyclopentyl-2-((3-fluoro-4-(piperazin-1-yl)phenyl)amino)-1'-methyl-5,8-dihydro-7H-spiro[pyrido[2,3-d]pyrimidine-6,3'-pyrrolidine]-2',5',7-trione (Compound D27)

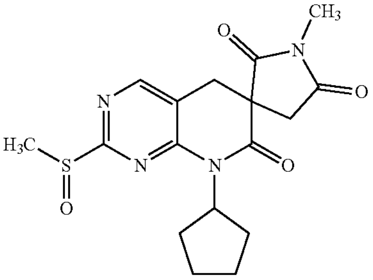

48F

+

-continued

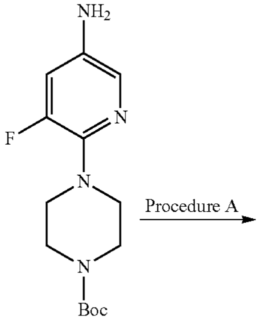

6

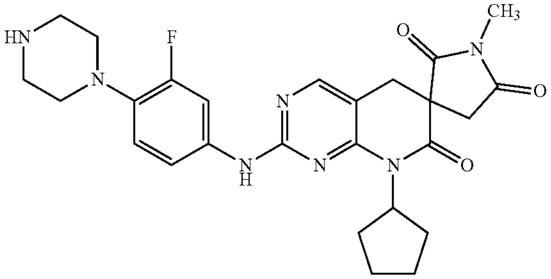

Compound D27

Compound D27 was synthesized from sulfoxide 48F and following the general procedure A, 4 mg (6% yield). MS(ESI) m/z 508.3 $(M+H)^+$. $^1$H NMR (600 MHz, Chloroform-d) δ 8.08 (s, 1H), 7.58 (dd, J=14.5, 2.3 Hz, 1H), 7.10-7.01 (m, 2H), 6.92 (t, J=9.0 Hz, 1H), 5.37 (p, J=8.7 Hz, 1H), 3.33 (d, J=15.8 Hz, 1H), 3.16 (d, J=18.1 Hz, 1H), 3.10-3.06 (m, 3H), 3.05 (s, 2H), 3.04 (s, 4H), 2.84 (d, J=15.7 Hz, 1H), 2.54 (d, J=18.1 Hz, 1H), 2.20-2.10 (m, 1H), 2.08 (s, 1H), 2.06-2.01 (m, 1H), 1.98-1.83 (m, 4H), 1.25 (s, 1H), 0.91-0.76 (m, 2H).

Example 45: Compound D28

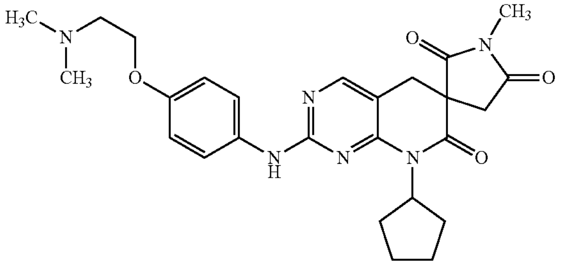 [SMILES: CN(C)CCOc1ccc(Nc2ncc3c(n2)N(C2CCCC2)C(=O)C2(CC(=O)N(C)C2=O)C3)cc1]

Synthesis of 8-cyclopentyl-2-((4-(2-(dimethylamino)ethoxy)phenyl)amino)-1'-methyl-5,8-dihydro-7H-spiro[pyrido[2,3-d]pyrimidine-6,3'-pyrrolidine]-2',5',7-trione (Compound D28)

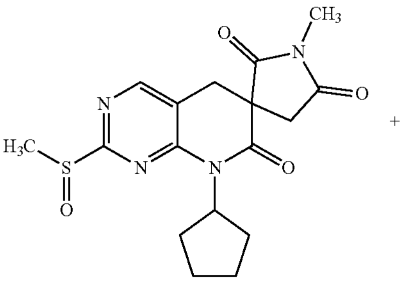

48F

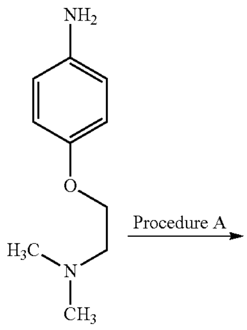

8

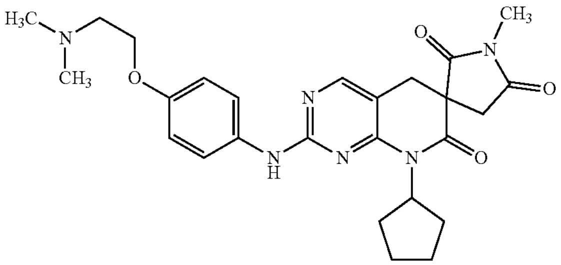

Compound D28

Compound D28 was synthesized from sulfoxide 48F and following the general procedure A, 40 mg (66% yield). MS(ESI) m/z 493.3 $(M+H)^+$. $^1$H NMR (600 MHz, Chloroform-d) δ 8.06 (s, 1H), 7.44 (d, J=8.9 Hz, 2H), 6.93 (s, 1H), 6.92-6.89 (m, 2H), 5.37 (q, J=8.8 Hz, 1H), 4.17 (t, J=5.3 Hz, 2H), 3.32 (d, J=15.8 Hz, 1H), 3.13 (d, J=18.1 Hz, 1H), 3.04 (s, 3H), 2.99 (s, 2H), 2.81 (d, J=15.7 Hz, 1H), 2.55 (s, 7H), 2.17-2.09 (m, 1H), 2.09-1.98 (m, 1H), 1.96-1.80 (m, 4H), 1.63-1.54 (m, 2H).

Example 46: Compound D29

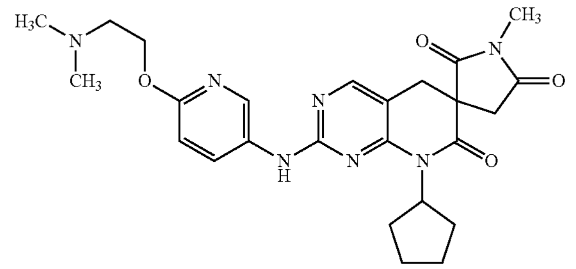 [SMILES: CN(C)CCOc1ccc(Nc2ncc3c(n2)N(C2CCCC2)C(=O)C2(CC(=O)N(C)C2=O)C3)cn1]

Synthesis of 8-cyclopentyl-2-((6-(2-(dimethylamino)ethoxy)pyridin-3-yl)amino)-1'-methyl-5,8-dihydro-7H-spiro[pyrido[2,3-d]pyrimidine-6,3'-pyrrolidine]-2',5',7-trione (Compound D29)

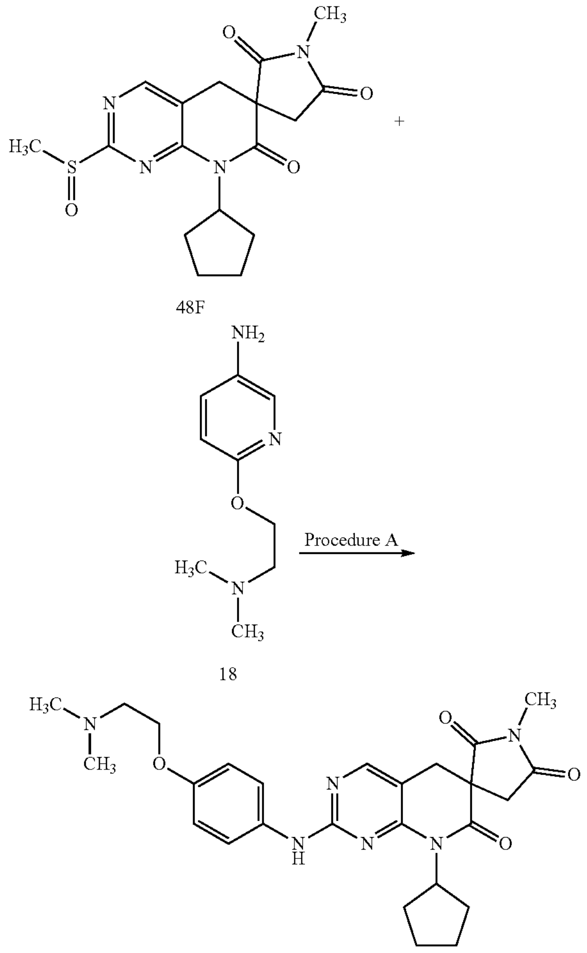

48F

18

Compound D28

Compound D29 was synthesized from sulfoxide 48F and following the general procedure A, 2 mg (3% yield). MS(ESI) m/z 494.3 $(M+H)^+$. $^1H$ NMR (600 MHz, Chloroform-d) δ 8.22 (d, J=2.6 Hz, 1H), 8.05 (s, 1H), 7.86 (dd, J=8.8, 2.6 Hz, 1H), 6.91 (s, 1H), 6.80 (d, J=8.9 Hz, 1H), 5.33 (p, J=8.6, 8.2 Hz, 1H), 4.43 (t, J=5.4 Hz, 2H), 3.31 (d, J=15.7 Hz, 1H), 3.16 (d, J=18.1 Hz, 1H), 3.04 (s, 3H), 2.84 (d, J=15.7 Hz, 1H), 2.79 (s, 2H), 2.53 (d, J=18.1 Hz, 1H), 2.39 (s, 6H), 2.14-2.08 (m, 1H), 2.06-1.99 (m, 1H), 1.97-1.62 (m, 4H), 1.62-1.53 (m, 2H).

Example 47: Compound D30

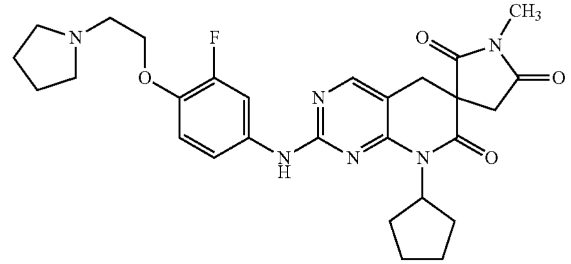 [SMILES: CN1C(=O)CC2(Cc3cnc(Nc4ccc(OCCN5CCCC5)c(F)c4)nc3N(C3CCCC3)C2=O)C1=O]

Synthesis of 8-cyclopentyl-2-((3-fluoro-4-(2-(pyrrolidin-1-yl)ethoxy)phenyl)amino)-1'-methyl-5,8-dihydro-7H-spiro[pyrido[2,3-d]pyrimidine-6,3'-pyrrolidine]-2',5',7-trione (Compound D30)

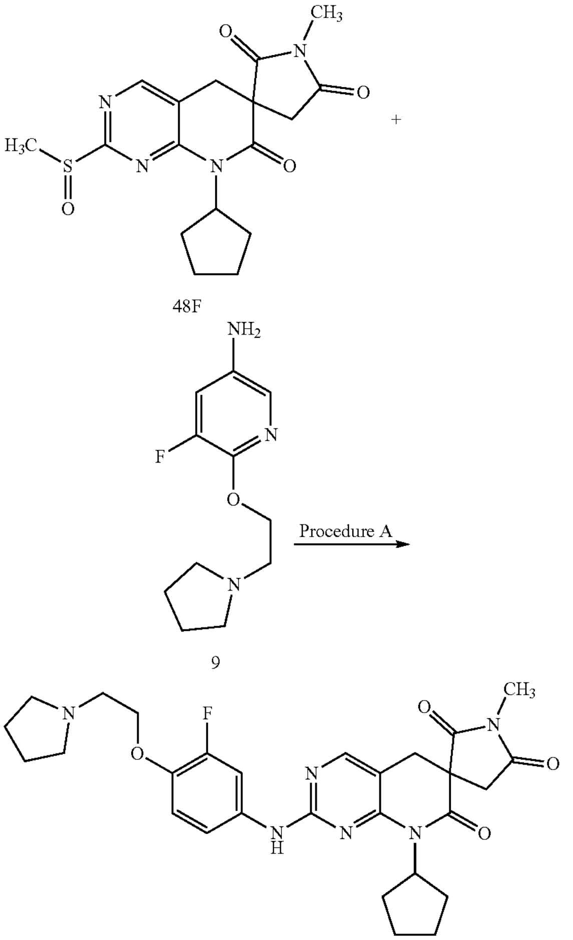

48F

9

Compound D30

Compound D30 was synthesized from sulfoxide 48F and following the general procedure A, 6 mg (9% yield). MS(ESI) m/z 537.3 $(M+H)^+$. $^1H$ NMR (600 MHz, Chloroform-d) δ 8.07 (s, 1H), 7.64 (dd, J=13.3, 2.5 Hz, 1H), 7.24 (s, 1H), 7.11-7.02 (m, 1H), 6.95 (t, J=9.0 Hz, 1H), 5.37 (p, J=8.7 Hz, 1H), 4.31 (t, J=5.2 Hz, 2H), 3.32 (d, J=16.1 Hz, 1H), 3.27 (s, 2H), 3.17 (d, J=18.1 Hz, 1H), 3.10 (s, 4H), 3.04 (s, 3H), 2.85 (d, J=15.8 Hz, 1H), 2.54 (d, J=18.1 Hz, 1H), 2.17-2.09 (m, 1H), 2.07 (d, J=7.8 Hz, 1H), 2.02-1.96 (m, 4H), 1.96-1.85 (m, 4H), 1.66-1.57 (m, 2H).

Example 48: Compound D31

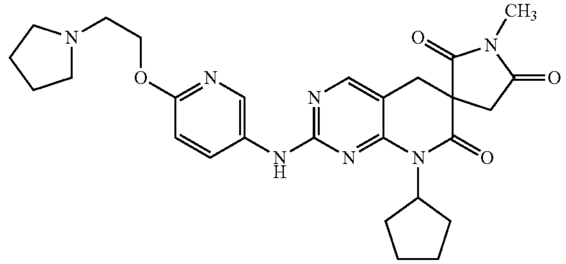 [SMILES: CN1C(=O)CC2(Cc3cnc(Nc4ccc(OCCN5CCCC5)nc4)nc3N(C3CCCC3)C2=O)C1=O]

Synthesis of 8-cyclopentyl-1'-methyl-2-((6-(2-(pyrrolidin-1-yl)ethoxy)pyridin-3-yl)amino)-5,8-dihydro-7H-spiro[pyrido[2,3-d]pyrimidine-6,3'-pyrrolidine]-2',5',7-trione (Compound D31)

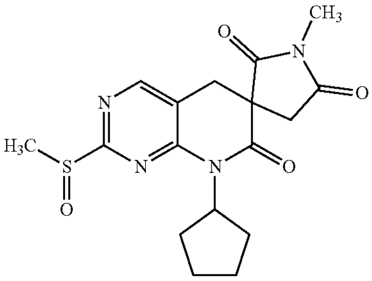

48F

+

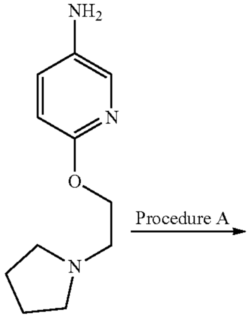

19

Procedure A

-continued

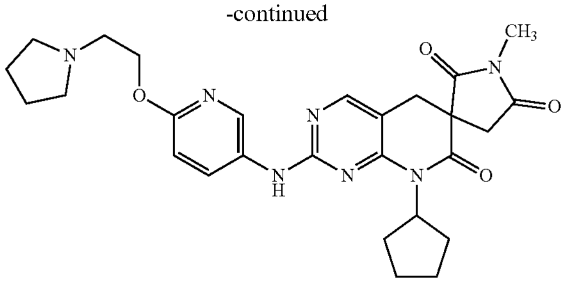

Compound D31

Compound D31 was synthesized from sulfoxide 48F and following the general procedure A, 14 mg (21% yield). MS(ESI) m/z 520.3 $(M+H)^+$. $^1H$ NMR (600 MHz, Chloroform-d) δ 8.23 (d, J=2.6 Hz, 1H), 8.05 (s, 1H), 7.90 (dd, J=8.8, 2.7 Hz, 1H), 7.03 (s, 1H), 6.78 (d, J=8.8 Hz, 1H), 5.33 (p, J=8.7 Hz, 1H), 4.67-4.56 (m, 2H), 3.34 (s, 1H), 3.31 (d, J=15.9 Hz, 1H), 3.18 (d, J=18.1 Hz, 1H), 3.03 (s, 3H), 2.85 (d, J=15.8 Hz, 1H), 2.54 (d, J=18.1 Hz, 1H), 2.17 (s, 3H), 2.14-2.08 (m, 1H), 2.03 (s, 5H), 1.94-1.81 (m, 6H), 1.62-1.53 (m, 2H).

Example 4

Enantiomeric Examples

Step 1: Separation of two enantiomers of tert-butyl 8-cyclopentyl-2-(methylthio)-2',7-dioxo-7,8-dihydro-5H-spiro[pyrido[2,3-d]pyrimidine-6,3'-pyrrolidine]-1'-carboxylate (1-H Analytical Chiral Column Chromatography Column: ChiralPak IC 4.6×250 mm 5 μm; Mobile Phase: Acetonitrile Flow Rate: 1.0 mL/min; wavelengths: 254 nm and 280 nm Retention Times ($t_R$): 5.06 min. (Enantiomer-1, E1), 8.95 min. (Enantiomer-2, E2)

Preparative Chiral Chromatography Conditions

Column: Chiralpak IC 21×250 mm, 5 micron; Mobile phase: Acetonitrile; Flow rate: 4 mL/min; Wavelength: 254 nm Standard chromatographic techniques were used to isolate the required two enantiomers, E1 and E2 as off-white solids (concentrated and lyophilized).

About 10 g of racemic 1-H was used to isolate the following amounts:

Enantiomer-1 (E1): Yield: 4.25 g (42%), Purity: >98%; Optical purity: % ee>99%

Enantiomer-2 (E2): Yield: 4.35 g (43%); Purity: >98%; Optical purity: % ee>99%

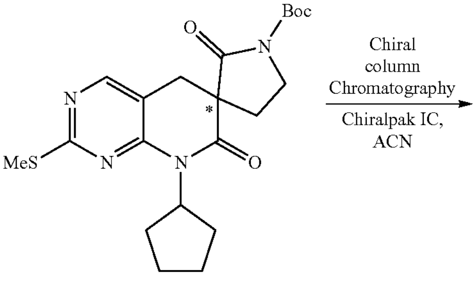

Racemic (1-H)

-continued

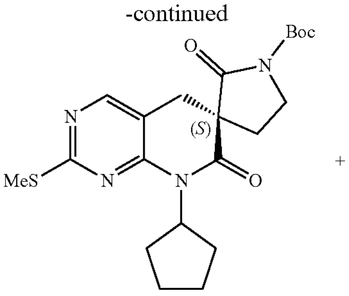

Enantiomer-1
(E1), $t_R$: 5.06 min

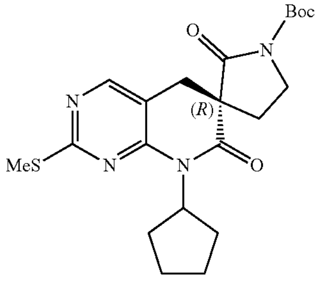

Enantiomer-2
(E2), $t_R$: 8.95 min

Synthesis of tert-butyl 8-cyclopentyl-2-(methylsulfinyl)-2',7-dioxo-7,8-dihydro-5H-spiro[pyrido[2,3-d]pyrimidine-6,3'-pyrrolidine]-1'-carboxylate (E1-sulfoxide)

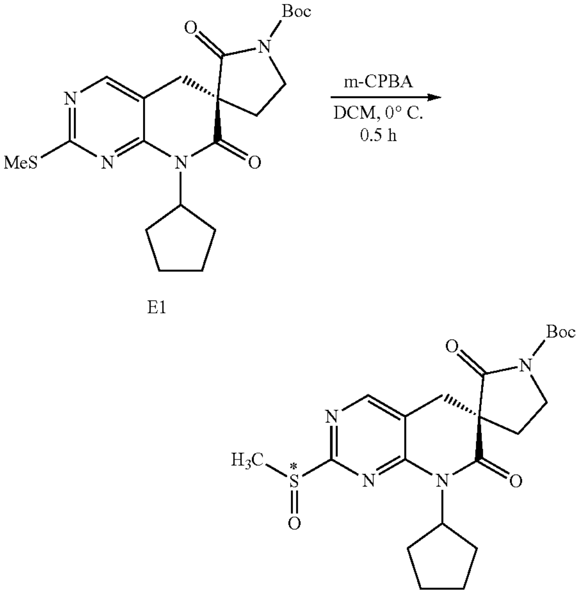

E1

E1-sulfoxide

E1-sulfoxide (diastereomers) was synthesized according to the procedure described for making racemic sulfoxide 1-I. Yield: 750 mg (97%)

MS(ESI) m/z 449.2 $(M+H)^+$. $^1$H NMR (600 MHz, Chloroform-d) δ 8.50 (d, J=13.1 Hz, 1H), 5.45 (dp, J=17.6, 9.0 Hz, 1H), 3.94-3.75 (m, 2H), 3.51-3.35 (m, 1H), 2.94 (s, 3H), 2.92-2.87 (m, 1H), 2.56 (ddd, J=13.0, 7.6, 3.7 Hz, 0.5H), 2.49 (ddd, J=13.0, 7.4, 3.7 Hz, 0.5H), 2.15-1.95 (m, 4H), 1.95-1.83 (m, 3H), 1.69 (s, 2H), 1.53 (s, 9H).

Synthesis of tert-butyl 8-cyclopentyl-2-(methylsulfinyl)-2',7-dioxo-7,8-dihydro-5H-spiro[pyrido[2,3-d]pyrimidine-6,3'-pyrrolidine]-1'-carboxylate (E2-sulfoxide)

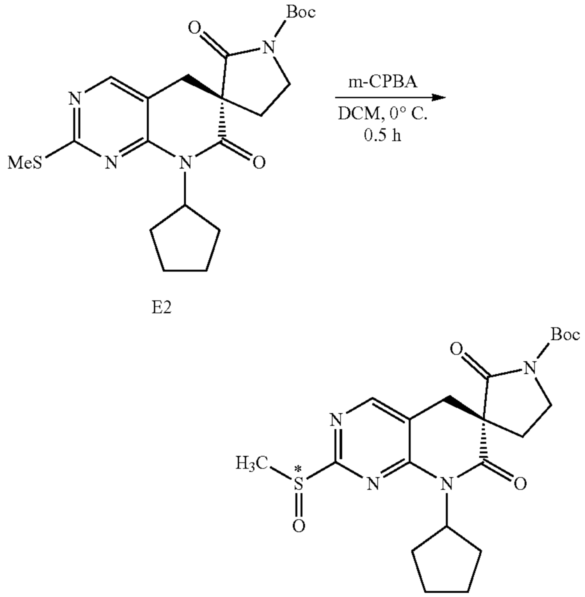

E2

E2-sulfoxide

E2-sulfoxide (diastereomers) were synthesized according to the procedure described for making racemic sulfoxide 1-I. Yield: 760 mg (98%).

MS(ESI) m/z 449.2 $(M+H)^+$. $^1$H NMR (600 MHz, Chloroform-d) δ 8.50 (d, J=13.0 Hz, 1H), 5.45 (dp, J=17.5, 9.1 Hz, 1H), 3.95-3.76 (m, 2H), 3.47-3.37 (m, 1H), 2.94 (s, 3H), 2.90 (d, J=17.1 Hz, 1H), 2.56 (ddd, J=13.0, 7.6, 3.7 Hz, 0.5H), 2.49 (ddd, J=13.1, 7.4, 3.7 Hz, 0.5H), 2.16-1.95 (m, 4H), 1.94-1.83 (m, 3H), 1.79 (s, 2H), 1.53 (d, J=2.2 Hz, 9H).

Example 1: Compound D49 (E1 of Compound D11)

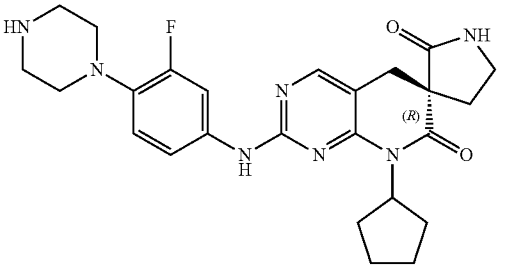

Synthesis of (R)-8-cyclopentyl-2-((3-fluoro-4-(piperazin-1-yl)phenyl)amino)-5,8-dihydro-7H-spiro[pyrido[2,3-d]pyrimidine-6,3'-pyrrolidine]-2',7-dione (Compound D49)

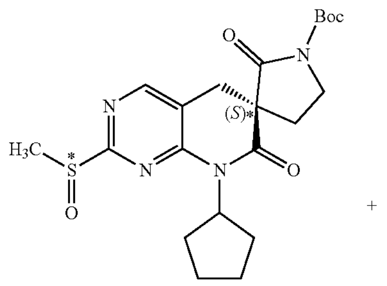

E1-Sulfoxide

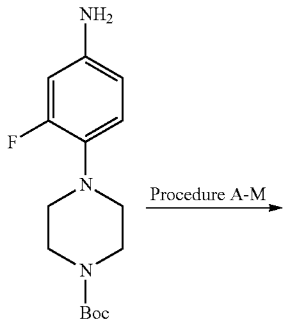

6

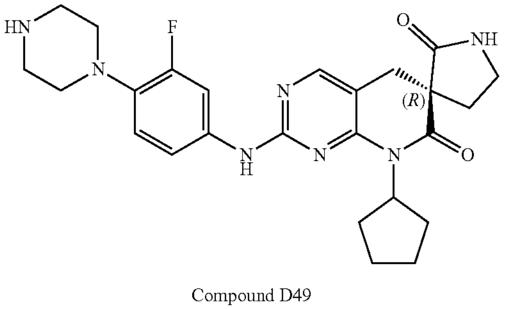

Compound D49

Compound D49 was synthesized starting from E1-sulfoxide, following the general procedure A-M, 32 mg (44% yield). MS(ESI) m/z 480.3 $(M+H)^+$. $^1H$ NMR (600 MHz, DMSO-$d_6$) δ 9.48 (s, 1H), 8.09 (s, 1H), 7.91 (s, 1H), 7.68 (dd, J=15.4, 2.3 Hz, 1H), 7.27 (d, J=7.5 Hz, 1H), 6.97 (t, J=9.4 Hz, 1H), 5.28 (p, J=8.7 Hz, 1H), 3.17-3.13 (m, 6H), 3.10-3.02 (m, 4H), 2.98 (d, J=15.9 Hz, 1H), 2.71 (d, J=15.9 Hz, 1H), 2.38-2.31 (m, 1H), 2.03-1.92 (m, 2H), 1.88-1.78 (m, 3H), 1.78-1.68 (m, 2H), 1.54-1.42 (m, 2H).

Example 2: Compound D50 (E2 of Compound D11)

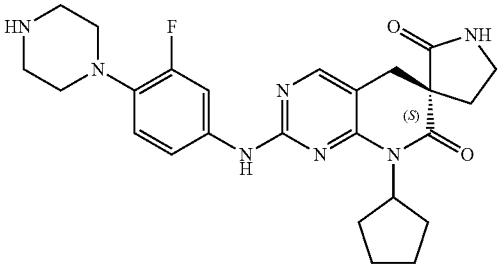

Synthesis of (S)-8-cyclopentyl-2-((3-fluoro-4-(piperazin-1-yl)phenyl)amino)-5,8-dihydro-7H-spiro[pyrido[2,3-d]pyrimidine-6,3'-pyrrolidine]-2',7-dione (Compound D50)

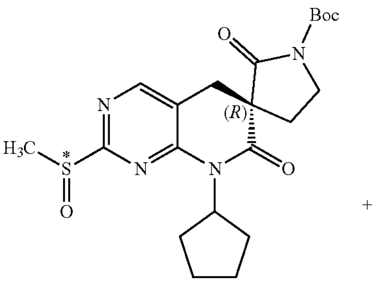

E2-Sulfoxide

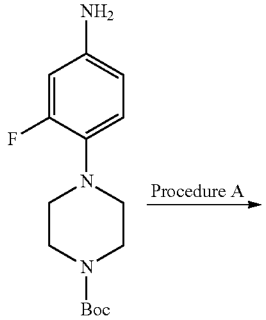

6

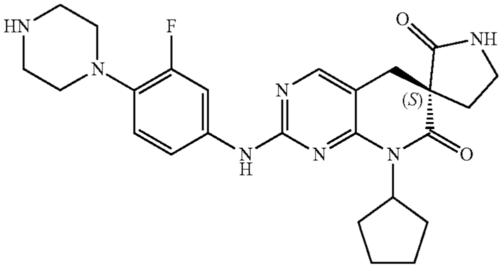

Compound D50

Compound D50 was synthesized starting from E2-sulfoxide following the general procedure A-M, 11 mg (15% yield). MS(ESI) m/z 480.3 $(M+H)^+$. $^1H$ NMR (600 MHz, DMSO-$d_6$) δ 9.47 (s, 1H), 8.09 (s, 1H), 7.91 (s, 1H), 7.67

(dd, J=15.4, 2.3 Hz, 1H), 7.27 (d, J=7.3 Hz, 1H), 6.96 (t, J=9.4 Hz, 1H), 5.28 (p, J=8.8 Hz, 1H), 3.14-3.07 (m, 5H), 3.03 (d, J=4.9 Hz, 4H), 2.98 (d, J=15.9 Hz, 1H), 2.70 (d, J=15.9 Hz, 1H), 2.34 (ddd, J=13.0, 7.8, 5.1 Hz, 1H), 1.98 (ddd, J=15.2, 12.5, 7.8 Hz, 2H), 1.84 (q, J=10.2, 8.2 Hz, 4H), 1.78-1.68 (m, 2H), 1.53-1.43 (m, 2H).

Example 3: Compound D51 (E1 of Compound D12)

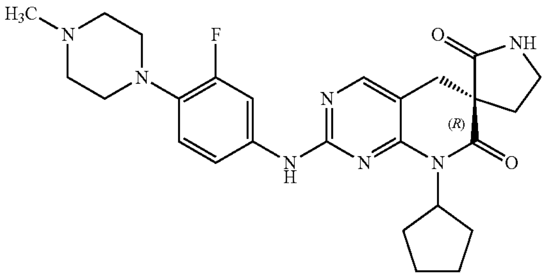

Synthesis of (R)-8-cyclopentyl-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (Compound D51)

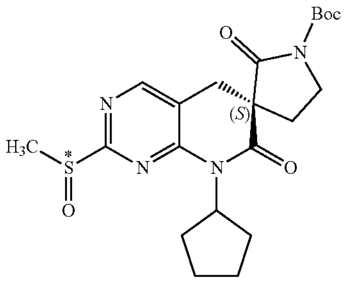

E1-sulfoxide

+

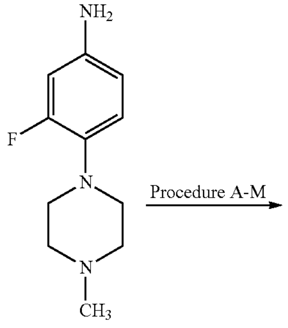

14

-continued

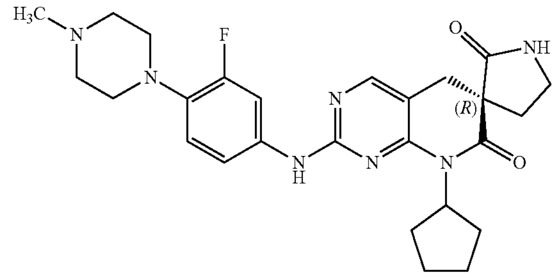

Compound D51

Compound D51 was synthesized starting from E1-sulfoxide, following the general procedure A-M, 18 mg (24% yield). MS(ESI) m/z 494.3 $(M+H)^+$. $^1H$ NMR (600 MHz, DMSO-$d_6$) δ 9.47 (s, 1H), 8.09 (s, 1H), 7.91 (s, 1H), 7.67 (dd, J=15.4, 2.1 Hz, 1H), 7.27 (d, J=7.6 Hz, 1H), 6.96 (t, J=9.4 Hz, 1H), 5.28 (p, J=8.7 Hz, 1H), 3.22-3.12 (m, 4H), 3.07 (s, 4H), 2.98 (d, J=15.9 Hz, 1H), 2.70 (d, J=15.9 Hz, 1H), 2.65 (s, 2H), 2.42 (S, 3H), 2.39-2.30 (m, 1H), 2.05-1.93 (m, 2H), 1.88-1.78 (m, 3H), 1.73 (s, 2H), 1.54-1.43 (m, 2H).

Example 4: Compound D52 (E2 of Compound D12)

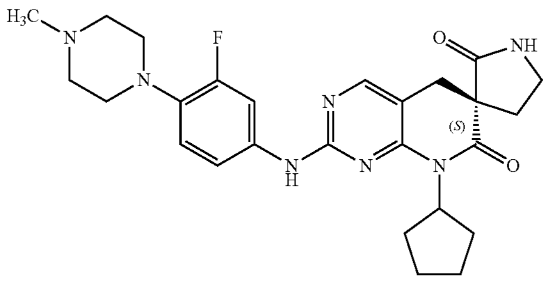

Synthesis of (S)-8-cyclopentyl-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (Compound D52)

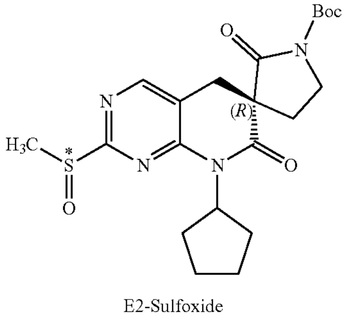

E2-Sulfoxide

+

-continued

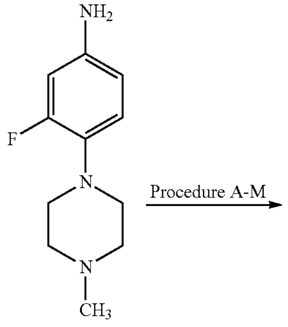

14

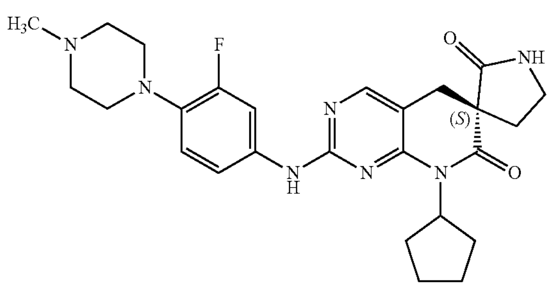

Compound D52

Compound D52 was synthesized starting from E2-sulfoxide following the general procedure A-M, 21 mg (28% yield). MS(ESI) m/z 494.3 $(M+H)^+$. $^1H$ NMR (600 MHz, DMSO-$d_6$) δ 9.48 (s, 1H), 8.09 (s, 1H), 7.91 (s, 1H), 7.68 (dd, J=15.4, 2.2 Hz, 1H), 7.27 (d, J=7.5 Hz, 1H), 6.97 (t, J=9.4 Hz, 1H), 5.28 (p, J=8.7 Hz, 1H), 3.21-3.01 (m, 8H), 2.98 (d, J=15.9 Hz, 1H), 2.76-2.67 (m, 3H), 2.48-2.40 (m, 3H), 2.38-2.30 (m, 1H), 2.03-1.93 (m, 2H), 1.88-1.78 (m, 3H), 1.78-1.68 (m, 2H), 1.52-1.43 (m, 2H).

Example 5: Compound D53 (E1 of Compound D10)

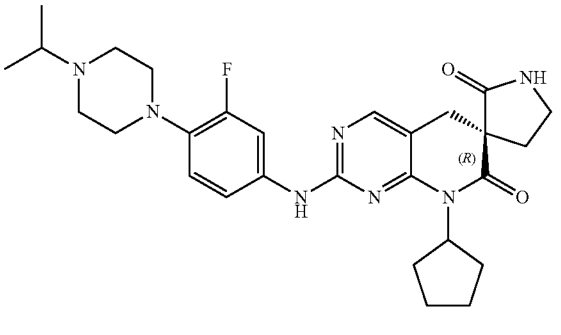

Synthesis of (R)-8-cyclopentyl-2-((3-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (Compound D53)

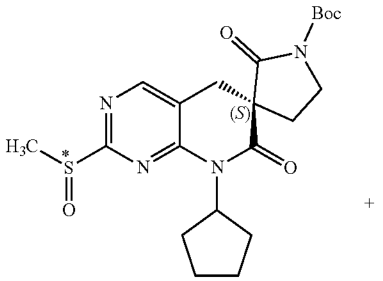

E1-Sulfoxide

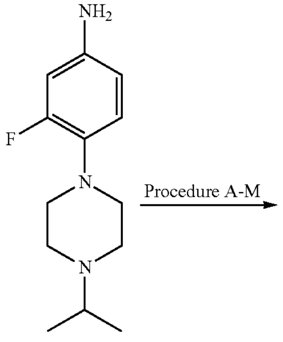

15

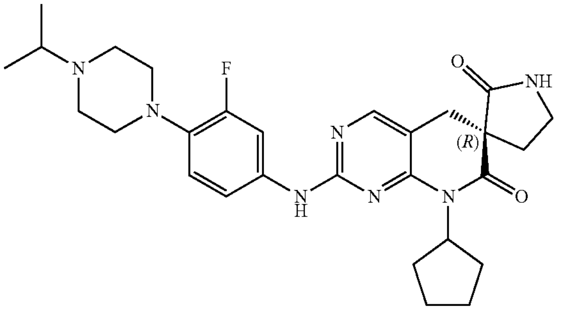

Compound D53

Compound D53 was synthesized starting from E1-sulfoxide following the general procedure A-M, 31 mg (40% yield). MS(ESI) m/z 522.4 $(M+H)^+$. $^1H$ NMR (600 MHz, DMSO-$d_6$) δ 9.55 (s, 1H), 8.16 (s, 1H), 7.98 (s, 1H), 7.76 (d, J=12.6 Hz, 1H), 7.34 (s, 1H), 7.05 (s, 1H), 5.42-5.30 (m, 1H), 3.47 (d, J=27.7 Hz, 4H), 3.29-3.12 (m, 4H), 3.05 (d, J=15.8 Hz, 1H), 3.02 (s, 2H), 2.77 (d, J=15.9 Hz, 1H), 2.46-2.36 (m, 2H), 2.11-1.97 (m, 2H), 1.96-1.84 (m, 3H), 1.84-1.75 (m, 2H), 1.60-1.50 (m, 2H), 1.26 (d, J=6.5 Hz, 6H).

Example 6: Compound D54 (E2 of Compound D10)

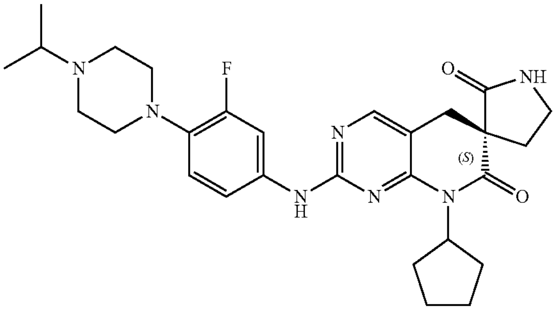

Synthesis of (S)-8-cyclopentyl-2-((3-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (Compound D54)

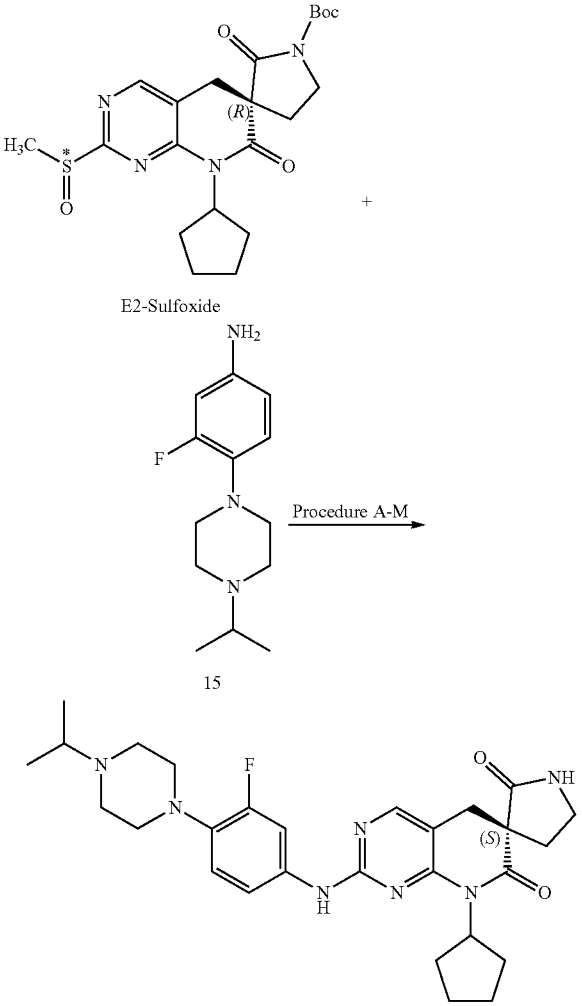

E2-Sulfoxide

15

Compound D54

Compound D54 was synthesized starting from E2-sulfoxide following the general procedure A-M, 16 mg (21% yield). MS(ESI) m/z 522.4 $(M+H)^+$. $^1H$ NMR (600 MHz, DMSO-$d_6$) δ 9.39 (s, 1H), 8.08 (s, 1H), 7.91 (s, 1H), 7.61 (dd, J=15.5, 2.0 Hz, 1H), 7.23 (d, J=8.2 Hz, 1H), 6.88 (t, J=9.4 Hz, 1H), 5.27 (p, J=8.6 Hz, 1H), 3.21-3.10 (m, 3H), 2.98 (d, J=15.8 Hz, 1H), 2.86 (s, 3H), 2.69 (d, J=15.8 Hz, 1H), 2.64-2.56 (m, 1H), 2.51 (s, 4H), 2.36-2.28 (m, 1H), 2.02-1.91 (m, 2H), 1.90-1.77 (m, 3H), 1.72 (s, 2H), 1.53-1.42 (m, 2H), 0.93 (d, J=6.5 Hz, 6H).

Example 7: Compound D55 (E1 of Compound D3)

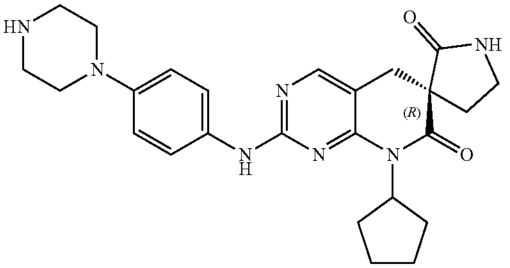

Step 1: Synthesis of (R)-8-cyclopentyl-2-((4-(piperazin-1-yl)phenyl)amino)-5,8-dihydro-7H-spiro[pyrido[2,3-d]pyrimidine-6,3'-pyrrolidine]-2',7-dione (Compound D55)

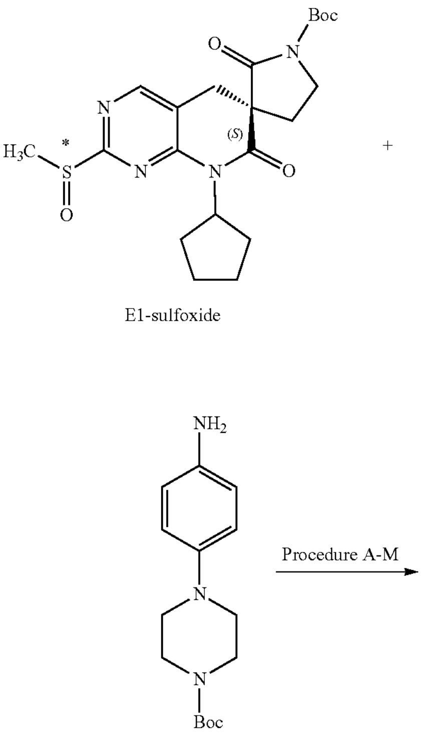

E1-sulfoxide

2

-continued

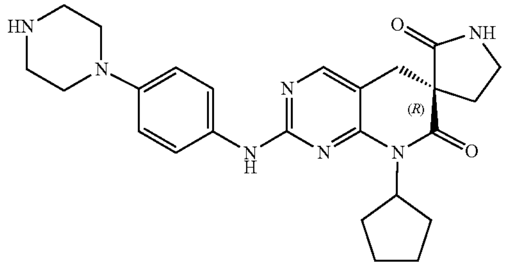

Compound D55

Compound D55 was synthesized starting from E1-sulfoxide, following the general procedure A-M, 40 mg (58% yield). MS(ESI) m/z 462.3 $(M+H)^+$. $^1H$ NMR (600 MHz, DMSO-$d_6$) δ 9.18 (s, 1H), 8.62 (s, 2H), 8.03 (s, 1H), 7.90 (s, 1H), 7.50 (d, J=8.9 Hz, 2H), 6.87 (d, J=9.0 Hz, 2H), 5.27 (p, J=8.7 Hz, 1H), 3.22-3.11 (m, 10H), 2.96 (d, J=15.8 Hz, 1H), 2.67 (d, J=15.8 Hz, 1H), 2.32 (ddd, J=12.8, 7.8, 5.0 Hz, 1H), 2.02-1.92 (m, 2H), 1.88-1.75 (m, 3H), 1.75-1.66 (m, 2H), 1.51-1.41 (m, 2H).

Example 8: Compound D56 (E2 of Compound D3)

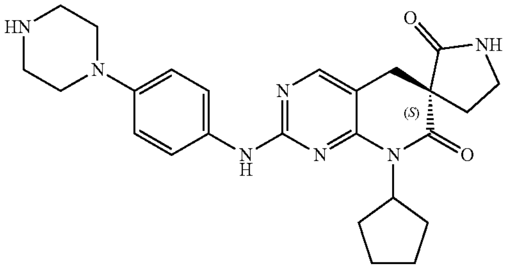

Synthesis of (S)-8-cyclopentyl-2-((4-(piperazin-1-yl)phenyl)amino)-5,8-dihydro-7H-spiro[pyrido[2,3-d]pyrimidine-6,3'-pyrrolidine]-2',7-dione (Compound D56)

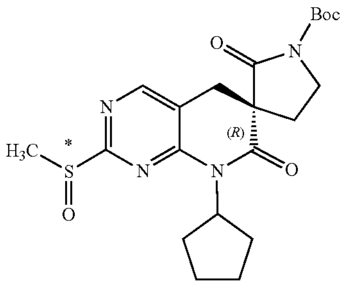

E2-sulfoxide

+

-continued

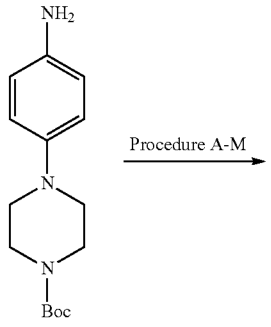

2

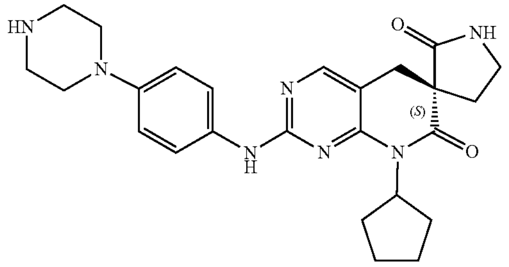

Compound D56

Compound D56 was synthesized starting from E2-sulfoxide following the general procedure A-M, 18 mg (26% yield). MS(ESI) m/z 462.3 $(M+H)^+$. $^1H$ NMR (600 MHz, DMSO-$d_6$) δ 9.16 (s, 1H), 8.03 (s, 1H), 7.90 (s, 1H), 7.48 (d, J=9.0 Hz, 2H), 6.86 (d, J=9.0 Hz, 2H), 5.27 (p, J=8.6 Hz, 1H), 3.17-3.11 (m, 6H), 3.10 (d, J=5.6 Hz, 4H), 2.96 (d, J=15.8 Hz, 1H), 2.66 (d, J=15.8 Hz, 1H), 2.35-2.27 (m, 1H), 2.00-1.92 (m, 2H), 1.87-1.75 (m, 3H), 1.70 (d, J=3.3 Hz, 2H), 1.52-1.42 (m, 2H).

Example 9: Compound D57 (E1)

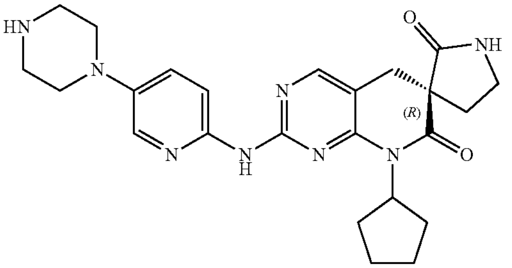

Step 1: Synthesis of (R)-8-cyclopentyl-2-((5-(piperazin-1-yl)pyridin-2-yl)amino)-5,8-dihydro-7H-spiro[pyrido[2,3-d]pyrimidine-6,3'-pyrrolidine]-2',7-dione (Compound D57)

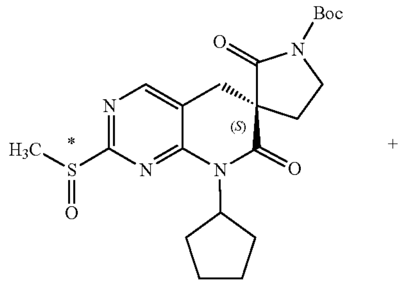

E1-sulfoxide

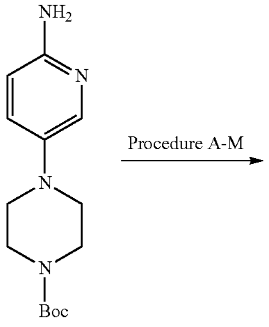

1

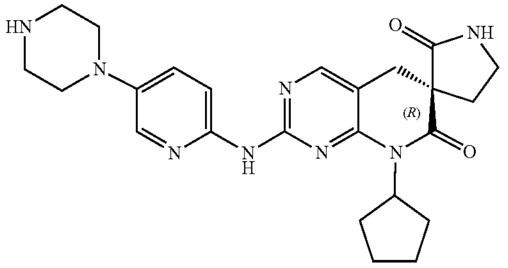

Compound D57

Compound D57 was synthesized starting from E1-sulfoxide, following the general procedure A-M, 22 mg (32% yield). MS(ESI) m/z 463.3 $(M+H)^+$. $^1H$ NMR (600 MHz, DMSO-$d_6$) δ 9.35 (s, 1H), 8.16 (s, 1H), 8.03-7.93 (m, 3H), 7.43 (dd, J=9.1, 3.0 Hz, 1H), 5.33 (p, J=8.9 Hz, 1H), 3.27-3.19 (m, 3H), 3.17 (s, 4H), 3.09-3.02 (m, 4H), 2.77 (d, J=15.9 Hz, 1H), 2.44-2.37 (m, 2H), 2.05 (s, 2H), 1.87 (s, 2H), 1.81-1.72 (m, 2H), 1.60-1.50 (m, 2H).

Example 10: Compound D58 (E2)

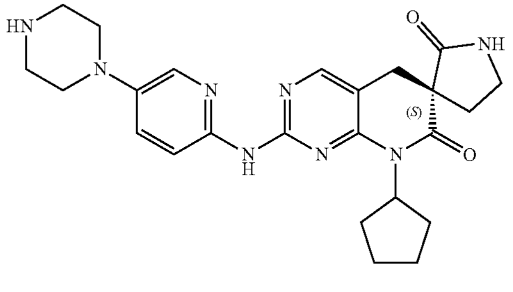

Step 1: Synthesis of (S)-8-cyclopentyl-2-((5-(piperazin-1-yl)pyridin-2-yl)amino)-5,8-dihydro-7H-spiro[pyrido[2,3-d]pyrimidine-6,3'-pyrrolidine]-2',7-dione (Compound D58)

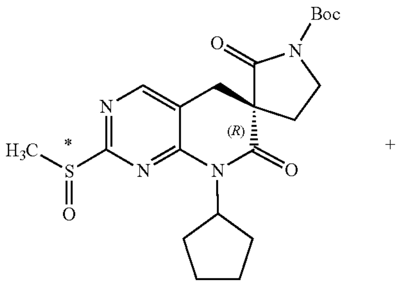

E2-sulfoxide

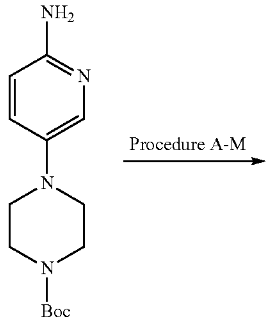

1

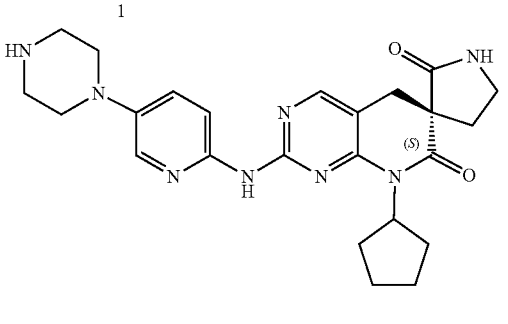

Compound D58

Compound D58 was synthesized starting from E2-sulfoxide, following the general procedure A-M, 5 mg (7% yield). MS(ESI) m/z 463.3 $(M+H)^+$. $^1H$ NMR (600 MHz, DMSO- $d_6$) δ 9.35 (s, 1H), 8.16 (s, 1H), 8.03-7.93 (m, 3H), 7.43 (dd, J=9.1, 3.0 Hz, 1H), 5.33 (p, J=8.9 Hz, 1H), 3.27-3.19 (m, 3H), 3.17 (s, 4H), 3.09-3.02 (m, 4H), 2.77 (d, J=15.9 Hz, 1H), 2.44-2.37 (m, 2H), 2.05 (s, 2H), 1.87 (s, 2H), 1.81-1.72 (m, 2H), 1.60-1.50 (m, 2H).

Example-59 (VP-NR10-308B, SPV-480)

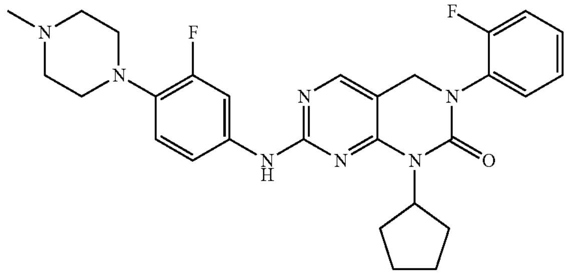 [SMILES: CN1CCN(c2ccc(Nc3ncc4c(n3)N(C3CCCC3)C(=O)N(c3ccccc3F)C4)cc2F)CC1]

Step 1: Synthesis 1-cyclopentyl-3-(2-fluorophenyl)-7-(methylsulfinyl)-3,4-dihydropyrimido[4,5-d]pyrimidin-2(1H)-one (59-D)

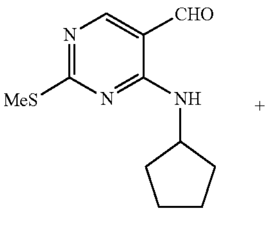

1

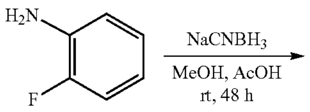

59-A

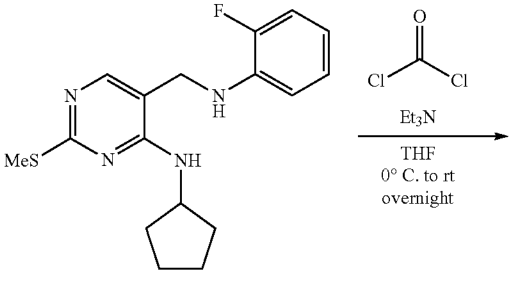

59-B

-continued

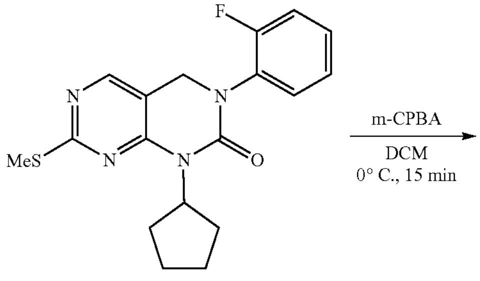

59-C

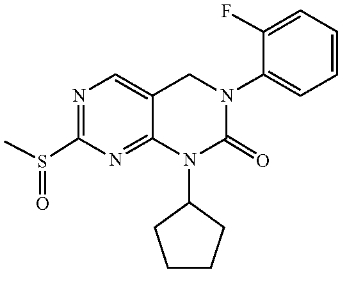

59-D

Synthesis of 59-B: (Ref: Bioorganic and medicinal chemistry 24 (11), 2549-2558,2016): A solution of 1 (2.00 g, 8.4 mmol) and 59-A (1 g, 9.2 mmol) in MeOH (50 mL) and AcOH (1 mL, 16.8 mmol) was stirred at rt for 30 minutes. Sodium cyanoborohydride (2.6 g, 42 mmol) was added portion wise and the reaction mixture was stirred at rt for 72 h. The reaction mixture was concentrated, diluted with DCM (50 mL), washed with saturated aqueous sodium bicarbonate (50 mL) and brine (50 mL), dried over sodium sulfate, and concentrated under reduced pressure. The crude product was further purified on column (0 to 100% EA in hexane) to give pure 59-B (0.66 g, 23%). MS(ESI) m/z 333.1 $(M+H)^+$ Synthesis of 59-C: (Ref: WO200024744): A mixture of 59-B (0.66 g, 2 mmol) and triethylamine (0.7 mL, 5 mmol) in 10 ml of tetrahydrofuran was added dropwise to an ice-cooled solution of phosgene (15% solution in toluene, 2.6 mL, 4 mmol) in 10 ml of tetrahydrofuran. After one hour, 10 ml of aqueous ammonium chloride solution and extracted with ethyl acetate (3×20 ml). The phases were separated, the organic phase was dried over sodium sulfate, filtered and then evaporated. The residue was further purified on column (Hexane/EA) to give 59-C as a white solid (0.43 g, 60%). MS(ESI) m/z 359.1 $(M+H)^{+1}$H NMR (600 MHz, Chloroform-d) δ 8.08 (s, 1H), 7.42-7.28 (m, 2H), 7.24-7.14 (m, 2H), 5.34-5.23 (m, 1H), 4.61 (s, 2H), 2.57 (s, 3H), 2.28-2.19 (m, 2H), 2.00-1.89 (m, 4H), 1.64-1.56 (m, 2H).

Synthesis of 59-D: To a solution of 59-C (0.43 g, 1.2 mmol) in 30 mL DCM was added m-CPBA (0.29 g, 1.26 mmol) in one portion at 0° C. After stirring for 15 min, reaction mixture was washed with Sat. $NaHCO_3$ and brine. The organic layer was dried over sodium sulfate, concentrated, dried and used as such for next step 9 (0.42 g, 95% yield). MS(ESI) m/z 375.2 $(M+H)^+$.

Step 2: Synthesis of 1-cyclopentyl-7-((3-fluoro-4-(4-methylpiperazin-1-yl)phenyl)amino)-3-(2-fluorophenyl)-3,4-dihydropyrimido[4,5-d]pyrimidin-2(1H)-one (Example-59)

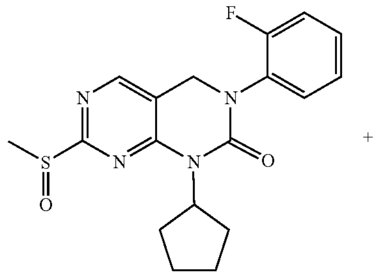

59-D

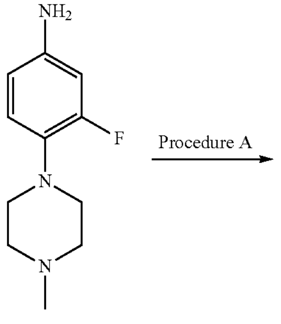

14

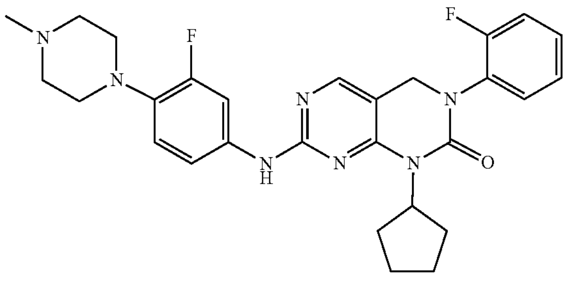

Example-59

Example-59 was synthesized following the general procedure A-X, 13 mg (25% yield). MS(ESI) m/z 520.2 $(M+H)^+$. $^1H$ NMR (600 MHz, DMSO-$d_6$) δ 9.49 (s, 1H), 8.09 (d, J=1.0 Hz, 1H), 7.66 (dd, J=15.5, 2.4 Hz, 1H), 7.45 (td, J=7.9, 1.7 Hz, 1H), 7.31 (dddd, J=8.4, 6.9, 5.0, 1.8 Hz, 1H), 7.29-7.18 (m, 2H), 6.92 (t, J=9.4 Hz, 1H), 5.12 (p, J=8.8 Hz, 1H), 4.56 (s, 2H), 2.92 (s, 3H), 2.58-2.54 (m, 1H), 2.54 (s, 1H), 2.44 (s, 3H), 2.35-2.30 (m, 1H), 2.24 (s, 3H), 2.13-1.99 (m, 2H), 1.89-1.71 (m, 3H), 1.54-1.40 (m, 2H).

Example-60 (VP-NR11-8C, SPV-481)

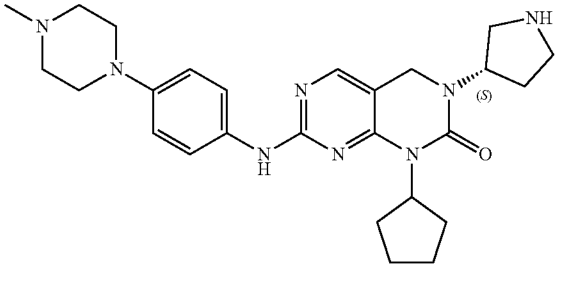

Step 1: Synthesis of tert-butyl (3S)-3-(1-cyclopentyl-7-(methylsulfinyl)-2-oxo-1,4-dihydropyrimido[4,5-d]pyrimidin-3(2H)-yl)pyrrolidine-1-carboxylate (60-D)

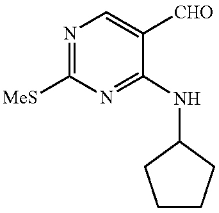

1-A

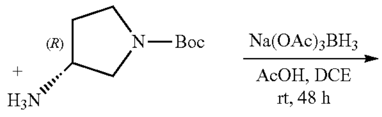

60-A

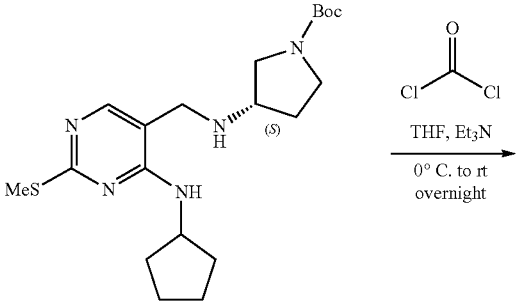

60-B

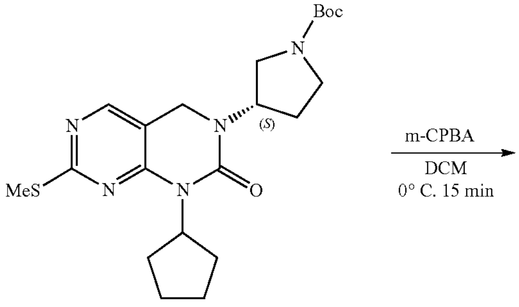

60-C

-continued

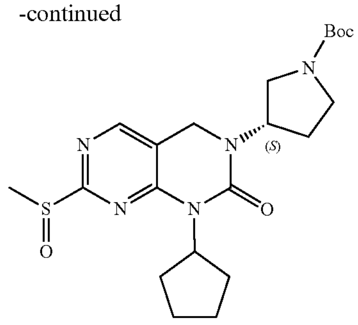

60-D

Synthesis of 60-B: (Ref: WO2011123536): To compound 1-A (1.00 g, 4.2 mmol) in 1,2-dichloroethane (20 mL) was added 60-A (0.94 g, 5.05 mmol), acetic acid (0.73 mL, 12.6 mmol), and sodium triacetoxyborohydride (1.8 g, 8.4 mmol). The reaction mixture was stirred at rt for 48 h, diluted with ethyl acetate (50 mL), washed with saturated aqueous sodium bicarbonate (50 mL) and brine (50 mL), dried over sodium sulfate, and concentrated under reduced pressure. The crude product was further purified on column (0 to 100% EA in hexane) to give pure 60-B (0.7 g, 41%). MS(ESI) m/z 408.2 $(M+H)^+$.

Synthesis of 60-C: (Ref: WO200024744): A mixture of 60-B (0.7 g, 1.7 mmol) and triethylamine (0.6 mL, 4.25 mmol) in 10 ml of tetrahydrofuran was added dropwise to an ice-cooled solution of phosgene (15% solution in toluene, 2.2 mL, 3.4 mmol) in 10 ml of tetrahydrofuran. After one hour, 10 ml of aqueous ammonium chloride solution and extracted with ethyl acetate (3×20 ml). The phases were separated, the organic phase was dried over sodium sulfate, filtered and then evaporated. The residue was further purified on column (Hexane/EA) to give 60-C as a white solid (0.5 g, 68%). MS(ESI) m/z 434.3 $(M+H)^+$.

Synthesis of 60-D: To a solution of 4 (0.5 g, 1.15 mmol) in 50 mL DCM was added m-CPBA (0.27 g, 1.2 mmol) in one portion at 0° C. After stirring for 15 min, reaction mixture was washed with Sat. $NaHCO_3$ and brine. The organic layer was dried over sodium sulfate, concentrated, dried and used as such for next step 60-D (0.48 g, 94% yield). MS(ESI) m/z 450.2 $(M+H)^+$.

Step 2: (S)-1-cyclopentyl-7-((4-(4-methylpiperazin-1-yl)phenyl)amino)-3-(pyrrolidin-3-yl)-3,4-dihydropyrimido[4,5-d]pyrimidin-2(1H)-one (Example-60)

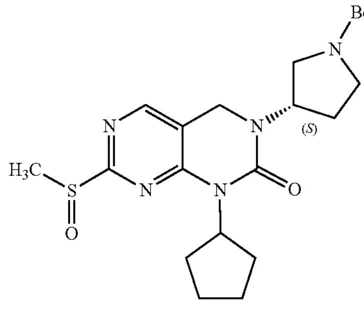

60-D

+

-continued

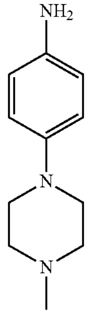

3

Procedure-A

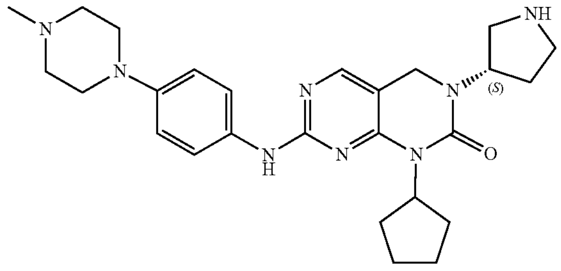

Example-60

Example-60 was synthesized following the general procedure A, 11 mg (23% yield). MS(ESI) m/z 477.2 $(M+H)^+$. $^1H$ NMR (600 MHz, DMSO-$d_6$) δ 9.14 (s, 1H), 8.70 (s, 3H), 8.00 (s, 1H), 7.51-7.41 (m, 2H), 6.90-6.82 (m, 2H), 5.04 (p, J=8.8 Hz, 1H), 4.66 (p, J=8.0 Hz, 1H), 4.19 (s, 2H), 3.39-3.32 (m, 3H), 3.21-3.15 (m, 2H), 3.14-3.08 (m, 2H), 3.01 (s, 6H), 2.60 (s, 2H), 2.14-1.97 (m, 4H), 1.81-1.74 (m, 2H), 1.74-1.67 (m, 2H), 1.52-1.40 (m, 2H).

Example-61 (VP-NR11-11, SPV-482)

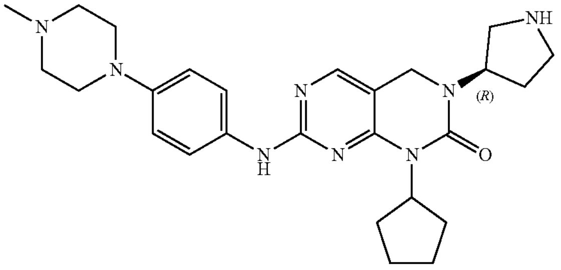

Step 1: Synthesis of tert-butyl (3R)-3-(1-cyclopentyl-7-(methylsulfinyl)-2-oxo-1,4-dihydropyrimido[4,5-d]pyrimidin-3(2H)-yl)pyrrolidine-1-carboxylate (61-D)

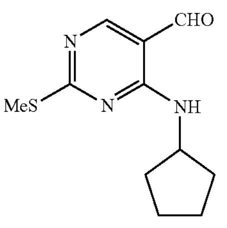

1

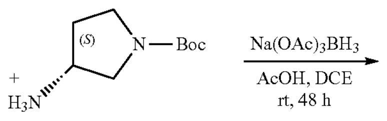

61-A

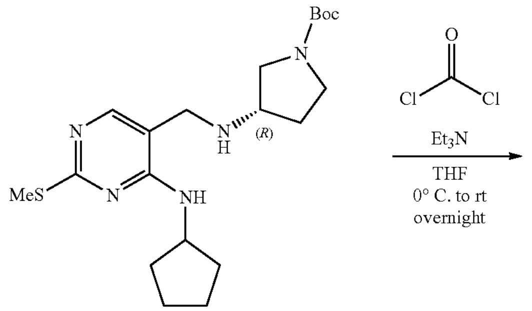

61-B

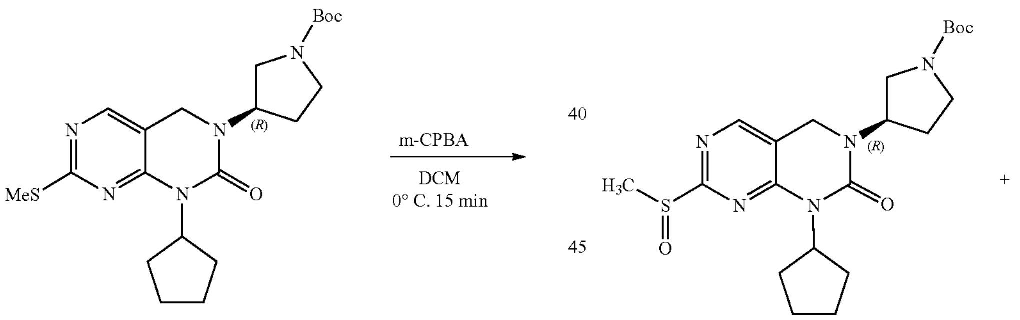

61-C

61-D

Synthesis of 61-B: (Ref: WO2011123536): To compound 1 (2.00 g, 8.4 mmol) in 1,2-dichloroethane (40 mL) was added 61-A (3.8 g, 10.1 mmol), acetic acid (1 mL, 33.6 mmol), and sodium triacetoxyborohydride (7.1 g, 33.6 mmol). The reaction mixture was stirred at rt for overnight, diluted with ethyl acetate (50 mL), washed with saturated aqueous sodium bicarbonate (50 mL) and brine (50 mL), dried over sodium sulfate, and concentrated under reduced pressure. The crude product was further purified on column (0 to 100% EA in hexane) to give pure 61-B (1.2 g, 35%). MS(ESI) m/z 408.3 $(M+H)^+$ Synthesis of 61-B: (Ref: WO200024744): A mixture of 61-B (1.2 g, 2.9 mmol) and triethylamine (1 mL, 7.25 mmol) in 10 ml of tetrahydrofuran was added dropwise to an ice-cooled solution of phosgene (15% solution in toluene, 3.7 mL, 5.8 mmol) in 10 ml of tetrahydrofuran. After one hour, 10 ml of aqueous ammonium chloride solution and extracted with ethyl acetate (3×20 ml). The phases were separated, the organic phase was dried over sodium sulfate, filtered and then evaporated. The residue was further purified on column (Hexane/EA) to give 61-C as a white solid (0.9 g, 75%). MS(ESI) m/z 434.3 $(M+H)^+$ Synthesis of 61-C: To a solution of 61-C (0.76 g, 1.75 mmol) in 50 mL DCM was added m-CPBA (0.41 g, 1.8 mmol) in one portion at 0° C. After stirring for 15 min, reaction mixture was washed with Sat. $NaHCO_3$ and brine. The organic layer was dried over sodium sulfate, concentrated, dried and used as such for next step 61-D (0.74 g, 95% yield). MS(ESI) m/z 450.2 $(M+H)^+$.

Step 2: (R)-1-cyclopentyl-7-((4-(4-methylpiperazin-1-yl)phenyl)amino)-3-(pyrrolidin-3-yl)-3,4-dihydropyrimido[4,5-d]pyrimidin-2(1H)-one (Example-61)

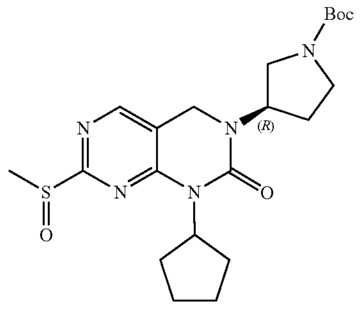

61-D

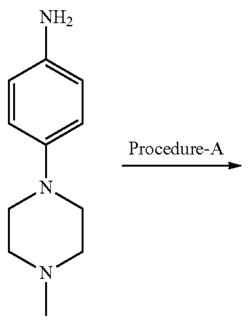

3

-continued

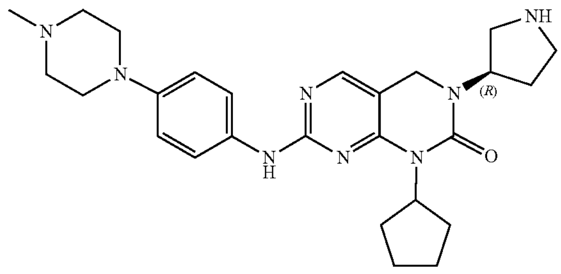

Example-61

Example-61 was synthesized following the general procedure A, 5 mg (10% yield). MS(ESI) m/z 477.2 $(M+H)^+$. $^1H$ NMR (600 MHz, DMSO-$d_6$) δ 9.18 (s, 1H), 8.06 (s, 1H), 7.51 (d, J=8.6 Hz, 2H), 6.93-6.86 (m, 2H), 5.15-5.03 (m, 1H), 4.73 (p, J=8.0 Hz, 1H), 4.25 (s, 2H), 3.45-3.39 (m, 1H), 3.28-3.23 (m, 2H), 3.23-3.13 (m, 3H), 2.97-2.64 (m, 5H), 2.50 (s, 5H), 2.23-2.01 (m, 4H), 1.88-1.74 (m, 3H), 1.59-1.43 (m, 2H).

Example-62 (VP-NR11-127, SPV-483)

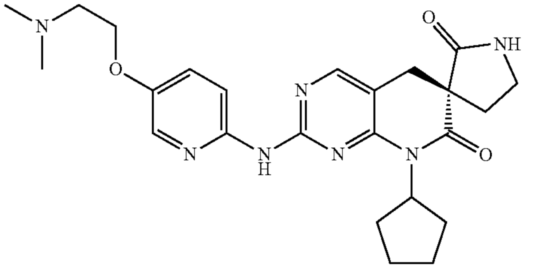 [SMILES: CN(C)CCOc1ccc(Nc2ncc3c(n2)N(C2CCCC2)C(=O)[C@]2(CCNC2=O)C3)nc1]

Step 1: Synthesis of (S)-8-cyclopentyl-2-((5-(2-(dimethylamino)ethoxy)pyridin-2-yl)amino)-5,8-dihydro-7H-spiro[pyrido[2,3-d]pyrimidine-6,3'-pyrrolidine]-2',7-dione (Example-62)

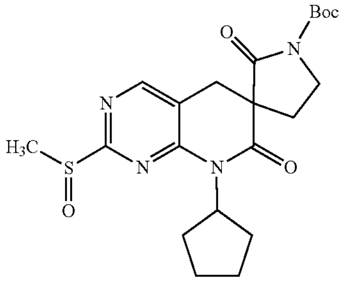

E2-sulfoxide

+

-continued

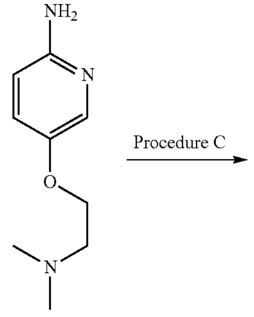

21

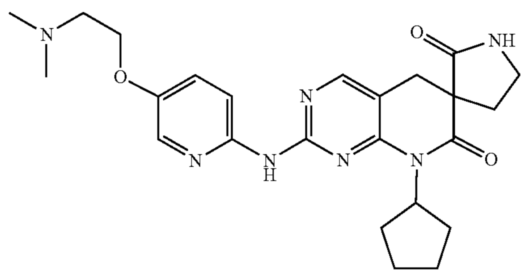

Example-62

Example-62 was synthesized following the general procedure C, 5 mg (11% yield). MS(ESI) m/z 466.2 $(M+H)^+$.

Example-63 (VP-7-49C, SPV-381)

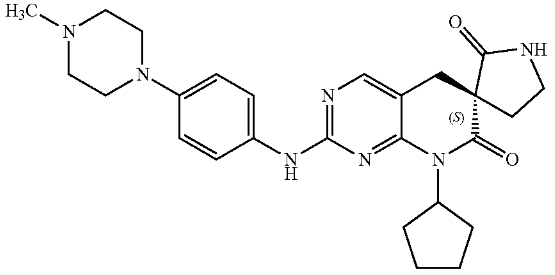

Step 1: Synthesis of (S)-8-cyclopentyl-2-((4-(4-methylpiperazin-1-yl)phenyl)amino)-5,8-dihydro-7H-spiro[pyrido[2,3-d]pyrimidine-6,3'-pyrrolidine]-2',7-dione (Example-63)

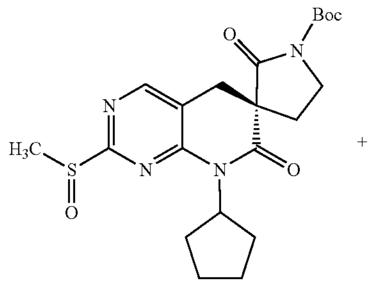

E2-sulfoxide

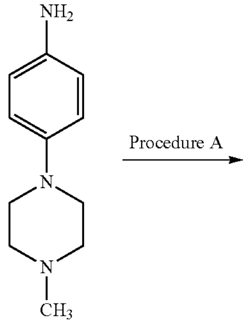

3

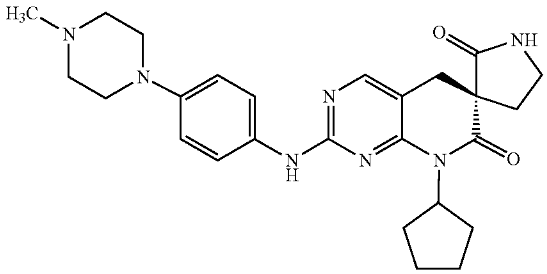

Example-63

Example-63 was synthesized following the general procedure A, 15 mg (16% yield). MS(ESI) m/z 476.2 $(M+H)^+$.

Example-64 (VP-7-50A, SPV-382)

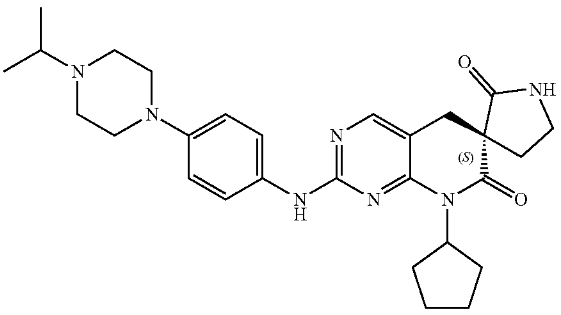

Step 1: Synthesis of (S)-8-cyclopentyl-2-((4-(4-isopropylpiperazin-1-yl)phenyl)amino)-5,8-dihydro-7H-spiro[pyrido[2,3-d]pyrimidine-6,3'-pyrrolidine]-2',7-dione (Example-64)

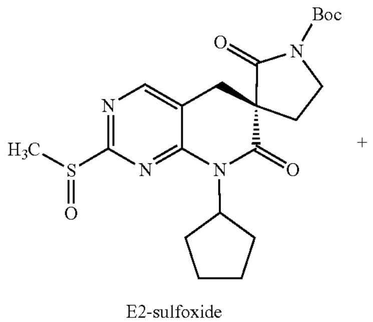

E2-sulfoxide

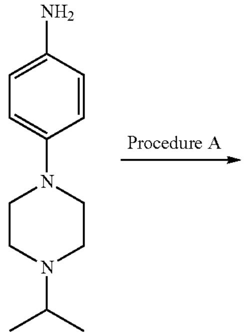

12

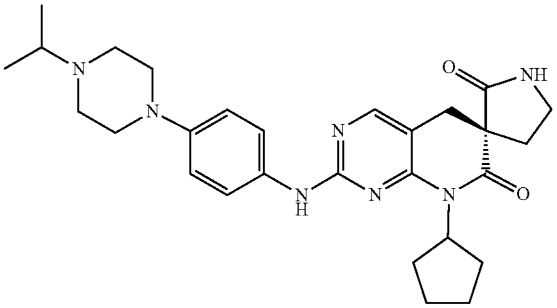

Example-64

Example-64 was synthesized following the general procedure A, 16 mg (32% yield). MS(ESI) m/z 504.2 $(M+H)^+$. $^1$H NMR (600 MHz, DMSO-$d_6$) δ 9.15 (s, 1H), 8.09 (s, 1H), 7.97 (s, 1H), 7.49 (d, J=8.5 Hz, 2H), 6.86 (d, J=8.5 Hz, 2H), 5.34 (t, J=8.8 Hz, 1H), 3.27-3.16 (m, 3H), 3.09-2.99 (m, 4H), 2.71 (d, J=15.6 Hz, 1H), 2.69-2.62 (m, 1H), 2.62-2.54 (m, 4H), 2.36 (ddd, J=12.8, 7.8, 4.8 Hz, 1H), 2.07-1.97 (m, 2H), 1.94-1.80 (m, 3H), 1.80-1.70 (m, 2H), 1.57-1.46 (m, 2H), 1.00 (d, J=6.5 Hz, 6H).

Example-65 (VP-7-53D, SPV-383)

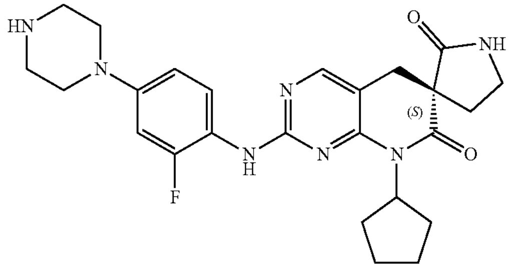

Step 1: Synthesis of (S)-8-cyclopentyl-2-((2-fluoro-4-(piperazin-1-yl)phenyl)amino)-5,8-dihydro-7H-spiro[pyrido[2,3-d]pyrimidine-6,3'-pyrrolidine]-2',7-dione (Example-65)

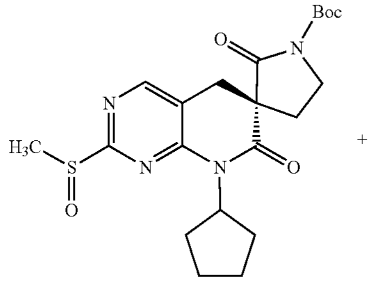

E2-sulfoxide

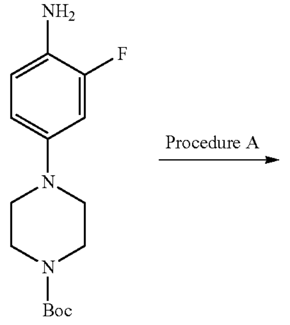

29

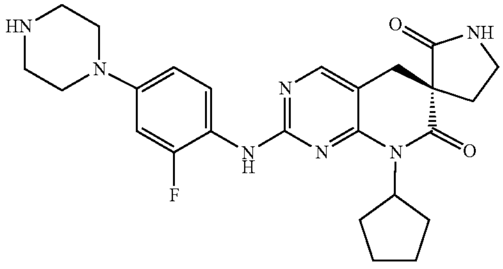

Example-65

Example-65 was synthesized following the general procedure A, 6 mg (13% yield). MS(ESI) m/z 480.2 $(M+H)^+$. $^1$H NMR (600 MHz, DMSO-$d_6$) δ 8.71 (s, 1H), 8.04 (s, 1H), 7.96 (s, 1H), 7.36 (t, J=9.0 Hz, 1H), 6.91 (dd, J=13.6, 2.7 Hz, 1H), 6.79 (dd, J=8.8, 2.7 Hz, 1H), 5.21 (t, J=9.0 Hz, 1H), 3.26-3.16 (m, 8H), 3.00 (d, J=15.7 Hz, 1H), 2.70 (d, J=15.7 Hz, 1H), 2.34 (ddd, J=12.8, 7.8, 4.8 Hz, 1H), 2.02-1.95 (m, 2H), 1.90 (dt, J=13.8, 7.3 Hz, 1H), 1.71-1.53 (m, 5H), 1.41 (s, 3H).

Example-66 (VP-7-54, SPV-384)

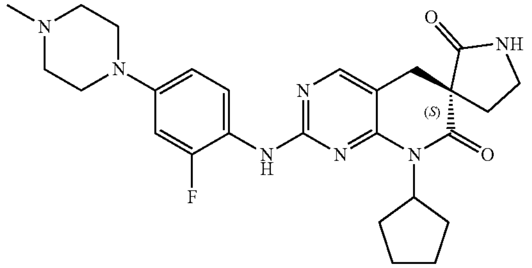

Step 1: Synthesis of (S)-8-cyclopentyl-2-((2-fluoro-4-(4-methylpiperazin-1-yl)phenyl)amino)-5,8-dihydro-7H-spiro[pyrido[2,3-d]pyrimidine-6,3'-pyrrolidine]-2',7-dione (Example-66)

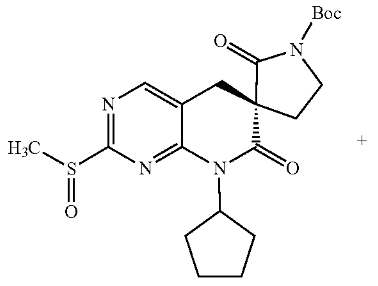

E2-sulfoxide

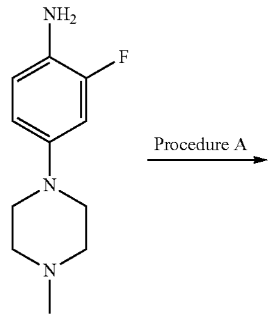

16

-continued

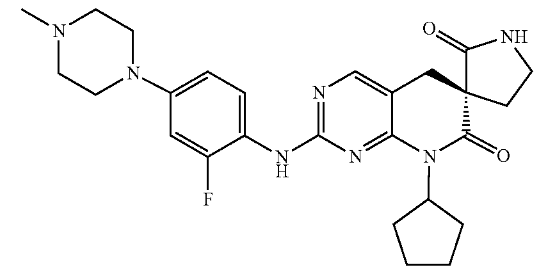

Example-66

Example-66 was synthesized following the general procedure A, 3 mg (6% yield). MS(ESI) m/z 494.2 $(M+H)^+$.

Example-67 (VP-7-55, SPV-385)

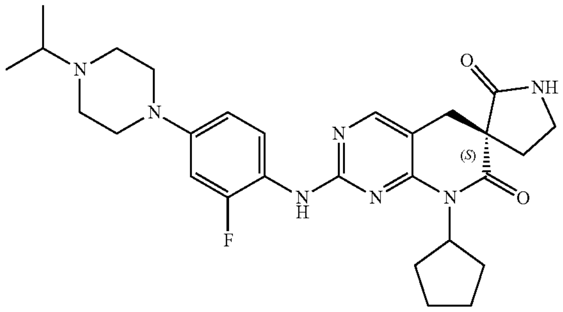

Step 1: Synthesis of (S)-8-cyclopentyl-2-((2-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (Example-67)

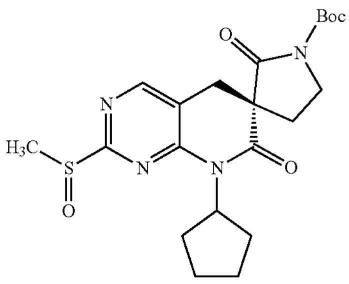

E2-sulfoxide

+

-continued

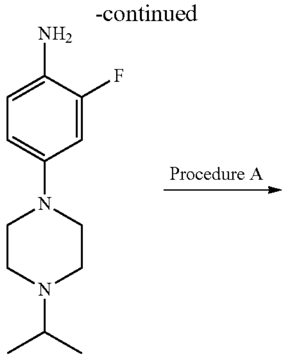

17

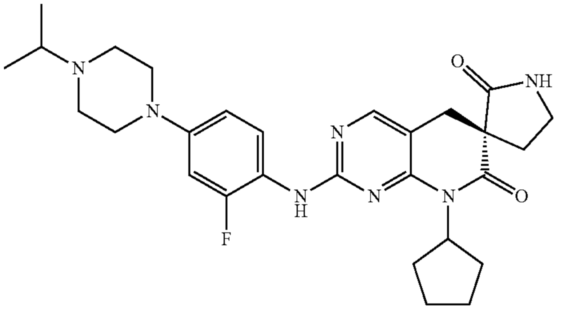

Example-67

Example-67 was synthesized following the general procedure A, 3 mg (6% yield). MS(ESI) m/z 522.2 $(M+H)^+$.

Example-68 (VP-7-56, SPV-386)

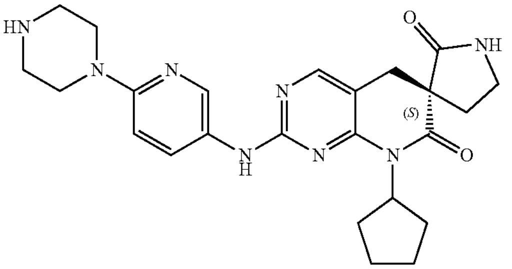

Step 1: Synthesis of (S)-8-cyclopentyl-2-((6-(piperazin-1-yl)pyridin-3-yl)amino)-5,8-dihydro-7H-spiro[pyrido[2,3-d]pyrimidine-6,3'-pyrrolidine]-2',7-dione (Example-68)

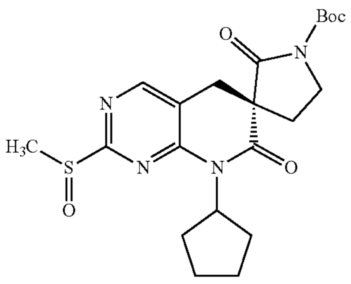

E2-sulfoxide

+

-continued

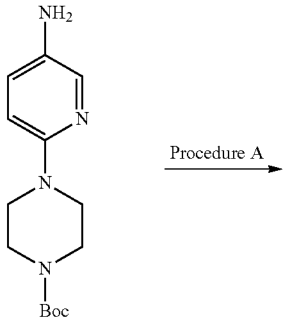

4

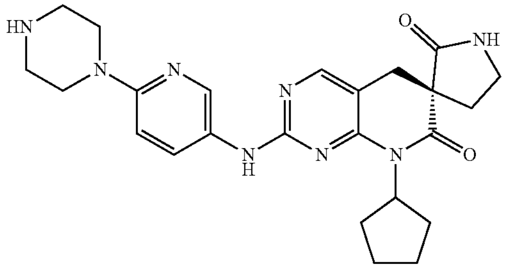

Example-68

Example-68 was synthesized following the general procedure A, 12 mg (26% yield). MS(ESI) m/z 463.2 $(M+H)^+$. $^1H$ NMR (600 MHz, DMSO-$d_6$) δ 9.16 (s, 1H), 8.34 (d, J=2.7 Hz, 1H), 8.03 (s, 1H), 7.90 (s, 1H), 7.83 (dd, J=9.1, 2.8 Hz, 1H), 6.84 (d, J=9.1 Hz, 1H), 5.24 (p, J=8.8 Hz, 1H), 3.55-3.50 (m, 4H), 3.12-3.07 (m, 4H), 2.96 (d, J=15.7 Hz, 1H), 2.84 (d, J=7.1 Hz, 1H), 2.67 (d, J=15.7 Hz, 1H), 2.32 (ddd, J=12.8, 7.8, 4.9 Hz, 1H), 1.99-1.92 (m, 2H), 1.88-1.80 (m, 2H), 1.80-1.76 (m, 2H), 1.72-1.65 (m, 2H), 1.48-1.42 (m, 2H).

Example-69 (VP-7-57, SPV-387)

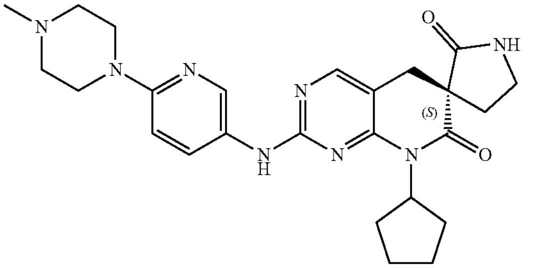

Step 1: Synthesis of (S)-8-cyclopentyl-2-((6-(4-methylpiperazin-1-yl)pyridin-3-yl)amino)-5,8-dihydro-7H-spiro[pyrido[2,3-d]pyrimidine-6,3'-pyrrolidine]-2',7-dione (Example-69)

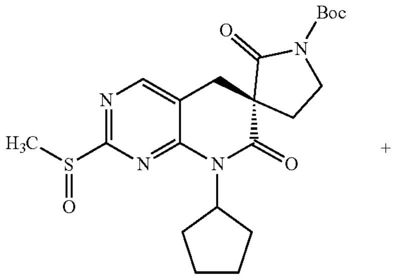

E2-sulfoxide

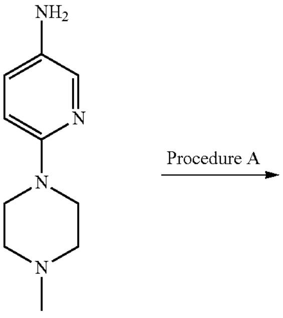

5

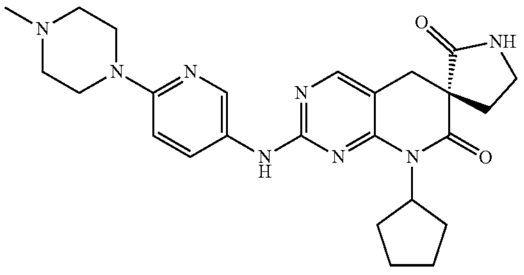

Example-69

Example-69 was synthesized following the general procedure A, 10 mg (21% yield). MS(ESI) m/z 477.2 $(M+H)^+$. $^1H$ NMR (600 MHz, DMSO-$d_6$) δ 9.16 (s, 1H), 8.34 (d, J=2.7 Hz, 1H), 8.03 (s, 1H), 7.90 (s, 1H), 7.83 (dd, J=9.0, 2.8 Hz, 1H), 6.85 (d, J=9.1 Hz, 1H), 5.25 (p, J=8.8 Hz, 1H), 3.20-3.11 (m, 4H), 3.04 (s, 3H), 2.96 (d, J=15.7 Hz, 2H), 2.71-2.62 (m, 3H), 2.32 (ddd, J=12.8, 7.8, 4.9 Hz, 1H), 2.00-1.91 (m, 2H), 1.88-1.81 (m, 2H), 1.81-1.74 (m, 2H), 1.73-1.60 (m, 3H), 1.50-1.38 (m, 3H).

Example-70 (VP-7-58, SPV-430)

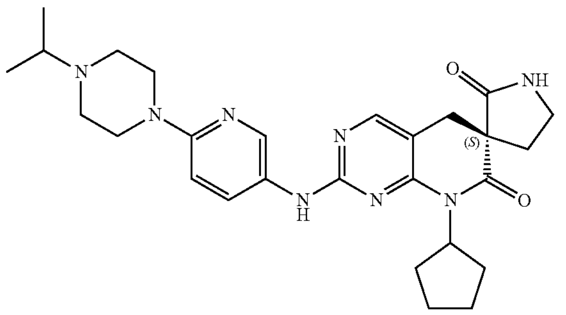

Step 1: Synthesis of (S)-8-cyclopentyl-2-((6-(4-isopropylpiperazin-1-yl)pyridin-3-yl)amino)-5,8-dihydro-7H-spiro[pyrido[2,3-d]pyrimidine-6,3'-pyrrolidine]-2',7-dione (Example-70)

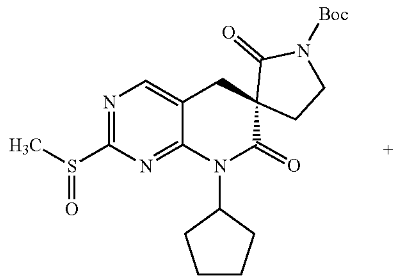

E2-sulfoxide

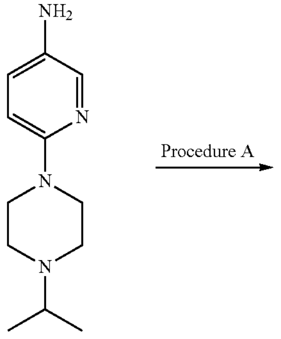

13

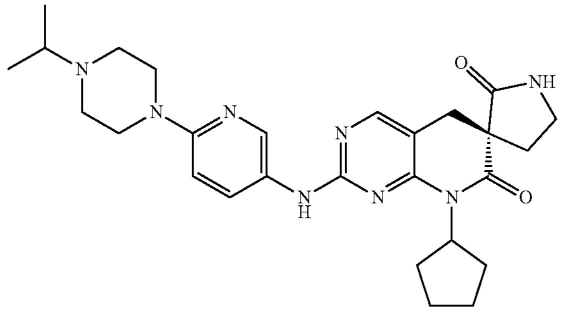

Example-70

Example-70 was synthesized following the general procedure A, 7 mg (14% yield). MS(ESI) m/z 505.2 $(M+H)^+$.

$^1H$ NMR (600 MHz, DMSO-$d_6$) δ 9.13 (s, 1H), 8.33 (s, 1H), 8.08 (s, 1H), 7.97 (s, 1H), 7.80 (d, J=9.0 Hz, 1H), 6.81 (d, J=9.1 Hz, 1H), 5.30 (t, J=8.9 Hz, 1H), 3.37 (s, 3H), 3.26-3.13 (m, 3H), 3.02 (d, J=15.7 Hz, 1H), 2.72 (d, J=15.7 Hz, 1H), 2.50 (s, 4H), 2.37 (ddd, J=12.8, 7.6, 4.6 Hz, 2H), 2.07-1.95 (m, 2H), 1.91 (ddd, J=13.7, 8.0, 6.2 Hz, 1H), 1.83 (s, 2H), 1.78-1.67 (m, 2H), 1.56-1.43 (m, 2H), 1.06-0.87 (m, 6H).

Example-71 (VP-7-131, SPV-388)

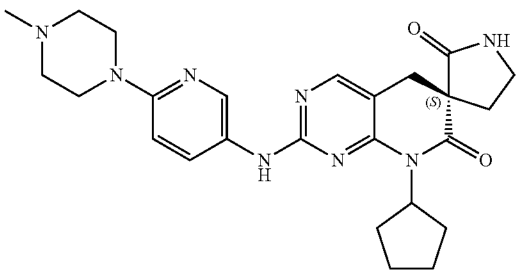

Step 1: Synthesis of (S)-8-cyclopentyl-2-((5-(4-methylpiperazin-1-yl)pyridin-2-yl)amino)-5,8-dihydro-7H-spiro[pyrido[2,3-d]pyrimidine-6,3'-pyrrolidine]-2',7-dione (Example-71)

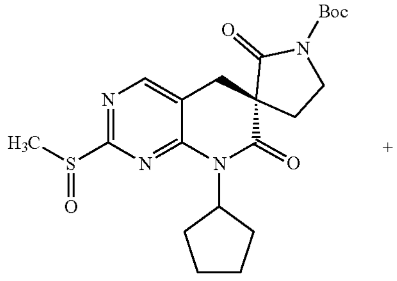

E2-sulfoxide

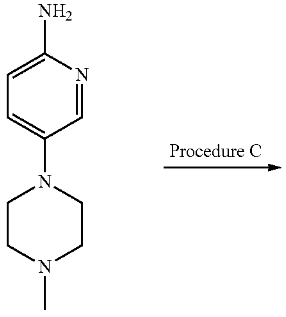

10

-continued

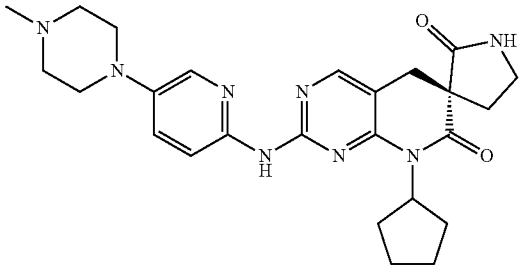

Example-71

Example-71 was synthesized following the general procedure C, 3 mg (6% yield). MS(ESI) m/z 477.2 $(M+H)^+$. $^1H$ NMR (600 MHz, DMSO-$d_6$) δ 9.22 (s, 1H), 8.08 (s, 1H), 7.90 (d, J=2.9 Hz, 2H), 7.86 (d, J=9.1 Hz, 1H), 7.34 (dd, J=9.1, 3.1 Hz, 1H), 5.26 (p, J=8.8 Hz, 1H), 3.20-3.12 (m, 2H), 3.06-3.02 (m, 4H), 2.98 (d, J=15.7 Hz, 1H), 2.69 (d, J=15.7 Hz, 1H), 2.41-2.37 (m, 4H), 2.32 (ddd, J=9.7, 7.8, 4.9 Hz, 1H), 2.15 (s, 3H), 2.03-1.93 (m, 2H), 1.88-1.83 (m, 1H), 1.82-1.77 (m, 2H), 1.74-1.65 (m, 2H), 1.51-1.43 (m, 2H).

Example-72 (VP-7-132, SPV-389)

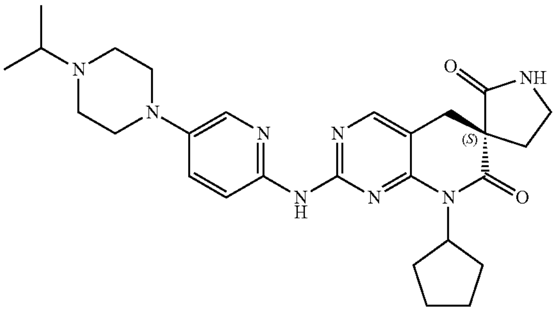

Step 1: Synthesis of (S)-8-cyclopentyl-2-((5-(4-isopropylpiperazin-1-yl)pyridin-2-yl)amino)-5,8-dihydro-7H-spiro[pyrido[2,3-d]pyrimidine-6,3'-pyrrolidine]-2',7-dione (Example-72)

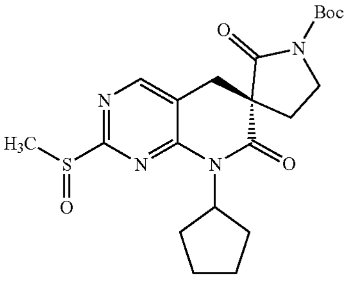

E2-Sulfoxide

+

-continued

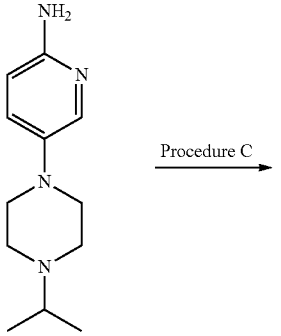

11

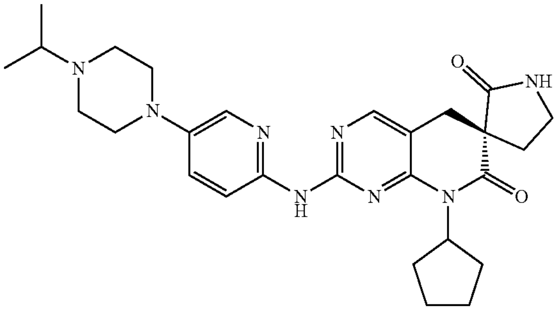

Example-72

Example-72 was synthesized following the general procedure C, 6 mg (12% yield). MS(ESI) m/z 505.2 $(M+H)^+$. $^1H$ NMR (600 MHz, DMSO-$d_6$) δ 9.28 (s, 1H), 8.15 (s, 1H), 8.03-7.94 (m, 2H), 7.92 (d, J=9.1 Hz, 1H), 7.40 (dd, J=9.1, 3.1 Hz, 1H), 5.33 (p, J=8.8 Hz, 1H), 3.27-3.17 (m, 2H), 3.15-3.07 (m, 4H), 3.05 (d, J=15.7 Hz, 1H), 2.76 (d, J=15.7 Hz, 1H), 2.68 (p, J=6.5 Hz, 1H), 2.60-2.55 (m, 4H), 2.39 (ddd, J=12.7, 7.9, 4.9 Hz, 1H), 2.09-2.00 (m, 2H), 1.95-1.82 (m, 3H), 1.81-1.71 (m, 2H), 1.58-1.49 (m, 2H), 1.01 (d, J=6.5 Hz, 6H).

Example-73 (VP-7-133, SPV-390)

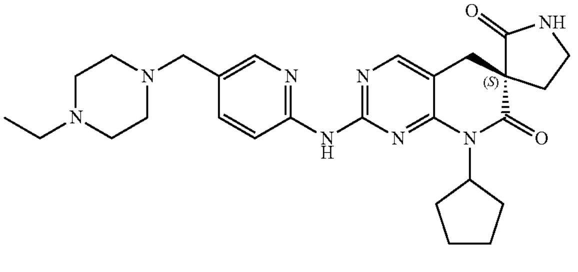

Step 1: Synthesis of (S)-8-cyclopentyl-2-((5-((4-ethylpiperazin-1-yl)methyl)pyridin-2-yl)amino)-5,8-dihydro-7H-spiro[pyrido[2,3-d]pyrimidine-6,3'-pyrrolidine]-2',7-dione (Example-73)

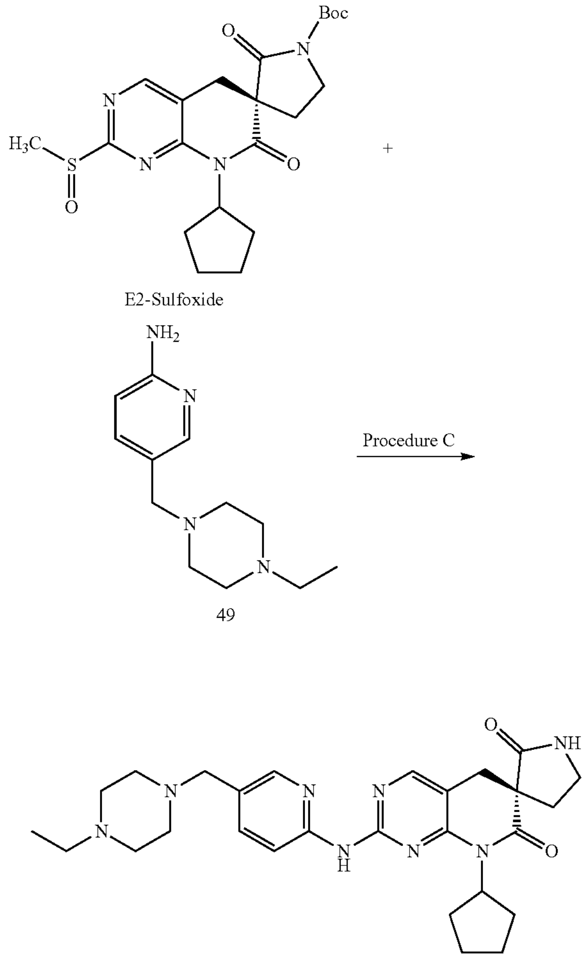

E2-Sulfoxide

49

Example-73

Example-73 was synthesized following the general procedure C, 3 mg (6% yield). MS(ESI) m/z 505.2 $(M+H)^+$.

Example-74 (VP-7-146, SPV-391)

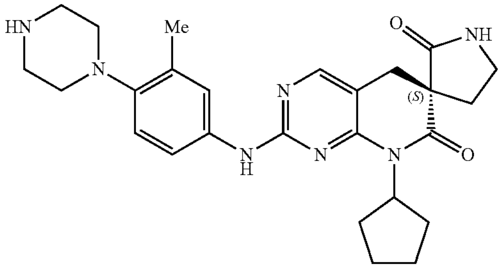

Step 1: Synthesis of (S)-8-cyclopentyl-2-((3-methyl-4-(piperazin-1-yl)phenyl)amino)-5,8-dihydro-7H-spiro[pyrido[2,3-d]pyrimidine-6,3'-pyrrolidine]-2',7-dione (Example-74)

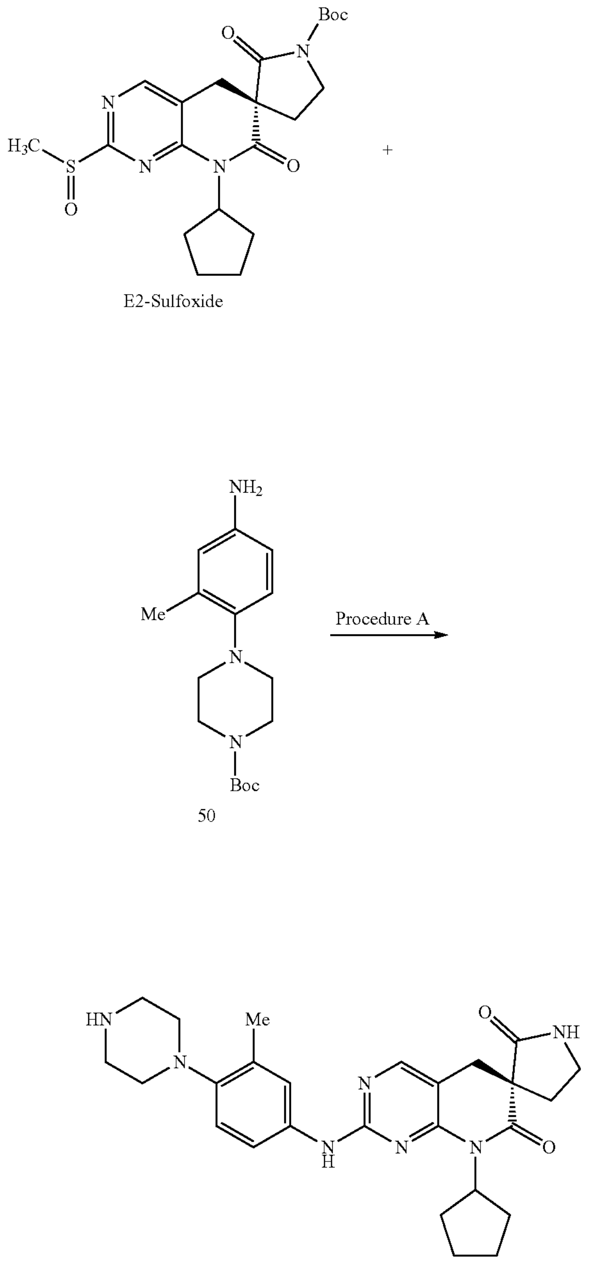

E2-Sulfoxide

50

Example-74

Example-74 was synthesized following the general procedure A, 21 mg (44% yield). MS(ESI) m/z 476.2 $(M+H)^+$. $^1$H NMR (600 MHz, DMSO-$d_6$) δ 9.32 (s, 1H), 8.13 (s, 1H), 7.98 (s, 1H), 7.62 (d, J=2.6 Hz, 1H), 7.43-7.38 (m, 1H), 6.98 (d, J=8.6 Hz, 1H), 5.36 (p, J=8.8 Hz, 1H), 3.24-3.17 (m, 6H), 3.04 (d, J=15.7 Hz, 1H), 2.99-2.95 (m, 4H), 2.75 (d, J=15.8 Hz, 1H), 2.40 (ddd, J=12.9, 7.8, 4.9 Hz, 1H), 2.24 (s, 3H), 2.06-1.99 (m, 2H), 1.95-1.83 (m, 3H), 1.83-1.77 (m, 2H), 1.56-1.50 (m, 2H).

Example-75 (VP-7-141, SPV-392)

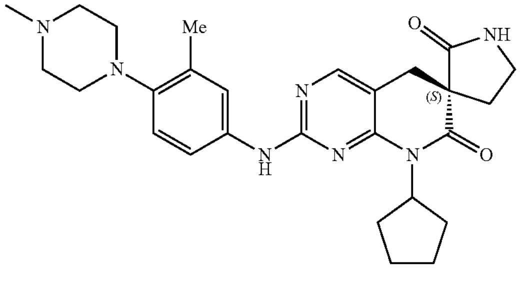

Step 1: Synthesis of (S)-8-cyclopentyl-2-((3-methyl-4-(4-methylpiperazin-1-yl)phenyl)amino)-5,8-dihydro-7H-spiro[pyrido[2,3-d]pyrimidine-6,3'-pyrrolidine]-2',7-dione (Example-75)

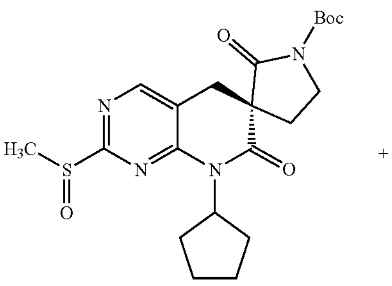

E2-Sulfoxide

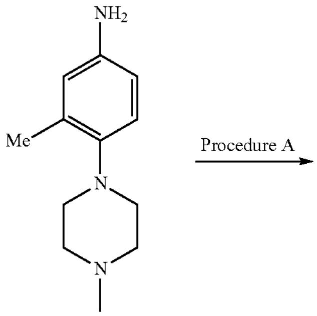

51

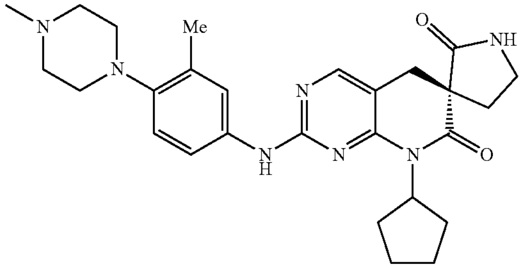

Example-75

Example-75 was synthesized following the general procedure A, 15 mg (31% yield). MS(ESI) m/z 490.2 $(M+H)^+$. $^1H$ NMR (600 MHz, DMSO-$d_6$) δ 9.32 (s, 1H), 8.13 (s, 1H), 7.97 (s, 1H), 7.62 (d, J=2.6 Hz, 1H), 7.40 (dd, J=8.9, 2.7 Hz, 1H), 6.99 (d, J=8.7 Hz, 1H), 5.36 (p, J=8.8 Hz, 1H), 3.28-3.18 (m, 4H), 3.04 (d, J=15.7 Hz, 2H), 2.96 (s, 3H), 2.82 (s, 3H), 2.75 (d, J=15.8 Hz, 1H), 2.40 (ddd, J=12.7, 7.7, 4.8 Hz, 2H), 2.25 (s, 3H), 2.08-1.98 (m, 2H), 1.95-1.84 (m, 4H), 1.83-1.74 (m, 2H), 1.58-1.49 (m, 2H).

Example-76 (VP-7-59, SPV-393)

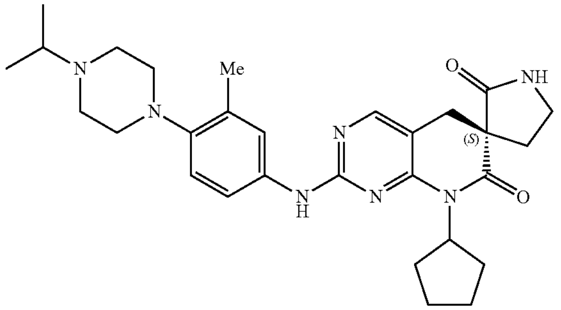

Step 1: Synthesis of (S)-8-cyclopentyl-2-((4-(4-isopropylpiperazin-1-yl)-3-methylphenyl)amino)-5,8-dihydro-7H-spiro[pyrido[2,3-d]pyrimidine-6,3'-pyrrolidine]-2',7-dione (Example-76)

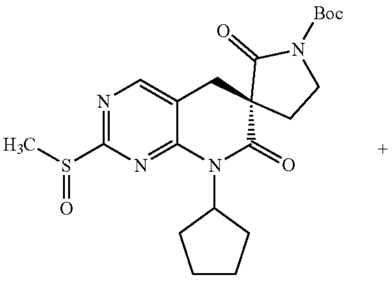

E2-Sulfoxide

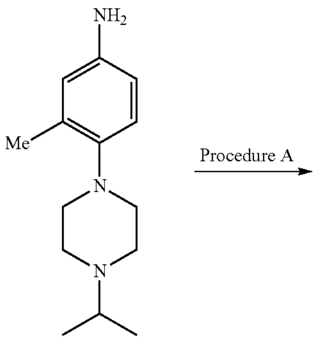

43

-continued

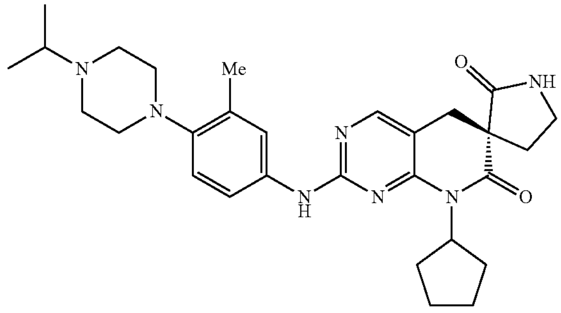

Example-76

Example-76 was synthesized following the general procedure A, 10 mg (19% yield). MS(ESI) m/z 518.3 $(M+H)^+$. $^1H$ NMR (600 MHz, DMSO-$d_6$) δ 9.24 (s, 1H), 8.11 (s, 1H), 7.97 (s, 1H), 7.56 (d, J=2.6 Hz, 1H), 7.38-7.33 (m, 1H), 6.94 (d, J=8.6 Hz, 1H), 5.36 (p, J=8.8 Hz, 1H), 3.27-3.17 (m, 3H), 3.03 (d, J=15.7 Hz, 1H), 2.80-2.76 (m, 4H), 2.73 (d, J=15.7 Hz, 1H), 2.71-2.64 (m, 1H), 2.57 (s, 3H), 2.37 (ddd, J=12.8, 7.8, 4.8 Hz, 1H), 2.22 (s, 3H), 2.06-1.99 (m, 2H), 1.95-1.87 (m, 2H), 1.87-1.83 (m, 1H), 1.83-1.76 (m, 2H), 1.57-1.49 (m, 2H), 1.01 (d, J=6.5 Hz, 6H).

Example-77 (VP-7-147, SPV-394)

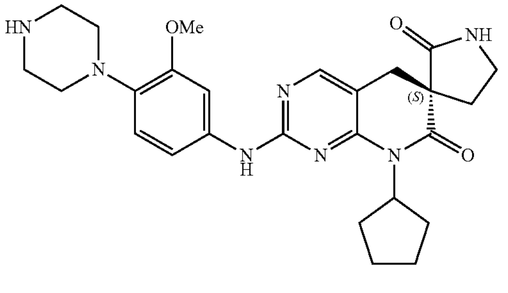

Step 1: Synthesis of (S)-8-cyclopentyl-2-((3-methoxy-4-(piperazin-1-yl)phenyl)amino)-5,8-dihydro-7H-spiro[pyrido[2,3-d]pyrimidine-6,3'-pyrrolidine]-2',7-dione (Example-77)

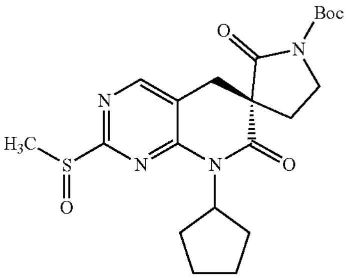

E2-Sulfoxide

+

-continued

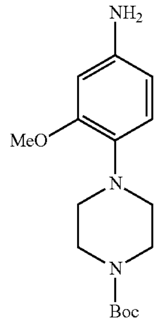

78

Procedure A

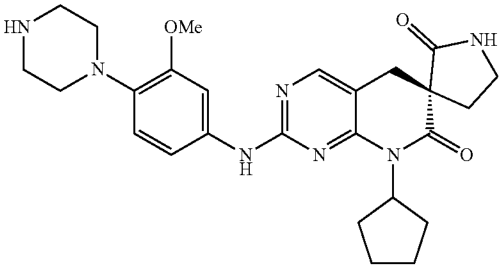

Example-77

Example-77 was synthesized following the general procedure A, 11 mg (22% yield). MS(ESI) m/z 492.2 $(M+H)^+$. $^1H$ NMR (600 MHz, DMSO-$d_6$) δ 9.17 (s, 1H), 8.05 (s, 1H), 7.90 (s, 1H), 7.27 (d, J=2.4 Hz, 1H), 7.13 (d, J=8.4 Hz, 1H), 6.74 (d, J=8.6 Hz, 1H), 5.33 (p, J=8.8 Hz, 1H), 3.69 (s, 3H), 2.97 (d, J=15.7 Hz, 1H), 2.82 (s, 7H), 2.67 (d, J=15.7 Hz, 1H), 2.31 (ddd, J=12.9, 7.9, 4.8 Hz, 2H), 1.99-1.90 (m, 2H), 1.88-1.76 (m, 3H), 1.74-1.66 (m, 2H), 1.49-1.40 (m, 2H).

Example-78 (VP-7-142, SPV-395)

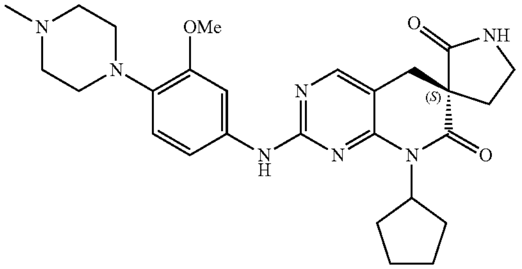

Step 1: Synthesis of (S)-8-cyclopentyl-2-((3-methoxy-4-(4-methylpiperazin-1-yl)phenyl)amino)-5,8-dihydro-7H-spiro[pyrido[2,3-d]pyrimidine-6,3'-pyrrolidine]-2',7-dione (Example-78)

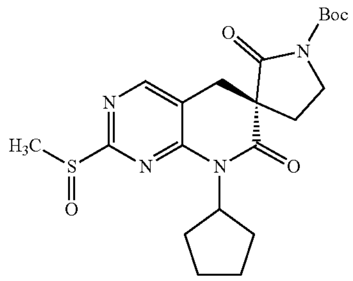

+

E2-Sulfoxide

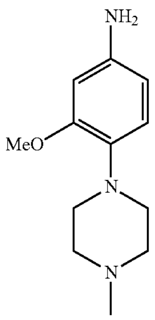

52

Procedure A

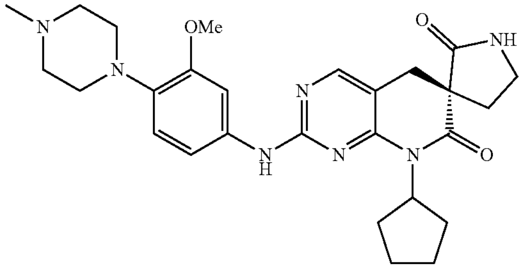

Example-78

Example-78 was synthesized following the general procedure A, 11 mg (22% yield). MS(ESI) m/z 506.2 $(M+H)^+$. $^1$H NMR (600 MHz, DMSO-$d_6$) δ 9.24 (s, 1H), 8.06 (s, 1H), 7.91 (s, 1H), 7.34 (d, J=2.3 Hz, 1H), 7.17 (dd, J=8.7, 2.3 Hz, 1H), 6.80 (d, J=8.6 Hz, 1H), 5.33 (p, J=8.8 Hz, 1H), 3.71 (s, 3H), 3.22-3.11 (m, 5H), 2.97 (d, J=15.8 Hz, 1H), 2.75 (s, 3H), 2.69 (d, J=15.8 Hz, 1H), 2.43 (s, 4H), 2.33 (ddd, J=12.9, 7.8, 4.9 Hz, 1H), 1.99-1.90 (m, 2H), 1.88-1.77 (m, 4H), 1.75-1.67 (m, 2H), 1.45 (q, J=6.6, 6.1 Hz, 2H).

Example-79 (VP-7-60, SPV-396)

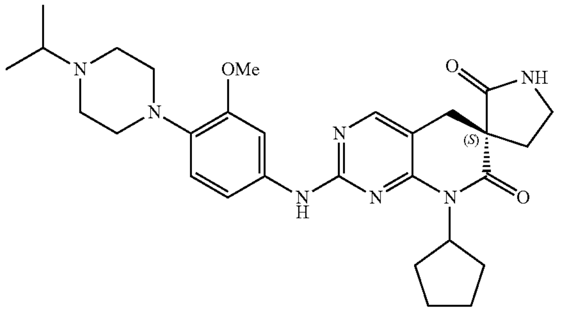

Step 1: Synthesis of (S)-8-cyclopentyl-2-((4-(4-isopropylpiperazin-1-yl)-3-methoxyphenyl)amino)-5,8-dihydro-7H-spiro[pyrido[2,3-d]pyrimidine-6,3'-pyrrolidine]-2',7-dione Example-79

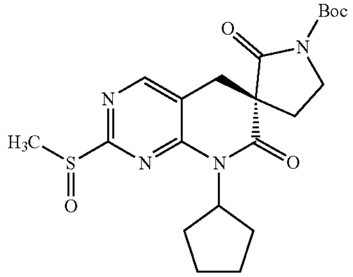

+

E2-Sulfoxide

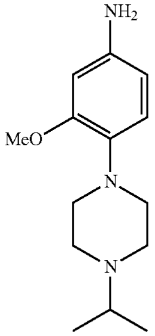

57

Procedure A

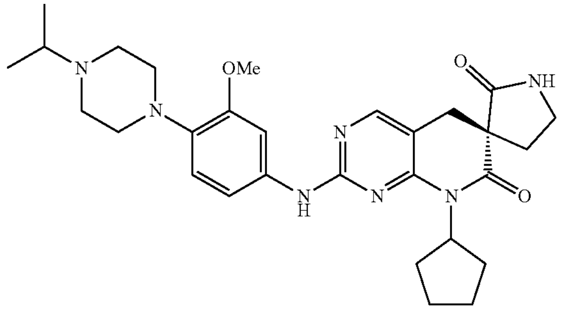

Example-79

Example-79 was synthesized following the general procedure A, 8 mg (15% yield). MS(ESI) m/z 534.2 $(M+H)^+$. $^1H$ NMR (600 MHz, DMSO-$d_6$) δ 9.15 (s, 1H), 8.05 (s, 1H), 7.90 (s, 1H), 7.27 (d, J=2.3 Hz, 1H), 7.13-7.09 (m, 1H), 6.72 (d, J=8.6 Hz, 1H), 5.33 (p, J=8.8 Hz, 1H), 3.69 (s, 3H), 3.20-3.11 (m, 2H), 2.97 (d, J=15.7 Hz, 1H), 2.83 (s, 4H), 2.66 (d, J=15.7 Hz, 1H), 2.62-2.53 (m, 1H), 2.43 (s, 4H), 2.30 (ddd, J=12.8, 7.8, 4.8 Hz, 1H), 1.99-1.90 (m, 2H), 1.88-1.75 (m, 3H), 1.74-1.67 (m, 2H), 1.47-1.41 (m, 2H), 0.93 (d, J=6.5 Hz, 6H).

Example-80 (VP-7-144, SPV-397)

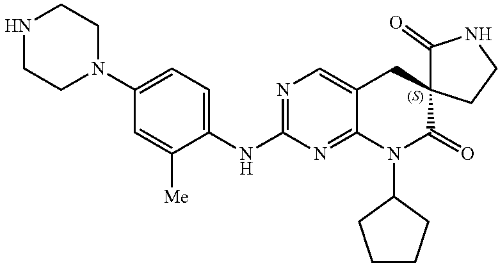

Step 1: Synthesis of (S)-8-cyclopentyl-2-((2-methyl-4-(piperazin-1-yl)phenyl)amino)-5,8-dihydro-7H-spiro[pyrido[2,3-d]pyrimidine-6,3'-pyrrolidine]-2',7-dione (Example-80)

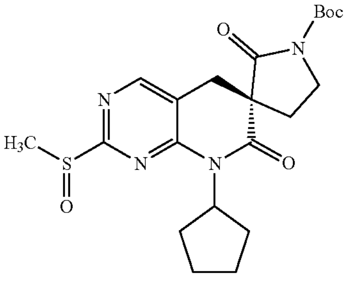

E2-Sulfoxide

+

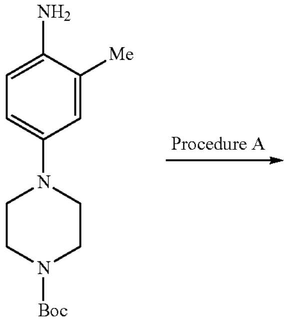

58

-continued

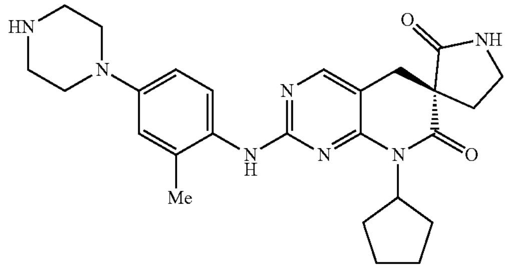

Example-80

Example-80 was synthesized following the general procedure A, 4 mg (8% yield). MS(ESI) m/z 476.2 $(M+H)^+$. $^1H$ NMR (600 MHz, DMSO-$d_6$) δ 8.47 (s, 1H), 8.00 (s, 1H), 7.95 (s, 1H), 7.18 (d, J=8.6 Hz, 1H), 6.84 (d, J=2.9 Hz, 1H), 6.77 (dd, J=8.7, 2.9 Hz, 1H), 5.22-5.17 (m, 1H), 3.26-3.21 (m, 2H), 3.21-3.16 (m, 4H), 3.13-3.08 (m, 4H), 2.99 (d, J=15.6 Hz, 1H), 2.67 (d, J=15.6 Hz, 1H), 2.33 (ddd, J=12.7, 7.8, 4.7 Hz, 1H), 2.15 (s, 3H), 2.00-1.86 (m, 3H), 1.65-1.54 (m, 4H), 1.40-1.34 (m, 2H).

Example-81 (VP-7-139, SPV-398)

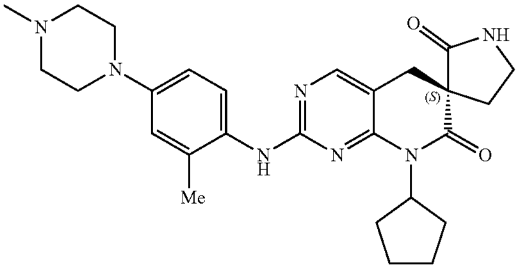

Step 1: Synthesis of (S)-8-cyclopentyl-2-((2-methyl-4-(4-methylpiperazin-1-yl)phenyl)amino)-5,8-dihydro-7H-spiro[pyrido[2,3-d]pyrimidine-6,3'-pyrrolidine]-2',7-dione (Example-81)

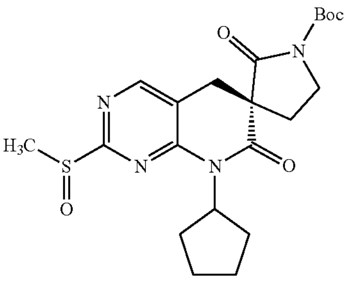

E2-Sulfoxide

+

-continued

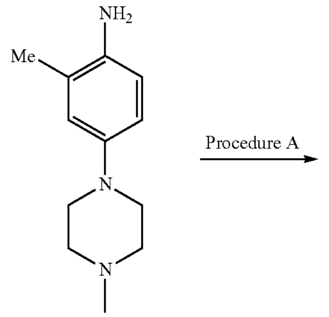

56

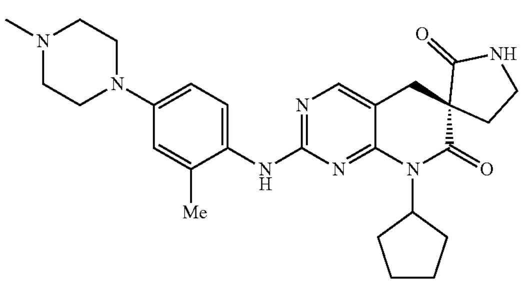

Example-81

Example-81 was synthesized following the general procedure A, 9 mg (18% yield). MS(ESI) m/z 490.2 $(M+H)^+$. $^1H$ NMR (600 MHz, DMSO-$d_6$) δ 8.40 (s, 1H), 7.90 (d, J=27.4 Hz, 2H), 7.11 (d, J=8.6 Hz, 1H), 6.78 (d, J=2.9 Hz, 1H), 6.71 (dd, J=8.7, 2.9 Hz, 1H), 5.13 (s, 1H), 3.20-3.08 (m, 4H), 3.05-2.85 (m, 4H), 2.63-2.51 (m, 3H), 2.43 (s, 4H), 2.26 (ddd, J=12.8, 7.8, 4.7 Hz, 1H), 2.08 (s, 3H), 1.93-1.75 (m, 3H), 1.54 (s, 4H), 1.31 (s, 2H).

Example-82 (VP-7-125, SPV-399)

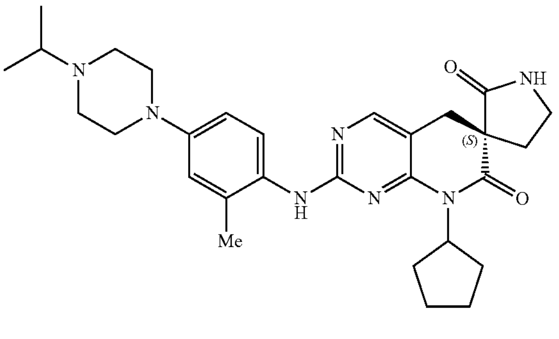

Step 1: Synthesis of (S)-8-cyclopentyl-2-((4-(4-isopropylpiperazin-1-yl)-2-methylphenyl)amino)-5,8-dihydro-7H-spiro[pyrido[2,3-d]pyrimidine-6,3'-pyrrolidine]-2',7-dione (Example-82)

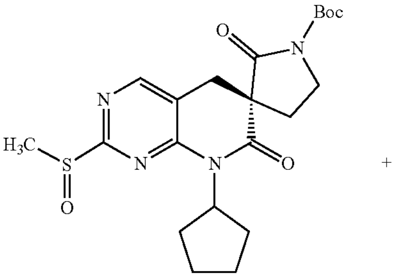

E2-Sulfoxide

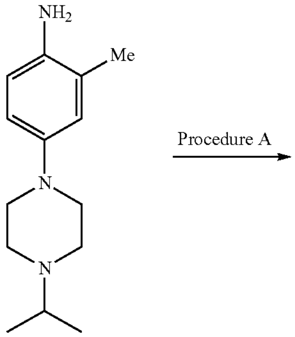

79

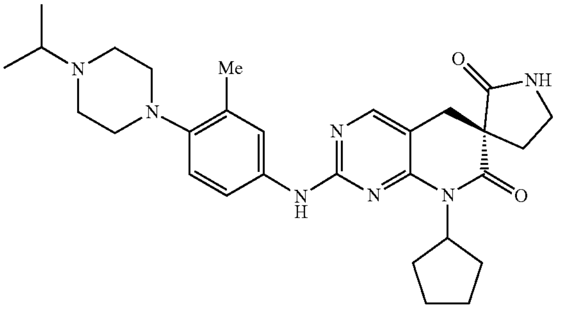

Example-82

Example-82 was synthesized following the general procedure A, 5 mg (10% yield). MS(ESI) m/z 518.2 $(M+H)^+$. $^1H$ NMR (600 MHz, DMSO-$d_6$) δ 8.35 (s, 1H), 7.92 (s, 1H), 7.88 (s, 1H), 7.05 (d, J=8.7 Hz, 1H), 6.72 (d, J=2.8 Hz, 1H), 6.65 (dd, J=8.7, 2.9 Hz, 1H), 5.12 (t, J=9.1 Hz, 1H), 3.19-3.08 (m, 4H), 3.03-2.98 (m, 4H), 2.91 (d, J=15.6 Hz, 1H), 2.62-2.56 (m, 2H), 2.52-2.48 (m, 4H), 2.24 (ddd, J=12.7, 7.8, 4.6 Hz, 1H), 2.06 (s, 3H), 1.90-1.84 (m, 2H), 1.84-1.82 (m, 1H), 1.52 (s, 2H), 1.33-1.27 (m, 2H), 0.93 (d, J=6.5 Hz, 6H).

Example-83 (VP-7-145, SPV-400)

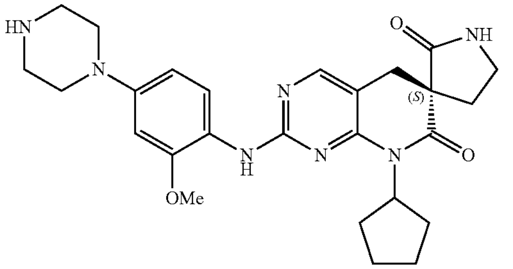

Step 1: Synthesis of (S)-8-cyclopentyl-2-((2-methoxy-4-(piperazin-1-yl)phenyl)amino)-5,8-dihydro-7H-spiro[pyrido[2,3-d]pyrimidine-6,3'-pyrrolidine]-2',7-dione (Example-83)

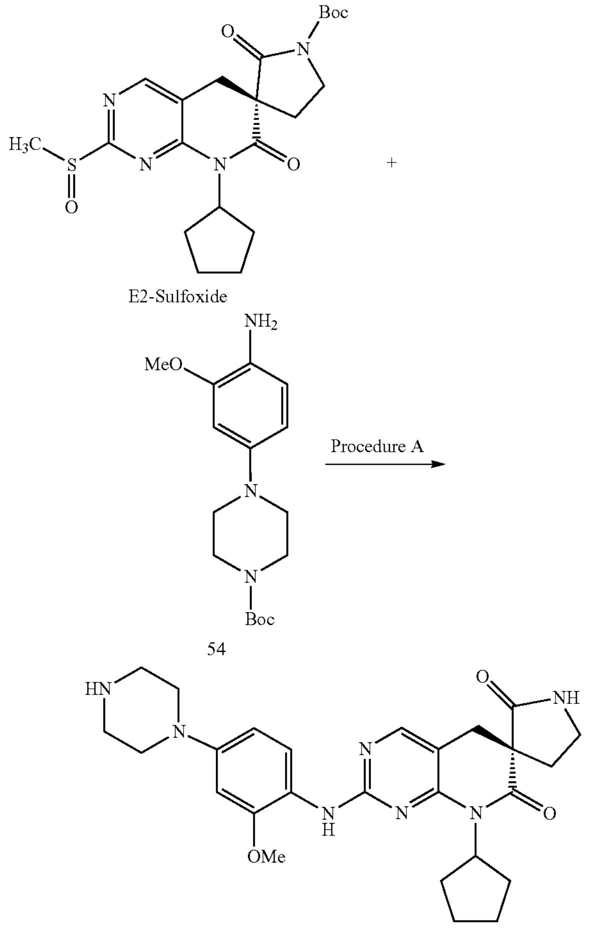

E2-Sulfoxide

54

Example-83

Example-83 was synthesized following the general procedure A, 15 mg (31% yield). MS(ESI) m/z 492.2 $(M+H)^+$. $^1H$ NMR (600 MHz, DMSO-$d_6$) δ 7.98 (s, 1H), 7.89 (s, 1H), 7.86 (s, 1H), 7.53 (d, J=8.6 Hz, 1H), 6.60 (d, J=2.5 Hz, 1H), 6.44 (dd, J=8.7, 2.6 Hz, 1H), 5.17 (p, J=8.9 Hz, 1H), 3.73 (s, 3H), 3.20-3.10 (m, 6H), 3.09-3.04 (m, 4H), 2.94 (d, J=15.7 Hz, 1H), 2.64 (d, J=15.7 Hz, 1H), 2.34-2.23 (m, 1H), 1.97-1.88 (m, 2H), 1.87-1.80 (m, 1H), 1.67-1.57 (m, 4H), 1.44-1.36 (m, 2H).

Example-84 (VP-7-140, SPV-401)

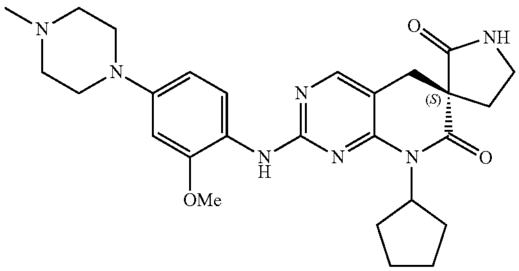

Step 1: Synthesis of (S)-8-cyclopentyl-2-((2-methoxy-4-(4-methylpiperazin-1-yl)phenyl)amino)-5,8-dihydro-7H-spiro[pyrido[2,3-d]pyrimidine-6,3'-pyrrolidine]-2',7-dione (Example-84)

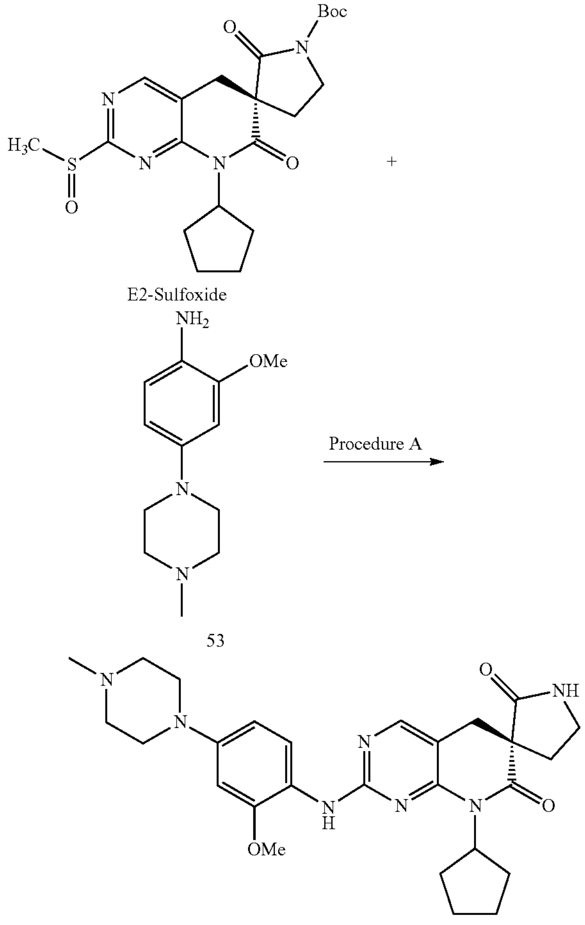

E2-Sulfoxide

53

Example-84

Example-84 was synthesized following the general procedure A, 14 mg (27% yield). MS(ESI) m/z 506.2 $(M+H)^+$. $^1H$ NMR (600 MHz, DMSO-$d_6$) δ 8.04 (s, 1H), 7.96 (s, 1H), 7.88 (s, 1H), 7.55 (d, J=8.7 Hz, 1H), 6.62 (d, J=2.6 Hz, 1H), 6.47 (dd, J=8.7, 2.6 Hz, 1H), 5.23 (p, J=8.5 Hz, 1H), 3.78 (s, 3H), 3.27-3.17 (m, 2H), 3.13 (s, 4H), 3.00 (d, J=15.6 Hz, 1H), 2.69 (d, J=15.7 Hz, 1H), 2.50 (s, 4H), 2.34 (ddd, J=12.8, 7.8, 4.8 Hz, 1H), 2.26 (s, 3H), 2.04-1.93 (m, 2H), 1.93-1.86 (m, 1H), 1.77-1.63 (m, 4H), 1.51-1.40 (m, 2H).

Example-85 (VP-7-126, SPV-402)

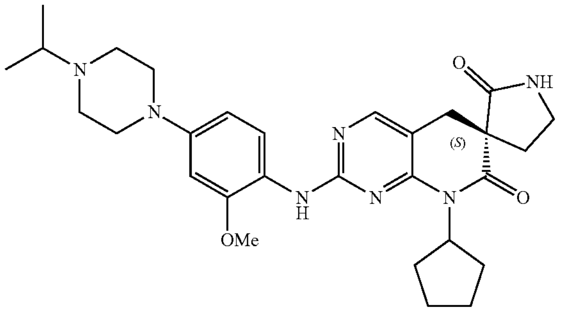

Step 1: Synthesis of (S)-8-cyclopentyl-2-((4-(4-isopropylpiperazin-1-yl)-2-methoxyphenyl)amino)-5,8-dihydro-7H-spiro[pyrido[2,3-d]pyrimidine-6,3'-pyrrolidine]-2',7-dione Example-85

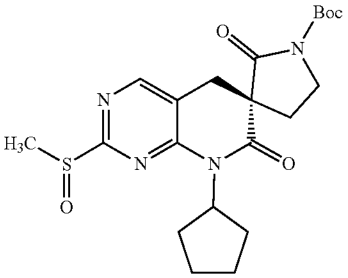

E2-Sulfoxide

+

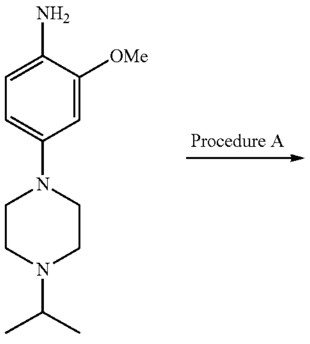

55

-continued

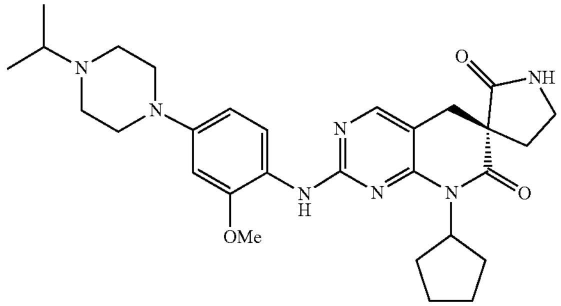

Example-85

Example-85 was synthesized following the general procedure A, 3 mg (6% yield). MS(ESI) m/z 534.2 $(M+H)^+$. $^1H$ NMR (600 MHz, DMSO-$d_6$) δ 7.97 (s, 1H), 7.89 (s, 1H), 7.82 (s, 1H), 7.46 (d, J=8.7 Hz, 1H), 6.54 (d, J=2.6 Hz, 1H), 6.39 (dd, J=8.7, 2.6 Hz, 1H), 5.16 (p, J=8.8 Hz, 1H), 3.71 (s, 3H), 3.19-3.08 (m, 2H), 3.08-2.98 (m, 4H), 2.93 (d, J=15.7 Hz, 1H), 2.67-2.57 (m, 2H), 2.56-2.48 (m, 4H), 2.27 (ddd, J=12.8, 7.8, 4.7 Hz, 1H), 1.99-1.87 (m, 2H), 1.87-1.80 (m, 1H), 1.72-1.52 (m, 4H), 1.46-1.30 (m, 2H), 0.94 (d, J=6.5 Hz, 6H).

Example-86 (VP-7-166, SPV-403)

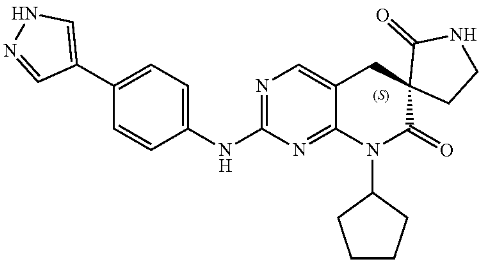

Step 1: Synthesis of (S)-2-((4-(1H-pyrazol-4-yl)phenyl)amino)-8-cyclopentyl-5,8-dihydro-7H-spiro[pyrido[2,3-d]pyrimidine-6,3'-pyrrolidine]-2',7-dione (Example-86)

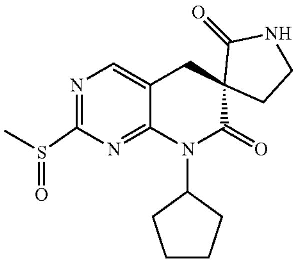

E2-Sulfoxide

+

-continued

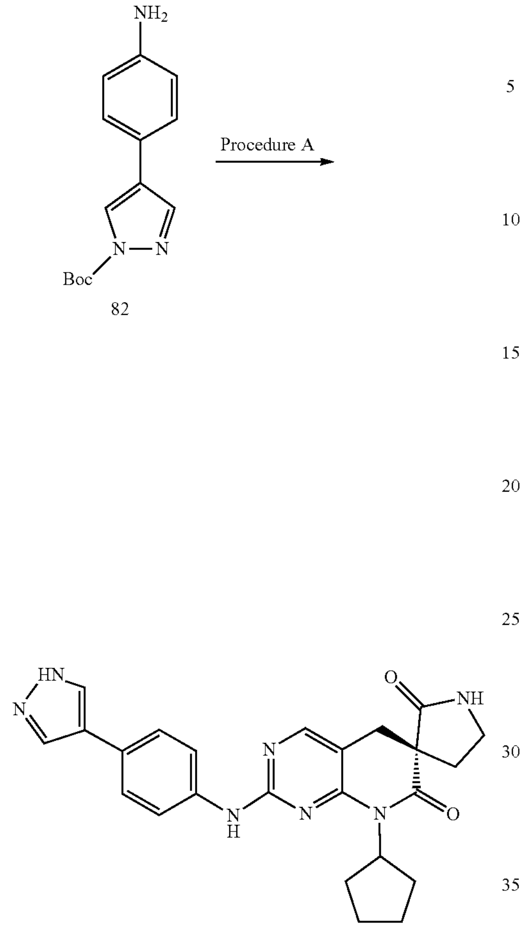

82

Example-86

Example-86 was synthesized following the general procedure A, 9 mg (20% yield). MS(ESI) m/z 444.2 $(M+H)^+$. $^1H$ NMR (600 MHz, DMSO-$d_6$) δ 12.77 (s, 1H), 9.36 (s, 1H), 8.09 (s, 1H), 8.02 (s, 1H), 7.91 (s, 1H), 7.79 (s, 1H), 7.62 (d, J=8.4 Hz, 2H), 7.44 (d, J=8.3 Hz, 2H), 5.31 (p, J=8.8 Hz, 1H), 3.21-3.12 (m, 2H), 2.98 (d, J=15.6 Hz, 1H), 2.69 (d, J=15.7 Hz, 1H), 2.32 (td, J=7.9, 4.0 Hz, 1H), 2.02-1.92 (m, 2H), 1.89-1.78 (m, 3H), 1.78-1.69 (m, 2H), 1.53-1.42 (m, 2H).

Example-87 (VP-7-167, SPV-404)

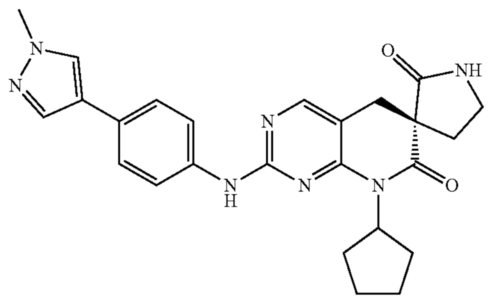 [SMILES: Cn1cc(-c2ccc(Nc3ncc4c(n3)N(C3CCCC3)C(=O)[C@]3(CCNC3=O)C4)cc2)cn1]

Step 1: Synthesis of (S)-8-cyclopentyl-2-((4-(1-methyl-1H-pyrazol-4-yl)phenyl)amino)-5,8-dihydro-7H-spiro[pyrido[2,3-d]pyrimidine-6,3'-pyrrolidine]-2',7-dione (Example-87)

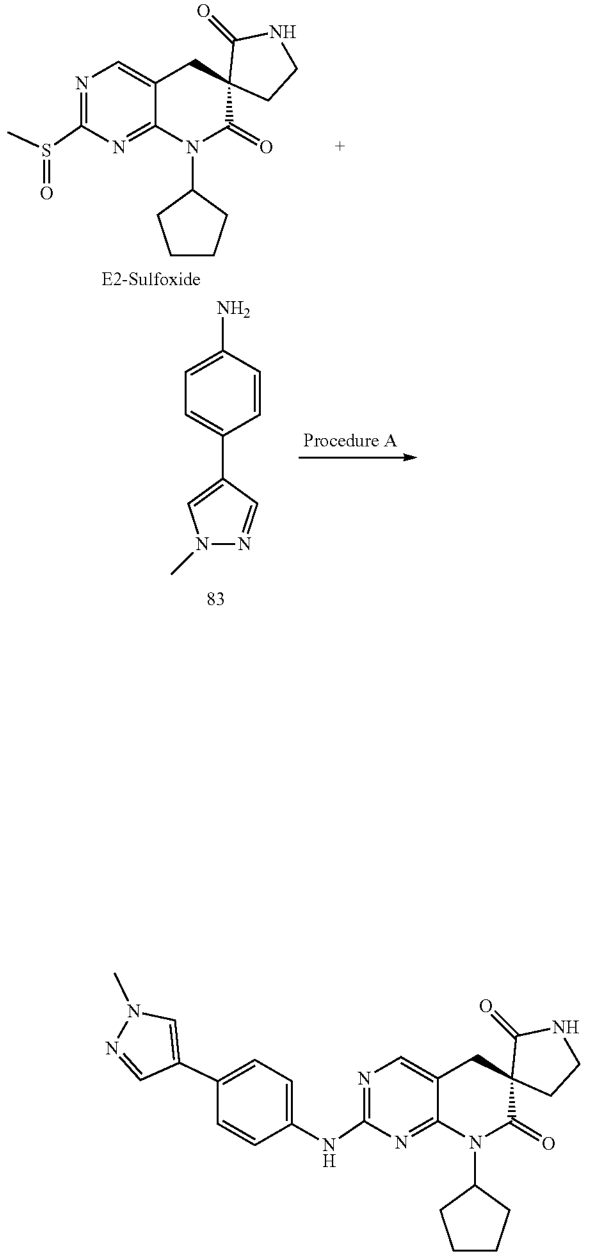

E2-Sulfoxide

83

Example-87

Example-87 was synthesized following the general procedure A, 12 mg (26% yield). MS(ESI) m/z 458.2 $(M+H)^+$. $^1H$ NMR (600 MHz, DMSO-$d_6$) δ 9.37 (s, 1H), 8.09 (s, 1H), 7.97 (s, 1H), 7.91 (s, 1H), 7.71 (s, 1H), 7.66-7.58 (m, 2H), 7.39 (d, J=8.6 Hz, 2H), 5.31 (p, J=8.8 Hz, 1H), 3.78 (s, 3H), 3.21-3.12 (m, 2H), 2.98 (d, J=15.7 Hz, 1H), 2.69 (d, J=15.7 Hz, 1H), 2.33 (ddd, J=12.8, 7.8, 4.9 Hz, 1H), 2.04-1.92 (m, 2H), 1.89-1.78 (m, 3H), 1.78-1.67 (m, 2H), 1.55-1.42 (m, 2H).

Example-88 (VP-7-172, SPV-405)

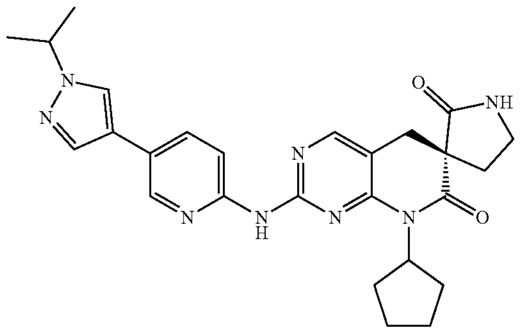 [SMILES: CC(C)n1cc(-c2ccc(Nc3ncc4c(n3)N(C3CCCC3)C(=O)[C@]3(CCNC3=O)C4)nc2)cn1]

Step 1: Synthesis of (S)-8-cyclopentyl-2-((5-(1-isopropyl-1H-pyrazol-4-yl)pyridin-2-yl)amino)-5,8-dihydro-7H-spiro[pyrido[2,3-d]pyrimidine-6,3'-pyrrolidine]-2',7-dione (Example-88)

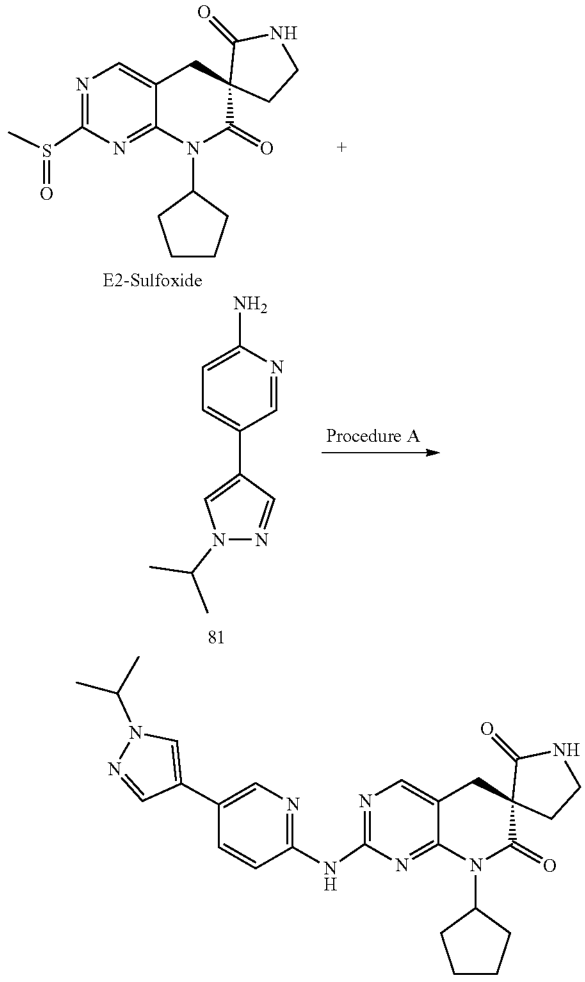

E2-Sulfoxide

81

Example-88

Example-88 was synthesized following the general procedure A, 16 mg (33% yield). MS(ESI) m/z 487.2 $(M+H)^+$.

$^1H$ NMR (600 MHz, DMSO-$d_6$) δ 9.56 (s, 1H), 8.47 (d, J=2.5 Hz, 1H), 8.19 (s, 1H), 8.15 (s, 1H), 8.06 (d, J=8.7 Hz, 1H), 7.92 (s, 1H), 7.87 (dd, J=8.6, 2.5 Hz, 1H), 7.82 (s, 1H), 5.29 (p, J=8.8 Hz, 1H), 4.44 (p, J=6.7 Hz, 1H), 3.20-3.13 (m, 2H), 3.01 (d, J=15.7 Hz, 1H), 2.74 (d, J=15.8 Hz, 1H), 2.38-2.30 (m, 1H), 2.05-1.95 (m, 2H), 1.89-1.80 (m, 3H), 1.78-1.67 (m, 2H), 1.55-1.45 (m, 2H), 1.38 (d, J=6.7 Hz, 6H).

Example-89 (VP-7-175, SPV-406)

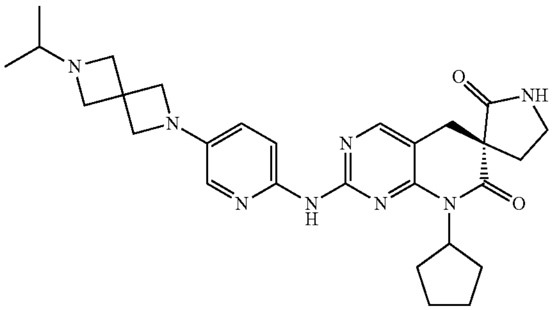

Step 1: (S)-8-cyclopentyl-2-((5-(6-isopropyl-2,6-diazaspiro[3.3]heptan-2-yl)pyridin-2-yl)amino)-5,8-dihydro-7H-spiro[pyrido[2,3-d]pyrimidine-6,3'-pyrrolidine]-2',7-dione (Example-89)

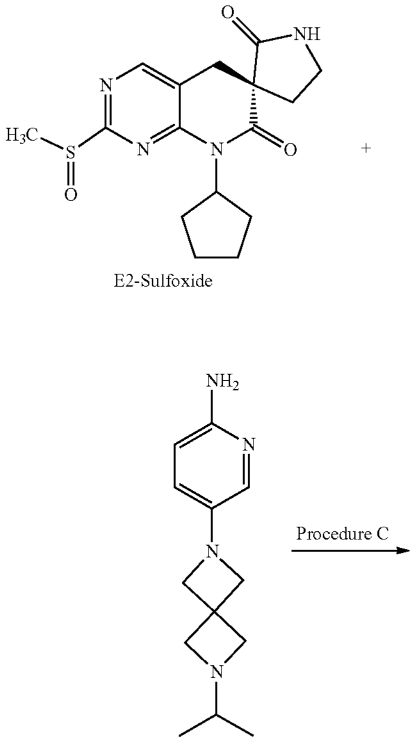

E2-Sulfoxide

62

-continued

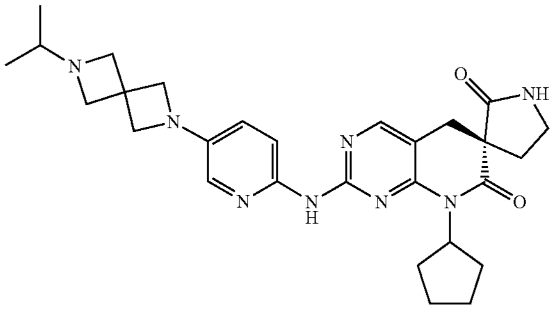 [SMILES: CC(C)N1CC2(CN(c3ccc(Nc4ncc5c(n4)N(C4CCCC4)C(=O)[C@]4(CCNC4=O)C5)nc3)C2)C1]

Example-89

Example-89 was synthesized following the general procedure A, 11 mg (21% yield). MS(ESI) m/z 517.2 $(M+H)^+$. $^1H$ NMR (600 MHz, DMSO-$d_6$) δ 9.18 (s, 1H), 8.06 (s, 1H), 7.91 (s, 1H), 7.81 (d, J=8.9 Hz, 1H), 7.53 (d, J=3.0 Hz, 1H), 6.91 (dd, J=8.8, 3.0 Hz, 1H), 5.25 (p, J=8.8 Hz, 1H), 4.20 (s, 2H), 3.99 (s, 1H), 3.87 (s, 1H), 3.33 (s, 3H), 3.22-3.11 (m, 3H), 2.97 (d, J=15.7 Hz, 1H), 2.69 (d, J=15.9 Hz, 1H), 2.33 (ddd, J=12.8, 7.8, 4.9 Hz, 1H), 2.02-1.92 (m, 2H), 1.88-1.81 (m, 2H), 1.81-1.76 (m, 2H), 1.73-1.65 (m, 2H), 1.50-1.42 (m, 2H), 1.04 (d, J=6.4 Hz, 6H).

Example-90 (VP-7-162, SPV-407)

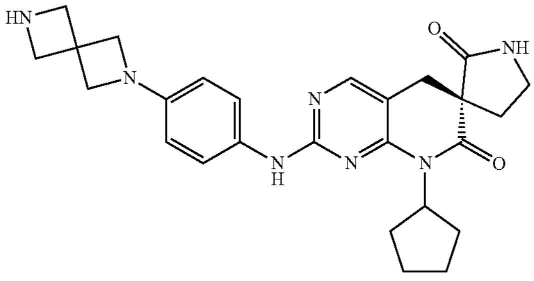 [SMILES: O=C1NCC[C@@]12Cc1cnc(Nc3ccc(N4CC5(CNC5)C4)cc3)nc1N(C1CCCC1)C2=O]

Step 1: (S)-2-((4-(2,6-diazaspiro[3.3]heptan-2-yl)phenyl)amino)-8-cyclopentyl-5,8-dihydro-7H-spiro[pyrido[2,3-d]pyrimidine-6,3'-pyrrolidine]-2',7-dione (Example-90)

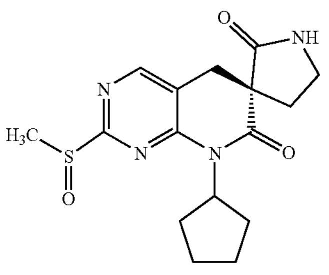

E2-Sulfoxide

+

-continued

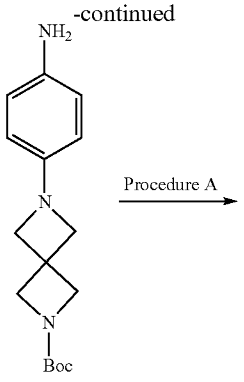

28

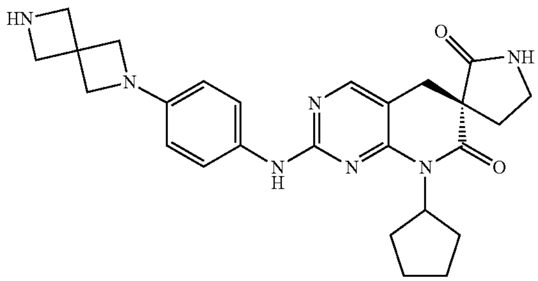

Example-90

Example-90 was synthesized following the general procedure A, 6 mg (13% yield). MS(ESI) m/z 474.2 $(M+H)^+$. $^1H$ NMR (600 MHz, DMSO-$d_6$) δ 8.92 (s, 1H), 7.98 (s, 1H), 7.89 (s, 1H), 7.29 (d, J=8.6 Hz, 2H), 6.52 (d, J=8.7 Hz, 2H), 5.39 (s, 1H), 5.25 (p, J=8.8 Hz, 1H), 3.59 (s, 4H), 3.50 (s, 2H), 3.15-3.09 (m, 4H), 2.94 (d, J=15.6 Hz, 1H), 2.63 (d, J=15.7 Hz, 1H), 2.33-2.26 (m, 1H), 2.00-1.92 (m, 2H), 1.88-1.81 (m, 1H), 1.81-1.73 (m, 2H), 1.73-1.63 (m, 2H), 1.49-1.39 (m, 2H).

Example-91 (VP-7-163, SPV-408)

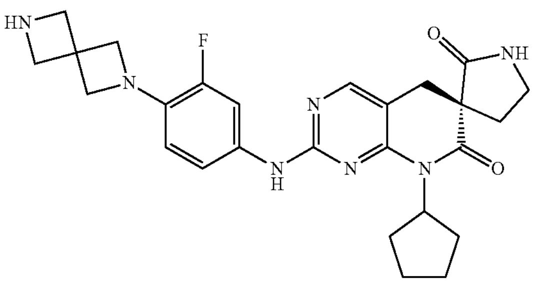 [SMILES: O=C1NCC[C@@]12Cc1cnc(Nc3ccc(N4CC5(CNC5)C4)c(F)c3)nc1N(C1CCCC1)C2=O]

Step 1: (S)-8-cyclopentyl-2-((3-fluoro-4-(2,6-diazaspiro[3.3]heptan-2-yl)phenyl)amino)-5,8-dihydro-7H-spiro[pyrido[2,3-d]pyrimidine-6,3'-pyrrolidine]-2',7-dione (Example-91)

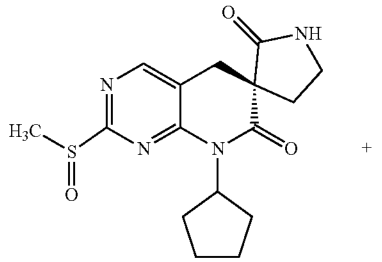

E2-Sulfoxide

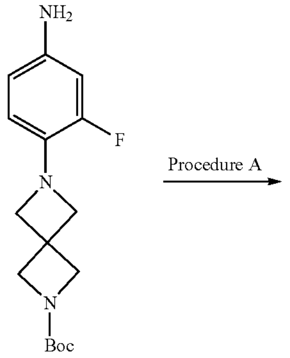

26

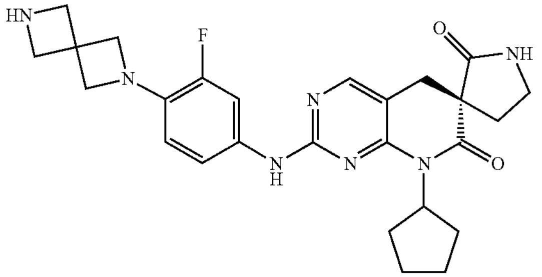

Example-91

Example-91 was synthesized following the general procedure A, 11 mg (22% yield). MS(ESI) m/z 492.2 $(M+H)^+$. $^1H$ NMR (600 MHz, DMSO-$d_6$) δ 9.21 (s, 1H), 8.10 (s, 1H), 7.97 (s, 1H), 7.55 (dd, J=14.4, 2.3 Hz, 1H), 7.17 (d, J=9.1 Hz, 1H), 6.72 (t, J=9.5 Hz, 1H), 5.37-5.29 (m, 1H), 5.21-5.15 (m, 1H), 3.60 (s, 2H), 3.56 (s, 1H), 3.28-3.17 (m, 6H), 3.03 (d, J=15.7 Hz, 1H), 2.72 (d, J=15.7 Hz, 1H), 2.37 (ddd, J=12.8, 7.5, 4.6 Hz, 1H), 2.08-1.98 (m, 2H), 1.95-1.86 (m, 3H), 1.81-1.71 (m, 2H), 1.58-1.47 (m, 2H).

Example-92 (VP-7-62B, SPV-409)

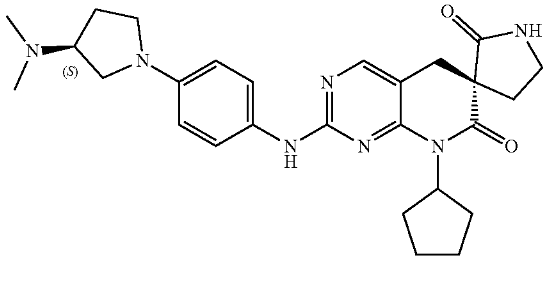

Step 1: Synthesis of (S)-8-cyclopentyl-2-((4-((S)-3-(dimethylamino)pyrrolidin-1-yl)phenyl)amino)-5,8-dihydro-7H-spiro[pyrido[2,3-d]pyrimidine-6,3'-pyrrolidine]-2',7-dione (Example-92)

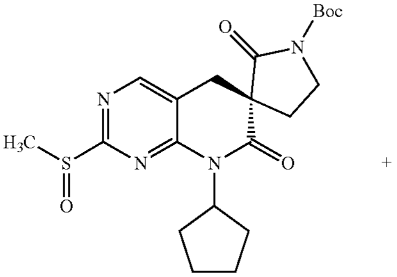

E2-Sulfoxide

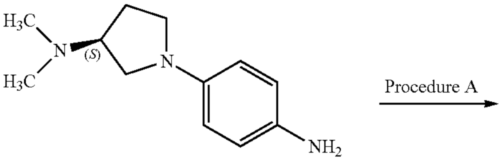

33

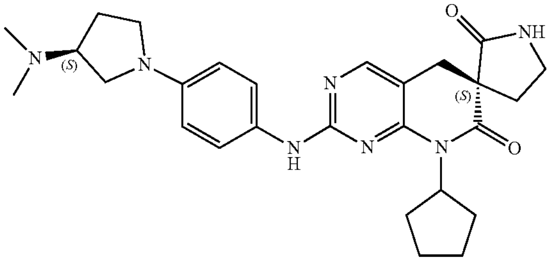

Example-92

Example-92 was synthesized following the general procedure A, 13 mg (27% yield). MS(ESI) m/z 490.2 $(M+H)^+$. $^1H$ NMR (600 MHz, DMSO-$d_6$) δ 8.92 (s, 1H), 7.99 (s, 1H), 7.89 (s, 1H), 7.35 (d, J=8.6 Hz, 2H), 6.42 (d, J=8.9 Hz, 2H), 5.26 (p, J=8.9 Hz, 1H), 3.32 (dd, J=9.1, 7.3 Hz, 2H), 3.19-3.11 (m, 3H), 2.98-2.91 (m, 2H), 2.74 (p, J=6.7, 5.7 Hz, 1H), 2.62 (d, J=15.7 Hz, 1H), 2.28 (ddd, J=12.8, 7.8, 4.7 Hz, 1H), 2.14 (s, 6H), 2.10-2.03 (m, 1H), 1.99-1.91 (m, 2H), 1.87-1.80 (m, 1H), 1.80-1.75 (m, 2H), 1.75-1.63 (m, 3H), 1.50-1.38 (m, 2H).

Example-93 (VP-7-66A, SPV-410)

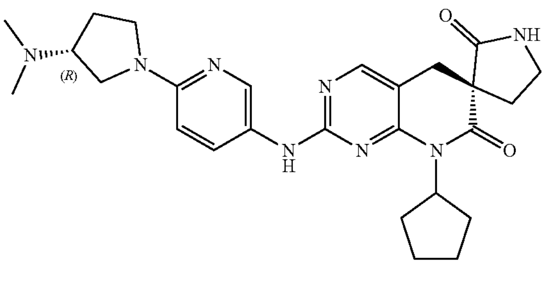

Step 1: Synthesis of (S)-8-cyclopentyl-2-((6-((R)-3-(dimethylamino)pyrrolidin-1-yl)pyridin-3-yl)amino)-5,8-dihydro-7H-spiro[pyrido[2,3-d]pyrimidine-6,3'-pyrrolidine]-2',7-dione (Example-93)

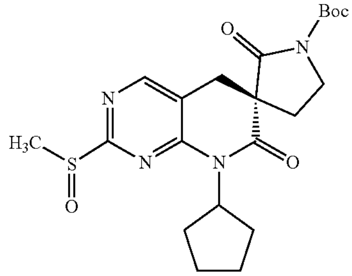

+

E2-Sulfoxide

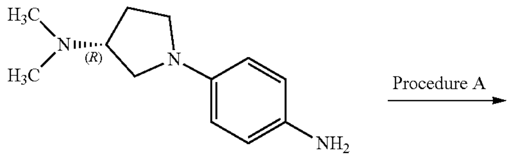

109

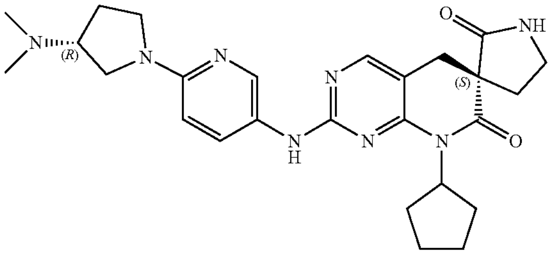

Example-93

Example-93 was synthesized following the general procedure A, 13 mg (27% yield). MS(ESI) m/z 491.2 $(M+H)^+$. $^1$H NMR (600 MHz, DMSO-$d_6$) δ 8.92 (s, 1H), 7.99 (s, 1H), 7.89 (s, 1H), 7.35 (d, J=8.6 Hz, 2H), 6.42 (d, J=8.9 Hz, 2H), 5.26 (p, J=8.9 Hz, 1H), 3.32 (dd, J=9.1, 7.3 Hz, 2H), 3.19-3.11 (m, 3H), 2.98-2.91 (m, 2H), 2.74 (p, J=6.7, 5.7 Hz, 1H), 2.62 (d, J=15.7 Hz, 1H), 2.28 (ddd, J=12.8, 7.8, 4.7 Hz, 1H), 2.14 (s, 6H), 2.10-2.03 (m, 1H), 1.99-1.91 (m, 2H), 1.87-1.80 (m, 1H), 1.80-1.75 (m, 2H), 1.75-1.63 (m, 3H), 1.50-1.38 (m, 2H).

Example-94 (VP-6-67B, SPV-411)

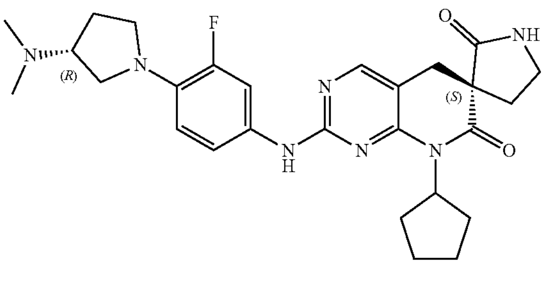

Step 1: Synthesis of (S)-8-cyclopentyl-2-((4-((R)-3-(dimethylamino)pyrrolidin-1-yl)-3-fluorophenyl)amino)-5,8-dihydro-7H-spiro[pyrido[2,3-d]pyrimidine-6,3'-pyrrolidine]-2',7-dione (Example-94)

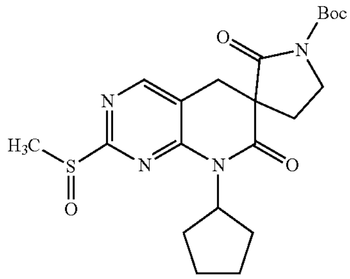

+

E2-Sulfoxide

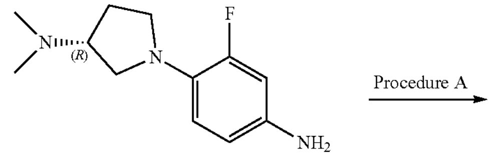

110

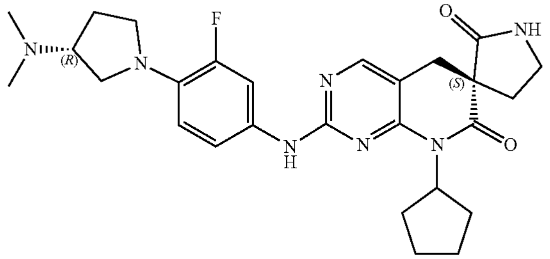

Example-94

Example-94 was synthesized following the general procedure A, 14 mg (27% yield). MS(ESI) m/z 508.2 $(M+H)^+$. $^1$H NMR (600 MHz, DMSO-$d_6$) δ 9.33 (s, 1H), 8.07 (s, 1H), 7.91 (s, 1H), 7.61 (dd, J=16.2, 2.4 Hz, 1H), 7.21 (dd, J=8.7, 2.4 Hz, 1H), 6.74 (t, J=9.5 Hz, 1H), 5.27 (p, J=8.8 Hz, 1H), 3.36 (d, J=6.5 Hz, 2H), 3.22-3.11 (m, 4H), 2.97 (d, J=15.7 Hz, 1H), 2.69 (d, J=15.8 Hz, 2H), 2.43 (s, 6H), 2.37-2.30 (m, 1H), 2.26-2.18 (m, 1H), 2.03-1.93 (m, 3H), 1.88-1.78 (m, 3H), 1.77-1.69 (m, 2H), 1.52-1.43 (m, 2H).

Example-95 (VP-7-68, SPV-412)

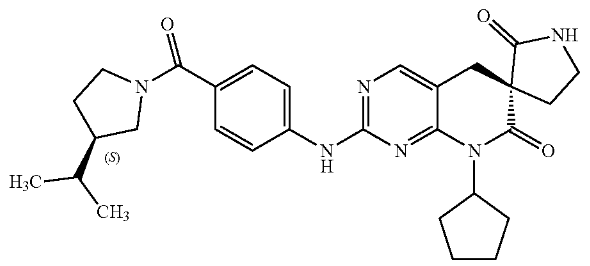

Step 1: (S)-8-cyclopentyl-2-((4-((S)-3-(dimethylamino)pyrrolidine-1-carbonyl)phenyl)amino)-5,8-dihydro-7H-spiro[pyrido[2,3-d]pyrimidine-6,3'-pyrrolidine]-2',7-dione (Example-95)

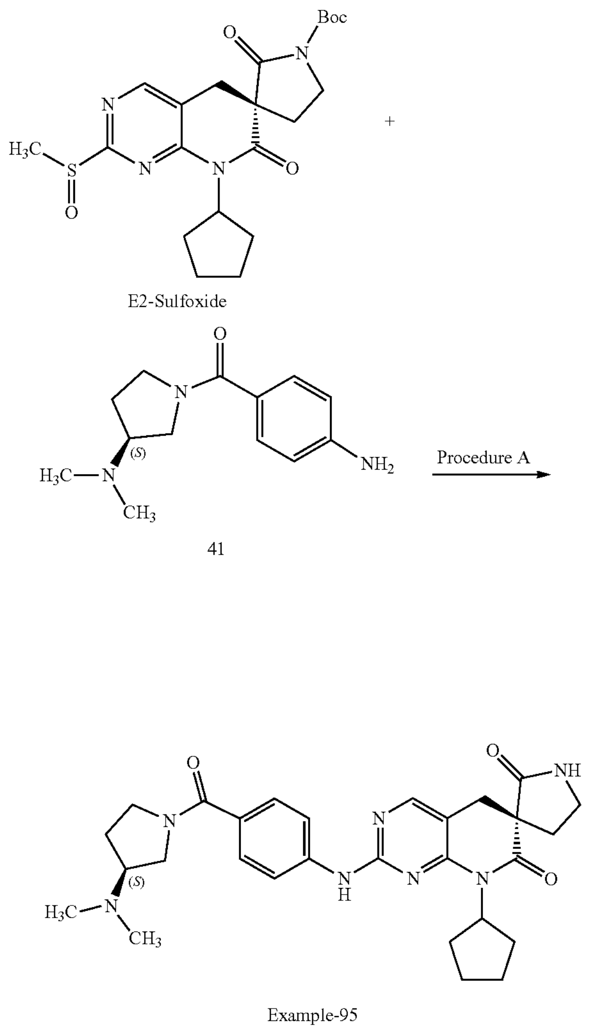

E2-Sulfoxide

41

Example-95

Example-95 was synthesized following the general procedure A, 2 mg (4% yield). MS(ESI) m/z 518.2 $(M+H)^+$.

Example-96 (VP-7-74B, SPV-413)

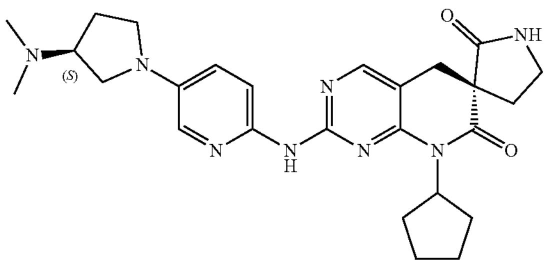

Step 1: Synthesis of (S)-8-cyclopentyl-2-((5-((S)-3-(dimethylamino)pyrrolidin-1-yl)pyridin-2-yl)amino)-5,8-dihydro-7H-spiro[pyrido[2,3-d]pyrimidine-6,3'-pyrrolidine]-2',7-dione (Example-96)

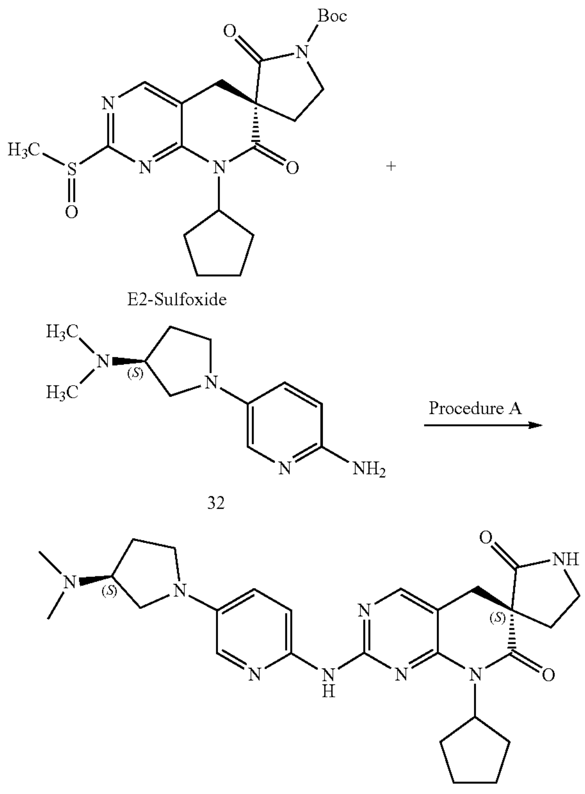

E2-Sulfoxide

32

Example-96

Example-96 was synthesized following the general procedure A, 4 mg (8% yield). MS(ESI) m/z 491.2 $(M+H)^+$. $^1H$ NMR (600 MHz, DMSO-$d_6$) δ 9.03 (s, 1H), 8.30-8.21 (m, 1H), 8.06 (s, 1H), 7.97 (s, 1H), 7.76 (dd, J=8.9, 2.7 Hz, 1H), 6.47 (d, J=9.0 Hz, 1H), 5.29 (s, 1H), 3.74-3.66 (m, 1H), 3.60-3.52 (m, 1H), 3.26-3.17 (m, 4H), 3.01 (d, J=15.7 Hz, 1H), 2.71 (d, J=15.7 Hz, 1H), 2.50 (s, 6H), 2.39-2.34 (m, 2H), 2.24 (s, 1H), 2.06-1.97 (m, 2H), 1.94-1.87 (m, 2H), 1.82 (s, 2H), 1.77-1.68 (m, 2H), 1.50 (q, J=6.0 Hz, 2H).

Example-97 (VP-7-82, SPV-414)

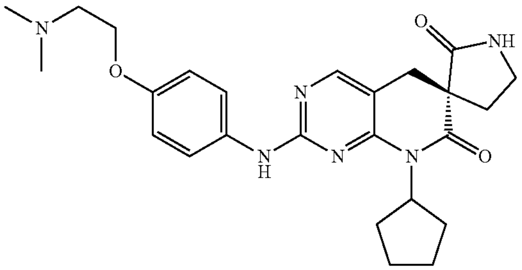 [SMILES: CN(C)CCOc1ccc(Nc2ncc3c(n2)N(C2CCCC2)C(=O)[C@]2(CCNC2=O)C3)cc1]

Step 1: Synthesis of (S)-8-cyclopentyl-2-((4-(2-(dimethylamino)ethoxy)phenyl)amino)-5,8-dihydro-7H-spiro[pyrido[2,3-d]pyrimidine-6,3'-pyrrolidine]-2',7-dione (Example-97)

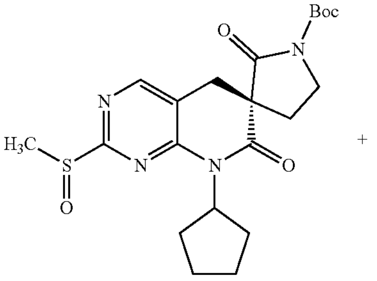

E2-Sulfoxide

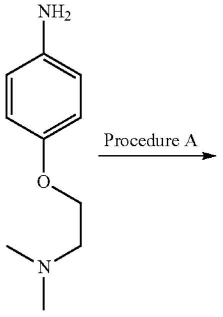

63

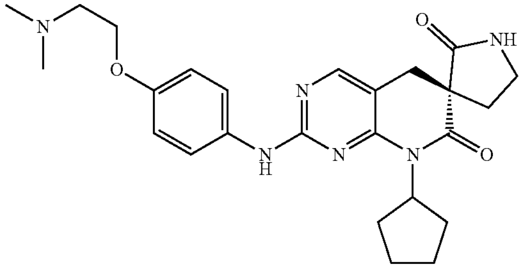

Example-97

Example-97 was synthesized following the general procedure A, 16 mg (35% yield). MS(ESI) m/z 465.2 $(M+H)^+$. $^1H$ NMR (600 MHz, DMSO-$d_6$) δ 9.23 (s, 1H), 8.04 (s, 1H), 7.90 (s, 1H), 7.54 (d, J=8.6 Hz, 2H), 6.87 (d, J=8.8 Hz, 2H), 5.28 (p, J=8.8 Hz, 1H), 4.15 (t, J=5.1 Hz, 2H), 3.20-3.12 (m, 3H), 2.97 (d, J=15.7 Hz, 1H), 2.73-2.63 (m, 7H), 2.32 (ddd, J=12.8, 7.8, 4.9 Hz, 1H), 2.01-1.93 (m, 2H), 1.88-1.78 (m, 4H), 1.75-1.65 (m, 2H), 1.52-1.40 (m, 2H).

Example-98 (VP-7-165, SPV-415)

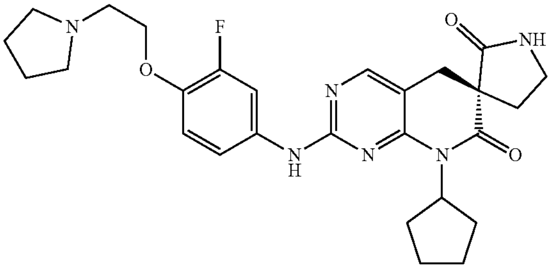 [SMILES: O=C1NCC[C@@]12Cc1cnc(Nc3ccc(OCCN4CCCC4)c(F)c3)nc1N(C1CCCC1)C2=O]

Step 1: Synthesis of (S)-8-cyclopentyl-2-((3-fluoro-4-(2-(pyrrolidin-1-yl)ethoxy)phenyl)amino)-5,8-dihydro-7H-spiro[pyrido[2,3-d]pyrimidine-6,3'-pyrrolidine]-2',7-dione (Example-98)

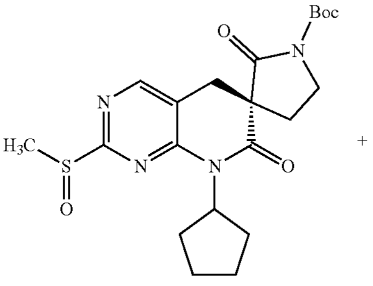

E2-Sulfoxide

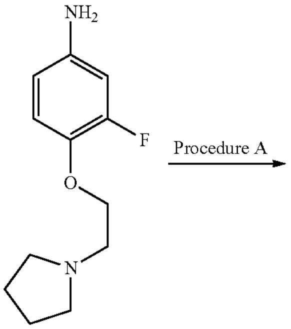

9

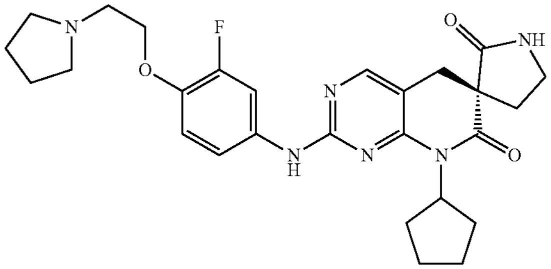

Example-98

Example-98 was synthesized following the general procedure A, 15 mg (29% yield). MS(ESI) m/z 509.2 $(M+H)^+$.

$^1$H NMR (600 MHz, DMSO-$d_6$) δ 9.38 (s, 1H), 8.08 (s, 1H), 7.91 (s, 1H), 7.65 (dd, J=14.3, 2.6 Hz, 1H), 7.28-7.21 (m, 1H), 7.03 (t, J=9.4 Hz, 1H), 5.27 (p, J=8.8 Hz, 1H), 4.01 (t, J=5.9 Hz, 2H), 3.21-3.12 (m, 4H), 2.98 (d, J=15.7 Hz, 1H), 2.76-2.65 (m, 3H), 2.32 (ddd, J=12.8, 7.9, 4.9 Hz, 1H), 2.02-1.91 (m, 2H), 1.88-1.76 (m, 5H), 1.75-1.68 (m, 2H), 1.61 (p, J=3.1 Hz, 4H), 1.52-1.43 (m, 2H).

Example-99 (VP-7-96B, SPV-416)

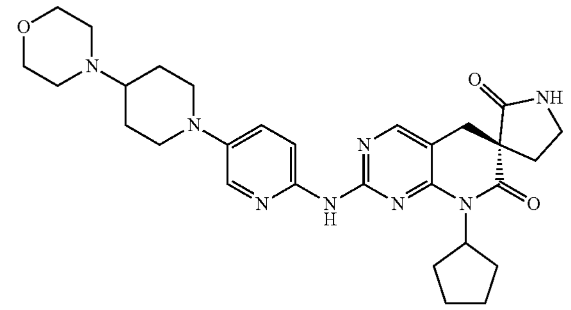 [SMILES: O=C1NCC[C@@]12Cc1cnc(Nc3ccc(N4CCC(N5CCOCC5)CC4)cn3)nc1N(C1CCCC1)C2=O]

Step 1: Synthesis of (S)-8-cyclopentyl-2-((5-(4-morpholinopiperidin-1-yl)pyridin-2-yl)amino)-5,8-dihydro-7H-spiro[pyrido[2,3-d]pyrimidine-6,3'-pyrrolidine]-2',7-dione (Example-99)

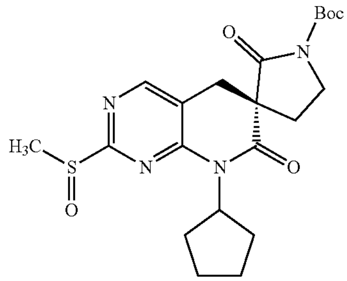

E2-Sulfoxide

+

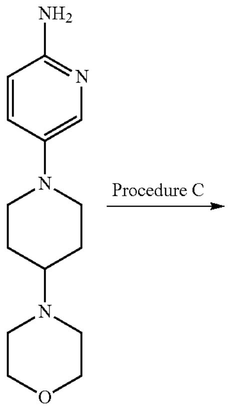

35

-continued

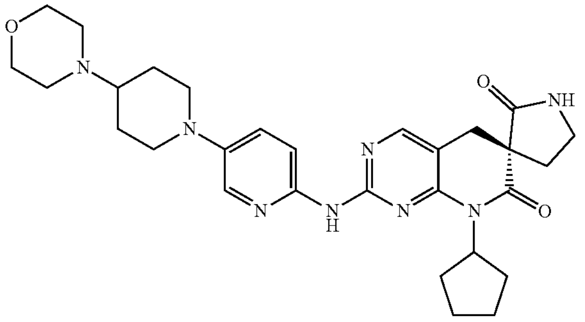

Example-99

Example-99 was synthesized following the general procedure C, 3 mg (5% yield). MS(ESI) m/z 547.2 (M+H)$^+$. $^1$H NMR (600 MHz, DMSO-$d_6$) δ 9.27 (s, 1H), 8.15 (s, 1H), 7.98 (d, J=3.4 Hz, 2H), 7.91 (d, J=9.1 Hz, 1H), 7.41 (dd, J=9.1, 3.1 Hz, 1H), 5.33 (p, J=8.9 Hz, 1H), 3.66 (d, J=12.0 Hz, 2H), 3.58 (t, J=4.6 Hz, 4H), 3.27-3.18 (m, 3H), 3.05 (d, J=15.8 Hz, 1H), 2.76 (d, J=15.8 Hz, 1H), 2.69-2.59 (m, 3H), 2.43-2.34 (m, 2H), 2.30-2.22 (m, 1H), 2.11-2.00 (m, 2H), 1.95-1.81 (m, 5H), 1.76 (s, 2H), 1.60-1.44 (m, 4H).

Example-100 (VP-7-98B, SPV-417)

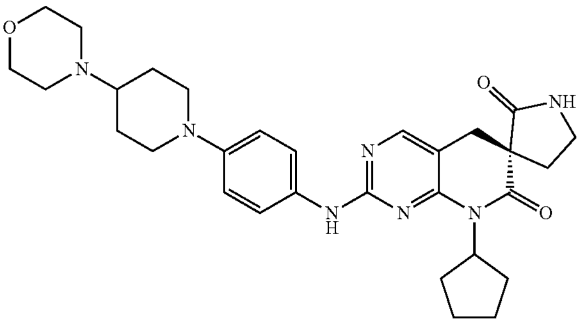 [SMILES: O=C1NCC[C@@]12Cc1cnc(Nc3ccc(N4CCC(N5CCOCC5)CC4)cc3)nc1N(C1CCCC1)C2=O]

Step 1: Synthesis of (S)-8-cyclopentyl-2-((4-(4-morpholinopiperidin-1-yl)phenyl)amino)-5,8-dihydro-7H-spiro[pyrido[2,3-d]pyrimidine-6,3'-pyrrolidine]-2',7-dione (Example-100)

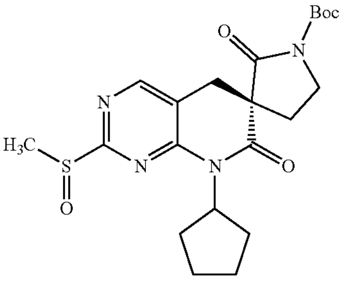

E2-Sulfoxide

+

-continued

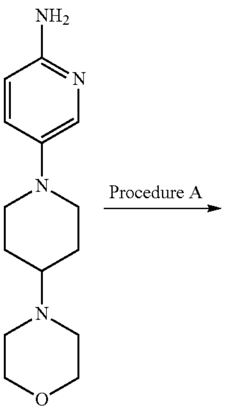

37

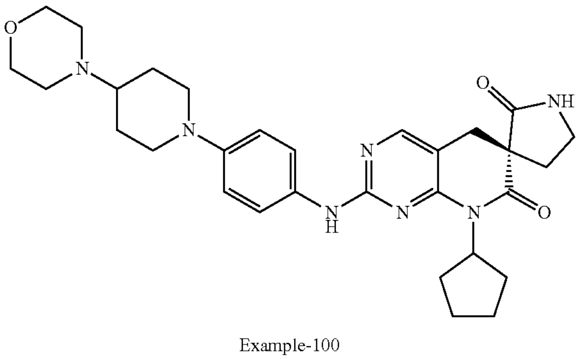

Example-100

Example-100 was synthesized following the general procedure A, 20 mg (36% yield). MS(ESI) m/z 546.2 $(M+H)^+$. $^1H$ NMR (600 MHz, DMSO-$d_6$) δ 9.08 (s, 1H), 8.02 (s, 1H), 7.90 (s, 1H), 7.42 (d, J=8.7 Hz, 2H), 6.81 (d, J=8.7 Hz, 2H), 5.31-5.23 (m, 1H), 3.55 (s, 7H), 3.21-3.10 (m, 3H), 2.95 (d, J=15.6 Hz, 1H), 2.65 (d, J=15.7 Hz, 1H), 2.56-2.49 (m, 3H), 2.30 (ddd, J=12.8, 7.7, 4.8 Hz, 2H), 2.01-1.91 (m, 2H), 1.88-1.76 (m, 6H), 1.73-1.66 (m, 2H), 1.50-1.43 (m, 4H).

Example-101 (VP-7-84B, SPV-431)

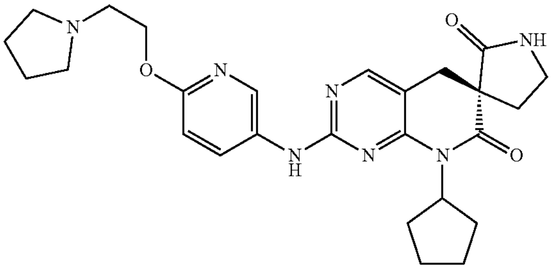 [SMILES: O=C1NCC[C@@]12Cc1cnc(Nc3ccc(OCCN4CCCC4)nc3)nc1N(C1CCCC1)C2=O]

Step 1: Synthesis of (S)-8-cyclopentyl-2-((6-(2-(pyrrolidin-1-yl)ethoxy)pyridin-3-yl)amino)-5,8-dihydro-7H-spiro[pyrido[2,3-d]pyrimidine-6,3'-pyrrolidine]-2',7-dione (Example-101)

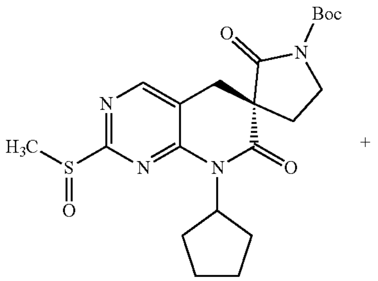

E2-Sulfoxide

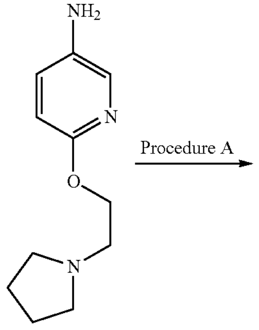

22

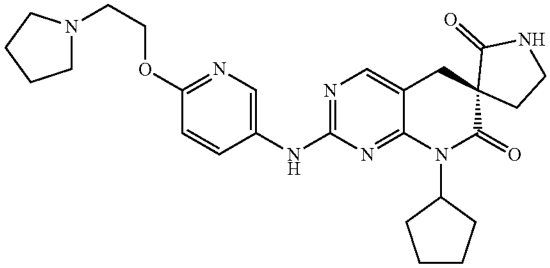

Example-101

Example-101 was synthesized following the general procedure A, 10 mg (20% yield). MS(ESI) m/z 492.2 $(M+H)^+$. $^1H$ NMR (600 MHz, DMSO-$d_6$) δ 9.31 (s, 1H), 8.36 (d, J=2.7 Hz, 1H), 8.06 (s, 1H), 7.94 (dd, J=9.0, 2.8 Hz, 1H), 7.91 (s, 1H), 6.77 (d, J=8.8 Hz, 1H), 5.31-5.20 (m, 1H), 4.42-4.34 (m, 2H), 3.21-3.10 (m, 4H), 3.03 (s, 2H), 2.97 (d, J=15.7 Hz, 1H), 2.69 (d, J=15.8 Hz, 1H), 2.43 (s, 2H), 2.33 (ddd, J=12.8, 7.8, 4.8 Hz, 1H), 2.00-1.90 (m, 2H), 1.87-1.74 (m, 7H), 1.74-1.61 (m, 2H), 1.51-1.39 (m, 2H).

Example-102 (VP-7-86B, SPV-432)

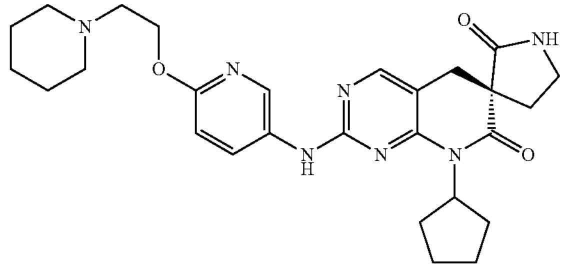 [SMILES: O=C1NCC[C@@]12Cc1cnc(Nc3ccc(OCCN4CCCCC4)nc3)nc1N(C1CCCC1)C2=O]

Step 1: Synthesis of (S)-8-cyclopentyl-2-((6-(2-(piperidin-1-yl)ethoxy)pyridin-3-yl)amino)-5,8-dihydro-7H-spiro[pyrido[2,3-d]pyrimidine-6,3'-pyrrolidine]-2',7-dione (Example-102)

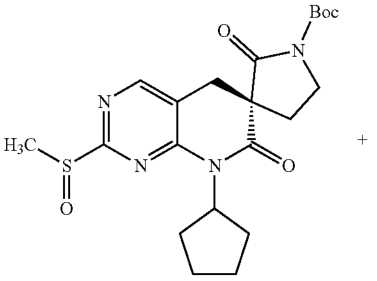

E2-Sulfoxide

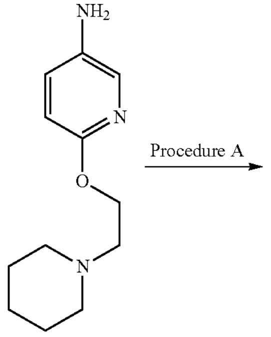

20

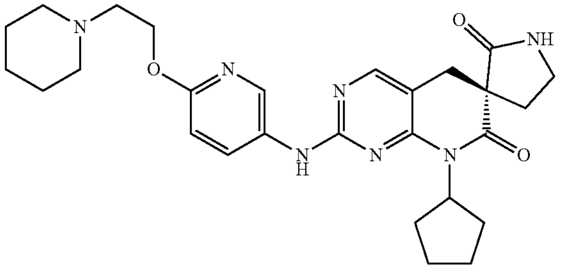

Example-102

Example-102 was synthesized following the general procedure A, 9 mg (18% yield). MS(ESI) m/z 506.2 $(M+H)^+$. $^1H$ NMR (600 MHz, DMSO-$d_6$) δ 9.34 (s, 1H), 8.39 (d, J=2.8 Hz, 1H), 8.06 (s, 1H), 7.97 (dd, J=8.9, 2.7 Hz, 1H), 7.91 (s, 1H), 6.80 (d, J=8.9 Hz, 1H), 5.26 (p, J=9.0 Hz, 1H), 4.49 (t, J=5.1 Hz, 2H), 3.48-3.40 (m, 4H), 3.22-3.11 (m, 3H), 2.97 (d, J=15.8 Hz, 1H), 2.93 (d, J=11.2 Hz, 2H), 2.70 (d, J=15.8 Hz, 1H), 2.34 (ddd, J=13.0, 7.9, 5.1 Hz, 1H), 1.99-1.89 (m, 2H), 1.87-1.73 (m, 5H), 1.73-1.65 (m, 2H), 1.65-1.57 (m, 3H), 1.51-1.41 (m, 2H).

Example-103 (VP-7-97B, SPV-433)

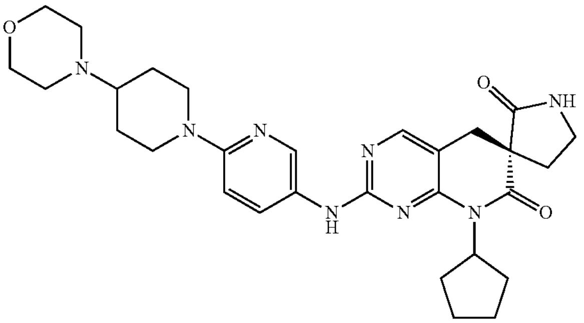 [SMILES: O=C1NCC[C@@]12Cc1cnc(Nc3ccc(N4CCC(N5CCOCC5)CC4)nc3)nc1N(C1CCCC1)C2=O]

Step 1: Synthesis of (S)-8-cyclopentyl-2-((6-(4-morpholinopiperidin-1-yl)pyridin-3-yl)amino)-5,8-dihydro-7H-spiro[pyrido[2,3-d]pyrimidine-6,3'-pyrrolidine]-2',7-dione (Example-103)

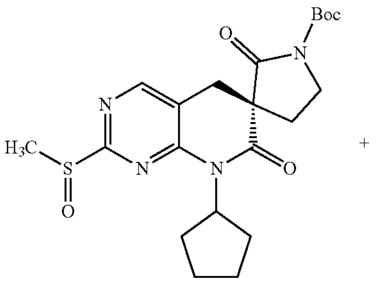

E2-Sulfoxide

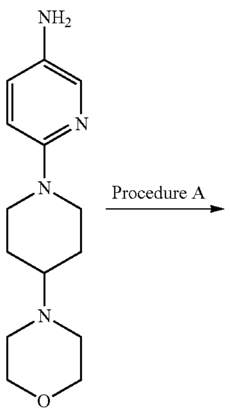

35

-continued

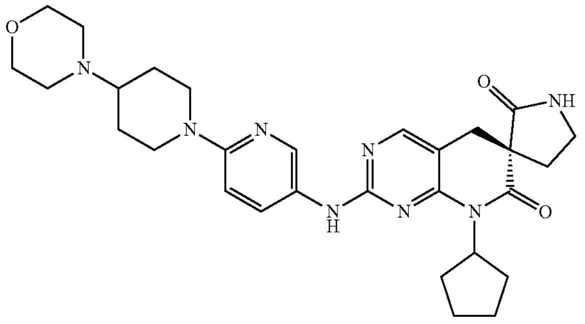

Example-103

Example-103 was synthesized following the general procedure A, 18 mg (33% yield). MS(ESI) m/z 547.2 $(M+H)^+$. $^1H$ NMR (600 MHz, DMSO-$d_6$) δ 9.04 (s, 1H), 8.24 (d, J=2.7 Hz, 1H), 8.01 (s, 1H), 7.90 (s, 1H), 7.73-7.68 (m, 1H), 6.76 (d, J=9.1 Hz, 1H), 5.26-5.20 (m, 1H), 4.18-4.13 (m, 2H), 3.51 (s, 5H), 3.21-3.10 (m, 3H), 2.95 (d, J=15.6 Hz, 1H), 2.71-2.62 (m, 4H), 2.30 (ddd, J=12.8, 7.7, 4.6 Hz, 2H), 1.99-1.91 (m, 2H), 1.79-1.73 (m, 3H), 1.70-1.63 (m, 3H), 1.48-1.39 (m, 3H), 1.32 (s, 1H), 1.21-1.16 (m, 2H).

Example-104 (VP-7-168, SPV-435)

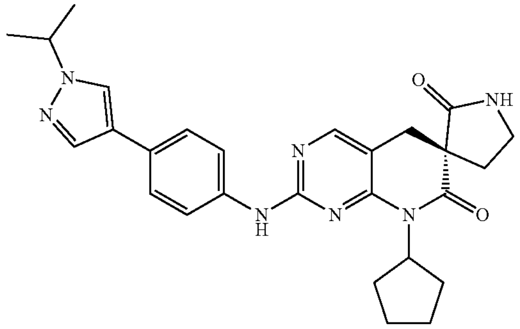 [SMILES: CC(C)n1cc(-c2ccc(Nc3ncc4c(n3)N(C3CCCC3)C(=O)[C@]3(CCNC3=O)C4)cc2)cn1]

Step 1: Synthesis of (S)-8-cyclopentyl-2-((5-(1-isopropyl-1H-pyrazol-4-yl)pyridin-2-yl)amino)-5,8-dihydro-7H-spiro[pyrido[2,3-d]pyrimidine-6,3'-pyrrolidine]-2',7-dione (Example-104)

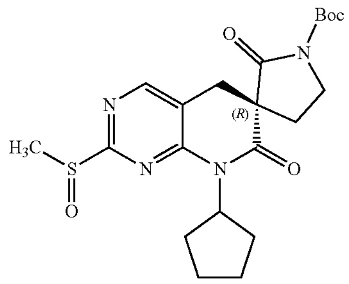

E2-Sulfoxide

+

-continued

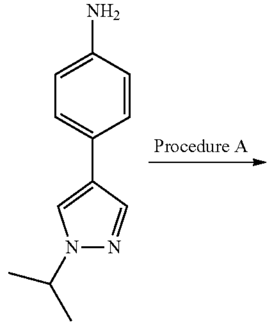

84

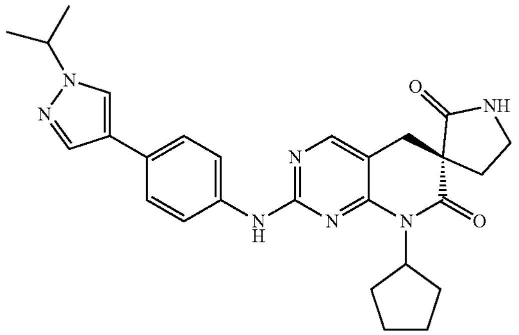

Example-104

Example-104 was synthesized following the general procedure A, 4 mg (8% yield). MS(ESI) m/z 586.2 $(M+H)^+$. $^1H$ NMR (600 MHz, DMSO-$d_6$) δ 9.37 (s, 1H), 8.09 (s, 1H), 8.05 (s, 1H), 7.91 (s, 1H), 7.72 (s, 1H), 7.62 (d, J=8.5 Hz, 2H), 7.44-7.39 (m, 2H), 5.31 (p, J=8.8 Hz, 1H), 4.46-4.38 (m, 1H), 3.22-3.11 (m, 2H), 2.99 (d, J=15.6 Hz, 1H), 2.69 (d, J=15.7 Hz, 1H), 2.33 (ddd, J=12.9, 7.8, 4.9 Hz, 1H), 2.03-1.94 (m, 2H), 1.89-1.79 (m, 3H), 1.78-1.70 (m, 2H), 1.54-1.46 (m, 2H), 1.37 (d, J=6.7 Hz, 6H).

Example-105 (VP-7-87, SPV-438)

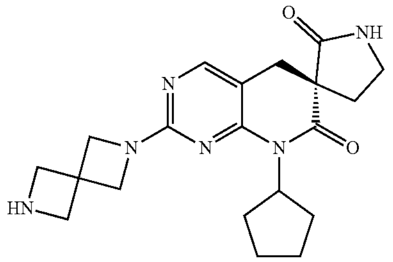 [SMILES: O=C1NCC[C@@]12Cc1cnc(N3CC4(CNC4)C3)nc1N(C1CCCC1)C2=O]

Step 1: Synthesis of (S)-8-cyclopentyl-2-(2,6-diazaspiro[3.3]heptan-2-yl)-5,8-dihydro-7H-spiro[pyrido[2,3-d]pyrimidine-6,3'-pyrrolidine]-2',7-dione (Example-105)

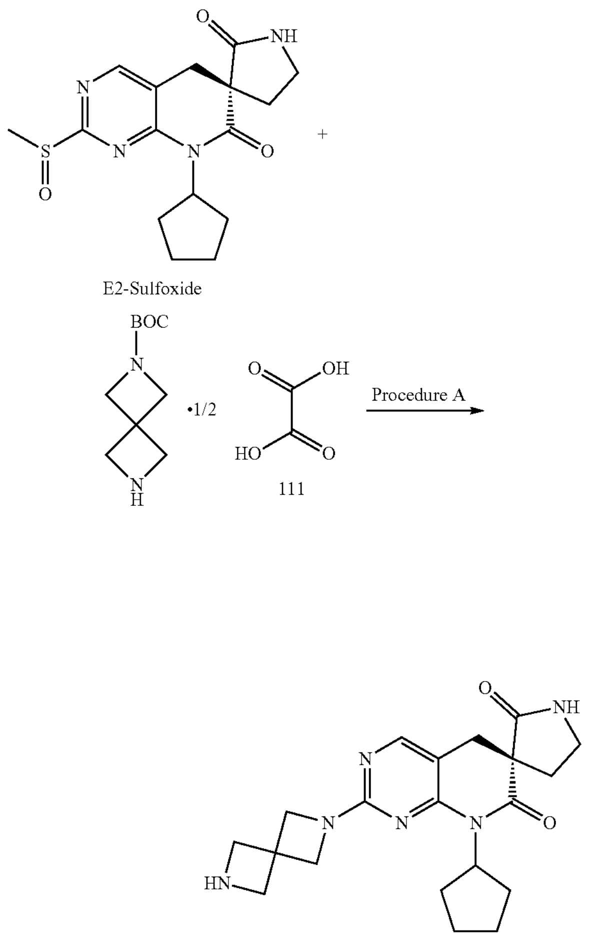

E2-Sulfoxide

111

Example-105

Example-105 was synthesized following the general procedure A, 9 mg (24% yield). MS(ESI) m/z 383.2 $(M+H)^+$.

Example-106 (VP-8-297, SPV-460)

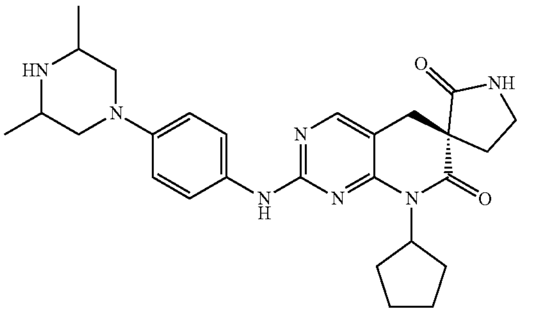 [SMILES: CC1CN(c2ccc(Nc3ncc4c(n3)N(C3CCCC3)C(=O)[C@]3(CCNC3=O)C4)cc2)CC(C)N1]

Step 1: Synthesis of (6S)-8-cyclopentyl-2-((4-(3,5-dimethylpiperazin-1-yl)phenyl)amino)-5,8-dihydro-7H-spiro[pyrido[2,3-d]pyrimidine-6,3'-pyrrolidine]-2',7-dione (Example-106)

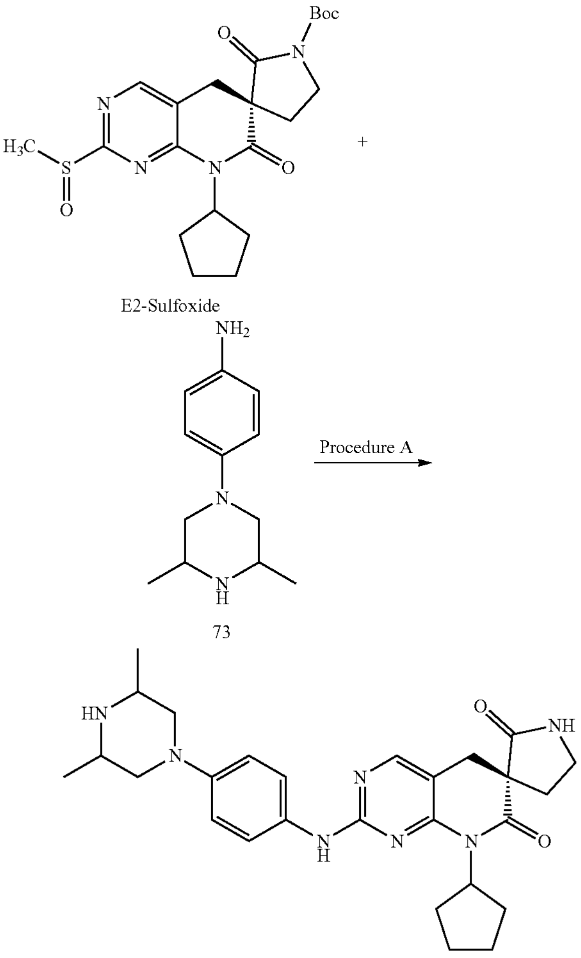

E2-Sulfoxide

73

Example-106

Example-106 was synthesized following the general procedure A, 50 mg (51% yield). MS(ESI) m/z 490.2 $(M+H)^+$.

Example-107 (VP-8-307E, SPV-462)

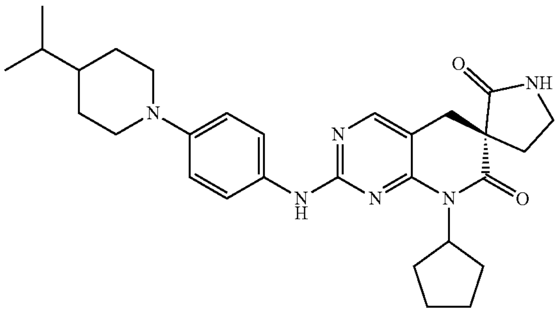

Step 1: Synthesis of (S)-8-cyclopentyl-2-((4-(4-isopropylpiperidin-1-yl)phenyl)amino)-5,8-dihydro-7H-spiro[pyrido[2,3-d]pyrimidine-6,3'-pyrrolidine]-2',7-dione (Example-107)

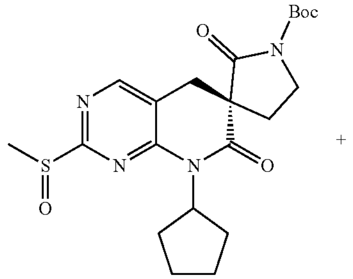

E2-Sulfoxide

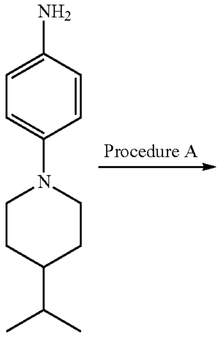

74

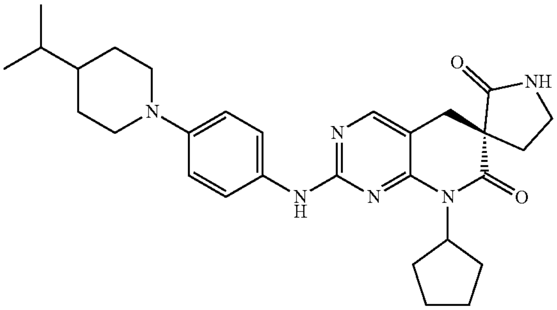 [SMILES: CC(C)C1CCN(c2ccc(Nc3ncc4c(n3)N(C3CCCC3)C(=O)[C@]3(CCNC3=O)C4)cc2)CC1]

Example-107

Example-107 was synthesized following the general procedure A, 4 mg (8% yield). MS(ESI) m/z 503.2 $(M+H)^+$. $^1H$ NMR (600 MHz, DMSO-$d_6$) δ 9.14 (s, 1H), 8.08 (s, 1H), 7.97 (s, 1H), 7.51-7.44 (m, 2H), 6.90-6.82 (m, 2H), 5.34 (p, J=8.8 Hz, 1H), 3.64-3.58 (m, 2H), 3.28-3.17 (m, 2H), 3.05-2.99 (m, 1H), 2.71 (d, J=15.7 Hz, 1H), 2.49 (s, 3H), 2.36 (ddd, J=12.8, 8.0, 5.0 Hz, 1H), 2.08-1.98 (m, 2H), 1.94-1.87 (m, 1H), 1.85 (s, 1H), 1.80-1.74 (m, 2H), 1.71 (dt, J=12.6, 2.6 Hz, 2H), 1.56-1.49 (m, 2H), 1.44 (h, J=6.7 Hz, 1H), 1.34-1.22 (m, 2H), 1.16-1.07 (m, 1H), 0.88 (d, J=6.8 Hz, 6H).

Example-108 (VP-8-308, SPV-463)

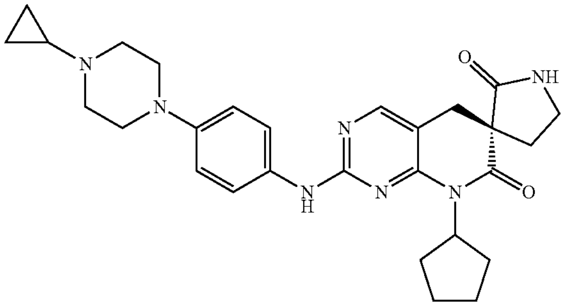 [SMILES: O=C1NCC[C@@]12Cc1cnc(Nc3ccc(N4CCN(C5CC5)CC4)cc3)nc1N(C1CCCC1)C2=O]

Step 1: Synthesis of (S)-8-cyclopentyl-2-((4-(4-cyclopropylpiperazin-1-yl)phenyl)amino)-5,8-dihydro-7H-spiro[pyrido[2,3-d]pyrimidine-6,3'-pyrrolidine]-2',7-dione (Example-108)

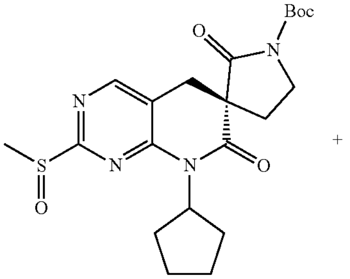

E2-Sulfoxide

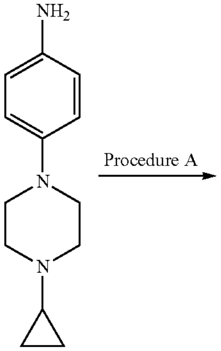

75

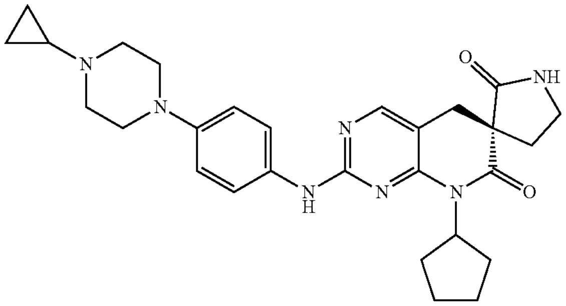

Example-108

Example-108 was synthesized following the general procedure A, 33 mg (66% yield). MS(ESI) m/z 502.2 $(M+H)^+$.

$^1$H NMR (600 MHz, DMSO-$d_6$) δ 9.16 (s, 1H), 8.09 (s, 1H), 7.97 (s, 1H), 7.53-7.44 (m, 2H), 6.94-6.81 (m, 2H), 5.34 (p, J=8.7 Hz, 1H), 3.28-3.18 (m, 2H), 3.07-2.98 (m, 4H), 2.75-2.69 (m, 1H), 2.69-2.64 (m, 3H), 2.42-2.29 (m, 2H), 2.07-1.96 (m, 2H), 1.95-1.88 (m, 2H), 1.85 (s, 2H), 1.81-1.70 (m, 2H), 1.68-1.62 (m, 1H), 1.59-1.48 (m, 2H), 0.46-0.41 (m, 2H), 0.35-0.31 (m, 2H).

Example-109 (VP-8-287, SPV-464)

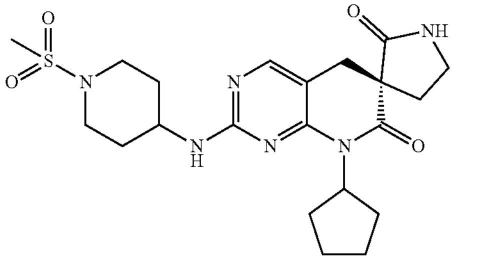 [SMILES: CS(=O)(=O)N1CCC(Nc2ncc3c(n2)N(C2CCCC2)C(=O)[C@]2(CCNC2=O)C3)CC1]

Step 1: Synthesis of (S)-8-cyclopentyl-2-((1-(methylsulfonyl)piperidin-4-yl)amino)-5,8-dihydro-7H-spiro[pyrido[2,3-d]pyrimidine-6,3'-pyrrolidine]-2',7-dione (Example-109)

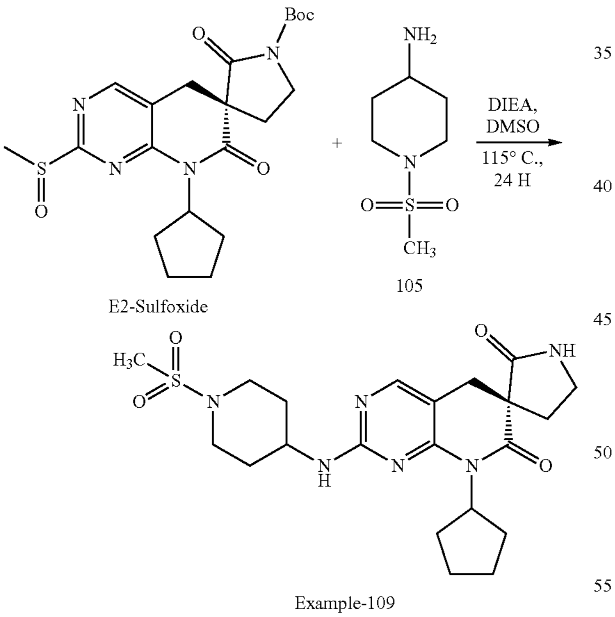

E2-Sulfoxide

105

Example-109

Example-109 was synthesized following the general procedure A (used DIEA and DMSO in the place of TFA and isopropanol), 29 mg (63% yield). MS(ESI) m/z 463.2 $(M+H)^+$. $^1$H NMR (600 MHz, DMSO-$d_6$) δ 7.96 (d, J=19.7 Hz, 1H), 7.03 (s, 1H), 5.33 (s, 1H), 3.81 (s, 1H), 3.62-3.50 (m, 2H), 3.26-3.15 (m, 2H), 2.97 (d, J=15.6 Hz, 1H), 2.87 (s, 2H), 2.86-2.81 (m, 1H), 2.64 (d, J=15.6 Hz, 1H), 2.50 (s, 4H), 2.36-2.28 (m, 1H), 2.01 (s, 1H), 1.98-1.92 (m, 2H), 1.90-1.84 (m, 2H), 1.78-1.68 (m, 2H), 1.60-1.45 (m, 3H).

Example-110 (VP-8-275, SPV-466)

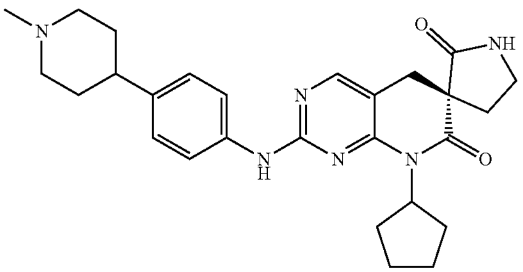 [SMILES: CN1CCC(c2ccc(Nc3ncc4c(n3)N(C3CCCC3)C(=O)[C@]3(CCNC3=O)C4)cc2)CC1]

Step 1: Synthesis of (S)-8-cyclopentyl-2-((4-(1-methylpiperidin-4-yl)phenyl)amino)-5,8-dihydro-7H-spiro[pyrido[2,3-d]pyrimidine-6,3'-pyrrolidine]-2',7-dione (Example-110)

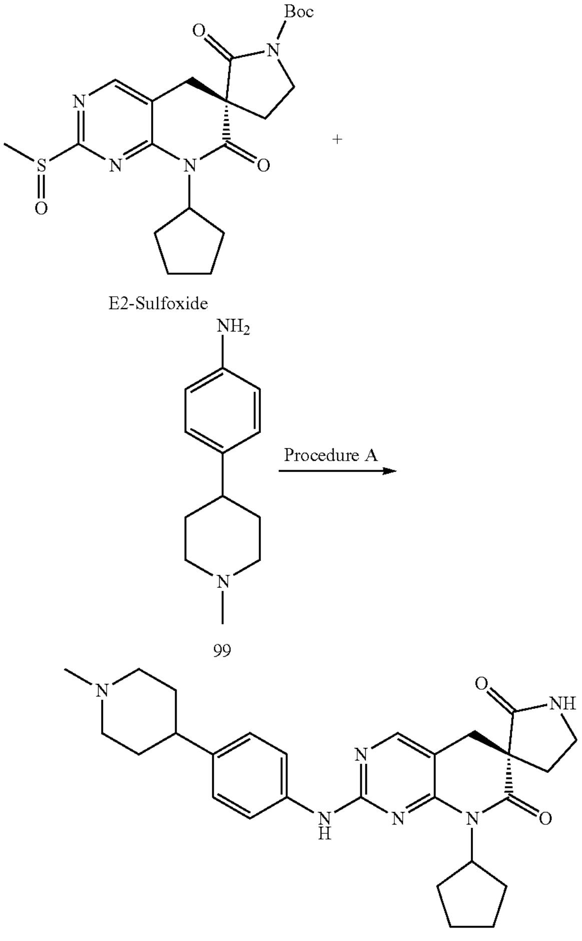

E2-Sulfoxide

99

Example-110

Example-110 was synthesized following the general procedure A, 6 mg (13% yield). MS(ESI) m/z 475.2 $(M+H)^+$. $^1$H NMR (600 MHz, DMSO-$d_6$) δ 9.34 (s, 1H), 8.13 (s, 1H), 7.97 (s, 1H), 7.65-7.55 (m, 2H), 7.18-7.11 (m, 2H), 5.36 (p, J=8.8 Hz, 1H), 3.27-3.18 (m, 2H), 3.04 (d, J=15.7 Hz, 1H), 2.88-2.82 (m, 1H), 2.74 (d, J=15.7 Hz, 1H), 2.50 (s, 2H), 2.42-2.35 (m, 2H), 2.19 (s, 3H), 2.07-1.99 (m, 2H), 1.99-1.92 (m, 2H), 1.90-1.82 (m, 2H), 1.81-1.73 (m, 2H), 1.74-1.68 (m, 2H), 1.68-1.59 (m, 2H), 1.58-1.50 (m, 2H).

Example-111 (VP-8-178, SPV-467)

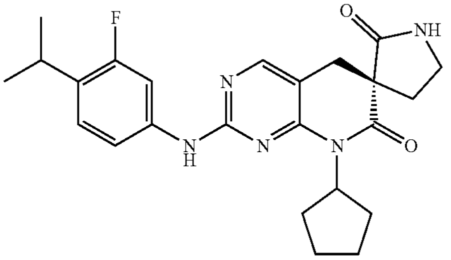 [SMILES: CC(C)c1ccc(Nc2ncc3c(n2)N(C2CCCC2)C(=O)[C@]2(CCNC2=O)C3)cc1F]

Step 1: Synthesis of (S)-8-cyclopentyl-2-((3-fluoro-4-isopropylphenyl)amino)-5,8-dihydro-7H-spiro [pyrido[2,3-d]pyrimidine-6,3'-pyrrolidine]-2',7-dione (Example-111)

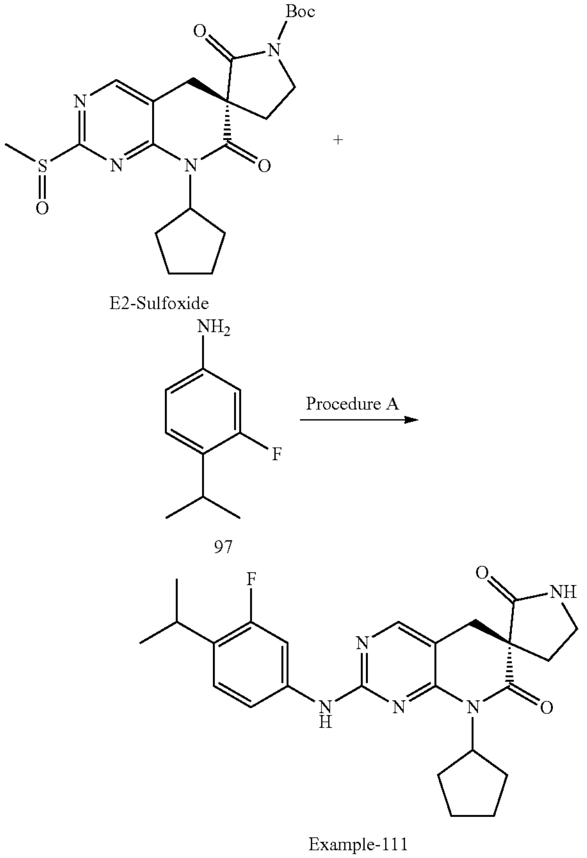

Example-111 was synthesized following the general procedure A, 18 mg (40% yield). MS(ESI) m/z 438.2 $(M+H)^+$. $^1H$ NMR (600 MHz, DMSO-$d_6$) δ 9.58 (s, 1H), 8.18 (s, 1H), 7.98 (s, 1H), 7.69 (dd, J=13.9, 2.2 Hz, 1H), 7.34 (dd, J=8.5, 2.2 Hz, 1H), 7.20 (t, J=8.7 Hz, 1H), 5.36 (p, J=8.8 Hz, 1H), 3.30-3.18 (m, 3H), 3.12-3.08 (m, 1H), 3.05 (d, 1H), 2.77 (d, J=15.8 Hz, 1H), 2.41 (ddd, J=12.8, 7.8, 4.9 Hz, 1H), 2.08-2.00 (m, 2H), 1.95-1.85 (m, 3H), 1.85-1.77 (m, 2H), 1.60-1.50 (m, 2H), 1.20 (d, J=6.9 Hz, 5H).

Example-112 (VP-8-96B, SPV-469)

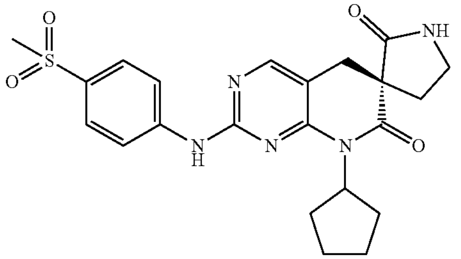 [SMILES: CS(=O)(=O)c1ccc(Nc2ncc3c(n2)N(C2CCCC2)C(=O)[C@]2(CCNC2=O)C3)cc1]

Step 1: Synthesis of (S)-8-cyclopentyl-2-((4-(methylsulfonyl)phenyl)amino)-5,8-dihydro-7H-spiro [pyrido[2,3-d]pyrimidine-6,3'-pyrrolidine]-2',7-dione (Example-112)

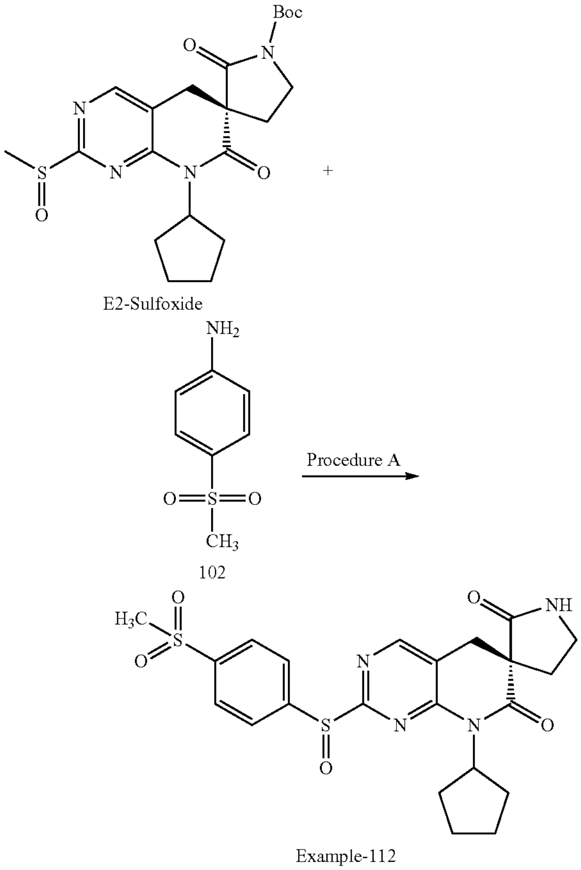

Example-112 was synthesized following the general procedure A, 7 mg (15% yield). MS(ESI) m/z 456.2 $(M+H)^+$. $^1H$ NMR (600 MHz, DMSO-$d_6$) δ 9.95 (s, 1H), 8.18 (s, 1H), 7.96-7.87 (m, 3H), 7.79-7.70 (m, 2H), 5.32 (p, J=8.7 Hz, 1H), 3.22-3.12 (m, 2H), 3.09 (s, 3H), 3.02 (d, J=15.8 Hz, 1H), 2.76 (d, J=15.9 Hz, 1H), 2.40-2.34 (m, 1H), 2.01-1.91 (m, 2H), 1.91-1.81 (m, 3H), 1.81-1.70 (m, 2H), 1.56-1.47 (m, 2H).

Example-113 (VP-8-97A, SPV-470)

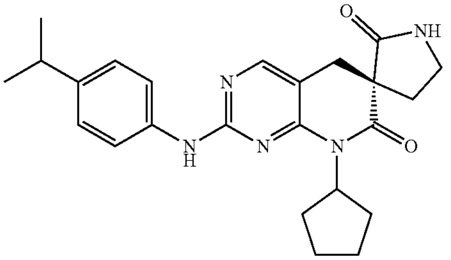 [SMILES: CC(C)c1ccc(Nc2ncc3c(n2)N(C2CCCC2)C(=O)[C@]2(CCNC2=O)C3)cc1]

Step 1: Synthesis of (S)-8-cyclopentyl-2-((4-isopropylphenyl)amino)-5,8-dihydro-7H-spiro[pyrido[2,3-d]pyrimidine-6,3'-pyrrolidine]-2',7-dione (Example-113)

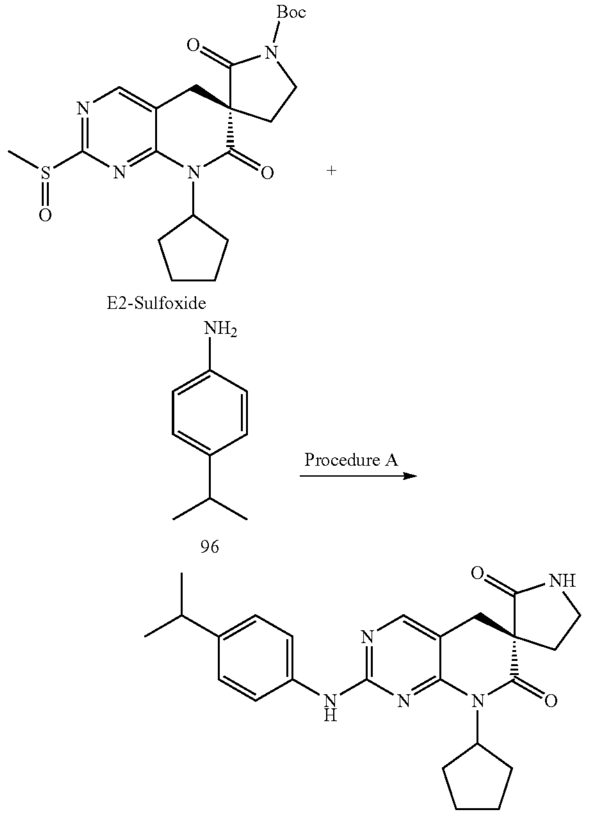

E2-Sulfoxide

96

Example-113

Example-113 was synthesized following the general procedure A, 30 mg (36% yield). MS(ESI) m/z 420.2 $(M+H)^+$. $^1$H NMR (600 MHz, DMSO-$d_6$) δ 9.34 (s, 1H), 8.15 (s, 1H), 8.00 (s, 1H), 7.66-7.59 (m, 2H), 7.20-7.14 (m, 2H), 5.38 (p, J=8.8 Hz, 1H), 3.30-3.21 (m, 2H), 3.10-3.03 (m, 1H), 2.86 (h, J=6.9 Hz, 1H), 2.76 (d, J=15.7 Hz, 1H), 2.40 (ddd, J=12.8, 7.8, 4.8 Hz, 1H), 2.11-2.00 (m, 2H), 1.97-1.85 (m, 3H), 1.85-1.76 (m, 2H), 1.61-1.51 (m, 2H), 1.21 (d, J=6.9 Hz, 6H).

Example-114 (VP-8-98A, SPV-471)

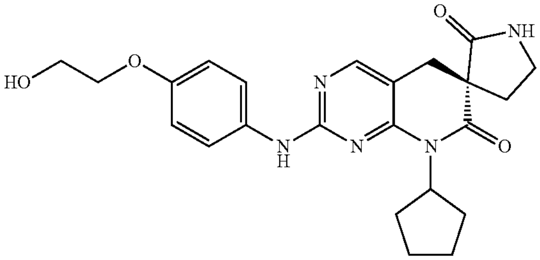 [SMILES: O=C1NCC[C@@]12Cc1cnc(Nc3ccc(OCCO)cc3)nc1N(C1CCCC1)C2=O]

Step 1: Synthesis of (S)-8-cyclopentyl-2-((4-(2-hydroxyethoxy)phenyl)amino)-5,8-dihydro-7H-spiro[pyrido[2,3-d]pyrimidine-6,3'-pyrrolidine]-2',7-dione (Example-114)

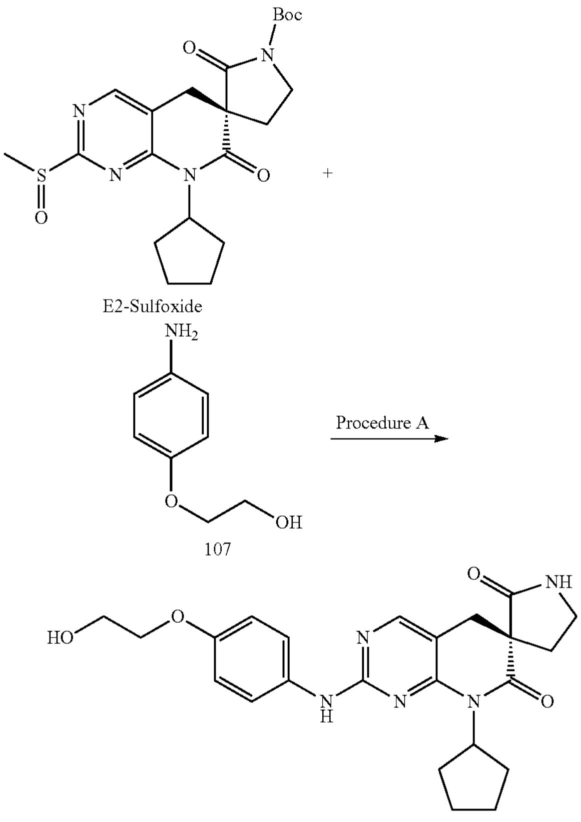

E2-Sulfoxide

107

Example-114

Example-114 was synthesized following the general procedure A, 53 mg (30% yield). MS(ESI) m/z 438.2 $(M+H)^+$. $^1$H NMR (600 MHz, DMSO-$d_6$) δ 9.16 (s, 1H), 8.03 (s, 1H), 7.90 (s, 1H), 7.55-7.43 (m, 2H), 6.86-6.77 (m, 2H), 5.27 (p, J=8.8 Hz, 1H), 4.76 (t, J=5.6 Hz, 1H), 3.87 (t, J=5.1 Hz, 2H), 3.63 (q, J=5.3 Hz, 2H), 3.22-3.11 (m, 2H), 2.96 (d, 1H), 2.66

(d, J=15.7 Hz, 1H), 2.30 (ddd, J=12.8, 7.8, 4.7 Hz, 1H), 2.03-1.90 (m, 2H), 1.91-1.75 (m, 3H), 1.75-1.64 (m, 2H), 1.53-1.42 (m, 2H).

Example-115 (VP-8-112A, SPV-472)

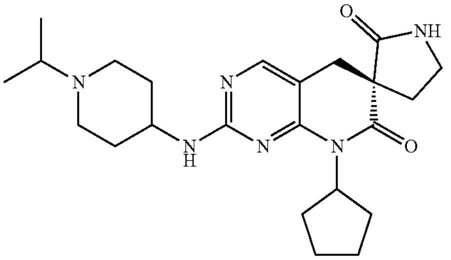 [SMILES: CC(C)N1CCC(Nc2ncc3c(n2)N(C2CCCC2)C(=O)[C@]2(CCNC2=O)C3)CC1]

Step 1: Synthesis of (S)-8-cyclopentyl-2-((1-isopropylpiperidin-4-yl)amino)-5,8-dihydro-7H-spiro[pyrido[2,3-d]pyrimidine-6,3'-pyrrolidine]-2',7-dione (Example-115)

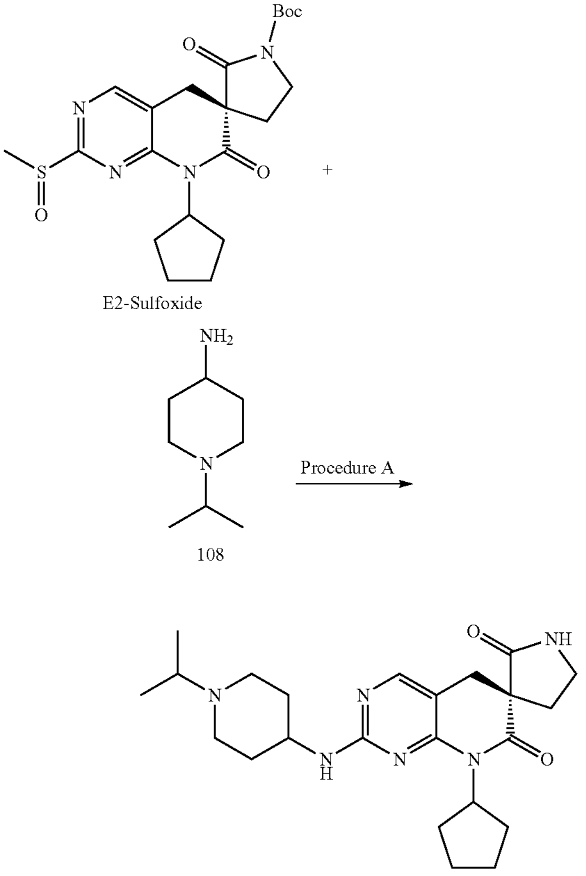

E2-Sulfoxide

108

Example-115

Example-115 was synthesized following the general procedure A, 15 mg (35% yield). MS(ESI) m/z 427.2 $(M+H)^+$.

Example-116 (VP-8-113C, SPV-473)

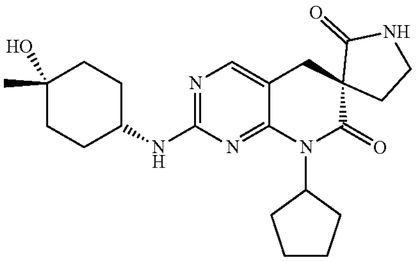

Step 1: Synthesis of (S)-8-cyclopentyl-2-(((1s,4R)-4-hydroxy-4-methylcyclohexyl)amino)-5,8-dihydro-7H-spiro[pyrido[2,3-d]pyrimidine-6,3'-pyrrolidine]-2',7-dione (Example-116)

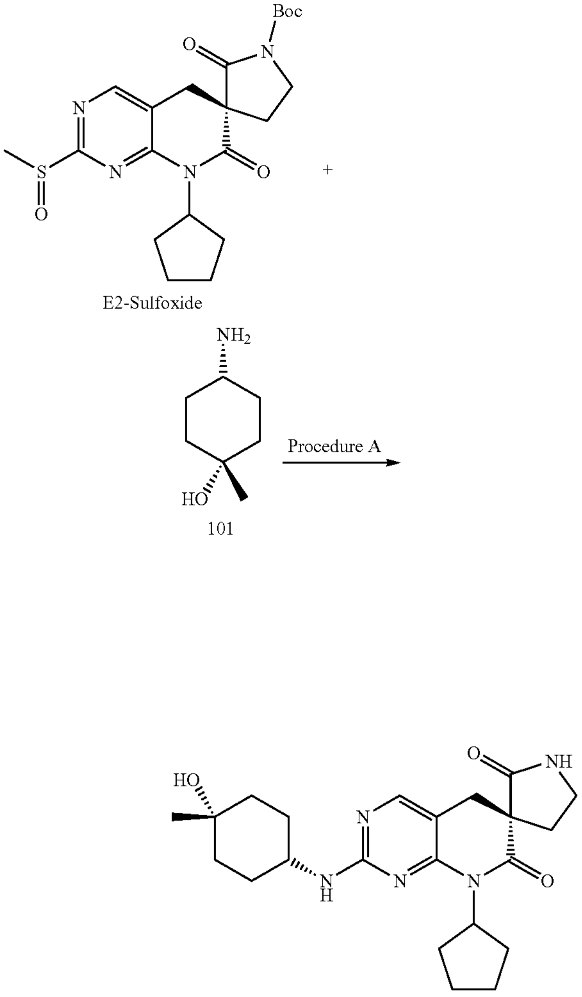

E2-Sulfoxide

101

Example-116

Example-116 was synthesized following the general procedure A, 2 mg (5% yield). MS(ESI) m/z 414.2 $(M+H)^+$.

Example-117 (VP-8-77A, SPV-475)

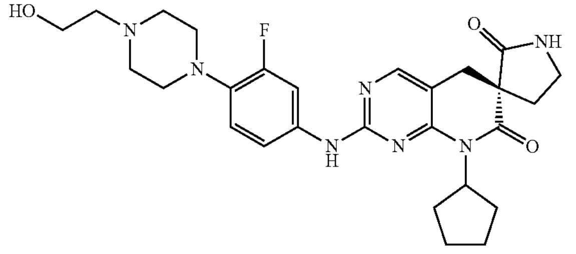 [SMILES: O=C1NCC[C@@]12Cc1cnc(Nc3ccc(N4CCN(CCO)CC4)c(F)c3)nc1N(C1CCCC1)C2=O]

Step 1: Synthesis of (S)-8-cyclopentyl-2-((3-fluoro-4-(4-(2-hydroxyethyl)piperazin-1-yl)phenyl)amino)-5,8-dihydro-7H-spiro[pyrido[2,3-d]pyrimidine-6,3'-pyrrolidine]-2',7-dione (Example-117)

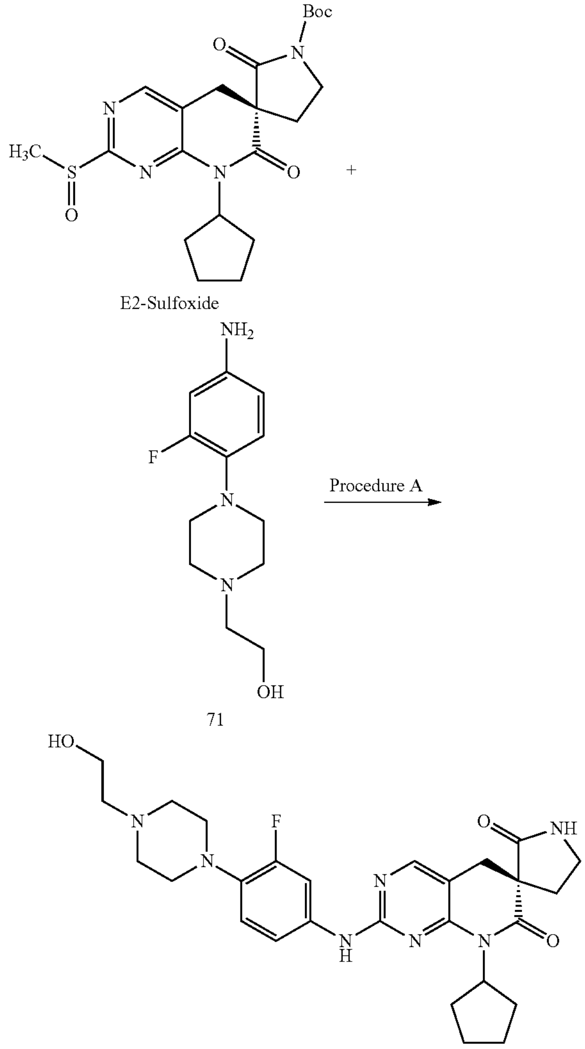

E2-Sulfoxide

71

Example-117

Example-117 was synthesized following the general procedure A, 22 mg (21% yield). MS(ESI) m/z 524.2 $(M+H)^+$.

Example-118 (VP-8-81B, SPV-477)

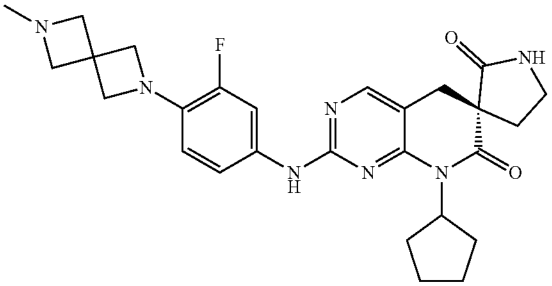 [SMILES: CN1CC2(C1)CN(c1ccc(Nc3ncc4c(n3)N(C3CCCC3)C(=O)[C@]3(CCNC3=O)C4)cc1F)C2]

Step 1: (S)-8-cyclopentyl-2-((3-fluoro-4-(6-methyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (Example-118)

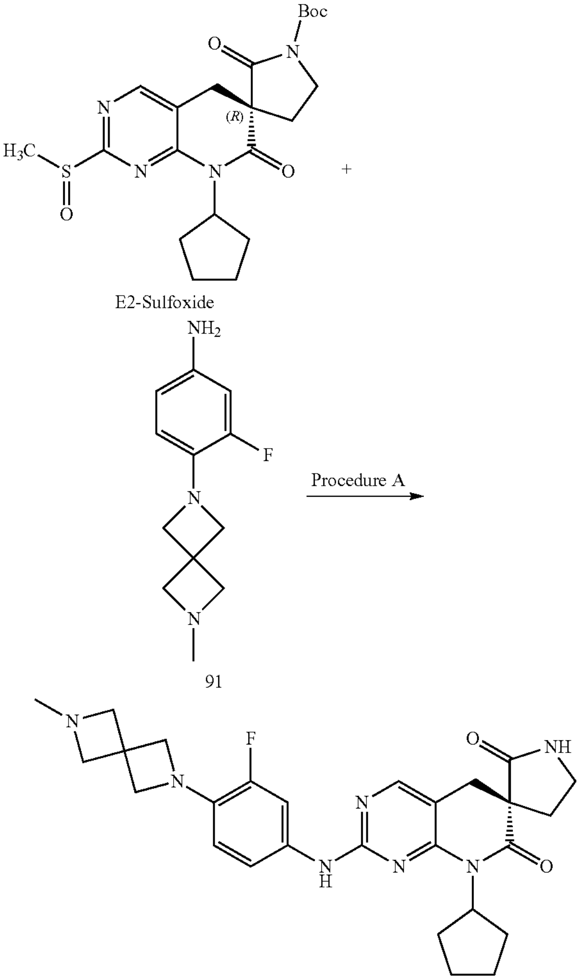

E2-Sulfoxide

91

Example-118

Example-118 was synthesized following the general procedure A, 23 mg (23% yield). MS(ESI) m/z 506.2 $(M+H)^+$. $^1H$ NMR (600 MHz, DMSO-$d_6$) δ 9.27 (s, 1H), 8.11 (s, 1H), 8.01-7.95 (m, 1H), 7.60 (dtd, J=14.3, 5.9, 2.4 Hz, 1H), 7.22-7.15 (m, 1H), 6.77 (dt, J=55.7, 9.6 Hz, 1H), 5.36-5.30 (m, 1H), 4.12-4.01 (m, 2H), 3.84-3.74 (m, 2H), 3.61 (s, 1H), 3.51 (s, 1H), 3.30 (s, 2H), 3.28-3.19 (m, 3H), 3.03 (d, J=15.7 Hz, 1H), 2.82-2.72 (m, 3H), 2.44-2.36 (m, 1H), 2.10-2.00 (m, 2H), 1.95-1.83 (m, 3H), 1.83-1.74 (m, 2H), 1.60-1.48 (m, 2H).

Example-119 (VP-8-82B, SPV-478)

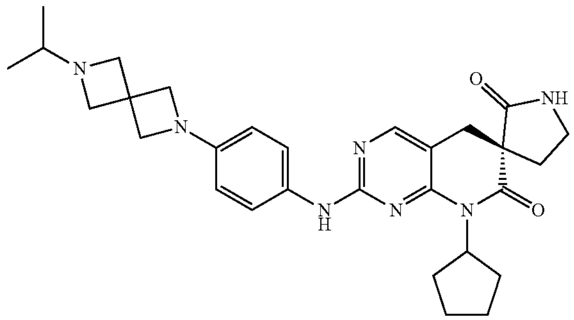 [SMILES: CC(C)N1CC2(CN(c3ccc(Nc4ncc5c(n4)N(C4CCCC4)C(=O)[C@]4(CCNC4=O)C5)cc3)C2)C1]

Step 1: (S)-8-cyclopentyl-2-((4-(6-isopropyl-2,6-diazaspiro[3.3]heptan-2-yl)phenyl)amino)-5,8-dihydro-7H-spiro[pyrido[2,3-d]pyrimidine-6,3'-pyrrolidine]-2',7-dione (Example-119)

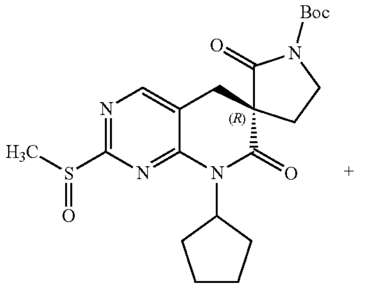

E2-Sulfoxide

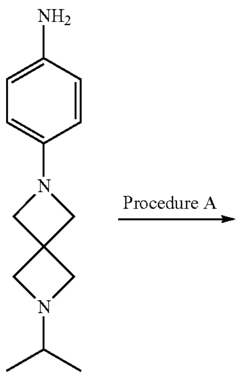

93

-continued

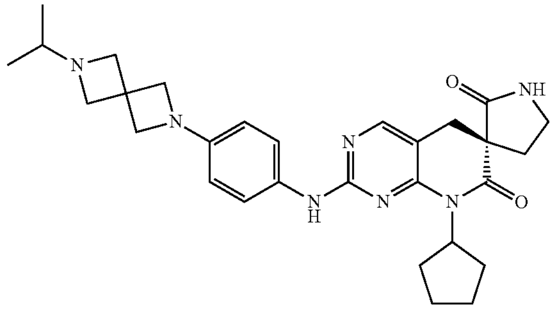

Example-119

Example-119 was synthesized following the general procedure A, 10 mg (10% yield). MS(ESI) m/z 516.2 $(M+H)^+$.

Example-120 (VP-8-58C, SPV-485)

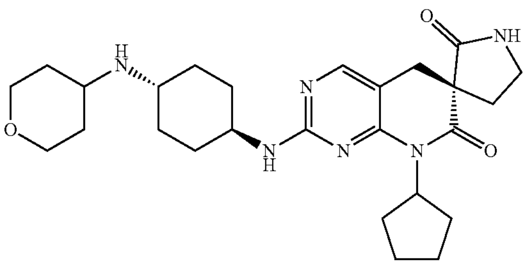 [SMILES: O=C1NCC[C@@]12Cc1cnc(N[C@H]3CC[C@H](NC4CCOCC4)CC3)nc1N(C1CCCC1)C2=O]

Step 1: Synthesis of (S)-8-cyclopentyl-2-(((1r,4S)-4-((tetrahydro-2H-pyran-4-yl)amino)cyclohexyl)amino)-5,8-dihydro-7H-spiro[pyrido[2,3-d]pyrimidine-6,3'-pyrrolidine]-2',7-dione (Example-120)

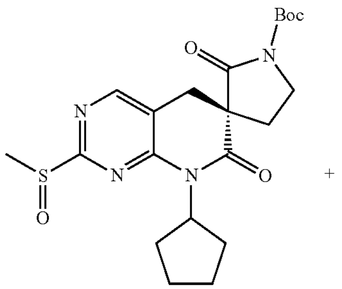

E2-Sulfoxide

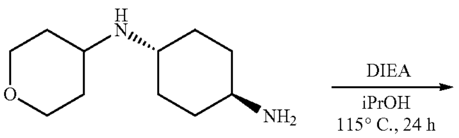

76

-continued

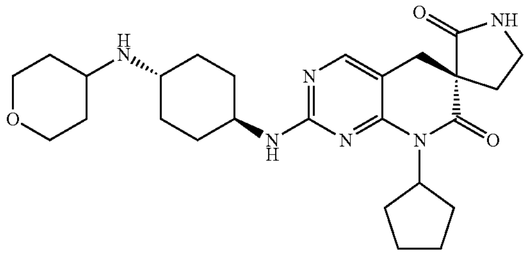

Example-120

Example-120 was synthesized following slightly modified procedure A (used DIEA in the place of TFA), 6 mg (13% yield). MS(ESI) m/z 483.2 $(M+H)^+$. $^1H$ NMR (600 MHz, DMSO-$d_6$) δ 7.89 (s, 1H), 5.24 (s, 1H), 3.86-3.77 (m, 1H), 3.53 (s, 1H), 3.27 (s, 1 OH), 3.18-3.07 (m, 1H), 2.89 (d, J=15.6 Hz, 1H), 2.56 (d, J=15.7 Hz, 1H), 2.44 (s, 9H), 2.30-2.20 (m, 1H), 2.00-1.86 (m, 2H), 1.86-1.72 (m, 2H), 1.72-1.58 (m, 1H), 1.58-1.40 (m, 1H), 1.40-1.14 (m, 2H).

Example-121 (VP-7-109B (racemic), SPV-418)

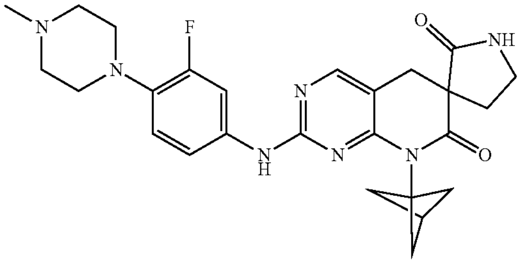 [SMILES: CN1CCN(c2ccc(Nc3ncc4c(n3)N(C35CC(C3)C5)C(=O)C3(CCNC3=O)C4)cc2F)CC1]

Step 1: Synthesis of tert-butyl-8-(bicyclo[1,1,1]pentan-1-yl)-2-(methylsulfinyl)-2',7-dioxo-7,8-dihydro-5H-spiro[pyrido[2,3-d]pyrimidine-6,3'-pyrrolidine]-1'-carboxylate (121-J)

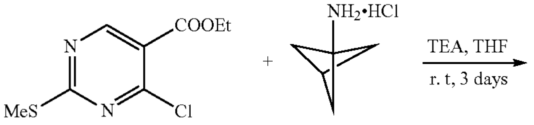

121-A 121-B

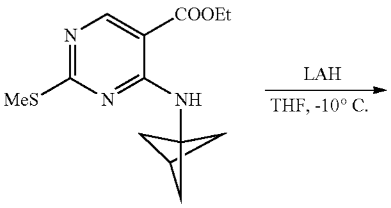

121-C

-continued

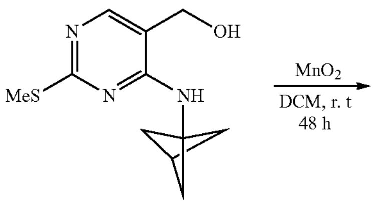

121-D

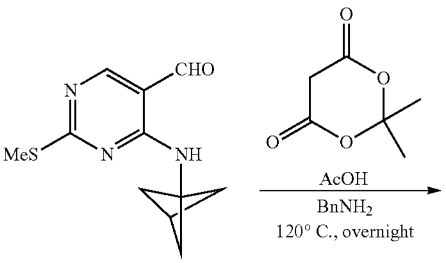

121-E

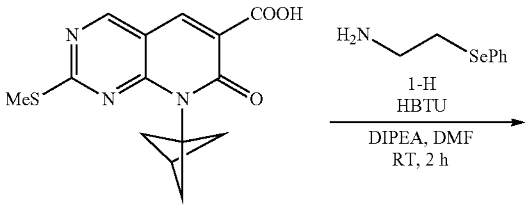

121-F

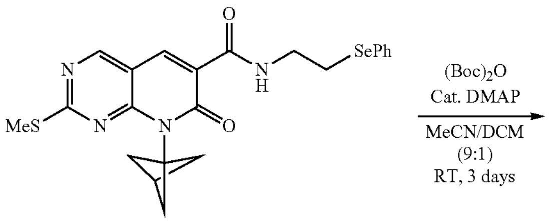

121-G

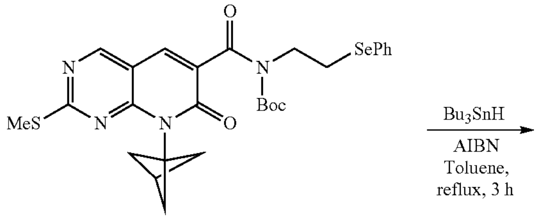

121-H

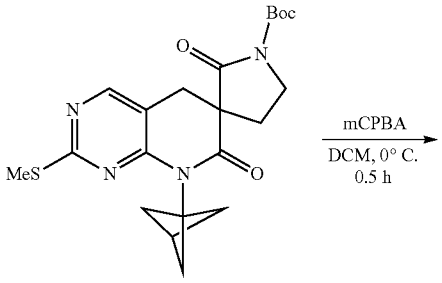

121-I

-continued

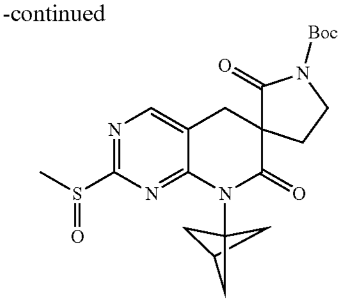

121-J

Synthesis of 121-C: (Ref: WO2012145569): 4-Chloro-2-methylsulfanyl-pyrimidine-5-carboxylic acid ethyl ester 1-A (48 g, 202 mmol) was dissolved in THF (1 L) to which triethylamine (102 g, 1010 mmol) and compound 121-B (25 g, 202 mmol) were added and stirred for 3 days at room temperature. The precipitated salts were filtered, and the solvent is evaporated in vacuo. The resultant oil was dissolved in ethyl acetate and washed with sodium bicarbonate and then dried over $Na_2SO_4$. The salts were filtered, and the solvent was evaporated in vacuum to obtain the product 121-C (46.4 g, 80% yield). MS(ESI) m/z 280.2 $[M+H]^+$.

Synthesis of 121-0: (Part in Ref: JMC 2014, 57, 578-599): Lithium aluminum hydride (2 g, 54 mmol) was suspended in anhydrous THF (100 mL) under nitrogen atmosphere and cooled to −10° C. with dry ice. The compound 121-C (10 g, 36 mmol) was dissolved in anhydrous THF (100 mL) and added dropwise to the cooled $LiAlH_4$ solution while keeping the reaction temperature below −10° C. The reaction was brought to room temperature and stirred for 1 h. The reaction was quenched by the addition of water (5 mL), 10% NaOH (20 mL), and then water (15 mL) again. The white solid that precipitated was filtered and the filtrate evaporated in vacuo to afford the product 121-D (6.8 g, 80% yield). MS(ESI) m/z 238.2 $[M+H]^+$.

Synthesis of 121-E: (Part in Ref: JMC 2014, 57, 578-599): The compound 121-D (18 g, 76 mmol) was dissolved in dichloromethane (400 mL) to which manganese dioxide ($MnO_2$) (99 g, 1140 mmol) was added and stirred for 48 h. The solids were removed by filtration through a Celite pad and washed with dichloromethane. Solvent evaporated under reduced pressure to get the product 121-E (14.4 g, 80% yield). MS(ESI) m/z 236.2 $[M+H]^+$.

Synthesis of 121-F: (Part in WO 2008032162): To compound 121-E (5 g, 21 mmol) and Meldrums acid (3.7 g, 26 mmol) in acetic added (50 mL) was added Benzyl amine (0.2 g, 2.1 mmol) and refluxed for overnight. After completion of the reaction cooled to room temperature and diluted with hexane and solid formed was filtered and washed with water and dried to get the product 121-F (4.5 g, 70% yield). MS(ESI) m/z 304.0 $[M+H]^+$. $^1H$ NMR (600 MHz, Chloroform-d) δ 13.67 (s, 1H), 8.80 (s, 1H), 8.76 (s, 1H), 2.75 (s, 6H), 2.71 (s, 1H), 2.68 (s, 3H).

Synthesis of 121-G: (WO 2010020675): To a mixture of Compound 121-F (4.4 g, 14.5 mmol), HBTU (6.1 g, 15.9 mmol) and diisopropylethylamine (7.6 mL, 43.5 mmol) in DMF (20 mL) was added compound 1-H (3.5 g, 17.4 mmol) and the reaction mixture was stirred for 2 h at room temperature. After completion, the reaction mixture was diluted with water (200 mL) and the solid formed was filtered and washed with water (2×100 mL) and dried to give compound 121-G (6.7 g, 96% yield) as a solid. MS(ESI) m/z 487.1 $[M+H]^+$. $^1H$ NMR (600 MHz, Chloroform-d) δ 9.60 (s, 1H), 8.71 (s, 1H), 8.68 (s, 1H), 7.60-7.54 (m, 2H), 7.28-7.24 (m, 2H), 7.24-7.18 (m, 1H), 3.72 (q, J=6.8 Hz, 2H), 3.13 (t, J=7.1 Hz, 2H), 2.73 (s, 6H), 2.67 (s, 1H), 2.65 (s, 3H).

Synthesis of 121-H: (WO 2012069680): To a stirred solution of compound 121-G (6.5 g, 13.4 mmol) in MeCN/DCM (9:1) were added Boc anhydride (15 g, 67 mmol) and DMAP (1.6 g, 13.3 mmol) and the reaction mixture was stirred for 3 days. After completion of the reaction, the solvents were removed under reduced pressure and purified by column chromatography (0 to 20% ethyl acetate in hexanes) to give compound 121-H (6.9 g, 89% yield) as a gummy liquid. MS(ESI) m/z 587.1 $[M+H]^+$.

Synthesis of 121-I: (Kyei et al., *Tetrahedron Lett.* 45(48): 8931-8934 (2004)). The selenide compound 121-H (5 g, 8.5 mmol) was dissolved in anhydrous toluene (100 mL), purged with argon and heated to 110° C. while stirring. A solution of tributyl tin hydride (4.5 mL, 17.1 mmol) and AIBN (700 mg, 5.3 mmol) was dissolved in toluene (50 mL) and added dropwise to the above selenide over a period of 2 h. The reaction mixture was stirred at that temperature for additional 1 h and then cooled to room temperature, diluted with EtOAc (750 mL), washed with water (2×100 mL), brine (1×100 mL), dried ($Na_2SO_4$) and then concentrated to give the crude product, which was subjected for $SiO_2$ column chromatography (0 to 100% EtOAc in n-hexanes) to afford 121-I (1.9 g, 50%) as an off-white solid. MS(ESI) m/z 431.1 $[M+H]^+$. $^1H$ NMR (600 MHz, Chloroform-d) δ 8.18 (s, 1H), 3.79 (dd, J=8.8, 5.2 Hz, 2H), 3.35 (d, J=15.9 Hz, 1H), 2.64 (d, J=15.9 Hz, 1H), 2.56 (s, 4H), 2.53-2.47 (m, 6H), 2.33 (dt, J=13.3, 5.2 Hz, 1H), 1.82 (dt, J=13.2, 8.8 Hz, 1H), 1.53 (s, 9H).

Synthesis of 121-J: To a solution of 121-I (1.9 g, 4.4 mmol) in DCM (200 mL) at 0° C. was added mCPBA (1.1 g of ~77%, 4.8 mmol, 1.1 eq.) in one portion. The resulting mixture was stirred at the same temperature for 30 min. The reaction mixture was washed with saturated $NaHCO_3$ solution (3×30 mL), water (1×30 mL), and brine (1×30 mL) respectively. The organic layer is then dried over sodium sulfate, filtered, and concentrated under reduced pressure to give 121-J (1 g, quantitative). MS(ESI) m/z 447.2 $(M+H)^+$ $.]^+$.

Step 2: Synthesis of 8-(bicyclo[1.1.1]pentan-1-yl)-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (Example-121)

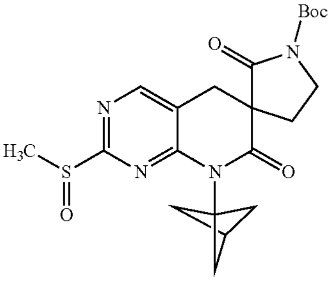

121-J

+

-continued

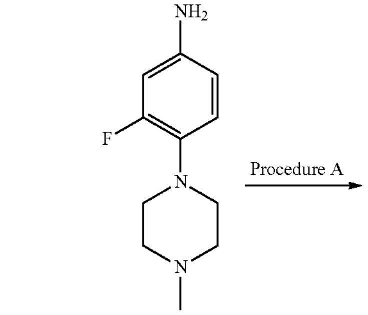

14

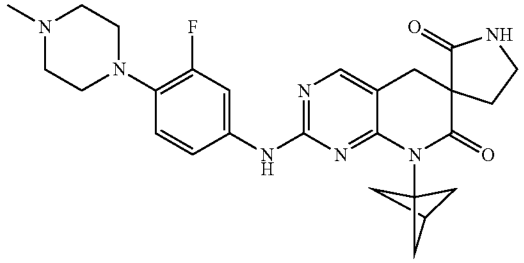

Example-121

Example-121 was synthesized following the general procedure A, 14 mg (29% yield). MS(ESI) m/z 492.2 $(M+H)^+$. $^1H$ NMR (600 MHz, DMSO-$d_6$) δ 9.26 (s, 1H), 8.07 (s, 1H), 7.92 (s, 1H), 7.66 (dd, J=15.2, 2.4 Hz, 1H), 7.27 (dd, J=8.7, 2.5 Hz, 1H), 6.96 (t, J=9.4 Hz, 1H), 3.20-3.11 (m, 3H), 3.02 (s, 4H), 2.93 (d, J=15.7 Hz, 2H), 2.67 (d, J=15.7 Hz, 1H), 2.58-2.48 (m, 2H), 2.47 (s, 1H), 2.43 (s, 3H), 2.38 (s, 6H), 2.37-2.30 (m, 2H).

Enantiomeric Examples

Step 1: Separation of two enantiomers of tert-butyl 8-(bicyclo[1.1.1]pentan-1-yl)-2-(methylthio)-2',7-dioxo-7,8-dihydro-5H-spiro[pyrido[2,3-d]pyrimidine-6,3'-pyrrolidine]-1'-carboxylate (121-I)

Preparative Chiral Chromatography Conditions:

Column: Chiralpak IC, 21×250 mm, 5 micron; Mobile phase: Acetonitrile;

Flow Rate: 4.0 mL/min; wavelengths: 254 nm and 280 nm Retention Times ($t_R$): 4:50 min. (Enantiomer-1 of 121-I), 9:80 min. (Enantiomer-2 of 121-I)

Standard chromatographic techniques were used to isolate the required two enantiomers, E1 and E2 as off-white solids (concentrated and lyophilized).

About 8 g of racemic 121-I was used to isolate the following amounts:

Enantiomer-1 of 121-I (E1): Yield: 3.4 g (42%), Purity: >98%; Optical purity: % ee>98%

Enantiomer-2 of 121-I (E2): Yield: 3.4 g (42%); Purity: >98%; Optical purity: % ee>98%

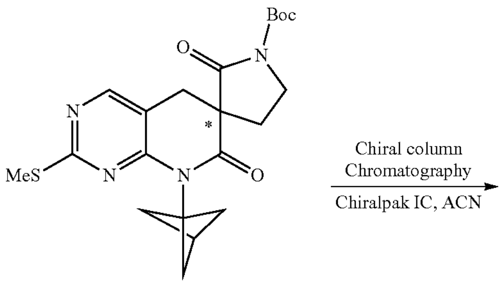

Racemic (121-I)

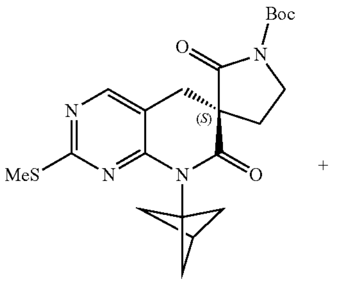

Enantiomer-1 (121-I-E1)
(E1), $t_R$: 4.5 min

+

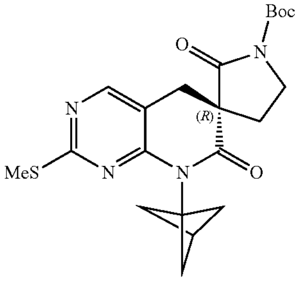

Enantiomer-2 (121-I-E2)
(E2), $t_R$: 9.8 min

Ref: VP-7-192E2 Enantiomer-2 (121-I-E2)

Synthesis of tert-butyl tert-butyl 8-(bicyclo[1.1.1]pentan-1-yl)-2-(methylthio)-2',7-dioxo-7,8-dihydro-5H-spiro[pyrido[2,3-d]pyrimidine-6,3'-pyrrolidine]-1'-carboxylate (121-I-E1sulfoxide)

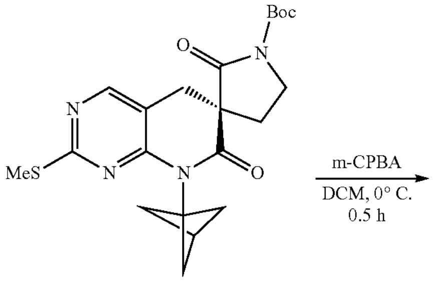

121-I-E1

-continued

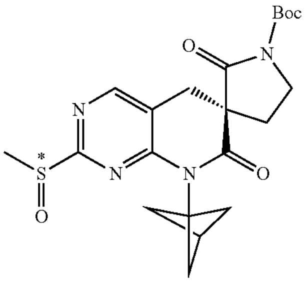

121-I-E1-sulfoxide

E1-sulfoxide (diastereomers) was synthesized according to the procedure described for making racemic sulfoxide 121-J. Yield: 700 mg (97%)

MS(ESI) m/z 447.2 $(M+H)^+$.

Synthesis of tert-butyl (6R)-8-cyclopentyl-2-(methylsulfinyl)-2',7-dioxo-7,8-dihydro-5H-spiro[pyrido[2,3-d]pyrimidine-6,3'-pyrrolidine]-1'-carboxylate (121-I-E2-sulfoxide)

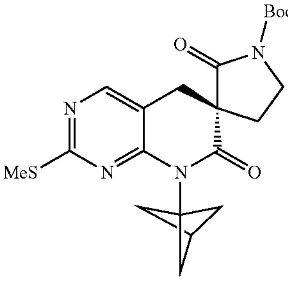

121-I-E2

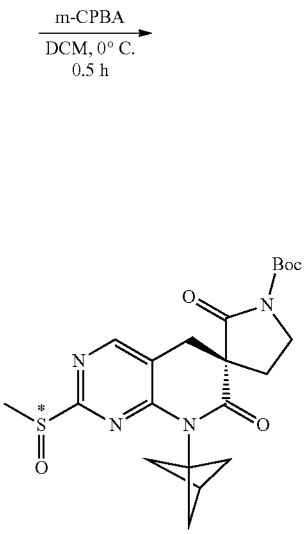

121-I-E2-sulfoxide

121-I-E2-sulfoxide (diastereomers) were synthesized according to the procedure described for making racemic sulfoxide 121-J. Yield: 760 mg (98%).

MS(ESI) m/z 447.2 $(M+H)^+$. $^1$H NMR (600 MHz, Chloroform-d) δ 8.52-8.46 (m, 1H), 3.90-3.78 (m, 2H), 3.38 (ddd, J=16.3, 11.0, 1.0 Hz, 1H), 2.94 (d, J=4.7 Hz, 3H), 2.89 (ddd, J=16.3, 10.7, 1.0 Hz, 1H), 2.59 (d, J=2.6 Hz, 1H), 2.54 (s, 4H), 2.53-2.51 (m, 3H), 1.88 (dt, J=13.2, 8.6 Hz, 1H), 1.53 (d, J=1.1 Hz, 9H).

Example-122 (VP-7-110B-E2, SPV-419)

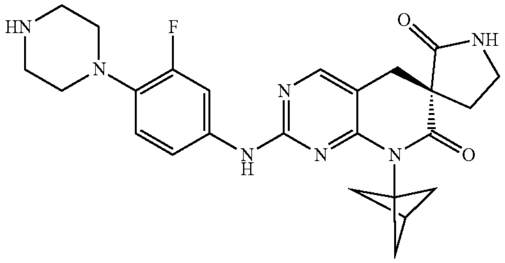 [SMILES: O=C1NCC[C@@]12Cc1cnc(Nc3ccc(N4CCNCC4)c(F)c3)nc1N(C13CC(C1)C3)C2=O]

Step 1: Synthesis of (S)-8-(bicyclo[1.1.1]pentan-1-yl)-2-((3-fluoro-4-(piperazin-1-yl)phenyl)amino)-5,8-dihydro-7H-spiro[pyrido[2,3-d]pyrimidine-6,3'-pyrrolidine]-2',7-dione Example-122

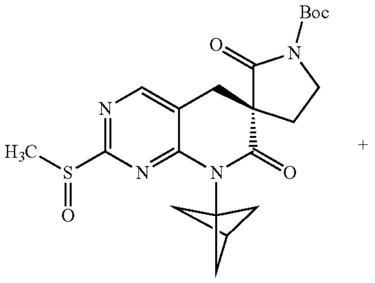

121-I-E2-Sulfoxide

+

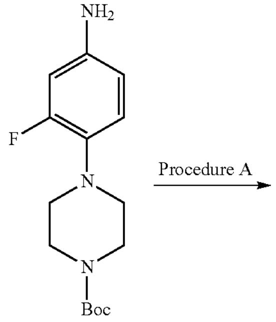

6

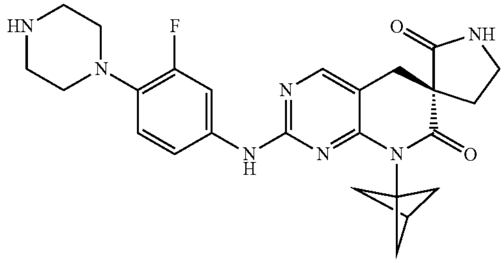

Example-122

Example-122 was synthesized following the general procedure A, 5 mg (10% yield). MS(ESI) m/z 478.2 $(M+H)^+$. $^1$H NMR (600 MHz, DMSO-$d_6$) δ 9.30 (s, 1H), 8.64 (s, 2H), 8.07 (s, 1H), 7.92 (s, 1H), 7.68 (dd, J=15.2, 2.5 Hz, 1H), 7.29

(dd, J=8.9, 2.5 Hz, 1H), 6.99 (t, J=9.4 Hz, 1H), 3.24-3.11 (m, 7H), 3.11-3.02 (m, 4H), 2.94 (d, J=15.7 Hz, 1H), 2.68 (d, J=15.8 Hz, 1H), 2.47 (s, 2H), 2.38 (s, 6H)

Example-123 (VP-7-111B-E2, SPV-420)

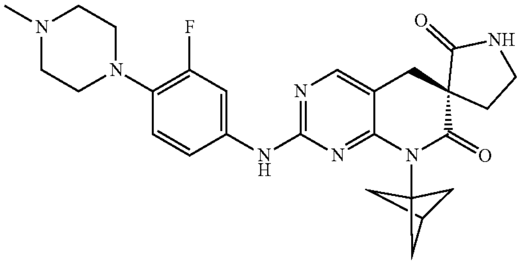 [SMILES: CN1CCN(c2ccc(Nc3ncc4c(n3)N(C35CC(C3)C5)C(=O)[C@]3(CCNC3=O)C4)cc2F)CC1]

Step 1: Synthesis of (S)-8-(bicyclo[1.1.1]pentan-1-yl)-2-((3-fluoro-4-(4-methylpiperazin-1-yl)phenyl) amino)-5,8-dihydro-7H-spiro[pyrido[2,3-d]pyrimidine-6,3'-pyrrolidine]-2',7-dione (Example-123)

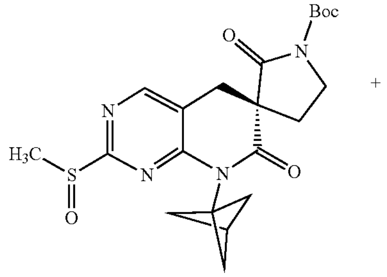

121-I-E2-Sulfoxide

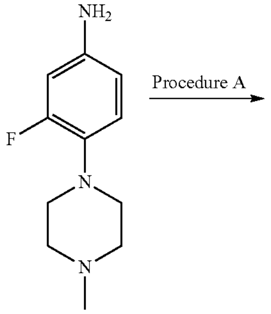

14

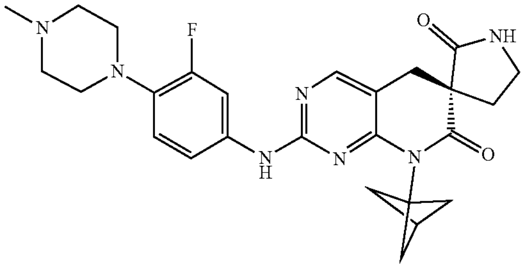

Example-123

Example-123 was synthesized following the general procedure A, 7 mg (14% yield). MS(ESI) m/z 492.2 $(M+H)^+$. $^1H$ NMR (600 MHz, DMSO-$d_6$) δ 9.24 (s, 1H), 8.07 (s, 1H), 7.92 (s, 1H), 7.67-7.61 (m, 1H), 7.26 (dd, J=8.7, 2.4 Hz, 1H), 6.94 (t, J=9.4 Hz, 1H), 3.20-3.11 (m, 3H), 2.98 (s, 4H), 2.93 (d, J=15.7 Hz, 1H), 2.74 (s, 4H), 2.66 (d, J=15.7 Hz, 1H), 2.47 (s, 3H), 2.38 (s, 7H), 2.35-2.31 (m, 1H).

Example-124 (VP-7-113-E2, SPV-421)

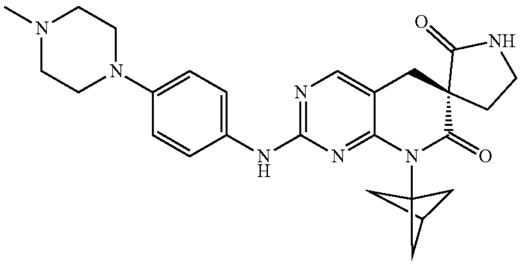 [SMILES: CN1CCN(c2ccc(Nc3ncc4c(n3)N(C35CC(C3)C5)C(=O)[C@]3(CCNC3=O)C4)cc2)CC1]

Step 1: Synthesis of (S)-8-(bicyclo[1.1.1]pentan-1-yl)-2-((4-(4-methylpiperazin-1-yl)phenyl)amino)-5,8-dihydro-7H-spiro[pyrido[2,3-d]pyrimidine-6,3'-pyrrolidine]-2',7-dione (Example-124)

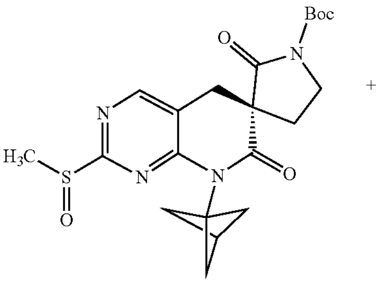

121-I-E2-Sulfoxide

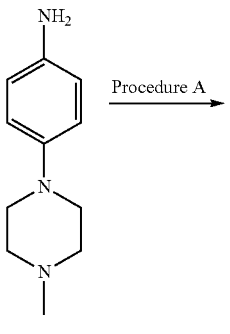

3

-continued

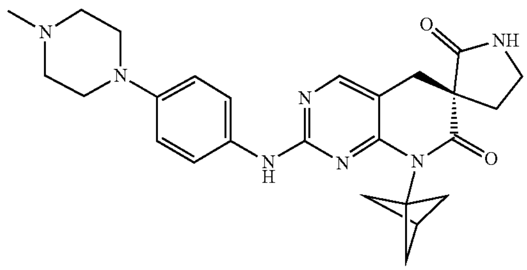

Example-124

Example-124 was synthesized following the general procedure A, 12 mg (26% yield). MS(ESI) m/z 474.2 $(M+H)^+$. $^1H$ NMR (600 MHz, DMSO-$d_6$) δ 8.98 (s, 1H), 8.00 (s, 1H), 7.90 (s, 1H), 7.44 (d, J=8.4 Hz, 2H), 6.85 (d, J=8.6 Hz, 2H), 3.20-3.06 (m, 7H), 2.91 (d, J=15.6 Hz, 2H), 2.84 (s, 4H), 2.62 (d, J=15.6 Hz, 1H), 2.49 (s, 3H), 2.35 (s, 6H), 2.32-2.27 (m, 1H).

Example-125 (VP-7-114-E2, SPV-422)

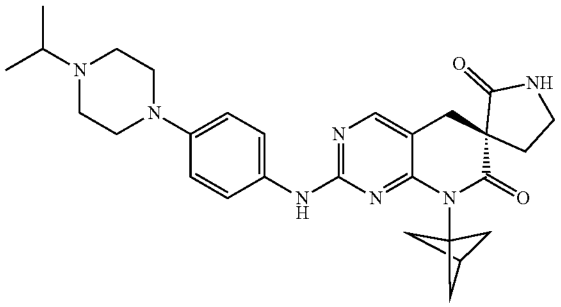 [SMILES: CC(C)N1CCN(c2ccc(Nc3ncc4c(n3)N(C35CC(C3)C5)C(=O)[C@]3(CCNC3=O)C4)cc2)CC1]

Step 1: Synthesis of (S)-8-(bicyclo[1.1.1]pentan-1-yl)-2-((4-(4-isopropylpiperazin-1-yl)phenyl)amino)-5,8-dihydro-7H-spiro[pyrido[2,3-d]pyrimidine-6,3'-pyrrolidine]-2',7-dione (Example-125)

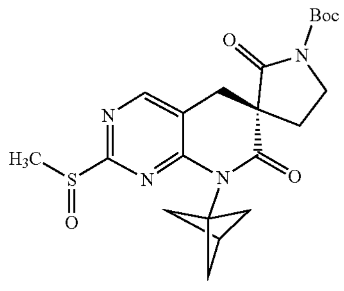

121-I-E2-Sulfoxide

+

-continued

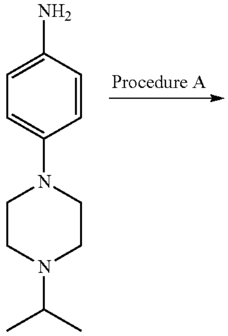

12

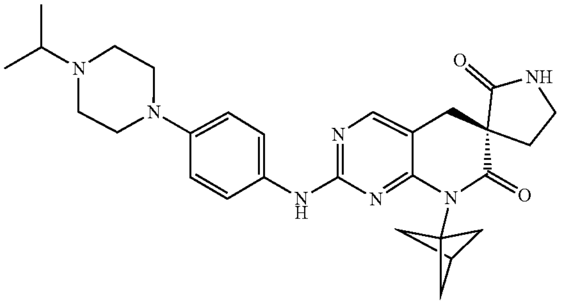

Example-125

Example-125 was synthesized following the general procedure A, 10 mg (20% yield). MS(ESI) m/z 502.2 $(M+H)^+$. $^1H$ NMR (600 MHz, DMSO-$d_6$) δ 9.08 (s, 1H), 8.07 (s, 1H), 7.98 (s, 1H), 7.64-7.50 (m, 2H), 6.96 (d, J=7.8 Hz, 2H), 3.77 (s, 2H), 3.52 (s, 2H), 3.27-3.15 (m, 3H), 2.98 (d, J=15.6 Hz, 1H), 2.94 (s, 2H), 2.70 (d, J=15.6 Hz, 1H), 2.50 (s, 3H), 2.42 (s, 6H), 2.40-2.35 (m, 1H), 1.91-1.86 (m, 1H), 1.29 (s, 6H).

Example-126 (VP-7-115-E2, SPV-423)

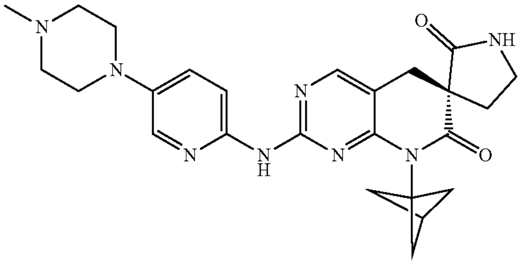 [SMILES: CN1CCN(c2ccc(Nc3ncc4c(n3)N(C35CC(C3)C5)C(=O)[C@]3(CCNC3=O)C4)nc2)CC1]

Step 1: Synthesis of (S)-8-(bicyclo[1.1.1]pentan-1-yl)-2-((5-(4-methylpiperazin-1-yl)pyridin-2-yl)amino)-5,8-dihydro-7H-spiro[pyrido[2,3-d]pyrimidine-6,3'-pyrrolidine]-2',7-dione (Example-126)

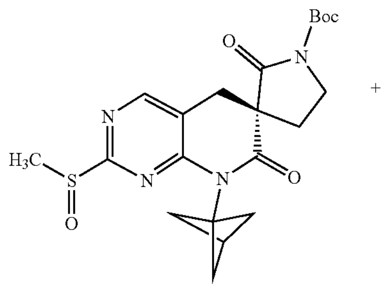

121-I-E2-Sulfoxide

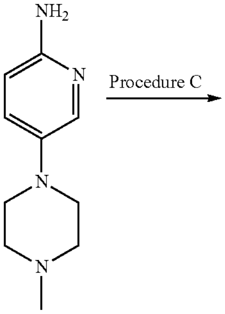

10

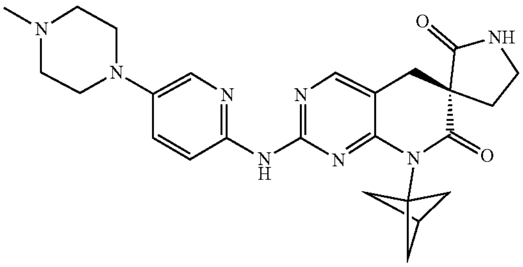

Example-126

Example-126 was synthesized following the general procedure C, 4 mg (9% yield). MS(ESI) m/z 475.2 $(M+H)^+$. $^1H$ NMR (600 MHz, DMSO-$d_6$) δ 8.62 (s, 1H), 7.99-7.93 (m, 1H), 7.91 (s, 1H), 7.85 (d, J=3.0 Hz, 1H), 7.60 (s, 1H), 7.31 (dd, J=9.1, 3.1 Hz, 1H), 3.17-3.10 (m, 2H), 3.05-3.01 (m, 4H), 2.92-2.86 (m, 1H), 2.82 (d, J=15.1 Hz, 1H), 2.71 (d, J=15.1 Hz, 1H), 2.43 (s, 4H), 2.38 (s, 1H), 2.33-2.25 (m, 1H), 2.19 (s, 3H), 2.05 (s, 5H), 1.86-1.79 (m, 1H).

Example-127 (VP-7-116-E2, SPV-424)

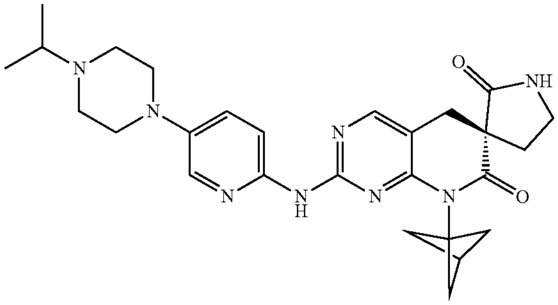 [SMILES: CC(C)N1CCN(c2ccc(Nc3ncc4c(n3)N(C35CC(C3)C5)C(=O)[C@]3(CCNC3=O)C4)nc2)CC1]

Step 1: Synthesis of (S)-8-(bicyclo[1.1.1]pentan-1-yl)-2-((5-(4-isopropylpiperazin-1-yl)pyridin-2-yl)amino)-5,8-dihydro-7H-spiro[pyrido[2,3-d]pyrimidine-6,3'-pyrrolidine]-2',7-dione (Example-127)

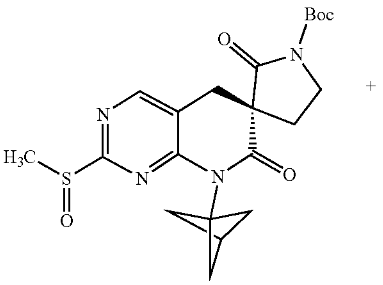

121-I-E2-Sulfoxide

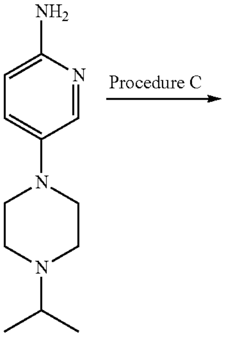

11

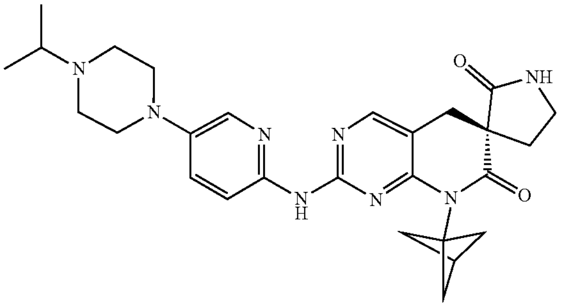

Example-127

Example-127 was synthesized following the general procedure C, 4 mg (8% yield). MS(ESI) m/z 503.2 $(M+H)^+$.

Example-128 (VP-7-117-E2, SPV-425)

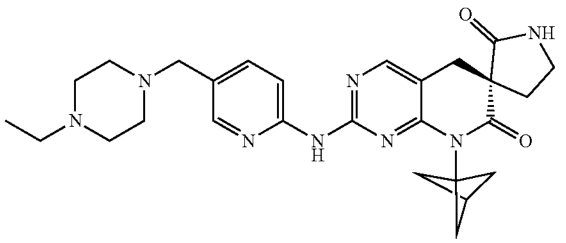 [SMILES: CCN1CCN(Cc2ccc(Nc3ncc4c(n3)N(C35CC(C3)C5)C(=O)[C@]3(CCNC3=O)C4)nc2)CC1]

Step 1: Synthesis of (S)-8-(bicyclo[1.1.1]pentan-1-yl)-2-((5-((4-ethylpiperazin-1-yl)methyl)pyridin-2-yl)amino)-5,8-dihydro-7H-spiro[pyrido[2,3-d]pyrimidine-6,3'-pyrrolidine]-2',7-dione (Example-128)

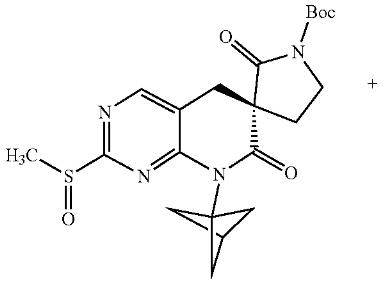

121-I-E2-Sulfoxide

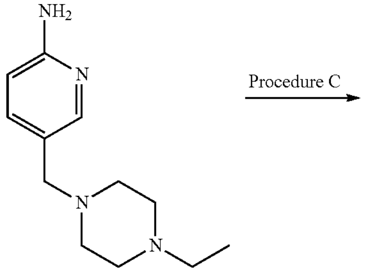

49

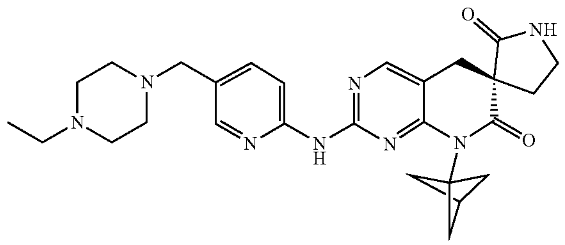

Example-128

Example-128 was synthesized following the general procedure C, 5 mg (10% yield). MS(ESI) m/z 503.2 $(M+H)^+$.

Example-129 (VP-7-112-E2, SPV-434)

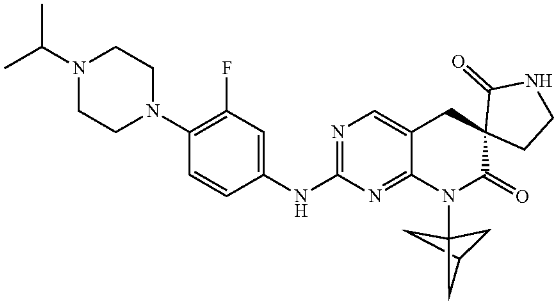 [SMILES: CC(C)N1CCN(c2ccc(Nc3ncc4c(n3)N(C35CC(C3)C5)C(=O)[C@]3(CCNC3=O)C4)cc2F)CC1]

Step 1: Synthesis of (S)-8-(bicyclo[1.1.1]pentan-1-yl)-2-((3-fluoro-4-(4-isopropylpiperazin-1-yl)phenyl)amino)-5,8-dihydro-7H-spiro[pyrido[2,3-d]pyrimidine-6,3'-pyrrolidine]-2',7-dione (Example-129)

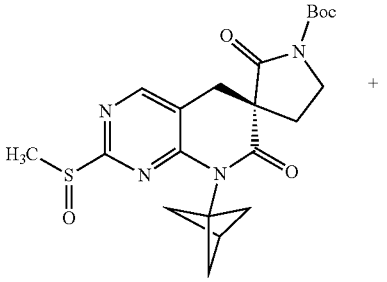

121-I-E2-Sulfoxide

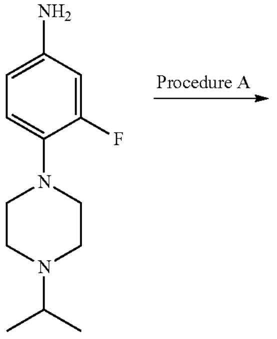

15

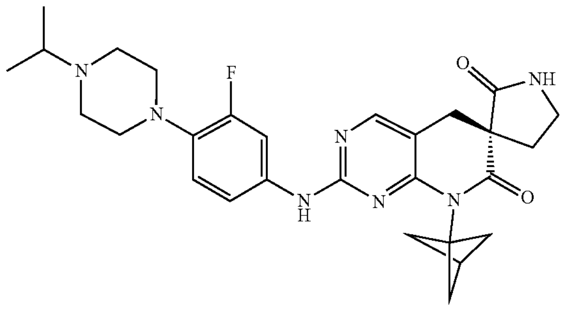

Example-129

Example-129 was synthesized following the general procedure A, 10 mg (19% yield). MS(ESI) m/z 520.2 $(M+H)^+$. $^1H$ NMR (600 MHz, DMSO-$d_6$) δ 9.24 (s, 1H), 8.06 (s, 1H), 7.92 (s, 1H), 7.64 (d, J=15.2 Hz, 1H), 7.26 (d, J=8.7 Hz, 1H), 6.93 (s, 1H), 3.21-3.10 (m, 3H), 3.00-2.80 (m, 4H), 2.66 (d, J=15.6 Hz, 1H), 2.46 (s, 1H), 2.43 (s, 6H), 2.38 (s, 5H), 2.36-2.30 (m, 1H), 1.86-1.79 (m, 1H), 1.51-0.72 (m, 6H).

Example-130 (VP-NR11-130-E2, SPV-484)

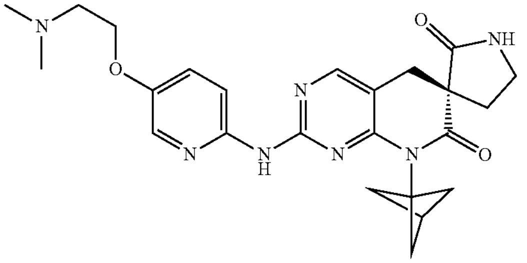 [SMILES: CN(C)CCOc1ccc(Nc2ncc3c(n2)N(C24CC(C2)C4)C(=O)[C@]2(CCNC2=O)C3)nc1]

Step 1: Synthesis of (S)-8-(bicyclo[1.1.1]pentan-1-yl)-2-((5-(2-(dimethylamino)ethoxy)pyridin-2-yl)amino)-5,8-dihydro-7H-spiro[pyrido[2,3-d]pyrimidine-6,3'-pyrrolidine]-2',7-dione (Example-130)

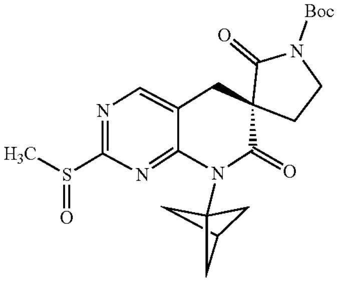

+

121-I-E2-Sulfoxide

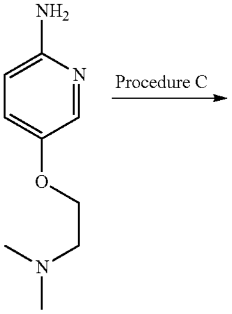

21

-continued

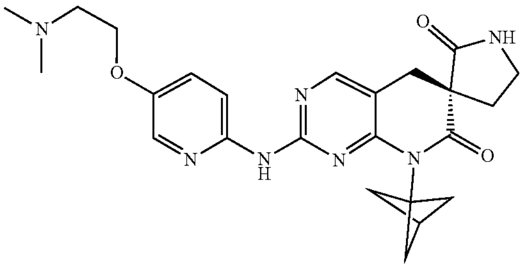

Example-130

Example-130 was synthesized following the general procedure A, 13 mg (28% yield). MS(ESI) m/z 464.2 $(M+H)^+$. $^1H$ NMR (600 MHz, DMSO-$d_6$) δ 9.61 (s, 1H), 8.15 (s, 1H), 8.09-8.03 (m, 1H), 7.99 (s, 1H), 7.46 (dd, J=9.1, 3.1 Hz, 1H), 4.23 (s, 2H), 3.27-3.19 (m, 3H), 3.01 (d, J=15.7 Hz, 1H), 2.79-2.71 (m, 1H), 2.63-2.59 (m, 1H), 2.56 (s, 2H), 2.50 (s, 6H), 2.45 (s, 3H), 2.43-2.35 (m, 2H), 2.07 (s, 2H).

Example-131 (VP-8-298B-E2, SPV-461)

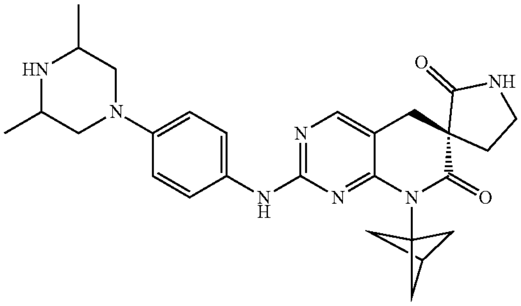 [SMILES: CC1CN(c2ccc(Nc3ncc4c(n3)N(C35CC(C3)C5)C(=O)[C@]3(CCNC3=O)C4)cc2)CC(C)N1]

Step 1: Synthesis of (6S)-8-(bicyclo[1.1.1]pentan-1-yl)-2-((4-(3,5-dimethylpiperazin-1-yl)phenyl)amino)-5,8-dihydro-7H-spiro[pyrido[2,3-d]pyrimidine-6,3'-pyrrolidine]-2',7-dione (Example-131)

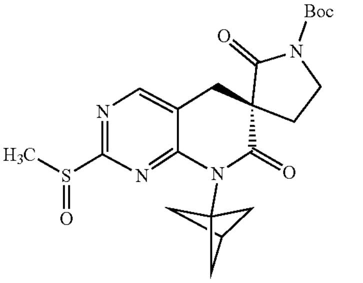

+

121-I-E2-Sulfoxide

-continued

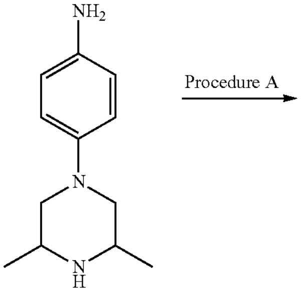

73

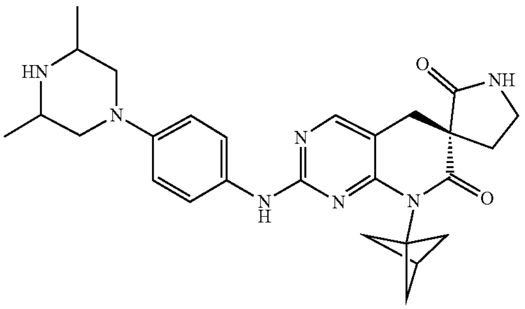

Example-131

Example-131 was synthesized following the general procedure A, 30 mg (30% yield). MS(ESI) m/z 488.2 $(M+H)^+$. $^1H$ NMR (600 MHz, DMSO-$d_6$) δ 8.98 (s, 1H), 8.06 (s, 1H), 7.97 (s, 1H), 7.45 (d, J=8.6 Hz, 2H), 6.90-6.83 (m, 2H), 3.43 (dd, J=11.6, 2.7 Hz, 2H), 3.26-3.18 (m, 2H), 2.97 (d, J=15.6 Hz, 1H), 2.89-2.81 (m, 2H), 2.68 (d, J=15.8 Hz, 1H), 2.41 (s, 5H), 2.40-2.32 (m, 2H), 2.10-2.02 (m, 2H), 1.93-1.85 (m, 2H), 1.01 (d, J=6.3 Hz, 6H).

Example-132 (VP-8-288-E2, SPV-465)

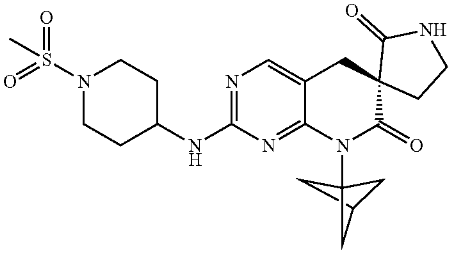 [SMILES: CS(=O)(=O)N1CCC(Nc2ncc3c(n2)N(C24CC(C2)C4)C(=O)[C@]2(CCNC2=O)C3)CC1]

Step 1: Synthesis of (S)-8-(bicyclo[1.1.1]pentan-1-yl)-2-((1-(methylsulfonyl)piperidin-4-yl)amino)-5,8-dihydro-7H-spiro[pyrido[2,3-d]pyrimidine-6,3'-pyrrolidine]-2',7-dione (Example-132)

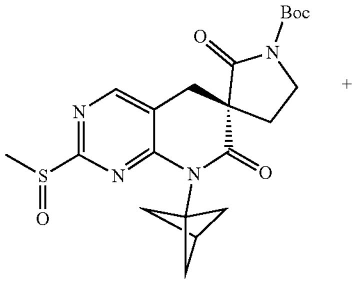

121-I-E2-Sulfoxide

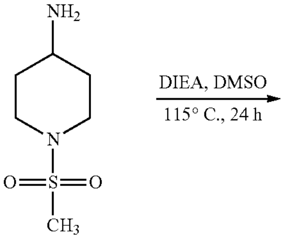

105

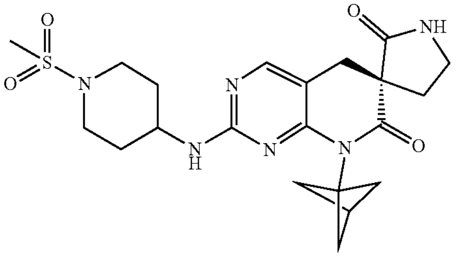

Example-132

Example-132 was synthesized following the procedure of Example-109, 24 mg (52% yield). MS(ESI) m/z 461.2 $(M+H)^+$. $^1H$ NMR (600 MHz, DMSO-$d_6$) δ 7.89 (d, J=5.4 Hz, 1H), 6.99 (s, 2H), 3.72 (s, 1H), 3.49 (dd, J=11.5, 4.2 Hz, 3H), 3.13 (dtd, J=16.5, 9.3, 5.6 Hz, 2H), 2.86 (d, J=15.5 Hz, 1H), 2.81 (s, 2H), 2.80-2.73 (m, 2H), 2.54 (d, J=15.5 Hz, 1H), 2.46 (s, 1H), 2.36 (s, 5H), 2.25 (ddd, J=12.8, 7.8, 4.8 Hz, 1H), 1.93-1.85 (m, 2H), 1.83-1.77 (m, 1H), 1.52-1.42 (m, 2H).

Example-133 (VP-8-93C-E2, SPV-474)

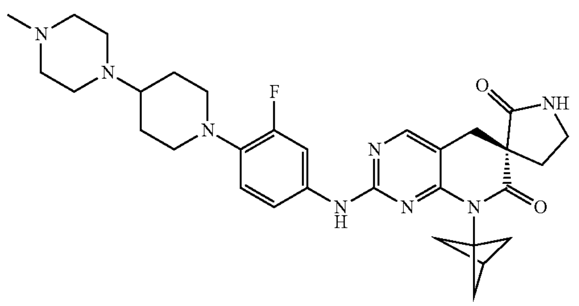 [SMILES: CN1CCN(C2CCN(c3ccc(Nc4ncc5c(n4)N(C46CC(C4)C6)C(=O)[C@]4(CCNC4=O)C5)cc3F)CC2)CC1]

Step 1: Synthesis of (S)-8-(bicyclo[1.1.1]pentan-1-yl)-2-((3-fluoro-4-(4-(4-methylpiperazin-1-yl)piperidin-1-yl)phenyl)amino)-5,8-dihydro-7H-spiro[pyrido[2,3-d]pyrimidine-6,3'-pyrrolidine]-2',7-dione (Example-133)

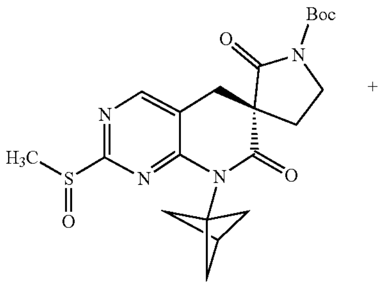

121-I-E2-Sulfoxide

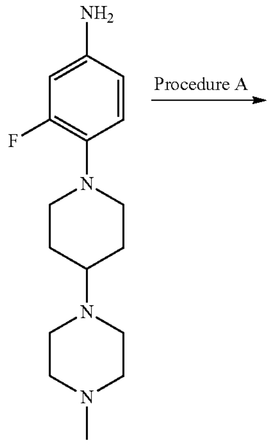

67

-continued

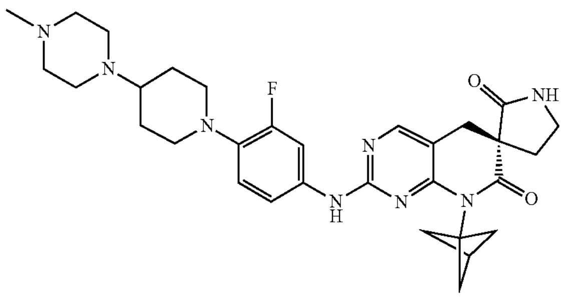

Example-133

Example-133 was synthesized following the general procedure A, 4 mg (7% yield). MS(ESI) m/z 575.2 $(M+H)^+$.

Example-134 (VP-8-79B-E2, SPV-476)

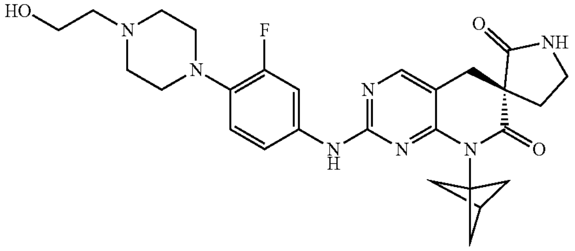 [SMILES: O=C1NCC[C@@]12Cc1cnc(Nc3ccc(N4CCN(CCO)CC4)c(F)c3)nc1N(C13CC(C1)C3)C2=O]

Step 1: Synthesis of (S)-8-(bicyclo[1.1.1]pentan-1-yl)-2-((3-fluoro-4-(4-(2-hydroxyethyl)piperazin-1-yl)phenyl)amino)-5,8-dihydro-7H-spiro[pyrido[2,3-d]pyrimidine-6,3'-pyrrolidine]-2',7-dione (Example-134)

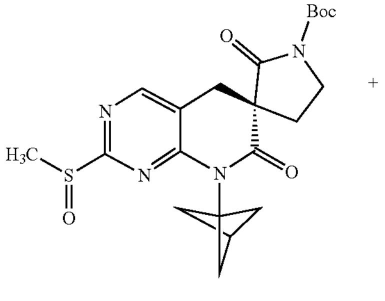

121-I-E2-Sulfoxide

-continued

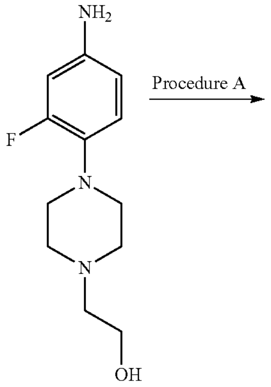

71

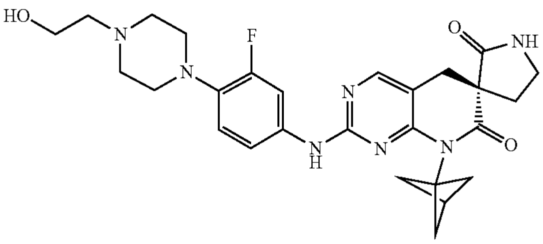

Example-135

Example-134 was synthesized following the general procedure A, 13 mg (25% yield). MS(ESI) m/z 522.2 $(M+H)^+$.

Example-135 (VP-8-59C-E2, SPV-486)

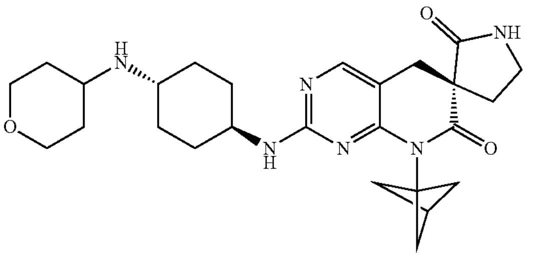 [SMILES: O=C1NCC[C@@]12Cc1cnc(N[C@H]3CC[C@H](NC4CCOCC4)CC3)nc1N(C13CC(C1)C3)C2=O]

Step 1: Synthesis of (S)-8-(bicyclo[1.1.1]pentan-1-yl)-2-(((1r,4S)-4-((tetrahydro-2H-pyran-4-yl)amino)cyclohexyl)amino)-5,8-dihydro-7H-spiro[pyrido[2,3-d]pyrimidine-6,3'-pyrrolidine]-2',7-dione (Example-135)

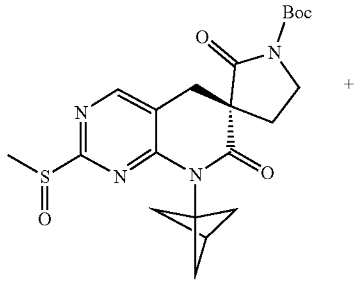

121-I-E2-Sulfoxide

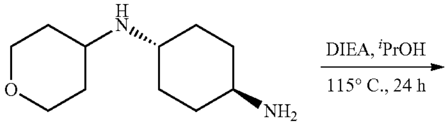

76

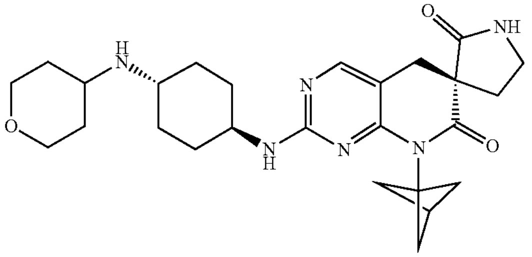

Example-135

Example-135 was synthesized following slightly modified general procedure A (used DIEA in the place of TFA), 7 mg (15% yield). MS(ESI) m/z 481.2 $(M+H)^+$. $^1$H NMR (600 MHz, DMSO-$d_6$) δ 7.88 (d, J=4.5 Hz, 1H), 3.88-3.78 (m, 1H), 3.54 (s, 1H), 3.27 (s, 7H), 3.18-3.08 (m, 2H), 2.85 (d, J=15.5 Hz, 1H), 2.54 (d, 1H), 2.44 (s, 7H), 2.48-2.45 (m, 1H), 2.37 (s, 3H), 2.35-2.30 (m, 1H), 2.25 (dt, J=13.1, 6.9 Hz, 1H), 2.06-1.95 (m, 1H), 1.90 (s, 1H), 1.83-1.75 (m, 1H), 1.36 (s, 1H), 1.26 (s, 2H).

Example-136 (VP-7-118-E1, SPV-436)

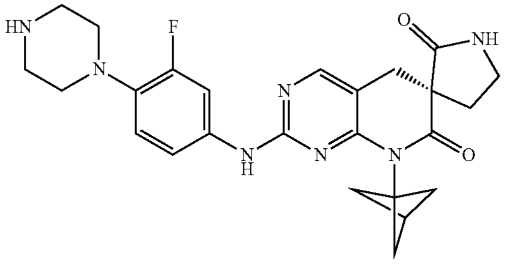 [SMILES: O=C1NCC[C@]12Cc1cnc(Nc3ccc(N4CCNCC4)c(F)c3)nc1N(C13CC(C1)C3)C2=O]

Step 1: Synthesis of (R)-8-(bicyclo[1.1.1]pentan-1-yl)-2-((3-fluoro-4-(piperazin-1-yl)phenyl)amino)-5,8-dihydro-7H-spiro[pyrido[2,3-d]pyrimidine-6,3'-pyrrolidine]-2',7-dione (Example-136)

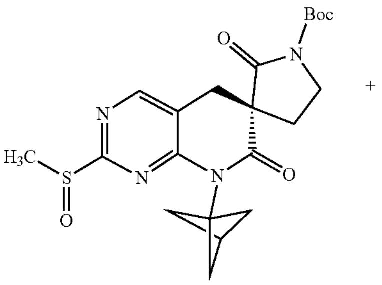

121-I-E2-Sulfoxide

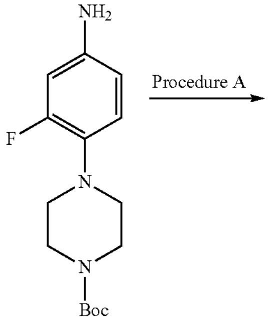

XX

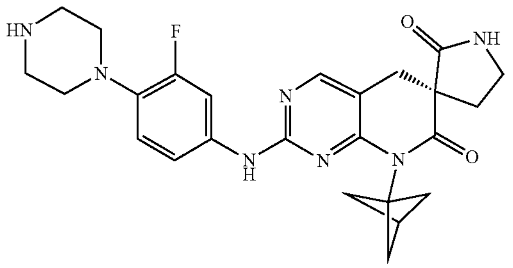

Example-136

Example-136 was synthesized following the general procedure A, 9 mg (19% yield). MS(ESI) m/z 478.2 $(M+H)^+$. $^1H$ NMR (600 MHz, DMSO-$d_6$) δ 9.25 (s, 1H), 8.07 (s, 1H), 7.92 (s, 1H), 7.65 (dd, J=15.1, 2.4 Hz, 1H), 7.30-7.23 (m, 1H), 6.95 (t, J=9.4 Hz, 1H), 3.06-2.99 (m, 5H), 3.00-2.90 (m, 6H), 2.67 (d, J=15.7 Hz, 1H), 2.47 (s, 1H), 2.38 (s, 6H), 2.36-2.31 (m, 2H).

Example-137 (VP-7-119B-E1, SPV-437)

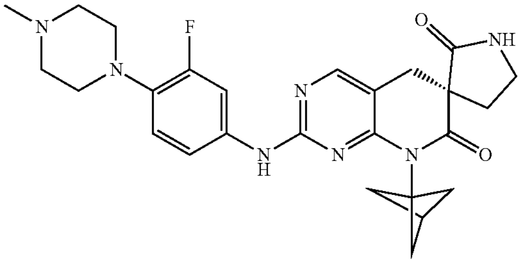

Step 1: Synthesis of (R)-8-(bicyclo[1.1.1]pentan-1-yl)-2-((3-fluoro-4-(4-methylpiperazin-1-yl)phenyl)amino)-5,8-dihydro-7H-spiro[pyrido[2,3-d]pyrimidine-6,3'-pyrrolidine]-2',7-dione (Example-137)

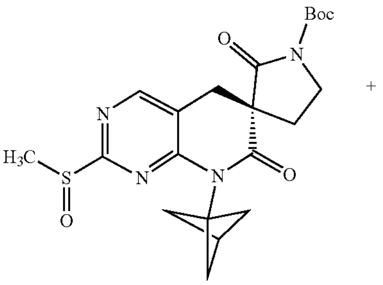

121-I-E2-Sulfoxide

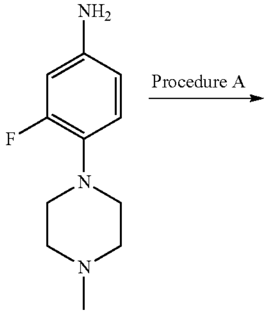

14

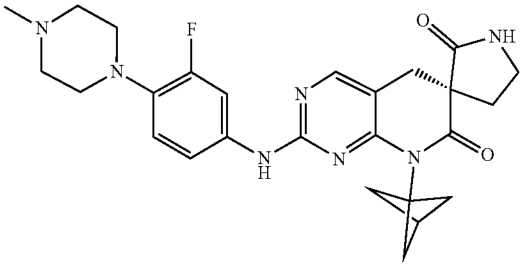

Example-137

Example-137 was synthesized following the general procedure A, 9 mg (18% yield). MS(ESI) m/z 492.2 $(M+H)^+$. $^1H$ NMR (600 MHz, DMSO-$d_6$) δ 9.28 (s, 1H), 8.07 (s, 1H), 7.92 (s, 1H), 7.68 (dd, J=15.3, 2.4 Hz, 1H), 7.28 (dd, J=8.8, 2.5 Hz, 1H), 6.98 (t, J=9.4 Hz, 1H), 3.20-3.12 (m, 5H), 2.94

(d, J=15.7 Hz, 1H), 2.75-2.63 (m, 4H), 2.47 (s, 1H), 2.43 (s, 4H), 2.38 (s, 6H), 2.37-2.30 (m, 2H), 1.87-1.79 (m, 1H).

Example 5

Inhibition Assays

Inhibition assays were performed using microfluidic LabChip 300 Drug Discovery System from Caliper Life Sciences. The assays were performed in six-point to 12-point concentration-response format ($IC_{50}$) (Nanosyn, Santa Clara, CA). The assay has a total volume of 10 μL consisting of 5 μL of enzyme and buffer and 5 μL of substrate and buffer. The test compounds were diluted in 100% dimethylsulfoxide (DMSO) using 3-fold dilution steps. The compounds were diluted in 100% dimethylsulfoxide (DMSO) and plated at 100-fold greater than the screening composition and serially diluted using 3-fold dilution steps. Compounds were tested in a single well for each dilution and the final concentration of DMSO was maintained at 1%.

The assay buffer contained 100 mM HEPES, pH 7.5, 0.01% Triton X-100, 0.1% bovine serum albumin (BSA), 5 mM $MgCl_2$; 1 mM dithiothreitol (DTT), 10 μM sodium orthovanadate, and 10 μM β-glycerophosphate.

The assay was conducted by adding 5 μL of enzyme, adenosine triphosphate (ATP) and buffer to an assay plate. A 100 nL aliquot of the diluted compounds were added to the plate. The assay was initiated by the addition of 5 μL of phosphoenolpyruvate substrate (PEP) in buffer. Specific concentrations for the enzyme, ATP, and PEP are shown in Table 1. The assays was incubated at 25° C. for 3 min for CDK2, CDK4 and CDK6 or 17 min for CDK9. The reaction was terminated by the addition of EDTA. The plates were analyzed using a Caliper LabChip 3000.

TABLE 1

Inhibition Assay Components and Concentrations

| Enzyme | Vendor | ENZ Stock Conc (μM) | ENZ Assay Conc (nM) | ATP Conc (μM) | PEP Conc (μM) | Assay Time |
|---|---|---|---|---|---|---|
| CDK2-CYCLINA | Millipore | 1.8 | 0.1 | 50 | 1 | 3 |
| CDK2-CYCLINE | Millipore | 0.93 | 0.15 | 100 | 1 | 3 |
| CDK4-CYCLIND1 | Invitrogen | 3.5 | 1 | 200 | 1 | 3 |
| CDK6-CYCLIND3 | Carna | 3.13 | 2 | 300 | 1 | 3 |
| CDK9-CYCLINT1 | Carna | 2.86 | 5 | 10 | 1 | 17 |

Figure 2:
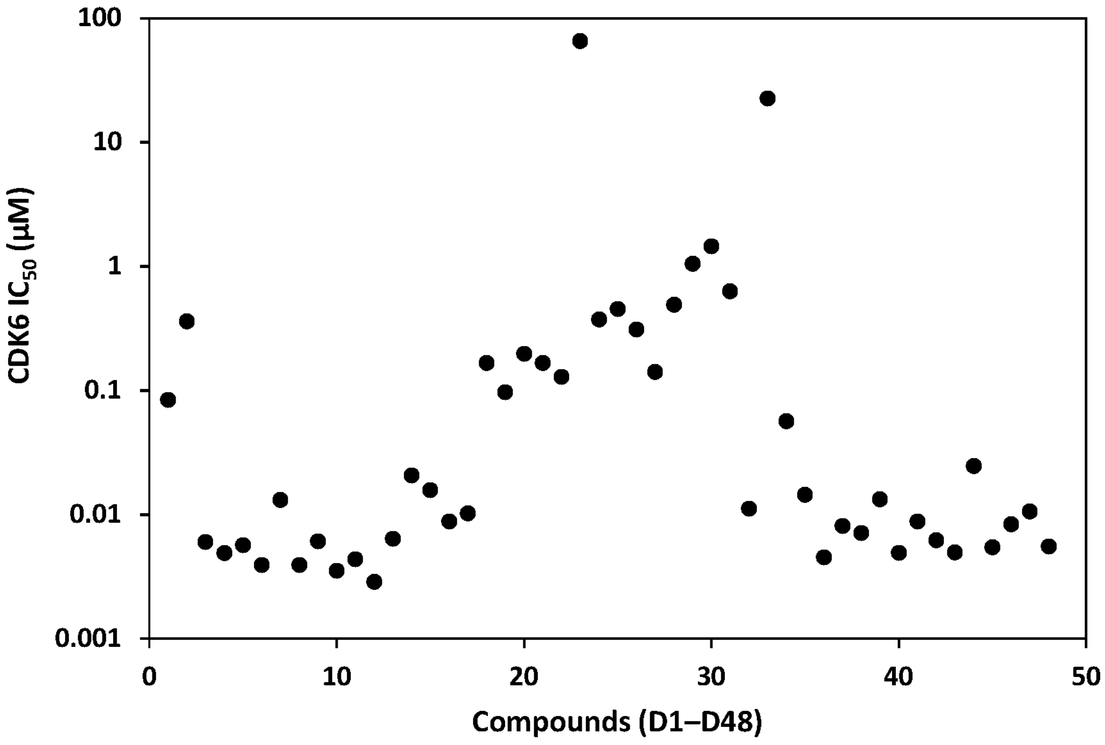
FIG. 2 shows CDK6 inhibition data for Compounds D1-D48. The plotted data is shown in Table 2.

Results for controls and compounds described herein are shown in the table below. The results are graphically shown in FIG. 1 (CDK4) and FIG. 2 (CDK6).

Example 6

Additional inhibition assays were performed as described above. The data is shown in Tables 4a and 4b.

TABLE 4a

Inhibition Assay Results

| Compound | CDK1/B $IC_{50}$ (μM) | CDK2 CyclinA $IC_{50}$ (μM) | CDK4 CyclinD1 $IC_{50}$ (μM) | CDK6 CyclinD3 $IC_{50}$ (μM) | CDK7 CyclinH $IC_{50}$ (μM) | CDK9 CyclinT1 IC50 (μM) |
|---|---|---|---|---|---|---|
| D144 | | 0.0292 | 0.00073 | 0.00154 | 0.229 | 0.00484 |
| D145 | | 0.0217 | 0.000784 | 0.00165 | 0.153 | 0.00502 |
| D146 | | 0.273 | 0.00419 | 0.00812 | 1.12 | 0.0248 |
| D147 | | 0.951 | 0.0732 | 0.188 | 4.26 | 0.518 |
| D148 | | 83.2 | 1.27 | 4.67 | >100 | 6.25 |
| D149 | | 0.0356 | 0.00122 | 0.00282 | 0.34 | 0.00752 |
| D150 | | 0.0529 | 0.00116 | 0.00234 | 0.402 | 0.00686 |
| D152 | | 1.71 | 0.00118 | 0.00164 | 19 | 0.12 |
| D153 | | 2.44 | 0.00294 | 0.00362 | 18.4 | 0.316 |
| D154 | | 2.14 | 0.00205 | 0.00234 | 13.5 | 0.163 |
| D155 | | 3.44 | 0.00622 | 0.00858 | 14.7 | 1.18 |
| D156 | | 0.0198 | 0.00092 | 0.0023 | 0.166 | 0.00391 |
| D157 | | 0.0183 | 0.000908 | 0.00151 | 0.164 | 0.00367 |
| D158 | | 0.0222 | 0.00104 | 0.00217 | 0.12 | 0.00525 |
| D159 | | 0.035 | 0.00162 | 0.00447 | 0.318 | 0.00734 |
| D160 | | 0.0335 | 0.0012 | 0.00341 | 0.157 | 0.00641 |
| D161 | | 0.0305 | 0.00129 | 0.00388 | 0.157 | 0.00727 |
| D162 | | 0.382 | 0.00534 | 0.0104 | 3.24 | 0.0619 |
| D163 | | 0.338 | 0.00902 | 0.0106 | 2.63 | 0.0651 |
| D164 | | 0.744 | 0.00905 | 0.0137 | 3.16 | 0.0719 |
| D165 | | 0.775 | 0.0292 | 0.0585 | 7.3 | 0.236 |
| D166 | | 1.86 | 0.0387 | 0.0792 | 13.9 | 0.307 |
| D167 | | 2.9 | 0.069 | 0.111 | 12 | 0.418 |
| D168 | | 0.0554 | 0.0152 | 0.03 | 3.1 | 0.00652 |
| D169 | | 0.0335 | 0.00589 | 0.00937 | 2.82 | 0.00292 |

TABLE 4a-continued

| Inhibition Assay Results | | | | | | |
|---|---|---|---|---|---|---|
| Compound | CDK1/B $IC_{50}$ (μM) | CDK2 CyclinA $IC_{50}$ (μM) | CDK4 CyclinD1 $IC_{50}$ (μM) | CDK6 CyclinD3 $IC_{50}$ (μM) | CDK7 CyclinH $IC_{50}$ (μM) | CDK9 CyclinT1 IC50 (μM) |
| D170 | | 8.56 | 0.0423 | 0.0531 | >100 | 0.39 |
| D171 | | 2.84 | 0.00198 | 0.00378 | 26.5 | 0.271 |
| D172 | | 0.0795 | 0.00272 | 0.0066 | 0.673 | 0.00481 |
| D173 | | 0.11 | 0.00537 | 0.0116 | 0.682 | 0.00574 |
| D174 | | 0.0609 | 0.00152 | 0.00316 | 0.505 | 0.00693 |
| D175 | | 0.0571 | 0.00156 (0.00083) | 0.0026 | 0.465 | 0.00362 |
| D176 | | 0.0333 | 0.00112 (0.00064) | 0.00207 | 0.126 | 0.00273 |
| D177 | | 0.05 | 0.00472 | 0.0139 | 2.94 | 0.0191 |
| D178 | | 0.127 | 0.00103 | 0.00188 | 1.13 | 0.00425 |
| D179 | | 0.0675 | 0.00127 | 0.00215 | 0.321 | 0.00185 |
| D180 | | 0.0987 | 0.00179 | 0.00435 | 0.266 | 0.00284 |
| D181 | | 0.0292 | 0.00073 | 0.00154 | 0.229 | 0.00484 |
| D182 | | 0.0217 | 0.000784 | 0.00165 | 0.153 | 0.00502 |
| D183 | | 0.273 | 0.00419 | 0.00812 | 1.12 | 0.0248 |
| D184 | | 0.951 | 0.0732 | 0.188 | 4.26 | 0.518 |
| D185 | | 83.2 | 1.27 | 4.67 | >100 | 6.25 |
| D186 | | 0.0356 | 0.00122 | 0.00282 | 0.34 | 0.00752 |
| D187 | | 0.0529 | 0.00116 | 0.00234 | 0.402 | 0.00686 |
| D188 | | 1.71 | 0.00118 | 0.00164 | 19 | 0.12 |
| D189 | | 2.44 | 0.00294 | 0.00362 | 18.4 | 0.316 |
| D190 | | 2.14 | 0.00205 | 0.00234 | 13.5 | 0.163 |
| D151 | | 3.44 | 0.00622 | 0.00858 | 14.7 | 1.18 |
| D191 | | 0.0198 | 0.00092 | 0.0023 | 0.166 | 0.00391 |
| D192 | | 0.0183 | 0.000908 | 0.00151 | 0.164 | 0.00367 |
| D193 | | 0.0222 | 0.00104 | 0.00217 | 0.12 | 0.00525 |
| D194 | | 0.035 | 0.00162 | 0.00447 | 0.318 | 0.00734 |
| D195 | | 0.0335 | 0.0012 | 0.00341 | 0.157 | 0.00641 |
| D196 | | 0.0305 | 0.00129 | 0.00388 | 0.157 | 0.00727 |
| D197 | | 0.382 | 0.00534 | 0.0104 | 3.24 | 0.0619 |
| D198 | | 0.338 | 0.00902 | 0.0106 | 2.63 | 0.0651 |
| D199 | | 0.744 | 0.00905 | 0.0137 | 3.16 | 0.0719 |
| D200 | | 0.775 | 0.0292 | 0.0585 | 7.3 | 0.236 |
| D201 | | 1.86 | 0.0387 | 0.0792 | 13.9 | 0.307 |
| D202 | | 2.9 | 0.069 | 0.111 | 12 | 0.418 |
| D117 | | 0.0554 | 0.0152 | 0.03 | 3.1 | 0.00652 |
| D123 | | 0.0335 | 0.00589 | 0.00937 | 2.82 | 0.00292 |
| D135 | | 8.56 | 0.0423 | 0.0531 | >100 | 0.39 |
| D130 | | 2.84 | 0.00198 | 0.00378 | 26.5 | 0.271 |
| D114 | | 0.0795 | 0.00272 | 0.0066 | 0.673 | 0.00481 |
| D115 | | 0.11 | 0.00537 | 0.0116 | 0.682 | 0.00574 |
| D116 | | 0.0609 | 0.00152 | 0.00316 | 0.505 | 0.00693 |
| D125 | | 0.0571 | 0.00156 (0.00083) | 0.0026 | 0.465 | 0.00362 |
| D126 | | 0.0333 | 0.00112 (0.00064) | 0.00207 | 0.126 | 0.00273 |
| D88 | | 0.05 | 0.00472 | 0.0139 | 2.94 | 0.0191 |
| D97 | | 0.127 | 0.00103 | 0.00188 | 1.13 | 0.00425 |
| D99 | | 0.0675 | 0.00127 | 0.00215 | 0.321 | 0.00185 |
| D101 | | 0.0987 | 0.00179 | 0.00435 | 0.266 | 0.00284 |
| D102 | | 5.82 | 0.0043 | 0.00679 | 40.9 | 0.818 |
| D105 | 0.172 | 0.0545 | <0.0032 | | 0.134 | <0.0032 |
| D80 | >10 | 7.59 | 0.00343 | | >10 | >10 |
| D71 | >10 | >10 | 1.96 | | >10 | >10 |
| D74 | >10 | >10 | 2.74 | | >10 | >10 |
| D138 | >10 | >10 | 0.00458 | | >10 | 0.204 |
| D148 | >10 | >10 | 0.188 | | >10 | 0.987 |
| D92 | 0.219 | 0.153 | 0.00556 | | 0.343 | <0.0032 |
| D93 | 1.1 | 0.723 | 0.0333 | | 1.5 | 0.0161 |

TABLE 4b

| Inhibition Assay Results | | |
|---|---|---|
| Compound | CDK4 $IC_{50}$ (μM) | CDK6 $IC_{50}$ (μM) |
| Staurosporine | 0.0535 | 0.0619 |
| Ribociclib | 0.00908 | 0.0243 |
| D1 | 0.027 | 0.0841 |

TABLE 4b-continued

Inhibition Assay Results

| | | |
|---|---|---|
| D2 | 0.0836 | 0.36 |
| D3 | 0.00281 | 0.00603 |
| D4 | 0.00222 | 0.0049 |
| D5 | 0.00264 | 0.00567 |
| D6 | 0.00188 | 0.00394 |
| D7 | 0.00868 | 0.0131 |
| D8 | 0.00206 | 0.00392 |
| D9 | 0.00299 | 0.00611 |
| D10 | 0.0015 | 0.00353 |
| D11 | 0.00209 | 0.00438 |
| D12 | 0.00183 | 0.00286 |
| D13 | 0.00335 | 0.00638 |
| D14 | 0.0107 | 0.0207 |
| D15 | 0.00708 | 0.0158 |
| D16 | 0.00525 | 0.00881 |
| D17 | 0.00441 | 0.0102 |
| D18 | 0.053 | 0.166 |
| D19 | 0.0336 | 0.0972 |
| D20 | 0.0507 | 0.198 |
| D21 | 0.0512 | 0.166 |
| D22 | 0.0286 | 0.129 |
| D23 | 17.1 | 65.4 |
| D24 | 0.127 | 0.373 |
| D25 | 0.135 | 0.455 |
| D26 | 0.105 | 0.311 |
| D27 | 0.0348 | 0.141 |
| D28 | 0.155 | 0.491 |
| D29 | 0.367 | 1.05 |
| D30 | 0.472 | 1.45 |
| D31 | 0.185 | 0.628 |
| D32 | 0.00516 | 0.0112 |
| D33 | 9.34 | 22.6 |
| D34 | 0.0446 | 0.0565 |
| D35 | 0.00701 | 0.0144 |
| D36 | 0.00196 | 0.00453 |
| D37 | 0.00318 | 0.00812 |
| D38 | 0.00387 | 0.0071 |
| D39 | 0.00729 | 0.0133 |
| D40 | 0.00212 | 0.00493 |
| D41 | 0.00461 | 0.00879 |
| D42 | 0.00272 | 0.00619 |
| D43 | 0.00242 | 0.00495 |
| D44 | 0.012 | 0.0246 |
| D45 | 0.00268 | 0.00546 |
| D46 | 0.00323 | 0.00836 |
| D47 | 0.00337 | 0.0106 |
| D48 | 0.00195 | 0.00553 |

| Compound | CDK1/B $IC_{50}$ (μM) | CDK2 CyclinA $IC_{50}$ (μM) | CDK4 CyclinD1 $IC_{50}$ (μM) | CDK6 CyclinD3 $IC_{50}$ (μM) | CDK7 CyclinH $IC_{50}$ (μM) | CDK9 CyclinT1 IC50 (μM) |
|---|---|---|---|---|---|---|
| D80 | >10 | 7.59 | 0.00343 | | >10 | >10 |
| D71 | >10 | >10 | 1.96 | | >10 | >10 |
| D74 | >10 | >10 | 2.74 | | >10 | >10 |
| D138 | >10 | >10 | 0.00458 | | >10 | 0.204 |
| D144 | | 0.0292 | 0.00073 | 0.00154 | 0.229 | 0.00484 |
| D145 | | 0.0217 | 0.000784 | 0.00165 | 0.153 | 0.00502 |
| D146 | | 0.273 | 0.00419 | 0.00812 | 1.12 | 0.0248 |
| D147 | | 0.951 | 0.0732 | 0.188 | 4.26 | 0.518 |
| D148 | | 83.2 | 1.27 | 4.67 | >100 | 6.25 |
| D149 | | 0.0356 | 0.00122 | 0.00282 | 0.34 | 0.00752 |
| D150 | | 0.0529 | 0.00116 | 0.00234 | 0.402 | 0.00686 |
| D151 | | | 0.00175 | 0.0028 | | |
| D153 | | 2.44 | 0.00294 | 0.00362 | 18.4 | 0.316 |
| D154 | | 2.14 | 0.00205 | 0.00234 | 13.5 | 0.163 |
| D155 | | 3.44 | 0.00622 | 0.00858 | 14.7 | 1.18 |
| D156 | | 0.0198 | 0.00092 | 0.0023 | 0.166 | 0.00391 |
| D157 | | 0.0183 | 0.000908 | 0.00151 | 0.164 | 0.00367 |
| D158 | | 0.0222 | 0.00104 | 0.00217 | 0.12 | 0.00525 |
| D159 | | 0.035 | 0.00162 | 0.00447 | 0.318 | 0.00734 |
| D160 | | 0.0335 | 0.0012 | 0.00341 | 0.157 | 0.00641 |
| D161 | | 0.0305 | 0.00129 | 0.00388 | 0.157 | 0.00727 |
| D162 | | 0.382 | 0.00534 | 0.0104 | 3.24 | 0.0619 |
| D163 | | 0.338 | 0.00902 | 0.0106 | 2.63 | 0.0651 |
| D164 | | 0.744 | 0.00905 | 0.0137 | 3.16 | 0.0719 |
| D165 | | 0.775 | 0.0292 | 0.0585 | 7.3 | 0.236 |

TABLE 4b-continued

| Inhibition Assay Results | | | | | | |
|---|---|---|---|---|---|---|
| D166 | | 1.86 | 0.0387 | 0.0792 | 13.9 | 0.307 |
| D167 | | 2.9 | 0.069 | 0.111 | 12 | 0.418 |
| D168 | | 0.0554 | 0.0152 | 0.03 | 3.1 | 0.00652 |
| D169 | | 0.0335 | 0.00589 | 0.00937 | 2.82 | 0.00292 |
| D170 | | 8.56 | 0.0423 | 0.0531 | >100 | 0.39 |
| D171 | | 2.84 | 0.00198 | 0.00378 | 26.5 | 0.271 |
| D172 | | 0.0795 | 0.00272 | 0.0066 | 0.673 | 0.00481 |
| D173 | | 0.11 | 0.00537 | 0.0116 | 0.682 | 0.00574 |
| D174 | | 0.0609 | 0.00152 | 0.00316 | 0.505 | 0.00693 |
| D175 | | 0.0571 | 0.00156 | 0.0026 | 0.465 | 0.00362 |
| | | | (0.00083) | | | |
| D176 | | 0.0333 | 0.00112 | 0.00207 | 0.126 | 0.00273 |
| | | | (0.00064) | | | |
| D177 | | 0.05 | 0.00472 | 0.0139 | 2.94 | 0.0191 |
| D178 | | 0.127 | 0.00103 | 0.00188 | 1.13 | 0.00425 |
| D179 | | 0.0675 | 0.00127 | 0.00215 | 0.321 | 0.00185 |
| D180 | | 0.0987 | 0.00179 | 0.00435 | 0.266 | 0.00284 |
| D181 | | 5.82 | 0.0043 | 0.00679 | 40.9 | 0.818 |
| D182 | | 0.115 | <0.00056 | <0.00056 | 0.591 | 0.0162 |
| D191 | | | 0.00627 | 0.0112 | | |
| D192 | | | 0.00458 | 0.00852 | | |
| D193 | | | 0.00154 | 0.00232 | | |
| D195 | | | 0.023 | 0.0337 | | |
| D198 | | | 8.86 | 16.2 | | |
| D199 | 0.353 | 0.0746 | <0.0032 | | 0.406 | 0.00374 |
| D201 | 2.85 | 0.424 | 0.00504 | | 2.97 | 0.00785 |
| D202 | 0.295 | 0.0404 | <0.0032 | | 0.276 | >10 |
| D117 | 0.00446 | <0.0032 | <0.0032 | | 0.215 | 0.00351 |
| D135 | 0.205 | 0.0898 | <0.0032 | | 0.222 | 0.00431 |
| D130 | 1.06 | 0.242 | 0.016 | | >10 | 0.0123 |
| D114 | 0.0379 | <0.0032 | <0.0032 | | 1.67 | <0.0032 |
| D115 | 0.563 | 0.135 | 0.00576 | | >10 | 0.00903 |
| D116 | 0.232 | 0.0313 | <0.0032 | | 3.45 | <0.0032 |
| D125 | 1.16 | 1.14 | 0.0114 | | 0.557 | 0.0205 |
| D126 | 2.2 | 0.803 | 0.0227 | | >10 | 0.0254 |
| D97 | 0.222 | 0.0566 | <0.0032 | | 0.111 | <0.0032 |
| D101 | 0.167 | 0.0368 | <0.0032 | | 0.162 | <0.0032 |
| D102 | 0.464 | 0.126 | <0.0032 | | 0.642 | <0.0032 |
| D92 | 0.219 | 0.153 | 0.00556 | | 0.343 | <0.0032 |
| D183 | | 2.43 | 0.0229 | 0.0662 | 2.34 | 0.0768 |
| D184 | | 1.4 | 0.0196 | 0.0435 | 1.69 | 0.0468 |
| | | | (0.0111) | | | |
| D185 | | 1.06 | 0.0156 | 0.0312 | 1.17 | 0.0367 |
| D186 | | 1.49 | 0.0139 | 0.0387 | 2.32 | 0.0615 |
| D187 | | 1.37 | 0.0145 | 0.0336 | 1.68 | 0.0607 |
| D188 | | >100 | 10.6 | 21.7 | >100 | >100 |
| D189 | | >100 | 28.7 | 41.6 | >100 | 17.7 |
| D190 | | >100 | 11.4 | 34.2 | >100 | 21.8 |
| D194 | | | 0.0174 | 0.0312 | | |
| D148 | >10 | >10 | 0.188 | | >10 | 0.987 |
| D200 | 8.67 | 3.42 | 0.0397 | | 3.77 | 0.0726 |
| D123 | 0.022 | 0.00419 | <0.0032 | | 0.88 | 0.0193 |
| D99 | 2.91 | 1.09 | 0.0133 | | 1.24 | 0.0281 |
| D93 | 1.1 | 0.723 | 0.0333 | | 1.5 | 0.0161 |
| D196 | | | 1.25 | 2.4 | | |
| D197 | | | 2.22 | 5.38 | | |
| D198 | | | 8.86 | 16.2 | | |
| D152 | | 1.71 | 0.00118 | 0.00164 | 19 | 0.12 |
| D105 | 0.172 | 0.0545 | <0.0032 | | 0.134 | <0.0032 |

Example 7

Biological Activity of Purified Enantiomers

Enantiomers of compounds D11, D12, D10, and D3 were separated as described above and analyzed in CDK Inhibition Assays. The assays were conducted as described above for the racemates.

Figure 3:
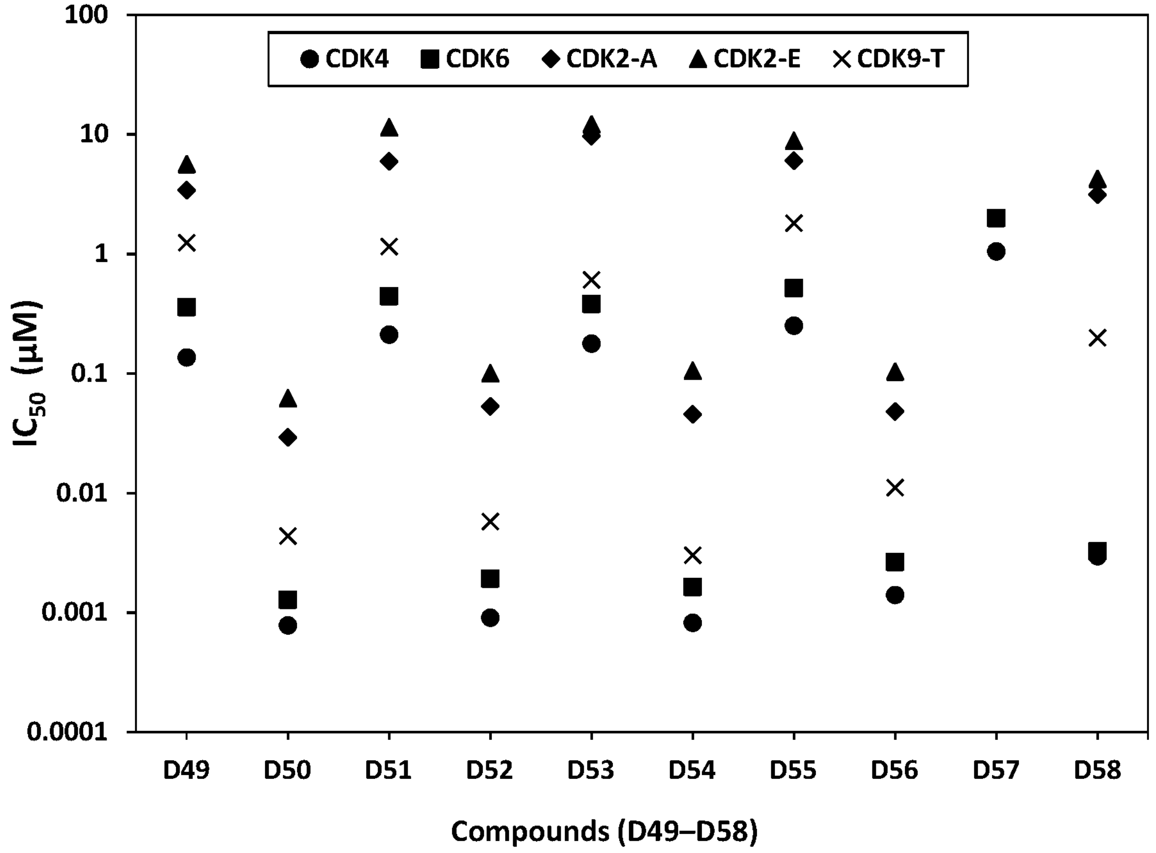
FIG. 3 shows CDK4 and CDK6 inhibition data for Compounds D49-D58. The plotted data is shown in Table 3.

Results for controls and compounds described herein are shown in the table below. The results are graphically shown in FIG. 3.

TABLE 3

Enantiomer Inhibition Assay Results

| Compound | Racemate Activity CDK4 CDK6 (nM) | CDK4 (E1/E2) (μM) | CDK6 (E1/E2) (μM) | CDK2-A (E1/E2) (μM) | CDK2-E (E1/E2) (μM) | CDK9-T (E1/E2) μM |
|---|---|---|---|---|---|---|
| Staurosporine | 31.8/29.1 | 0.0535 | 0.0619 | 0.00126 | 0.00223 | 0.00543 |
| Ribociclib | 8.05/19.9 | 0.00908 | 0.0243 | >10 | >10 | 0.487 |
| D49 (E1 of D11) | 2.1/3.5 | 0.136 | 0.36 | 3.41 | 5.66 | 1.24 |
| D50 (E2 of D11) | 2.1/3.5 | 0.00078 | 0.00129 | 0.0291 | 0.0624 | 0.00437 |
| D51 (E1 of D12 | 1.8/2.9 | 0.211 | 0.444 | 5.94 | 11.5 | 1.15 |
| D52 (E2 of D12) | 1.8/2.9 | 0.000904 | 0.00194 | 0.0531 | 0.101 | 0.00575 |
| D53 (E1 of D10) | 1.5/3.5 | 0.178 | 0.384 | 9.67 | 12.1 | 0.605 |
| D54 (E2 of D10) | 1.5/3.5 | 0.000822 | 0.00165 | 0.0456 | 0.106 | 0.00302 |
| D55 (E1 of D3) | 2.81/6.03 | 0.251 | 0.519 | 6.0 | 8.88 | 1.8 |
| D56 (E2 of D3) | 2.81/6.03 | 0.0014 | 0.00267 | 0.0482 | 0.104 | 0.0111 |
| D57 (E1) | N/A | 1.05 | 2.01 | >100 | >100 | >100 |
| D58 (E2) | N/A | 0.00296 | 0.00326 | 3.12 | 4.24 | 0.198 |

Example 8

2D Cell Proliferation Assay

Viability of the cells was analyzed by using the CellTiter-Blue® Cell Viability Assay (Promega), and was performed according to manufacturer's instructions. Briefly, cells were harvested from exponential phase cultures (Chapter 6.6), counted and plated in 96-well flat-bottom microtiter plates at a cell density of 4,000-60,000 cells/well in a volume of 140 μl per well. After a 24 hours recovery period, 10 μL cell culture medium (six control wells/plate) or culture medium with test compound were added (Chapter 6.2). The compounds were applied at five concentrations in full-log increments up to 100 μM in duplicate. Cultures were incubated at 37° C. and 5% $CO_2$ in a humidified atmosphere for another three days. After three days of treatment, 20 μl/well CellTiter-Blue® reagent was added. Following incubation with CellTiter-Blue® reagent for up to four hours, fluorescence (FU) was measured by using the Enspire Multimode Plate Reader (excitation λ=570 nm, emission λ=600 nm). For calculations, the mean values of duplicate/sextuplicate (untreated control) data were used.

Data Evaluation for Efficacy Assessment

An assay was considered fully evaluable if the following quality control criteria were fulfilled:

- control/background ratio>3.0-Z'-factor calculated within the assay plate>0.5 [7]—coefficient of variation in the growth control wells <30%

Drug effects were expressed in terms of the percentage of the fluorescence signal, obtained by comparison of the mean signal in the treated wells with the mean signal of the untreated controls (expressed by the test-versus-control value, T/C-value [%]):

$$\frac{T}{C}[\%] = \frac{\text{mean florescence } signal_{treated\ group}}{\text{mean florescence } signal_{control\ group}} \cdot 100$$

IC values are reported as relative $IC_{50}$ values and absolute $IC_{50}$ and $IC_{70}$ values. The absolute $IC_{50}$ value reflects the concentration of the test compound that achieves T/C=50%. The absolute $IC_{70}$ value gives the concentration of the test compound that achieves T/C=30%. The relative $IC_{50}$ value is the concentration of test compound that gives a response halfway between the top and bottom plateau of the sigmoidal concentration-response curve (inflection point of the curve). Calculation was done by 4parameter non-linear curve fit (Oncotest Data Warehouse Software).

If an $IC_{50}$ or $IC_{70}$ value could not be determined within the examined dose range (because a compound was either too active or lacked activity), the lowest or highest concentration studied was used for calculation of the geometric mean value.

The overall potency of a compound was determined by the geometric mean $IC_{50}/IC_{70}$ values of all individual $IC_{50}/IC_{70}$ values. In the heatmap representation of $IC_{50}$ and $IC_{70}$ values, the distribution of the $IC_{50}$ or $IC_{70}$ values obtained for a test compound in the individual cell lines is given in relation to the geometric mean $IC_{50}$ or $IC_{70}$ value, obtained over all PDX models tested. The individual IC values range from 1/32-fold geometric mean IC (corresponding to very potent compound activity or high tumor sensitivity) to 32-fold geometric mean IC (corresponding to lack of compound activity or tumor resistance). The heatmap presentation, therefore, represents an antiproliferative "fingerprint" profile of a test compound. Results are shown in Table 5.

TABLE 5

Tumor Sensitivity Results

| Cell Line | SPV414 D179 | SPV383 D146 | SPV413 D178 | SPV389 D154 |
|---|---|---|---|---|
| BXF 5637 | 0.143 | 1.49 | 34.26 | 17.57 |
| CEXF HeLa | 0.268 | 1.57 | 36.93 | 72.59 |
| CNXF U-87 MG | 100 | 10.81 | 75.49 | 100 |
| CXF Caco-2 | 100 | 23 | 100 | 100 |
| CXF COLO 205 | 0.101 | 0.577 | 6.22 | 4.76 |
| CXF HCT-15 | 1.414 | 2.054 | 29.48 | 22.07 |
| CXF HT-29 | 0.562 | 8.979 | 31.75 | 29.88 |
| GXA MKN45 | 0.112 | 3.119 | 47.34 | 47.79 |
| LEXFAL MOLT-4 | 0.177 | | | |
| LEXFAM MV4-11 | 0.01 | 0.01 | 0.01 | 0.01 |
| LEXFCL MEC-1 | 0.447 | 0.142 | 37.036 | 9.695 |
| LEXFCM K-562 | 0.355 | 4.943 | 75.735 | 84.39 |
| LIXAH HLE | 0.103 | 0.928 | 21.308 | 21.504 |
| LIXAH SNU-398 | 0.025 | 0.251 | 0.608 | 6.841 |
| LIXFH Hep G2 | 0.037 | 0.341 | 5.313 | 8.137 |
| LIXFH HEP-3B | 0.171 | 3.669 | 67.76 | 78.86 |
| LXFA A549 | 3.306 | 3.405 | 69.87 | 79.24 |
| LXFA NCl-H1975 | 0.029 | 0.356 | 16.65 | 26.32 |
| LXFE Calu-1 | 1.249 | 5.96 | 78.56 | 48.68 |
| LXFL NCl-H1299 | 0.353 | 8.903 | 30.08 | 37.33 |
| LXFL NCl-H460 | 0.274 | 2.129 | 63.37 | 35.26 |
| LYXFNH Daudi | | 0.162 | | |
| LYXFNH U-937 | 0.01 | 0.01 | 0.01 | 0.01 |
| MAXFHER BT-474 | 0.125 | 5.555 | 67.92 | 81.09 |
| MAXFHER SK-BR-3 | 0.328 | 1.016 | 31.94 | 13.8 |
| MAXFLB MCF7 (ER+) | 0.057 | 1.045 | 31.99 | 29.81 |
| MAXFLB T47D (ER+) | 0.829 | 1.633 | 46.21 | 97.39 |
| MAXFTN BT-549 | 0.252 | 2.312 | 16.63 | 19.55 |
| MAXFTN MDA-MB-231 (ER−) | 0.053 | 0.703 | 2.453 | 4.857 |
| MAXFTN MDA-MB-453 | 0.057 | 0.327 | 1.999 | 7.684 |
| MAXFTN MDA-MB-468 (ER−) | 0.681 | 0.925 | 68.19 | 72.88 |
| MAXFTN ZR-75-1 (ER+) | 0.409 | 9.025 | 88.15 | 100 |
| MEXF A2058 | 0.174 | 1.532 | 60.4 | 14.46 |
| MEXF A-375 | 0.061 | 0.263 | 0.769 | 0.254 |
| MEXF M14 | 0.268 | 1.579 | 24.59 | 21.4 |
| MEXF MDA-MB-435 | 0.102 | 0.875 | 18.27 | 15.95 |
| MEXF WM-266-4 | 0.272 | 6.22 | 74.44 | 81.27 |
| MMXF U-266 | 0.814 | 4.553 | 62.32 | 78.54 |
| OVXF SK-OV-3 | 0.772 | 8.263 | 76.74 | 59.86 |
| PAXF BxPC-3 | 0.116 | 0.756 | 12.13 | 2.869 |
| PAXF MIA-Pa-Ca-2 | 0.163 | 6.296 | 65.94 | 73.87 |
| PRXF 22Rv1 | 0.021 | 0.138 | 0.447 | 1.424 |
| PRXF DU-145 | 0.047 | 0.544 | 19.23 | 30.64 |
| PRXF LNCaP | 0.024 | 0.349 | 20.84 | 31.12 |
| PRXF VCap | 0.037 | 1.256 | 21.07 | 25.36 |
| UXF EFE-184 | 0.244 | 2.077 | 22.63 | 34.63 |
| UXF MFE-319 | 0.144 | 1.135 | 11.29 | 5.43 |
| Geomean abs. IC50 value [μM]: | 0.205 | 1.237 | 16.455 | 16.983 |

| Cell Line | SPV372 D50 | SPV411 D176 | SPV374 D52 | SPV382 D145 | SPV393 D158 | SPV376 D54 | SPV381 D144 |
|---|---|---|---|---|---|---|---|
| LEXFAL MOLT-4 | 0.101 | 0.097 | | 0.084 | | | |
| LEXFAM MV4-11 | 0.010 | 0.028 | 0.010 | 0.010 | 0.038 | 0.010 | 0.010 |
| LXFA A549 | 0.338 | 0.440 | 0.257 | 0.148 | 0.554 | 1.396 | 1.290 |
| LXFL NCl-H1299 | 0.187 | 0.229 | 0.151 | 0.108 | 0.257 | 0.212 | 0.219 |
| MAXFLB MCF7 | 0.080 | 0.062 | 0.122 | 0.088 | 0.055 | 0.188 | 0.114 |
| MAXFTN MDA-MB-231 | 0.150 | 0.172 | 0.318 | 0.300 | | | |
| MAXFTN ZR-75-1 | 23.27 | 0.648 | 0.925 | 100.0 | 5.52 | 10.32 | 100.0 |
| MEXF WM-266-4 | 0.046 | 0.548 | 0.509 | 0.047 | 0.451 | 0.331 | 0.358 |
| Geomean abs. IC50 value [μM]: | 0.173 | 0.179 | 0.184 | 0.189 | 0.301 | 0.352 | 0.475 |

Example 9

PK Data

Nonclinical pharmacokinetic (PK) parameters of lead CDK4/6/9 inhibitors were determined in an intravenous (IV) and oral study (p.o.) conducted in rats. Lead compounds were each administered as a single oral dose at 100 mg/kg or by IV bolus via the caudal vein at the dose of 30 mg/kg. Blood samples were collected at 0.25, 0.5, 1, 2, 4, 8, 12, and 24 hours post i.v. administration, and at 1, 2, 4, 8, 24 and 48 hours post oral administration. Plasma was processed for drug concentration analysis using a validated LCMS/MS method, and PK parameters were calculated by using WinNonlin. Lead compounds exhibited excellent exposure following oral administration with oral bioavailability >36% for all compounds, and two compounds >43%. The results are shown in Table 6. High exposure level and excellent bioavailability enable a once-daily oral dose regimen.

TABLE 6

PK Data SPV374, SPV382, SPV414

| | IV BOLUS 30 MG/KG N = 3 | | | ORAL ADMINISTRATION 100 MG/KG N = 3 | | | | |
|---|---|---|---|---|---|---|---|---|
| | $C_{max}$ ng/ml | Clearance L/hr/kg | $T_{1/2}$ hr | $C_{max}$ | $T_{1/2}$ hr | MRT hr | AUC ng · hr/ml | BIOAVAILABILITY F %* |
| SPV374 (D52) | 6363 | 1.16 | 4.45 | 4353 | 7.1 | 5.48 | 37657 | 43.9 |
| SPV382 (D145) | 7730 | 2.11 | 1.93 | 4470 | 5.6 | 4.37 | 21542 | 43.8 |
| SPV414 (D179) | 6200 | 2.3 | 2.26 | 3357 | 3.1 | 2.99 | 14172 | 36.3 |

Example 10

Crystal Structure of Enantiomer 2

A crystal specimen of Enantiomer 2 ($C_{21}H_{28}N_4O_4S$) with approximate dimensions 0.325 mm×0.348 mm×0.353 mm was used for the X-ray crystallographic analysis. Earlier specimens shattered when placed in the coldstream at 100 K. The temperature was then adjusted to 150 K and a new specimen mounted. The X-ray intensity data were measured on a Bruker-Nonius X8 Kappa APEX II system equipped with a fine-focus sealed tube (MoKα, λ=0.71073 Å) and a graphite monochromator.

The total exposure time was 13.35 hours. Frames were integrated with the Bruker SAINT software package using a narrow-frame algorithm. Bruker SAINT. Bruker AXS Inc., Madison, WI, USA. The integration of the data using a monoclinic unit cell yielded a total of 22808 reflections to a maximum θ angle of 30.99° (0.69 Å resolution), of which 7200 were independent (average redundancy: 3.168, completeness: 99.9%, $R_{int}$=2.75%, $R_{sig}$=3.07%) and 5759 (79.99%) were greater than 2σ($F^2$). Table 4 provides parameters for the unit cell and data collection. The unit cell dimensions of a=12.5547(8) Å, b=6.3677(4) Å, c=14.3460 (9) Å, β=100.2090(10°), volume=1128.73(12) Å$^3$, are based upon the refinement of the XYZ-centroids of 9452 reflections above 20 σ(l) with 5.726°<2θ<61.04°. Data were corrected for absorption effects using the Multi-Scan method (SADABS). Krause et al., *J. Appl. Cryst.* 48: 3-10 (2015). The ratio of minimum to maximum apparent transmission was 0.943. The calculated minimum and maximum transmission coefficients (based on crystal size) are 0.9400 and 0.9450.

TABLE 7

Crystal Data for Enantiomer 2

| | | |
|---|---|---|
| Chemical formula | $C_{21}H_{28}N_4O_4S$ | |
| Temperature | 150(2) K | |
| Wavelength | 0.71073 Å | |
| Crystal size | 0.325 × 0.348 × 0.353 mm | |
| Crystal system | monoclinic | |
| Space group | P21 | |
| Unit cell dimensions | a = 12.5547(8) Å | α = 90° |
| | b = 6.3677(4) Å | β = 100.2090(10)° |
| | c = 14.3460(9) Å | γ = 90° |
| Volume | 1128.73(12) Å$^3$ | |
| Z | 2 | |
| Density (calculated) | 1.273 g/cm$^3$ | |
| Absorption coefficient | 0.177 mm$^{-1}$ | |
| F(000) | 460 | |

The structure was solved and refined using the Bruker SHELXTL Software Package, using the space group $P2_1$, with Z=2 for the formula unit, $C_{21}H_{28}N_4O_4S$. Sheldrick, *Acta Cryst., A* 71: 3-8 (2015). The final anisotropic full-matrix least-squares refinement on $F^2$ with 321 variables converged at R1=4.64%, for the observed data and wR2=12.16% for all data. The goodness-of-fit was 1.023. The largest peak in the final difference electron density synthesis was 0.655 $e^-/Å^3$ and the largest hole was −0.501 $e^-/Å^3$ with an RMS deviation of 0.045 e/A$^3$. Based on the final model, the calculated density was 1.273 g/cm$^3$ and F(000), 460 $e^-$. Table 5 provides parameters for the molecular structure and refinement statistics.

TABLE 8

Data Collection and Structure Refinement for Enantiomer 2

| | |
|---|---|
| Diffractometer | Bruker-Nonius X8 Kappa APEX II |
| Radiation source | fine-focus sealed tube (MoKα, λ = 0.71073 Å) |
| Theta range for data collection | 1.99 to 30.99° |
| Index ranges | −18 <= h <= 17, −9 <= k <= 9, −20 <= l <= 20 |
| Reflections collected | 22808 |
| Independent reflections | 7200 [$R_{(int)}$ = 0.0275] |
| Coverage of independent reflections | 99.9% |
| Absorption correction | Multi-Scan |
| Max. and min. transmission | 0.9450 and 0.9400 |
| Structure solution technique | Direct methods |
| Structure solution program | SHELXT 2014/5 (Sheldrick, 2014) |
| Refinement method | Full-matrix least-squares on $F^2$ |

TABLE 8-continued

| Data Collection and Structure Refinement for Enantiomer 2 | | |
|---|---|---|
| Refinement program | SHELXL-2017/1 (Sheldrick, 2017) | |
| Function minimized | $\Sigma$ w($Fo^2$ − $Fc^2$)$^2$ | |
| Data/restraints/parameters | 7200/72/321 | |
| Goodness-of-fit on $F^2$ | 1.023 | |
| Final R indices | 5759 data; I > 2σ(I) | R1 = 0.0464, $wR^2$ = 0.1100 |
| | all data | R1 = 0.0637, $wR^2$ = 0.1216 |
| Weighting scheme | w = $1/[\sigma^2(Fo^2) + (0.0552P)^2 + 0.3233P]$ where P = $(Fo^2 + 2Fc^2)/3$ | |
| Absolute structure parameter | −0.02(2) | |
| Largest diff. peak and hole | 0.655 and −0.501 eÅ$^{-3}$ | |
| R.M.S. deviation from mean | 0.045 eÅ$^{-3}$ | |

Figure 4:
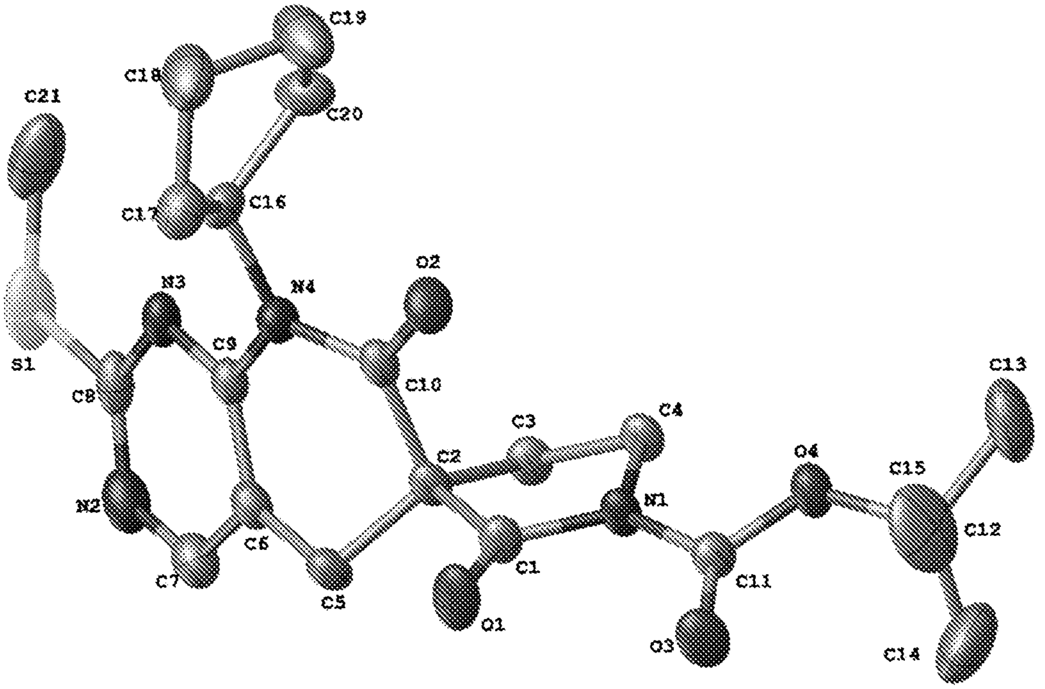
FIG. 4A: Thermal ellipsoid plot (50% probability) for Enantiomer 2 prepared using OLEX2. Dolomanov et al., *J. Appl. Cryst.* 42: 339-341 (2009). Only the major conformation of the cylcopentyl ring is shown. H atoms are excluded for clarity.
FIG. 4B: Close-up view of thermal ellipsoid plot (25% probability, H atoms hidden for clarity) of disordered cyclopentyl ring of Enantiomer 2. The major conformation (0.53) is in dark color, while the minor conformer (0.47) is highlighted in green.
Figure 4:
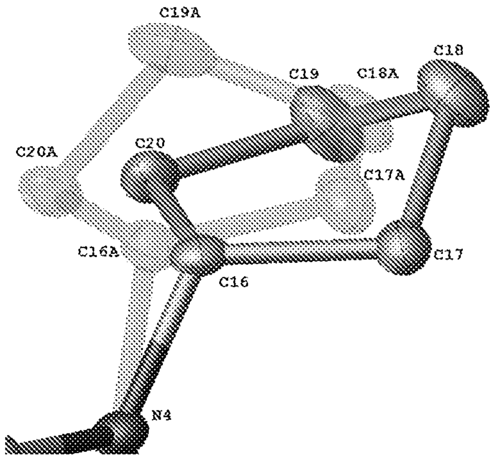
Figure 5:
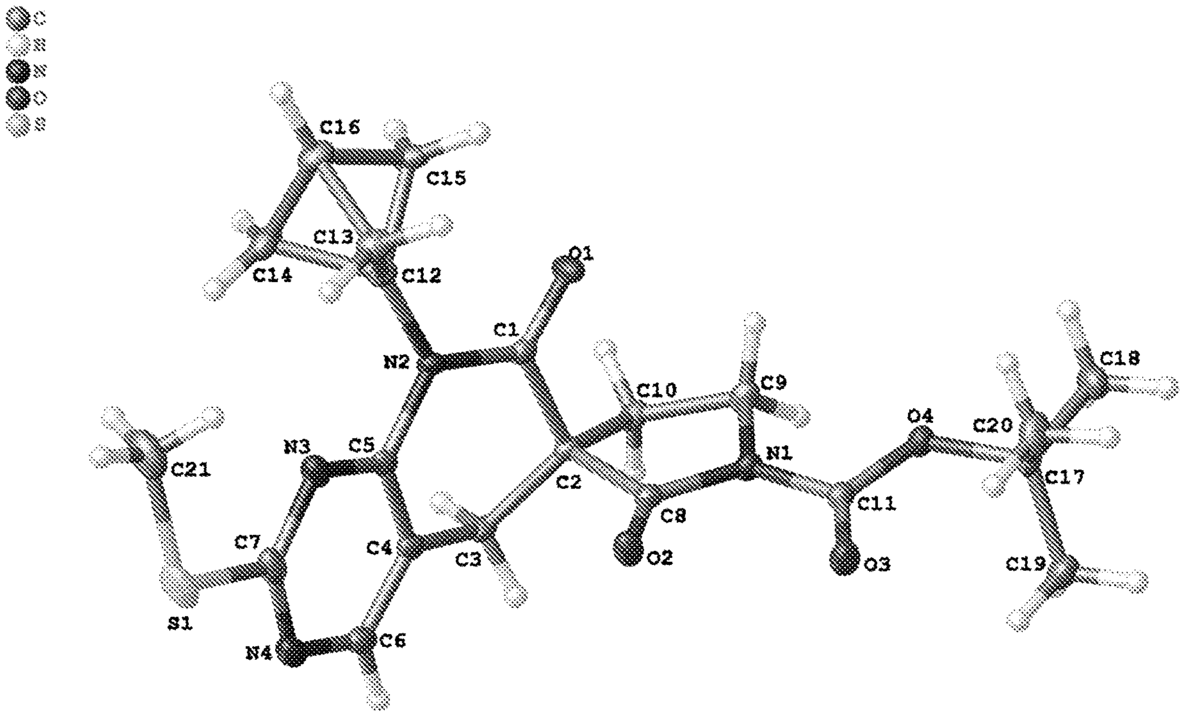
FIG. 5: shows a thermal ellipsoid plot[1] of VP-7-192E2. ([1] Dolomanov, O. V.; Bourhis, L. J; Gildea, R. J.; Howard, J. A. K; Puschman, H., OLEX2: A complete structure solution, refinement and analysis program (2009). J. Appl. Cryst., 42, 339-341).

The absolute stereochemistry of the structure, (R at C2) was determined based on anomalous dispersion in the diffraction data, based on methods by Flack and Parsons and confirms the specimen was enantiomerically pure. Parsons et al., *Acta Cryst*. B69: 249-259 (2013); Parsons et al., *Acta Cryst. A* 68: 736-749 (2012). The structure is shown below and the thermal ellipsoid plot is shown in FIG. 4A. Atomic coordinates and isotropic displacement parameters are shown in Table 6.

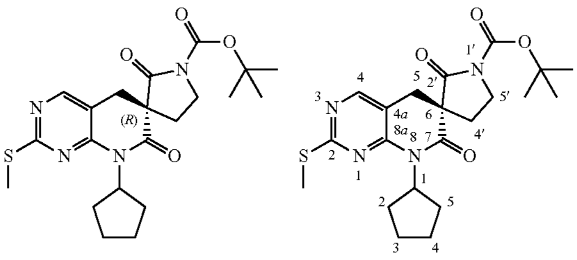

tert-butyl (R)-8-cyclopentyl-2-(methylthio)-2′,7-dioxo-7,8-dihydro-5H-spiro[pyrido[2,3-d]pyrimidine-6,3′-pyrrolidine]-1′-carboxylate Refinement of the structure revealed positional disorder in the cyclopentyl ring of the compound, evident as residual electron density, and misshapen thermal ellipsoids in that region of the structure. Modeling of the disorder revealed two conformations of the C5 ring, with nearly equal populations (0.53, 0.47), as shown in FIG. 4B. Model restraints (SAME, SADI, RIGU from SHELXTL) were employed to maintain a chemically reasonable and consistent structure for the two conformations of the ring.

TABLE 9

Atomic Coordinates and Equivalent Isotropic Displacement Parameters (Å$^2$) for Enantiomer 2.

| Atom | x/a | y/b | z/c | U(eq) |
|---|---|---|---|---|
| S1 | 0.16382(8) | 0.98406(12) | 0.58908(7) | 0.0603(3) |
| O1 | 0.38237(17) | 0.0392(3) | 0.30013(17) | 0.0458(5) |
| O2 | 0.25515(15) | 0.6225(3) | 0.19486(12) | 0.0382(4) |
| O3 | 0.55493(17) | 0.1250(3) | 0.20497(14) | 0.0409(5) |
| O4 | 0.59554(15) | 0.8310(3) | 0.13061(13) | 0.0354(4) |
| N1 | 0.49238(17) | 0.8020(3) | 0.23983(14) | 0.0261(4) |
| N2 | 0.2856(2) | 0.3146(4) | 0.60744(16) | 0.0397(5) |
| N3 | 0.18891(18) | 0.2502(3) | 0.45108(16) | 0.0323(5) |
| N4 | 0.20675(16) | 0.4711(3) | 0.32424(14) | 0.0301(4) |

TABLE 9-continued

Atomic Coordinates and Equivalent Isotropic Displacement Parameters (Å$^2$) for Enantiomer 2.

| Atom | x/a | y/b | z/c | U(eq) |
|---|---|---|---|---|
| C1 | 0.4156(2) | 0.8644(4) | 0.29170(18) | 0.0291(5) |
| C2 | 0.3798(2) | 0.6688(3) | 0.34022(17) | 0.0270(5) |
| C3 | 0.4714(2) | 0.5115(3) | 0.33466(17) | 0.0284(5) |
| C4 | 0.5120(2) | 0.5733(3) | 0.24460(18) | 0.0279(5) |
| C5 | 0.3621(2) | 0.7234(4) | 0.43988(18) | 0.0336(5) |
| C6 | 0.3119(2) | 0.5384(4) | 0.47962(17) | 0.0301(5) |
| C7 | 0.3317(2) | 0.4819(5) | 0.57355(18) | 0.0364(5) |
| C8 | 0.2177(2) | 0.2079(4) | 0.5431(2) | 0.0351(6) |
| C9 | 0.23662(19) | 0.4165(4) | 0.41997(17) | 0.0268(4) |
| C10 | 0.2751(2) | 0.5898(4) | 0.27916(17) | 0.0280(5) |
| C11 | 0.5495(2) | 0.9402(4) | 0.19132(16) | 0.0271(5) |
| C12 | 0.6739(3) | 0.9301(5) | 0.0782(2) | 0.0504(8) |
| C13 | 0.6954(4) | 0.7540(8) | 0.0132(3) | 0.0797(14) |
| C14 | 0.7713(3) | 0.9908(10) | 0.1489(3) | 0.0853(15) |
| C15 | 0.6222(4) | 0.1117(7) | 0.0192(3) | 0.0773(13) |
| C21 | 0.0840(3) | 0.8727(6) | 0.4889(4) | 0.0737(13) |
| C16 | 0.1013(8) | 0.4042(15) | 0.2663(6) | 0.0311(18) |
| C17 | 0.0277(5) | 0.5844(12) | 0.2239(5) | 0.0388(13) |
| C18 | 0.9589(5) | 0.4832(13) | 0.1364(4) | 0.0541(18) |
| C19 | 0.0419(16) | 0.348(3) | 0.0999(9) | 0.057(4) |
| C20 | 0.1117(6) | 0.2514(10) | 0.1847(4) | 0.0399(14) |
| C16A | 0.1172(11) | 0.3458(19) | 0.2682(8) | 0.038(3) |
| C17A | 0.0354(6) | 0.4810(18) | 0.2031(6) | 0.055(2) |
| C18A | 0.0239(18) | 0.380(3) | 0.1049(11) | 0.064(4) |
| C19A | 0.0579(6) | 0.1565(16) | 0.1268(6) | 0.064(3) |
| C20A | 0.1526(6) | 0.1709(13) | 0.2075(6) | 0.0451(18) |

U(eq) is defined as one third of the trace of the orthogonalized $U_{ij}$ tensor.

Example 11 (VP-7-192E2, Compound D203)

Crystal Structure of VP-7-192E2

A colorless plate-like specimen of $C_{21}H_{26}N_4O_4S$, approximate dimensions 0.033 mm×0.124 mm×0.228 mm, was used for the X-ray crystallographic analysis. The X-ray intensity data were measured on a Bruker D8 VENTURE system equipped with a Incoatec IμS 3.0 microfocus sealed tube (Cu Kα, λ=1.54178 Å) and a multilayer mirror monochromator.

The total exposure time was 1.51 hours. The frames were integrated with the Bruker SAINT software package using a narrow-frame algorithm. The integration of the data using an orthorhombic unit cell yielded a total of 18528 reflections to a maximum θ angle of 77.31° (0.79 Å resolution), of which 4377 were independent (average redundancy 4.233, completeness=99.3%, $R_{int}$=3.51%, $R_{sig}$=3.43%) and 4296 (98.15%) were greater than 2σ($F_2$). The final cell constants of a=9.5061(2) Å, b=10.7343(2) Å, c=20.5677(3) Å, volume=2098.76(7) Å$^3$, are based upon the refinement of the XYZ-centroids of 1384 reflections above 20 σ(I) with 8.599°<2θ<101.0°. Data were corrected for absorption effects using the Multi-Scan method (SADABS). The ratio of minimum to maximum apparent transmission was 0.772. The calculated minimum and maximum transmission coefficients (based on crystal size) are 0.7010 and 0.9470.

The structure was solved and refined using the Bruker SHELXTL Software Package, using the space group P212121 with Z=4 for the formula unit, $C_{21}H_{26}N_4O_4S$. The final anisotropic full-matrix least-squares refinement on F2 with 276 variables converged at R1=2.60%, for the observed data and wR2=6.87% for all data. The goodness-of-fit was 1.058. The largest peak in the final difference electron density synthesis was 0.276 e−/Å$^3$ and the largest hole was −0.178 e−/Å$^3$ with an RMS deviation of 0.039 e−/Å$^3$. On the basis of the final model, the calculated density was 1.363 g/cm$^3$ and F(000), 912 e$^-$.

TABLE 10

| Crystal Data for VP-7-192E2 | | |
|---|---|---|
| Chemical formula | $C_{21}H_{26}N_4O_4S$ | |
| Formula weight | 130.52 g/mol | |
| Temperature | 100(2) K | |
| Wavelength | 1.54178 Å | |
| Crystal size | 0.033 × 0.124 × 0.228 mm | |
| Crystal habit | Colorless plate | |
| Crystal system | orthorhombic | |
| Space group | $F2_12_12_1$ | |
| Unit cell dimensions | a = 9.5061(2) Å | α = 90° |
| | b = 10.7343(2) Å | β = 90° |
| | c = 20.5677(3) Å | γ = 90° |
| Volume | 2098.76(7) $Å^3$ | |
| Z | 4 | |
| Density (calculated) | 1.363 $g/cm^3$ | |
| Absorption coefficient | 1.674 $mm^{-1}$ | |
| F(000) | 912 | |

TABLE 11

| Data Collection and Structure Refinement for VP-7-192E2 | | |
|---|---|---|
| Diffractometer | Bruker D8 VENTURE | |
| Radiation source | Incoatec IμS 3.0 microfocus sealed tube (Cu Kα, λ = 1.54178 Å) | |
| Theta range for data collection | 4.30 to 77.31° | |
| Index ranges | −8 <= h <= 12, −13 <= k <= 12, −25 <= l <= 26 | |
| Reflections collected | 18528 | |
| Independent reflections | 4377 [R(int) = 0.0351] | |
| Coverage of independent reflections | 99.3% | |
| Absorption correction | Multi-Scan | |
| Max. and min. transmission | 0.9470 and 0.7010 | |
| Structure solution technique | Direct methods | |
| Structure solution program | SHELXT 2014/5 (Sheldrick, 2014) | |
| Refinement method | Full-matrix least-squares on $F^2$ | |
| Refinement program | SHELXL-2018/3 (Sheldrick, 2018) | |
| Function minimized | $\Sigma\ w(Fo^2 - Fc^2)^2$ | |
| Data/restraints/ parameters | 4377/0/276 | |
| Goodness-of-fit on $F^2$ | 1.058 | |
| Δ/σmax | 0.001 | |
| Final R indices | 4296 data; I > 2σ(I) | R1 = 0.0260, $wR^2$ = 0.0684 |
| | all data | R1 = 0.0264, $wR^2$ = 0.0687 |
| Weighting scheme | $w = 1/[\sigma^2(Fo^2) + (0.0395P)^2 + 0.2263P]$ where $P = (Fo^2 + 2Fc^2)/3$ | |
| Absolute structure parameter | 0.028 (16) | |
| Largest diff. peak and hole | 0.276 and −0.178 $eÅ^{-3}$ | |
| R.M.S. deviation from mean | 0.039 $eÅ^{-3}$ | |

The absolute stereochemistry of the structure (R at C2) was determined based on anomalous dispersion in the diffraction data, using methods by Flack and Parsons.[2] The value of this parameter refined to approximately 2.8% (Flack X=0.028(16) using TWIN/BASF refinement), suggesting that a minor component of S enantiomer is present in the specimen.

[2] Parson et al., Acta Cryst. B69: 249-259 (2013); Parsons et al., Acta Cryst. A 68: 736-749 (2012)

TABLE 12

Atomic Coordinates and Equivalent Isotropic Displacement Parameters ($Å^2$) for VP-7-192E2.

| Atom | x/a | y/b | z/c | U(eq) |
|---|---|---|---|---|
| S1 | 0.89771(6) | 0.24731(5) | 0.95514(2) | 0.03042(13) |
| O1 | 0.63588(12) | 0.55546(12) | 0.66516(6) | 0.0187(3) |
| O2 | 0.52567(14) | 0.22006(11) | 0.71192(6) | 0.0208(3) |
| O3 | 0.42421(14) | 0.11730(11) | 0.59832(6) | 0.0206(3) |
| O4 | 0.34910(11) | 0.26606(10) | 0.52796(5) | 0.0156(2) |
| N1 | 0.40483(14) | 0.32216(12) | 0.62914(6) | 0.0143(2) |
| N2 | 0.70596(13) | 0.48342(12) | 0.76413(6) | 0.0128(3) |
| N3 | 0.78923(15) | 0.37114(13) | 0.85317(7) | 0.0176(3) |
| N4 | 0.63354(18) | 0.25970(15) | 0.92398(7) | 0.0250(3) |
| C1 | 0.60810(16) | 0.49952(14) | 0.71468(7) | 0.0127(3) |
| C2 | 0.46205(16) | 0.43934(15) | 0.72324(7) | 0.0133(3) |
| C3 | 0.42143(17) | 0.42591(15) | 0.79487(7) | 0.0162(3) |
| C4 | 0.54003(18) | 0.37420(15) | 0.83364(8) | 0.0166(3) |
| C5 | 0.67841(17) | 0.40769(14) | 0.81859(7) | 0.0139(3) |
| C6 | 0.5249(2) | 0.29769(17) | 0.88721(8) | 0.0220(3) |
| C7 | 0.7594(2) | 0.29974(17) | 0.90480(8) | 0.0214(3) |
| C8 | 0.47067(15) | 0.31137(15) | 0.68941(7) | 0.0137(3) |
| C9 | 0.35565(16) | 0.45036(15) | 0.61531(8) | 0.0162(3) |
| C10 | 0.35218(16) | 0.50969(16) | 0.68295(8) | 0.0160(3) |
| C11 | 0.39526(17) | 0.22291(14) | 0.58511(7) | 0.0142(3) |
| C12 | 0.84157(16) | 0.54574(14) | 0.76009(8) | 0.0137(3) |
| C13 | 0.98890(17) | 0.48687(16) | 0.74871(9) | 0.0193(3) |
| C14 | 0.90831(18) | 0.62668(17) | 0.81424(8) | 0.0211(3) |
| C15 | 0.88398(17) | 0.64813(16) | 0.71098(9) | 0.0202(3) |
| C16 | 0.01321(16) | 0.63004(16) | 0.75639(9) | 0.0196(3) |
| C17 | 0.32569(17) | 0.17762(16) | 0.47300(8) | 0.0178(3) |
| C18 | 0.27929(19) | 0.26463(19) | 0.41891(8) | 0.0243(4) |
| C19 | 0.2096(2) | 0.08589(18) | 0.49061(9) | 0.0239(4) |
| C20 | 0.4627(2) | 0.11234(19) | 0.45543(9) | 0.0264(4) |
| C21 | 0.0428(2) | 0.3429(2) | 0.92975(9) | 0.0318(4) |

U(eq) is defined as one third of the trace of the orthogonalized $U_{ij}$ tensor.

TABLE 13

| Bond lengths (Å) for VP-7-192E2 | | | |
|---|---|---|---|
| S1—C7 | 1.7653(19) | S1—C21 | 1.797(2) |
| O1—C1 | 1.2114(19) | O2—C8 | 1.203(2) |
| O3—C11 | 1.198(2) | O4—C11 | 1.3375(19) |
| O4—C17 | 1.4928(18) | N1—C8 | 1.3935(19) |
| N1—C11 | 1.4014(19) | N1—C9 | 1.481(2) |
| N2—C1 | 1.389(2) | N2—C5 | 1.4086(19) |
| N2—C12 | 1.4547(19) | N3—C5 | 1.330(2) |
| N3—C7 | 1.340(2) | N4—C7 | 1.331(3) |
| N4—C6 | 1.343(3) | C1—C2 | 1.541(2) |
| C2—C3 | 1.530(2) | C2—C10 | 1.532(2) |
| C2—C8 | 1.542(2) | C3—C4 | 1.488(2) |
| C3—H3A | 0.99 | C3—H3B | 0.99 |
| C4—C6 | 1.382(2) | C4—C5 | 1.398(2) |
| C6—H6 | 0.95 | C9—C10 | 1.530(2) |
| C9—H9A | 0.99 | C9—H9B | 0.99 |
| C10—H10A | 0.99 | C10—H10B | 0.99 |
| C12—C15 | 1.546(2) | C12—C14 | 1.548(2) |
| C12—C13 | 1.554(2) | C13—C16 | 1.562(2) |
| C13—H13A | 0.99 | C13—H13B | 0.99 |
| C14—C16 | 1.553(2) | C14—H14A | 0.99 |
| C14—H14B | 0.99 | C15—C16 | 1.555(2) |
| C15—H15A | 0.99 | C15—H15B | 0.99 |
| C16—H16 | 1.0 | C17—C18 | 1.518(2) |
| C17—C20 | 1.522(2) | C17—C19 | 1.523(2) |
| C18—H18A | 0.98 | C18—H18B | 0.98 |
| C18—H18C | 0.98 | C19—H19A | 0.98 |
| C19—H19B | 0.98 | C19—H19C | 0.98 |
| C20—H20A | 0.98 | C20—H20B | 0.98 |
| C20—H20C | 0.98 | C21—H21A | 0.98 |
| C21—H21B | 0.98 | C21—H21C | 0.98 |

TABLE 14

| Bond angles (°) for VP-7-192E2 | | | |
|---|---|---|---|
| C7—S1—C21 | 102.66(9) | C11—O4—C17 | 119.61(12) |
| C8—N1—C11 | 122.74(13) | C8—N1—C9 | 112.95(12) |
| C11—N1—C9 | 124.18(13) | C1—N2—C5 | 121.97(13) |
| C1—N2—C12 | 119.64(12) | C5—N2—C12 | 118.40(12) |
| C5—N3—C7 | 115.16(15) | C7—N4—C6 | 115.23(15) |
| O1—C1—N2 | 122.08(14) | O1—C1—C2 | 120.01(13) |
| N2—C1—C2 | 117.87(12) | C3—C2—C10 | 113.28(13) |
| C3—C2—C1 | 112.13(12) | C10—C2—C1 | 110.22(12) |
| C3—C2—C8 | 111.35(13) | C10—C2—C8 | 103.37(12) |
| C1—C2—C8 | 105.90(12) | C4—C3—C2 | 111.09(13) |
| C4—C3—H3A | 109.4 | C2—C3—H3A | 109.4 |
| C4—C3—H3B | 109.4 | C2—C3—H3B | 109.4 |
| H3A—C3—H3B | 108.0 | C6—C4—C5 | 115.28(16) |
| C6—C4—C3 | 124.76(16) | C5—C4—C3 | 119.88(14) |
| N3—C5—C4 | 123.42(14) | N3—C5—N2 | 116.62(14) |
| C4—C5—N2 | 119.96(14) | N4—C6—C4 | 123.33(17) |
| N4—C6—H6 | 118.3 | C4—C6—H6 | 118.3 |
| N4—C7—N3 | 127.54(16) | N4—C7—S1 | 113.12(13) |
| N3—C7—S1 | 119.33(14) | O2—C8—N1 | 127.23(15) |
| O2—C8—C2 | 125.11(14) | N1—C8—C2 | 107.66(13) |
| N1—C9—C10 | 102.64(13) | N1—C9—H9A | 111.2 |
| C10—C9—H9A | 111.2 | N1—C9—H9B | 111.2 |
| C10—C9—H9B | 111.2 | H9A—C9—H9B | 109.2 |
| C9—C10—C2 | 105.78(12) | C9—C10—H10A | 110.6 |
| C2—C10—H10A | 110.6 | C9—C10—H10B | 110.6 |
| C2—C10—H10B | 110.6 | H10A—C10—H10B | 108.7 |
| O3—C11—O4 | 127.05(14) | O3—C11—N1 | 123.92(14) |
| O4—C11—N1 | 109.02(13) | N2—C12—C15 | 126.53(13) |
| N2—C12—C14 | 125.45(13) | C15—C12—C14 | 87.95(12) |
| N2—C12—C13 | 128.33(13) | C15—C12—C13 | 87.46(12) |
| C14—C12—C13 | 88.12(12) | C12—C13—C16 | 73.62(11) |
| C12—C13—H13A | 116.2 | C16—C13—H13A | 116.2 |
| C12—C13—H13B | 116.2 | C16—C13—H13B | 116.2 |
| H13A—C13—H13B | 113.2 | C12—C14—C16 | 74.04(11) |
| C12—C14—H14A | 116.1 | C16—C14—H14A | 116.1 |
| C12—C14—H14B | 116.1 | C16—C14—H14B | 116.1 |
| H14A—C14—H14B | 113.1 | C12—C15—C16 | 74.03(11) |

TABLE 15

| Bond angles (°) for VP-7-192E2 | | | |
|---|---|---|---|
| C12—C15—H15A | 116.1 | C16—C15—H15A | 116.1 |
| C12—C15—H15B | 116.1 | C16—C15—H15B | 116.1 |
| H15A—C15—H15B | 113.1 | C14—C16—C15 | 87.47(12) |
| C14—C16—C13 | 87.69(12) | C15—C16—C13 | 86.86(12) |
| C14—C16—H16 | 127.1 | C15—C16—H16 | 127.1 |
| C13—C16—H16 | 127.1 | O4—C17—C18 | 101.94(13) |
| O4—C17—C20 | 110.18(13) | C18—C17—C20 | 110.97(14) |
| O4—C17—C19 | 109.83(13) | C18—C17—C19 | 111.20(14) |
| C20—C17—C19 | 112.25(15) | C17—C18—H18A | 109.5 |
| C17—C18—H18B | 109.5 | H18A—C18—H18B | 109.5 |
| C17—C18—H18C | 109.5 | H18A—C18—H18C | 109.5 |
| H18B—C18—H18C | 109.5 | C17—C19—H19A | 109.5 |
| C17—C19—H19B | 109.5 | H19A—C19—H19B | 109.5 |
| C17—C19—H19C | 109.5 | H19A—C19—H19C | 109.5 |
| H19B—C19—H19C | 109.5 | C17—C20—H20A | 109.5 |
| C17—C20—H20B | 109.5 | H20A—C20—H20B | 109.5 |
| C17—C20—H20C | 109.5 | H20A—C20—H20C | 109.5 |
| H20B—C20—H20C | 109.5 | S1—C21—H21A | 109.5 |
| S1—C21—H21B | 109.5 | H21A—C21—H21B | 109.5 |
| S1—C21—H21C | 109.5 | H21A—C21—H21C | 109.5 |
| H21B—C21—H21C | 109.5 | | |

TABLE 16

| Torsion angles (°) for VP-7-192E2 | | | |
|---|---|---|---|
| C5—N2—C1—O1 | −173.32(14) | C12—N2—C1—O1 | 6.5(2) |
| C5—N2—C1—C2 | 4.4(2) | C12—N2—C1—C2 | −175.77(13) |
| O1—C1—C2—C3 | −154.32(15) | N2—C1—C2—C3 | 27.87(19) |
| O1—C1—C2—C10 | −27.13(19) | N2—C1—C2—C10 | 155.07(13) |
| O1—C1—C2—C8 | 84.04(17) | N2—C1—C2—C8 | −93.76(15) |
| C10—C2—C3—C4 | −171.53(13) | C1—C2—C3—C4 | −46.00(18) |
| C8—C2—C3—C4 | 72.47(16) | C2—C3—C4—C6 | −147.30(15) |
| C2—C3—C4—C5 | 36.0(2) | C7—N3—C5—C4 | −0.6(2) |
| C7—N3—C5—N2 | 179.70(14) | C6—C4—C5—N3 | −0.9(2) |
| C3—C4—C5—N3 | 176.03(14) | C6—C4—C5—N2 | 178.73(14) |
| C3—C4—C5—N2 | −4.3(2) | C1—N2—C5—N3 | 162.00(14) |
| C12—N2—C5—N3 | −17.79(19) | C1—N2—C5—C4 | −17.7(2) |
| C12—N2—C5—C4 | 162.53(14) | C7—N4—C6—C4 | −0.8(2) |
| C5—C4—C6—N4 | 1.7(2) | C3—C4—C6—N4 | −175.08(16) |
| C6—N4—C7—N3 | −1.0(3) | C6—N4—C7—S1 | 179.77(12) |
| C5—N3—C7—N4 | 1.7(3) | C5—N3—C7—S1 | −179.10(12) |
| C21—S1—C7—N4 | −167.05(13) | C21—S1—C7—N3 | 13.65(17) |
| C11—N1—C8—O2 | −0.5(2) | C9—N1—C8—O2 | −176.61(16) |
| C11—N1—C8—C2 | 179.15(13) | C9—N1—C8—C2 | 3.03(16) |
| C3—C2—C8—O2 | −44.1(2) | C10—C2—C8—O2 | −166.09(15) |
| C1—C2—C8—O2 | 78.00(19) | C3—C2—C8—N1 | 136.22(13) |
| C10—C2—C8—N1 | 14.27(15) | C1—C2—C8—N1 | −101.64(13) |
| C8—N1—C9—C10 | −18.97(16) | C11—N1—C9—C10 | 164.96(13) |
| N1—C9—C10—C2 | 27.02(15) | C3—C2—C10—C9 | −146.16(13) |
| C1—C2—C10—C9 | 87.28(14) | C8—C2—C10—C9 | −25.53(15) |
| C17—O4—C11—O3 | 1.5(2) | C17—O4—C11—N1 | −178.21(12) |
| C8—N1—C11—O3 | 10.8(2) | C9—N1—C11—O3 | −173.49(15) |
| C8—N1—C11—O4 | −169.43(13) | C9—N1—C11—O4 | 6.3(2) |
| C1—N2—C12—C15 | 10.7(2) | C5—N2—C12—C15 | −169.53(15) |
| C1—N2—C12—C14 | 128.87(17) | C5—N2—C12—C14 | −51.3(2) |
| C1—N2—C12—C13 | −110.36(18) | C5—N2—C12—C13 | 69.4(2) |
| N2—C12—C13—C16 | −179.13(17) | C15—C12—C13—C16 | 44.44(12) |
| C14—C12—C13—C16 | −43.59(12) | N2—C12—C14—C16 | −178.61(16) |
| C15—C12—C14—C16 | −43.73(11) | C13—C12—C14—C16 | 43.80(12) |
| N2—C12—C15—C16 | 177.72(16) | C14—C12—C15—C16 | 43.64(11) |
| C13—C12—C15—C16 | −44.57(11) | C12—C14—C16—C15 | 43.43(11) |
| C12—C14—C16—C13 | −43.53(11) | C12—C15—C16—C14 | −43.51(11) |
| C12—C15—C16—C13 | 44.31(11) | C12—C13—C16—C14 | 43.45(11) |
| C12—C13—C16—C15 | −44.14(11) | C11—O4—C17—C18 | −178.36(13) |
| C11—O4—C17—C20 | −60.50(18) | C11—O4—C17—C19 | 63.66(18) |

TABLE 17

Anisotropic atomic displacement parameters (Å2) for VP-7-192E2.

| Atom | $U_{11}$ | $U_{22}$ | $U_{33}$ | $U_{23}$ | $U_{13}$ | $U_{12}$ |
|---|---|---|---|---|---|---|
| S1 | 0.0432(3) | 0.0297(3) | 0.01842(19) | 0.00726(17) | −0.00519(17) | 0.0090(2) |
| O1 | 0.0155(5) | 0.0234(6) | 0.0172(5) | 0.0057(4) | −0.0007(4) | −0.0039(4) |
| O2 | 0.0326(6) | 0.0129(6) | 0.0168(5) | −0.0004(4) | −0.0042(5) | 0.0018(5) |
| O3 | 0.0306(6) | 0.0122(6) | 0.0191(5) | −0.0011(4) | −0.0046(5) | −0.0001(5) |
| O4 | 0.0176(5) | 0.0136(5) | 0.0155(5) | −0.0020(4) | −0.0025(4) | −0.0005(4) |
| N1 | 0.0152(5) | 0.0114(6) | 0.0163(6) | −0.0012(5) | −0.0010(5) | 0.0000(5) |
| N2 | 0.0134(6) | 0.0104(6) | 0.0145(6) | 0.0013(5) | 0.0012(5) | −0.0015(5) |
| N3 | 0.0248(7) | 0.0137(7) | 0.0143(6) | −0.0002(5) | −0.0010(5) | 0.0022(5) |
| N4 | 0.0411(9) | 0.0189(7) | 0.0151(6) | 0.0019(6) | −0.0004(6) | −0.0078(6) |
| C1 | 0.0126(7) | 0.0098(7) | 0.0155(6) | −0.0012(5) | 0.0009(5) | −0.0003(6) |
| C2 | 0.0127(7) | 0.0117(7) | 0.0154(7) | −0.0010(5) | 0.0019(5) | −0.0024(5) |
| C3 | 0.0154(7) | 0.0177(8) | 0.0155(7) | −0.0038(6) | 0.0047(6) | −0.0063(6) |
| C4 | 0.0235(7) | 0.0123(8) | 0.0141(7) | −0.0033(6) | 0.0030(6) | −0.0046(6) |
| C5 | 0.0209(7) | 0.0076(7) | 0.0133(6) | −0.0021(5) | 0.0012(6) | −0.0011(6) |
| C6 | 0.0323(9) | 0.0179(8) | 0.0157(7) | −0.0030(6) | 0.0045(6) | −0.0096(7) |
| C7 | 0.0344(9) | 0.0157(8) | 0.0140(7) | −0.0017(6) | −0.0018(6) | 0.0023(7) |
| C8 | 0.0141(7) | 0.0129(7) | 0.0142(6) | −0.0009(6) | 0.0021(5) | −0.0025(6) |
| C9 | 0.0156(7) | 0.0119(7) | 0.0211(7) | −0.0010(6) | −0.0032(6) | 0.0021(5) |
| C10 | 0.0115(6) | 0.0154(7) | 0.0211(7) | −0.0025(6) | −0.0003(5) | −0.0005(6) |
| C11 | 0.0146(6) | 0.0131(7) | 0.0148(6) | −0.0018(5) | 0.0010(5) | −0.0016(5) |
| C12 | 0.0120(6) | 0.0119(7) | 0.0173(7) | 0.0008(5) | −0.0002(5) | −0.0003(6) |
| C13 | 0.0132(7) | 0.0189(8) | 0.0259(7) | −0.0005(6) | 0.0019(6) | 0.0019(6) |
| C14 | 0.0166(7) | 0.0213(8) | 0.0253(8) | −0.0071(6) | 0.0009(7) | −0.0042(6) |
| C15 | 0.0146(7) | 0.0174(8) | 0.0286(8) | 0.0067(6) | 0.0004(6) | −0.0034(6) |
| C16 | 0.0124(7) | 0.0186(8) | 0.0276(8) | −0.0010(7) | 0.0009(6) | −0.0017(6) |
| C17 | 0.0190(7) | 0.0194(8) | 0.0151(7) | −0.0056(6) | −0.0028(6) | −0.0026(6) |
| C18 | 0.0243(8) | 0.0306(10) | 0.0181(7) | 0.0033(7) | −0.0039(6) | −0.0051(7) |

TABLE 17-continued

| Anisotropic atomic displacement parameters (Å2) for VP-7-192E2. | | | | | | |
|---|---|---|---|---|---|---|
| Atom | $U_{11}$ | $U_{22}$ | $U_{33}$ | $U_{23}$ | $U_{13}$ | $U_{12}$ |
| C19 | 0.0266(8) | 0.0207(9) | 0.0244(8) | −0.0011(7) | −0.0049(7) | −0.0071(7) |
| C20 | 0.0257(8) | 0.0312(10) | 0.0224(8) | −0.0097(7) | −0.0011(7) | 0.0050(7) |
| C21 | 0.0328(10) | 0.0419(12) | 0.0209(8) | 0.0018(8) | −0.0046(7) | 0.0119(8) |

TABLE 18

| Hydrogen atomic coordinates and isotropic atomic displacement parameters (Å2) for VP-7-192E2. | | | | |
|---|---|---|---|---|
| Atom | x/a | y/b | z/c | U(eq) |
| H3A | 0.3947 | 0.5084 | 0.8125 | 0.019 |
| H3B | 0.3389 | 0.3701 | 0.7986 | 0.019 |
| H6 | 0.4331 | 0.2706 | 0.8986 | 0.026 |
| H9A | 0.2610 | 0.4499 | 0.5952 | 0.019 |
| H9B | 0.4219 | 0.4947 | 0.5863 | 0.019 |
| H10A | 0.2576 | 0.5010 | 0.7026 | 0.019 |
| H10B | 0.3760 | 0.5993 | 0.6804 | 0.019 |
| H13A | 1.0062 | 0.4519 | 0.7049 | 0.023 |
| H13B | 1.0256 | 0.4337 | 0.7842 | 0.023 |
| H14A | 0.9403 | 0.5817 | 0.8536 | 0.025 |
| H14B | 0.8596 | 0.7059 | 0.8243 | 0.025 |
| H15A | 0.8338 | 0.7286 | 0.7150 | 0.024 |
| H15B | 0.8962 | 0.6209 | 0.6653 | 0.024 |
| H16 | 1.1050 | 0.6754 | 0.7544 | 0.023 |
| H18A | 0.2586 | 0.2160 | 0.3797 | 0.036 |
| H18B | 0.3547 | 0.3243 | 0.4096 | 0.036 |
| H18C | 0.1946 | 0.3097 | 0.4325 | 0.036 |
| H19A | 0.1886 | 0.0331 | 0.4530 | 0.036 |
| H19B | 0.1248 | 0.1319 | 0.5032 | 0.036 |
| H19C | 0.2406 | 0.0337 | 0.5270 | 0.036 |
| H20A | 0.4493 | 0.0636 | 0.4156 | 0.04 |
| H20B | 0.4904 | 0.0568 | 0.4910 | 0.04 |
| H20C | 0.5364 | 0.1746 | 0.4484 | 0.04 |
| H21A | 1.1286 | 0.3159 | 0.9521 | 0.048 |
| H21B | 1.0232 | 0.4301 | 0.9406 | 0.048 |
| H21C | 1.0558 | 0.3348 | 0.8827 | 0.048 |

What is claimed:

1. A compound or a pharmaceutically acceptable salt thereof, wherein the compound is of Formula (I) or (II):

(I)

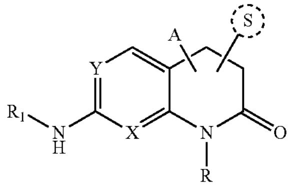

or (II)

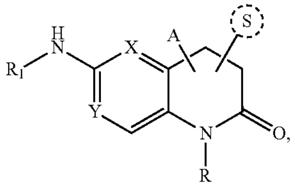

wherein A is none, Me, CO, or gem-difluoro;

X and Y are independently, C—H, N, or C—F;

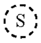 is:

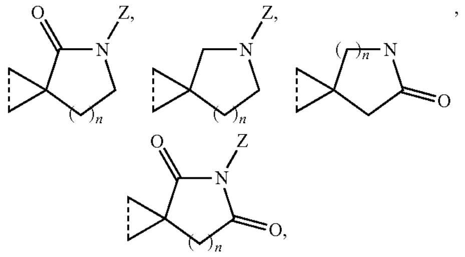

bonded in a spiro-manner, where Z is H, Me, $CH_2CH_2OH$, $CH_2CH_2CN$, $CH_2CH_2F$, $COCH_3$, or $COCH{=}CH_2$; and n is 0, 1, 2, or 3;

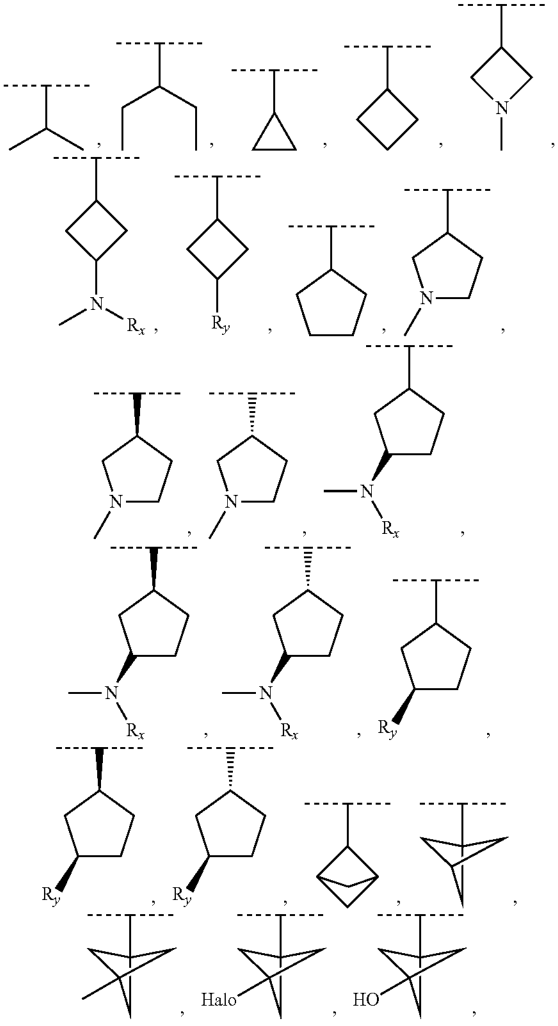

-continued
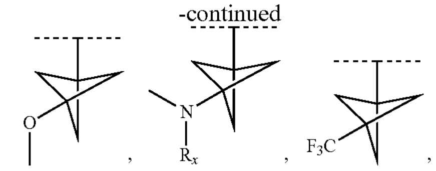
,
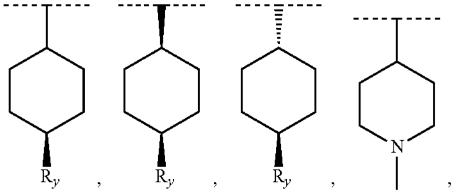
,
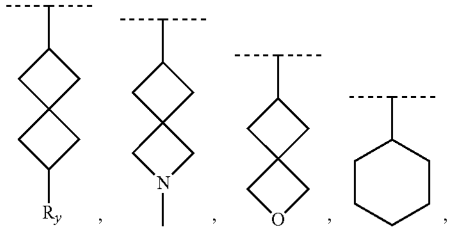
,
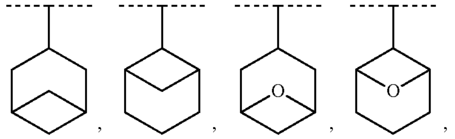
,
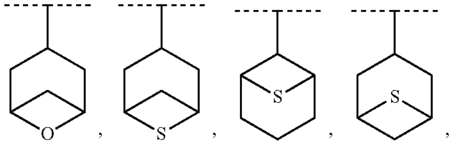
,
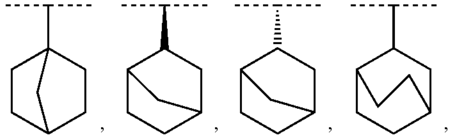
,
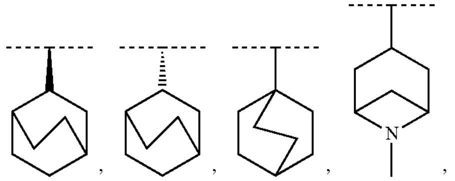
,
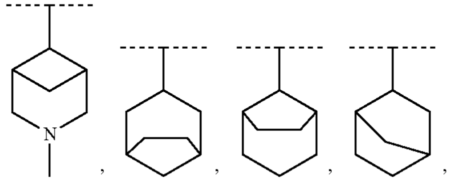
,
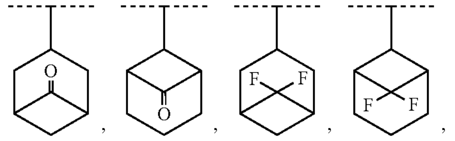
,
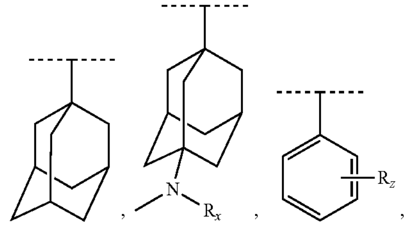
,
-continued
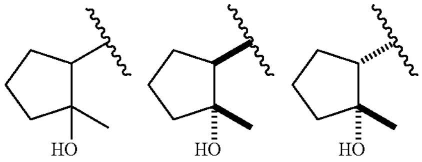
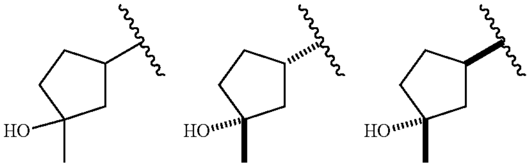
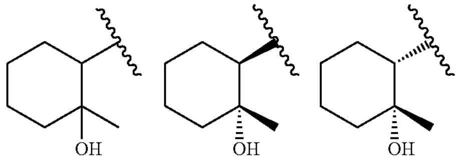
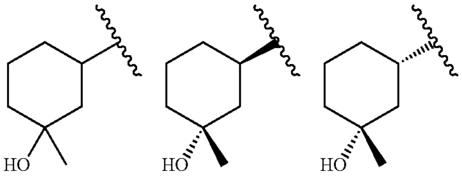
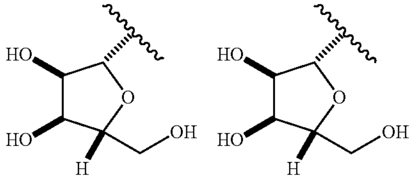
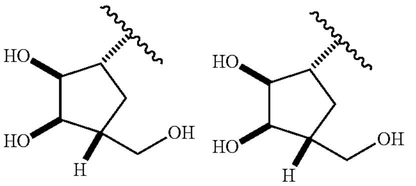
or
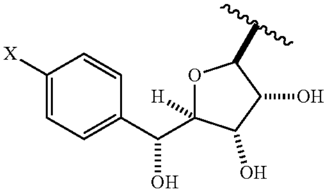
X = F, Cl
R is —$(CH_2)_mCH_3$,
where $R_x$ is H or Me, $R_y$ is Me, OH, or OMe; $R_z$ is H, Me, OMe, OH, $NH_2$, F, or $CF_3$; and m is 1 to 11; and
$R_1$ is:
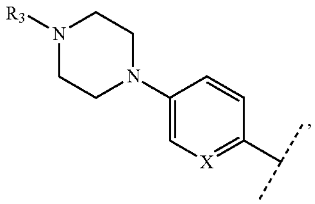
, -continued
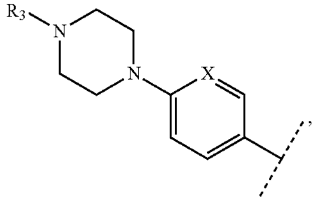
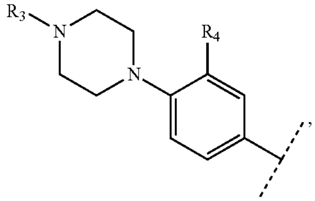
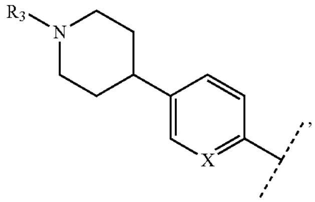
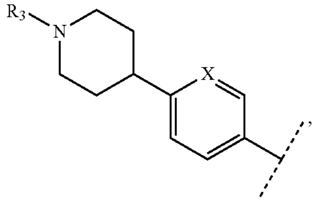
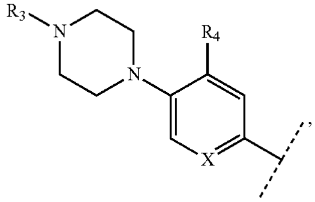
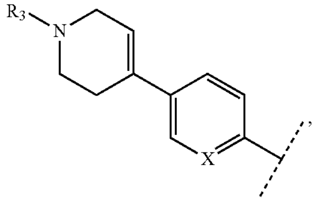
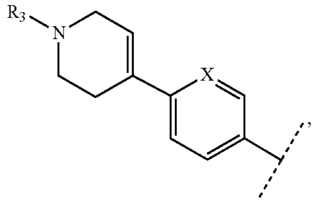
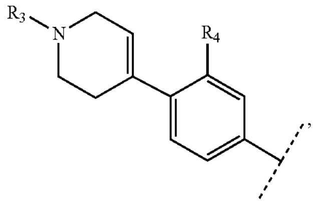
-continued
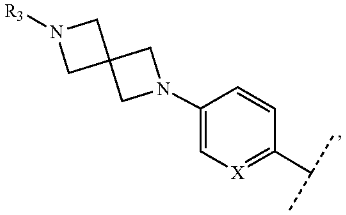
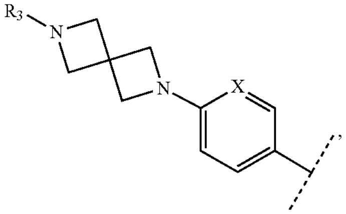
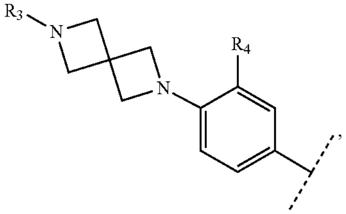
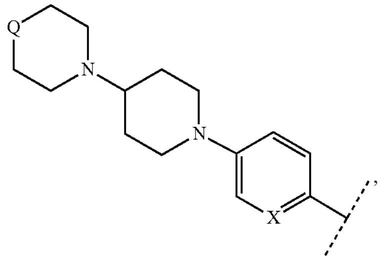
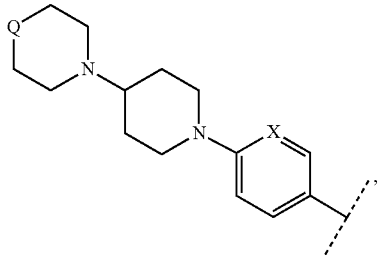
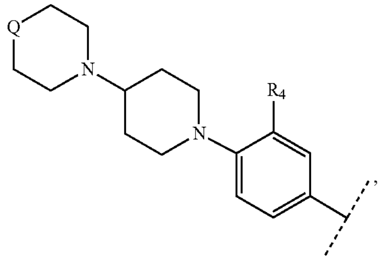
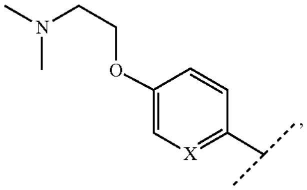

-continued
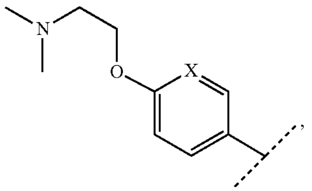
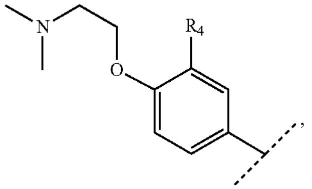
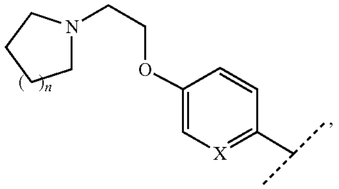
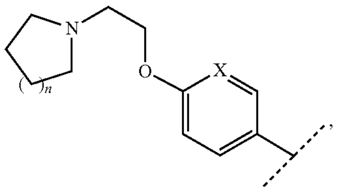
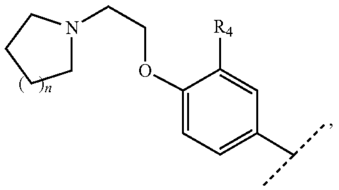
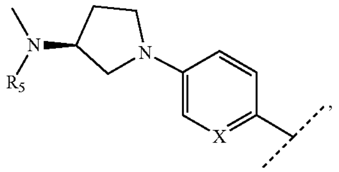
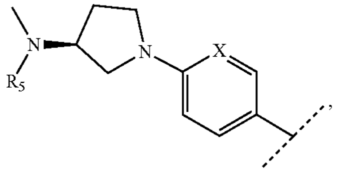
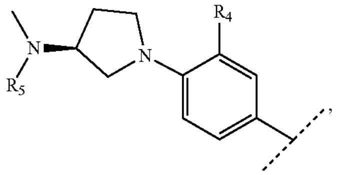
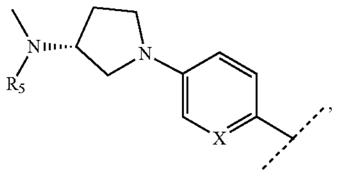
-continued
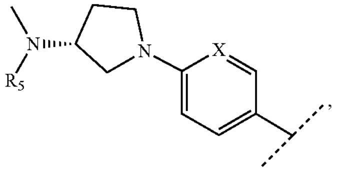
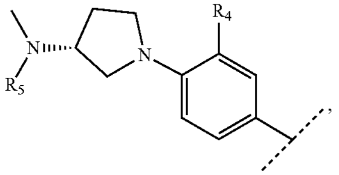
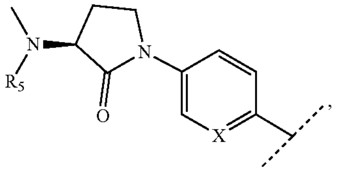
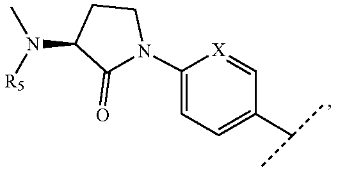
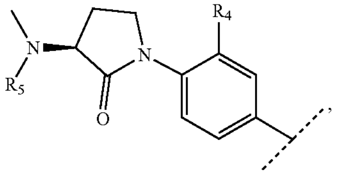
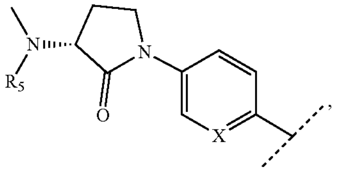
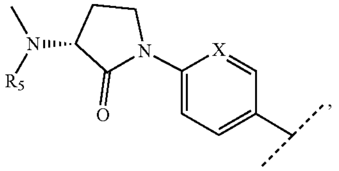
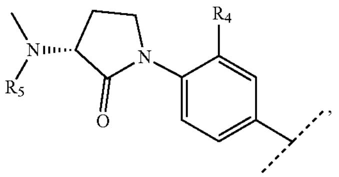
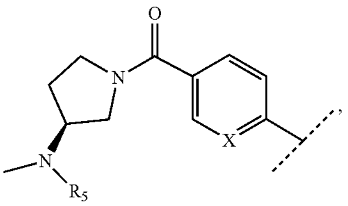

-continued
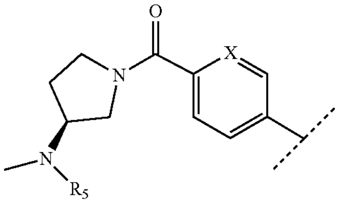,
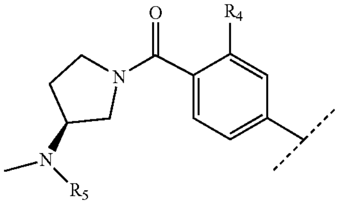,
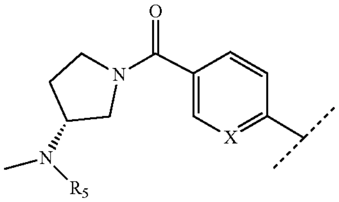,
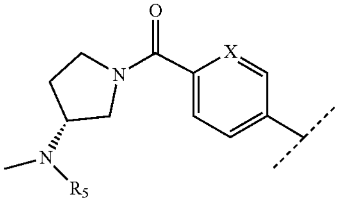,
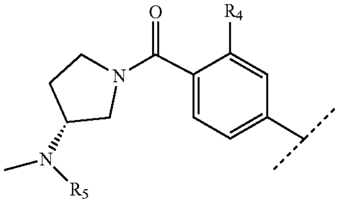,
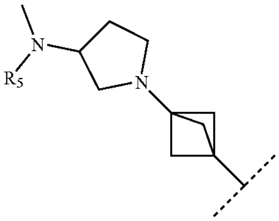,
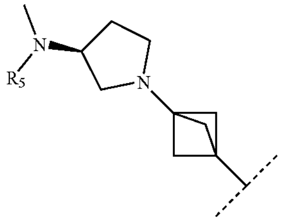,
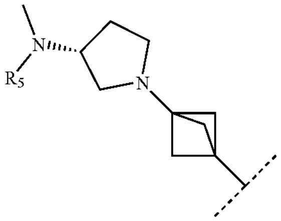,
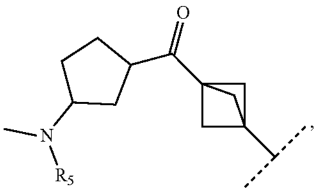,
-continued
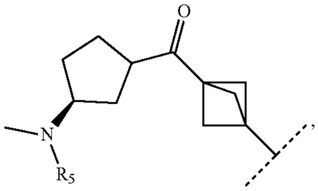,
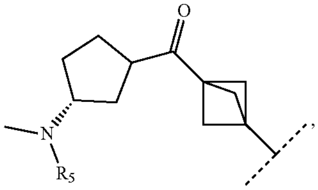,
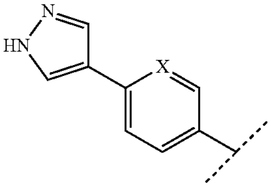,
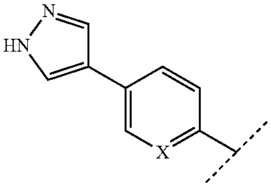,
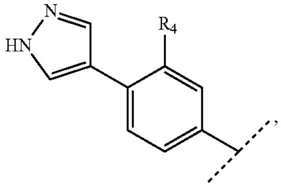,
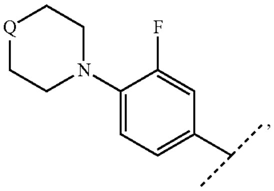,
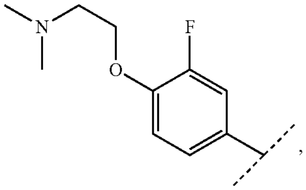,
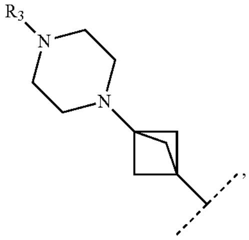,
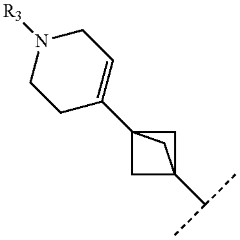,
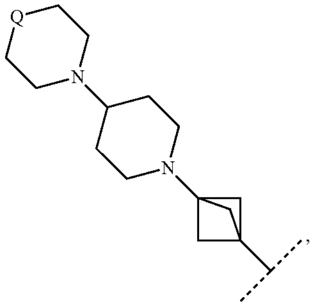,
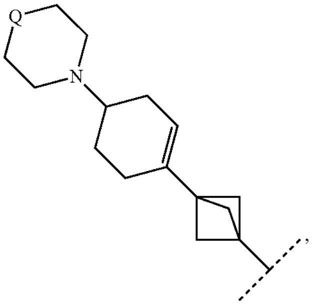, -continued
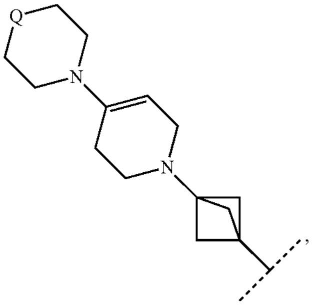,
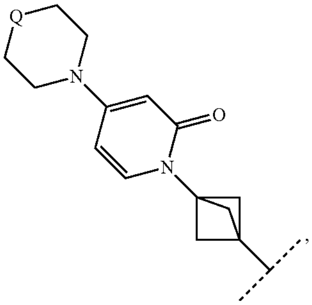,
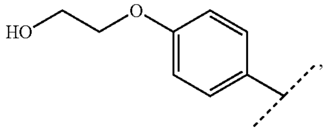,
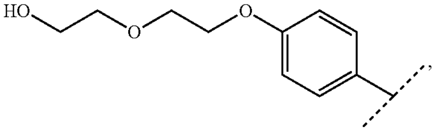,
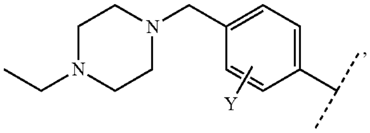,
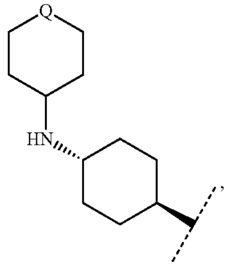, 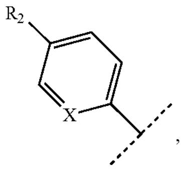,
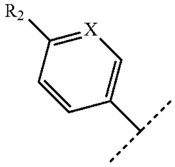, 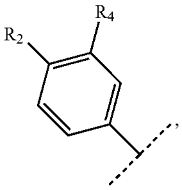, 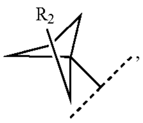,
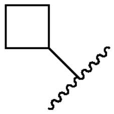 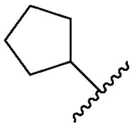 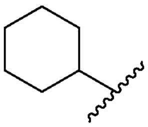 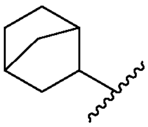
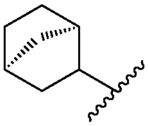 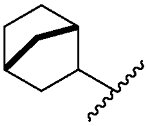 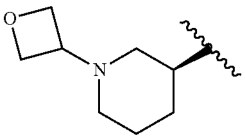
-continued
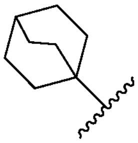 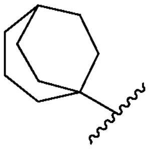 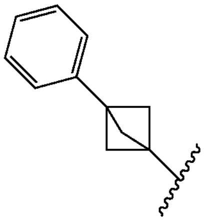
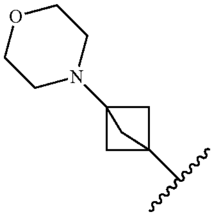 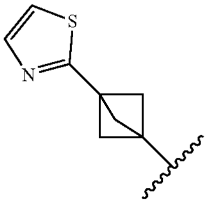
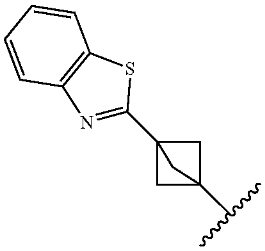 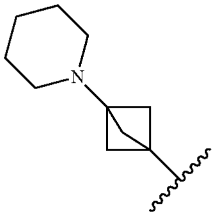
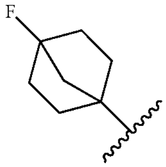 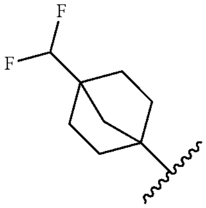
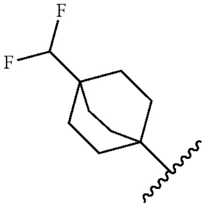 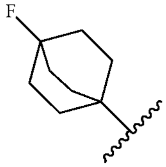 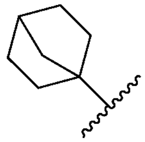
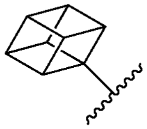 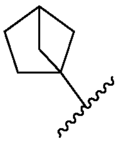 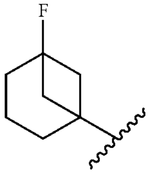
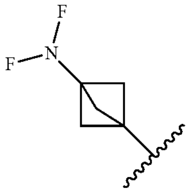 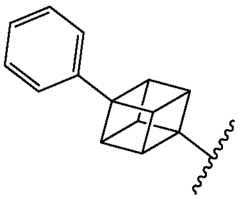
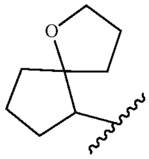 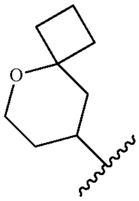 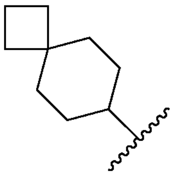

-continued
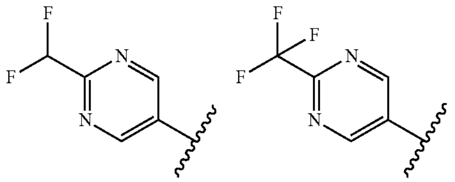
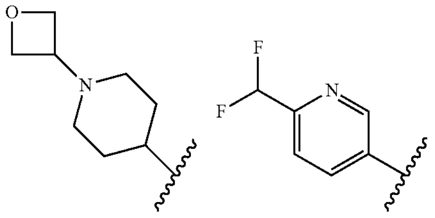
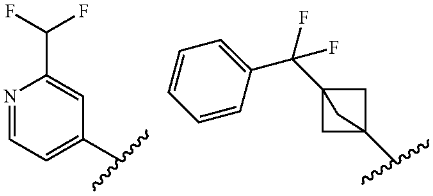
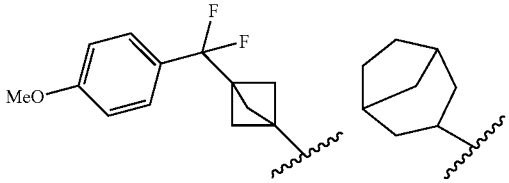
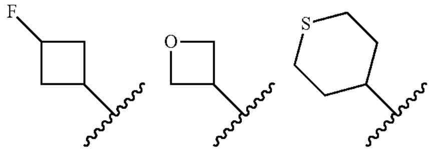
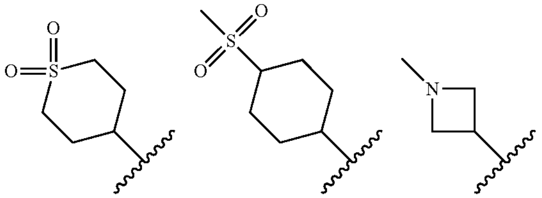
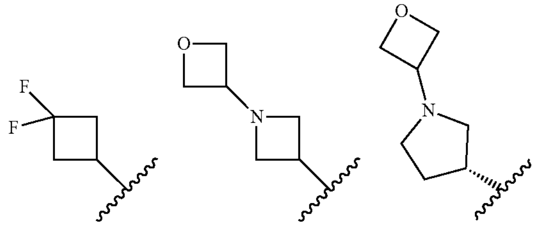
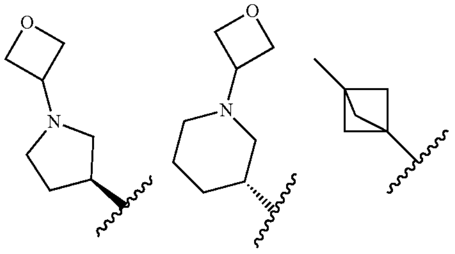
-continued
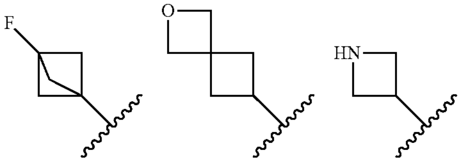
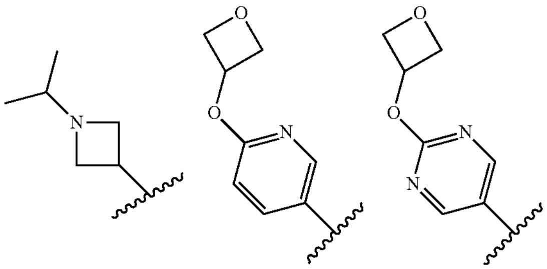
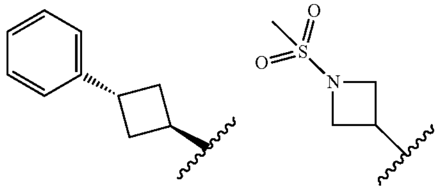
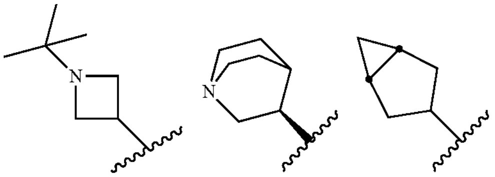
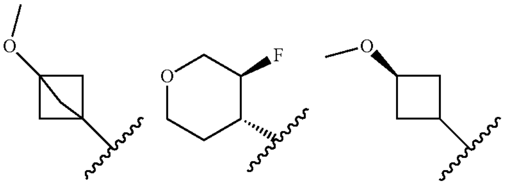
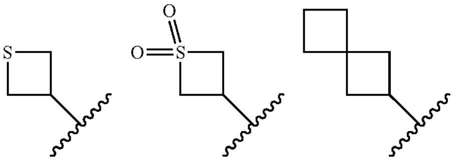
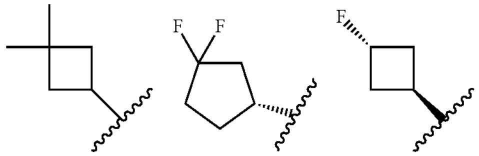
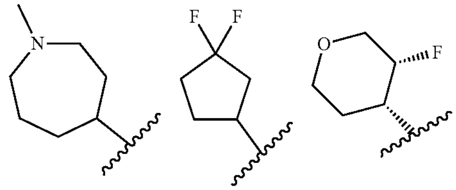
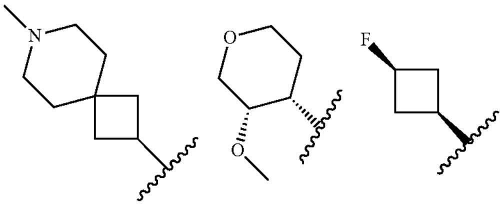

-continued
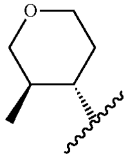
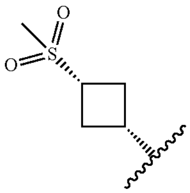
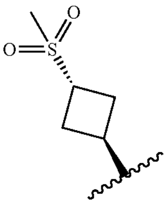
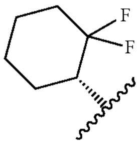
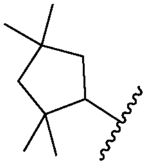
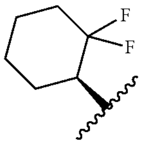
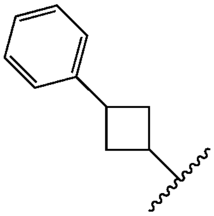
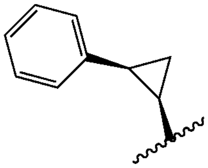
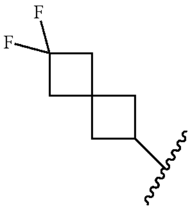
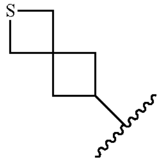
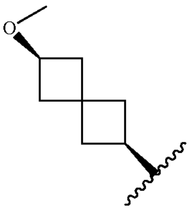
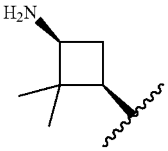
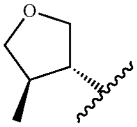
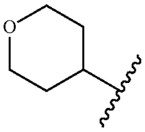
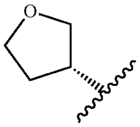
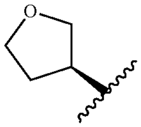
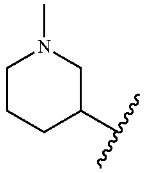
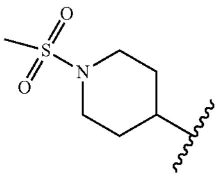
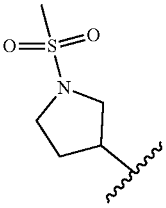
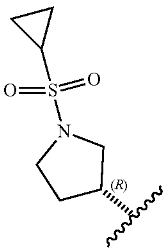
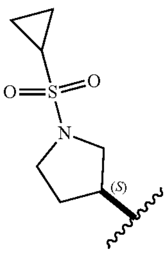
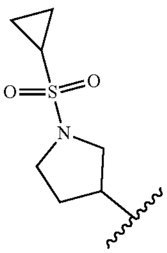
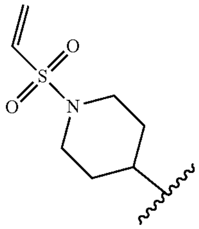
-continued
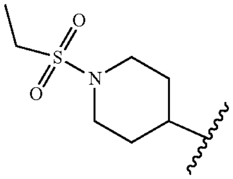
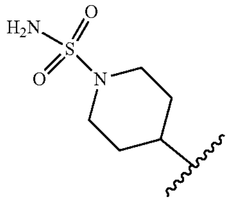
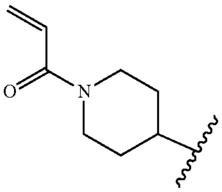
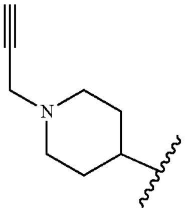
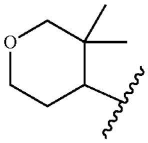
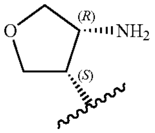
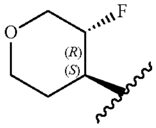
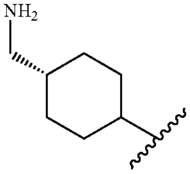
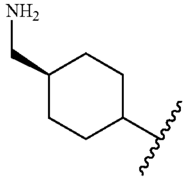
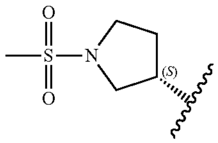
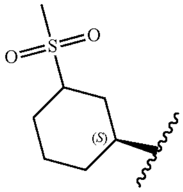
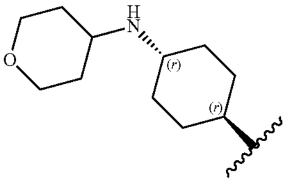
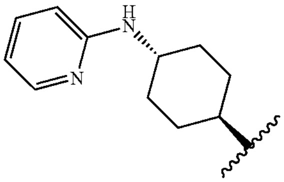
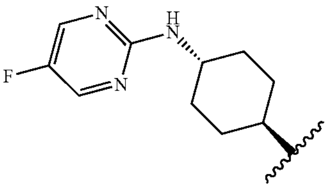
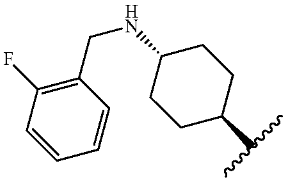
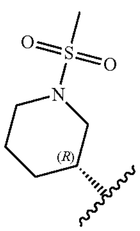

-continued
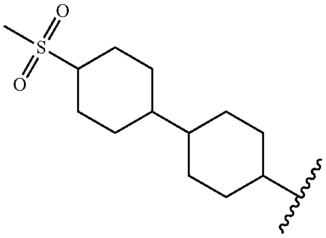
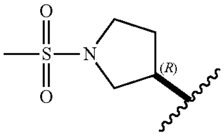
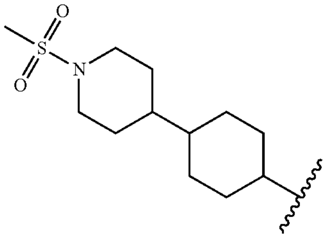
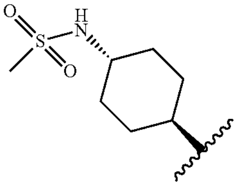
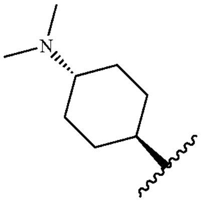
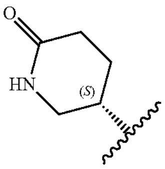
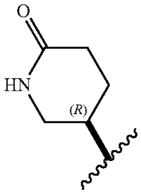
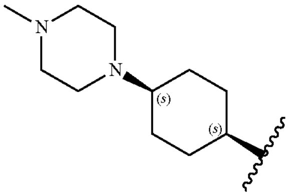
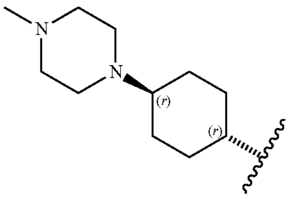
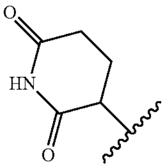
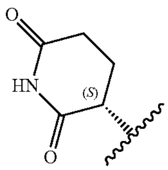
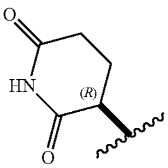
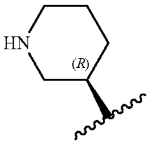
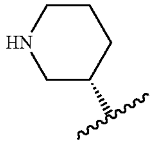
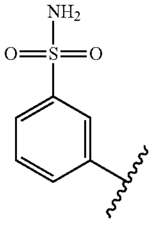
-continued
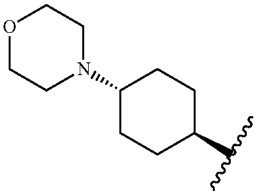
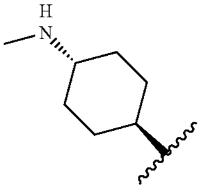
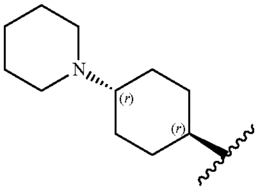
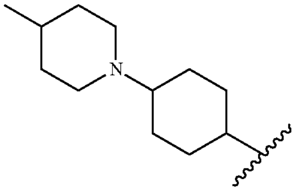
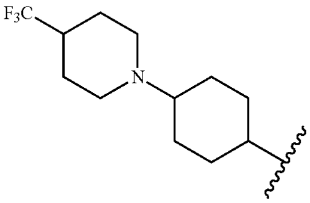
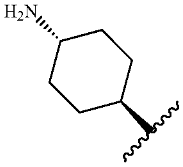
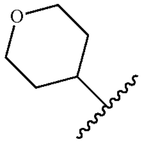
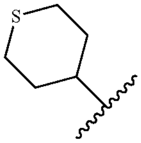
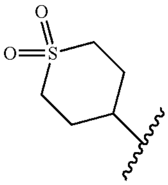
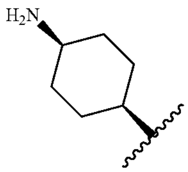
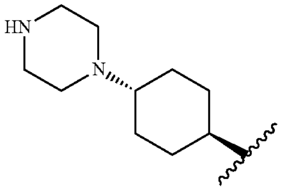
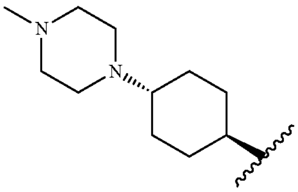
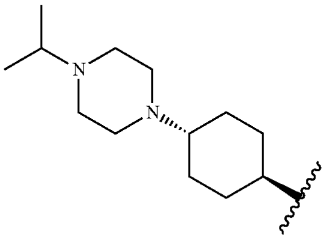
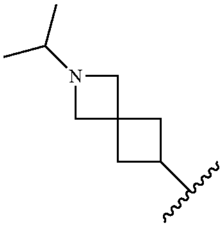
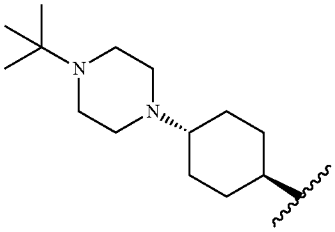

-continued
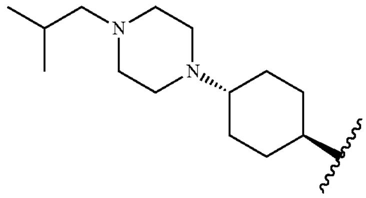
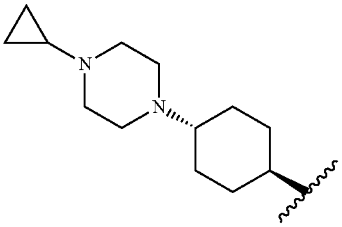
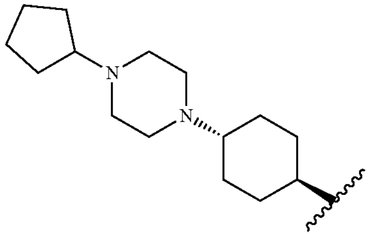
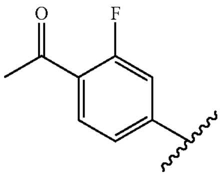
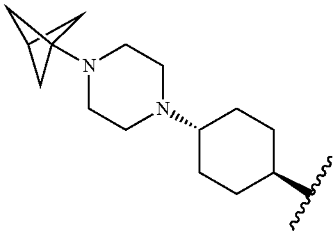
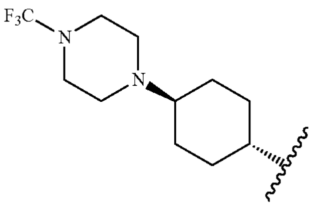
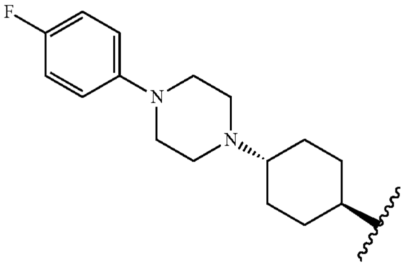
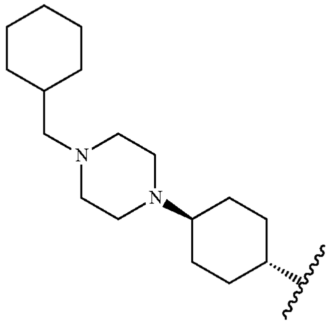
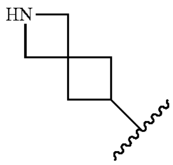
-continued
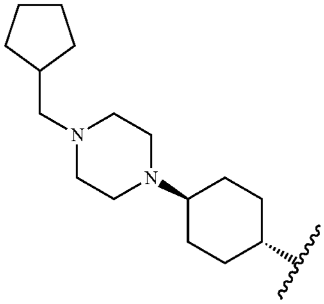
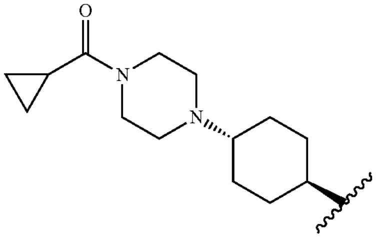
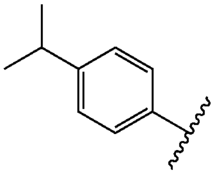
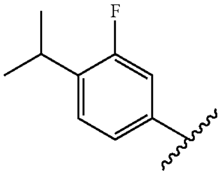
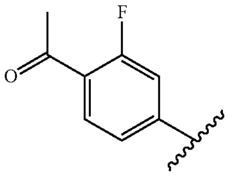
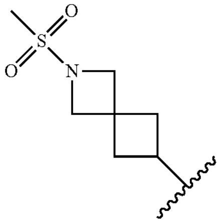
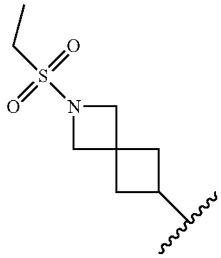
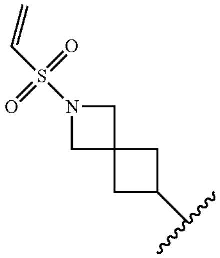
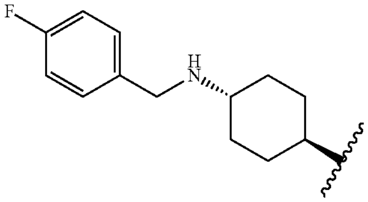
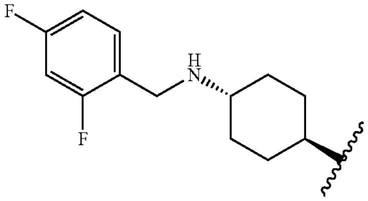

-continued
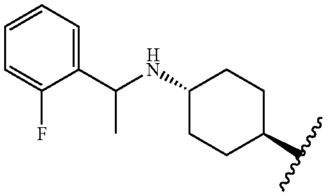
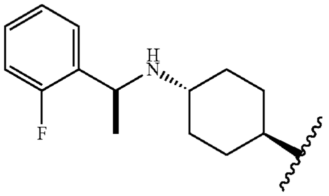
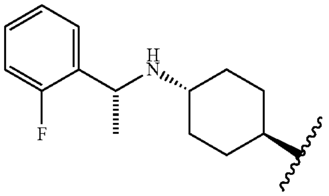
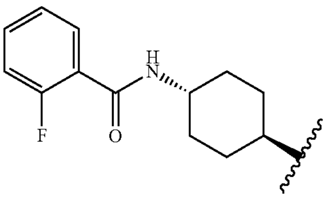
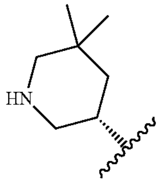
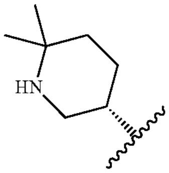
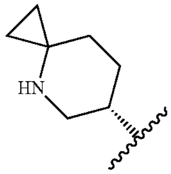
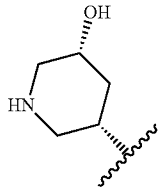
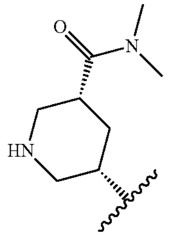
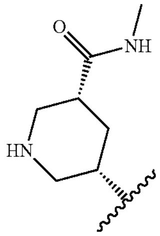
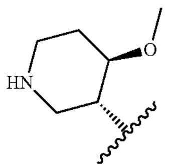
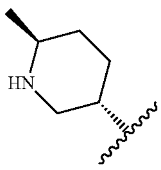
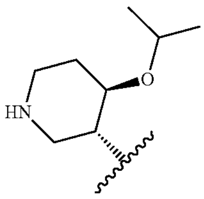
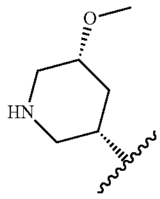
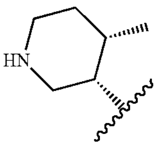
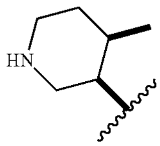
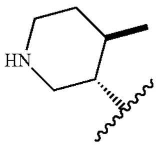
-continued
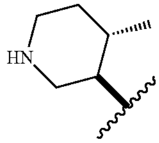
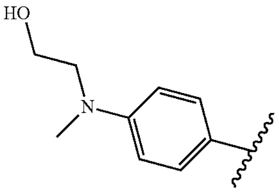
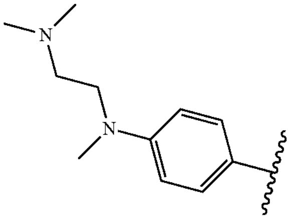
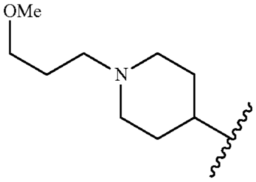
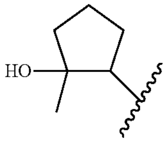
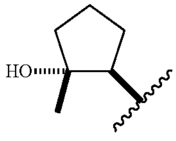
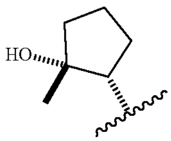
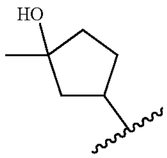
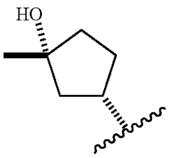
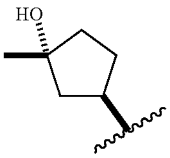
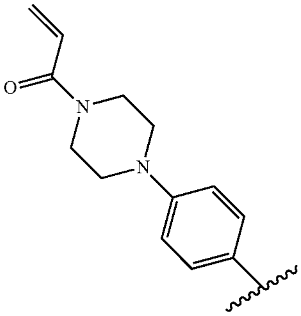
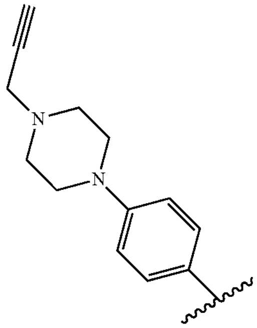
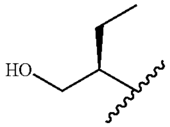
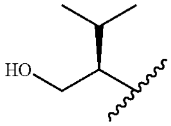
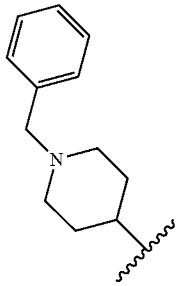
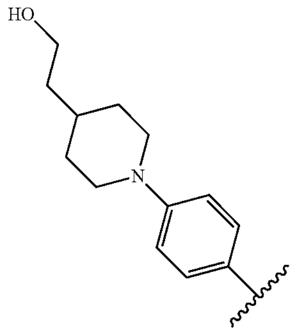

-continued
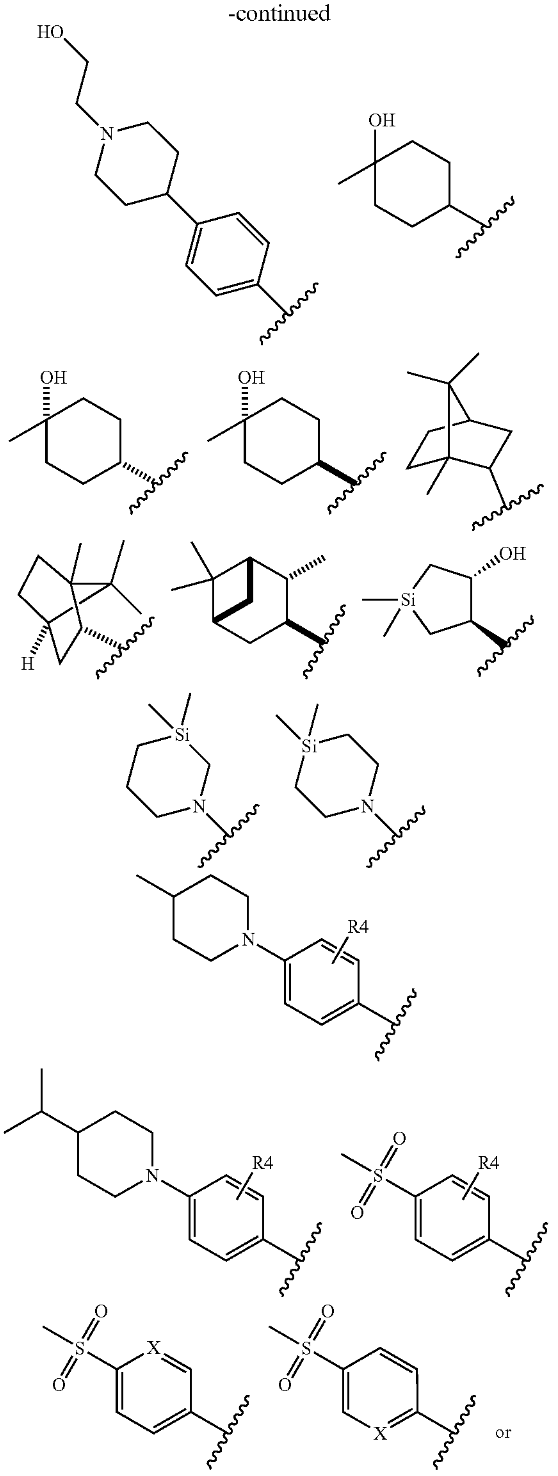
or
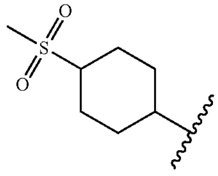
where $R_3$ is H, Me, $CH_2CH_2OH$, isopropyl, isobutyl, or bicyclo[1.1.1]pentane;
$R_4$ is H, Me, OMe, $CF_3$, or $CHF_2$;
$R_5$ is H or Me;
$Y_1$ is H, $NH_2$, F, Me, OMe, $CF_3$, or $CHF_2$;
Q is O or S;
p is 1, 2, or 3; and
$R_2$ is:
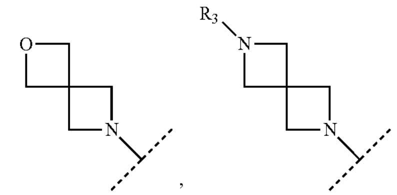
, ,
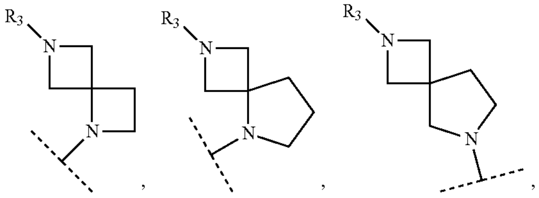
, , ,
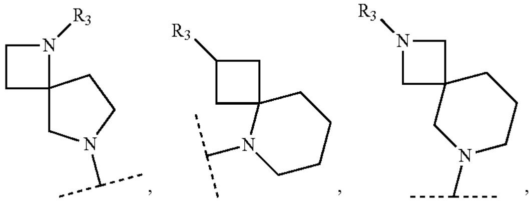
, , ,
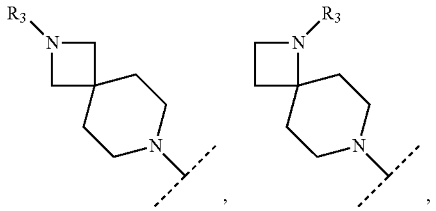
, ,
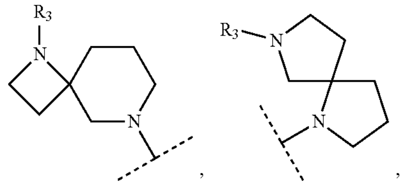
, ,
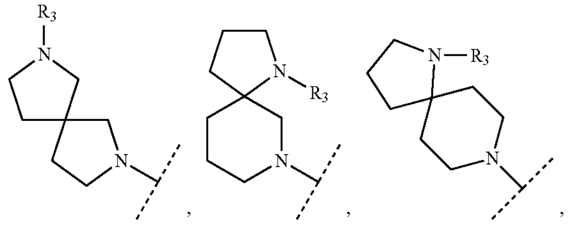
, , ,
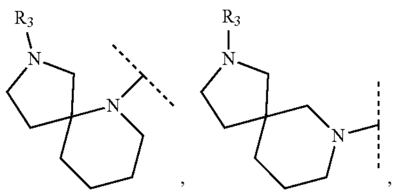
, , -continued
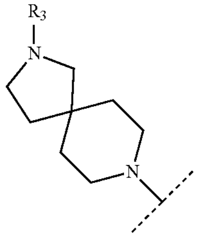, 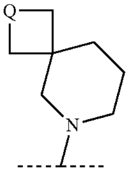,
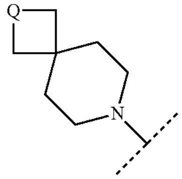, 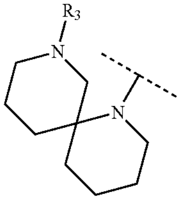,
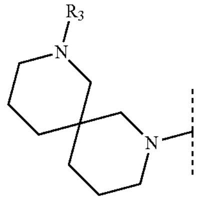, 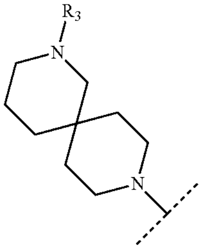,
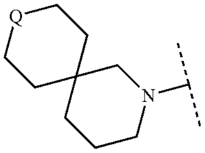, 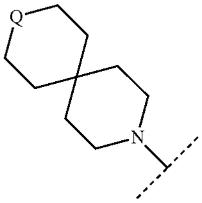,
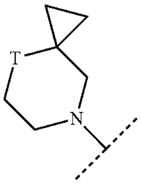, 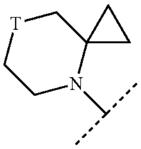, 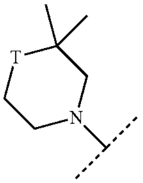,
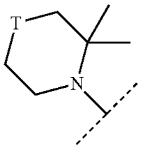, 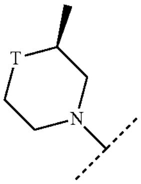, 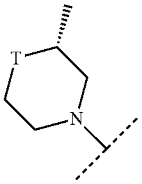,
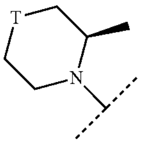, 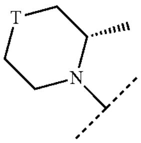, 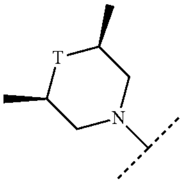,
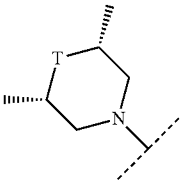, 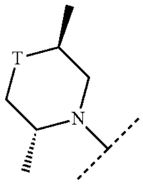, 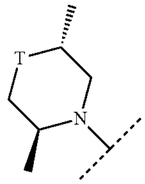,
-continued
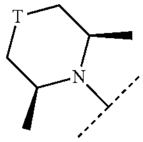, 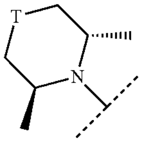, 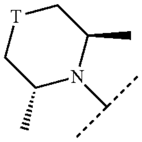,
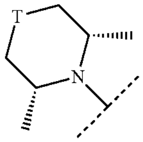, 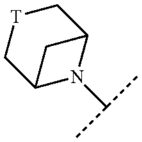, 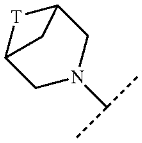,
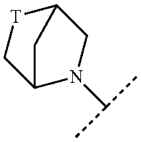, 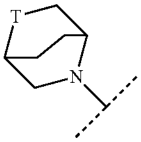, 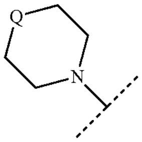, or
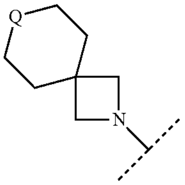,
where T is O, NH, NMe, N-isopropyl, or N-isobutyl.
2. The compound of claim 1 or the pharmaceutically acceptable salt thereof, wherein
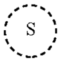 is 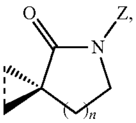, 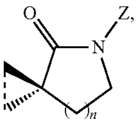, 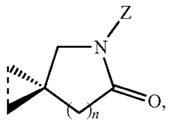, 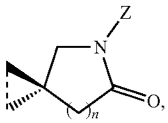, 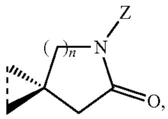, 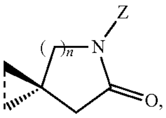, 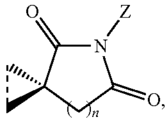, or 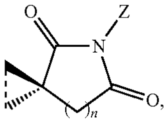,
bonded in a spiro-manner, where Z is H, Me, $CH_2CH_2OH$, $CH_2CH_2CN$, $CH_2CH_2F$, $COCH_3$, or $COCH{=}CH_2$; and n is 0, 1, 2, or 3.
3. The compound of claim 1 or the pharmaceutically acceptable salt thereof, wherein R is
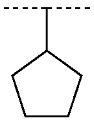.

4. The compound of claim 1 or the pharmaceutically acceptable salt thereof, wherein $R_1$ is:

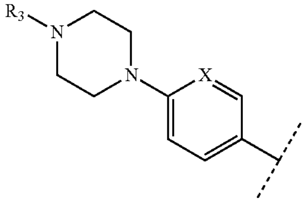

,

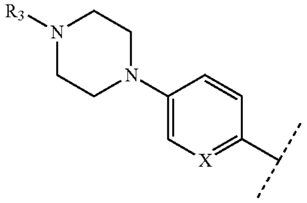

,

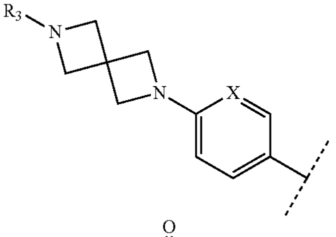

, or

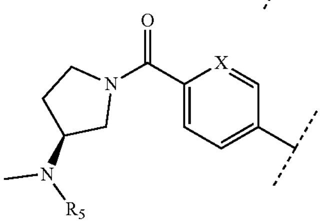

, where $R_3$ is H, Me, $CH_2CH_2OH$, isopropyl, isobutyl, or bicyclo[1.1.1]pentane; $R_5$ is H or Me; and X is C—H, N, or C—F.

5. The compound of claim 1 or the pharmaceutically acceptable salt thereof, wherein the compound is of Formula (I):

(I)

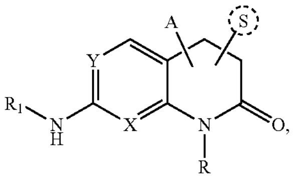

where A is none; and X and Y are independently, C—H or N.

6. The compound of claim 5 or the pharmaceutically acceptable salt thereof, wherein

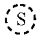 is 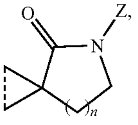

bonded in a spiro-manner; where Z is H, Me, or $CH_2CH_2OH$; and n is 0, 1, 2, or 3.

7. The compound of claim 5 or the pharmaceutically acceptable salt thereof, wherein R is

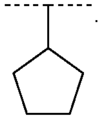

.

8. The compound of claim 5 or the pharmaceutically acceptable salt thereof, wherein $R_1$ is:

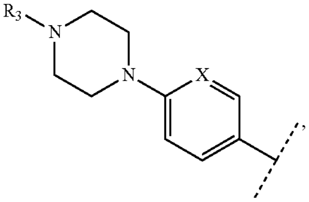

,

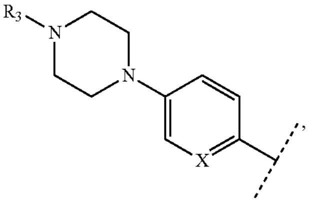

,

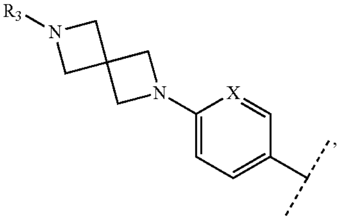

, or

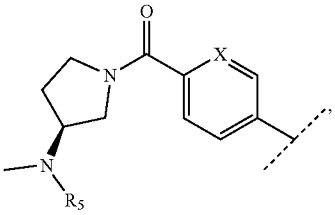

, where $R_3$ is H, Me, $CH_2CH_2OH$, isopropyl, isobutyl, or bicyclo[1.1.1]pentane; $R_5$ is H or Me; and X is C—H, N, or C—F.

9. A compound or a pharmaceutically acceptable salt thereof, wherein the compound is of Formulae (VII)-(XVIII):

(VII)

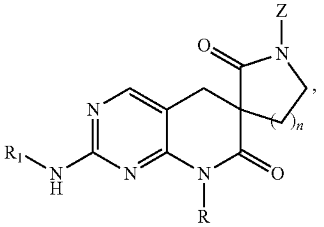

-continued
(VIII)
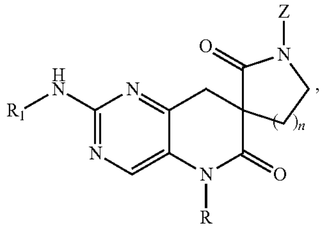
(IX)
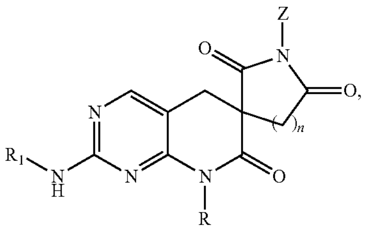
(X)
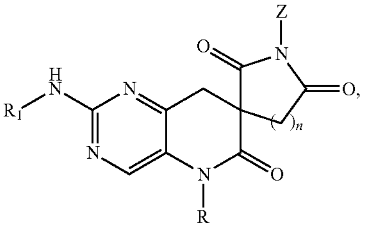
(XI)
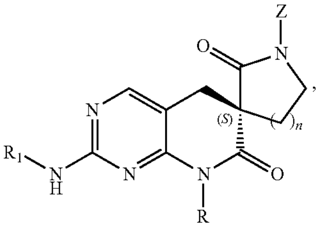
(XII)
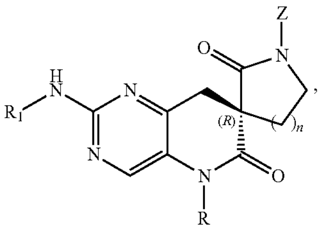
(XIII)
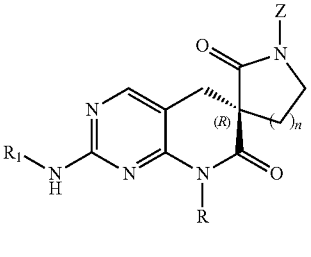
-continued
(XIV)
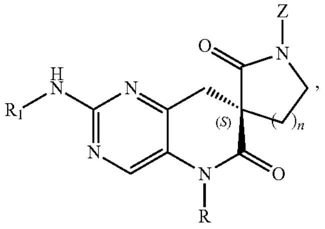
(XV)
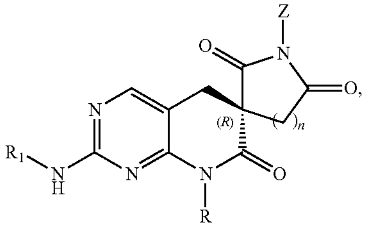
(XVI)
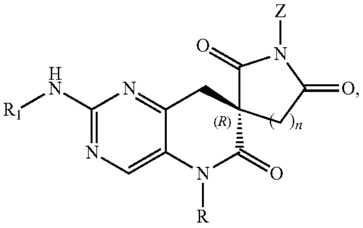
(XVII)
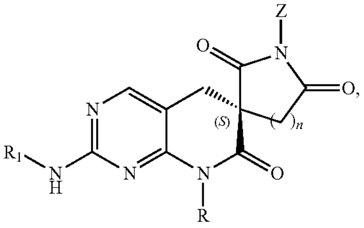
or
(XVIII)
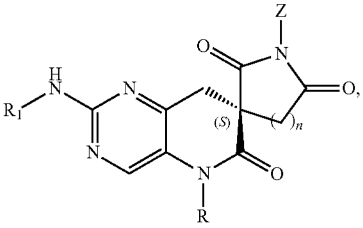
(XVIII), wherein Z is H, Me, or $CH_2CH_2OH$; and n is 0, 1, 2, or 3;
R is $(CH_2)_mCH_3$,
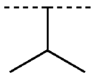 , 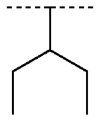 , 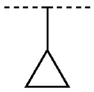 , 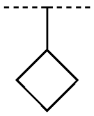 ,
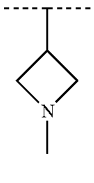 , 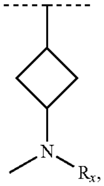 , 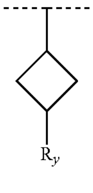 , 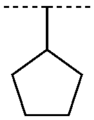 , -continued
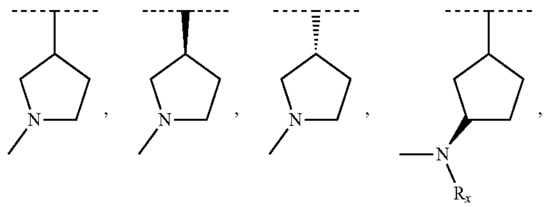
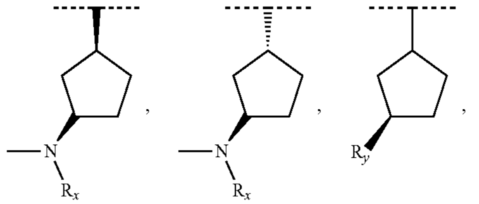
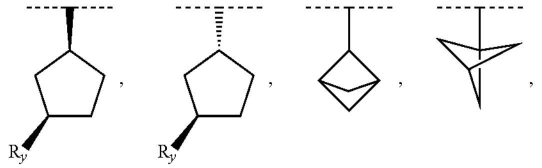
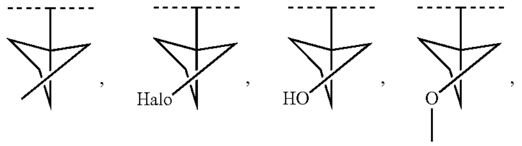
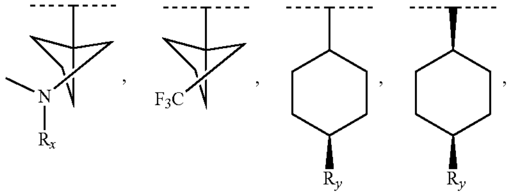
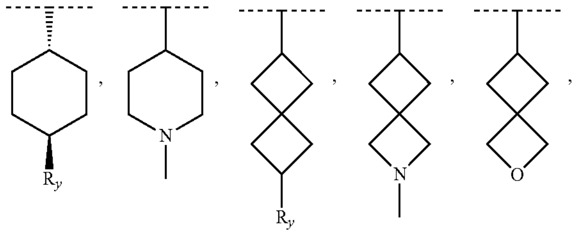
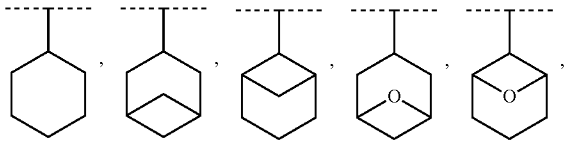
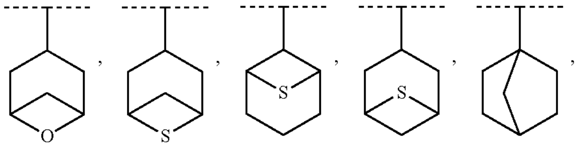
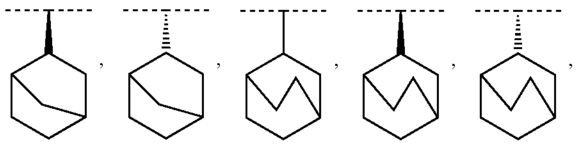
-continued
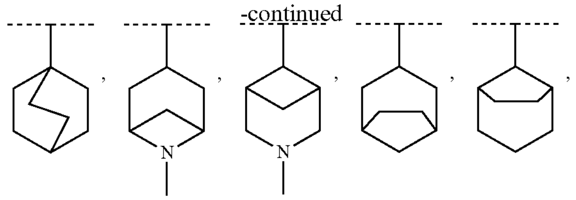
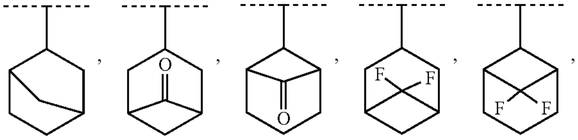
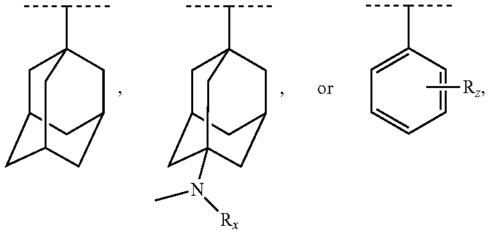
where $R_x$ is H or Me, $R_y$ is Me, OH, or OMe; $R_z$ is H, Me, OMe, OH, $NH_2$, F, or $CF_3$; and me is 1 to 11; and
$R_1$ is:
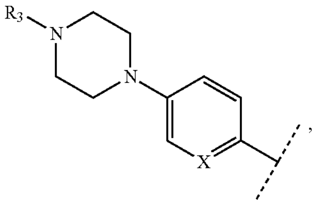
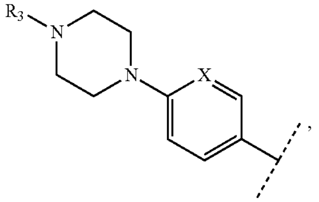
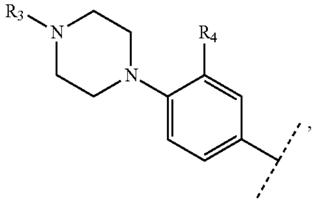
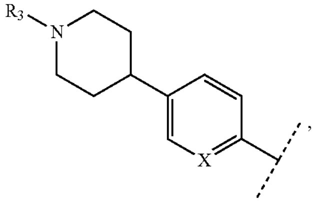
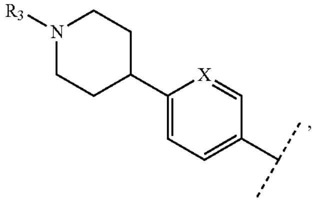

-continued
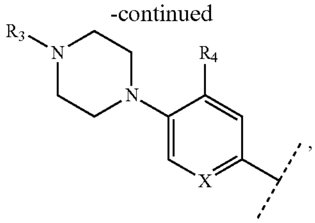
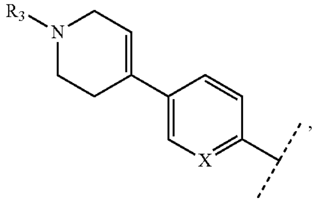
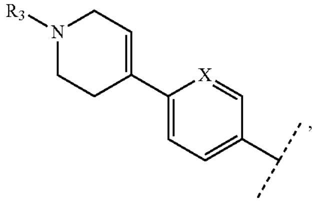
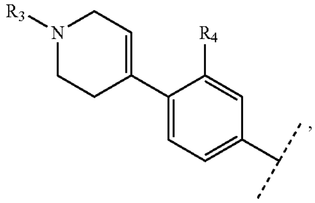
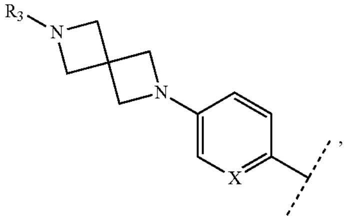
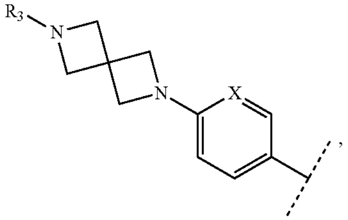
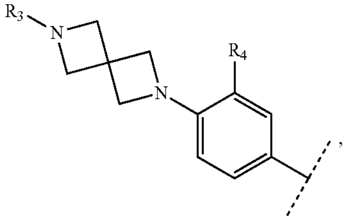
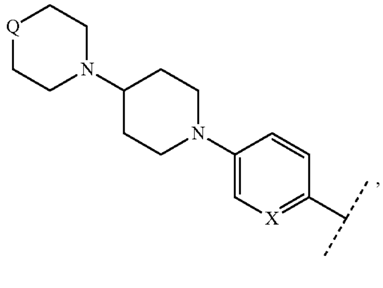
-continued
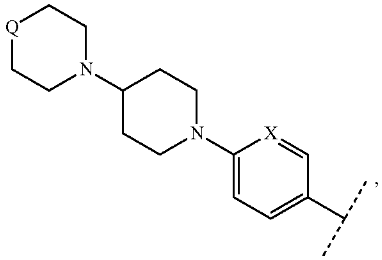
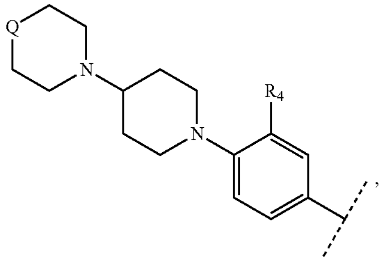
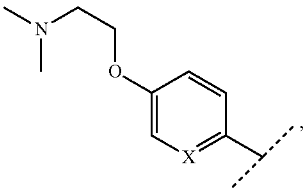
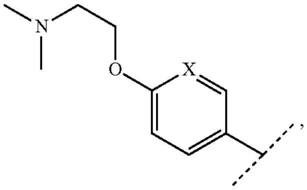
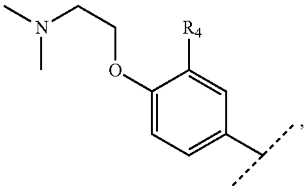
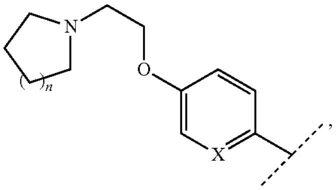
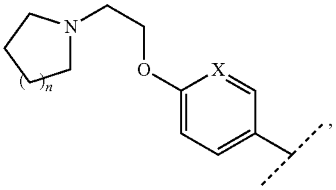
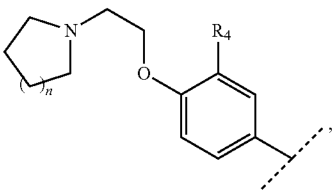

-continued
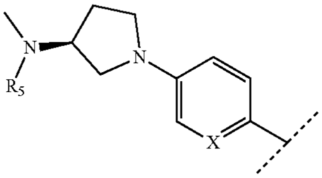
,
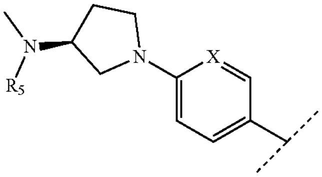
,
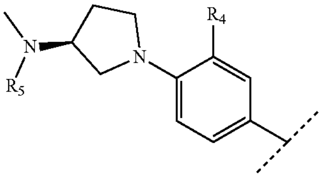
,
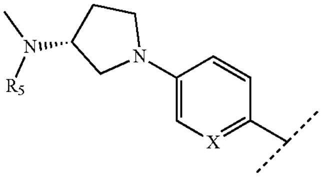
,
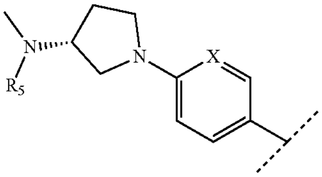
,
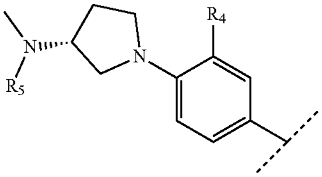
,
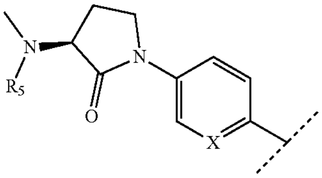
,
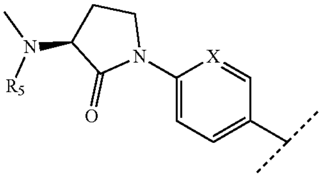
,
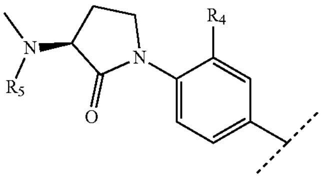
,
-continued
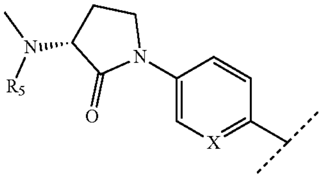
,
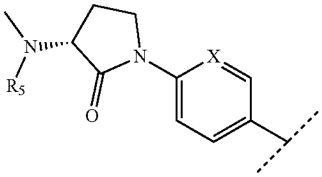
,
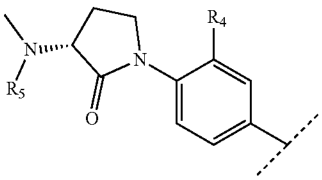
,
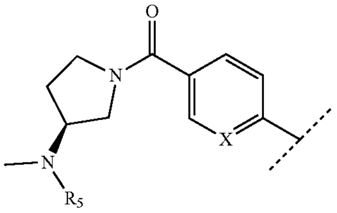
,
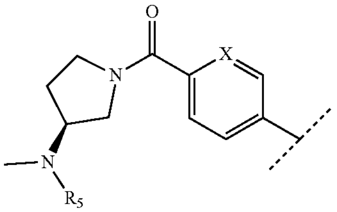
,
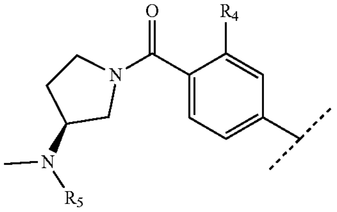
,
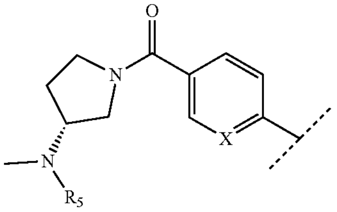
,
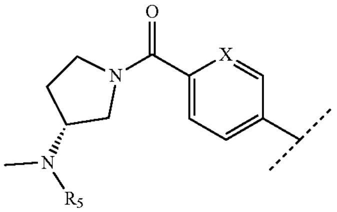
, -continued
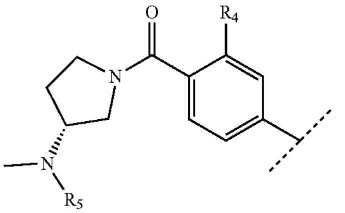
,
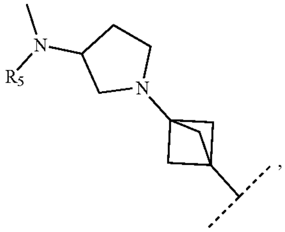
,
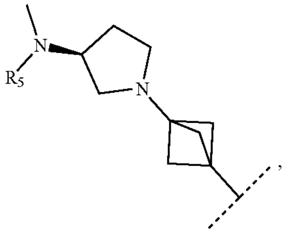
,
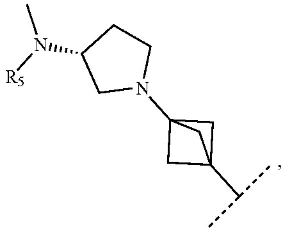
,
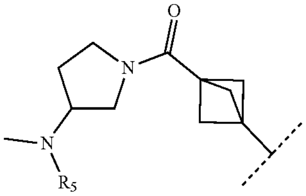
,
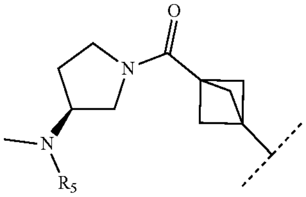
,
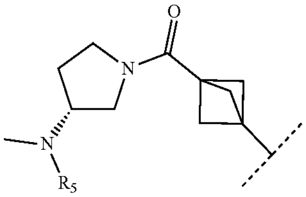
,
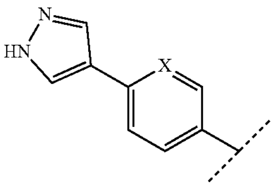
,
-continued
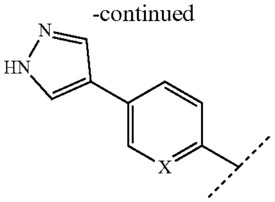
,
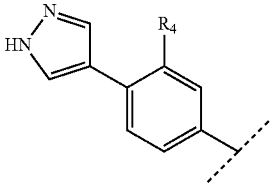
,
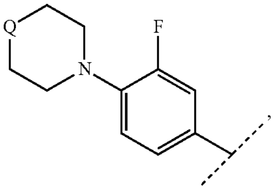
,
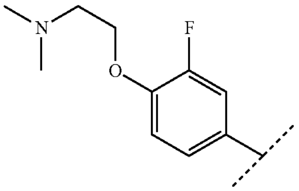
,
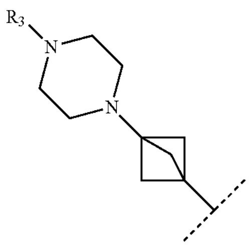
,
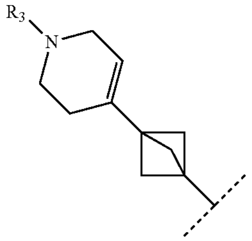
,
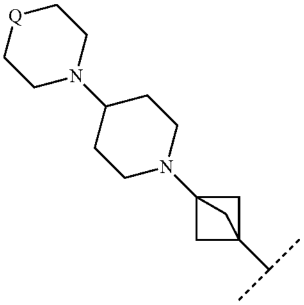
,
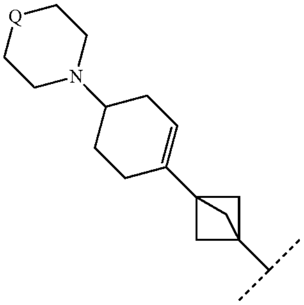
,
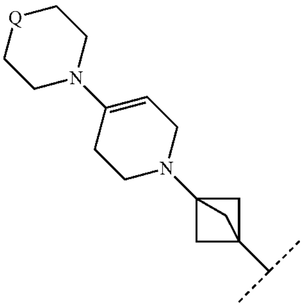
, -continued
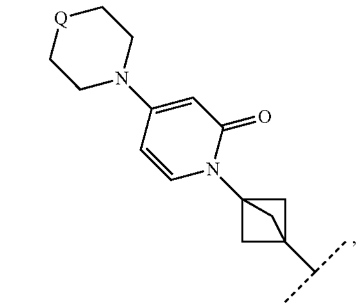
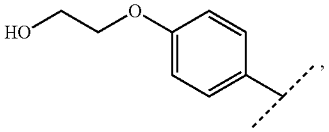
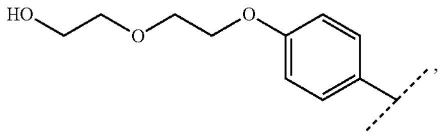
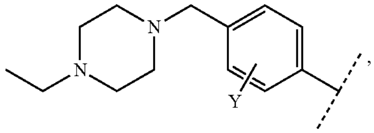
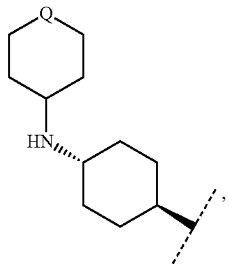
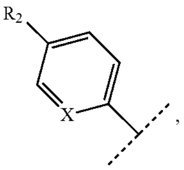
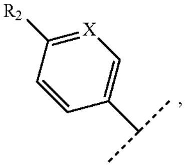
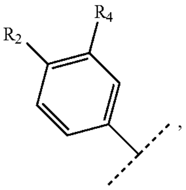
or
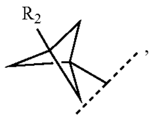
where $R_3$ is H, Me, $CH_2CH_2OH$, isopropyl, isobutyl, or bicyclo[1.1.1]pentane;
$R_4$ is H, Me, OMe, $CF_3$, or $CHF_2$;
$R_5$ is H or Me;
X is C—H, N, or C—F;
$Y_1$ is H, $NH_2$, F, Me, OMe, $CF_3$, or $CHF_2$;
Q is O or S;
p is 1, 2, or 3; and
$R_2$ is:
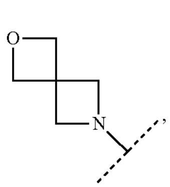
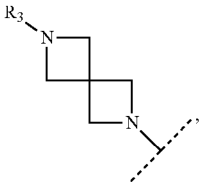
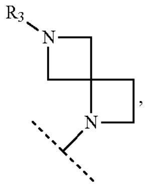
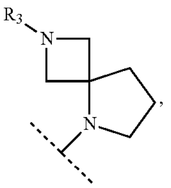
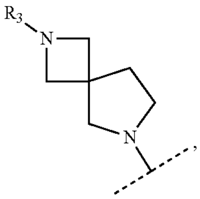
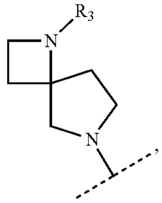
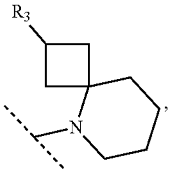
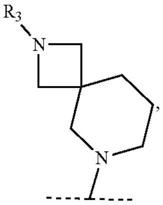
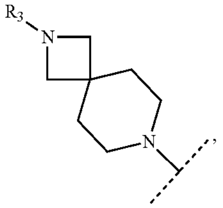
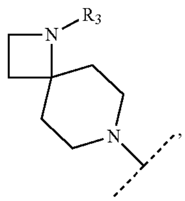
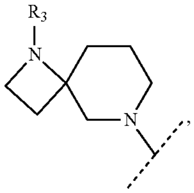
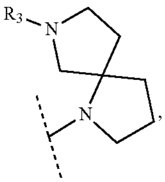
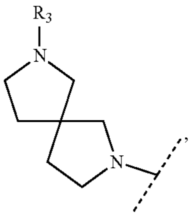
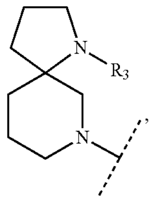
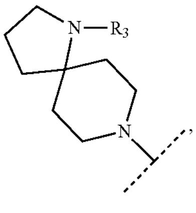
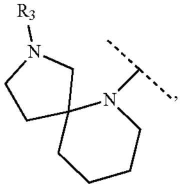

-continued
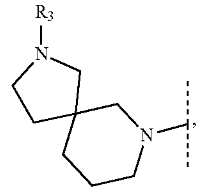 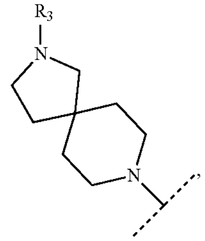
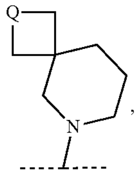 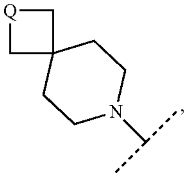
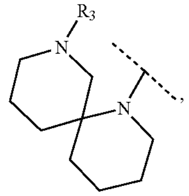 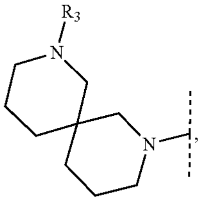
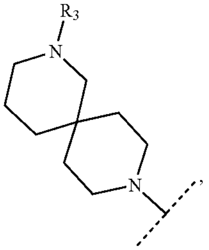 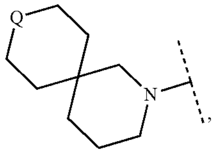
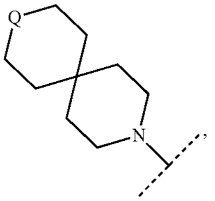 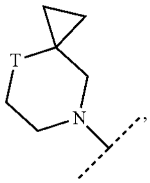
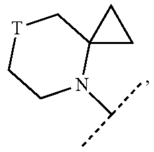 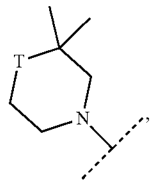
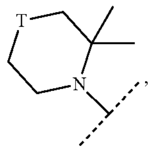 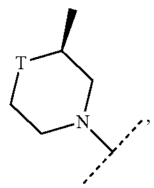
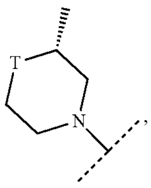 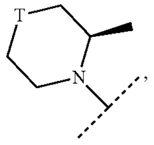
-continued
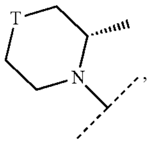 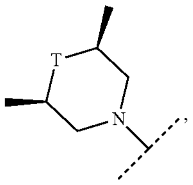
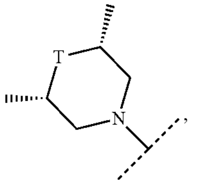 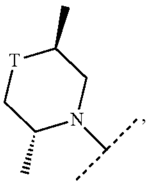
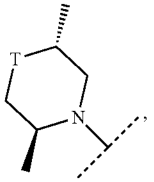 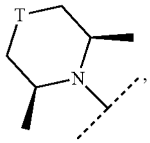
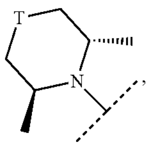 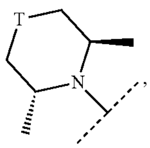
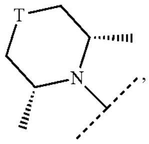 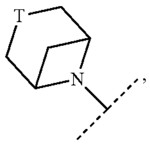
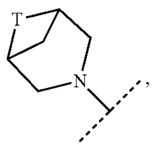 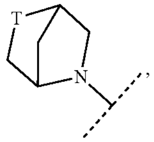
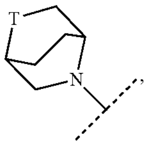 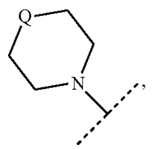 or
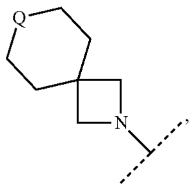
where T is O, NH, NMe, N-isopropyl, or N-isobutyl.
10. The compound of claim 9 or the pharmaceutically acceptable salt thereof, wherein the compound is of Formulae (VII), (XI), or (XIII):

(VII)

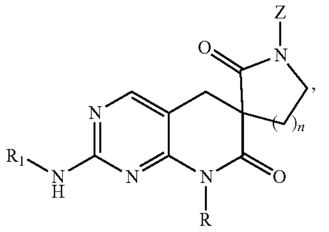

(XI)

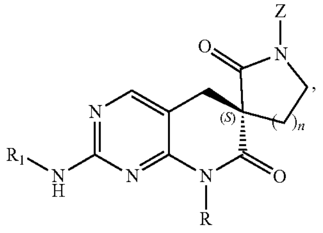

or (XIII)

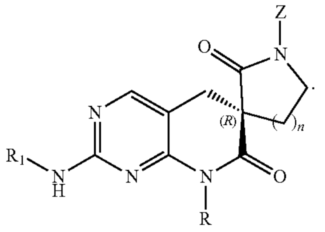

11. The compound of claim 10 or the pharmaceutically acceptable salt thereof, wherein R is

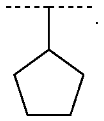

12. The compound of claim 10 or the pharmaceutically acceptable salt thereof, wherein $R_1$ is:

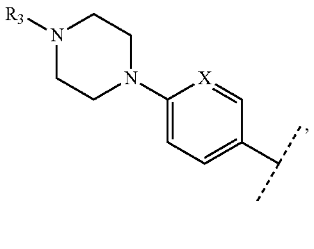

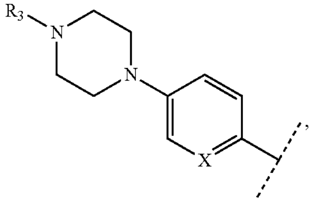

-continued

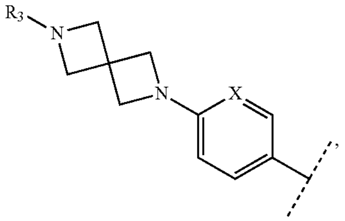

or

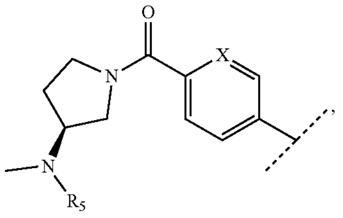

where $R_3$ is H, Me, $CH_2CH_2OH$, isopropyl, isobutyl, or bicyclo[1.1.1]pentane; $R_5$ is H or Me; and X is C—H, N, or C—F.

13. A compound selected from D1-D48 or pharmaceutically acceptable salts thereof:

(D1)

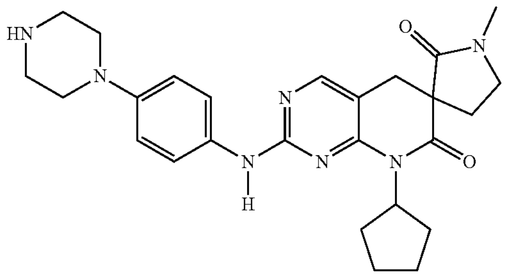

(D2)

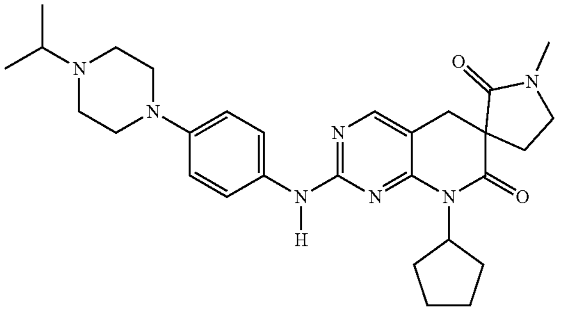

(D3)

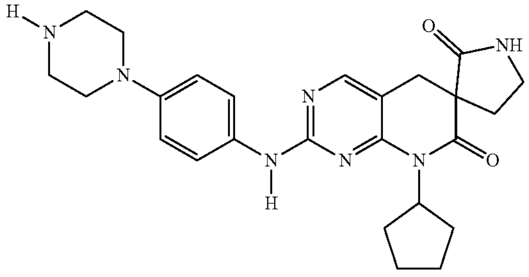

-continued
(D4)
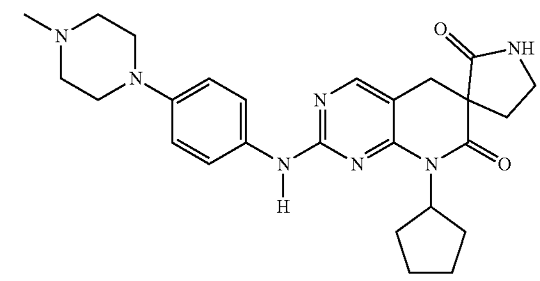
(D5)
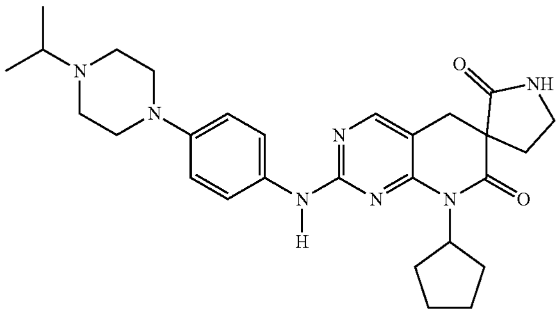
(D6)
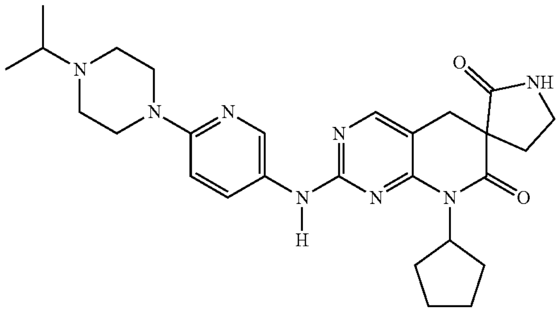
(D7)
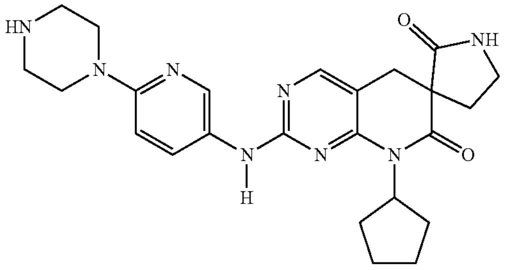
(D8)
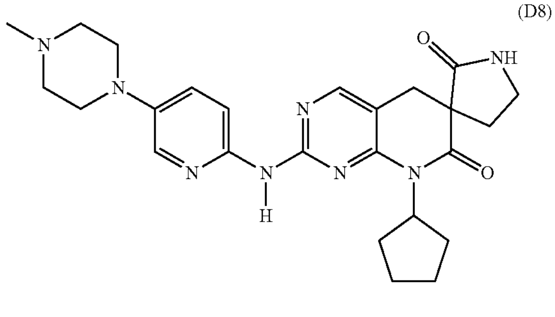
-continued
(D9)
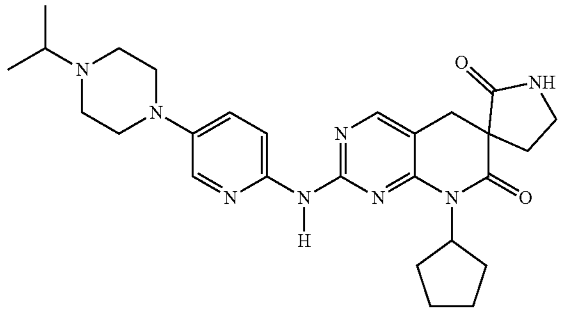
(D10)
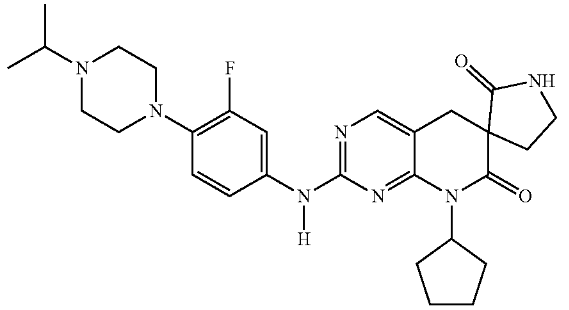
(D11)
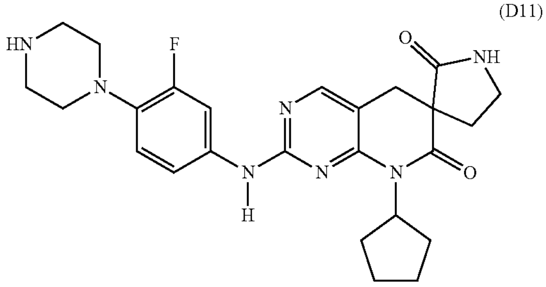
(D12)
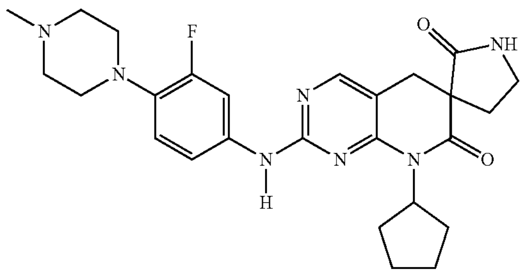
(D13)
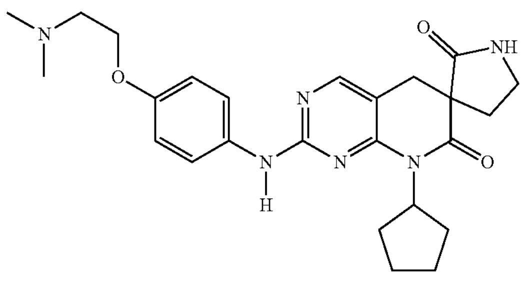

-continued
(D14)
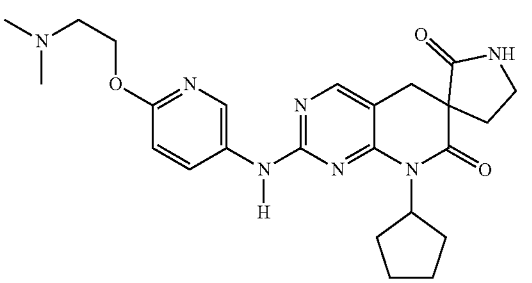
(D15)
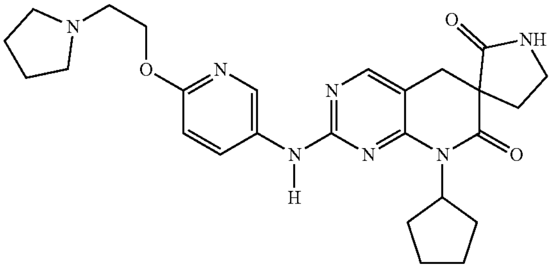
(D16)
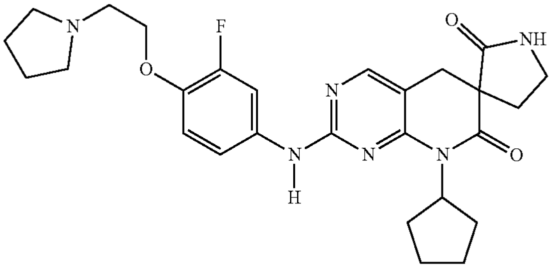
(D17)
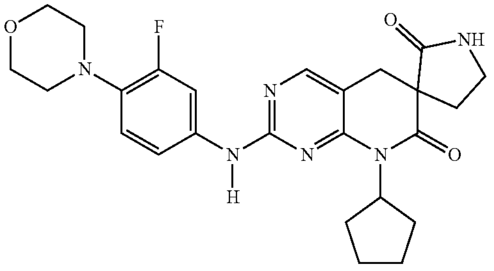
(D18)
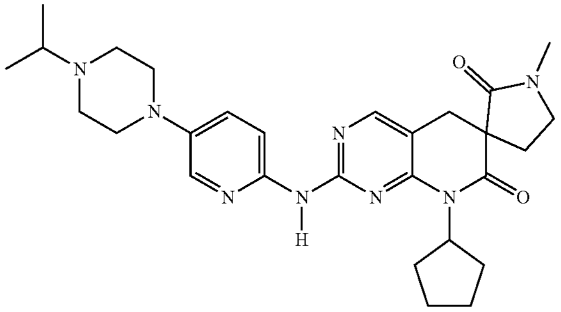
-continued
(D19)
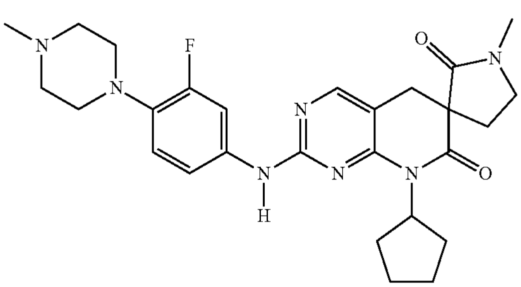
(D20)
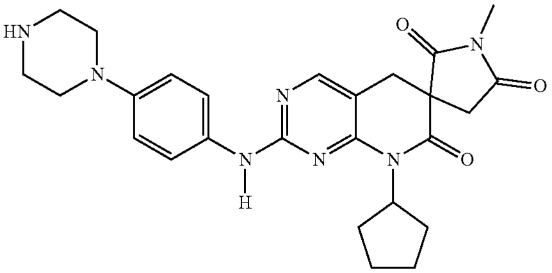
(D21)
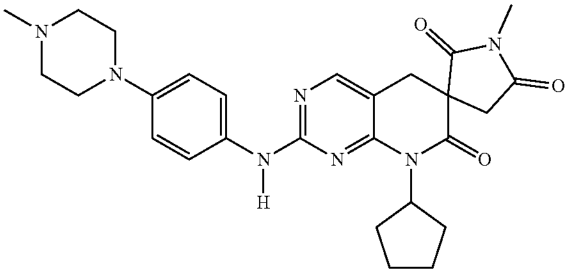
(D22)
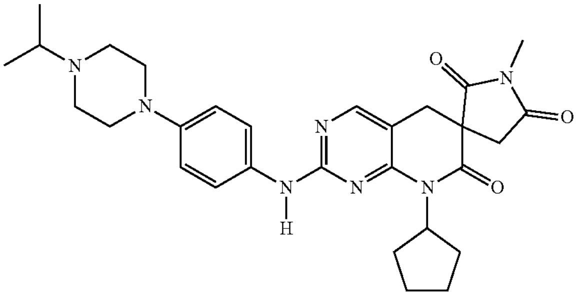
(D23)
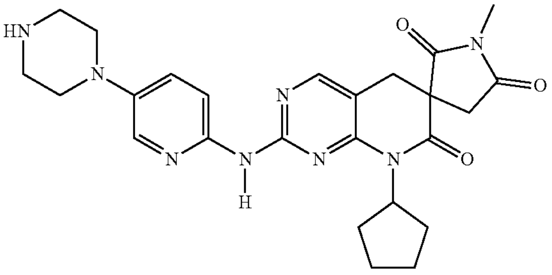

-continued
(D24)
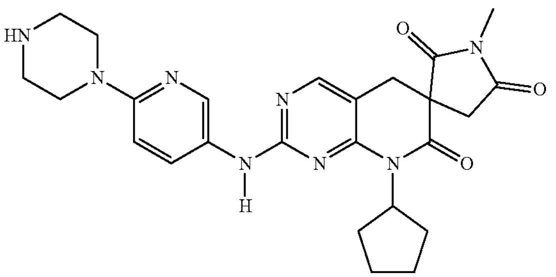
(D25)
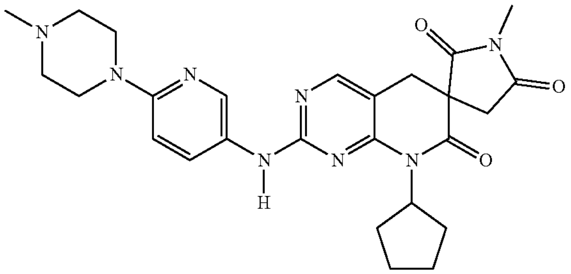
(D26)
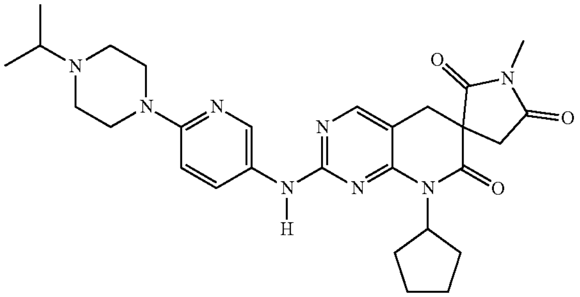
(D27)
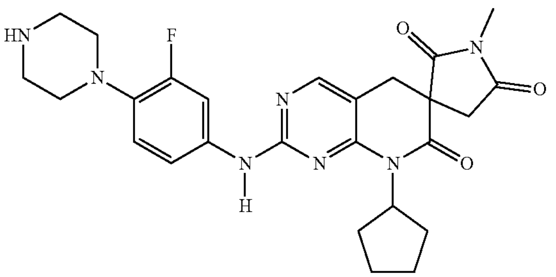
(D28)
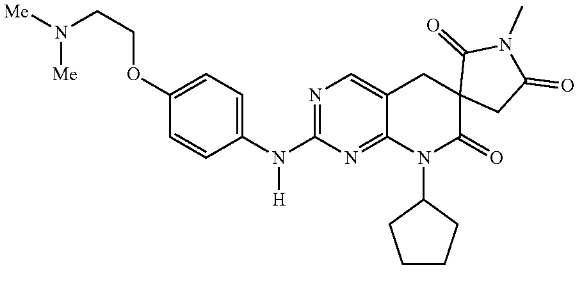
-continued
(D29)
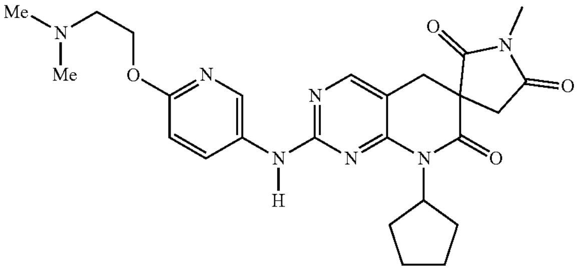
(D30)
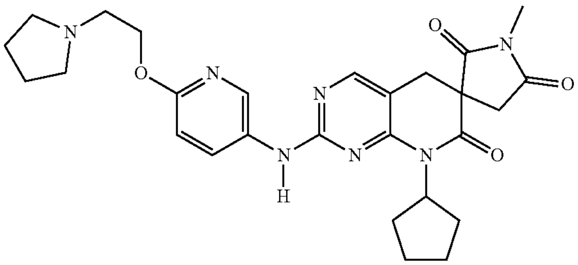
(D31)
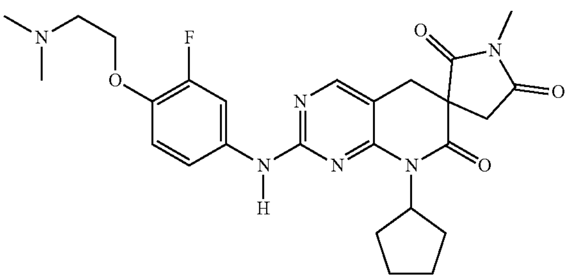
(D32)
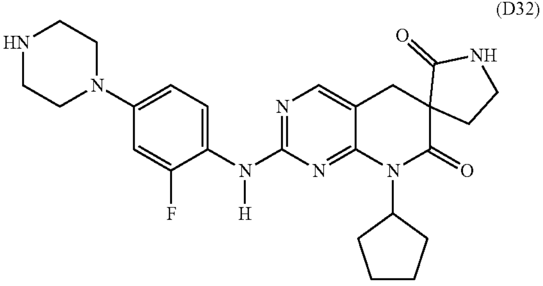
(D33)
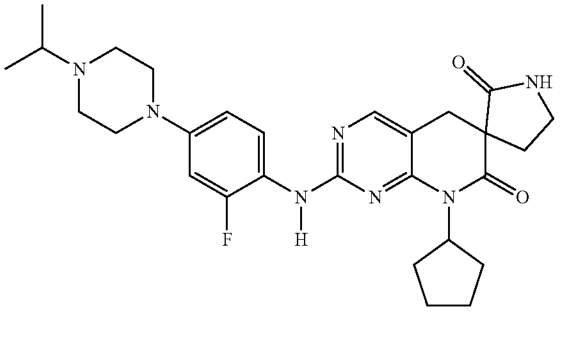

-continued
(D34)
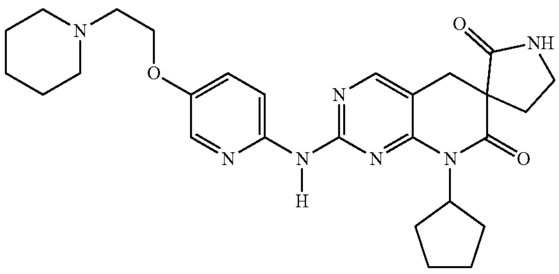
(D35)
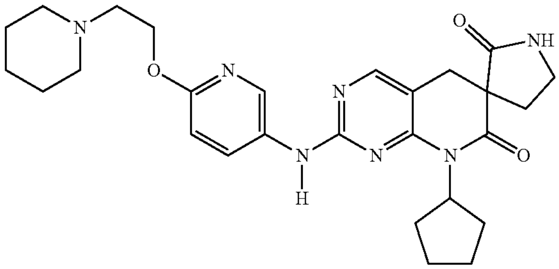
(D36)
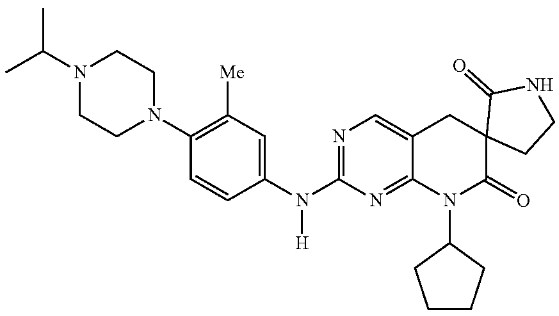
(D37)
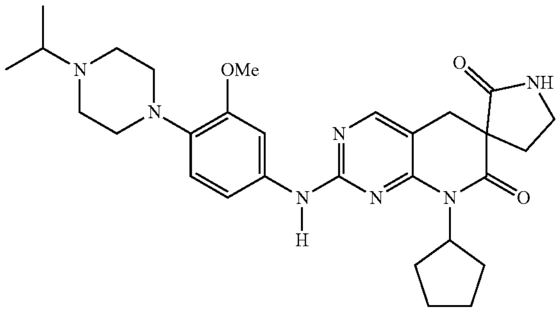
(D38)
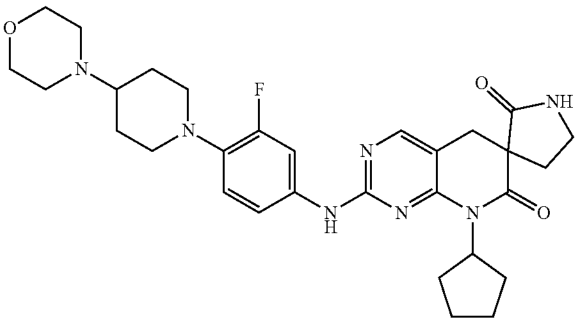
-continued
(D39)
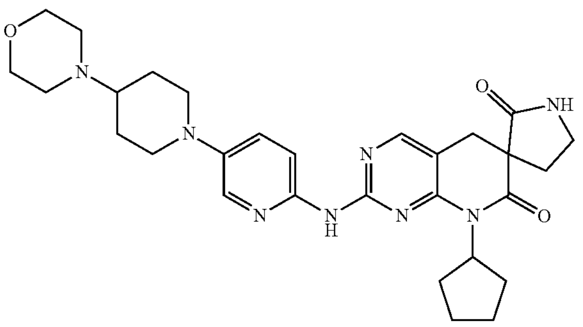
(D40)
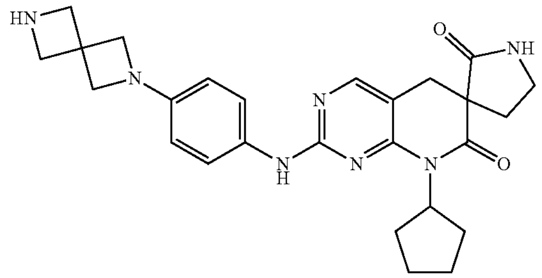
(D41)
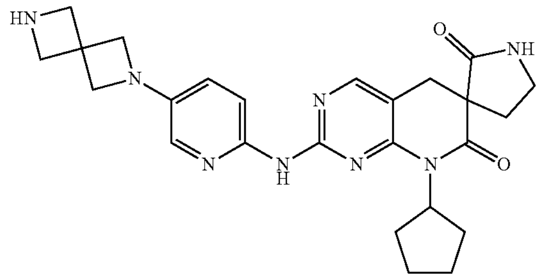
(D42)
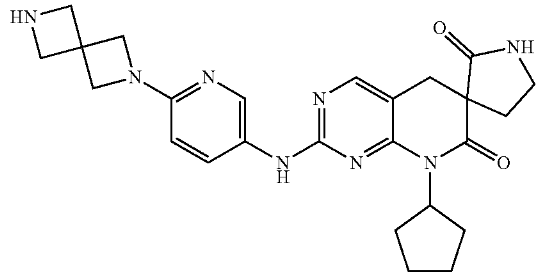
(D43)
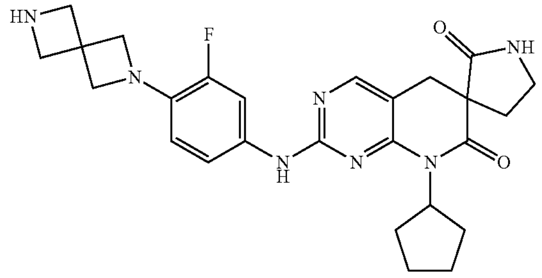

-continued (D44)

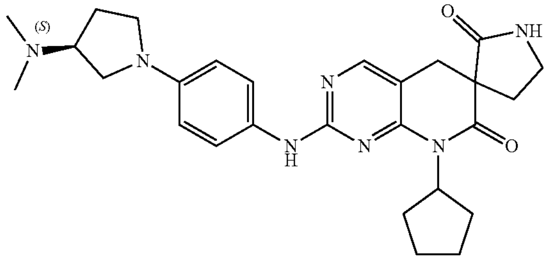

(D45)

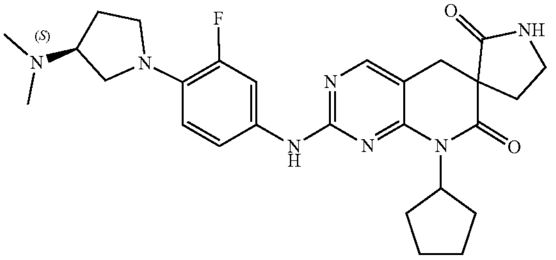

(D46)

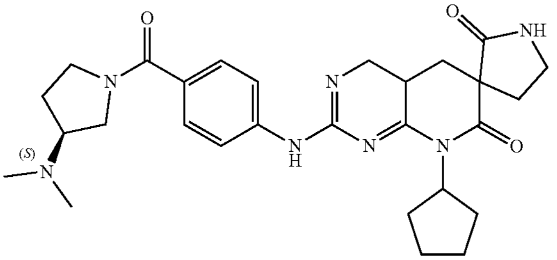

(D47)

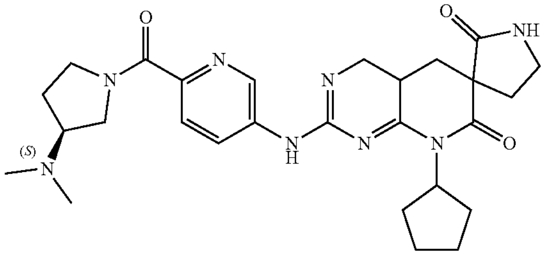

or (D48)

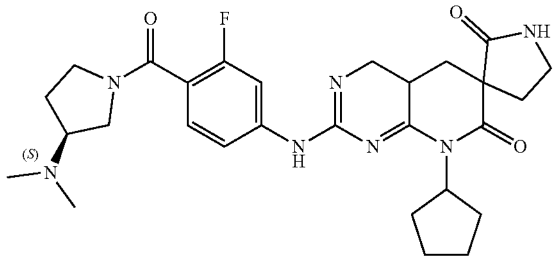

.

14. A pharmaceutical composition comprising one or more of Compounds D1-D48 as defined in claim 13, or a pharmaceutically acceptable salt thereof and one or more pharmaceutically acceptable excipients.

15. A method of treating cancer or providing a chemotherapeutic protective effect comprising administering an effective amount of one or more of Compounds D1-D48 as defined in claim 13, or a pharmaceutically acceptable salt thereof, to a subject in need thereof.

16. A compound selected from Compounds D49-D69, D87-D93, D95-D197, D199-D202 or pharmaceutically acceptable salts thereof:

(D49)

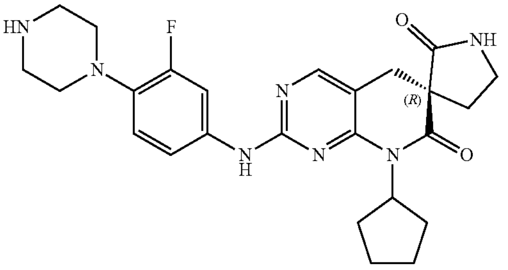

Enantiomer I (E1) of D11

(D50)

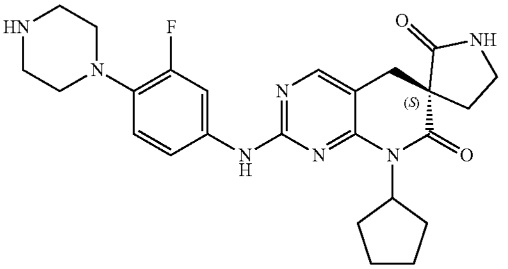

Enantiomer II (E2) of D11

(D51)

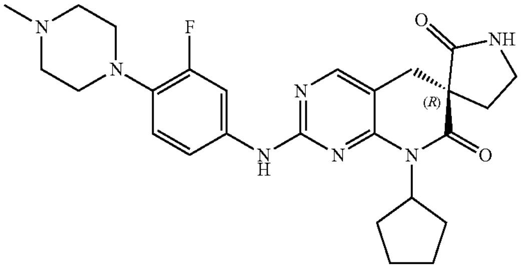

Enantiomer I (E1) of D12

(D52)

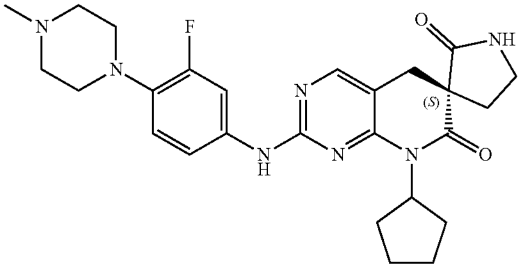

Enantiomer II (E2) of D12

-continued
(D53)
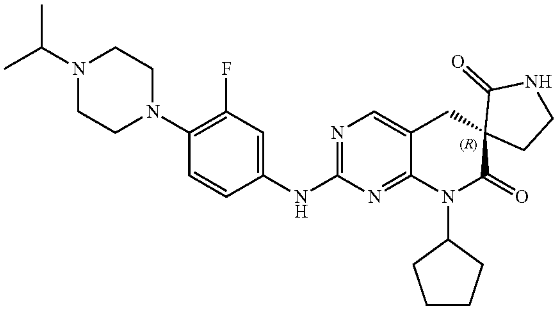
Enantiomer I (E1) of D10
(D54)
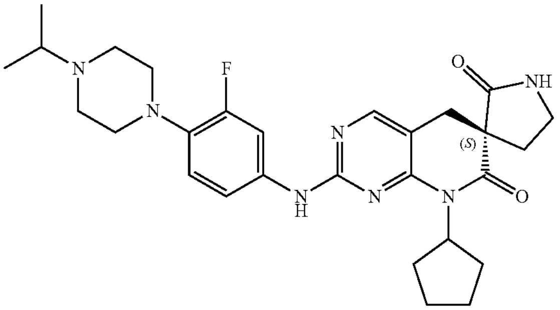
Enantiomer II (E2) of D10
(D55)
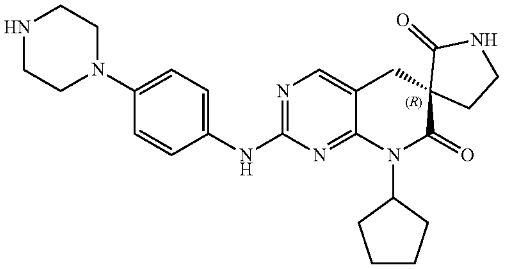
Enantiomer I (E1) of D3
(D56)
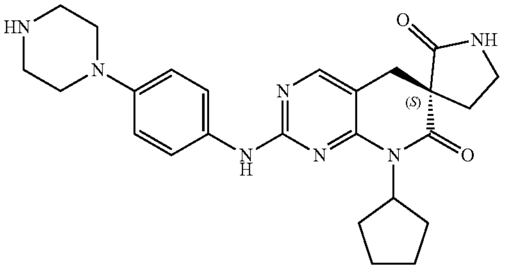
Enantiomer II (E2) of D3
-continued
(D57)
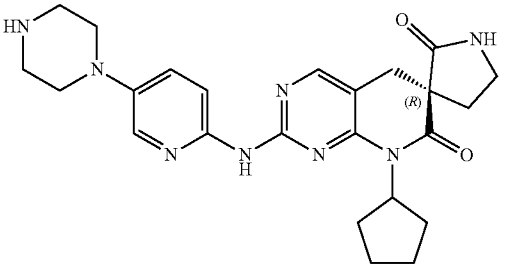
Enantiomer I (E1)
(D58)
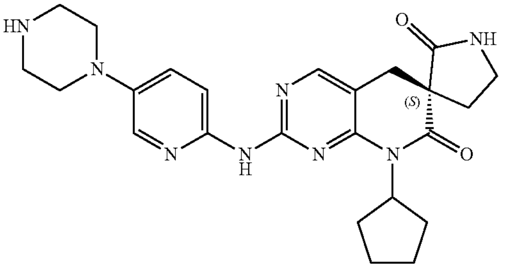
Enantiomer II (E2)
(D59)
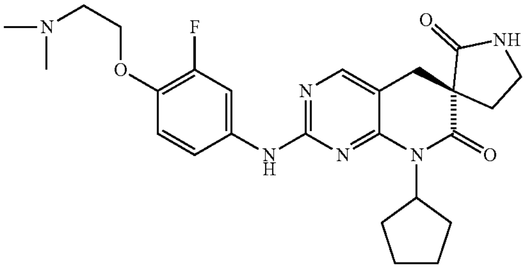
(D60)
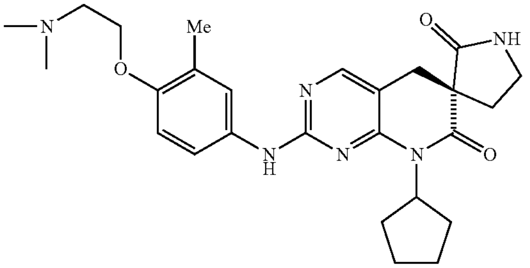
(D61)
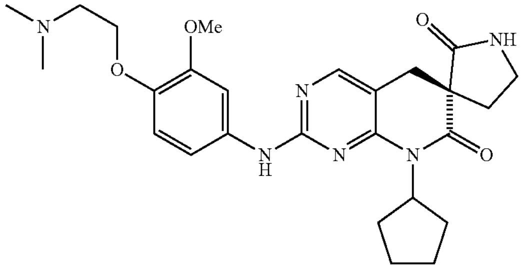

-continued
(D62)
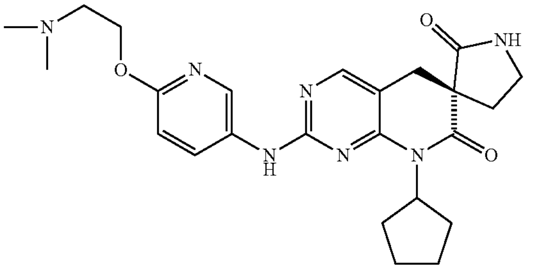
(D63)
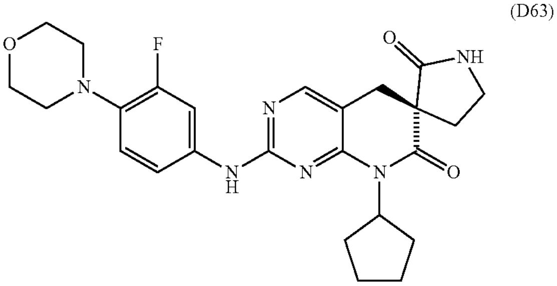
(D64)
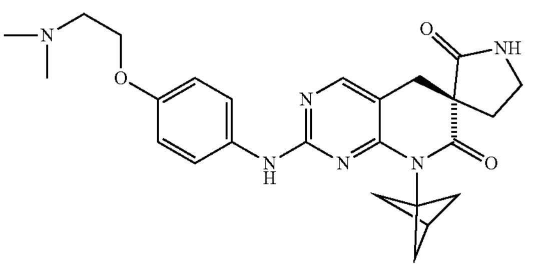
(D65)
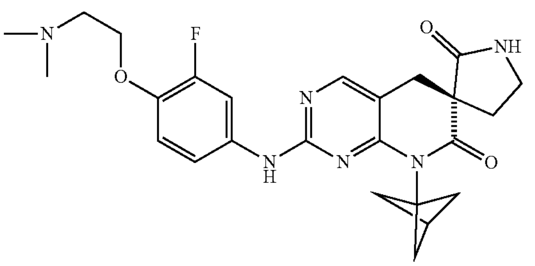
(D66)
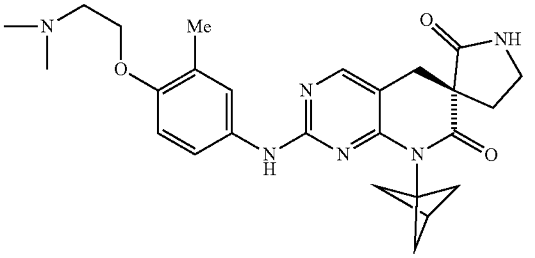
-continued
(D67)
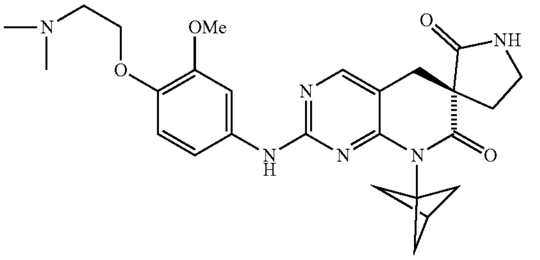
(D68)
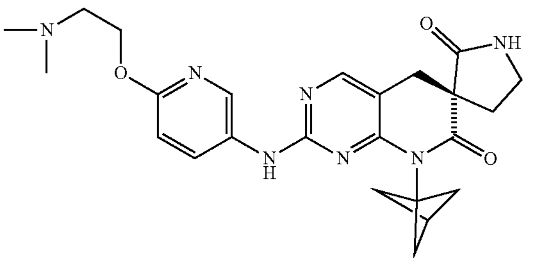
(D69)
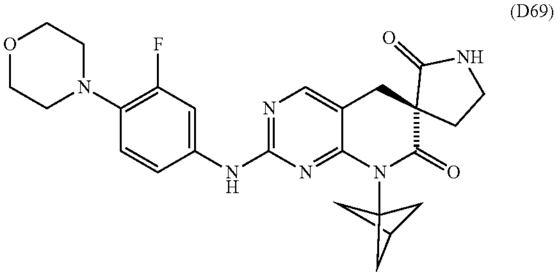
(D70)
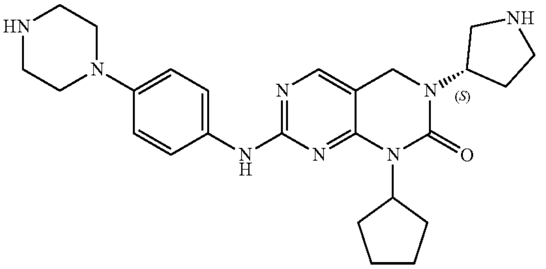
(D86)
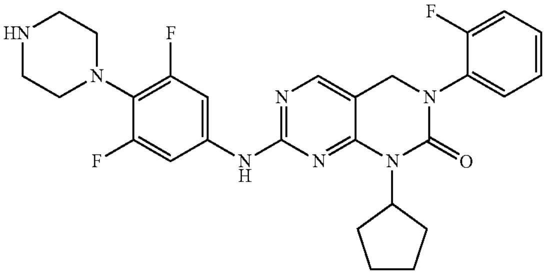

-continued
(D87)
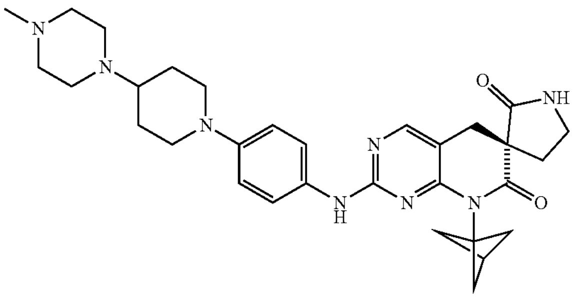
(D88)
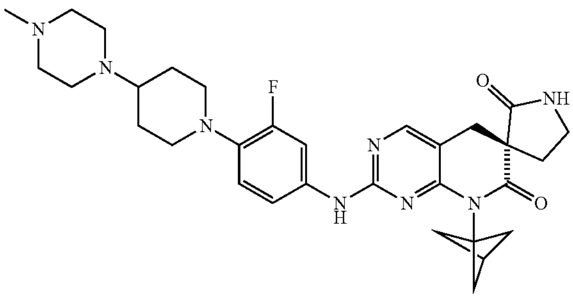
(D89)
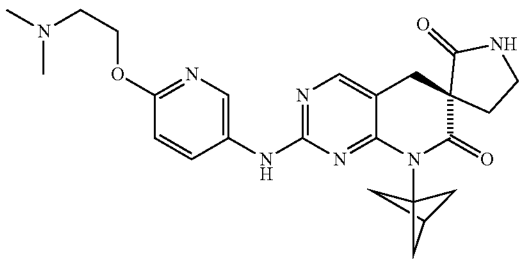
(D90)
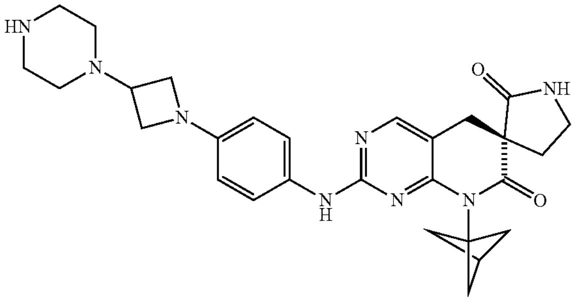
(D91)
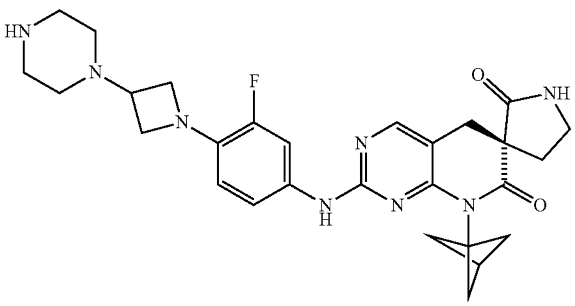
-continued
(D92)
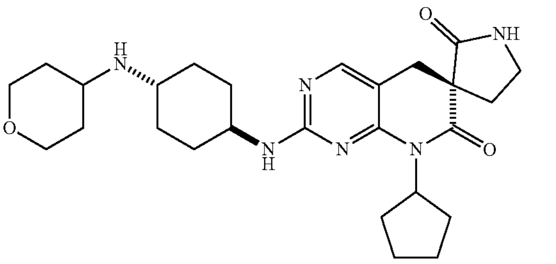
(D93)
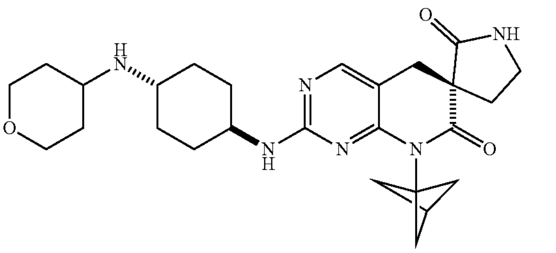
(D94)
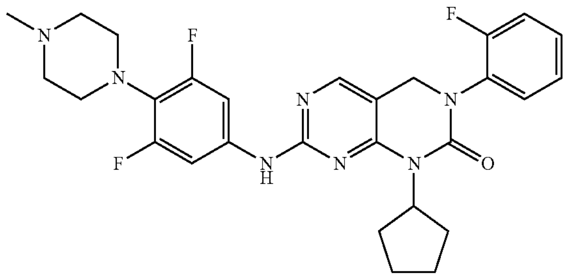
(D95)
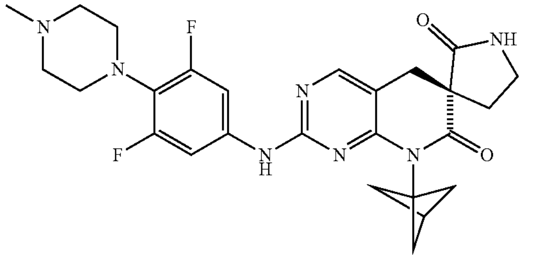
(D96)
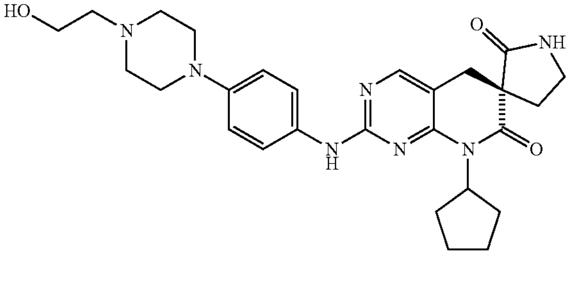

-continued
(D97)
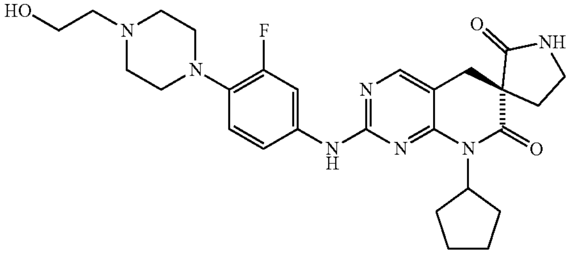
(D98)
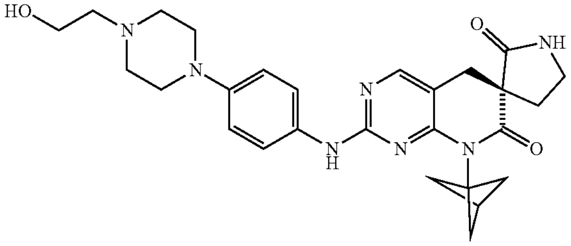
(D99)
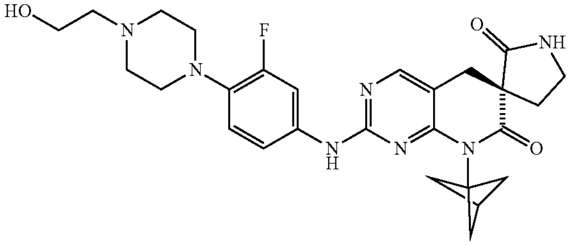
(D100)
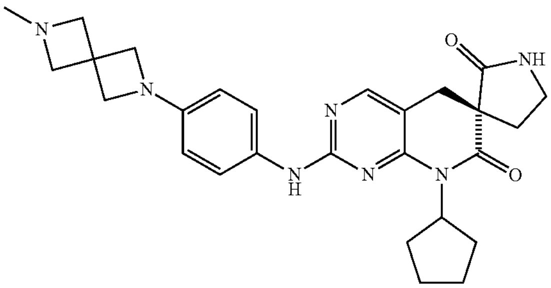
(D101)
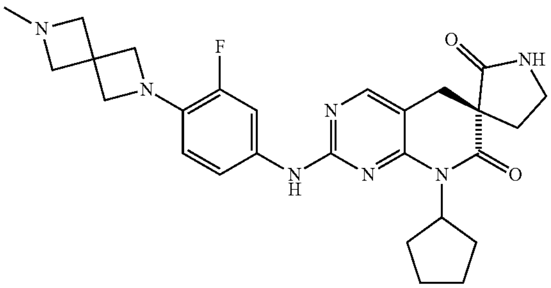
-continued
(D102)
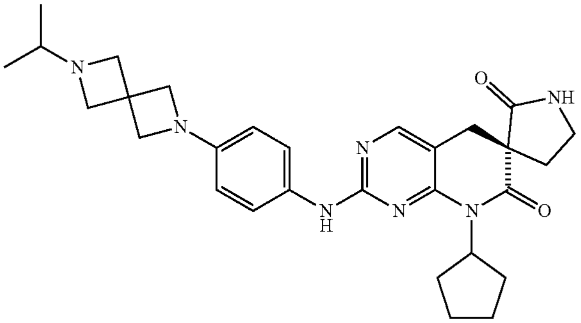
(D103)
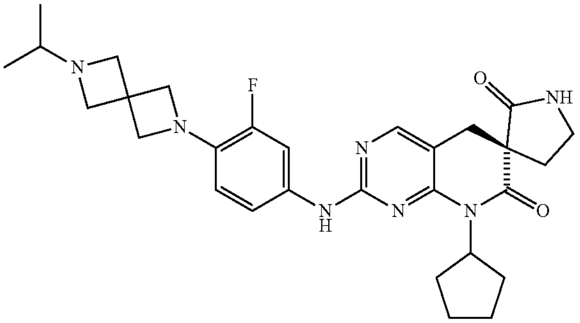
(D104)
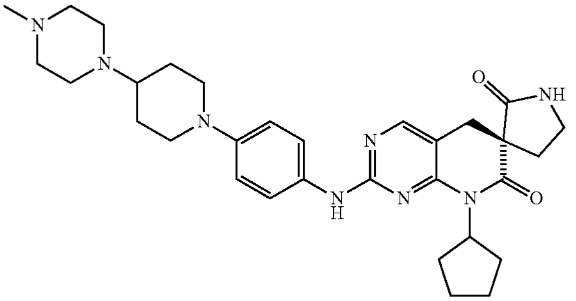
(D105)
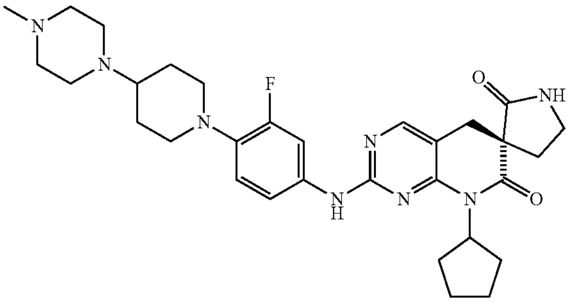

-continued
(D106)
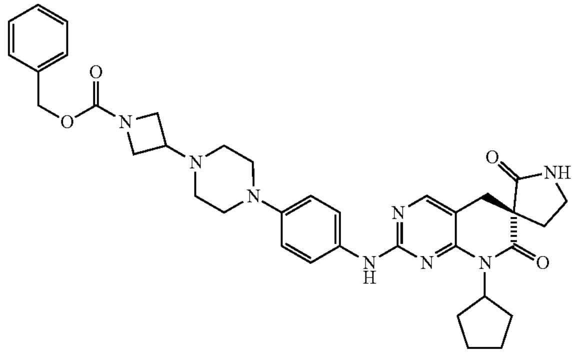
(D107)
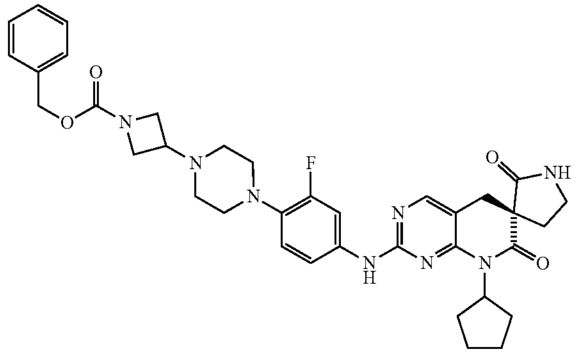
(D108)
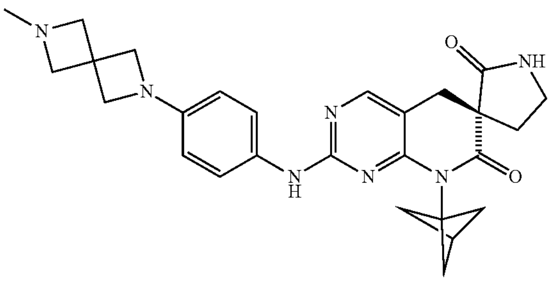
(D109)
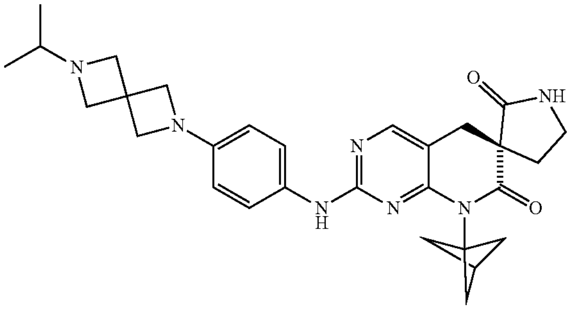
-continued
(D110)
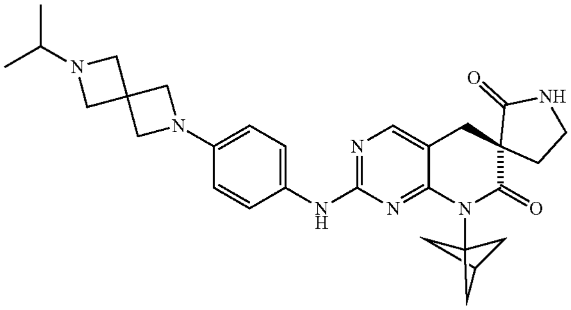
(D111)
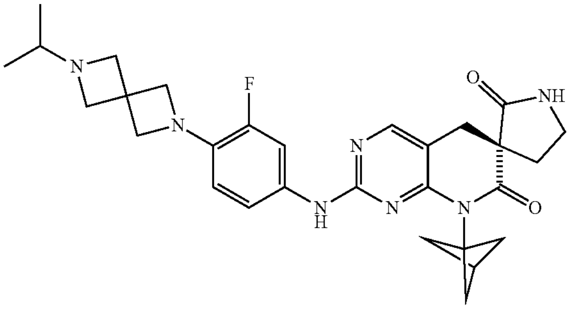
(D112)
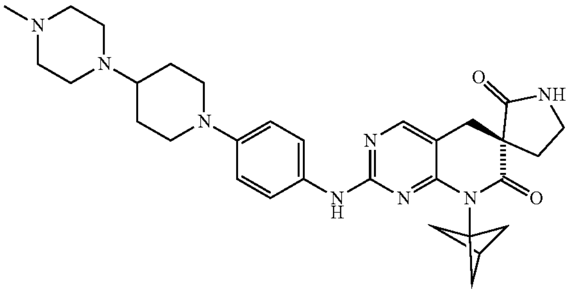
(D113)
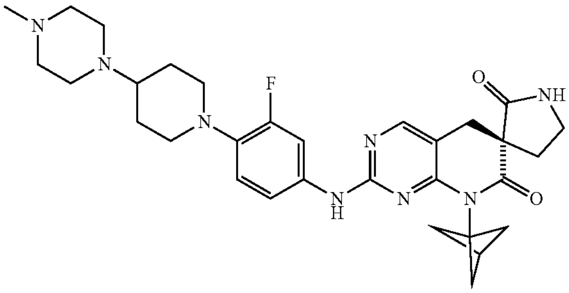
(D114)
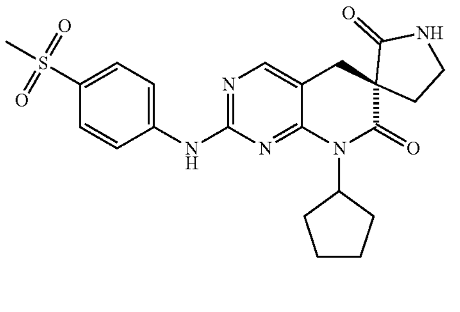

-continued
(D115)
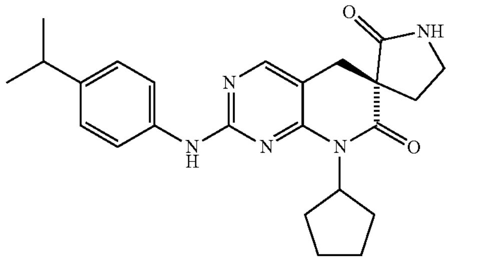
(D116)
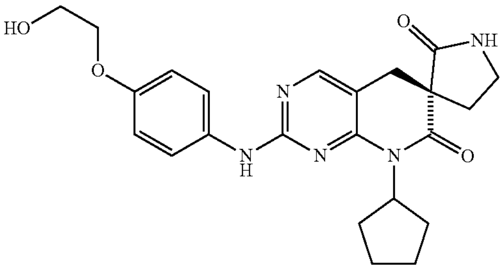
(D117)
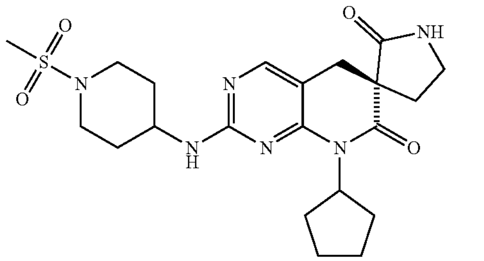
(D118)
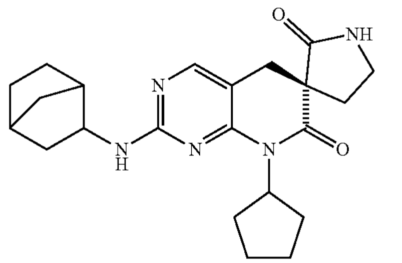
(D119)
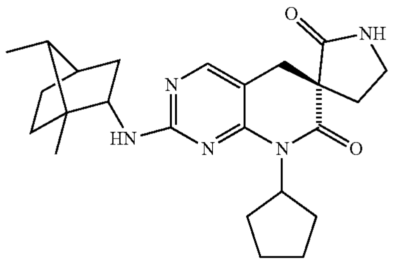
(D120)
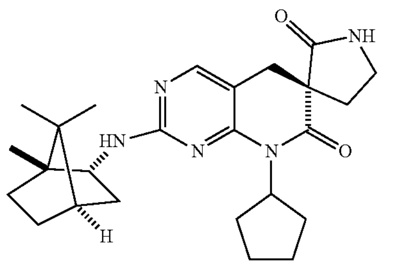
-continued
(D121)
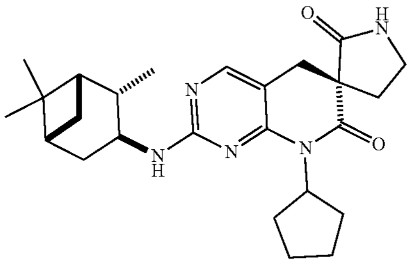
(D122)
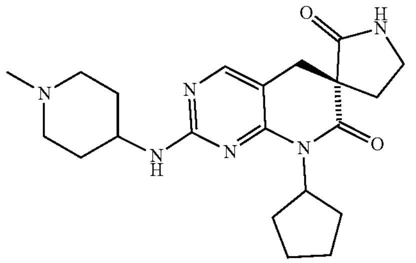
(D123)
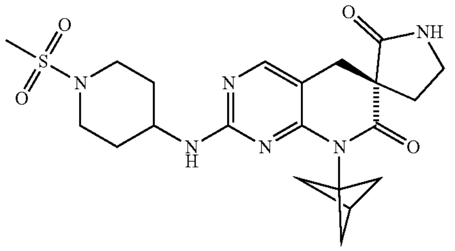
(D124)
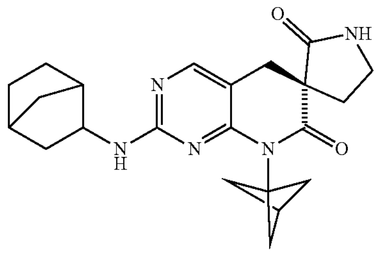
(D125)
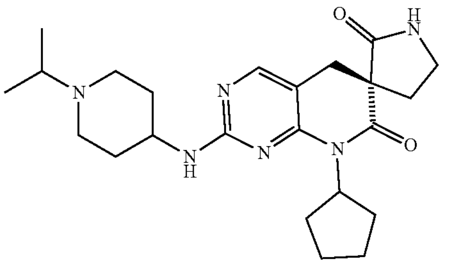
(D126)
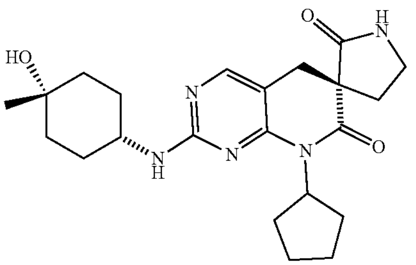

-continued
(D127)
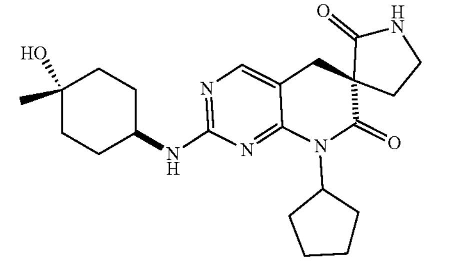
(D128)
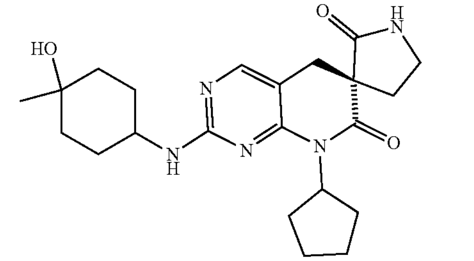
(D129)
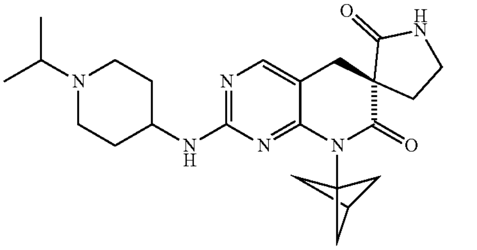
(D130)
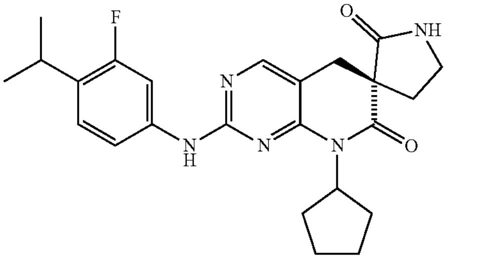
(D131)
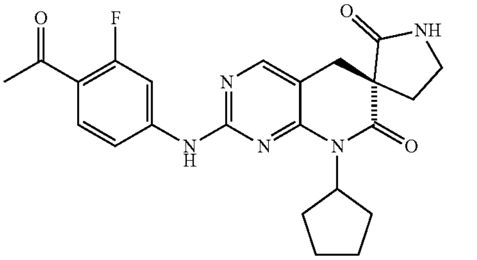
(D132)
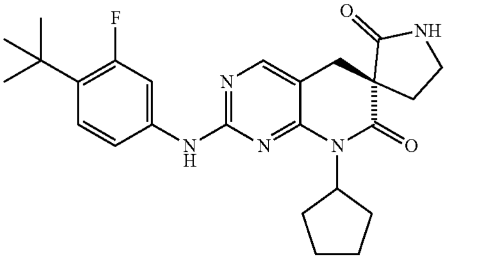
-continued
(D133)
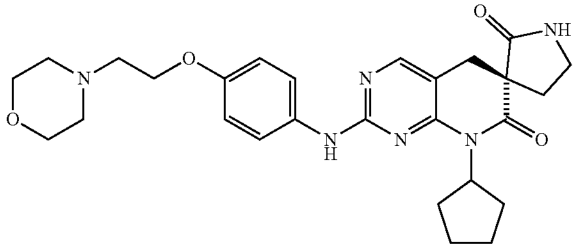
(D134)
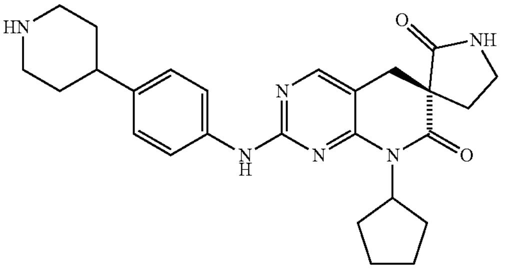
(D135)
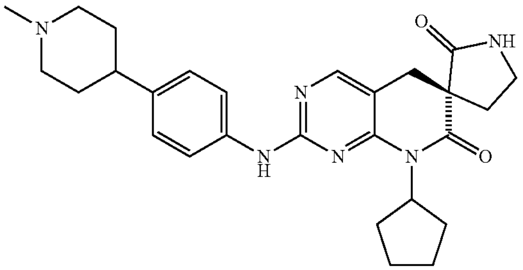
(D136)
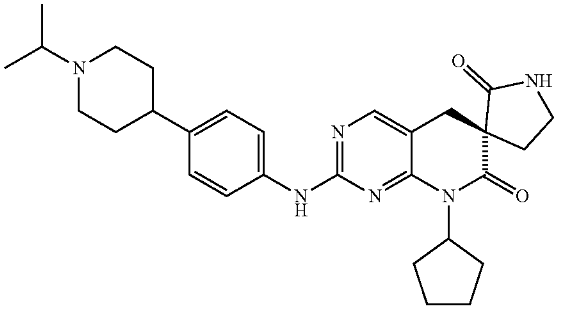
(D137)
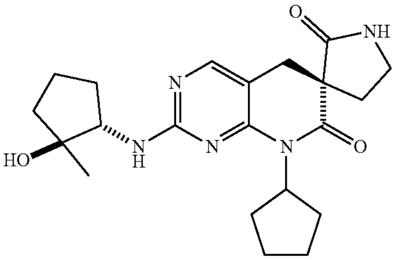

-continued
(D138)
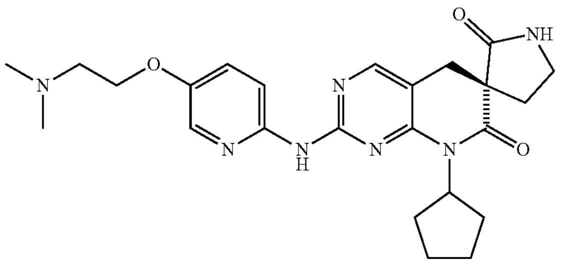
(D139)
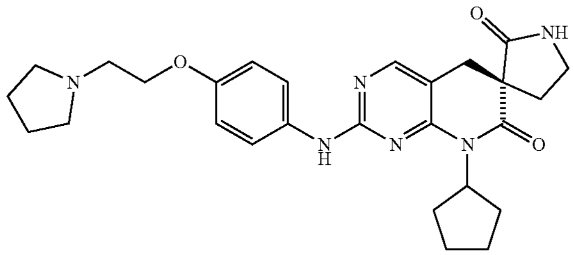
(D140)
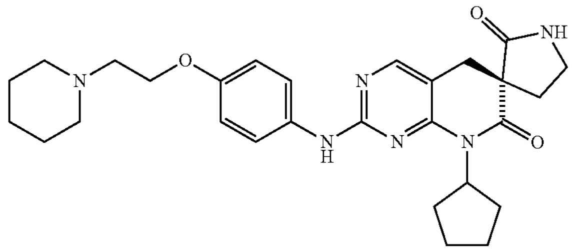
(D141)
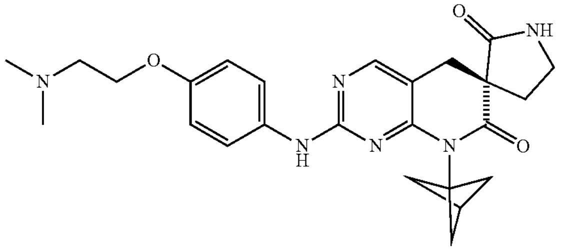
(D142)
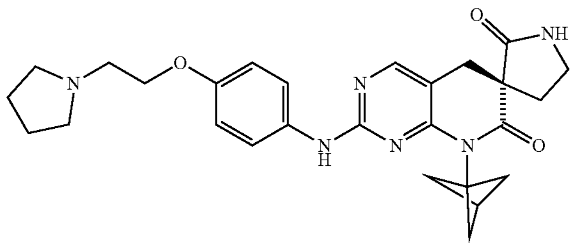
-continued
(D143)
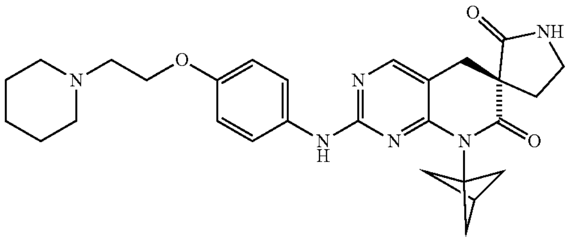
(D144)
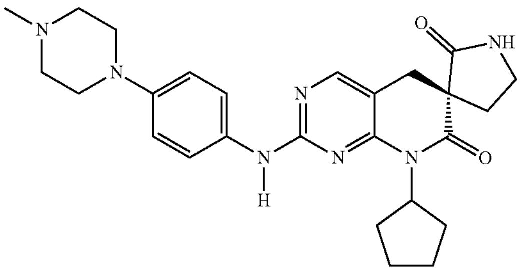
(D145)
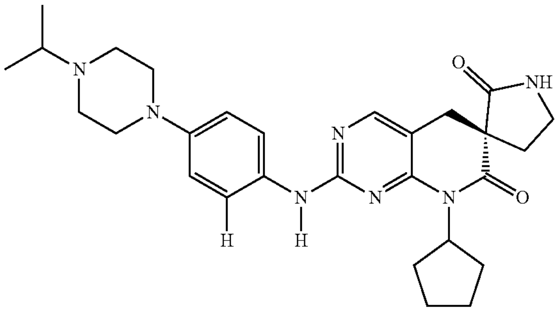
(D146)
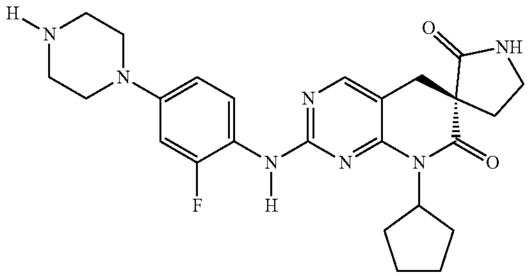
(D147)
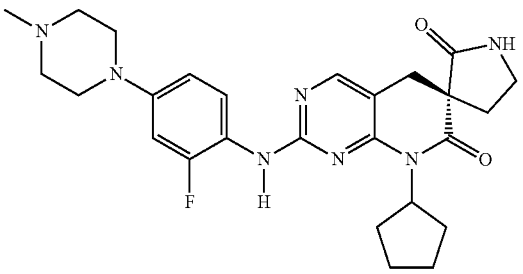

-continued
(D148)
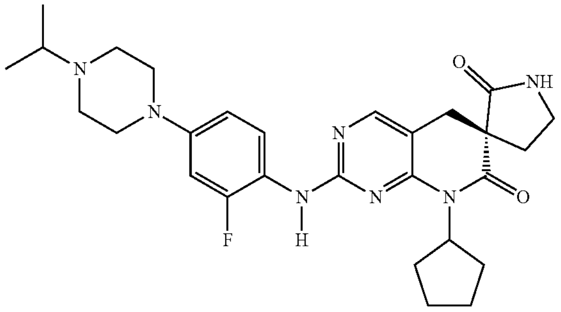
(D149)
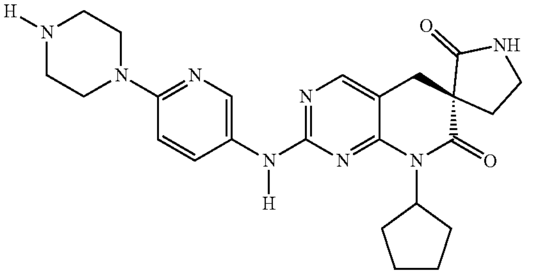
(D150)
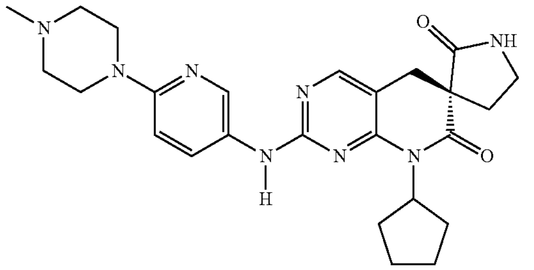
(D151)
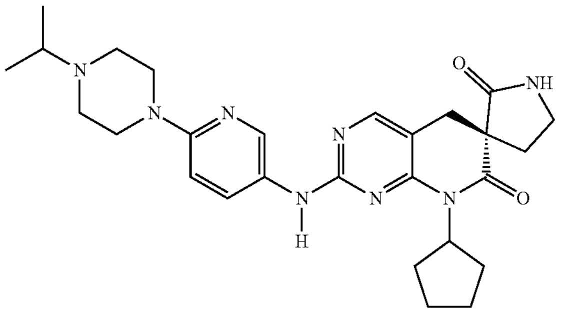
(D152)
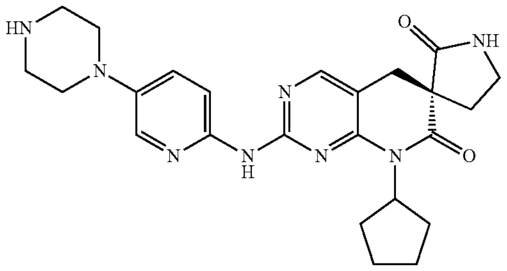
-continued
(D153)
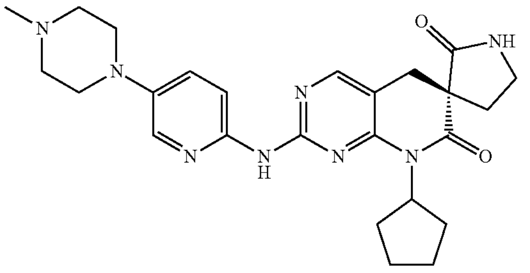
(D154)
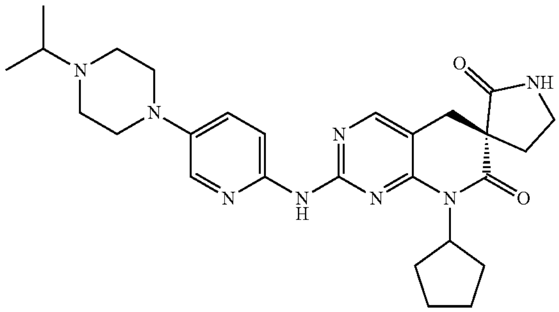
(D155)
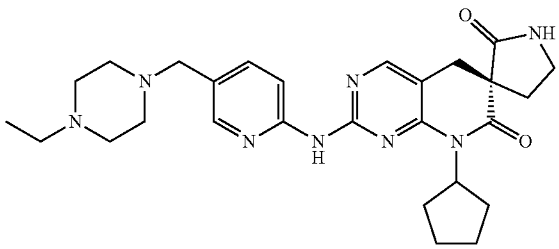
(D156)
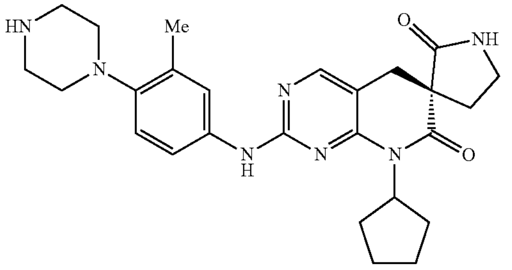
(D157)
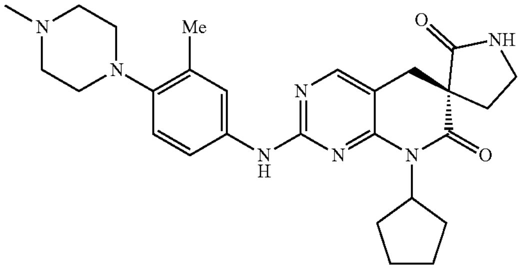

-continued
(D158)
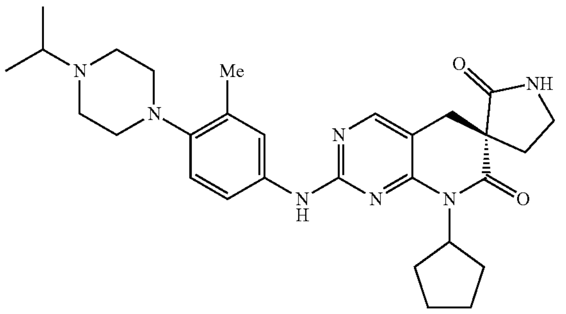
(D159)
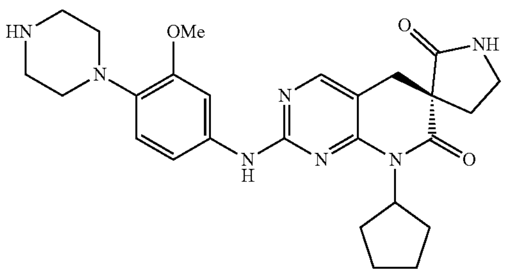
(D160)
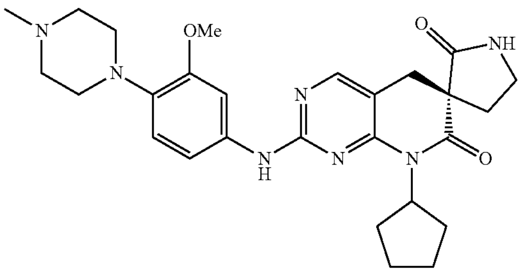
(D161)
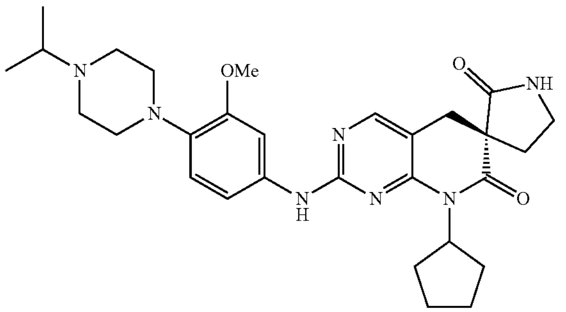
(D162)
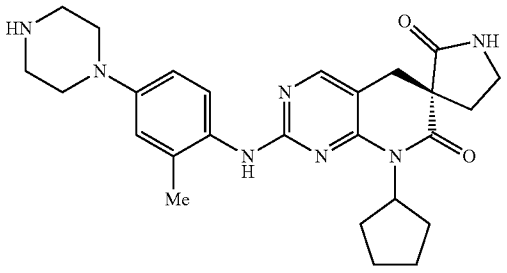
-continued
(D163)
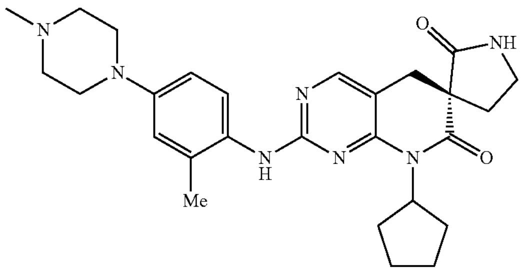
(D164)
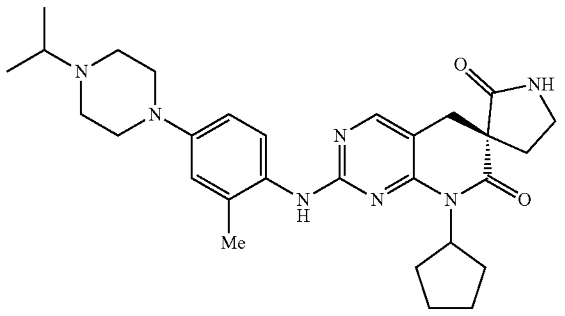
(D165)
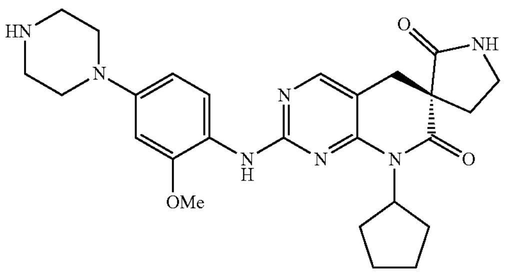
(D166)
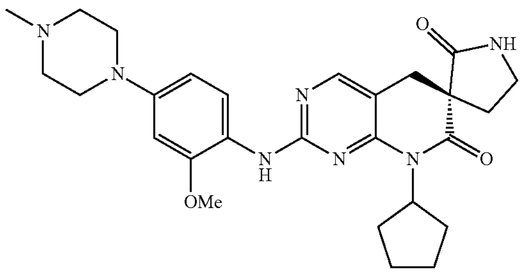
(D167)
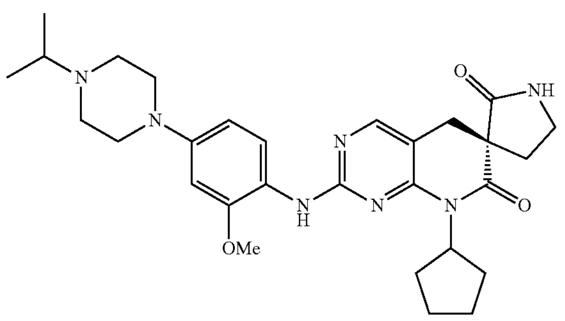

-continued
(D168)
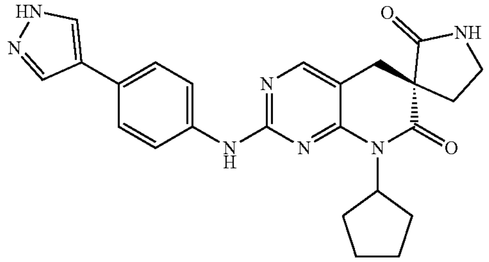
(D169)
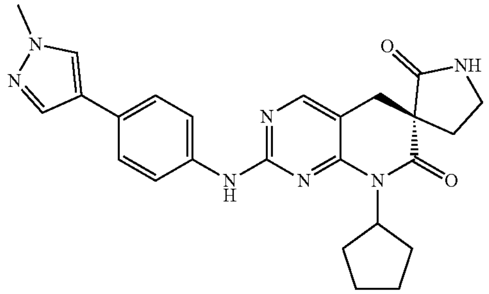
(D170)
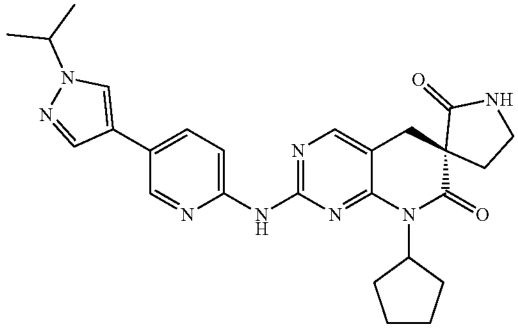
(D171)
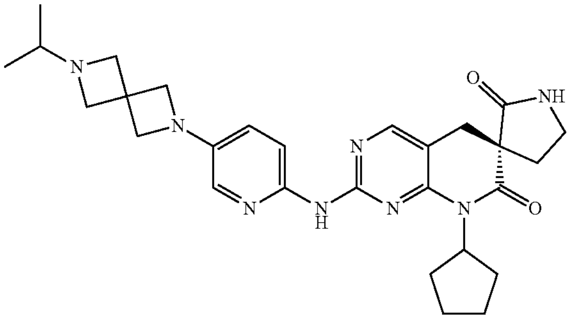
(D172)
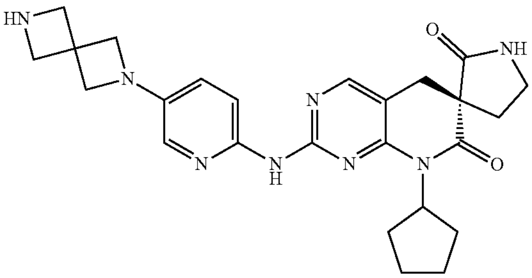
-continued
(D173)
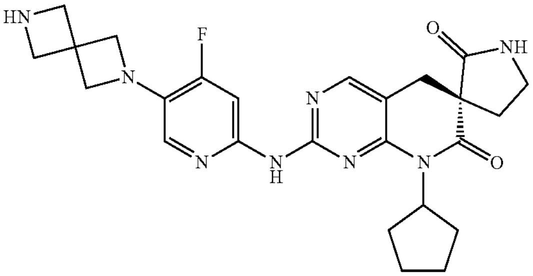
(D174)
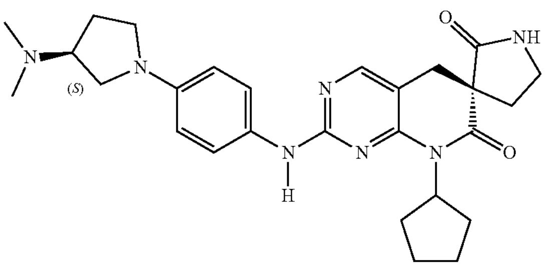
(D175)
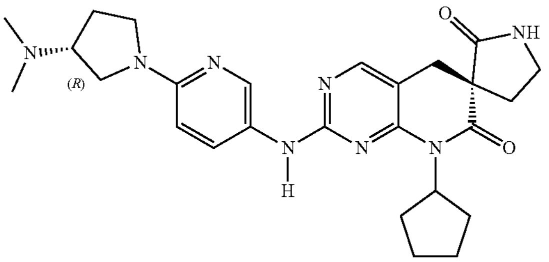
(D176)
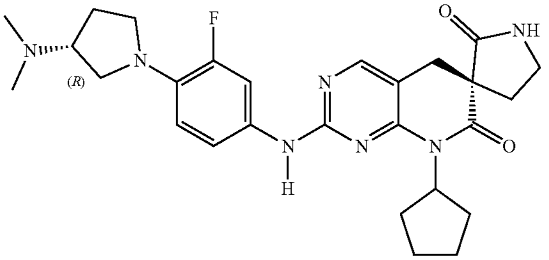
(D177)
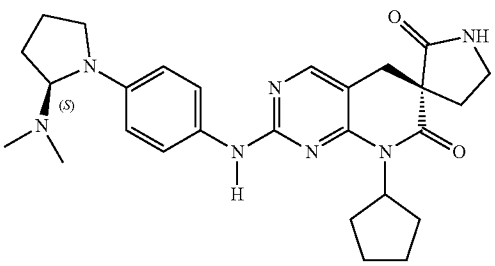

-continued
(D178)
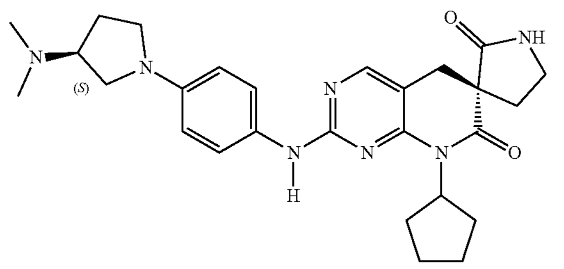
(D179)
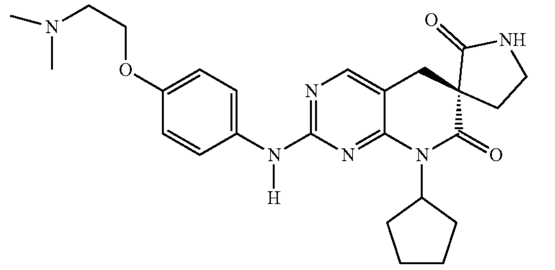
(D180)
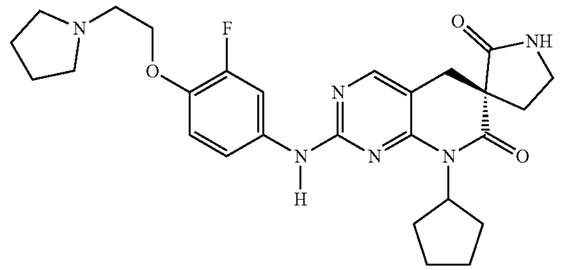
(D181)
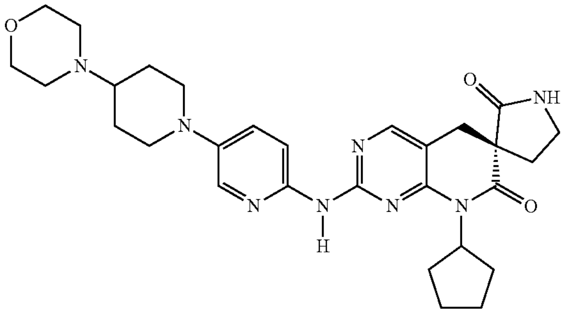
(D182)
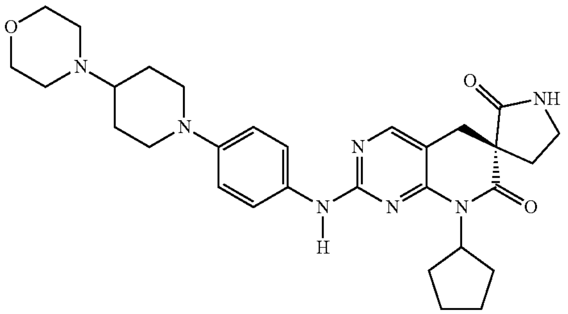
-continued
(D183)
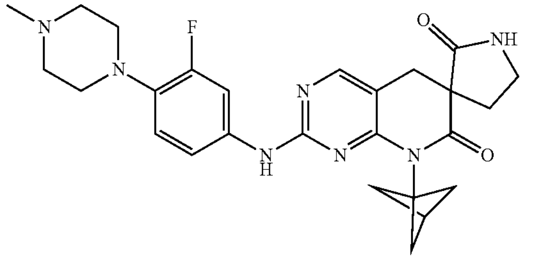
Racemic
(D184)
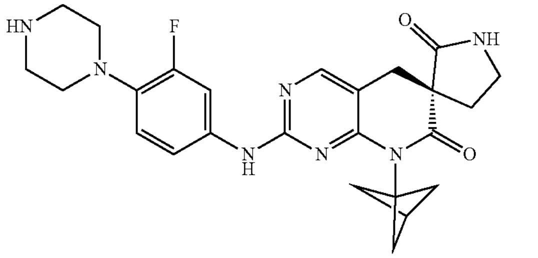
E2
(D185)
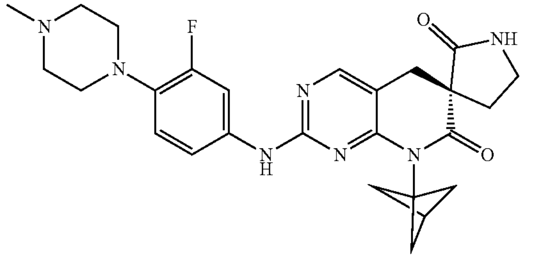
E2
(D186)
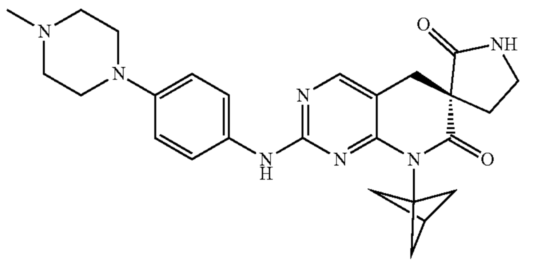
E2
(D187)
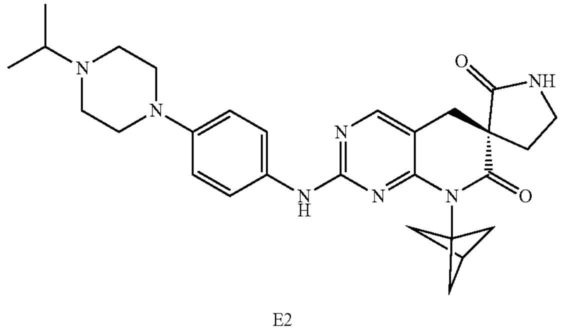
E2

-continued
(D188)
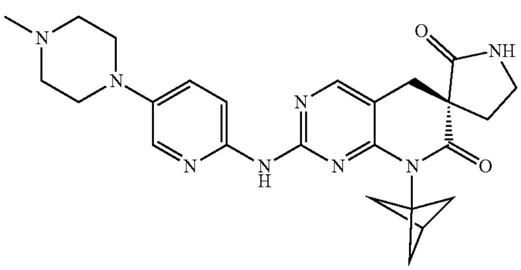
E2
(D189)
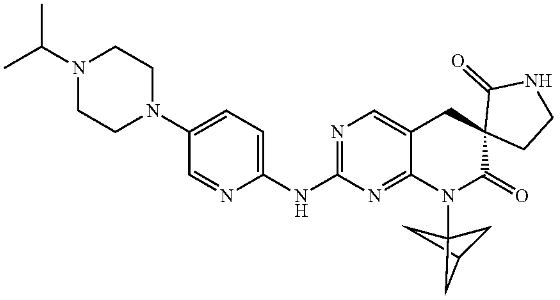
E2
(D190)
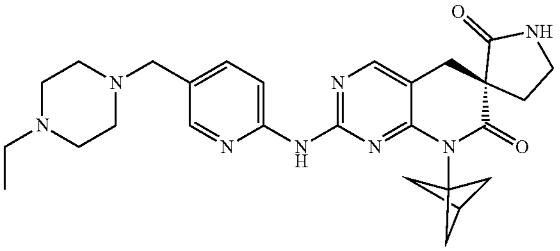
E2
(D191)
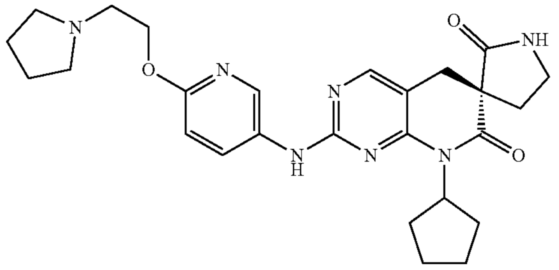
(D192)
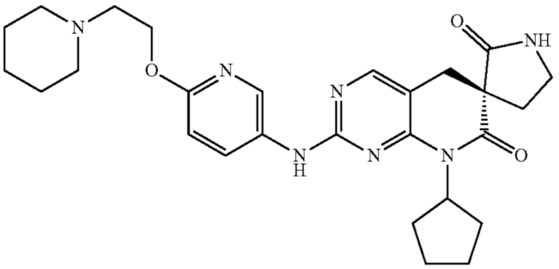
-continued
(D193)
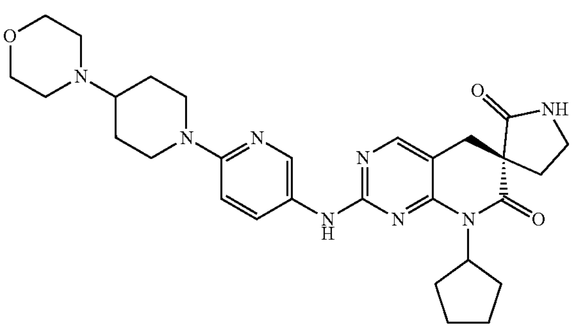
(D194)
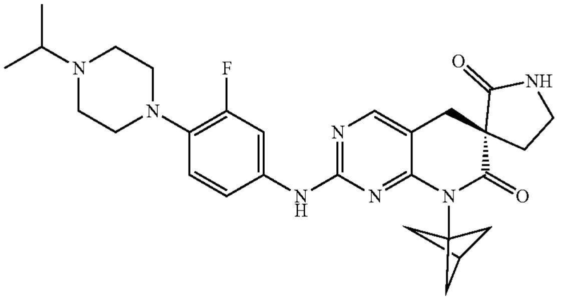
E2
(D195)
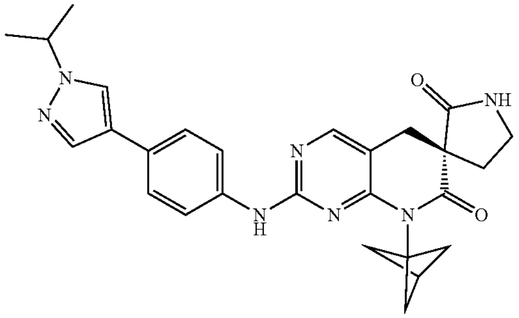
E2
(D196)
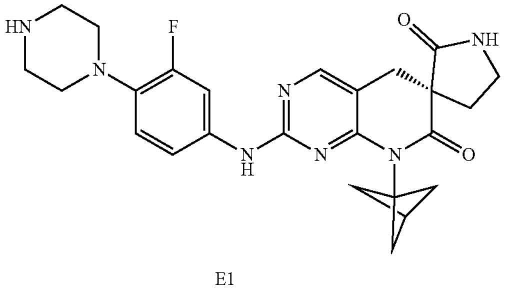
E1

-continued (D197)

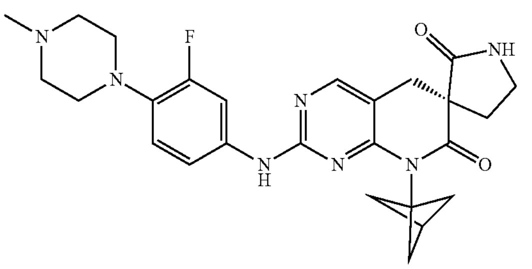

E1

(D198)

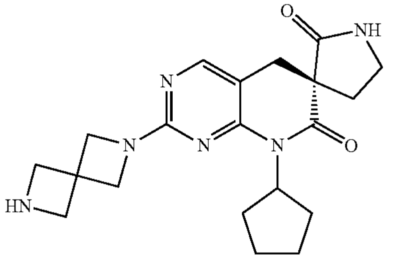

(D199)

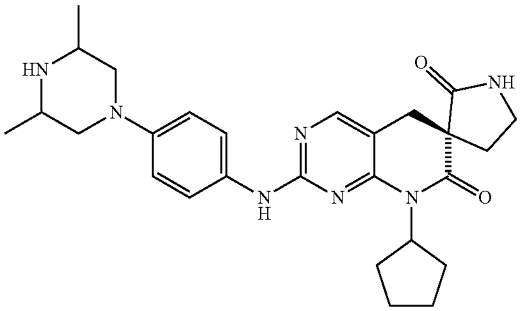

(D200)

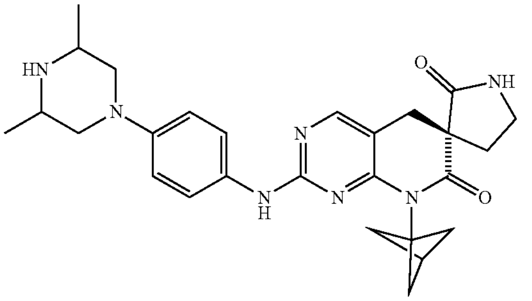

(D201)

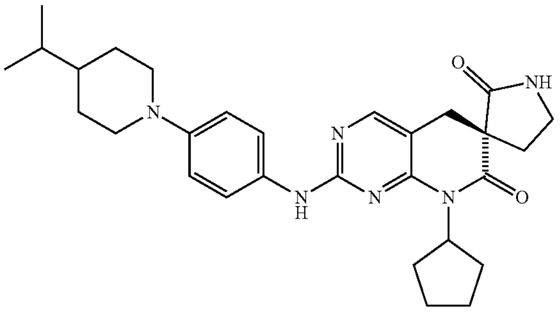

-continued (202)

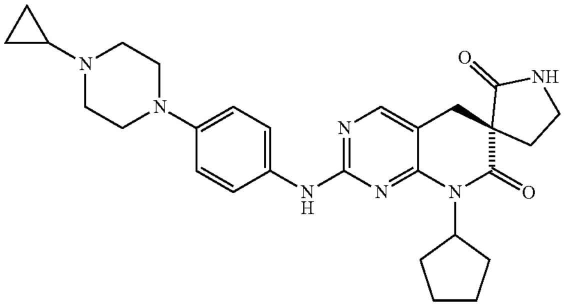

(203)

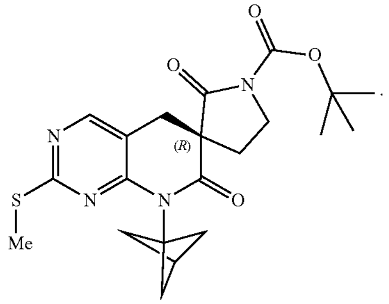

17. A pharmaceutical composition comprising one or more of Compounds D49-D69, D87-D93, D95-D197, D199-D202 as defined in claim 16, or a pharmaceutically acceptable salt thereof and one or more pharmaceutically acceptable excipients.

18. A method of treating cancer or providing a chemo-therapeutic protective effect comprising administering an effective amount of one or more of Compounds D49-D69 D87-D93, D95-D197, D199-D202 as defined in claim 16, or a pharmaceutically acceptable salt thereof, to a subject in need thereof.

19. A pharmaceutical composition comprising one or more compounds as defined in claim 9, or a pharmaceutically acceptable salt thereof and one or more pharmaceutically acceptable excipients.

20. The compound of claim 10 or the pharmaceutically acceptable salt thereof, wherein R is

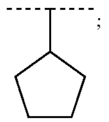

and wherein $R_1$ is

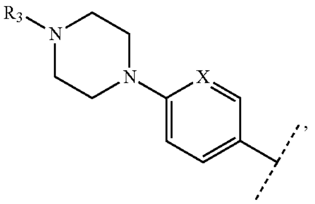

-continued

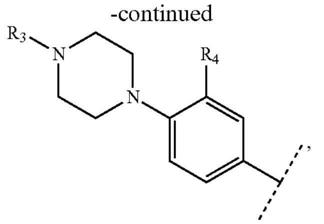

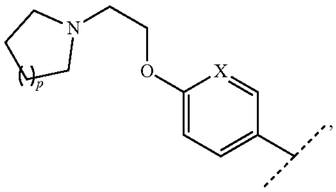

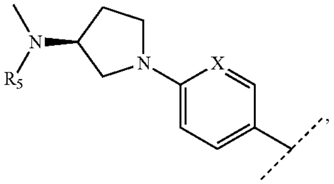

or

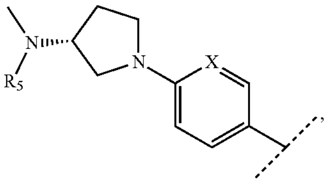

where $R_3$ is H, Me, $CH_2CH_2OH$, isopropyl, or isobutyl; $R_4$ is Me; $R_5$ is H or Me; and X is C—H, N, or C—F; and p is 1.

21. The compound of claim 20 or the pharmaceutically acceptable salt thereof, wherein the compound is of formula (XI)

(XI)

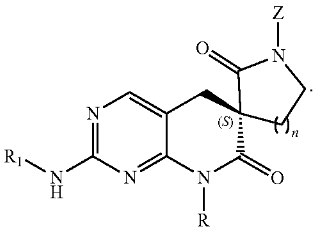

22. A pharmaceutical composition comprising one or more compounds as defined in claim 21, or a pharmaceutically acceptable salt thereof and one or more pharmaceutically acceptable excipients.

23. A method of treating cancer or providing a chemotherapeutic protective effect comprising administering an effective amount of one or more as defined in claim 21 to a subject in need thereof.

* * * * *